(12) United States Patent
Flasinski

(10) Patent No.: US 12,071,628 B2
(45) Date of Patent: Aug. 27, 2024

(54) PLANT REGULATORY ELEMENTS AND USES THEREOF

(71) Applicant: Monsanto Technology LLC, St. Louis, MO (US)

(72) Inventor: Stanislaw Flasinski, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 17/821,123

(22) Filed: Aug. 19, 2022

(65) Prior Publication Data

US 2023/0145023 A1 May 11, 2023

Related U.S. Application Data

(62) Division of application No. 16/900,717, filed on Jun. 12, 2020, now Pat. No. 11,466,282, which is a division of application No. 15/798,319, filed on Oct. 30, 2017, now Pat. No. 10,752,910, which is a division of application No. 14/686,602, filed on Apr. 14, 2015, now Pat. No. 9,834,777, which is a division of application No. 13/428,994, filed on Mar. 23, 2012, now Pat. No. 9,062,316.

(60) Provisional application No. 61/467,875, filed on Mar. 25, 2011.

(51) Int. Cl.
   *C12N 15/82* (2006.01)
   *C12N 15/113* (2010.01)

(52) U.S. Cl.
   CPC ........ *C12N 15/8216* (2013.01); *C12N 15/113* (2013.01); *C12N 15/8222* (2013.01)

(58) Field of Classification Search
   None
   See application file for complete search history.

(56) References Cited

U.S. PATENT DOCUMENTS

| | | | |
|---|---|---|---|
| 5,633,441 A | 5/1997 | De Greef et al. | |
| 6,054,574 A | 4/2000 | Quail et al. | |
| 6,596,925 B1 | 7/2003 | Perera et al. | |
| 6,878,818 B1 | 4/2005 | Goldsbrough et al. | |
| 7,211,711 B2 | 5/2007 | Perera et al. | |
| 7,518,034 B2 | 4/2009 | Perera et al. | |
| 7,622,641 B2 * | 11/2009 | McCutchen | C12N 9/1092 |
| | | | 800/300 |
| 7,816,581 B2 | 10/2010 | Gilbertson et al. | |
| 7,932,374 B2 | 4/2011 | Perera et al. | |
| 9,062,316 B2 | 6/2015 | Flasinski | |
| 10,752,910 B2 | 8/2020 | Flasinski | |
| 11,466,282 B2 | 10/2022 | Flasinski | |
| 2002/0042932 A1 | 4/2002 | Back et al. | |
| 2002/0046415 A1 | 4/2002 | Albert et al. | |
| 2002/0192813 A1 | 12/2002 | Conner et al. | |
| 2003/0154509 A1 | 8/2003 | Pascal et al. | |
| 2005/0198712 A1 | 9/2005 | Betts et al. | |
| 2008/0263721 A9 | 10/2008 | Boukharov et al. | |
| 2010/0058495 A1 * | 3/2010 | Abbitt | C12N 15/113 |
| | | | 800/278 |
| 2010/0199371 A1 | 8/2010 | Castle et al. | |
| 2011/0023183 A1 | 1/2011 | Neal et al. | |
| 2011/0177228 A1 | 7/2011 | Alexandrov et al. | |
| 2015/0167012 A1 | 6/2015 | Flasinski | |
| 2016/0289693 A1 | 10/2016 | Flasinski | |
| 2018/0057833 A1 | 3/2018 | Flasinski | |
| 2018/0105823 A1 | 4/2018 | Flasinski | |
| 2020/0032289 A1 | 1/2020 | Anderson et al. | |
| 2020/0080096 A1 | 3/2020 | Flasinski et al. | |

FOREIGN PATENT DOCUMENTS

| | | |
|---|---|---|
| CA | 2822289 | 6/2012 |
| CL | 1646-04 | 6/2004 |
| EP | 1953232 | 8/2008 |
| RU | 2181380 | 4/2002 |
| RU | 2326167 | 6/2008 |
| WO | WO 99/46976 | 9/1999 |
| WO | WO 99/58659 A2 | 11/1999 |
| WO | WO 01/94394 A2 | 12/2001 |
| WO | WO 2006/101938 | 9/2006 |
| WO | WO 2006/101938 A1 | 9/2006 |
| WO | 2007112326 | 10/2007 |
| WO | WO 2008/064289 A2 | 5/2008 |
| WO | WO 2009/126470 | 10/2009 |
| WO | WO 2009/149304 A2 | 12/2009 |
| WO | WO 2010/144385 A1 | 12/2010 |

OTHER PUBLICATIONS

U.S. Appl. No. 15/668,668, filed Aug. 3, 2017, Flasinski.
Christensen et al., "Maize polyubiquitin genes: structure, thermal perturbation of expression and transcript splicing, and promoter activity following transfer to protoplasts by electroporation," *Plant Molec Biol*, 18(4):675-689, 1992.
EMBL Accession No. CW082733, dated May 19, 2010.
EMBL Accession No. CW0938, XP002685119, dated May 19, 2010.
Frank et al., "Drought and rust effects on gene expression in the dominant plant species of tallgrass prairie, *Andropogon gerardii*," abstract 16, <http://www.k-state.edu/ecogen/PosterAbstracts-2006.pdf>, 2006.

(Continued)

*Primary Examiner* — Medina A Ibrahim

(74) *Attorney, Agent, or Firm* — Dentons US LLP; Judith Koehler

(57) ABSTRACT

The present invention provides novel DNA molecules and constructs, including their nucleotide sequences, useful for modulating gene expression in plants and plant cells. The invention also provides transgenic plants, plant cells, plant parts, seeds, and commodity products comprising the DNA molecules operably linked to heterologous transcribable polynucleotides, along with methods of their use.

19 Claims, 31 Drawing Sheets

Specification includes a Sequence Listing.

(56) References Cited

OTHER PUBLICATIONS

Frank, "Rust and drought effects on the gene expression and phytohormone concentration in Big Bluestem," thesis, Kansas State University, p. 24, <http://hdl.handle.net/2097/393>, 2007.
GenBank Accession No. X04753, "Potato light-inducible tissue-specific ST-LS1 gene," <http://www.ncbi.nlm.nih.gov/nuccore/X04753>, accessed on Nov. 1, 2012.
International Search Report and Written Opinion issued in PCT/US2012/029990 dated Oct. 29, 2012.
Kim et al., "A 20 nucleotide upstream element is essential for the nopaline synthase (nos) promoter activity," Plant Molecular Biology 24:105-117, 1994.
Vettore et al., "The molecular and functional characterization of an Opaque2 homologue gene from Coix and a new classification of plant bZIP proteins," Plant Molecular Biology 36(2):249-263, 1998.
Wang et al., "Rice ubiquitin promoters: deletion analysis and potential usefulness in plant transformation systems," Plant Cell Reproduction 22:129-134, 2003.
Chilean Office Action regarding 27-7-13, dated Feb. 16, 2015.
Kosugi et al., "Two of three promoter elements identified in a rice gene for proliferating cell nuclear antigen are essential for meristematic tissue-specific expression," The Plant Journal 7(6):877-886, 1995.
Dolferus et al., "Differential interactions of promoter elements in stress response of the Arabidopsis Adh gene", Plant Physiol., 105:1075-1087, 1994.
Donald et al., "Mutation of either G box or I box sequences profoundly affects expression from the Arabidopsis rbcS-1A promoter", The EMBO Journal, 9(6): 1717-1726, 1990.
USPTO: Non-final Office Action regarding U.S. Appl. No. 14/625,566 dated Jan. 20, 2017.
Christensen, et al., "Maize polyubiquitin genes: structure, thermal perturbation of expression and transcript splicing, and promoter activity following transfer to protoplasts by electroporation", Plant Molecular Biology 18: 675-689, 1992.
GenBank Accession No. EU161568, dated Dec. 7, 2007.
GenBank Accession No. EU161573, dated Dec. 7, 2007.
Himmelbach et al., "A Set of Modular Binary Vecgtors for Transformation of Cereals," Plant Physiology 145:1192-1200, 2007.
Response to Non-Final Office Action regarding U.S. Appl. No. 14/625,566, dated Apr. 19, 2017.
USPTO: Notice of Allowance and Fee(s) Due regarding U.S. Appl. No. 14/625,566, dated May 26, 2017.
USPTO: Notice of Allowability regarding U.S. Appl. No. 14/686,602, dated Oct. 12, 2017.
Decision on Grant of Patent for Invention regarding Russian Application No. 2013147604, dated Nov. 14, 2017.
USPTO: Non-Final Office Action regarding U.S. Appl. No. 15/179,635, dated Nov. 22, 2017.
GenBank Accession No. AY37338, dated Nov. 25, 2003.
GenBank Accession No. DQ141598, dated Sep. 6, 2005.
Lee et al., "Enhanced octopamine synthesis through the ectopic expression of tyrosine decarboxylase in rice plants," Plant Science 176:46-50, 2009.
USPTO: Final Office Action regarding U.S. Appl. No. 15/179,635, dated Apr. 6, 2018.
Doebley, "Molecular Evidence for Gene Flow among Zea Species," BioScience 40(6):443-448, 1990.
Streatfield et al., "Analysis of the maize polyubiquitin-1 promoter heat shock elements and generation of promoter variants with modified expression characteristics," Transgenic Research 13:299-312, 2004.
Response to Final Office Action regarding U.S. Appl. No. 15/179,635, dated Jul. 6, 2018.
USPTO: Advisory Action regarding U.S. Appl. No. 15/179,635, dated Jul. 23, 2018.
USPTO: Non-Final Office Action regarding U.S. Appl. No. 15/179,635, dated Sep. 11, 2018.
USPTO: Notice of Allowance and Fee(s) Due regarding U.S. Appl. No. 15/668,668, dated Oct. 1, 2018.
Christensen et al, "Ubiquitin promoter-based vectors for high-level expression of selectable and/or screenable marker genes in monocotyledonous plants," Transgenic Research 5:213-218, 1996.
USPTO: Non-Final Office Action regarding U.S. Appl. No. 15/798,326, dated Nov. 28, 2018.
Response to Non-Final Office Action regarding U.S. Appl. No. 15/179,635, dated Dec. 11, 2018.
Response to Non-Final Office Action regarding U.S. Appl. No. 15/798,326, dated Feb. 25, 2019.
USPTO: Final Office Action regarding U.S. Appl. No. 15/179,635, dated Jan. 23, 2019.
Response to Final Office Action regarding U.S. Appl. No. 15/179,635, dated Jul. 1, 2019.
USPTO: Final Office Action regarding U.S. Appl. No. 15/798,326, dated May 24, 2019.
Response to Final Office Action regarding U.S. Appl. No. 15/798,326, dated Aug. 22, 2019.
Notice of Allowance regarding U.S. Appl. No. 15/798,326, dated Sep. 6, 2019.
USPTO: Non-Final Office Action regarding U.S. Appl. No. 15/179,635, dated Nov. 4, 2019.
Response to Non-Final Office Action regarding U.S. Appl. No. 15/179,635, dated Mar. 2, 2020.
USPTO: Notice of Allowance regarding U.S. Appl. No. 15/179,635, dated Mar. 27, 2020.
GenBank Accession No. AY342393. Zea diploperennis polyubiquitin-1 (Ubi-1) gene, promoter region and 5' UTR. Published Aug. 1, 2004. pp. 1-2.
Response to Non-Final Office Action regarding U.S. Appl. No. 15/179,635, dated Feb. 2, 2018.
USPTO: Corrected Notice of Allowability regarding U.S. Appl. No. 15/798,319, dated Jul. 2, 2020.
GenBank Accession No. NC_012879.1, dated Nov. 16, 2009.
Office Action regarding Ukraine App. No. a201803687, mailed Feb. 8, 2024.

\* cited by examiner

```
P-ANDge.Ubq1-1:1:9      ------------------------------------------------------------
P-ANDge.Ubq1-1:1:8      ------------------------------------------------------------
P-ANDge.Ubq1-1:1:11     AGCAGACTCGCATTATCGATGGAGGGGTGGGTTTAGAACCCTGAAAACTGGTACTGTTTC
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------

P-ANDge.Ubq1-1:1:9      ------------------------------------------------------------
P-ANDge.Ubq1-1:1:8      ------------------------------------------------------------
P-ANDge.Ubq1-1:1:11     GAACTGAAAAACACTGTAGCACTTTTCGTTTGTTTGTGGTAAATATTATCTTACTATGGT
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------

P-ANDge.Ubq1-1:1:9      ------------------------------------------------------------
P-ANDge.Ubq1-1:1:8      ------------------------------------------------------------
P-ANDge.Ubq1-1:1:11     CTAACTAGGCTCAAAAGAATCGTCTCGCAATGTACATCTAAATTATGCAATTAGTTATTT
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------

P-ANDge.Ubq1-1:1:9      ------------------------------------------------------------
P-ANDge.Ubq1-1:1:8      ------------------------------------------------------------
P-ANDge.Ubq1-1:1:11     TGTTTACCTGCATTTCATACTCCGAGCATGCGTCTTTTGGTACATTTAATGCTTCGATGT
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------

P-ANDge.Ubq1-1:1:9      ------------------------------------------------------------
P-ANDge.Ubq1-1:1:8      ------------------------------------------------------------
P-ANDge.Ubq1-1:1:11     GATGGGAATTTTAAAAATTTTGGAGAAAAGTTGGTTTCTAAACACCCCCGAGGACGAAAT
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------

P-ANDge.Ubq1-1:1:9      ------------------------------------------------------------
P-ANDge.Ubq1-1:1:8      ------------------------------------------------------------
P-ANDge.Ubq1-1:1:11     TGGATTCGGTCTTTGACGCGGATGCAGCAACTGCAGTGCGCAGGATACCATCTTAGCCGT
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------
```

FIG. 1a

```
P-ANDge.Ubq1-1:1:9    ------------------------------------------------------------
P-ANDge.Ubq1-1:1:8    ------------------------------------------------------------
P-ANDge.Ubq1-1:1:11   TGCGTCGAAGTTCGCTTTGCTAACGTTTTGAGAAAATTAAACCAGCTTTGACCAACGTGA
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   ------------------------------------------------------------

P-ANDge.Ubq1-1:1:9    ------------------------------------------------------------
P-ANDge.Ubq1-1:1:8    ------------------------------------------------------------
P-ANDge.Ubq1-1:1:11   GACGAGCGCCTTACGTGGCAGTGTAATGGAACCGGGCACGGCAAGTTTGACGCTGTAGTG
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   ------------------------------------------------------------

P-ANDge.Ubq1-1:1:9    ----------CTCGTTACGTTTGGCACAACTTAGTTGAATCCGGCTTCCGGCAAACTATAT
P-ANDge.Ubq1-1:1:8    ------------------------------------------------------------
P-ANDge.Ubq1-1:1:11   TTAGCCGGTCTCGTTACGTTTGGCACAACTTAGTTGAATCCGGCTTCCGGCAAACTATAT
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   ------------------------------------------------------------

P-ANDge.Ubq1-1:1:9    GGCAAGTTAGACCCAAGTGTGAGCCGGCCACCGCAAGTTATTGGGACATTATACGTAGGA
P-ANDge.Ubq1-1:1:8    ------------------------------------------------------------
P-ANDge.Ubq1-1:1:11   GGCAAGTTAGACCCAAGTGTGAGCCGGCCACCGCAAGTTATTGGGACATTATACGTAGGA
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   ------------------------------------------------------------

P-ANDge.Ubq1-1:1:9    AGCAAGTGTATAATAAGAATATGAGATAATGTAAGCAGCTATATGAATCATCACGTCATA
P-ANDge.Ubq1-1:1:8    ------------------------------------------------------------
P-ANDge.Ubq1-1:1:11   AGCAAGTGTATAATAAGAATATGAGATAATGTAAGCAGCTATATGAATCATCACGTCATA
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   ------------------------------------------------------------

P-ANDge.Ubq1-1:1:9    TTTATGTTAAGATGAAGAGGATAGAATAAACGGTATGTAAATTTATAGCGAGTGATAGAC
P-ANDge.Ubq1-1:1:8    ------------------------------------------------------------
P-ANDge.Ubq1-1:1:11   TTTATGTTAAGATGAAGAGGATAGAATAAACGGTATGTAAATTTATAGCGAGTGATAGAC
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   ------------------------------------------------------------
```

FIG. 1b

```
P-ANDge.Ubq1-1:1:9     GGGCACAAGGCCTCCTAGCTATTTCCATAAATCGGATTTTGTAAGAACAAAAAAGAGGAC
P-ANDge.Ubq1-1:1:8     ------------------------------------------------------------
P-ANDge.Ubq1-1:1:11    GGGCACAAGGCCTCCTAGCTATTTCCATAAATCGGATTTTGTAAGAACAAAAAAGAGGAC
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     TTATTATAAGAGAATGTGGTAAGTAAGTATACTCTCTCCGTTTCAAATTATAAGTTGTTT
P-ANDge.Ubq1-1:1:8     ------------------------------------------------------------
P-ANDge.Ubq1-1:1:11    TTATTATAAGAGAATGTGGTAAGTAAGTATACTCTCTCCGTTTCAAATTATAAGTTGTTT
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     TGATTTTTTGGTACATCTATTTTACTATGCATTAGATATAATAATGTGTCTAGATACAT
P-ANDge.Ubq1-1:1:8     ------------------------------------------------------------
P-ANDge.Ubq1-1:1:11    TGATTTTTTGGTACATCTATTTTACTATGCATTAGATATAATAATGTGTCTAGATACAT
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     AACAAAATGGATGAATCAAAAAAGTCAAAGTGATTTACAATTTGGAACGGAGAGAGTAAG
P-ANDge.Ubq1-1:1:8     ------------------------------------------------------------
P-ANDge.Ubq1-1:1:11    AACAAAATGGATGAATCAAAAAAGTCAAAGTGATTTACAATTTGGAACGGAGAGAGTAAG
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    -----------------------------------------------------------G

P-ANDge.Ubq1-1:1:9     TTCAAGCCGTCAAGGCACTTCTATGCAACCACAGTCAACTTGAATGCCGCTTGAGTGCCT
P-ANDge.Ubq1-1:1:8     ------------------------------------------------------------
P-ANDge.Ubq1-1:1:11    TTCAAGCCGTCAAGGCACTTCTATGCAACCACAGTCAACTTGAATGCCGCTTGAGTGCCT
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    TTCAAGCCGTCAAGGCACTTCTATGCAACCACAGTCAACTTGAATGCCGCTTGAGTGCCT

P-ANDge.Ubq1-1:1:9     TCTCAAGTTTTTTTTCTTGCAAAAATCATTTCTTTTTTTAAAAAAGTATAATTTGGA
P-ANDge.Ubq1-1:1:8     ---------------------------------------------------------
P-ANDge.Ubq1-1:1:11    TCTCAAGTTTTTTTTCTTGCAAAAATCATTTCTTTTTTTAAAAAAGTATAATTTGGA
P-ANDge.Ubq1-1:1:12    ---------------------------------------------------------
P-ANDge.Ubq1-1:1:13    ---------------------------------------------------------
P-ANDge.Ubq1-1:1:14    ---------------------------------------------------------
P-ANDge.Ubq1-1:1:10    TCTCAAGTTTTTTTTCTTGCAAAAATCATTTCTTTTTTTAAAAAAGTATAATTTGGA
```

FIG. 1c

```
P-ANDge.Ubq1-1:1:9      TCGTGCAAATTTCTCTCTAGGTGTGTGTGTGACTGTGTGAGTAACAATTTCTCTAGTTGT
P-ANDge.Ubq1-1:1:8      ------------------------------------------------------------
P-ANDge.Ubq1-1:1:11     TCGTGCAAATTTCTCTCTAGGTGTGTGTGTGACTGTGTGAGTAACAATTTCTCTAGTTGT
P-ANDge.Ubq1-1:1:12     ---------------------------------------------------TCTAGTTGT
P-ANDge.Ubq1-1:1:13     ------------------------------------------------------------
P-ANDge.Ubq1-1:1:14     ------------------------------------------------------------
P-ANDge.Ubq1-1:1:10     TCGTGCAAATTTCTCTCTAGGTGTGTGTGTGACTGTGTGAGTAACAATTTCTCTAGTTGT

P-ANDge.Ubq1-1:1:9      GCGCGACTGCTGCTTACTTTGGAGATTACAATATCTTTCTAAAATGCTTCGATTACTTAT
P-ANDge.Ubq1-1:1:8      ------------------------------------------------------------
P-ANDge.Ubq1-1:1:11     GCGCGACTGCTGCTTACTTTGGAGATTACAATATCTTTCTAAAATGCTTCGATTACTTAT
P-ANDge.Ubq1-1:1:12     GCGCGACTGCTGCTTACTTTGGAGATTACAATATCTTTCTAAAATGCTTCGATTACTTAT
P-ANDge.Ubq1-1:1:13     ------------------------------------------------------------
P-ANDge.Ubq1-1:1:14     ------------------------------------------------------------
P-ANDge.Ubq1-1:1:10     GCGCGACTGCTGCTTACTTTGGAGATTACAATATCTTTCTAAAATGCTTCGATTACTTAT

P-ANDge.Ubq1-1:1:9      TTATAAACCGTCTCTAAGGCCAATTGCTCAAGATTCATTCAACAATTGAAACGTCTCACA
P-ANDge.Ubq1-1:1:8      ------------------------------------------------------------
P-ANDge.Ubq1-1:1:11     TTATAAACCGTCTCTAAGGCCAATTGCTCAAGATTCATTCAACAATTGAAACGTCTCACA
P-ANDge.Ubq1-1:1:12     TTATAAACCGTCTCTAAGGCCAATTGCTCAAGATTCATTCAACAATTGAAACGTCTCACA
P-ANDge.Ubq1-1:1:13     ------------------------------------------------------------
P-ANDge.Ubq1-1:1:14     ------------------------------------------------------------
P-ANDge.Ubq1-1:1:10     TTATAAACCGTCTCTAAGGCCAATTGCTCAAGATTCATTCAACAATTGAAACGTCTCACA

P-ANDge.Ubq1-1:1:9      TGATTAAATCATATAAAGTTTCTAAGTCTTGTTTGACAAGATTTTTTAGATTTTCATCT
P-ANDge.Ubq1-1:1:8      ------------------------------------------------------------
P-ANDge.Ubq1-1:1:11     TGATTAAATCATATAAAGTTTCTAAGTCTTGTTTGACAAGATTTTTTAGATTTTCATCT
P-ANDge.Ubq1-1:1:12     TGATTAAATCATATAAAGTTTCTAAGTCTTGTTTGACAAGATTTTTTAGATTTTCATCT
P-ANDge.Ubq1-1:1:13     ------------------------------------------------------------
P-ANDge.Ubq1-1:1:14     ------------------------------------------------------------
P-ANDge.Ubq1-1:1:10     TGATTAAATCATATAAAGTTTCTAAGTCTTGTTTGACAAGATTTTTTAGATTTTCATCT

P-ANDge.Ubq1-1:1:9      AAATTGGATGAAACTATCAAACACTAATTTTAAAAAATATAAGAGAAGCTCCGGAGATAA
P-ANDge.Ubq1-1:1:8      ------------------------------------------------------------
P-ANDge.Ubq1-1:1:11     AAATTGGATGAAACTATCAAACACTAATTTTAAAAAATATAAGAGAAGCTCCGGAGATAA
P-ANDge.Ubq1-1:1:12     AAATTGGATGAAACTATCAAACACTAATTTTAAAAAATATAAGAGAAGCTCCGGAGATAA
P-ANDge.Ubq1-1:1:13     ------------------------------------------------------------
P-ANDge.Ubq1-1:1:14     ------------------------------------------------------------
P-ANDge.Ubq1-1:1:10     AAATTGGATGAAACTATCAAACACTAATTTTAAAAAATATAAGAGAAGCTCCGGAGATAA

P-ANDge.Ubq1-1:1:9      AAGGTCGTCTATGTTATTATAAGAGTAAAGTCGTCTATTCTCTTCGTCCCAACATATATA
P-ANDge.Ubq1-1:1:8      ------------------------------------------------------------
P-ANDge.Ubq1-1:1:11     AAGGTCGTCTATGTTATTATAAGAGTAAAGTCGTCTATTCTCTTCGTCCCAACATATATA
P-ANDge.Ubq1-1:1:12     AAGGTCGTCTATGTTATTATAAGAGTAAAGTCGTCTATTCTCTTCGTCCCAACATATATA
P-ANDge.Ubq1-1:1:13     ------------------------------------------------------------
P-ANDge.Ubq1-1:1:14     ------------------------------------------------------------
P-ANDge.Ubq1-1:1:10     AAGGTCGTCTATGTTATTATAAGAGTAAAGTCGTCTATTCTCTTCGTCCCAACATATATA
```

FIG. 1d

```
P-ANDge.Ubq1-1:1:9      ATTCTAAGCATGAATTGCTTTCTTTTTGGACAAAAGGAGCATGCCACAACACAAGAATGA
P-ANDge.Ubq1-1:1:8      ---------------------------------------------------CACAAGAATGA
P-ANDge.Ubq1-1:1:11     ATTCTAAGCATGAATTGCTTTCTTTTTGGACAAAAGGAGCATGCCACAACACAAGAATGA
P-ANDge.Ubq1-1:1:12     ATTCTAAGCATGAATTGCTTTCTTTTTGGACAAAAGGAGCATGCCACAACACAAGAATGA
P-ANDge.Ubq1-1:1:13     ------------------------------------------------------------
P-ANDge.Ubq1-1:1:14     ------------------------------------------------------------
P-ANDge.Ubq1-1:1:10     ATTCTAAGCATGAATTGCTTTCTTTTTGGACAAAAGGAGCATGCCACAACACAAGAATGA

P-ANDge.Ubq1-1:1:9      TGTCACCGTCATGCTTGGATCCTTTTATGGTAAAGCTTCACCTTCTATAATCTAACAATA
P-ANDge.Ubq1-1:1:8      TGTCACCGTCATGCTTGGATCCTTTTATGGTAAAGCTTCACCTTCTATAATCTAACAATA
P-ANDge.Ubq1-1:1:11     TGTCACCGTCATGCTTGGATCCTTTTATGGTAAAGCTTCACCTTCTATAATCTAACAATA
P-ANDge.Ubq1-1:1:12     TGTCACCGTCATGCTTGGATCCTTTTATGGTAAAGCTTCACCTTCTATAATCTAACAATA
P-ANDge.Ubq1-1:1:13     ------------------------------------------------------------
P-ANDge.Ubq1-1:1:14     ------------------------------------------------------------
P-ANDge.Ubq1-1:1:10     TGTCACCGTCATGCTTGGATCCTTTTATGGTAAAGCTTCACCTTCTATAATCTAACAATA

P-ANDge.Ubq1-1:1:9      GAGAAATCAGGGAAAAATCATGTTTTGGTTGTTTTTATTTCTAACCTCCACAATAACTTT
P-ANDge.Ubq1-1:1:8      GAGAAATCAGGGAAAAATCATGTTTTGGTTGTTTTTATTTCTAACCTCCACAATAACTTT
P-ANDge.Ubq1-1:1:11     GAGAAATCAGGGAAAAATCATGTTTTGGTTGTTTTTATTTCTAACCTCCACAATAACTTT
P-ANDge.Ubq1-1:1:12     GAGAAATCAGGGAAAAATCATGTTTTGGTTGTTTTTATTTCTAACCTCCACAATAACTTT
P-ANDge.Ubq1-1:1:13     ------------------------------------------------------------
P-ANDge.Ubq1-1:1:14     ------------------------------------------------------------
P-ANDge.Ubq1-1:1:10     GAGAAATCAGGGAAAAATCATGTTTTGGTTGTTTTTATTTCTAACCTCCACAATAACTTT

P-ANDge.Ubq1-1:1:9      GGTTTACCATTTTTTGTTTGATTTTAGTTTTAGAGAAGCGTTTATAACAGGACCTAAAAT
P-ANDge.Ubq1-1:1:8      GGTTTACCATTTTTTGTTTGATTTTAGTTTTAGAGAAGCGTTTATAACAGGACCTAAAAT
P-ANDge.Ubq1-1:1:11     GGTTTACCATTTTTTGTTTGATTTTAGTTTTAGAGAAGCGTTTATAACAGGACCTAAAAT
P-ANDge.Ubq1-1:1:12     GGTTTACCATTTTTTGTTTGATTTTAGTTTTAGAGAAGCGTTTATAACAGGACCTAAAAT
P-ANDge.Ubq1-1:1:13     ------------------------------------------------------------
P-ANDge.Ubq1-1:1:14     ------------------------------------------------------------
P-ANDge.Ubq1-1:1:10     GGTTTACCATTTTTTGTTTGATTTTAGTTTTAGAGAAGCGTTTATAACAGGACCTAAAAT

P-ANDge.Ubq1-1:1:9      CTTTTTTCAGTACACAGTACAACGCAGACGCTCATACACGCACGCACACTCACCTCTATG
P-ANDge.Ubq1-1:1:8      CTTTTTTCAGTACACAGTACAACGCAGACGCTCATACACGCACGCACACTCACCTCTATG
P-ANDge.Ubq1-1:1:11     CTTTTTTCAGTACACAGTACAACGCAGACGCTCATACACGCACGCACACTCACCTCTATG
P-ANDge.Ubq1-1:1:12     CTTTTTTCAGTACACAGTACAACGCAGACGCTCATACACGCACGCACACTCACCTCTATG
P-ANDge.Ubq1-1:1:13     ------------------------------------------------------------
P-ANDge.Ubq1-1:1:14     ------------------------------------------------------------
P-ANDge.Ubq1-1:1:10     CTTTTTTCAGTACACAGTACAACGCAGACGCTCATACACGCACGCACACTCACCTCTATG

P-ANDge.Ubq1-1:1:9      AACACACGTAAGAAAACCCTACACCTTGAGCACCTTCGAAGGACTGAGCCGGTAAATATA
P-ANDge.Ubq1-1:1:8      AACACACGTAAGAAAACCCTACACCTTGAGCACCTTCGAAGGACTGAGCCGGTAAATATA
P-ANDge.Ubq1-1:1:11     AACACACGTAAGAAAACCCTACACCTTGAGCACCTTCGAAGGACTGAGCCGGTAAATATA
P-ANDge.Ubq1-1:1:12     AACACACGTAAGAAAACCCTACACCTTGAGCACCTTCGAAGGACTGAGCCGGTAAATATA
P-ANDge.Ubq1-1:1:13     ------------------------------------------------------------
P-ANDge.Ubq1-1:1:14     ------------------------------------------------------------
P-ANDge.Ubq1-1:1:10     AACACACGTAAGAAAACCCTACACCTTGAGCACCTTCGAAGGACTGAGCCGGTAAATATA
```

FIG. 1e

```
P-ANDge.Ubq1-1:1:9    GAGATTCTCGAAGTCACTATTAGCGCCTCGTTGTCAACGGGAATGTCGCTTACCACTTAA
P-ANDge.Ubq1-1:1:8    GAGATTCTCGAAGTCACTATTAGCGCCTCGTTGTCAACGGGAATGTCGCTTACCACTTAA
P-ANDge.Ubq1-1:1:11   GAGATTCTCGAAGTCACTATTAGCGCCTCGTTGTCAACGGGAATGTCGCTTACCACTTAA
P-ANDge.Ubq1-1:1:12   GAGATTCTCGAAGTCACTATTAGCGCCTCGTTGTCAACGGGAATGTCGCTTACCACTTAA
P-ANDge.Ubq1-1:1:13   -------------------------------GTCAACGGGAATGTCGCTTACCACTTAA
P-ANDge.Ubq1-1:1:14   ------------------------------------------------------------
P-ANDge.Ubq1-1:1:10   GAGATTCTCGAAGTCACTATTAGCGCCTCGTTGTCAACGGGAATGTCGCTTACCACTTAA

P-ANDge.Ubq1-1:1:9    AGCATAACGCCGAGAAATCCCGTAATAAATCCAGTAAAATACGAGCACCCGTGCCAAGTT
P-ANDge.Ubq1-1:1:8    AGCATAACGCCGAGAAATCCCGTAATAAATCCAGTAAAATACGAGCACCCGTGCCAAGTT
P-ANDge.Ubq1-1:1:11   AGCATAACGCCGAGAAATCCCGTAATAAATCCAGTAAAATACGAGCACCCGTGCCAAGTT
P-ANDge.Ubq1-1:1:12   AGCATAACGCCGAGAAATCCCGTAATAAATCCAGTAAAATACGAGCACCCGTGCCAAGTT
P-ANDge.Ubq1-1:1:13   AGCATAACGCCGAGAAATCCCGTAATAAATCCAGTAAAATACGAGCACCCGTGCCAAGTT
P-ANDge.Ubq1-1:1:14   ------------------------------------------------------------
P-ANDge.Ubq1-1:1:10   AGCATAACGCCGAGAAATCCCGTAATAAATCCAGTAAAATACGAGCACCCGTGCCAAGTT

P-ANDge.Ubq1-1:1:9    GAATATTTGAACCCGAGTGGGTAGATTCCACCGCAAAGGACCTAACCAGATCATTTCGCA
P-ANDge.Ubq1-1:1:8    GAATATTTGAACCCGAGTGGGTAGATTCCACCGCAAAGGACCTAACCAGATCATTTCGCA
P-ANDge.Ubq1-1:1:11   GAATATTTGAACCCGAGTGGGTAGATTCCACCGCAAAGGACCTAACCAGATCATTTCGCA
P-ANDge.Ubq1-1:1:12   GAATATTTGAACCCGAGTGGGTAGATTCCACCGCAAAGGACCTAACCAGATCATTTCGCA
P-ANDge.Ubq1-1:1:13   GAATATTTGAACCCGAGTGGGTAGATTCCACCGCAAAGGACCTAACCAGATCATTTCGCA
P-ANDge.Ubq1-1:1:14   ------------------------------------------------------------
P-ANDge.Ubq1-1:1:10   GAATATTTGAACCCGAGTGGGTAGATTCCACCGCAAAGGACCTAACCAGATCATTTCGCA

P-ANDge.Ubq1-1:1:9    AACAGGAACTAAAATCGGTAGAGAGCCCAGACAAAAGCCTTTCCTAAGAGCCACTCCAGT
P-ANDge.Ubq1-1:1:8    AACAGGAACTAAAATCGGTAGAGAGCCCAGACAAAAGCCTTTCCTAAGAGCCACTCCAGT
P-ANDge.Ubq1-1:1:11   AACAGGAACTAAAATCGGTAGAGAGCCCAGACAAAAGCCTTTCCTAAGAGCCACTCCAGT
P-ANDge.Ubq1-1:1:12   AACAGGAACTAAAATCGGTAGAGAGCCCAGACAAAAGCCTTTCCTAAGAGCCACTCCAGT
P-ANDge.Ubq1-1:1:13   AACAGGAACTAAAATCGGTAGAGAGCCCAGACAAAAGCCTTTCCTAAGAGCCACTCCAGT
P-ANDge.Ubq1-1:1:14   ------------------------------------------------------------
P-ANDge.Ubq1-1:1:10   AACAGGAACTAAAATCGGTAGAGAGCCCAGACAAAAGCCTTTCCTAAGAGCCACTCCAGT

P-ANDge.Ubq1-1:1:9    GGAAGCCCCTACTTTAGGTATAAAATGCAATACTAGTGGGGCTCCTAAATAAACTTCTAT
P-ANDge.Ubq1-1:1:8    GGAAGCCCCTACTTTAGGTATAAAATGCAATACTAGTGGGGCTCCTAAATAAACTTCTAT
P-ANDge.Ubq1-1:1:11   GGAAGCCCCTACTTTAGGTATAAAATGCAATACTAGTGGGGCTCCTAAATAAACTTCTAT
P-ANDge.Ubq1-1:1:12   GGAAGCCCCTACTTTAGGTATAAAATGCAATACTAGTGGGGCTCCTAAATAAACTTCTAT
P-ANDge.Ubq1-1:1:13   GGAAGCCCCTACTTTAGGTATAAAATGCAATACTAGTGGGGCTCCTAAATAAACTTCTAT
P-ANDge.Ubq1-1:1:14   ------------------------------------------------------------
P-ANDge.Ubq1-1:1:10   GGAAGCCCCTACTTTAGGTATAAAATGCAATACTAGTGGGGCTCCTAAATAAACTTCTAT

P-ANDge.Ubq1-1:1:9    TTTTCATGGCCTTCTAAAATTCACTCCCAAACCCCTAGCTATAGAAGTCTCTTATCCATC
P-ANDge.Ubq1-1:1:8    TTTTCATGGCCTTCTAAAATTCACTCCCAAACCCCTAGCTATAGAAGTCTCTTATCCATC
P-ANDge.Ubq1-1:1:11   TTTTCATGGCCTTCTAAAATTCACTCCCAAACCCCTAGCTATAGAAGTCTCTTATCCATC
P-ANDge.Ubq1-1:1:12   TTTTCATGGCCTTCTAAAATTCACTCCCAAACCCCTAGCTATAGAAGTCTCTTATCCATC
P-ANDge.Ubq1-1:1:13   TTTTCATGGCCTTCTAAAATTCACTCCCAAACCCCTAGCTATAGAAGTCTCTTATCCATC
P-ANDge.Ubq1-1:1:14   ---------------------CACTCCCAAACCCCTAGCTATAGAAGTCTCTTATCCATC
P-ANDge.Ubq1-1:1:10   TTTTCATGGCCTTCTAAAATTCACTCCCAAACCCCTAGCTATAGAAGTCTCTTATCCATC
                                           ***************************************
```

FIG. 1f

```
P-ANDge.Ubq1-1:1:9      CTCTAAATAAAAATGGGAGTCTATTTTATTTCACCAGAGTTGATCGTAAATTTAGTCTCT
P-ANDge.Ubq1-1:1:8      CTCTAAATAAAAATGGGAGTCTATTTTATTTCACCAGAGTTGATCGTAAATTTAGTCTCT
P-ANDge.Ubq1-1:1:11     CTCTAAATAAAAATGGGAGTCTATTTTATTTCACCAGAGTTGATCGTAAATTTAGTCTCT
P-ANDge.Ubq1-1:1:12     CTCTAAATAAAAATGGGAGTCTATTTTATTTCACCAGAGTTGATCGTAAATTTAGTCTCT
P-ANDge.Ubq1-1:1:13     CTCTAAATAAAAATGGGAGTCTATTTTATTTCACCAGAGTTGATCGTAAATTTAGTCTCT
P-ANDge.Ubq1-1:1:14     CTCTAAATAAAAATGGGAGTCTATTTTATTTCACCAGAGTTGATCGTAAATTTAGTCTCT
P-ANDge.Ubq1-1:1:10     CTCTAAATAAAAATGGGAGTCTATTTTATTTCACCAGAGTTGATCGTAAATTTAGTCTCT
                        ************************************************************

P-ANDge.Ubq1-1:1:9      CAAATTTTATAAGTTGAGGGTAGAGGATGACTGGAGTTGCTCTAAACGGACCTATCTTCA
P-ANDge.Ubq1-1:1:8      CAAATTTTATAAGTTGAGGGTAGAGGATGACTGGAGTTGCTCTAAACGGACCTATCTTCA
P-ANDge.Ubq1-1:1:11     CAAATTTTATAAGTTGAGGGTAGAGGATGACTGGAGTTGCTCTAAACGGACCTATCTTCA
P-ANDge.Ubq1-1:1:12     CAAATTTTATAAGTTGAGGGTAGAGGATGACTGGAGTTGCTCTAAACGGACCTATCTTCA
P-ANDge.Ubq1-1:1:13     CAAATTTTATAAGTTGAGGGTAGAGGATGACTGGAGTTGCTCTAAACGGACCTATCTTCA
P-ANDge.Ubq1-1:1:14     CAAATTTTATAAGTTGAGGGTAGAGGATGACTGGAGTTGCTCTAAACGGACCTATCTTCA
P-ANDge.Ubq1-1:1:10     CAAATTTTATAAGTTGAGGGTAGAGGATGACTGGAGTTGCTCTAAACGGACCTATCTTCA
                        ************************************************************

P-ANDge.Ubq1-1:1:9      AGTGACCTCAGTGAGCCCGTTTAACGGCGTCGACAAGTTTAATCTAACGGACACCAACCA
P-ANDge.Ubq1-1:1:8      AGTGACCTCAGTGAGCCCGTTTAACGGCGTCGACAAGTTTAATCTAACGGACACCAACCA
P-ANDge.Ubq1-1:1:11     AGTGACCTCAGTGAGCCCGTTTAACGGCGTCGACAAGTTTAATCTAACGGACACCAACCA
P-ANDge.Ubq1-1:1:12     AGTGACCTCAGTGAGCCCGTTTAACGGCGTCGACAAGTTTAATCTAACGGACACCAACCA
P-ANDge.Ubq1-1:1:13     AGTGACCTCAGTGAGCCCGTTTAACGGCGTCGACAAGTTTAATCTAACGGACACCAACCA
P-ANDge.Ubq1-1:1:14     AGTGACCTCAGTGAGCCCGTTTAACGGCGTCGACAAGTTTAATCTAACGGACACCAACCA
P-ANDge.Ubq1-1:1:10     AGTGACCTCAGTGAGCCCGTTTAACGGCGTCGACAAGTTTAATCTAACGGACACCAACCA
                        ************************************************************

P-ANDge.Ubq1-1:1:9      GAGAAGAGAACCACCGCCAGCGCCGAGCCAAGCGACGTTGACATCTTGGCGCGGCACGGC
P-ANDge.Ubq1-1:1:8      GAGAAGAGAACCACCGCCAGCGCCGAGCCAAGCGACGTTGACATCTTGGCGCGGCACGGC
P-ANDge.Ubq1-1:1:11     GAGAAGAGAACCACCGCCAGCGCCGAGCCAAGCGACGTTGACATCTTGGCGCGGCACGGC
P-ANDge.Ubq1-1:1:12     GAGAAGAGAACCACCGCCAGCGCCGAGCCAAGCGACGTTGACATCTTGGCGCGGCACGGC
P-ANDge.Ubq1-1:1:13     GAGAAGAGAACCACCGCCAGCGCCGAGCCAAGCGACGTTGACATCTTGGCGCGGCACGGC
P-ANDge.Ubq1-1:1:14     GAGAAGAGAACCACCGCCAGCGCCGAGCCAAGCGACGTTGACATCTTGGCGCGGCACGGC
P-ANDge.Ubq1-1:1:10     GAGAAGAGAACCACCGCCAGCGCCGAGCCAAGCGACGTTGACATCTTGGCGCGGCACGGC
                        ************************************************************

P-ANDge.Ubq1-1:1:9      ATCTCCCTGGCGTCTGGCCCCCTCTCGAGACTTCCGCTCCACCTCCCACCGGTGGCGGTT
P-ANDge.Ubq1-1:1:8      ATCTCCCTGGCGTCTGGCCCCCTCTCGAGACTTCCGCTCCACCTCCCACCGGTGGCGGTT
P-ANDge.Ubq1-1:1:11     ATCTCCCTGGCGTCTGGCCCCCTCTCGAGACTTCCGCTCCACCTCCCACCGGTGGCGGTT
P-ANDge.Ubq1-1:1:12     ATCTCCCTGGCGTCTGGCCCCCTCTCGAGACTTCCGCTCCACCTCCCACCGGTGGCGGTT
P-ANDge.Ubq1-1:1:13     ATCTCCCTGGCGTCTGGCCCCCTCTCGAGACTTCCGCTCCACCTCCCACCGGTGGCGGTT
P-ANDge.Ubq1-1:1:14     ATCTCCCTGGCGTCTGGCCCCCTCTCGAGACTTCCGCTCCACCTCCCACCGGTGGCGGTT
P-ANDge.Ubq1-1:1:10     ATCTCCCTGGCGTCTGGCCCCCTCTCGAGACTTCCGCTCCACCTCCCACCGGTGGCGGTT
                        ************************************************************
```

FIG. 1g

```
P-ANDge.Ubq1-1:1:9     TCCAAGTCCGTTCCGCCTCCTCTCACACGGCACGAAACCGTGACGGGCACCGGCAGCACG
P-ANDge.Ubq1-1:1:8     TCCAAGTCCGTTCCGCCTCCTCTCACACGGCACGAAACCGTGACGGGCACCGGCAGCACG
P-ANDge.Ubq1-1:1:11    TCCAAGTCCGTTCCGCCTCCTCTCACACGGCACGAAACCGTGACGGGCACCGGCAGCACG
P-ANDge.Ubq1-1:1:12    TCCAAGTCCGTTCCGCCTCCTCTCACACGGCACGAAACCGTGACGGGCACCGGCAGCACG
P-ANDge.Ubq1-1:1:13    TCCAAGTCCGTTCCGCCTCCTCTCACACGGCACGAAACCGTGACGGGCACCGGCAGCACG
P-ANDge.Ubq1-1:1:14    TCCAAGTCCGTTCCGCCTCCTCTCACACGGCACGAAACCGTGACGGGCACCGGCAGCACG
P-ANDge.Ubq1-1:1:10    TCCAAGTCCGTTCCGCCTCCTCTCACACGGCACGAAACCGTGACGGGCACCGGCAGCACG
                       ************************************************************

P-ANDge.Ubq1-1:1:9     GGGGGATTCCTTTCCCACCGCTCCTTCCCTTTCCCTTCCTCTCCCGCCGCTATAAATAGC
P-ANDge.Ubq1-1:1:8     GGGGGATTCCTTTCCCACCGCTCCTTCCCTTTCCCTTCCTCTCCCGCCGCTATAAATAGC
P-ANDge.Ubq1-1:1:11    GGGGGATTCCTTTCCCACCGCTCCTTCCCTTTCCCTTCCTCTCCCGCCGCTATAAATAGC
P-ANDge.Ubq1-1:1:12    GGGGGATTCCTTTCCCACCGCTCCTTCCCTTTCCCTTCCTCTCCCGCCGCTATAAATAGC
P-ANDge.Ubq1-1:1:13    GGGGGATTCCTTTCCCACCGCTCCTTCCCTTTCCCTTCCTCTCCCGCCGCTATAAATAGC
P-ANDge.Ubq1-1:1:14    GGGGGATTCCTTTCCCACCGCTCCTTCCCTTTCCCTTCCTCTCCCGCCGCTATAAATAGC
P-ANDge.Ubq1-1:1:10    GGGGGATTCCTTTCCCACCGCTCCTTCCCTTTCCCTTCCTCTCCCGCCGCTATAAATAGC
                       ************************************************************

P-ANDge.Ubq1-1:1:9     CAGCCCCATCCCCAGCTTCTTTC
P-ANDge.Ubq1-1:1:8     CAGCCCCATCCCCAGCTTCTTTC
P-ANDge.Ubq1-1:1:11    CAGCCCCATCCCCAGCTTCTTTC
P-ANDge.Ubq1-1:1:12    CAGCCCCATCCCCAGCTTCTTTC
P-ANDge.Ubq1-1:1:13    CAGCCCCATCCCCAGCTTCTTTC
P-ANDge.Ubq1-1:1:14    CAGCCCCATCCCCAGCTTCTTTC
P-ANDge.Ubq1-1:1:10    CAGCCCCATCCCCAGCTTCTTTC
                       ***********************
```

FIG. 1h

```
P-ERIra.Ubq1-1:1:9     ------------------------------------------------------------
P-ERIra.Ubq1-1:1:10    GTGGCCAGCTTTTGTTCTAGTTCAACGGCCCCGGCCTTCCGGGCACCTAATACCCTAATT
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     ------------------------------------------------------------
P-ERIra.Ubq1-1:1:10    AATCTATTGCAGCTAACCTCAAAAGAAATGCATTTGCAGTTGTCTGTCCCAATCAATCTA
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     ------------------------------------------------------------
P-ERIra.Ubq1-1:1:10    CTAGCAGACTTACATTATAGATGGAGGAAATTAAATTCAGCCTTTGACGTGGATGCAACA
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     ------------------------------------------------------------
P-ERIra.Ubq1-1:1:10    ACTGCACTGCACAGGATACCATCTTAGCCGTTGTGTCAAAGTTTGCTTTGCTAAACGTTT
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     ------------------------------------------------------------
P-ERIra.Ubq1-1:1:10    TGAGAAAACCAGCTTTGACCAACGCGAGATGAGCGCCTTACGTTTGGCACAATGTAATGT
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     ------------------------------------------------------------
P-ERIra.Ubq1-1:1:10    AATCCGGCACGGCAAGTTAGACTCTGTAGTGTTAGCCGGCCTCTTTACGTTTGGCATAGT
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------
```

FIG. 2a

```
P-ERIra.Ubq1-1:1:9    ------------------------------------------------------------
P-ERIra.Ubq1-1:1:10   TTAATTGAATCCGGCATGGCAAGTTAGACCGTAGTGTGAGCCGGCCAACGCAAGTTATTA
P-ERIra.Ubq1-1:1:8    ------------------------------------------------------------
P-ERIra.Ubq1-1:1:11   ------------------------------------------------------------
P-ERIra.Ubq1-1:1:12   ------------------------------------------------------------
P-ERIra.Ubq1-1:1:13   ------------------------------------------------------------

P-ERIra.Ubq1-1:1:9    ---------GTATAAGAGCAAGTGTATTGTCACGTGATATTTATGTTGAGATGAAGAAGAG
P-ERIra.Ubq1-1:1:10   TGACATATGTATAAGAGCAAGTGTATTGTCACGTGATATTTATGTTGAGATGAAGAAGAG
P-ERIra.Ubq1-1:1:8    ------------------------------------------------------------
P-ERIra.Ubq1-1:1:11   ------------------------------------------------------------
P-ERIra.Ubq1-1:1:12   ------------------------------------------------------------
P-ERIra.Ubq1-1:1:13   ------------------------------------------------------------

P-ERIra.Ubq1-1:1:9    AAAATAAACAGCCTGCAAATTTATAGCGAGTGATAGATGGGCACAAGGCTTCCTATTTCT
P-ERIra.Ubq1-1:1:10   AAAATAAACAGCCTGCAAATTTATAGCGAGTGATAGATGGGCACAAGGCTTCCTATTTCT
P-ERIra.Ubq1-1:1:8    ------------------------------------------------------------
P-ERIra.Ubq1-1:1:11   ------------------------------------------------------------
P-ERIra.Ubq1-1:1:12   ------------------------------------------------------------
P-ERIra.Ubq1-1:1:13   ------------------------------------------------------------

P-ERIra.Ubq1-1:1:9    TAAATCAGACTTTGTAAGAACAAAAAAAGGACTTATAAGAGAATGGGATAAACCATATAT
P-ERIra.Ubq1-1:1:10   TAAATCAGACTTTGTAAGAACAAAAAAAGGACTTATAAGAGAATGGGATAAACCATATAT
P-ERIra.Ubq1-1:1:8    ------------------------------------------------------------
P-ERIra.Ubq1-1:1:11   ------------------------------------------------------------
P-ERIra.Ubq1-1:1:12   ------------------------------------------------------------
P-ERIra.Ubq1-1:1:13   ------------------------------------------------------------

P-ERIra.Ubq1-1:1:9    CAATGGTGTAGTATGTTAGTATGCATTAAGATCTGACTATTATATGAGTGAGTTGTTAAA
P-ERIra.Ubq1-1:1:10   CAATGGTGTAGTATGTTAGTATGCATTAAGATCTGACTATTATATGAGTGAGTTGTTAAA
P-ERIra.Ubq1-1:1:8    ------------------------------------------------------------
P-ERIra.Ubq1-1:1:11   ------------------------------------------------------------
P-ERIra.Ubq1-1:1:12   ------------------------------------------------------------
P-ERIra.Ubq1-1:1:13   ------------------------------------------------------------

P-ERIra.Ubq1-1:1:9    TTCATTTTAGGTGACATGGCCCGGTTAAATTATTAGCCATACCCTAACAGCTCTAAAAAA
P-ERIra.Ubq1-1:1:10   TTCATTTTAGGTGACATGGCCCGGTTAAATTATTAGCCATACCCTAACAGCTCTAAAAAA
P-ERIra.Ubq1-1:1:8    ------------------------------------------------------------
P-ERIra.Ubq1-1:1:11   ------------------------------------------------------------
P-ERIra.Ubq1-1:1:12   ------------------------------------------------------------
P-ERIra.Ubq1-1:1:13   ------------------------------------------------------------
```

FIG. 2b

```
P-ERIra.Ubq1-1:1:9     GATATATTCGTTGAGGCACTTTTATGCAACCACATAGTCAACTTGAATGCCGCTTGAGTG
P-ERIra.Ubq1-1:1:10    GATATATTCGTTGAGGCACTTTTATGCAACCACATAGTCAACTTGAATGCCGCTTGAGTG
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     CGTTCTCAAGTTTTTTTTCTTGCAAATTACGCTTTTTTAAGAAAGTATAATTTGGATCGT
P-ERIra.Ubq1-1:1:10    CGTTCTCAAGTTTTTTTTCTTGCAAATTACGCTTTTTTAAGAAAGTATAATTTGGATCGT
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     GCGATTTTTTTCTCTAGGTGTGCGTGACTGTGTGAGTAACAATTTTGGATCTCAGAAAG
P-ERIra.Ubq1-1:1:10    GCGATTTTTTTCTCTAGGTGTGCGTGACTGTGTGAGTAACAATTTTGGATCTCAGAAAG
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     GTAATAAAAGAATAATACTGCTGCCTACTTTGAGGATTACAATATCTTTCTCTAAAATGT
P-ERIra.Ubq1-1:1:10    GTAATAAAAGAATAATACTGCTGCCTACTTTGAGGATTACAATATCTTTCTCTAAAATGT
P-ERIra.Ubq1-1:1:8     ------------------------------------------------------------
P-ERIra.Ubq1-1:1:11    -----------------CTGCTGCCTACTTTGAGGATTACAATATCTTTCTCTAAAATGT
P-ERIra.Ubq1-1:1:12    ------------------------------------------------------------
P-ERIra.Ubq1-1:1:13    ------------------------------------------------------------

P-ERIra.Ubq1-1:1:9     TTTGGTTTGTTATTTAAACCGTCTTTAAGGCCAATTGCTCAAGATTCATTCAACAATTGA
P-ERIra.Ubq1-1:1:10    TTTGGTTTGTTATTTAAACCGTCTTTAAGGCCAATTGCTCAAGATTCATTCAACAATTGA
P-ERIra.Ubq1-1:1:8     ------------------------------------------------------------
P-ERIra.Ubq1-1:1:11    TTTGGTTTGTTATTTAAACCGTCTTTAAGGCCAATTGCTCAAGATTCATTCAACAATTGA
P-ERIra.Ubq1-1:1:12    ------------------------------------------------------------
P-ERIra.Ubq1-1:1:13    ------------------------------------------------------------

P-ERIra.Ubq1-1:1:9     AACGTCTCACATGATTAAATCATATAAGGTTGCTAAGGTCTTGTTTGACAAGGTTTTTTT
P-ERIra.Ubq1-1:1:10    AACGTCTCACATGATTAAATCATATAAGGTTGCTAAGGTCTTGTTTGACAAGGTTTTTTT
P-ERIra.Ubq1-1:1:8     ------------------------------------------------------------
P-ERIra.Ubq1-1:1:11    AACGTCTCACATGATTAAATCATATAAGGTTGCTAAGGTCTTGTTTGACAAGGTTTTTTT
P-ERIra.Ubq1-1:1:12    ------------------------------------------------------------
P-ERIra.Ubq1-1:1:13    ------------------------------------------------------------
```

FIG. 2c

```
P-ERIra.Ubq1-1:1:9      TGTGGAAATTTCATCTAAATTTTTGAGTGAAACTATCAAATACTAATTTAAAAAAGGCAA
P-ERIra.Ubq1-1:1:10     TGTGGAAATTTCATCTAAATTTTTGAGTGAAACTATCAAATACTAATTTAAAAAAGGCAA
P-ERIra.Ubq1-1:1:8      ------------------------------------------------------------
P-ERIra.Ubq1-1:1:11     TGTGGAAATTTCATCTAAATTTTTGAGTGAAACTATCAAATACTAATTTAAAAAAGGCAA
P-ERIra.Ubq1-1:1:12     ------------------------------------------------------------
P-ERIra.Ubq1-1:1:13     ------------------------------------------------------------

P-ERIra.Ubq1-1:1:9      ATTTTGCTGGAGGACACTGCAGAAACGTGTAATTGGCCGGCACAAACCGCCAAACGGAGA
P-ERIra.Ubq1-1:1:10     ATTTTGCTGGAGGACACTGCAGAAACGTGTAATTGGCCGGCACAAACCGCCAAACGGAGA
P-ERIra.Ubq1-1:1:8      ------------------------------------------------------------
P-ERIra.Ubq1-1:1:11     ATTTTGCTGGAGGACACTGCAGAAACGTGTAATTGGCCGGCACAAACCGCCAAACGGAGA
P-ERIra.Ubq1-1:1:12     ------------------------------------------------------------
P-ERIra.Ubq1-1:1:13     ------------------------------------------------------------

P-ERIra.Ubq1-1:1:9      ATTTGCCCAGTACCATTATAAATTCATGATAAATTCATGGTTGTTTGCCAGTGGGGCTAG
P-ERIra.Ubq1-1:1:10     ATTTGCCCAGTACCATTATAAATTCATGATAAATTCATGGTTGTTTGCCAGTGGGGCTAG
P-ERIra.Ubq1-1:1:8      ------------------------------------------------------------
P-ERIra.Ubq1-1:1:11     ATTTGCCCAGTACCATTATAAATTCATGATAAATTCATGGTTGTTTGCCAGTGGGGCTAG
P-ERIra.Ubq1-1:1:12     ------------------------------------------------------------
P-ERIra.Ubq1-1:1:13     ------------------------------------------------------------

P-ERIra.Ubq1-1:1:9      GGTTCCTCGCGTATGGTGCGGAATGTGGTTTGGTTCGACCAACTCGAACTCAATCCGATC
P-ERIra.Ubq1-1:1:10     GGTTCCTCGCGTATGGTGCGGAATGTGGTTTGGTTCGACCAACTCGAACTCAATCCGATC
P-ERIra.Ubq1-1:1:8      ------------------------------------------------------------
P-ERIra.Ubq1-1:1:11     GGTTCCTCGCGTATGGTGCGGAATGTGGTTTGGTTCGACCAACTCGAACTCAATCCGATC
P-ERIra.Ubq1-1:1:12     ------------------------------------------------------------
P-ERIra.Ubq1-1:1:13     ------------------------------------------------------------

P-ERIra.Ubq1-1:1:9      CAAAGGGGCATCAATAGTCATTTTAGAAAGTTTCTCTCTCCCGAGCAGTGGAAATGATTA
P-ERIra.Ubq1-1:1:10     CAAAGGGGCATCAATAGTCATTTTAGAAAGTTTCTCTCTCCCGAGCAGTGGAAATGATTA
P-ERIra.Ubq1-1:1:8      ------------------------------------------------------------
P-ERIra.Ubq1-1:1:11     CAAAGGGGCATCAATAGTCATTTTAGAAAGTTTCTCTCTCCCGAGCAGTGGAAATGATTA
P-ERIra.Ubq1-1:1:12     ------------------------------------------------------------
P-ERIra.Ubq1-1:1:13     ------------------------------------------------------------

P-ERIra.Ubq1-1:1:9      TTCTATTTGGCGCGATGTCCACCGGCAAACAACCACGAATTTGTAATGGTACTAGGCAAA
P-ERIra.Ubq1-1:1:10     TTCTATTTGGCGCGATGTCCACCGGCAAACAACCACGAATTTGTAATGGTACTAGGCAAA
P-ERIra.Ubq1-1:1:8      ------------------CCACCGGCAAACAACCACGAATTTGTAATGGTACTAGGCAAA
P-ERIra.Ubq1-1:1:11     TTCTATTTGGCGCGATGTCCACCGGCAAACAACCACGAATTTGTAATGGTACTAGGCAAA
P-ERIra.Ubq1-1:1:12     ------------------------------------------------------------
P-ERIra.Ubq1-1:1:13     ------------------------------------------------------------
```

FIG. 2d

```
P-ERIra.Ubq1-1:1:9     TTCTCCGTTTGGCGGTGTGTGCCGGCCAATTACACGTTTTTGCGGTGTCCTCCGACAAAA
P-ERIra.Ubq1-1:1:10    TTCTCCGTTTGGCGGTGTGTGCCGGCCAATTACACGTTTTTGCGGTGTCCTCCGACAAAA
P-ERIra.Ubq1-1:1:8     TTCTCCGTTTGGCGGTGTGTGCCGGCCAATTACACGTTTTTGCGGTGTCCTCCGACAAAA
P-ERIra.Ubq1-1:1:11    TTCTCCGTTTGGCGGTGTGTGCCGGCCAATTACACGTTTTTGCGGTGTCCTCCGACAAAA
P-ERIra.Ubq1-1:1:12    ------------------------------------------------------------
P-ERIra.Ubq1-1:1:13    ------------------------------------------------------------

P-ERIra.Ubq1-1:1:9     TTTGCCTTTTAAAAACAATTTTATAAGAGAAGCTCCGGAGATAAAAGGCCGTCAATGTTA
P-ERIra.Ubq1-1:1:10    TTTGCCTTTTAAAAACAATTTTATAAGAGAAGCTCCGGAGATAAAAGGCCGTCAATGTTA
P-ERIra.Ubq1-1:1:8     TTTGCCTTTTAAAAACAATTTTATAAGAGAAGCTCCGGAGATAAAAGGCCGTCAATGTTA
P-ERIra.Ubq1-1:1:11    TTTGCCTTTTAAAAACAATTTTATAAGAGAAGCTCCGGAGATAAAAGGCCGTCAATGTTA
P-ERIra.Ubq1-1:1:12    ------------------------------------------------------------
P-ERIra.Ubq1-1:1:13    ------------------------------------------------------------

P-ERIra.Ubq1-1:1:9     CAAGAGTGAAGTCGTCTACTCCCTCCATCCCAAAAAATGTAATTCTAAGTATGAGTTGTA
P-ERIra.Ubq1-1:1:10    CAAGAGTGAAGTCGTCTACTCCCTCCATCCCAAAAAATGTAATTCTAAGTATGAGTTGTA
P-ERIra.Ubq1-1:1:8     CAAGAGTGAAGTCGTCTACTCCCTCCATCCCAAAAAATGTAATTCTAAGTATGAGTTGTA
P-ERIra.Ubq1-1:1:11    CAAGAGTGAAGTCGTCTACTCCCTCCATCCCAAAAAATGTAATTCTAAGTATGAGTTGTA
P-ERIra.Ubq1-1:1:12    ------------------------------------------------------------
P-ERIra.Ubq1-1:1:13    ------------------------------------------------------------

P-ERIra.Ubq1-1:1:9     TTATTATTTTTGGACAAAAGGAGTATACCACAAGAATGATATCATCGTCATGCTTAGATC
P-ERIra.Ubq1-1:1:10    TTATTATTTTTGGACAAAAGGAGTATACCACAAGAATGATATCATCGTCATGCTTAGATC
P-ERIra.Ubq1-1:1:8     TTATTATTTTTGGACAAAAGGAGTATACCACAAGAATGATATCATCGTCATGCTTAGATC
P-ERIra.Ubq1-1:1:11    TTATTATTTTTGGACAAAAGGAGTATACCACAAGAATGATATCATCGTCATGCTTAGATC
P-ERIra.Ubq1-1:1:12    --------------------------ACCACAAGAATGATATCATCGTCATGCTTAGATC
P-ERIra.Ubq1-1:1:13    ------------------------------------------------------------

P-ERIra.Ubq1-1:1:9     CTTTTTAGTAAAGCTTGAGCTTCTCTAAAAGTAGAGAAATTAGAAAAAAATCACGTTTTT
P-ERIra.Ubq1-1:1:10    CTTTTTAGTAAAGCTTGAGCTTCTCTAAAAGTAGAGAAATTAGAAAAAAATCACGTTTTT
P-ERIra.Ubq1-1:1:8     CTTTTTAGTAAAGCTTGAGCTTCTCTAAAAGTAGAGAAATTAGAAAAAAATCACGTTTTT
P-ERIra.Ubq1-1:1:11    CTTTTTAGTAAAGCTTGAGCTTCTCTAAAAGTAGAGAAATTAGAAAAAAATCACGTTTTT
P-ERIra.Ubq1-1:1:12    CTTTTTAGTAAAGCTTGAGCTTCTCTAAAAGTAGAGAAATTAGAAAAAAATCACGTTTTT
P-ERIra.Ubq1-1:1:13    ------------------------------------------------------------

P-ERIra.Ubq1-1:1:9     GTGGTCTTGATTTCTAGCCTCCACAAAATCTTTGGTTTTACATTTTTTGTTTGATTTTGG
P-ERIra.Ubq1-1:1:10    GTGGTCTTGATTTCTAGCCTCCACAAAATCTTTGGTTTTACATTTTTTGTTTGATTTTGG
P-ERIra.Ubq1-1:1:8     GTGGTCTTGATTTCTAGCCTCCACAAAATCTTTGGTTTTACATTTTTTGTTTGATTTTGG
P-ERIra.Ubq1-1:1:11    GTGGTCTTGATTTCTAGCCTCCACAAAATCTTTGGTTTTACATTTTTTGTTTGATTTTGG
P-ERIra.Ubq1-1:1:12    GTGGTCTTGATTTCTAGCCTCCACAAAATCTTTGGTTTTACATTTTTTGTTTGATTTTGG
P-ERIra.Ubq1-1:1:13    ------------------------------------------------------------
```

FIG. 2e

```
P-ERIra.Ubq1-1:1:9    TTTCAGAAGTCCTTATTTATATGTGCTAGTTTGGCAGCACTTAAAATCGTTAGAGAGAGC
P-ERIra.Ubq1-1:1:10   TTTCAGAAGTCCTTATTTATATGTGCTAGTTTGGCAGCACTTAAAATCGTTAGAGAGAGC
P-ERIra.Ubq1-1:1:8    TTTCAGAAGTCCTTATTTATATGTGCTAGTTTGGCAGCACTTAAAATCGTTAGAGAGAGC
P-ERIra.Ubq1-1:1:11   TTTCAGAAGTCCTTATTTATATGTGCTAGTTTGGCAGCACTTAAAATCGTTAGAGAGAGC
P-ERIra.Ubq1-1:1:12   TTTCAGAAGTCCTTATTTATATGTGCTAGTTTGGCAGCACTTAAAATCGTTAGAGAGAGC
P-ERIra.Ubq1-1:1:13   ------------------------------------------------------------

P-ERIra.Ubq1-1:1:9    CTAAACAAAAGCCTTTTCAAAACGACCTTGAGCCAGATTGGTTGATGGCCAAAATTTGAT
P-ERIra.Ubq1-1:1:10   CTAAACAAAAGCCTTTTCAAAACGACCTTGAGCCAGATTGGTTGATGGCCAAAATTTGAT
P-ERIra.Ubq1-1:1:8    CTAAACAAAAGCCTTTTCAAAACGACCTTGAGCCAGATTGGTTGATGGCCAAAATTTGAT
P-ERIra.Ubq1-1:1:11   CTAAACAAAAGCCTTTTCAAAACGACCTTGAGCCAGATTGGTTGATGGCCAAAATTTGAT
P-ERIra.Ubq1-1:1:12   CTAAACAAAAGCCTTTTCAAAACGACCTTGAGCCAGATTGGTTGATGGCCAAAATTTGAT
P-ERIra.Ubq1-1:1:13   ------------------------------------------------------------

P-ERIra.Ubq1-1:1:9    TGTCAAAACTTAGGCAAGCCAAGATTTTAGCAGCTATTTGGTTTGGTACCAAAATTTGCC
P-ERIra.Ubq1-1:1:10   TGTCAAAACTTAGGCAAGCCAAGATTTTAGCAGCTATTTGGTTTGGTACCAAAATTTGCC
P-ERIra.Ubq1-1:1:8    TGTCAAAACTTAGGCAAGCCAAGATTTTAGCAGCTATTTGGTTTGGTACCAAAATTTGCC
P-ERIra.Ubq1-1:1:11   TGTCAAAACTTAGGCAAGCCAAGATTTTAGCAGCTATTTGGTTTGGTACCAAAATTTGCC
P-ERIra.Ubq1-1:1:12   TGTCAAAACTTAGGCAAGCCAAGATTTTAGCAGCTATTTGGTTTGGTACCAAAATTTGCC
P-ERIra.Ubq1-1:1:13   -----------AGGCAAGCCAAGATTTTAGCAGCTATTTGGTTTGGTACCAAAATTTGCC
                                 *********************************************

P-ERIra.Ubq1-1:1:9    AATGATCTGTTCTTTTGCCTTTTCAACCGGTTTATCAGCCGTACTTCAGCTTATTCTCTC
P-ERIra.Ubq1-1:1:10   AATGATCTGTTCTTTTGCCTTTTCAACCGGTTTATCAGCCGTACTTCAGCTTATTCTCTC
P-ERIra.Ubq1-1:1:8    AATGATCTGTTCTTTTGCCTTTTCAACCGGTTTATCAGCCGTACTTCAGCTTATTCTCTC
P-ERIra.Ubq1-1:1:11   AATGATCTGTTCTTTTGCCTTTTCAACCGGTTTATCAGCCGTACTTCAGCTTATTCTCTC
P-ERIra.Ubq1-1:1:12   AATGATCTGTTCTTTTGCCTTTTCAACCGGTTTATCAGCCGTACTTCAGCTTATTCTCTC
P-ERIra.Ubq1-1:1:13   AATGATCTGTTCTTTTGCCTTTTCAACCGGTTTATCAGCCGTACTTCAGCTTATTCTCTC
                      ************************************************************

P-ERIra.Ubq1-1:1:9    TCACAGAACACTATTGAATCAGCCGAAAAGCCACCGCAGAACAGGACCAGTATCTCACAA
P-ERIra.Ubq1-1:1:10   TCACAGAACACTATTGAATCAGCCGAAAAGCCACCGCAGAACAGGACCAGTATCTCACAA
P-ERIra.Ubq1-1:1:8    TCACAGAACACTATTGAATCAGCCGAAAAGCCACCGCAGAACAGGACCAGTATCTCACAA
P-ERIra.Ubq1-1:1:11   TCACAGAACACTATTGAATCAGCCGAAAAGCCACCGCAGAACAGGACCAGTATCTCACAA
P-ERIra.Ubq1-1:1:12   TCACAGAACACTATTGAATCAGCCGAAAAGCCACCGCAGAACAGGACCAGTATCTCACAA
P-ERIra.Ubq1-1:1:13   TCACAGAACACTATTGAATCAGCCGAAAAGCCACCGCAGAACAGGACCAGTATCTCACAA
                      ************************************************************

P-ERIra.Ubq1-1:1:9    ATGGCATGCCAAATATACTCACCGTCAGTGAGCCCGTTTAACGGCGTCGACAAGTCTAAC
P-ERIra.Ubq1-1:1:10   ATGGCATGCCAAATATACTCACCGTCAGTGAGCCCGTTTAACGGCGTCGACAAGTCTAAC
P-ERIra.Ubq1-1:1:8    ATGGCATGCCAAATATACTCACCGTCAGTGAGCCCGTTTAACGGCGTCGACAAGTCTAAC
P-ERIra.Ubq1-1:1:11   ATGGCATGCCAAATATACTCACCGTCAGTGAGCCCGTTTAACGGCGTCGACAAGTCTAAC
P-ERIra.Ubq1-1:1:12   ATGGCATGCCAAATATACTCACCGTCAGTGAGCCCGTTTAACGGCGTCGACAAGTCTAAC
P-ERIra.Ubq1-1:1:13   ATGGCATGCCAAATATACTCACCGTCAGTGAGCCCGTTTAACGGCGTCGACAAGTCTAAC
                      ************************************************************
```

FIG. 2f

```
P-ERIra.Ubq1-1:1:9     GGCCACCAACCAGCGAACCACCAGCGTCAAGCTAGCCAAGCGAAGCAGACGGCCGAGACG
P-ERIra.Ubq1-1:1:10    GGCCACCAACCAGCGAACCACCAGCGTCAAGCTAGCCAAGCGAAGCAGACGGCCGAGACG
P-ERIra.Ubq1-1:1:8     GGCCACCAACCAGCGAACCACCAGCGTCAAGCTAGCCAAGCGAAGCAGACGGCCGAGACG
P-ERIra.Ubq1-1:1:11    GGCCACCAACCAGCGAACCACCAGCGTCAAGCTAGCCAAGCGAAGCAGACGGCCGAGACG
P-ERIra.Ubq1-1:1:12    GGCCACCAACCAGCGAACCACCAGCGTCAAGCTAGCCAAGCGAAGCAGACGGCCGAGACG
P-ERIra.Ubq1-1:1:13    GGCCACCAACCAGCGAACCACCAGCGTCAAGCTAGCCAAGCGAAGCAGACGGCCGAGACG
                       ************************************************************

P-ERIra.Ubq1-1:1:9     TTGACACCTTGGCGCGGGCATCTCTCTGGCCCCCTCTCGAGAGTTCCGCTCCACCTCCAC
P-ERIra.Ubq1-1:1:10    TTGACACCTTGGCGCGGGCATCTCTCTGGCCCCCTCTCGAGAGTTCCGCTCCACCTCCAC
P-ERIra.Ubq1-1:1:8     TTGACACCTTGGCGCGGGCATCTCTCTGGCCCCCTCTCGAGAGTTCCGCTCCACCTCCAC
P-ERIra.Ubq1-1:1:11    TTGACACCTTGGCGCGGGCATCTCTCTGGCCCCCTCTCGAGAGTTCCGCTCCACCTCCAC
P-ERIra.Ubq1-1:1:12    TTGACACCTTGGCGCGGGCATCTCTCTGGCCCCCTCTCGAGAGTTCCGCTCCACCTCCAC
P-ERIra.Ubq1-1:1:13    TTGACACCTTGGCGCGGGCATCTCTCTGGCCCCCTCTCGAGAGTTCCGCTCCACCTCCAC
                       ************************************************************

P-ERIra.Ubq1-1:1:9     TGGTGGCGGTTTCCAAGTCCGTTCCGCCTCCTGCTCCTCCTCACACGGCACGAAACCGTC
P-ERIra.Ubq1-1:1:10    TGGTGGCGGTTTCCAAGTCCGTTCCGCCTCCTGCTCCTCCTCACACGGCACGAAACCGTC
P-ERIra.Ubq1-1:1:8     TGGTGGCGGTTTCCAAGTCCGTTCCGCCTCCTGCTCCTCCTCACACGGCACGAAACCGTC
P-ERIra.Ubq1-1:1:11    TGGTGGCGGTTTCCAAGTCCGTTCCGCCTCCTGCTCCTCCTCACACGGCACGAAACCGTC
P-ERIra.Ubq1-1:1:12    TGGTGGCGGTTTCCAAGTCCGTTCCGCCTCCTGCTCCTCCTCACACGGCACGAAACCGTC
P-ERIra.Ubq1-1:1:13    TGGTGGCGGTTTCCAAGTCCGTTCCGCCTCCTGCTCCTCCTCACACGGCACGAAACCGTC
                       ************************************************************

P-ERIra.Ubq1-1:1:9     ACGGCACCGGCAGCACGGGGGATTCCTTTCCCACCGCTCCTTCCCTTTCCCTTCCTCGCC
P-ERIra.Ubq1-1:1:10    ACGGCACCGGCAGCACGGGGGATTCCTTTCCCACCGCTCCTTCCCTTTCCCTTCCTCGCC
P-ERIra.Ubq1-1:1:8     ACGGCACCGGCAGCACGGGGGATTCCTTTCCCACCGCTCCTTCCCTTTCCCTTCCTCGCC
P-ERIra.Ubq1-1:1:11    ACGGCACCGGCAGCACGGGGGATTCCTTTCCCACCGCTCCTTCCCTTTCCCTTCCTCGCC
P-ERIra.Ubq1-1:1:12    ACGGCACCGGCAGCACGGGGGATTCCTTTCCCACCGCTCCTTCCCTTTCCCTTCCTCGCC
P-ERIra.Ubq1-1:1:13    ACGGCACCGGCAGCACGGGGGATTCCTTTCCCACCGCTCCTTCCCTTTCCCTTCCTCGCC
                       ************************************************************

P-ERIra.Ubq1-1:1:9     CGCCGTTTTAAATAGCCAGCCCCATCCCCAGCTTCTCTCCCC
P-ERIra.Ubq1-1:1:10    CGCCGTTTTAAATAGCCAGCCCCATCCCCAGCTTCTCTCCCC
P-ERIra.Ubq1-1:1:8     CGCCGTTTTAAATAGCCAGCCCCATCCCCAGCTTCTCTCCCC
P-ERIra.Ubq1-1:1:11    CGCCGTTTTAAATAGCCAGCCCCATCCCCAGCTTCTCTCCCC
P-ERIra.Ubq1-1:1:12    CGCCGTTTTAAATAGCCAGCCCCATCCCCAGCTTCTCTCCCC
P-ERIra.Ubq1-1:1:13    CGCCGTTTTAAATAGCCAGCCCCATCCCCAGCTTCTCTCCCC
                       ******************************************
```

FIG. 2g

```
P-Sv.Ubq1-1:1:2    ------------------------------------------------------------
P-Sv.Ubq1-1:1:1    ACTGCCGCGACACGCCTCACTGGCGGGAGGGCTCCGAGCGCTCTCTCCCCGGCGGCCGGC
P-Sv.Ubq1-1:1:3    ------------------------------------------------------------

P-Sv.Ubq1-1:1:2    ------------------------------------------------------------
P-Sv.Ubq1-1:1:1    GGAGCAGCGATCTGGATTGGAGAGAATAGAGGAAAGAGAGGGAAAAGGAGAGAGATAGCG
P-Sv.Ubq1-1:1:3    ------------------------------------------------------------

P-Sv.Ubq1-1:1:2    ------------------------------------------------------------
P-Sv.Ubq1-1:1:1    CAAAGAGCTGAAAAGATAAGGTTGTGCGGGCTGTGGTGATTAGAGGACCACTAATCCCTC
P-Sv.Ubq1-1:1:3    ------------------------------------------------------------

P-Sv.Ubq1-1:1:2    ------------------------------------------------------------
P-Sv.Ubq1-1:1:1    CATCTCCTAATGACGCGGTGCCCAAGACCAGTGCCGCGGCACACCAGCGTCTAAGTGAAC
P-Sv.Ubq1-1:1:3    ------------------------------------------------------------

P-Sv.Ubq1-1:1:2    ------------------------------------------------------------
P-Sv.Ubq1-1:1:1    TTCCGCTAACCTTCCGGTCATTGCGCCTGAAAGATGTCATGTGGCGAGGCCCCCCTCTCA
P-Sv.Ubq1-1:1:3    ------------------------------------------------------------

P-Sv.Ubq1-1:1:2    ------------------------------------------------------------
P-Sv.Ubq1-1:1:1    GTAGATTGCCAACTGCCTACCGTGCCACTCTTCCATGCATGATTGCTCCCGTCTATCCCG
P-Sv.Ubq1-1:1:3    ------------------------------------------------------------

P-Sv.Ubq1-1:1:2    ------------------------------------------------------------
P-Sv.Ubq1-1:1:1    TTTCTCACAACAGATAGACAACAGTAAGCATCACTAAAGCAAGCATGTGTAGAACCTTAA
P-Sv.Ubq1-1:1:3    ------------------------------------------------------------

P-Sv.Ubq1-1:1:2    ---------------------------------------GCCGTTTTTGAAGTATCCAGGA
P-Sv.Ubq1-1:1:1    AAAAAGGCTTATACTACCAGTATACTATCAACCAGCATGCCGTTTTTGAAGTATCCAGGA
P-Sv.Ubq1-1:1:3    ------------------------------------------------------------

P-Sv.Ubq1-1:1:2    TTAGAAGCTTCTACTGCGCTTTTATATTATAGCTGTGGACCTGTGGTAACCTTTCTCTTT
P-Sv.Ubq1-1:1:1    TTAGAAGCTTCTACTGCGCTTTTATATTATAGCTGTGGACCTGTGGTAACCTTTCTCTTT
P-Sv.Ubq1-1:1:3    ------------------------------------------------------------

P-Sv.Ubq1-1:1:2    TGGCGCTTGCTTAATCTCGGCCGTGCTGGTCCATGCTTAGGCACTAGGCAGAGATAGAGC
P-Sv.Ubq1-1:1:1    TGGCGCTTGCTTAATCTCGGCCGTGCTGGTCCATGCTTAGGCACTAGGCAGAGATAGAGC
P-Sv.Ubq1-1:1:3    ------------------------------------------------------------

P-Sv.Ubq1-1:1:2    CGGGGGTGAATGGGGCTAAAGCTCAGCTGCTCGAGGGGCCGTGGGCTGGTTTCCACTAGC
P-Sv.Ubq1-1:1:1    CGGGGGTGAATGGGGCTAAAGCTCAGCTGCTCGAGGGGCCGTGGGCTGGTTTCCACTAGC
P-Sv.Ubq1-1:1:3    ------------------------------------------------------------

P-Sv.Ubq1-1:1:2    CTACAGCTGTGCCACGTGCGGCCGCGCAAGCCGAAGCAAGCACGCTGAGCCGTTGGACAG
P-Sv.Ubq1-1:1:1    CTACAGCTGTGCCACGTGCGGCCGCGCAAGCCGAAGCAAGCACGCTGAGCCGTTGGACAG
P-Sv.Ubq1-1:1:3    ------------------------------------------------------------
```

FIG. 3a

```
P-Sv.Ubq1-1:1:2    CTTGTCATAATGCCATTACGTGGATTACAGGTAACTGGCCCTGTAACTACTCGTTCGGCC
P-Sv.Ubq1-1:1:1    CTTGTCATAATGCCATTACGTGGATTACAGGTAACTGGCCCTGTAACTACTCGTTCGGCC
P-Sv.Ubq1-1:1:3    ------------------------------------------------------------

P-Sv.Ubq1-1:1:2    ATCATCAAACGACGACGTCCGCTAGGCGACGACACGGGTAATGCACGCAGCCACCCAGGC
P-Sv.Ubq1-1:1:1    ATCATCAAACGACGACGTCCGCTAGGCGACGACACGGGTAATGCACGCAGCCACCCAGGC
P-Sv.Ubq1-1:1:3    --------------------------------CACGGGTAATGCACGCAGCCACCCAGGC
                                                   ****************************

P-Sv.Ubq1-1:1:2    GCGCGCGCTAGCGGAGCACGGTCAGGTGACACGGGCGTCGTGACGCTTCCGAGTTGAAGG
P-Sv.Ubq1-1:1:1    GCGCGCGCTAGCGGAGCACGGTCAGGTGACACGGGCGTCGTGACGCTTCCGAGTTGAAGG
P-Sv.Ubq1-1:1:3    GCGCGCGCTAGCGGAGCACGGTCAGGTGACACGGGCGTCGTGACGCTTCCGAGTTGAAGG
                   ************************************************************

P-Sv.Ubq1-1:1:2    GGTTAACGCCAGAAACAGTGTTTGGCCAGGGTATGAACATAACAAAAAATATTCACACGA
P-Sv.Ubq1-1:1:1    GGTTAACGCCAGAAACAGTGTTTGGCCAGGGTATGAACATAACAAAAAATATTCACACGA
P-Sv.Ubq1-1:1:3    GGTTAACGCCAGAAACAGTGTTTGGCCAGGGTATGAACATAACAAAAAATATTCACACGA
                   ************************************************************

P-Sv.Ubq1-1:1:2    AAGAATGGAAGTATGGAGCTGCTACTGTGTAAATGCCAAGCAGGAAACTCACGCCCGCTA
P-Sv.Ubq1-1:1:1    AAGAATGGAAGTATGGAGCTGCTACTGTGTAAATGCCAAGCAGGAAACTCACGCCCGCTA
P-Sv.Ubq1-1:1:3    AAGAATGGAAGTATGGAGCTGCTACTGTGTAAATGCCAAGCAGGAAACTCACGCCCGCTA
                   ************************************************************

P-Sv.Ubq1-1:1:2    ACATCCAACGGCCAACAGCTCGACGTGCCGGTCAGCAGAGACATCGGAACACTGGTGATT
P-Sv.Ubq1-1:1:1    ACATCCAACGGCCAACAGCTCGACGTGCCGGTCAGCAGAGACATCGGAACACTGGTGATT
P-Sv.Ubq1-1:1:3    ACATCCAACGGCCAACAGCTCGACGTGCCGGTCAGCAGAGACATCGGAACACTGGTGATT
                   ************************************************************

P-Sv.Ubq1-1:1:2    GGTGGAGCCGGCAGTATGCGCCCCAGCACGGCCGAGGTGGTGGTGGCCCGTGGCCCTGCT
P-Sv.Ubq1-1:1:1    GGTGGAGCCGGCAGTATGCGCCCCAGCACGGCCGAGGTGGTGGTGGCCCGTGGCCCTGCT
P-Sv.Ubq1-1:1:3    GGTGGAGCCGGCAGTATGCGCCCCAGCACGGCCGAGGTGGTGGTGGCCCGTGGCCCTGCT
                   ************************************************************

P-Sv.Ubq1-1:1:2    GTCTGCGCGGCTCGGGACAACTTGAAACTGGGCCACCGCCTCGTCGCAACTCGCAACCCG
P-Sv.Ubq1-1:1:1    GTCTGCGCGGCTCGGGACAACTTGAAACTGGGCCACCGCCTCGTCGCAACTCGCAACCCG
P-Sv.Ubq1-1:1:3    GTCTGCGCGGCTCGGGACAACTTGAAACTGGGCCACCGCCTCGTCGCAACTCGCAACCCG
                   ************************************************************

P-Sv.Ubq1-1:1:2    TTGGCGGAAGAAAGGAATGGCTCGTAGGGGCCCGGGTAGAATCCAAGAATGTTGCGCTGG
P-Sv.Ubq1-1:1:1    TTGGCGGAAGAAAGGAATGGCTCGTAGGGGCCCGGGTAGAATCCAAGAATGTTGCGCTGG
P-Sv.Ubq1-1:1:3    TTGGCGGAAGAAAGGAATGGCTCGTAGGGGCCCGGGTAGAATCCAAGAATGTTGCGCTGG
                   ************************************************************

P-Sv.Ubq1-1:1:2    GCTTCGATTCACATAACATGGGCCTGAAGCTCTAAAACGACGGCCCGGTCACCGGGCGAT
P-Sv.Ubq1-1:1:1    GCTTCGATTCACATAACATGGGCCTGAAGCTCTAAAACGACGGCCCGGTCACCGGGCGAT
P-Sv.Ubq1-1:1:3    GCTTCGATTCACATAACATGGGCCTGAAGCTCTAAAACGACGGCCCGGTCACCGGGCGAT
                   ************************************************************
```

FIG. 3b

```
P-Sv.Ubq1-1:1:2    GGAAAGAGACCGGATCCTCCTCGTGAATTCTGGAAGGCCACACGAGAGCGACCCACCACC
P-Sv.Ubq1-1:1:1    GGAAAGAGACCGGATCCTCCTCGTGAATTCTGGAAGGCCACACGAGAGCGACCCACCACC
P-Sv.Ubq1-1:1:3    GGAAAGAGACCGGATCCTCCTTGTGAATTCTGGAAGGCCACACGAGAGCGACCCACCACC
                   ********************* **************************************

P-Sv.Ubq1-1:1:2    GACGCGGAGGAGTCGTGCGTGGTCCAACACGGCCGGCGGGCTGGGCTGCGACCTTAACCA
P-Sv.Ubq1-1:1:1    GACGCGGAGGAGTCGTGCGTGGTCCAACACGGCCGGCGGGCTGGGCTGCGACCTTAACCA
P-Sv.Ubq1-1:1:3    GACGCGGAGGAGTCGTGCGTGGTCCAACACGGCCGGCGGGCTGGGCTGCGACCTTAACCA
                   ************************************************************

P-Sv.Ubq1-1:1:2    GCAAGGCACGCCACGACCCGCCTCGCCCTCGAGGCATAAATACCCTCCCATCC
P-Sv.Ubq1-1:1:1    GCAAGGCACGCCACGACCCGCCTCGCCCTCGAGGCATAAATACCCTCCCATCC
P-Sv.Ubq1-1:1:3    GCAAGGCACGCCACGACCCGCCTCGCCCTCGAGGCATAAATACCCTCCCATCC
                   *****************************************************
```

FIG. 3c

```
EXP-Zm.UbqM1:1:2    GTCGTGCCCCTCTCTAGAGATAAAGAGCATTGCATGTCTAAAGTATAAAAAATTACCACA
EXP-Zm.UbqM1:1:5    GTCGTGCCCCTCTCTAGAGATAAAGAGCATTGCATGTCTAAAGTATAAAAAATTACCACA
EXP-Zm.UbqM1:1:1    GTCGTGCCCCTCTCTAGAGATAATGAGCATTGCATGTCTAAGTTATAAAAAATTACCACA
EXP-Zm.UbqM1:1:4    GTCGTGCCCCTCTCTAGAGATAAAGAGCATTGCATGTCTAAGTTATAAAAAATTACCACA
                    ***********************  ****************  ****************

EXP-Zm.UbqM1:1:2    TA--TTTTTTTGTCACACT--TATTTGAAGTGTAGTTTATCTATCTCTATACATATATTT
EXP-Zm.UbqM1:1:5    TA--TTTTTTTGTCACACT--TATTTGAAGTGTAGTTTATCTATCTCTATACATATATTT
EXP-Zm.UbqM1:1:1    TATTTTTTTTTGTCACACTTGTGTTTGAAGTGCAGTTTATCTATCTCTATACATATATTT
EXP-Zm.UbqM1:1:4    TA-TTTTTTTTGTCACACT--TGTTTGAAGTGCAGTTTATCTATCTTTATACATATATTT
                    **  *************    * ******** ************* *************

EXP-Zm.UbqM1:1:2    AAACTTCACTCTACAAATAATATAGTCTATAATACTAAAATAATATTAGTGTTTTAGAGG
EXP-Zm.UbqM1:1:5    AAACTTCACTCTACAAATAATATAGTCTATAATACTAAAATAATATTAGTGTTTTAGAGG
EXP-Zm.UbqM1:1:1    AAACTTCACTATATGAATAATATAGTCTATAGTATTAAAATAATATCAATGTTTTAGATG
EXP-Zm.UbqM1:1:4    AAACTTTACTCTACGAATAATATAATCTATAGTACTACAATAATATCAGTGTTTTAGAGA
                    ****** *** **   ********  ***** ** **  ******  * ********

EXP-Zm.UbqM1:1:2    ATCATATAAATAAACTGCTAGACATGGTCTAAAGGATAATTGAATATTTTGACAA-----
EXP-Zm.UbqM1:1:5    ATCATATAAATAAACTGCTAGACATGGTCTAAAGGATAATTGAATATTTTGACAA-----
EXP-Zm.UbqM1:1:1    ATTATATAACTGAACTGCTAGACATGGTCTAAAGGACAACCGAGTATTTTGACAACATGA
EXP-Zm.UbqM1:1:4    ATCATATAAATGAACAGTTAGACATGGTCTAAAGGACAATTGAGTATTTTGACAACAGGA
                    ** ****** * ***  * *****************  **   ** **********

EXP-Zm.UbqM1:1:2    -TCTACAGTTTTATCTTTTTAGTGTGCATGTGATCTCTCTGTTTTTTTTGCAAATAGCTT
EXP-Zm.UbqM1:1:5    -TCTACAGTTTTATCTTTTTAGTGTGCATGTGATCTCTCTGTTTTTTTTGCAAATAGCTT
EXP-Zm.UbqM1:1:1    CTCTACAGTTTTATCTTTTTAGTGTGCATGTGTTCTTT---TTACTTTTGCAAATAGCTT
EXP-Zm.UbqM1:1:4    CTCTACAGTTTTATCTTTTTAGTGTGCATGTGTTCTCCTT-TTTTTTTTGCAAATAGCTT
                     ******************************  ***      **  **************

EXP-Zm.UbqM1:1:2    GACCTATATAATACTTCATCCATTTTATTAGTACATCCATTTAGGATTTAGGGTTGATGG
EXP-Zm.UbqM1:1:5    GACCTATATAATACTTCATCCATTTTATTAGTACATCCATTTAGGATTTAGGGTTGATGG
EXP-Zm.UbqM1:1:1    CACCTATATAATACTTCATCCATTTTATTAGTACATCCATTT------------------
EXP-Zm.UbqM1:1:4    CACCTATATAATACTTCATCCATTTTATTAGTACATCCATTTAGGGTTTAGGGTTAATGG
                     *****************************************

EXP-Zm.UbqM1:1:2    TTTCTATAGACTAA--TTTTTAGTACATCCATTTTATTCT-TTTTAGTCTCTAAATTTTT
EXP-Zm.UbqM1:1:5    TTTCTATAGACTAA--TTTTTAGTACATCCATTTTATTCT-TTTTAGTCTCTAAATTTTT
EXP-Zm.UbqM1:1:1    ---------ACTAAA-TTTTTAGTACATCTATTTTATTCTATTTTAGCCTCTAAA-TTAA
EXP-Zm.UbqM1:1:4    TTTTTATAGACTAATTTTTTTAGTACATCTATTTTATTCTATTTTAGCCTCTAAA-TTAA
                             *****  ************ ********** ****** ******* **

EXP-Zm.UbqM1:1:2    TAAAACTAAAACTCTATTTTAG-TTTTTTATTTAATAATTTAGATATAAAATGAAATAAA
EXP-Zm.UbqM1:1:5    TAAAACTAAAACTCTATTTTAG-TTTTTTATTTAATAATTTAGATATAAAATGAAATAAA
EXP-Zm.UbqM1:1:1    GAAAACTAAAACTCTATTTTAG-TTTTTTATTTAATAATTTAGATATAAAATAGAATAAA
EXP-Zm.UbqM1:1:4    GAAAACTAAAACTCTATTTTAGTTTTTTTATTTAATAATTTAGATATAAAATAGAATAAA
                     ************ ****** ************************* ******
```

FIG. 4a

```
EXP-Zm.UbqM1:1:2    ATAAATTGACTACAAATAAAACAAATACCCTTTAAGAAA-TAAAAAAACTAAGCAAACAT
EXP-Zm.UbqM1:1:5    ATAAATTGACTACAAATAAAACAAATACCCTTTAAGAAA-TAAAAAAACTAAGCAAACAT
EXP-Zm.UbqM1:1:1    ATAAAGTGACTAAAAAATAACTAAATACCTTTTAAGAAA-TAAAAAAACTAAGGAACCAT
EXP-Zm.UbqM1:1:4    ATAAAGTGACTAAAAATTAAACAAATACCCTTTAAGAAATTAAAAAAACTAAGGAAACAT
                    *****  ****** ***   **   ******* ******** ************* ** ***

EXP-Zm.UbqM1:1:2    TTTTCTTGTTTCGAGTAGATAATGACAGGCTGTTCAACGCCGTCGACGAGTCTAACGGAC
EXP-Zm.UbqM1:1:5    TTTTCTTGTTTCGAGTAGATAATGACAGGCTGTTCAACGCCGTCGACGAGTCTAACGGAC
EXP-Zm.UbqM1:1:1    TTTTCTTGTTCCGAGTAGATAATGACAGCCTGTTCAACGCCGTCGACGAGTCTAACGGAC
EXP-Zm.UbqM1:1:4    TTTTCTTGTTTCGAGTAGATAATGCCAGCCTGTTAAACGCCGTCGACGAGTCTAACGGAC
                    ********** ************ *** *****  **********************

EXP-Zm.UbqM1:1:2    ACCAACCAGCGAACCAGCAGCGTCGCGTCGGGCCAAGCGAAGCAGACGGCACGGCATCTC
EXP-Zm.UbqM1:1:5    ACCAACCAGCGAACCAGCAGCGTCGCGTCGGGCCAAGCGAAGCAGACGGCACGGCATCTC
EXP-Zm.UbqM1:1:1    ACCAACCAGCGAACCAGCAGCGTCGCGTCGGGCCAAGCGAAGCAGACGGCACGGCATCTC
EXP-Zm.UbqM1:1:4    ACCAACCAGCGAACCAGCAGCGTCGCGTCGGGCCAAGCGAAGCAGACGGCACGGCATCTC
                    ************************************************************

EXP-Zm.UbqM1:1:2    TGTAGCTGCCTCTGGACCCCTCTCGAGAGTTCCGCTCCACCGTTGGACTTGCTCCGCTGT
EXP-Zm.UbqM1:1:5    TGTAGCTGCCTCTGGACCCCTCTCGAGAGTTCCGCTCCACCGTTGGACTTGCTCCGCTGT
EXP-Zm.UbqM1:1:1    TGTAGCTGCCTCTGGACCCCTCTCGAGAGTTCCGCTCCACCGTTGGACTTGCTCCGCTGT
EXP-Zm.UbqM1:1:4    TGTCGCTGCCTCTGGACCCCTCTCGAGAGTTCCGCTCCACCGTTGGACTTGCTCCGCTGT
                    *** ********************************************************

EXP-Zm.UbqM1:1:2    CGGCATCCAGAAATTGCGTGGCGGAGCGGCAGACGTGAGGCGGCACGGCAGGCGGCCTCT
EXP-Zm.UbqM1:1:5    CGGCATCCAGAAATTGCGTGGCGGAGCGGCAGACGTGAGGCGGCACGGCAGGCGGCCTCT
EXP-Zm.UbqM1:1:1    CGGCATCCAGAAATTGCGTGGCGGAGCGGCAGACGTGAGCCGGCACGGCAGGCGG-----
EXP-Zm.UbqM1:1:4    CGGCATCCAGAAATTGCGTGGCGGAGCGGCAGACGTGAGCCGGCACGGCAGGCGGCCTCC
                    ************************************** ***************

EXP-Zm.UbqM1:1:2    TCCTCCTCTCACGGCACCGGCAGCTACGGGGGATTCCTTTCCCACCGCTCCTTCGCTTTC
EXP-Zm.UbqM1:1:5    TCCTCCTCTCACGGCACCGGCAGCTACGGGGGATTCCTTTCCCACCGCTCCTTCGCTTTC
EXP-Zm.UbqM1:1:1    -CCTCCTCTCACGGCACCGGCAGCTACGGGGGATTCCTTTCCCACCGCTCCTTCGCTTTC
EXP-Zm.UbqM1:1:4    TCCTCCTCTCACGGCACCGGCAGCTACGGGGGATTCCTTTCCCACCGCTCCTTCGCTTTC
                     ***********************************************************

EXP-Zm.UbqM1:1:2    CCTTCCTCGCCCGCCGTAATAAATAGACACCCCCTCCACACCCTCTTTCCCCAACCTCGT
EXP-Zm.UbqM1:1:5    CCTTCCTCGCCCGCCGTAATAAATAGACACCCCCTCCACACCCTCTTTCCCCAACCTCGT
EXP-Zm.UbqM1:1:1    CCTTCCTCGCCCGCCGTAATAAATAG--ACCCCCTCCACACCCTCTTTCCCCAACCTCGT
EXP-Zm.UbqM1:1:4    CCTTCCTCGCCCGCCGTAATAAATAGACACCCCCTCCACACCTTCTTTCCCCAACCTCGT
                    **************************  ************* ******************

EXP-Zm.UbqM1:1:2    GTTCGTTCGGAGCGCACACACACGCAACCAGATCTCCCCCAAATCCAGCCGTCGGCACCT
EXP-Zm.UbqM1:1:5    GTTCGTTCGGAGCGCACACACACGCAACCAGATCTCCCCCAAATCCAGCCGTCGGCACCT
EXP-Zm.UbqM1:1:1    GTTCGTTCGGAGCGCGCACACACACAACCAGATCTCCCCCAAATCCACCCGTCGGCACCT
EXP-Zm.UbqM1:1:4    GTT-GTTCGGAGCGCACACACACACAACCAGATCTCCCCCAAATCCACCCGTCGGCACCT
                    *** ********** ******  ******************* *************
```

FIG. 4b

```
EXP-Zm.UbqM1:1:2    CCGCTTCAAGGTACGCCGCTCATCCTCCCCCCCCCCCTCTCTCTACCTTCTCTAGATCGG
EXP-Zm.UbqM1:1:5    CCGCTTCAAGGTACGCCGCTCATCCTCCCCCCCCCCCTCTCTCTACCTTCTCTAGATCGG
EXP-Zm.UbqM1:1:1    CCGCTTCAAGGTACGCCGCTCATCCTCCTCCCCCCCCTCTCTCTACCTTCTCTAGATCGG
EXP-Zm.UbqM1:1:4    CCGCTTCAAGGTACGCCGCTCATCCTCCCCCCCCC---CTCTCTACCTTCTCTAGATCGG
                    ***************************** ******   ********************

EXP-Zm.UbqM1:1:2    CGATCCGGTCCATGGTTAGGGCCCGGTAGTTCTACTTCTGTTCATGTTTGTGTTAGAGCA
EXP-Zm.UbqM1:1:5    CGATCCGGTCCATGGTTAGGGCCCGGTAGTTCTACTTCTGTTCATGTTTGTGTTAGAGCA
EXP-Zm.UbqM1:1:1    CGTTTCGGTCCATGGTTAGGGCCCGGTAGTTCTACTTCTGTTCATGTTTGTGTTAGATC-
EXP-Zm.UbqM1:1:4    CGTTCCGGTCCATGGTTAGGGCCCGGTAGTTCTACTTCTGTTCATGTTTGTGTTAGATC-
                    ** * **************************************************** *

EXP-Zm.UbqM1:1:2    AACATGTTCATGTT-------------------------CATGTTTGTGAT----------
EXP-Zm.UbqM1:1:5    AACATGTTCATGTT-------------------------CATGTTTGTGAT----------
EXP-Zm.UbqM1:1:1    --CGTGTTTGTGTTAGATCCGTGCTGCTAGATTTCGTACACGGATGCGACCTGTACATCA
EXP-Zm.UbqM1:1:4    --CGTGTTTGTGTTAGATCCGTGCTGCTAGCGTTCGTACACGGATGCGACCTGTACGTCA
                      * ****  ****                         **  *    ** ** **

EXP-Zm.UbqM1:1:2    GATGTGGTCTGGTTG--------GGCGGTCGTTCTAGATCGGAG----TAGGATACTGTTT
EXP-Zm.UbqM1:1:5    GATGTGGTCTGGTTG--------GGCGGTCGTTCTAGATCGGAG----TAGGATACTGTTT
EXP-Zm.UbqM1:1:1    GACATGTTCTGATTGCTAACTTGCCAGTGTTTCTCTTTGGGGAATCCTGGGA---TGGCT
EXP-Zm.UbqM1:1:4    GACACGTTCTGATTGCTAACTTGCCAGTGTTTCTCTTTGGGGAATCCTGGGA---TGGCT
                    **    * **** ***        *   * ** ** ****   * **    * ***  ** *

EXP-Zm.UbqM1:1:2    CAAGCT---------ACCTGGTGGATTT-----ATTAATTTTGTATCTGTATGT------
EXP-Zm.UbqM1:1:5    CAAGCT---------ACCTGGTGGATTT-----ATTAATTTTGTATCTGTATGT------
EXP-Zm.UbqM1:1:1    CTAGCCGTTCCGCAGACGGGATCGATTTCATGAATTTTTTTGTTTCGTTGCATAGGGTT
EXP-Zm.UbqM1:1:4    CTAGCCGTTCCGCAGACGGGATCGATTTCATG-ATTTTTTTGTTTCGTTGCATAGGGTT
                    * ***           **  * * *****    *** ****** **   *

EXP-Zm.UbqM1:1:2    --GTGTGCCATACATCTTCATAGTTACGAGTTTAAGATGATGGATGGAAATATCGATCTA
EXP-Zm.UbqM1:1:5    --GTGTGCCATACATCTTCATAGTTACGAGTTTAAGATGATGGATGGAAATATCGATCTA
EXP-Zm.UbqM1:1:1    TGGTTTGCCCTTTTCCTTTAT---------TTCAATAT-----------ATGCC------
EXP-Zm.UbqM1:1:4    TGGTTTGCCCTTTTCCTTTAT---------TTCAATAT-----------ATGCC------
                      ** **** *   *  ***  *         ** **  **             **  *

EXP-Zm.UbqM1:1:2    GGATAGGTATACATGTTGATGCGGGT--TTTACTGATGCATATACAGAGATGCTTTTTTT
EXP-Zm.UbqM1:1:5    GGATAGGTATACATGTTGATGCGGGT--TTTACTGATGCATATACAGAGATGCTTTTTTT
EXP-Zm.UbqM1:1:1    ------GTGCACTTGTTTGT-CGGGTCATCTTTTCATG----------------TTTTTT
EXP-Zm.UbqM1:1:4    ------GTGCACTTGTTTGT-CGGGTCATCTTTTCATGC---------------TTTTTT
                          **  **  ****  *  *****    *  * ***                 ******

EXP-Zm.UbqM1:1:2    CTCGCTTGGTTGTGATGATATGGTCTGGTTGGGCGGTCGTTCTAGATCGGAGTAGAATAC
EXP-Zm.UbqM1:1:5    CTCGCTTGGTTGTGATGATATGGTCTGGTTGGGCGGTCGTTCTAGATCGGAGTAGAATAC
EXP-Zm.UbqM1:1:1    TTGGCTTGGTTGTGATGATGTGGTCTGGTTGGGCGGTCGTTCTAGATCGGAGTAGAATAC
EXP-Zm.UbqM1:1:4    TTGTCTTGGTTGTGATGATGTGGTCTGGTTGGGCGGTCGTTCTAGATCGGAGAAGAATTC
                    *   ******************** *********************************** ***** *
```

FIG. 4c

```
EXP-Zm.UbqM1:1:2    TGTTTCAAACTACCTGGTGGATTTATTAAAGGATAAAGGGTCGTTCTAGATCGGAGTAGA
EXP-Zm.UbqM1:1:5    TGTTTCAAACTACCTGGTGGATTTATTAAAGGATAAAGGGTCGTTCTAGATCGGAGTAGA
EXP-Zm.UbqM1:1:1    TGTTTCAAACTACCTGGTGGATTTATTAA-------------------------------
EXP-Zm.UbqM1:1:4    TGTTTCAAACTACCTGGTGGATTTATTAA-------------------------------
                    *****************************

EXP-Zm.UbqM1:1:2    ATACTGTTTCAAACTACCTGGTGGATTTATTAAAGGATCTGTATGTATGTGCC-TACATC
EXP-Zm.UbqM1:1:5    ATACTGTTTCAAACTACCTGGTGGATTTATTAAAGGATCTGTATGTATGTGCC-TACATC
EXP-Zm.UbqM1:1:1    ----------------------------------AGGATCTGTATGTATGTGCCATACATC
EXP-Zm.UbqM1:1:4    ------------------------------TTTTGGATCTGTATGTGTGTGCCATACATA
                                                      *********** ****** *****

EXP-Zm.UbqM1:1:2    TTCATAGTTACGAGTTTAAGATGATGGATGGAAATATCGATCTAGGATAGGTATACATGT
EXP-Zm.UbqM1:1:5    TTCATAGTTACGAGTTTAAGATGATGGATGGAAATATCGATCTAGGATAGGTATACATGT
EXP-Zm.UbqM1:1:1    TTCATAGTTACGAGTTTAAGATGATGGATGGAAATATCGATCTAGGATAGGTATACATGT
EXP-Zm.UbqM1:1:4    TTCATAGTTACGAATTGAAGATGATGGATGGAAATATCGATCTAGGATAGGTATACATGT
                    ************* ** *******************************************

EXP-Zm.UbqM1:1:2    TGATGCGGGTTTTACTGATGCATATACAGAGATGCTTTTT-TTCGCTTGGTTGTGATGAT
EXP-Zm.UbqM1:1:5    TGATGCGGGTTTTACTGATGCATATACAGAGATGCTTTTT-TTCGCTTGGTTGTGATGAT
EXP-Zm.UbqM1:1:1    TGATGCGGGTTTTACTGATGCATATACAGAGATGCTTTTTTTTCGCTTGGTTGTGATGAT
EXP-Zm.UbqM1:1:4    TGATGCGGGTTTTACTGATGCATATACAGAGATGCTTTTTGTTCGCTTGGTTGTGATGAT
                    ****************************************  *****************

EXP-Zm.UbqM1:1:2    GTGGTCTGGTTGGGCGG--------TCGTTCTAGATCGGAGTAGAATACTGTTTCAAACT
EXP-Zm.UbqM1:1:5    GTGGTCTGGTTGGGCGG--------TCGTTCTAGATCGGAGTAGAATACTGTTTCAAACT
EXP-Zm.UbqM1:1:1    GTGGTCTGGTCGGGCGG--------TCGTTCTAGATCGGAGTAGAATACTGTTTCAAACT
EXP-Zm.UbqM1:1:4    GTGGTCTGGTTGGGCGGTCGTTCATTCGTTCTAGATCGGAGTAGAATACTGTTTCAAACT
                    ********** ******        ***********************************

EXP-Zm.UbqM1:1:2    ACCTGGTGGATTTATTAATTTTGTATCTTTATGTGTGTGCCATACATCTTCATAGTTACG
EXP-Zm.UbqM1:1:5    ACCTGGTGGATTTATTAATTTTGTATCTTTATGTGTGTGCCATACATCTTCATAGTTACG
EXP-Zm.UbqM1:1:1    ACCTGGTGGATTTATTAATTTTGGATCTGTATGTGTGT--CATACATCTTCATAGTTACG
EXP-Zm.UbqM1:1:4    ACCTGGTGTATTTATTAATTTTGGAACTGTATGTGTGTGTCATACATCTTCATAGTTACG
                    ********  *************  **  ** ********  ******************

EXP-Zm.UbqM1:1:2    AGTTTAAGATGATGGATGGAAATATTGATCTAGGATAGGTATACATGTTGATGTGGGTTT
EXP-Zm.UbqM1:1:5    AGTTTAAGATGATGGATGGAAATATTGATCTAGGATAGGTATACATGTTGATGTGGGTTT
EXP-Zm.UbqM1:1:1    AGTTTAA---GATCGATGGAAATATCGATCTAGGATAGGTATACATGTTGATGTGGGTTT
EXP-Zm.UbqM1:1:4    AGTTTAA---GATGGATGGAAATATCGATCTAGGATAGGTATACATGTTGATGTGGGTTT
                    *******   *** *********** **********************************

EXP-Zm.UbqM1:1:2    TACTGATGCATATACATGATGGCATATGCGGCATCTATTCATATGCTCTAACCTTGAGTA
EXP-Zm.UbqM1:1:5    TACTGATGCATATACATGATGGCATATGCGGCATCTATTCATATGCTCTAACCTTGAGTA
EXP-Zm.UbqM1:1:1    TACTGATGCATATAC---ATGGCATATGCAGCATCTATTCATATGCTCTAACCTTGAGTA
EXP-Zm.UbqM1:1:4    TACTGATGCATATACATGATGGCATATGCAGCATCTATTCATATGCTCTAACCTTGAGTA
                    ***************   ********** *******************************
```

FIG. 4d

```
EXP-Zm.UbqM1:1:2    CCTATCTATTATAATAAACAAGTATGTTTTATAATTATTTTGATCTTGATATACTTGGAT
EXP-Zm.UbqM1:1:5    CCTATCTATTATAATAAACAAGTATGTTTTATAATTATTTTGATCTTGATATACTTGGAT
EXP-Zm.UbqM1:1:1    CCTATCTATTATAATAAACAAGTATGTTTTATAATTATTTTGATCTTGATATACTTGGAT
EXP-Zm.UbqM1:1:4    CCTATCTATTATAATAAACAAGTATGTTTTATAATTATTTTGATCTTGATATACTTGGAT
                    ************************************************************

EXP-Zm.UbqM1:1:2    GATGGCATATGCAGCAGCTATATGTGGA-TTTTTTAGCCCTGCCTTCATACGCTATTTAT
EXP-Zm.UbqM1:1:5    GATGGCATATGCAGCAGCTATATGTGGA-TTTTTTAGCCCTGCCTTCATACGCTATTTAT
EXP-Zm.UbqM1:1:1    GATGGCATATGCAGCAGCTATATGTGGATTTTTTTAGCCCTGCCTTCATACGCTATTTAT
EXP-Zm.UbqM1:1:4    GATGGCATATGCAGCAGCTATATGTGGATTTTTTTAGCCCTGCCTTCATACGCTATTTAT
                    **************************** *******************************

EXP-Zm.UbqM1:1:2    TTGCTTGGTACTGTTTCTTTTGTCCGATGCTCACCCTGTTGTTGGGTGATACTTCTGCAG
EXP-Zm.UbqM1:1:5    TTGCTTGGTACTGTTTCTTTTGTCCGATGCTCACCCTGTTGTTGGTGATACTTCTGCAG
EXP-Zm.UbqM1:1:1    TTGCTTGGTACTGTTTCTTTTGT-CGATGCTCACCCTGTTGTTGGTGATACTTCTGCAG
EXP-Zm.UbqM1:1:4    TTGCTTGGTACTGTTTCTTTTGT-CGATGCTCACCCTGTTGTTGGTGATACTTCTGCAG
                    *********************** ******************** ***************
```

FIG. 4e

```
P-Sb.Ubq6-1:1:2    ------------------------------------------------------------
P-Sb.Ubq6-1:1:1    CATTAAAAGTCATTATGTGCATGCGTCGTAACTAACATGGATATGTTGCTGCACTATCTC

P-Sb.Ubq6-1:1:2    ----CACTAGCTGCGCATGATAAAGCCACAAGCCAAAATTAATTATTATGGGTGAGAATA
P-Sb.Ubq6-1:1:1    CTCGCACTAGCTGCGCATGATAAAGCCACAAGCCAAAATTAATTATTATGGGTGAGAATA
                       ********************************************************

P-Sb.Ubq6-1:1:2    AATACGTACCAGCACCGGCCATAGAAAAAGTACATTATTAAAGGTCTAATTTGGAAACAG
P-Sb.Ubq6-1:1:1    AATACGTACCAGCACCGGCCATAGAAAAAGTACATTATTAAAGGTCTAATTTGGAAACAG
                   ************************************************************

P-Sb.Ubq6-1:1:2    TCTGAAAACGACGTGCGCTGCAGAGGTAAATGTAATTTTCGGCACTAAAACCATTATCAA
P-Sb.Ubq6-1:1:1    TCTGAAAACGACGTGCGCTGCAGAGGTAAATGTAATTTTCGGCACTAAAACCATTATCAA
                   ************************************************************

P-Sb.Ubq6-1:1:2    CTAATTCATTCAATAACAGTTATTTAGAAAATGTATAGCTCGCTCTAAAAAAACAGTTTA
P-Sb.Ubq6-1:1:1    CTAATTCATTCAATAACAGTTATTTAGAAAATGTATAGCTCGCTCTAAAAAAACAGTTTA
                   ************************************************************

P-Sb.Ubq6-1:1:2    GAAAACAGTCAAAATAATTCGACCAACAAACAGTTAATAAGGTTCATTAAATATATAAT
P-Sb.Ubq6-1:1:1    GAAAACAGTCAAAATAATTCGACCAACAAACAGTTAATAAGGTTCATTAAATATATAAT
                   ************************************************************

P-Sb.Ubq6-1:1:2    GCACGGTGCTATTTGATCTTTTAAAGGAAAAAGAGGAATAGTCGTGGGCGCCAGGCGGGA
P-Sb.Ubq6-1:1:1    GCACGGTGCTATTTGATCTTTTAAAGGAAAAAGAGGAATAGTCGTGGGCGCCAGGCGGGA
                   ************************************************************

P-Sb.Ubq6-1:1:2    ATTGGGGCGCGGGAGTCTGCCGGACGACGCGTTCCGTCCGAACGGCCGGACCCGACGAGG
P-Sb.Ubq6-1:1:1    ATTGGGGCGCGGGAGTCTGCCGGACGACGCGTTCCGTCCGAACGGCCGGACCCGACGAGG
                   ************************************************************

P-Sb.Ubq6-1:1:2    CCCCCCCGCCGCCCCACGTCGCAGAACCGTCCGTGGGTGGTAATCTGGCCGGGTACACCA
P-Sb.Ubq6-1:1:1    CCCCCCCGCCGCCCCACGTCGCAGAACCGTCCGTGGGTGGTAATCTGGCCGGGTACACCA
                   ************************************************************

P-Sb.Ubq6-1:1:2    GCCGTCCCCTTGGGCGGCCTCACAGCACTGGGCTCACACGTGAGTTTTGTTCTGGGCTTC
P-Sb.Ubq6-1:1:1    GCCGTCCCCTTGGGCGGCCTCACAGCACTGGGCTCACACGTGAGTTTTGTTCTGGGCTTC
                   ************************************************************

P-Sb.Ubq6-1:1:2    GGATCGCACCATATGGGCCTCGGCATCAGAAAGACGGGGCCCGTCTGGGATAGAAGAGAC
P-Sb.Ubq6-1:1:1    GGATCGCACCATATGGGCCTCGGCATCAGAAAGACGGGGCCCGTCTGGGATAGAAGAGAC
                   ************************************************************
```

FIG. 5a

```
P-Sb.Ubq6-1:1:2    AGGAACCTCCTCGTGGATTCCAGAAGCCAGCCACGAGCGACCACCGACGCGGAGGATACT
P-Sb.Ubq6-1:1:1    AGGAACCTCCTCGTGGATTCCAGAAGCCAGCCACGAGCGACCACCGACGCGGAGGATACT
                   ************************************************************

P-Sb.Ubq6-1:1:2    CGTCGTCCAAGTCCAACACGGCGGGCGGGCGGGCGGACGCGTGGGCTGGGCTAACTGCCT
P-Sb.Ubq6-1:1:1    CGTCGTCCAAGTCCAACACGGCGGGCGGGCGGGCGGACGCGTGGGCTGGGCTAACTGCCT
                   ************************************************************

P-Sb.Ubq6-1:1:2    AACCTTAACCTCCAAGGCACGCCAAGGCCCGCTTCTCCCACCCGACATAAATATCCCCCC
P-Sb.Ubq6-1:1:1    AACCTTAACCTCCAAGGCACGCCAAGGCCCGCTTCTCCCACCCGACATAAATATCCCCCC
                   ************************************************************

P-Sb.Ubq6-1:1:2    ATCCAGGCAAGGCGC
P-Sb.Ubq6-1:1:1    ATCCAGGCAAGGCGC
                   ***************
```

FIG. 5b

```
P-SETit.Ubq1-1:1:4    ACTGCCGCGACACGCCTCACTGGCGGGAGGGCTCCGAGCGCTCTCTCCCCGGCGGCCGGC
P-SETit.Ubq1-1:1:3    ------------------------------------------------------------
P-SETit.Ubq1-1:1:1    ACTGCCGCGACACGCCTCACTGGCGGGAGGGCTCCGAGCGCTCTCTCCCCGGCGGCCGGC
P-SETit.Ubq1-1:1:2    ------------------------------------------------------------

P-SETit.Ubq1-1:1:4    GGAGCAGCGATCTGGATTGGAGAGAATAGAGGAAAGAGAGGGAAAAGGAGAGAGATAGCG
P-SETit.Ubq1-1:1:3    ------------------------------------------------------------
P-SETit.Ubq1-1:1:1    GGAGCAGCGATCTGGATTGGAGAGAATAGAGGAAAGAGAGGGAAAAGGAGAGAGATAGCG
P-SETit.Ubq1-1:1:2    ------------------------------------------------------------

P-SETit.Ubq1-1:1:4    CAAAGAGCTGAAAAGATAAGGTTGTGCGGGCTGTGGTGATTAGAGGACCACTAATCCCTC
P-SETit.Ubq1-1:1:3    ------------------------------------------------------------
P-SETit.Ubq1-1:1:1    CAAAGAGCTGAAAAGATAAGGTTGTGCGGGCTGTGGTGATTAGAGGACCACTAATCCCTC
P-SETit.Ubq1-1:1:2    ------------------------------------------------------------

P-SETit.Ubq1-1:1:4    CATCTCCTAATGACGCGGTGCCCAAGACCAGTGCCGCGGCACACCAGCGTCTAAGTGAAC
P-SETit.Ubq1-1:1:3    ------------------------------------------------------------
P-SETit.Ubq1-1:1:1    CATCTCCTAATGACGCGGTGCCCAAGACCAGTGCCGCGGCACACCAGCGTCTAAGTGAAC
P-SETit.Ubq1-1:1:2    ------------------------------------------------------------

P-SETit.Ubq1-1:1:4    TTCCGCTAACCTTCCGGTCATTGCGCCTGAAAGATGTCATGTGGCGAGGCCCCCCTCTCA
P-SETit.Ubq1-1:1:3    ------------------------------------------------------------
P-SETit.Ubq1-1:1:1    TTCCGCTAACCTTCCGGTCATTGCGCCTGAAAGATGTCATGTGGCGAGGCCCCCCTCTCA
P-SETit.Ubq1-1:1:2    ------------------------------------------------------------

P-SETit.Ubq1-1:1:4    GTAGATTGCCAACTGCCTACCGTGCCACTCTTCCATGCATGATTGCTCCCGTCTATCCCG
P-SETit.Ubq1-1:1:3    ------------------------------------------------------------
P-SETit.Ubq1-1:1:1    GTAGATTGCCAACTGCCTACCGTGCCACTCTTCCATGCATGATTGCTCCCGTCTATCCCG
P-SETit.Ubq1-1:1:2    ------------------------------------------------------------

P-SETit.Ubq1-1:1:4    TTTCTCACAACAGATAGACAACAGTAAGCATCACTAAAGCAAGCATGTGTAGAACCTTAA
P-SETit.Ubq1-1:1:3    ------------------------------------------------------------
P-SETit.Ubq1-1:1:1    TTTCTCACAACAGATAGACAACAGTAAGCATCACTAAAGCAAGCATGTGTAGAACCTTAA
P-SETit.Ubq1-1:1:2    ------------------------------------------------------------

P-SETit.Ubq1-1:1:4    AAAAAGGCTTATACTACCAGTATACTATCAACCAGCATGCCGTTTTTGAAGTATCCAGGA
P-SETit.Ubq1-1:1:3    ------------------------------------------------------------
P-SETit.Ubq1-1:1:1    AAAAAGGCTTATACTACCAGTATACTATCAACCAGCATGCCGTTTTTGAAGTATCCAGGA
P-SETit.Ubq1-1:1:2    ---------------------------------------GCCGTTTTTGAAGTATCCAGGA

P-SETit.Ubq1-1:1:4    TTAGAAGCTTCTACTGCGCTTTTATATTATAGCTGTGGACCCGTGGTAACCTTTCTCTTT
P-SETit.Ubq1-1:1:3    ------------------------------------------------------------
P-SETit.Ubq1-1:1:1    TTAGAAGCTTCTACTGCGCTTTTATATTATAGCTGTGGACCTGTGGTAACCTTTCTCTTT
P-SETit.Ubq1-1:1:2    TTAGAAGCTTCTACTGCGCTTTTATATTATAGCTGTGGACCTGTGGTAACCTTTCTCTTT

P-SETit.Ubq1-1:1:4    TGGCGCTTGCTTAATCTCGGCCGTGCTGGTCCATGCTTAGGCACTAGGCAGAGATAGAGC
P-SETit.Ubq1-1:1:3    ------------------------------------------------------------
P-SETit.Ubq1-1:1:1    TGGCGCTTGCTTAATCTCGGCCGTGCTGGTCCATGCTTAGGCACTAGGCAGAGATAGAGC
P-SETit.Ubq1-1:1:2    TGGCGCTTGCTTAATCTCGGCCGTGCTGGTCCATGCTTAGGCACTAGGCAGAGATAGAGC
```

FIG. 6a

```
P-SETit.Ubq1-1:1:4    CGGGGGTGAATGGGGCTAAAGCTCAGCTGCTCGAGGGGCCGTGGGCTGGTTTCCACTAGC
P-SETit.Ubq1-1:1:3    ------------------------------------------------------------
P-SETit.Ubq1-1:1:1    CGGGGGTGAATGGGGCTAAAGCTCAGCTGCTCGAGGGGCCGTGGGCTGGTTTCCACTAGC
P-SETit.Ubq1-1:1:2    CGGGGGTGAATGGGGCTAAAGCTCAGCTGCTCGAGGGGCCGTGGGCTGGTTTCCACTAGC

P-SETit.Ubq1-1:1:4    CTACAGCTGTGCCACGTGCGGCCGCGCAAGCCGAAGCAAGCACGCTGAGCCGTTGGACAG
P-SETit.Ubq1-1:1:3    ------------------------------------------------------------
P-SETit.Ubq1-1:1:1    CTACAGCTGTGCCACGTGCGGCCGCGCAAGCCGAAGCAAGCACGCTGAGCCGTTGGACAG
P-SETit.Ubq1-1:1:2    CTACAGCTGTGCCACGTGCGGCCGCGCAAGCCGAAGCAAGCACGCTGAGCCGTTGGACAG

P-SETit.Ubq1-1:1:4    CTTGTCATAATGCCATTACGTGGATTACACGTAACTGGCCCTGTAACTACTCGTTCGGCC
P-SETit.Ubq1-1:1:3    ------------------------------------------------------------
P-SETit.Ubq1-1:1:1    CTTGTCATAATGCCATTACGTGGATTACACGTAACTGGCCCTGTAACTACTCGTTCGGCC
P-SETit.Ubq1-1:1:2    CTTGTCATAATGCCATTACGTGGATTACACGTAACTGGCCCTGTAACTACTCGTTCGGCC

P-SETit.Ubq1-1:1:4    ATCATCAAACGACGACGTCCGCTAGGCGACGACACGGGTAATGCACGCAGCCACCCAGGC
P-SETit.Ubq1-1:1:3    --------------------------------CACGGGTAATGCACGCAGCCACCCAGGC
P-SETit.Ubq1-1:1:1    ATCATCAAACGACGACGTCCGCTAGGCGACGACACGGGTAATGCACGCAGCCACCCAGGC
P-SETit.Ubq1-1:1:2    ATCATCAAACGACGACGTCCGCTAGGCGACGACACGGGTAATGCACGCAGCCACCCAGGC
                                                      ****************************

P-SETit.Ubq1-1:1:4    GCGCGCGCTAGCGGAGCACGGTCAGGTGACACGGGCGTCGTGACGCTTCCGAGTTGAAGG
P-SETit.Ubq1-1:1:3    GCGCGCGCTAGCGGAGCACGGTCAGGTGACACGGGCGTCGTGACGCTTCCGAGTTGAAGG
P-SETit.Ubq1-1:1:1    GCGCGCGCTAGCGGAGCACGGTCAGGTGACACGGGCGTCGTGACGCTTCCGAGTTGAAGG
P-SETit.Ubq1-1:1:2    GCGCGCGCTAGCGGAGCACGGTCAGGTGACACGGGCGTCGTGACGCTTCCGAGTTGAAGG
                      ************************************************************

P-SETit.Ubq1-1:1:4    GGTTAACGCCAGAAACAGTGTTTGGCCAGGGTATGAACATAACAAAAAATATTCACACGA
P-SETit.Ubq1-1:1:3    GGTTAACGCCAGAAACAGTGTTTGGCCAGGGTATGAACATAACAAAAAATATTCACACGA
P-SETit.Ubq1-1:1:1    GGTTAACGCCAGAAACAGTGTTTGGCCAGGGTATGAACATAACAAAAAATATTCACACGA
P-SETit.Ubq1-1:1:2    GGTTAACGCCAGAAACAGTGTTTGGCCAGGGTATGAACATAACAAAAAATATTCACACGA
                      ************************************************************

P-SETit.Ubq1-1:1:4    AAGAATGGAAGTATGGAGCTGCTACTGTGTAAATGCCAAGCAGGAAACTCACGCCCGCTA
P-SETit.Ubq1-1:1:3    AAGAATGGAAGTATGGAGCTGCTACTGTGTAAATGCCAAGCAGGAAACTCACGCCCGCTA
P-SETit.Ubq1-1:1:1    AAGAATGGAAGTATGGAGCTGCTACTGTGTAAATGCCAAGCAGGAAACTCACGCCCGCTA
P-SETit.Ubq1-1:1:2    AAGAATGGAAGTATGGAGCTGCTACTGTGTAAATGCCAAGCAGGAAACTCACGCCCGCTA
                      ************************************************************

P-SETit.Ubq1-1:1:4    ACATCCAACGGCCAACAGCTCGACGTGCCGGTCAGCAGAGCATCGGAACACTGGTGATTG
P-SETit.Ubq1-1:1:3    ACATCCAACGGCCAACAGCTCGACGTGCCGGTCAGCAGAGCATCGGAACACTGGTGATTG
P-SETit.Ubq1-1:1:1    ACATCCAACGGCCAACAGCTCGACGTGCCGGTCAGCAGAGCATCGGAACACTGGTGATTG
P-SETit.Ubq1-1:1:2    ACATCCAACGGCCAACAGCTCGACGTGCCGGTCAGCAGAGCATCGGAACACTGGTGATTG
                      ************************************************************

P-SETit.Ubq1-1:1:4    GTGGAGCCGGCAGTATGCGCCCCAGCACGGCCGAGGTGGTGGTGGCCCGTGGCCCTGCTG
P-SETit.Ubq1-1:1:3    GTGGAGCCGGCAGTATGCGCCCCAGCACGGCCGAGGTGGTGGTGGCCCGTGGCCCTGCTG
P-SETit.Ubq1-1:1:1    GTGGAGCCGGCAGTATGCGCCCCAGCACGGCCGAGGTGGTGGTGGCCCGTGGCCCTGCTG
P-SETit.Ubq1-1:1:2    GTGGAGCCGGCAGTATGCGCCCCAGCACGGCCGAGGTGGTGGTGGCCCGTGGCCCTGCTG
                      ************************************************************
```

FIG. 6b

```
P-SETit.Ubq1-1:1:4    TCTGCGCGGCTCGGGACAACTTGAAACTGGGCCACCGCCTCGTCGCAACTCGCAACCCGT
P-SETit.Ubq1-1:1:3    TCTGCGCGGCTCGGGACAACTTGAAACTGGGCCACCGCCTCGTCGCAACTCGCAACCCGT
P-SETit.Ubq1-1:1:1    TCTGCGCGGCTCGGGACAACTTGAAACTGGGCCACCGCCTCGTCGCAACTCGCAACCCGT
P-SETit.Ubq1-1:1:2    TCTGCGCGGCTCGGGACAACTTGAAACTGGGCCACCGCCTCGTCGCAACTCGCAACCCGT
                      ************************************************************

P-SETit.Ubq1-1:1:4    TGGCGGAAGAAAGGAATGGCTCGTAGGGGCCCGGGTAGAATCGAAGAATGTTGCGCTGGG
P-SETit.Ubq1-1:1:3    TGGCGGAAGAAAGGAATGGCTCGTAGGGGCCCGGGTAGAATCGAAGAATGTTGCGCTGGG
P-SETit.Ubq1-1:1:1    TGGCGGAAGAAAGGAATGGCTCGTAGGGGCCCGGGTAGAATCGAAGAATGTTGCGCTGGG
P-SETit.Ubq1-1:1:2    TGGCGGAAGAAAGGAATGGCTCGTAGGGGCCCGGGTAGAATCGAAGAATGTTGCGCTGGG
                      ************************************************************

P-SETit.Ubq1-1:1:4    CTTCGATTCACATAACATGGGCCTGAAGCTCTAAAACGACGGCCCGGTCGCCGCGCGATG
P-SETit.Ubq1-1:1:3    CTTCGATTCACATAACATGGGCCTGAAGCTCTAAAACGACGGCCCGGTCGCCGCGCGATG
P-SETit.Ubq1-1:1:1    CTTCGATTCACATAACATGGGCCTGAAGCTCTAAAACGACGGCCCGGTCGCCGCGCGATG
P-SETit.Ubq1-1:1:2    CTTCGATTCACATAACATGGGCCTGAAGCTCTAAAACGACGGCCCGGTCGCCGCGCGATG
                      ************************************************************

P-SETit.Ubq1-1:1:4    GAAAGAGACCGGATCCTCCTCGTGAATTCTGGAAGGCCACACGAGAGCGACCCACCACCG
P-SETit.Ubq1-1:1:3    GAAAGAGACCGGATCCTCCTCGTGAATTCTGGAAGGCCACACGAGAGCGACCCACCACCG
P-SETit.Ubq1-1:1:1    GAAAGAGACCGGATCCTCCTCGTGAATTCTGGAAGGCCACACGAGAGCGACCCACCACCG
P-SETit.Ubq1-1:1:2    GAAAGAGACCGGATCCTCCTCGTGAATTCTGGAAGGCCACACGAGAGCGACCCACCACCG
                      ************************************************************

P-SETit.Ubq1-1:1:4    ACGCGGAGGAGTCGTGCGTGGTCCAACACGGCCGGCGGGCTGGGCTGCGACCTTAACCAG
P-SETit.Ubq1-1:1:3    ACGCGGAGGAGTCGTGCGTGGTCCAACACGGCCGGCGGGCTGGGCTGCGACCTTAACCAG
P-SETit.Ubq1-1:1:1    ACGCGGAGGAGTCGTGCGTGGTCCAACACGGCCGGCGGGCTGGGCTGCGACCTTAACCAG
P-SETit.Ubq1-1:1:2    ACGCGGAGGAGTCGTGCGTGGTCCAACACGGCCGGCGGGCTGGGCTGCGACCTTAACCAG
                      ************************************************************

P-SETit.Ubq1-1:1:4    CAAGGCACGCCACGACCCGCCCCGCCCTCGAGGCATAAATACCCTCCCATCC
P-SETit.Ubq1-1:1:3    CAAGGCACGCCACGACCCGCCCCGCCCTCGAGGCATAAATACCCTCCCATCC
P-SETit.Ubq1-1:1:1    CAAGGCACGCCACGACCCGCCCCGCCCTCGAGGCATAAATACCCTCCCATCC
P-SETit.Ubq1-1:1:2    CAAGGCACGCCACGACCCGCCCCGCCCTCGAGGCATAAATACCCTCCCATCC
                      ****************************************************
```

FIG. 6c

```
E-Cl.Ubq1-1:1:1    AGCAGACTCGCATTATCGATGGAGCTCTACCAAACTGGCCCTAGGCATTAACCTACCATG
P-Cl.Ubq1-1:1:1    AGCAGACTCGCATTATCGATGGAGCTCTACCAAACTGGCCCTAGGCATTAACCTACCATG
P-Cl.Ubq1-1:1:3    ------------------------------------------------------------
P-Cl.Ubq1-1:1:4    ------------------------------------------------------------
P-Cl.Ubq1-1:1:5    ------------------------------------------------------------

E-Cl.Ubq1-1:1:1    GATCACATCGTAAAAAAAAAACCCTACCATGGATCCTATCTGTTTTCTTTTTGCCCTGAA
P-Cl.Ubq1-1:1:1    GATCACATCGTAAAAAAAAAACCCTACCATGGATCCTATCTGTTTTCTTTTTGCCCTGAA
P-Cl.Ubq1-1:1:3    ------------------------------------------------------------
P-Cl.Ubq1-1:1:4    ----------------------------------CTATCTGTTTTCTTTTTGCCCTGAA
P-Cl.Ubq1-1:1:5    ------------------------------------------------------------

E-Cl.Ubq1-1:1:1    AGAGTGAAGTCATCATCATATTTACCATGGCGCGCGTAGGAGCGCTTCGTCGAAGACCCA
P-Cl.Ubq1-1:1:1    AGAGTGAAGTCATCATCATATTTACCATGGCGCGCGTAGGAGCGCTTCGTCGAAGACCCA
P-Cl.Ubq1-1:1:3    ------------------------------------------------------------
P-Cl.Ubq1-1:1:4    AGAGTGAAGTCATCATCATATTTACCATGGCGCGCGTAGGAGCGCTTCGTCGAAGACCCA
P-Cl.Ubq1-1:1:5    ------------------------------------------------------------

E-Cl.Ubq1-1:1:1    TAGGGGGGCGGTACTCGCACCGTGGTTGTTTCCTGTTATGTAATATCGGATGGGGGAGCA
P-Cl.Ubq1-1:1:1    TAGGGGGGCGGTACTCGCACCGTGGTTGTTTCCTGTTATGTAATATCGGATGGGGGAGCA
P-Cl.Ubq1-1:1:3    ------------------------------------------------------------
P-Cl.Ubq1-1:1:4    TAGGGGGGCGGTACTCGCACCGTGGTTGTTTCCTGTTATGTAATATCGGATGGGGGAGCA
P-Cl.Ubq1-1:1:5    ------------------------------------------------------------

E-Cl.Ubq1-1:1:1    GTCGGCTAGGTTGGTCCCATCGGTACTGGTCGTCCCCTAGTGCGCTAGATGCGCGATGTT
P-Cl.Ubq1-1:1:1    GTCGGCTAGGTTGGTCCCATCGGTACTGGTCGTCCCCTAGTGCGCTAGATGCGCGATGTT
P-Cl.Ubq1-1:1:3    ------------------------------------------------------------
P-Cl.Ubq1-1:1:4    GTCGGCTAGGTTGGTCCCATCGGTACTGGTCGTCCCCTAGTGCGCTAGATGCGCGATGTT
P-Cl.Ubq1-1:1:5    ------------------------------------------------------------

E-Cl.Ubq1-1:1:1    TGTCCTCAAAAACTCTTTTCTTCTTAATAACAATCATACGCAAATTTTTTGCGTATTCGA
P-Cl.Ubq1-1:1:1    TGTCCTCAAAAACTCTTTTCTTCTTAATAACAATCATACGCAAATTTTTTGCGTATTCGA
P-Cl.Ubq1-1:1:3    ------------------------------------------------------------
P-Cl.Ubq1-1:1:4    TGTCCTCAAAAACTCTTTTCTTCTTAATAACAATCATACGCAAATTTTTTGCGTATTCGA
P-Cl.Ubq1-1:1:5    ------------------------------------------------------------

E-Cl.Ubq1-1:1:1    GAAAAAAGAAGATTCTATCTGTTTTTTTTTGAAATGGCTCCAATTTATAGGAGGAGCC
P-Cl.Ubq1-1:1:1    GAAAAAAGAAGATTCTATCTGTTTTTTTTTGAAATGGCTCCAATTTATAGGAGGAGCC
P-Cl.Ubq1-1:1:3    ------------------------------------------------------------
P-Cl.Ubq1-1:1:4    GAAAAAAGAAGATTCTATCTGTTTTTTTTTGAAATGGCTCCAATTTATAGGAGGAGCC
P-Cl.Ubq1-1:1:5    ------------------------------------------------------------

E-Cl.Ubq1-1:1:1    CGTTTAACGGCGTCGACAAATCTAACGGACACCAACCAGCGAATGAGCGAACCCACCAGC
P-Cl.Ubq1-1:1:1    CGTTTAACGGCGTCGACAAATCTAACGGACACCAACCAGCGAATGAGCGAACCCACCAGC
P-Cl.Ubq1-1:1:3    ----------------CAAATCTAACGGACACCAACCAGCGAATGAGCGAACCCACCAGC
P-Cl.Ubq1-1:1:4    CGTTTAACGGCGTCGACAAATCTAACGGACACCAACCAGCGAATGAGCGAACCCACCAGC
P-Cl.Ubq1-1:1:5    ------------------------------------------------------------
```

FIG. 7a

```
E-Cl.Ubq1-1:1:1    GCCAAGCTAGCCAAGCGAAGCAGACGGCCGAGACGCTGACACCCTTGCCTTGGCGCGGCA
P-Cl.Ubq1-1:1:1    GCCAAGCTAGCCAAGCGAAGCAGACGGCCGAGACGCTGACACCCTTGCCTTGGCGCGGCA
P-Cl.Ubq1-1:1:3    GCCAAGCTAGCCAAGCGAAGCAGACGGCCGAGACGCTGACACCCTTGCCTTGGCGCGGCA
P-Cl.Ubq1-1:1:4    GCCAAGCTAGCCAAGCGAAGCAGACGGCCGAGACGCTGACACCCTTGCCTTGGCGCGGCA
P-Cl.Ubq1-1:1:5    ------------------------------------------------------------

E-Cl.Ubq1-1:1:1    TCTCCGTCGCTGGCTCGCTGGCTCTGGCCCCTTCGCGAGAGTTCCGGTCCACCTCCACCT
P-Cl.Ubq1-1:1:1    TCTCCGTCGCTGGCTCGCTGGCTCTGGCCCCTTCGCGAGAGTTCCGGTCCACCTCCACCT
P-Cl.Ubq1-1:1:3    TCTCCGTCGCTGGCTCGCTGGCTCTGGCCCCTTCGCGAGAGTTCCGGTCCACCTCCACCT
P-Cl.Ubq1-1:1:4    TCTCCGTCGCTGGCTCGCTGGCTCTGGCCCCTTCGCGAGAGTTCCGGTCCACCTCCACCT
P-Cl.Ubq1-1:1:5    ------------------------------------------------------------

E-Cl.Ubq1-1:1:1    GTGTCGGTTTCCAACTCCGTTCCGCCTTCGCGTGGGACTTGTTCCGTTCATCCGTTGGCG
P-Cl.Ubq1-1:1:1    GTGTCGGTTTCCAACTCCGTTCCGCCTTCGCGTGGGACTTGTTCCGTTCATCCGTTGGCG
P-Cl.Ubq1-1:1:3    GTGTCGGTTTCCAACTCCGTTCCGCCTTCGCGTGGGACTTGTTCCGTTCATCCGTTGGCG
P-Cl.Ubq1-1:1:4    GTGTCGGTTTCCAACTCCGTTCCGCCTTCGCGTGGGACTTGTTCCGTTCATCCGTTGGCG
P-Cl.Ubq1-1:1:5    ------------------------------------------------------------

E-Cl.Ubq1-1:1:1    GCATCCGGAAATTGCGTGGCGTAGAGCACGGGGCCCTCCTCTCACACGGCACGGAACCGT
P-Cl.Ubq1-1:1:1    GCATCCGGAAATTGCGTGGCGTAGAGCACGGGGCCCTCCTCTCACACGGCACGGAACCGT
P-Cl.Ubq1-1:1:3    GCATCCGGAAATTGCGTGGCGTAGAGCACGGGGCCCTCCTCTCACACGGCACGGAACCGT
P-Cl.Ubq1-1:1:4    GCATCCGGAAATTGCGTGGCGTAGAGCACGGGGCCCTCCTCTCACACGGCACGGAACCGT
P-Cl.Ubq1-1:1:5    ------------------------------------------------------------

E-Cl.Ubq1-1:1:1    CACGAGCTCACGGCACCGGCAGCACGGCGGGGATTCCTTCCCCACCACCGCTCCTTCCCT
P-Cl.Ubq1-1:1:1    CACGAGCTCACGGCACCGGCAGCACGGCGGGGATTCCTTCCCCACCACCGCTCCTTCCCT
P-Cl.Ubq1-1:1:3    CACGAGCTCACGGCACCGGCAGCACGGCGGGGATTCCTTCCCCACCACCGCTCCTTCCCT
P-Cl.Ubq1-1:1:4    CACGAGCTCACGGCACCGGCAGCACGGCGGGGATTCCTTCCCCACCACCGCTCCTTCCCT
P-Cl.Ubq1-1:1:5    ------------------------------------------------------------

E-Cl.Ubq1-1:1:1    TTCCCTTCCTCGCCCGCC------------------------------------------
P-Cl.Ubq1-1:1:1    TTCCCTTCCTCGCCCGCCATCATAAATAGCCACCCCTCCCAGCTTCCTTCGCCACAT
P-Cl.Ubq1-1:1:3    TTCCCTTCCTCGCCCGCCATCATAAATAGCCACCCCTCCCAGCTTCCTTCGCCACAT
P-Cl.Ubq1-1:1:4    TTCCCTTCCTCGCCCGCCATCATAAATAGCCACCCCTCCCAGCTTCCTTCGCCACAT
P-Cl.Ubq1-1:1:5    ---CCTTCCTCGCCCGCCATCATAAATAGCCACCCCTCCCAGCTTCCTTCGCCACAT
                      **************
```

FIG. 7b

Transgene Cassette Configuration 1
| Promoter or chimeric promoter [A] | Leader [B] | Intron [C] | Coding Region [D] | 3' UTR [E] |
Transgene Cassette Configuration 2
| Promoter or chimeric promoter [F] | Leader [G] | Intron [H] | Leader [I] | Coding Region [J] | 3' UTR [K] |
Transgene Cassette Configuration 3
| Promoter or chimeric promoter [L] | Leader [M] | Coding Region [N] | Intron [O] | Coding Region [P] | 3' UTR [Q] |
FIG. 8

PLANT REGULATORY ELEMENTS AND USES THEREOF

REFERENCE TO RELATED APPLICATIONS

This application is a divisional of U.S. patent application Ser. No. 16/900,717, filed Jun. 12, 2020, which is a divisional of U.S. patent application Ser. No. 15/798,319, filed Oct. 30, 2017, now issued as U.S. Pat. No. 10,752,910, which is a divisional of U.S. patent application Ser. No. 14/686,602, filed Apr. 14, 2015, now issued as U.S. Pat. No. 9,834,777, which is a divisional of U.S. patent application Ser. No. 13/428,994, filed Mar. 23, 2012, now issued as U.S. Pat. No. 9,062,316, which claims the benefit of U.S. Provisional Application No. 61/467,875, filed Mar. 25, 2011, each of which is herein incorporated by reference in its entirety.

INCORPORATION OF SEQUENCE LISTING

The sequence listing that is contained in the file named "MONS282USD7_ST.26.xml", which is 425 KB (as measured in Microsoft Windows®) and was created on Nov. 8, 2022, is filed herewith by electronic submission and is incorporated by reference herein.

FIELD OF THE INVENTION

The invention relates to the field of plant molecular biology and plant genetic engineering, and DNA molecules useful for modulating gene expression in plants.

BACKGROUND

Regulatory elements are genetic elements that regulate gene activity by modulating the transcription of an operably linked transcribable polynucleotide molecule. Such elements include promoters, leaders, introns, and 3' untranslated regions and are useful in the field of plant molecular biology and plant genetic engineering.

SUMMARY OF THE INVENTION

The present invention provides novel gene regulatory elements for use in plants. The present invention also provides DNA constructs comprising the regulatory elements. The present invention also provides transgenic plant cells, plants, and seeds comprising the regulatory elements. The sequences may be provided operably linked to a transcribable polynucleotide molecule. In one embodiment, the transcribable polynucleotide molecule may be heterologous with respect to a regulatory sequence provided herein. A regulatory element sequence provided by the invention thus may, in particular embodiments, be defined as operably linked to a heterologous transcribable polynucleotide molecule. The present invention also provides methods of making and using the regulatory elements, the DNA constructs comprising the regulatory elements, and the transgenic plant cells, plants, and seeds comprising the regulatory elements operably linked to a transcribable polynucleotide molecule.

Thus, in one aspect, the present invention provides a DNA molecule comprising a DNA sequence selected from the group consisting of: a) a sequence with at least about 85 percent sequence identity to any of SEQ ID NOs: 1-158 and 180-183; b) a sequence comprising any of SEQ ID NOs: 1-158 and 180-183; and c) a fragment of any of SEQ ID NOs: 1-158 and 180-183, wherein the fragment has gene-regulatory activity; wherein the sequence is operably linked to a heterologous transcribable polynucleotide molecule. In specific embodiments, the DNA molecule comprises at least about 90 percent, at least about 95 percent, at least about 98 percent, or at least about 99 percent sequence identity to the DNA sequence of any of SEQ ID NOs: 1-158 and 180-183. In certain embodiments of the DNA molecule, the DNA sequence comprises a regulatory element. In some embodiments the regulatory element comprises a promoter. In particular embodiments, the heterologous transcribable polynucleotide molecule comprises a gene of agronomic interest, such as a gene capable of providing herbicide resistance in plants, or a gene capable of providing plant pest resistance in plants.

The invention also provides a transgenic plant cell comprising a heterologous DNA construct provided by the invention, including a sequence of any of SEQ ID NOs: 1-158 and 180-183, or a fragment or variant thereof, wherein said sequence is operably linked to a heterologous transcribable polynucleotide molecule. In certain embodiments, the transgenic plant cell is a monocotyledonous plant cell. In other embodiments, the transgenic plant cell is a dicotyledonous plant cell.

Further provided by the invention is a transgenic plant, or part thereof, comprising a DNA molecule as provided herein, including a DNA sequence selected from the group consisting of: a) a sequence with at least 85 percent sequence identity to any of SEQ ID NOs: 1-158 and 180-183; b) a sequence comprising any of SEQ ID NOs: 1-158 and 180-183; and c) a fragment of any of SEQ ID NOs: 1-158 and 180-183, wherein the fragment has gene-regulatory activity; wherein the sequence is operably linked to a heterologous transcribable polynucleotide molecule. In specific embodiments, the transgenic plant may be a progeny plant of any generation that comprises the DNA molecule, relative to a starting transgenic plant comprising the DNA molecule. Still further provided is a transgenic seed comprising a DNA molecule according to the invention.

In yet another aspect, the invention provides a method of producing a commodity product comprising obtaining a transgenic plant or part thereof according to the invention and producing the commodity product therefrom. In one embodiment, a commodity product of the invention is protein concentrate, protein isolate, grain, starch, seeds, meal, flour, biomass, or seed oil. In another aspect, the invention provides a commodity produced using the above method. For instance, in one embodiment the invention provides a commodity product comprising a DNA molecule as provided herein, including a DNA sequence selected from the group consisting of: a) a sequence with at least 85 percent sequence identity to any of SEQ ID NOs: 1-158 and 180-183; b) a sequence comprising any of SEQ ID NOs: 1-158 and 180-183; and c) a fragment of any of SEQ ID NOs: 1-158 and 180-183, wherein the fragment has gene-regulatory activity; wherein the sequence is operably linked to a heterologous transcribable polynucleotide molecule.

In still yet another aspect, the invention provides a method of expressing a transcribable polynucleotide molecule that comprises obtaining a transgenic plant according to the invention, such as a plant comprising a DNA molecule as described herein, and cultivating plant, wherein a transcribable polynucleotide in the DNA molecule is expressed.

Throughout this specification and the claims, unless the context requires otherwise, the word "comprise" and its variations, such as "comprises" and "comprising," will be understood to imply the inclusion of a stated composition, step, and/or value, or group thereof, but not the exclusion of any other composition, step, and/or value, or group thereof.

BRIEF DESCRIPTION OF THE FIGURES

FIGS. 1 *a*-1 *h* depict alignment of promoter size variants corresponding to promoter elements isolated from the grass species *Andropogon gerardii*. In particular, FIGS. 1*a*-1*h* show alignment of the 2603 bp promoter sequence P-ANDge.Ubq1-1:1:11 (SEQ ID NO: 2), found in the transcriptional regulatory expression element group EXP-ANDge.Ubq1:1:9 (SEQ ID NO: 1), with promoter sequences derived via deletion analysis of P-ANDge.Ubq1-1:1:11. Deletion, for instance of the 5' end of P-ANDge.Ubq1-1:1:11, produced the promoter P-ANDge.Ubq1-1:1:9 (SEQ ID NO: 6), a 2114 bp sequence which is found within EXP-ANDge.Ubq1:1:7 (SEQ ID NO: 5). Other promoter sequences in FIG. 1 include P-ANDge.Ubq1-1:1:10 (SEQ ID NO: 9), a 1644 bp sequence comprised within EXP-ANDge.Ubq1:1:8 (SEQ ID NO: 8); P-ANDge.Ubq1-1:1:12 (SEQ ID NO: 11), a 1472 bp sequence comprised within EXP-ANDge.Ubq1:1:10 (SEQ ID NO: 10); P-ANDge.Ubq1-1:1:8 (SEQ ID NO: 13), a 1114 bp sequence comprised within EXP-ANDge.Ubq1:1:6 (SEQ ID NO: 12); P-ANDge.Ubq1-1:1:13 (SEQ ID NO: 15), a 771 bp sequence comprised within EXP-ANDge.Ubq1:1:11 (SEQ ID NO: 14); and P-ANDge.Ubq1-1:1:14 (SEQ ID NO: 17), a 482 bp sequence comprised within EXP-ANDge.Ubq1:1:12 (SEQ ID NO: 16). Asterisks indicate bases which are identical between the aligned sequences.

FIGS. 2 *a*-2 *g* depict alignment of promoter variants isolated from the grass *Saccharum ravennae* (*Erianthus ravennae*). In particular, FIGS. 2*a*-2*g* show an alignment of the 2536 bp promoter sequence P-ERIra.Ubq1-1:1:10 (SEQ ID NO: 19) (found, for instance, within the transcriptional regulatory expression element group EXP-ERIra.Ubq1 (SEQ ID NO: 18)) with promoter sequences derived from deletion analysis of P-ERIra.Ubq1-1:1:10: a 2014 bp promoter sequence P-ERIra.Ubq1-1:1:9 (SEQ ID NO: 23); a 1525 bp promoter sequence P-ERIra.Ubq1-1:1:11 (SEQ ID NO: 26); a 1044 bp promoter sequence P-ERIra.Ubq1-1:1:8 (SEQ ID NO: 28); a 796 bp sequence P-ERIra.Ubq1-1:1:12 (SEQ ID NO: 30); and a 511 bp sequence P-ERIra.Ubq1-1:1:13 (SEQ ID NO: 32). Asterisks indicate bases which are identical between the aligned sequence.

FIGS. 3 *a*-3 *c* depict alignment of promoter size variants corresponding to promoter elements isolated from the grass species *Setaria viridis*. In particular, FIGS. 3*a*-3*c* show an alignment of a 1493 bp promoter sequence, P-Sv.Ubq1-1:1:1 (SEQ ID NO: 34) with promoters derived from deletion analysis of the 5' end of P-Sv.Ubq1-1:1:1: a 1035 bp sized promoter P-Sv.Ubq1-1:1:2 (SEQ ID NO: 38); and a 681 bp promoter sequence P-Sv.Ubq1-1:1:3 (SEQ ID NO: 40). Asterisks indicate bases which are identical between the aligned sequences.

FIGS. 4 *a*-4 *e* depict alignment of transcriptional regulatory expression element group variants derived from the grass *Zea mays* subsp. *mexicana*. In particular, FIGS. 4*a*-4*e* compare a 2005 bp transcriptional regulatory expression element group termed EXP-Zm.UbgM1:1:2 (SEQ ID NO: 49) with allelic variant EXP-Zm.UbgM1:1:5 (SEQ ID NO: 53), as well as with size variants EXP-Zm.UbgM1:1:1 (SEQ ID NO: 41), which is 1922 bps in length, and EXP-Zm.UbgM1:1:4 (SEQ ID NO: 45), which is 1971 bps in length. Asterisks indicate bases which are identical between the aligned sequences.

FIGS. 5 *a*-5 *b* depict alignment of promoter size variants isolated from the grass *Sorghum bicolor*. In particular, FIGS. 5 *a*-5 *b* shows alignment of the 791 bp sized promoter element, P-Sb.Ubg6-1:1:2 (SEQ ID NO: 60) comprised within the transcriptional regulatory expression element group EXP-Sb.Ubg6 (SEQ ID NO: 59), with 855 bp promoter element P-Sb.Ubg6-1:1:1 (SEQ ID NO: 64) comprised within EXP-Sb.Ubg6:1:1 (SEQ ID NO: 63). Asterisks indicate bases which are identical between the aligned sequences.

FIGS. 6 *a*-6 *c* depict alignment of promoter size variants corresponding to promoter elements isolated from the grass *Setaria italica*. In particular, FIGS. 6 *a*-6 *c* show an alignment of the 1492 bp promoter variant P-SETit. Ubq1-1:1:1 (SEQ ID NO: 70) with 1492 bp promoter variant P-SETit. Ubq1-1:1:4 (SEQ ID NO: 74), 1034 bp promoter element P-SETit. Ubq1-1:1:2 (SEQ ID NO: 76), and 680 bp promoter element P-SETit.Ubq1-1:1:3 (SEQ ID NO: 78). Asterisks indicate bases which are identical between the aligned sequences.

FIGS. 7*a*-7*b* depict alignment of promoter size variants and an enhancer element corresponding to promoter elements isolated from the grass species *Coix lachryma-jobi*. In particular, FIGS. 7*a* and 7*b* show an alignment of the 837 bp promoter variant, P-Cl.Ubq1-1:1:1 (SEQ ID NO: 80) found within transcriptional regulatory expression element group EXP-Cl.Ubq1:1:1 (SEQ ID NO: 79), with an enhancer fragment derived from P-Cl.Ubq1-1:1:1, termed E-Cl.Ubq1:1:1 (SEQ ID NO: 89) that is 798 bp in length, as well as with three 5' end deletion variants of P-Cl.Ubq1-1:1:1: a 742 bp element P-Cl.Ubq1-1:1:4 (SEQ ID NO: 84); a 401 bp element P-Cl.Ubq1-1:1:3 (SEQ ID NO: 86); and a 54 bp minimal promoter element P-Cl.Ubq1-1:1:5 (SEQ ID NO: 88). Asterisks indicate bases which are identical between the aligned sequences.

FIG. 8 depicts transgene cassette configurations of the present invention.

BRIEF DESCRIPTION OF THE SEQUENCES

SEQ ID NOS: 1, 5, 8, 10, 12, 14, 16, 18, 22, 25, 27, 29, 31, 33, 37, 39, 41, 45, 49, 53, 55, 59, 63, 65, 69, 73, 75, 77, 79, 83, 85, 87, 90, 93, 95, 97, 98, 99, 100, 102, 104, 106, 108, 110, 112, 114, 115, 116, 117, 119, 121, 123, 124, 125, 126, 128, 130, 132, 133, 134, 136, 137, 139, 141, 143, 145, 147, 149, 151, 153, 155, 157, 180, 181 and 183 are sequences of transcriptional regulatory expression element groups or EXP sequences comprising a promoter sequence operably linked 5' to a leader sequence which is operably linked 5' to an intron sequence.

SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135 are promoter sequences.

SEQ ID NOS: 3, 20, 35, 43, 47, 51, 57, 61, 67, 71 and 81 are leader sequences.

SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 are intron sequences.

SEQ ID NO: 89 is the sequence of an enhancer.

DETAILED DESCRIPTION OF THE INVENTION

The invention disclosed herein provides polynucleotide molecules having beneficial gene regulatory activity from plant species. The design, construction, and use of these polynucleotide molecules are provided by the invention. The nucleotide sequences of these polynucleotide molecules are provided among SEQ ID NOs: 1-158 and 180-183. These polynucleotide molecules are, for instance, capable of affecting the expression of an operably linked transcribable polynucleotide molecule in plant tissues, and therefore selectively regulating gene expression, or activity of an encoded gene product, in transgenic plants. The present invention also provides methods of modifying, producing, and using the same. The invention also provides compositions, transformed host cells, transgenic plants, and seeds containing the promoters and/or other disclosed nucleotide sequences, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term "DNA sequence" refers to the nucleotide sequence of a DNA molecule. The nomenclature used herein corresponds to that of by Title 37 of the United States Code of Federal Regulations § 1.822, and set forth in the tables in WIPO Standard ST.25 (1998), Appendix 2, Tables 1 and 3.

As used herein, the term "isolated DNA molecule" refers to a DNA molecule at least partially separated from other molecules normally associated with it in its native or natural state. In one embodiment, the term "isolated" refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods well known to those skilled in the art can be used to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

As used herein, the term "sequence identity" refers to the extent to which two optimally aligned polynucleotide sequences or two optimally aligned polypeptide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. As used herein, the term "reference sequence" refers to a sequence provided as the polynucleotide sequences of SEQ ID NOs: 1-158 and 180-183.

As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence. Thus, one embodiment of the invention is a DNA molecule comprising a sequence that when optimally aligned to a reference sequence, provided herein as SEQ ID NOs: 1-158 and 180-183, has at least about 85 percent identity, at least about 90 percent identity, at least about 95 percent identity, at least about 96 percent identity, at least about 97 percent identity, at least about 98 percent identity, or at least about 99 percent identity to the reference sequence. In particular embodiments such sequences may be defined as having gene-regulatory activity.

Regulatory Elements

A regulatory element is a DNA molecule having gene regulatory activity, i.e. one that has the ability to affect the transcription and/or translation of an operably linked transcribable polynucleotide molecule. The term "gene regulatory activity" thus refers to the ability to affect the expression pattern of an operably linked transcribable polynucleotide molecule by affecting the transcription and/or translation of that operably linked transcribable polynucleotide molecule. As used herein, a transcriptional regulatory expression element group or "EXP" sequence may be comprised of expression elements, such as enhancers, promoters, leaders and introns, operably linked. Thus a transcriptional regulatory expression element group may be comprised, for instance, of a promoter operably linked 5' to a leader sequence, which is in turn operably linked 5' to an intron sequence. The intron sequence may be comprised of a sequence beginning at the point of the first intron/exon splice junction of the native sequence and further may be comprised of a small leader fragment comprising the second intron/exon splice junction so as to provide for proper intron/exon processing to facilitate transcription and proper processing of the resulting transcript. Leaders and introns may positively affect transcription of an operably linked transcribable polynucleotide molecule as well as translation of the resulting transcribed RNA. The pre-processed RNA molecule comprises leaders and introns, which may affect the post-transcriptional processing of the transcribed RNA and/or the export of the transcribed RNA molecule from the cell nucleus into the cytoplasm. Following post-transcriptional processing of the transcribed RNA molecule, the leader sequence may be retained as part of the final messenger RNA and may positively affect the translation of the messenger RNA molecule.

Regulatory elements such as promoters, leaders, introns, and transcription termination regions (or 3' UTRs) are DNA molecules that have gene regulatory activity and play an integral part in the overall expression of genes in living cells. The term "regulatory element" refers to a DNA molecule having gene regulatory activity, i.e. one that has the ability to affect the transcription and/or translation of an operably linked transcribable polynucleotide molecule. Isolated regulatory elements, such as promoters and leaders that function in plants are therefore useful for modifying plant phenotypes through the methods of genetic engineering.

Regulatory elements may be characterized by their expression pattern effects (qualitatively and/or quantitatively), e.g. positive or negative effects and/or constitutive or other effects such as by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable polynucleotide molecule.

As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression" is any pattern of translation of a transcribed RNA molecule into a protein molecule. Protein expression may be characterized by its temporal, spatial, developmental, or morphological qualities as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more heterologous DNA molecules. Promoters useful in practicing the present invention include SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135, or fragments or variants thereof. In specific embodiments of the invention, such molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent sequence for recognition and binding of the RNA polymerase II complex for initiation of transcription.

In one embodiment, fragments are provided of a promoter sequence disclosed herein. Promoter fragments may comprise promoter activity, as described above, and may be useful alone or in combination with other promoters and promoter fragments, such as in constructing chimeric promoters. In specific embodiments, fragments of a promoter are provided comprising at least about 50, 95, 150, 250, 500, 750, or at least about 1000 contiguous nucleotides, or longer, of a polynucleotide molecule having promoter activity disclosed herein.

Compositions derived from any of the promoters presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135, such as internal or 5' deletions, for example, can be produced using methods known in the art to improve or alter expression, including by removing elements that have either positive or negative effects on expression; duplicating elements that have positive or negative effects on expression; and/or duplicating or removing elements that have tissue or cell specific effects on expression. Compositions derived from any of the promoters presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135 comprised of 3' deletions in which the TATA box element or equivalent sequence thereof and downstream sequence is removed can be used, for example, to make enhancer elements. Further deletions can be made to remove any elements that have positive or negative; tissue specific; cell specific; or timing specific (such as, but not limited to, circadian rhythms) effects on expression. Any of the promoters presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135 and fragments or enhancers derived there from can be used to make chimeric transcriptional regulatory element compositions comprised of any of the promoters presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135 and the fragments or enhancers derived therefrom operably linked to other enhancers and promoters. The efficacy of the modifications, duplications or deletions described herein on the desired expression aspects of a particular transgene may be tested empirically in stable and transient plant assays, such as those described in the working examples herein, so as to validate the results, which may vary depending upon the changes made and the goal of the change in the starting molecule.

As used herein, the term "leader" refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. Promoter molecules of the present invention may thus be operably linked to their native leader or may be operably linked to a heterologous leader. Leaders useful in practicing the present invention include SEQ ID NOS: 3, 20, 35, 43, 47, 51, 57, 61, 67, 71 and 81 or fragments or variants thereof. In specific embodiments, such sequences may be provided defined as being capable of acting as a leader in a host cell, including, for example, a transgenic plant cell. In one embodiment such sequences are decoded as comprising leader activity.

The leader sequences (5' UTR) presented as SEQ ID NOS: 3, 20, 35, 43, 47, 51, 57, 61, 67, 71 and 81 may be comprised of regulatory elements or may adopt secondary structures that can have an effect on transcription or translation of a transgene. The leader sequences presented as SEQ ID NOS: 3, 20, 35, 43, 47, 51, 57, 61, 67, 71 and 81 can be used in accordance with the invention to make chimeric regulatory elements that affect transcription or translation of a transgene. In addition, the leader sequences presented as SEQ ID NOS: 3, 20, 35, 43, 47, 51, 57, 61, 67, 71 and 81 can be used to make chimeric leader sequences that affect transcription or translation of a transgene.

The introduction of a foreign gene into a new plant host does not always result in a high expression of the incoming gene. Furthermore, if dealing with complex traits, it is sometimes necessary to modulate several genes with spatially or temporarily different expression pattern.

Introns can principally provide such modulation. However multiple use of the same intron in one plant has shown to exhibit disadvantages. In those cases it is necessary to have a collection of basic control elements for the construction of appropriate recombinant DNA elements. As the available collection of introns known in the art with expression enhancing properties is limited, alternatives are needed.

Compositions derived from any of the introns presented as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 can be comprised of internal deletions or duplications of cis regulatory elements; and/or alterations of the 5' and 3' sequences comprising the intron/exon splice junctions can be used to improve expression or specificity of expression when operably linked to a promoter+leader or chimeric promoter+leader and coding sequence. Alterations of the 5' and 3' regions comprising the intron/exon splice junction can also be made to reduce the potential for introduction of false start and stop codons being produced in the resulting transcript after processing and splicing of the messenger RNA. The introns can be tested empirically as described in the working examples to determine the intron's effect on expression of a transgene.

In accordance with the invention a promoter or promoter fragment may be analyzed for the presence of known promoter elements, i.e. DNA sequence characteristics, such as a TATA-box and other known transcription factor binding site motifs. Identification of such known promoter elements may be used by one of skill in the art to design variants of the promoter having a similar expression pattern to the original promoter.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box or equivalent sequence. A promoter may naturally comprise one or more enhancer elements that affect the transcription of an operably linked polynucleotide sequence. An isolated enhancer element may also be fused to a promoter to produce a chimeric promoter cis-element, which confers an aspect of the overall modulation of gene expression. A promoter or promoter fragment may comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e. deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

In plants, the inclusion of some introns in gene constructs leads to increased mRNA and protein accumulation relative to constructs lacking the intron.

This effect has been termed "intron mediated enhancement" (IME) of gene expression (Mascarenhas et al., (1990) *Plant Mol. Biol.* 15:913-920). Introns known to stimulate expression in plants have been identified in maize genes (e.g. tubA1, Adh1, Sh1, Ubi1 (Jeon et al. (2000) *Plant Physiol.* 123:1005-1014; Callis et al. (1987) *Genes Dev.* 1:1183-1200; Vasil et al. (1989) *Plant Physiol.* 91:1575-1579; Christiansen et al. (1992) *Plant Mol. Biol.* 18:675-689) and in rice genes (e.g. salt, tpi: McElroy et al., *Plant Cell* 2:163-171 (1990); Xu et al., *Plant Physiol.* 106:459-467 (1994)). Similarly, introns from dicotyledonous plant genes like those from *petunia* (e.g. rbcS), potato (e.g. st-ls1) and from *Arabidopsis thaliana* (e.g. ubq3 and pat1) have been found to elevate gene expression rates (Dean et al. (1989) *Plant Cell* 1:201-208; Leon et al. (1991) *Plant Physiol.* 95:968-972; Norris et al. (1993) *Plant Mol Biol* 21:895-906; Rose and Last (1997) *Plant J.* 11:455-464). It has been shown that deletions or mutations within the splice sites of an intron reduce gene expression, indicating that splicing might be needed for IME (Mascarenhas et al. (1990) *Plant Mol Biol.* 15:913-920; Clancy and Hannah (2002) *Plant Physiol.* 130:918-929). However, that splicing per se is not required for a certain IME in dicotyledonous plants has been shown by point mutations within the splice sites of the pat1 gene from *A. thaliana* (Rose and Beliakoff (2000) *Plant Physiol.* 122:535-542).

Enhancement of gene expression by introns is not a general phenomenon because some intron insertions into recombinant expression cassettes fail to enhance expression (e.g. introns from dicot genes (rbcS gene from pea, phaseolin gene from bean and the stls-1 gene from *Solanum tuberosum*) and introns from maize genes (adh1 gene the ninth intron, hsp81 gene the first intron)) (Chee et al. (1986) *Gene* 41:47-57; Kuhlemeier et al. (1988) *Mol Gen Genet* 212:405-411; Mascarenhas et al. (1990) *Plant Mol. Biol.* 15:913-920; Sinibaldi and Mettler (1992) In WE Cohn, K Moldave, eds, *Progress in Nucleic Acid Research and Molecular Biology*, Vol 42. Academic Press, New York, pp 229-257; Vancanneyt et al. 1990 *Mol. Gen. Genet.* 220:245-250). Therefore, not each intron can be employed in order to manipulate the gene expression level of non-endogenous genes or endogenous genes in transgenic plants. What characteristics or specific sequence features must be present in an intron sequence in order to enhance the expression rate of a given gene is not known in the prior art and therefore from the prior art it is not possible to predict whether a given plant intron, when used heterologously, will cause enhancement of expression at the DNA level or at the transcript level (IME).

As used herein, the term "chimeric" refers to a single DNA molecule produced by fusing a first DNA molecule to a second DNA molecule, where neither first nor second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; an example would be the fusion of a promoter to an enhancer element. Thus, the design, construction, and use of chimeric promoters according to the methods disclosed herein for modulating the expression of operably linked transcribable polynucleotide molecules are encompassed by the present invention.

As used herein, the term "variant" refers to a second DNA molecule that is in composition similar, but not identical to, a first DNA molecule and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" can also encompass a regulatory element having a nucleotide sequence comprising a substitution, deletion and/ or insertion of one or more nucleotides of a reference sequence, wherein the derivative regulatory element has more or less or equivalent transcriptional or translational activity than the corresponding parent regulatory molecule. The regulatory element "variants" will also encompass variants arising from mutations that naturally occur in bacterial and plant cell transformation. In the present invention, a polynucleotide sequence provided as SEQ ID NOs: 1-158 and 180-183 may be used to create variants that are in composition similar, but not identical to, the polynucleotide sequence of the original regulatory element, while still maintaining the general functionality, i.e. same or similar expression pattern, of the original regulatory element. Production of such variants of the present invention is well within the ordinary skill of the art in light of the disclosure and is encompassed within the scope of the present invention. Chimeric regulatory element "variants" comprise the same constituent elements as a reference sequence but the constituent elements comprising the chimeric regulatory element may be operatively linked by various methods known in the art such as, restriction enzyme digestion and ligation, ligation independent cloning, modular assembly of PCR products during amplification, or direct chemical synthesis of the regulatory element as well as other methods known in the art. The resulting chimeric regulatory element "variant" can be comprised of the same, or variants of the same, constituent elements of the reference sequence but differ in the sequence or sequences that comprise the linking sequence or sequences which allow the constituent parts to be operatively linked. In the present invention, a polynucleotide sequence provided as SEQ ID NOs: 1-158 and 180-183 provide a reference sequence wherein the constituent elements that comprise the reference sequence may be joined by methods known in the art and may comprise substitutions, deletions and/or insertions of one or more nucleotides or mutations that naturally occur in bacterial and plant cell transformation.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell. The term includes an expression cassette isolated from any of the aforementioned molecules.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. A leader, for example, is operably linked to coding sequence when it is capable of serving as a leader for the polypeptide encoded by the coding sequence.

The constructs of the present invention may be provided, in one embodiment, as double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *A. tumefaciens* cells, permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known to those skilled in the art of plant transformation can function in the present invention.

Methods are known in the art for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells are well known to one skilled in the art, see, for example, *Molecular Cloning: A Laboratory Manual*, $3^{rd}$ edition Volumes 1, 2, and 3 (2000) J. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971, 908; 4,940,835; 4,769,061; and 4,757,011 in their entirety. These types of vectors have also been reviewed in the scientific literature (see, for example, Rodriguez, et al., *Vectors: A Survey of Molecular Cloning Vectors and Their Uses*, Butterworths, Boston, (1988) and Glick, et al., *Methods in Plant Molecular Biology and Biotechnology*, CRC Press, Boca Raton, FL (1993)). Typical vectors useful for expression of nucleic acids in higher plants are well known in the art and include vectors derived from the tumor-inducing (Ti) plasmid of *Agrobacterium tumefaciens* (Rogers, et al., *Methods in Enzymology* 153: 253-277 (1987)). Other recombinant vectors useful for plant transformation, including the pCaMVCN transfer control vector, have also been described in the scientific literature (see, for example, Fromm, et al., *Proc. Natl. Acad. Sci. USA* 82: 5824-5828 (1985)).

Various regulatory elements may be included in a construct including any of those provided herein. Any such regulatory elements may be provided in combination with other regulatory elements. Such combinations can be designed or modified to produce desirable regulatory features. In one embodiment, constructs of the present invention comprise at least one regulatory element operably linked to a transcribable polynucleotide molecule operably linked to a 3' UTR.

Constructs of the present invention may include any promoter or leader provided herein or known in the art. For example, a promoter of the present invention may be operably linked to a heterologous non-translated 5' leader such as one derived from a heat shock protein gene (see, for example, U.S. Pat. Nos. 5,659,122 and 5,362,865). Alternatively, a leader of the present invention may be operably linked to a heterologous promoter such as the Cauliflower Mosaic Virus 35S transcript promoter (see, U.S. Pat. No. 5,352,605).

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347). Introns useful in practicing the present invention include SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182. Further, when modifying intron/exon boundary sequences, it may be preferable to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The sequence around the 5' or 3' end splice junction sites of the intron can thus be modified in this manner.

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region (see, Fraley, et al., *Proc. Natl. Acad. Sci. USA,* 80: 4803-4807 (1983)); wheat hsp17 3' region; pea rubisco small subunit 3' region; cotton E6 3' region (U.S. Pat. No. 6,096,950); 3' regions disclosed in WO0011200A2; and the coixin 3' UTR (U.S. Pat. No. 6,635,806).

3' UTRs typically find beneficial use for the recombinant expression of specific genes. In animal systems, a machinery of 3' UTRs has been well defined (e.g. Zhao et al., *Microbiol Mol Biol Rev* 63:405-445 (1999); Proudfoot, *Nature* 322: 562-565 (1986); Kim et al., *Biotechnology Progress* 19:1620-1622 (2003); Yonaha and Proudfoot, *EMBO J.* 19:3770-3777 (2000); Cramer et al., *FEBS Letters* 498:179-182 (2001); Kuerstem and Goodwin, *Nature Reviews Genetics* 4:626-637 (2003)). Effective termination of RNA transcription is required to prevent unwanted transcription of trait-unrelated (downstream) sequences, which may interfere with trait performance. Arrangement of multiple gene expression cassettes in local proximity to one another (e.g. within one T-DNA) may cause suppression of gene expression of one or more genes in said construct in comparison to independent insertions (Padidam and Cao, *BioTechniques* 31:328-334 (2001). This may interfere with achieving adequate levels of expression, for instance in cases were strong gene expression from all cassettes is desired.

In plants, clearly defined polyadenylation signal sequences are not known. Hasegawa et al., *Plant J.* 33:1063-1072, (2003)) were not able to identify conserved polyadenylation signal sequences in both in vitro and in vivo systems in *Nicotiana sylvestris* and to determine the actual length of the primary (non-polyadenylated) transcript. A weak 3' UTR has the potential to generate read-through, which may affect the expression of the genes located in the neighboring expression cassettes (Padidam and Cao, *BioTechniques* 31:328-334 (2001)). Appropriate control of transcription termination can prevent read-through into sequences (e.g. other expression cassettes) localized downstream and can further allow efficient recycling of RNA polymerase, to improve gene expression. Efficient termination of transcription (release of RNA Polymerase II from the DNA) is pre-requisite for re-initiation of transcription and thereby directly affects the overall transcript level. Subsequent to transcription termination, the mature mRNA is released from the site of synthesis and template to the cytoplasm. Eukaryotic mRNAs are accumulated as poly(A) forms in vivo, so that it is difficult to detect transcriptional termination sites by conventional methods. However, prediction of functional and efficient 3' UTRs by bioinformatics methods is difficult in that there are no conserved sequences which would allow easy prediction of an effective 3' UTR.

From a practical standpoint, it is typically beneficial that a 3' UTR used in a transgene cassette possesses the following characteristics. The 3' UTR should be able to efficiently and effectively terminate transcription of the transgene and prevent read-through of the transcript into any neighboring DNA sequence which can be comprised of another transgene cassette as in the case of multiple cassettes residing in one T-DNA, or the neighboring chromosomal DNA into which the T-DNA has inserted. The 3' UTR should not cause a reduction in the transcriptional activity imparted by the promoter, leader and introns that are used to drive expression of the transgene. In plant biotechnology, the 3' UTR is often used for priming of amplification reactions of reverse transcribed RNA extracted from the transformed plant and used to (1) assess the transcriptional activity or expression of the transgene cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

3' UTRs useful in providing expression of a transgene in plants may be identified based upon the expression of expressed sequence tags (ESTs) in cDNA libraries made from messenger RNA isolated from seed, flower and other tissues derived from Big bluestem (*Andropogon gerardii*), Plume grass (*Saccharum ravennae* (*Erianthus ravennae*)), Green bristlegrass (*Setaria viridis*), Teosinte (*Zea mays* subsp. *mexicana*), Foxtail millet (*Setaria italica*), or *Coix*

(*Coix lacryma-jobi*). Libraries of cDNA are made from tissues isolated from selected plant species using methods known to those skilled in the art from flower tissue, seed, leaf and root. The resulting cDNAs are sequenced using various sequencing methods known in the art. The resulting ESTs are assembled into clusters using bioinformatics software such as clc_ref_assemble_complete version 2.01.37139 (CLC bio USA, Cambridge, Massachusetts 02142). Transcript abundance of each cluster is determined by counting the number of cDNA reads for each cluster. The identified 3' UTRs may be comprised of sequence derived from cDNA sequence as well as sequence derived from genomic DNA. The cDNA sequence is used to design primers, which are then used with GenomeWalker™ (Clontech Laboratories, Inc, Mountain View, CA) libraries constructed following the manufacturer's protocol to clone the 3' region of the corresponding genomic DNA sequence to provide a longer termination sequence. Analysis of relative transcript abundance either by direct counts or normalized counts of observed sequence reads for each tissue library can be used to infer properties about patters of expression. For example, some 3' UTRs may be found in transcripts seen in higher abundance in root tissue as opposed to leaf. This is suggestive that the transcript is highly expressed in root and that the properties of root expression may be attributable to the transcriptional regulation of the promoter, the lead, the introns or the 3' UTR. Empirical testing of 3' UTRs identified by the properties of expression within specific organs, tissues or cell types can result in the identification of 3' UTRs that enhance expression in those specific organs, tissues or cell types.

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442 (1987)) or the *Petunia hybrida* EPSPS CTP (CTP4) (See, della-Cioppa et al., *Proc. Natl. Acad. Sci. USA* 83:6873-6877 (1986)) has been show to target heterologous EPSPS protein sequences to chloroplasts in transgenic plants (See, U.S. Pat. Nos. 5,627,061; 5,633,435; and 5,312,910 and EP 0218571; EP 189707; EP 508909; and EP 924299).

Transcribable Polynucleotide Molecules

As used herein, the term "transcribable polynucleotide molecule" refers to any DNA molecule capable of being transcribed into a RNA molecule, including, but not limited to, those having protein coding sequences and those producing RNA molecules having sequences useful for gene suppression. A "transgene" refers to a transcribable polynucleotide molecule heterologous to a host cell at least with respect to its location in the genome and/or a transcribable polynucleotide molecule artificially incorporated into a host cell's genome in the current or any prior generation of the cell.

A promoter of the present invention may be operably linked to a transcribable polynucleotide molecule that is heterologous with respect to the promoter molecule. As used herein, the term "heterologous" refers to the combination of two or more polynucleotide molecules when such a combination is not normally found in nature. For example, the two molecules may be derived from different species and/or the two molecules may be derived from different genes, e.g. different genes from the same species or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of a RNA transcript is desired. Such expression of an RNA transcript may result in translation of the resulting mRNA molecule and thus protein expression. Alternatively, for example, a transcribable polynucleotide molecule may be designed to ultimately cause decreased expression of a specific gene or protein. In one embodiment, this may be accomplished by using a transcribable polynucleotide molecule that is oriented in the antisense direction. One of ordinary skill in the art is familiar with using such antisense technology. Briefly, as the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, one embodiment of the invention is a regulatory element of the present invention, such as those provided as SEQ ID NOs: 1-158 and 180-183, operably linked to a transcribable polynucleotide molecule so as to modulate transcription of the transcribable polynucleotide molecule at a desired level or in a desired pattern when the construct is integrated in the genome of a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule, double stranded RNA or other similar inhibitory RNA molecule in order to inhibit expression of a specific RNA molecule of interest in a target host cell.

Genes of Agronomic Interest

Transcribable polynucleotide molecules may be genes of agronomic interest. As used herein, the term "gene of agronomic interest" refers to a transcribable polynucleotide molecule that when expressed in a particular plant tissue, cell, or cell type confers a desirable characteristic, such as associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or RNAi molecule targeting a particular gene for suppression. The product of a gene of agronomic interest may act within the plant in order to cause an effect upon the plant physiology or metabolism or may be act as a pesticidal agent in the diet of a pest that feeds on the plant.

In one embodiment of the invention, a promoter of the present invention is incorporated into a construct such that the promoter is operably linked to a transcribable polynucleotide molecule that is a gene of agronomic interest. The expression of the gene of agronomic interest is desirable in order to confer an agronomically beneficial trait. A beneficial agronomic trait may be, for example, but is not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. Examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. USRE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. USRE37,543; 6,228,623; and U.S. Pat. Nos. 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristic or phenotype by encoding a RNA molecule that causes the targeted modulation of gene expression of an endogenous gene, for example via antisense (see e.g. U.S. Pat. No. 5,107,065); inhibitory RNA ("RNAi", including modulation of gene expression via miRNA-, siRNA-, trans-acting siRNA-, and phased sRNA-mediated mechanisms, e.g. as described in published applications US 2006/0200878 and US 2008/0066206, and in U.S. patent application Ser. No. 11/974,469); or cosuppression-mediated mechanisms. The RNA could also be a catalytic RNA molecule (e.g. a ribozyme or a riboswitch; see e.g. US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Publication No. US20070124836) and compositions isolated from nematode pests (U.S. Patent Publication No. US20070250947). Plant pests include, but are not limited to arthropod pests, nematode pests, and fungal or microbial pests. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule can include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding β-glucuronidase (GUS described in U.S. Pat. No. 5,599,670), green fluorescent protein and variants thereof (GFP described in U.S. Pat. Nos. 5,491,084 and 6,146,826), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include, but are not limited to: amino-methyl-phosphonic acid, glyphosate, glufosinate, sulfonylureas, imidazolinones, bromoxynil, dalapon, dicamba, cyclohexanedione, protoporphyrinogen oxidase inhibitors, and isoxasflutole herbicides. Transcribable polynucleotide molecules encoding proteins involved in herbicide tolerance are known in the art, and include, but are not limited to, a transcribable polynucleotide molecule encoding 5-enolpyruvylshikimate-3-phosphate synthase (EPSPS for glyphosate tolerance described in U.S. Pat. Nos. 5,627,061; 5,633,435; 6,040,497; and 5,094,945); a transcribable polynucleotide molecule encoding a glyphosate oxidoreductase and a glyphosate-N-acetyl transferase (GOX described in U.S. Pat. No. 5,463,175; GAT described in U.S. Patent publication No. 20030083480, and dicamba monooxygenase U.S. Patent publication No. 20030135879); a transcribable polynucleotide molecule encoding bromoxynil nitrilase (Bxn for Bromoxynil tolerance described in U.S. Pat. No. 4,810,648); a transcribable polynucleotide molecule encoding phytoene desaturase (crtI) described in Misawa, et al., *Plant Journal* 4:833-840 (1993) and Misawa, et al., *Plant Journal* 6:481-489 (1994) for norflurazon tolerance; a transcribable polynucleotide molecule encoding acetohydroxyacid synthase (AHAS, aka ALS) described in Sathasiivan, et al., *Nucl. Acids Res.* 18:2188-2193 (1990) for tolerance to sulfonylurea herbicides; and the bar gene described in DeBlock, et al., *EMBO Journal* 6:2513-2519 (1987) for glufosinate and bialaphos tolerance. The promoter molecules of the present invention can express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g. by ELISA), small active enzymes which are detectable in extracellular solution (e.g, alpha-amylase, beta-lactamase, phosphinothricin transferase), or proteins which are inserted or trapped in the cell wall (such as proteins which include a leader sequence such as that found in the expression unit of extension or tobacco pathogenesis related proteins also known as tobacco PR-S). Other possible selectable marker genes will be apparent to those of skill in the art and are encompassed by the present invention.

Cell Transformation

The invention is also directed to a method of producing transformed cells and plants which comprise a promoter operably linked to a transcribable polynucleotide molecule.

The term "transformation" refers to the introduction of nucleic acid into a recipient host. As used herein, the term "host" refers to bacteria, fungi, or plant, including any cells, tissue, organs, or progeny of the bacteria, fungi, or plant. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules.

There are many methods for introducing polynucleic acid molecules into plant cells. The method generally comprises the steps of selecting a suitable host cell, transforming the host cell with a recombinant vector, and obtaining the transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.* 42: 205 (1991)).

Technology for introduction of a DNA molecule into cells is well known to those of skill in the art. Methods and materials for transforming plant cells by introducing a plant DNA construct into a plant genome in the practice of this invention can include any of the well-known and demonstrated methods. Any transformation methods may be utilized to transform a host cell with one or more promoters and/or constructs of the present. Host cells may be any cell or organism such as a plant cell, algae cell, algae, fungal cell, fungi, bacterial cell, or insect cell. Preferred hosts and transformed cells include cells from: plants, *Aspergillus*, yeasts, insects, bacteria and algae.

Regenerated transgenic plants can be self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding*, John Wiley & Sons, NY, U. of CA, Davis, CA, 50-98 (1960); Simmonds, *Principles of crop improvement*, Longman, Inc., NY, 369-399 (1979); Sneep and Hendriksen, Plant breeding perspectives, Wageningen (ed), Center for Agricultural Publishing and Documentation (1979); Fehr, *Soybeans: Improvement, Production and Uses,* 2nd Edition, Monograph, 16:249 (1987); Fehr, *Principles of variety development, Theory and Technique*, (Vol. 1) and *Crop Species Soybean* (Vol 2), Iowa State Univ., Macmillan Pub. Co., NY, 360-376 (1987). Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, CA) reagents and methods as described by the manufacturer and PCR cycle times determined using the TaqMan® Testing Matrix. Alternatively, the Invader® (Third Wave Technologies, Madison, WI) reagents and methods as described by the manufacturer can be used transgene expression.

The seeds of the plants of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleotide molecule to its progeny. Progeny includes any regenerable plant part or seed comprising the transgene derived from an ancestor plant. The transgenic plant is preferably homozygous for the transformed polynucleotide molecule and transmits that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Commodity Products

The present invention provides a commodity product comprising DNA moleucles according to the invention. As used herein, a "commodity product" refers to any composition or product which is comprised of material derived from a plant, seed, plant cell or plant part comprising a DNA molecule of the invention. Commodity products may be sold to consumers and may be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animals consumption, oil, meal, flour, flakes, bran, fiber, milk, cheese, paper, cream, wine, and any other food for human consumption; and biomasses and fuel products. Viable commodity products include but are not limited to seeds and plant cells. Plants comprising a DNA moleucle according to the invention can thus be used to manufacture any commodity product typically acquired from plants or parts thereof.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1: Identification and Cloning of Regulatory Elements

Novel ubiquitin transcriptional regulatory elements, or transcriptional regulatory expression element group (EXP) sequences were identified and isolated from genomic DNA of the monocot species Big bluestem (*Andropogon gerardii*), Plume Grass (*Saccharum ravennae* (*Erianthus ravennae*)), Green bristlegrass (*Setaria viridis*), Teosinte (*Zea mays* subsp. *mexicana*), Foxtail millet (*Setaria italica*), and Coix (*Coix lacryma-jobi*).

Ubiquitin 1 transcript sequences were identified from each of the above species. The 5' untranslated region (5' UTR) of each of the Ubiquitin 1 transcripts was used to design primers to amplify the corresponding transcriptional regulatory elements for the identified Ubiquitin gene, which comprises a promoter, leader (5' UTR) and first intron operably linked. The primers were used with GenomeWalker™ (Clontech Laboratories, Inc, Mountain View, CA) libraries constructed following the manufacturer's protocol to clone the 5' region of the corresponding genomic DNA sequence. Ubiquitin transcriptional regulatory elements were also isolated from the monocot *Sorghum bicolor* using public sequences that are homologs to the Ubiquitin 4, 6 and 7 genes of *Zea mays*.

Using the identified sequences, a bioinformatic analysis was conducted to identify regulatory elements within the amplified DNA. Using the results of this analysis, regulatory elements were defined within the DNA sequences and primers designed to amplify the regulatory elements. The corresponding DNA molecule for each regulatory element was amplified using standard polymerase chain reaction conditions with primers containing unique restriction enzyme sites and genomic DNA isolated from *A. gerardii*, *S. ravennae*, *S. viridis*, *Z. mays* subsp. *mexicana*, *S. italica*, *C. lacryma-jobi*, and *S. bicolor*. The resulting DNA fragments were ligated into base plant expression vectors and sequenced. An analysis of the regulatory element TSS and intron/exon splice junctions was then done using transformed plant protoplasts. Briefly, the protoplasts were transformed with the plant expression vectors comprising the cloned DNA fragments operably linked to a heterologous transcribable polynucleotide molecule and the 5' RACE System for Rapid Amplification of cDNA Ends, Version 2.0 (Invitrogen, Carlsbad, California 92008) was used to confirm the regulatory element TSS and intron/exon splice junctions by analyzing the sequence of the mRNA transcripts produced thereby.

Sequences of the identified transcriptional regulatory expression element groups ("EXP's") are provided herein as SEQ ID NOS: 1, 5, 8, 10, 12, 14, 16, 18, 22, 25, 27, 29, 31, 33, 37, 39, 41, 45, 49, 53, 55, 59, 63, 65, 69, 73, 75, 77, 79, 83, 85, 87, 90, 93, 95, 97, 98, 99, 100, 102, 104, 106, 108, 110, 112, 114, 115, 116, 117, 119, 121, 123, 124, 125, 126, 128, 130, 132, 133, 134, 136, 137, 139, 141, 143, 145, 147, 149, 151, 153, 155, 157, 180, 181 and 183, as listed in Table 1 below. Promoter sequences are provided herein as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135. Leader sequences are provided herein as SEQ ID NOS: 3, 20, 35, 43, 47, 51, 57, 61, 67, 71 and 81. Intron sequences are provided herein as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182. An enhancer sequence is provided as SEQ ID NO: 89.

TABLE 1

Transcriptional regulatory expression element groups ("EXP's"),
promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| EXP-ANDge.Ubq1:1:9 | 1 | 3741 | *A. gerardii* | EXP: P-ANDge.Ubq1-1:1:11 (SEQ ID NO: 2); L-ANDge.Ubq1-1:1:2 (SEQ ID NO: 3); I-ANDge.Ubq1-1:1:3 (SEQ ID NO: 4). | |
| P-ANDge.Ubq1-1:1:11 | 2 | 2603 | *A. gerardii* | promoter | |
| L-ANDge.Ubq1-1:1:2 | 3 | 99 | *A. gerardii* | leader | |
| I-ANDge.Ubq1-1:1:3 | 4 | 1039 | *A. gerardii* | intron | |
| EXP-ANDge.Ubq1:1:7 | 5 | 3255 | *A. gerardii* | EXP: P-ANDge.Ubq1-1:1:9 (SEQ ID NO: 6); L-ANDge.Ubq1-1:1:2 (SEQ ID NO: 3); I-ANDge.Ubq1-1:1:4 (SEQ ID NO: 7). | pMON136264, PCR0145892, pMON140896, PCR41 |
| P-ANDge.Ubq1-1:1:9 | 6 | 2114 | *A. gerardii* | promoter | |
| I-ANDge.Ubq1-1:1:4 | 7 | 1042 | *A. gerardii* | intron | |
| EXP-ANDge.Ubq1:1:8 | 8 | 2785 | *A. gerardii* | EXP: P-ANDge.Ubq1-1:1:10 (SEQ ID NO: 9); L-ANDge.Ubq1-1:1:2 (SEQ ID NO: 3); I-ANDge.Ubq1-1:1:4 (SEQ ID NO: 7). | pMON140917, PCR42 |
| P-ANDge.Ubq1-1:1:10 | 9 | 1644 | *A. gerardii* | promoter | |
| EXP-ANDge.Ubq1:1:10 | 10 | 2613 | *A. gerardii* | EXP: P-ANDge.Ubq1-1:1:12 (SEQ ID NO: 11); L-ANDge.Ubq1-1:1:2 (SEQ ID NO: 3); I-ANDge.Ubq1-1:1:4 (SEQ ID NO: 7). | PCR0145815, PCR43 |
| P-ANDge.Ubq1-1:1:12 | 11 | 1472 | *A. gerardii* | promoter | |
| EXP-ANDge.Ubq1:1:6 | 12 | 2255 | *A. gerardii* | EXP: P-ANDge.Ubq1-1:1:8 (SEQ ID NO: 13); L-ANDge.Ubq1-1:1:2 (SEQ ID NO: 3); I-ANDge.Ubq1-1:1:4 (SEQ ID NO: 7). | pMON136259, PCR0145893, pMON140898, PCR44 |
| P-ANDge.Ubq1-1:1:8 | 13 | 1114 | *A. gerardii* | promoter | |
| EXP-ANDge.Ubq1:1:11 | 14 | 1912 | *A. gerardii* | EXP: P-ANDge.Ubq1-1:1:13 (SEQ ID NO: 15); L-ANDge.Ubq1-1:1:2 (SEQ ID NO: 3); I-ANDge.Ubq1-1:1:4 (SEQ ID NO: 7). | PCR0145817, pMON140899, PCR45 |
| P-ANDge.Ubq1-1:1:13 | 15 | 771 | *A. gerardii* | promoter | |
| EXP-ANDge.Ubq1:1:12 | 16 | 1623 | *A. gerardii* | EXP: P-ANDge.Ubq1-1:1:14 (SEQ ID NO: 17); L-ANDge.Ubq1-1:1:2 (SEQ ID NO: 3); I-ANDge.Ubq1-1:1:4 (SEQ ID NO: 7). | PCR0145819, pMON140900, PCR46 |
| P-ANDge.Ubq1-1:1:14 | 17 | 482 | *A. gerardii* | promoter | |
| EXP-ERIra.Ubq1 | 18 | 3483 | *E. ravennae* | EXP: P-ERIra.Ubq1-1:1:10 (SEQ ID NO: 19); L-ERIra.Ubq1-1:1:2 (SEQ ID NO: 20); I-ERIra.Ubq1-1:1:1 (SEQ ID NO: 21). | |
| P-ERIra.Ubq1-1:1:10 | 19 | 2536 | *E. ravennae* | promoter | |
| L-ERIra.Ubq1-1:1:2 | 20 | 94 | *E. ravennae* | leader | |
| I-ERIra.Ubq1-1:1:1 | 21 | 1041 | *E. ravennae* | intron | |
| EXP-ERIra.Ubq1:1:9 | 22 | 3152 | *E. ravennae* | EXP: P-ERIra.Ubq1-1:1:9 (SEQ ID NO: 23); L-ERIra.Ubq1-1:1:2 (SEQ ID NO: 20); I-ERIra.Ubq1-1:1:2 (SEQ ID NO: 24). | pMON136263, PCR0145896, pMON140904, PCR50 |
| P-ERIra.Ubq1-1:1:9 | 23 | 2014 | *E. ravennae* | promoter | |
| I-ERIra.Ubq1-1:1:2 | 24 | 1044 | *E. ravennae* | intron | |
| EXP-ERIra.Ubq1:1:10 | 25 | 2663 | *E. ravennae* | EXP: P-ERIra.Ubq1-1:1:11 (SEQ ID NO: 26); L-ERIra.Ubq1-1:1:2 (SEQ ID NO: 20); I-ERIra.Ubq1-1:1:2 (SEQ ID NO: 24). | PCR0145820, pMON140905, PCR51 |
| P-ERIra.Ubq1-1:1:11 | 26 | 1525 | *E. ravennae* | promoter | |
| EXP-ERIra.Ubq1:1:8 | 27 | 2182 | *E. ravennae* | EXP: P-ERIra.Ubq1-1:1:8 (SEQ ID NO: 28); L-ERIra.Ubq1-1:1:2 (SEQ ID NO: 20); I-ERIra.Ubq1-1:1:2 (SEQ ID NO: 24). | pMON136258, PCR0145897, pMON140906, PCR52, pMON142864, pMON142862 |
| P-ERIra.Ubq1-1:1:8 | 28 | 1044 | *E. ravennae* | promoter | |
| EXP-ERIra.Ubq1:1:11 | 29 | 1934 | *E. ravennae* | EXP: P-ERIra.Ubq1-1:1:12 (SEQ ID NO: 30); L-ERIra.Ubq1-1:1:2 (SEQ ID NO: 20); I-ERIra.Ubq1-1:1:2 (SEQ ID NO: 24). | PCR0145821, pMON140907, PCR53 |
| P-ERIra.Ubq1-1:1:12 | 30 | 796 | *E. ravennae* | promoter | |
| EXP-ERIra.Ubq1:1:12 | 31 | 1649 | *E. ravennae* | EXP: P-ERIra.Ubq1-1:1:13 (SEQ ID NO: 32); L-ERIra.Ubq1-1:1:2 (SEQ ID NO: 20); I-ERIra.Ubq1-1:1:2 (SEQ ID NO: 24). | PCR0145822, pMON140908, PCR54 |
| P-ERIra.Ubq1-1:1:13 | 32 | 511 | *E. ravennae* | promoter | |
| EXP-Sv.Ubq1:1:2 | 33 | 2631 | *S. viridis* | EXP: P-Sv.Ubq1-1:1:1 (SEQ ID NO: 34); L-Sv.Ubq1-1:1:2 (SEQ ID NO: 35); I-Sv.Ubq1-1:1:1 (SEQ ID NO: 36). | pMON140878, PCR0145909, pMON129203, pMON131958 |
| P-Sv.Ubq1-1:1:1 | 34 | 1493 | *S. viridis* | promoter | |
| L-Sv.Ubq1-1:1:2 | 35 | 127 | *S. viridis* | leader | |
| I-Sv.Ubq1-1:1:1 | 36 | 1011 | *S. viridis* | intron | |

TABLE 1-continued

Transcriptional regulatory expression element groups ("EXP's"),
promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| EXP-Sv.Ubq1:1:3 | 37 | 2173 | *S. viridis* | EXP: P-Sv.Ubq1-1:1:2 (SQ ID NO: 38); L-Sv.Ubq1-1:1:2 (SEQ ID NO: 35); I-Sv.Ubq1-1:1:1 (SEQ ID NO: 36). | PCR0145929, pMON129204 |
| P-Sv.Ubq1-1:1:2 | 38 | 1035 | *S. viridis* | promoter | |
| EXP-Sv.Ubq1:1:5 | 39 | 1819 | *S. viridis* | EXP: P-Sv.Ubq1-1:1:3 (SEQ ID NO: 40); L-Sv.Ubq1-1:1:2 (SEQ ID NO: 35); I-Sv.Ubq1-1:1:1 (SEQ ID NO: 36). | pMON129205, pMON131959 |
| P-Sv.Ubq1-1:1:3 | 40 | 681 | *S. viridis* | promoter | |
| EXP-Zm.UbqM1:1:1 (Allele-1) | 41 | 1922 | *Z. mays* subsp. *mexicana* | EXP: P-Zm.UbqM1-1:1:1 (SEQ ID NO: 42); L-Zm.UbqM1-1:1:1 (SEQ ID NO: 43); I-Zm.UbqM1-1:1:5 (SEQ ID NO: 44). | pMON140881, PCR0145914, pMON129210, pMON131961 |
| P-Zm.UbqM1-1:1:1 (Allele-1) | 42 | 850 | *Z. mays* subsp. *mexicana* | promoter | |
| L-Zm.UbqM1-1:1:1 (Allele-1) | 43 | 78 | *Z. mays* subsp. *mexicana* | leader | |
| I-Zm.UbqM1-1:1:5 (Allele-1) | 44 | 994 | *Z. mays* subsp. *mexicana* | intron | |
| EXP-Zm.UbqM1:1:4 (Allele-2) | 45 | 1971 | *Z. mays* subsp. *mexicana* | EXP: P-Zm.UbqM1-1:1:4 (SEQ ID NO: 46); L-Zm.UbqM1-1:1:5 (SEQ ID NO: 47); I-Zm.UbqM1-1:1:4 (SEQ ID NO: 48). | pMON140882, PCR0145915, pMON129212, pMON131963 |
| P-Zm.UbqM1-1:1:4 (Allele-2) | 46 | 887 | *Z. mays* subsp. *mexicana* | promoter | |
| L-Zm.UbqM1-1:1:5 (Allele-2) | 47 | 77 | *Z. mays* subsp. *mexicana* | leader | |
| I-Zm.UbqM1-1:1:4 (Allele-2) | 48 | 1007 | *Z. mays* subsp. *mexicana* | intron | |
| EXP-Zm.UbqM1:1:2 (Allele-3) | 49 | 2005 | *Z. mays* subsp. *mexicana* | EXP: P-Zm.UbqM1-1:1:5 (SEQ ID NO: 50); L-Zm.UbqM1-1:1:4 (SEQ ID NO: 51); I-Zm.UbqM1-1:1:11 (SEQ ID NO: 52). | PCR0145916, pMON129211, pMON131962, pMON132047 |
| P-Zm.UbqM1-1:1:5 (Allele-3) | 50 | 877 | *Z. mays* subsp. *mexicana* | promoter | |
| L-Zm.UbqM1-1:1:4 (Allele-3) | 51 | 78 | *Z. mays* subsp. *mexicana* | leader | |
| I-Zm.UbqM1-1:1:11 (Allele-3) | 52 | 1050 | *Z. mays* subsp. *mexicana* | intron | |
| EXP-Zm.UbqM1:1:5 (Allele-3) | 53 | 2005 | *Z. mays* subsp. *mexicana* | EXP: P-Zm.UbqM1-1:1:5 (SEQ ID NO: 50); L-Zm.UbqM1-1:1:4 (SEQ ID NO: 51); I-Zm.UbqM1-1:1:12 (SEQ ID NO: 54). | |
| I-Zm.UbqM1-1:1:12 (Allele-3) | 54 | 1050 | *Z. mays* subsp. *mexicana* | intron | |
| EXP-Sb.Ubq4:1:1 | 55 | 1632 | *S. bicolor* | EXP: P-Sb.Ubq4-1:1:1 (SEQ ID NO: 56); L-Sb.Ubq4-1:1:1 (SEQ ID NO: 57); I-Sb.Ubq4-1:1:1 (SEQ ID NO: 58). | pMON140886, PCR0145921, pMON129219, pMON132932 |
| P-Sb.Ubq4-1:1:1 | 56 | 401 | *S. bicolor* | promoter | |
| L-Sb.Ubq4-1:1:1 | 57 | 154 | *S. bicolor* | leader | |
| I-Sb.Ubq4-1:1:1 | 58 | 1077 | *S. bicolor* | intron | |
| EXP-Sb.Ubq6 | 59 | 2000 | *S. bicolor* | EXP: P-Sb.Ubq6-1:1:2 (SEQ ID NO: 60); L-Sb.Ubq6-1:1:1 (SEQ ID NO: 61); I-Sb.Ubq6-1:1:1 (SEQ ID NO: 62). | |
| P-Sb.Ubq6-1:1:2 | 60 | 791 | *S. bicolor* | promoter | |
| L-Sb.Ubq6-1:1:1 | 61 | 136 | *S. bicolor* | leader | |
| I-Sb.Ubq6-1:1:1 | 62 | 1073 | *S. bicolor* | intron | |
| EXP-Sb.Ubq6:1:1 | 63 | 2064 | *S. bicolor* | EXP: P-Sb.Ubq6-1:1:1 (SEQ ID NO: 64); L-Sb.Ubq6-1:1:1 (SEQ ID NO: 61); I-Sb.Ubq6-1:1:1 (SEQ ID NO: 62). | pMON140887, PCR0145920, pMON129218 |
| P-Sb.Ubq6-1:1:1 | 64 | 855 | *S. bicolor* | promoter | |
| EXP-Sb.Ubq7-1:1:1 | 65 | 2000 | *S. bicolor* | EXP: P-Sb.Ubq7-1:1:1 (SEQ ID NO: 66); L-Sb.Ubq7-1:1:1 (SEQ ID NO: 67); I-Sb.Ubq7-1:1:1 (SEQ ID NO: 68). | pMON132974 |
| P-Sb.Ubq7-1:1:1 | 66 | 565 | *S. bicolor* | promoter | |
| L-Sb.Ubq7-1:1:1 | 67 | 77 | *S. bicolor* | leader | |
| I-Sb.Ubq7-1:1:1 | 68 | 1358 | *S. bicolor* | intron | |
| EXP-SETit.Ubq1:1:1 | 69 | 2622 | *S. italica* | EXP: P-SETit.Ubq1-1:1:1 (SEQ ID NO: 70); L-SETit.Ubq1-1:1:1 (SEQ ID NO: 71); I-SETit.Ubq1-1:1:1 (SEQ ID NO: 72). | pMON140877, PCR0145900, pMON129200 |
| P-SETit.Ubq1-1:1:1 | 70 | 1492 | *S. italica* | promoter | |
| L-SETit.Ubq1-1:1:1 | 71 | 127 | *S. italica* | leader | |
| I-SETit.Ubq1-1:1:1 | 72 | 1003 | *S. italica* | intron | |

TABLE 1-continued

Transcriptional regulatory expression element groups ("EXP's"),
promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| EXP-SETit.Ubq1:1:4 | 73 | 2622 | S. italica | EXP: P-SETit.Ubq1-1:1:4 (SEQ ID NO: 74); L-SETit.Ubq1-1:1:1 (SEQ ID NO: 71); I-SETit.Ubq1-1:1:1 (SEQ ID NO: 72). | pMON132037 |
| P-SETit.Ubq1-1:1:4 | 74 | 1492 | S. italica | promoter | |
| EXP-SETit.Ubq1:1:2 | 75 | 2164 | S. italica | EXP: P-SETit.Ubq1-1:1:2 (SEQ ID NO: 76); L-SETit.Ubq1-1:1:1 (SEQ ID NO: 71); I-SETit.Ubq1-1:1:1 (SEQ ID NO: 72). | |
| P-SETit.Ubq1-1:1:2 | 76 | 1034 | S. italica | promoter | |
| EXP-SETit.Ubq1:1:3 | 77 | 1810 | S. italica | EXP: P-SETit.Ubq1-1:1:3 (SEQ ID NO: 78); L-SETit.Ubq1-1:1:1 (SEQ ID NO: 71); I-SETit.Ubq1-1:1:1 (SEQ ID NO: 72). | PCR0145905, pMON129202, pMON131957 |
| P-SETit.Ubq1-1:1:3 | 78 | 680 | S. italica | promoter | |
| EXP-Cl.Ubq1:1:1 | 79 | 1940 | C. lacryma-jobi | EXP: P-Cl.Ubq1-1:1:1 (SEQ ID NO: 80); L-Cl.Ubq1-1:1:1 (SEQ ID NO: 81); I-Cl.Ubq1-1:1:1 (SEQ ID NO: 82). | pMON140889, PCR0145922, pMON140913, PCR19, pMON129221, pMON146795, pMON146796, pMON146797, pMON146798, pMON146799, pMON132047, pMON146800, pMON146801, pMON146802 |
| P-Cl.Ubq1-1:1:1 | 80 | 837 | C. lacryma-jobi | promoter | |
| L-Cl.Ubq1-1:1:1 | 81 | 86 | C. lacryma-jobi | leader | |
| I-Cl.Ubq1-1:1:1 | 82 | 1017 | C. lacryma-jobi | intron | |
| EXP-Cl.Ubq1:1:3 | 83 | 1845 | C. lacryma-jobi | EXP: P-Cl.Ubq1-1:1:4 (SEQ ID NO: 84); L-Cl.Ubq1-1:1:1 (SEQ ID NO: 81); I-Cl.Ubq1-1:1:1 (SEQ ID NO: 82). | PCR0145945, pMON140914, PCR20 |
| P-Cl.Ubq1-1:1:4 | 84 | 742 | C. lacryma-jobi | promoter | |
| EXP-Cl.Ubq1:1:4 | 85 | 1504 | C. lacryma-jobi | EXP: P-Cl.Ubq1-1:1:3 (SEQ ID NO: 86); L-Cl.Ubq1-1:1:1 (SEQ ID NO: 81); I-Cl.Ubq1-1:1:1 (SEQ ID NO: 82). | PCR0145946, pMON140915, PCR21 |
| P-Cl.Ubq1-1:1:3 | 86 | 401 | C. lacryma-jobi | promoter | |
| EXP-Cl.Ubq1:1:5 | 87 | 1157 | C. lacryma-jobi | EXP: P-Cl.Ubq1-1:1:5 (SEQ ID NO: 88); L-Cl.Ubq1-1:1:1 (SEQ ID NO: 81); I-Cl.Ubq1-1:1:1 (SEQ ID NO: 82). | PCR0145947, pMON140916, PCR22 |
| P-Cl.Ubq1-1:1:5 | 88 | 54 | C. lacryma-jobi | promoter | |
| E-Cl.Ubq1-1:1:1 | 89 | 798 | C. lacryma-jobi | enhancer | |
| EXP-Cl.Ubq1:1:12 | 90 | 3393 | C. lacryma-jobi | EXP: P-Cl.Ubq1-1:1:9 (SEQ ID NO: 91); L-Cl.Ubq1-1:1:1 (SEQ ID NO: 81); I-Cl.Ubq1-1:1:7 (SEQ ID NO: 92) | pMON142729 |
| P-Cl.Ubq1-1:1:9 | 91 | 2287 | C. lacryma-jobi | Promoter | |
| I-Cl.Ubq1-1:1:7 | 92 | 1020 | C. lacryma-jobi | Intron | |
| EXP-Cl.Ubq1:1:16 | 93 | 3393 | C. lacryma-jobi | EXP: P-Cl.Ubq1-1:1:9 (SEQ ID NO: 91); L-Cl.Ubq1-1:1:1 (SEQ ID NO: 81); I-Cl.Ubq1-1:1:6 (SEQ ID NO: 94) | pMON146750, pMON142748 |
| I-Cl.Ubq1-1:1:6 | 94 | 1020 | C. lacryma-jobi | Intron | |
| EXP-Cl.Ubq1:1:11 | 95 | 2166 | C. lacryma-jobi | EXP: P-Cl.Ubq1-1:1:10 (SEQ ID NO: 96); L-Cl.Ubq1-1:1:1 (SEQ ID NO: 81); I-Cl.Ubq1-1:1:7 (SEQ ID NO: 92) | pMON142730 |
| P-Cl.Ubq1-1:1:10 | 96 | 1060 | C. lacryma-jobi | Promoter | |
| EXP-Cl.Ubq1:1:17 | 97 | 2166 | C. lacryma-jobi | EXP: P-Cl.Ubq1-1:1:10 (SEQ ID NO: 96); L-Cl.Ubq1-1:1:1 (SEQ ID NO: 81); I-Cl.Ubq1-1:1:6 (SEQ ID NO: 94) | pMON146751, pMON142749 |
| EXP-Cl.Ubq1:1:10 | 98 | 1943 | C. lacryma-jobi | EXP: P-Cl.Ubq1-1:1:1 (SEQ ID NO: 80); L-Cl.Ubq1-1:1:1 (SEQ ID NO: 81); I-Cl.Ubq1-1:1:6 (SEQ ID NO: 94) | pMON140889, PCR0145922, pMON140913, PCR19, pMON129221 |
| EXP-Cl.Ubq1:1:18 | 99 | 1943 | C. lacryma-jobi | EXP: P-Cl.Ubq1-1:1:1 (SEQ ID NO: 80); L-Cl.Ubq1-1:1:1 (SEQ ID NO: 81); I-Cl.Ubq1-1:1:7 (SEQ ID NO: 92) | pMON146795 |
| EXP-Cl.Ubq1:1:19 | 100 | 1943 | C. lacryma-jobi | EXP: P-Cl.Ubq1-1:1:1 (SEQ ID NO: 80); L-Cl.Ubq1-1:1:1 (SEQ ID NO: 81); I-Cl.Ubq1-1:1:8 (SEQ ID NO: 101) | pMON146796 |
| I-Cl.Ubq1-1:1:8 | 101 | 1020 | C. lacryma-jobi | Intron | |
| EXP-Cl.Ubq1:1:20 | 102 | 1943 | C. lacryma-jobi | EXP: P-Cl.Ubq1-1:1:1 (SEQ ID NO: 80); L-Cl.Ubq1-1:1:1 (SEQ ID NO: 81); I-Cl.Ubq1-1:1:9 (SEQ ID NO: 103) | pMON146797 |

TABLE 1-continued

Transcriptional regulatory expression element groups ("EXP's"),
promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| I-Cl.Ubq1-1:1:9 | 103 | 1020 | *C. lacryma-jobi* | Intron | |
| EXP-Cl.Ubq1:1:21 | 104 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:10 (SEQ ID NO: 105) | pMON146798 |
| I-Cl.Ubq1-1:1:10 | 105 | 1020 | *C. lacryma-jobi* | Intron | |
| EXP-Cl.Ubq1:1:22 | 106 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:11 (SEQ ID NO: 107) | pMON146799 |
| I-Cl.Ubq1-1:1:11 | 107 | 1020 | *C. lacryma-jobi* | Intron | |
| EXP-Cl.Ubq1:1:23 | 108 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:12 (SEQ ID NO: 109) | pMON132047, pMON146800 |
| I-Cl.Ubq1-1:1:12 | 109 | 1020 | *C. lacryma-jobi* | Intron | |
| EXP-Cl.Ubq1:1:24 | 110 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:13 (SEQ ID NO: 111) | pMON146801 |
| I-Cl.Ubq1-1:1:13 | 111 | 1020 | *C. lacryma-jobi* | Intron | |
| EXP-Cl.Ubq1:1:25 | 112 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:14 (SEQ ID NO: 113) | pMON146802 |
| I-Cl.Ubq1-1:1:14 | 113 | 1020 | *C. lacryma-jobi* | Intron | |
| EXP-Cl.Ubq1:1:13 | 114 | 1848 | *C. lacryma-jobi* | EXP: P-Cl.Ubq1-1:1:4 (SEQ ID NO: 84); L-Cl.Ubq1-1:1:1 (SEQ ID NO: 81); I-Cl.Ubq1-1:1:6 (SEQ ID NO: 94) | PCR0145945, pMON140914, PCR20 |
| EXP-Cl.Ubq1:1:14 | 115 | 1507 | *C. lacryma-jobi* | EXP: P-Cl.Ubq1-1:1:3 (SEQ ID NO: 86); L-Cl.Ubq1-1:1:1 (SEQ ID NO: 81); I-Cl.Ubq1-1:1:6 (SEQ ID NO: 94) | PCR0145946, pMON140915, PCR21 |
| EXP-Cl.Ubq1:1:15 | 116 | 1160 | *C. lacryma-jobi* | EXP: P-Cl.Ubq1-1:1:5 (SEQ ID NO: 88); L-Cl.Ubq1-1:1:1 (SEQ ID NO: 81); I-Cl.Ubq1-1:1:6 (SEQ ID NO: 94) | PCR0145947, pMON140916, PCR22 |
| EXP-SETit.Ubq1:1:5 | 117 | 2625 | *S. italica* | EXP: P-SETit.Ubq1-1:1:1 (SEQ ID NO: 70); L-SETit.Ubq1-1:1:1 (SEQ ID NO: 71); I-SETit.Ubq1-1:1:2 (SEQ ID NO: 118) | pMON140877, PCR0145900, pMON129200 |
| I-SETit.Ubq1-1:1:2 | 118 | 1006 | *S. italica* | Intron | |
| EXP-SETit.Ubq1:1:10 | 119 | 2625 | *S. italica* | EXP: P-SETit.Ubq1-1:1:4 (SEQ ID NO: 64); L-SETit.Ubq1-1:1:1 (SEQ ID NO: 71); I-SETit.Ubq1-1:1:3 (SEQ ID NO: 120) | pMON132037 |
| I-SETit.Ubq1-1:1:3 | 120 | 1006 | *S. italica* | Intron | |
| EXP-SETit.Ubq1:1:12 | 121 | 2625 | *S. italica* | EXP: P-SETit.Ubq1-1:1:4 (SEQ ID NO: 64); L-SETit.Ubq1-1:1:1 (SEQ ID NO: 71); I-SETit.Ubq1-1:1:4 (SEQ ID NO: 122) | |
| I-SETit.Ubq1-1:1:4 | 122 | 1006 | *S. italica* | Intron | |
| EXP-SETit.Ubq1:1:7 | 123 | 2167 | *S. italica* | EXP: P-SETit.Ubq1-1:1:2 (SEQ ID NO: 71); L-SETit.Ubq1-1:1:1 (SEQ ID NO: 71); I-SETit.Ubq1-1:1:2 (SEQ ID NO: 118) | PCR0145928, pMON129201 |
| EXP-SETit.Ubq1:1:6 | 124 | 1813 | *S. italica* | EXP: P-SETit.Ubq1-1:1:3 (SEQ ID NO: 73); L-SETit.Ubq1-1:1:1 (SEQ ID NO: 71); I-SETit.Ubq1-1:1:2 (SEQ ID NO: 118) | PCR0145905, pMON129202 |
| EXP-SETit.Ubq1:1:11 | 125 | 1813 | *S. italica* | EXP: P-SETit.Ubq1-1:1:3 (SEQ ID NO: 73); L-SETit.Ubq1-1:1:1 (SEQ ID NO: 71); I-SETit.Ubq1-1:1:3 (SEQ ID NO: 120) | pMON131957 |
| EXP-SETit.Ubq1:1:13 | 126 | 1813 | *S. italica* | EXP: P-SETit.Ubq1-1:1:3 (SEQ ID NO: 73); L-SETit.Ubq1-1:1:1 (SEQ ID NO: 71); I-SETit.Ubq1-1:1:5 (SEQ ID NO: 127) | |
| I-SETit.Ubq1-1:1:5 | 127 | 1006 | *S. italica* | Intron | |
| EXP-Sv.Ubq1:1:7 | 128 | 2634 | *S. viridis* | EXP: P-Sv.Ubq1-1:1:1 (SEQ ID NO: 34); L-Sv.Ubq1-1:1:2 (SEQ ID NO: 35); I-Sv.Ubq1-1:1:2 (SEQ ID NO: 129) | pMON140878, PCR0145909, pMON129203 |
| I-Sv.Ubq1-1:1:2 | 129 | 1014 | *S. viridis* | Intron | |
| EXP-Sv.Ubq1:1:11 | 130 | 2634 | *S. viridis* | EXP: P-Sv.Ubq1-1:1:1 (SEQ ID NO: 34); L-Sv.Ubq1-1:1:2 (SEQ ID NO: 35); I-Sv.Ubq1-1:1:3 (SEQ ID NO: 131) | pMON131958 |
| I-Sv.Ubq1-1:1:3 | 131 | 1014 | *S. viridis* | Intron | |
| EXP-Sv.Ubq1:1:8 | 132 | 2176 | *S. viridis* | EXP: P-Sv.Ubq1-1:1:2 (SEQ ID NO: 38); L-Sv.Ubq1-1:1:2 (SEQ ID NO: 35); I-Sv.Ubq1-1:1:2 (SEQ ID NO: 129) | PCR0145929, pMON129204 |
| EXP-Sv.Ubq1:1:9 | 133 | 1822 | *S. viridis* | EXP: P-Sv.Ubq1-1:1:3 (SEQ ID NO: 40); L-Sv.Ubq1-1:1:2 (SEQ ID NO: 35); I-Sv.Ubq1-1:1:2 (SEQ ID NO: 129) | pMON129205 |
| EXP-Sv.Ubq1:1:10 | 134 | 1822 | *S. viridis* | EXP: P-Sv.Ubq1-1:1:4 (SEQ ID NO: 135); L-Sv.Ubq1-1:1:2 (SEQ ID NO: 35); I-Sv.Ubq1-1:1:2 (SEQ ID NO: 129) | PCR0145911 |

TABLE 1-continued

Transcriptional regulatory expression element groups ("EXP's"),
promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| P-Sv.Ubq1-1:1:4 | 135 | 681 | S. viridis | Promoter | |
| EXP-Sv.Ubq1:1:12 | 136 | 1822 | S. viridis | EXP: P-Sv.Ubq1-1:1:3 (SEQ ID NO: 40); L-Sv.Ubq1-1:1:2 (SEQ ID NO: 35); I-Sv.Ubq1-1:1:3 (SEQ ID NO: 131) | pMON131959 |
| EXP-Zm.UbqM1:1:6 (Allele-1) | 137 | 1925 | Z. mays subsp. Mexicana | EXP: P-Zm.UbqM1-1:1:1 (SEQ ID NO: 42); L-Zm.UbqM1-1:1:1 (SEQ ID NO: 43); I-Zm.UbqM1-1:1:13 (SEQ ID NO: 138) | pMON140881, PCR0145914, pMON129210 |
| I-Zm.UbqM1-1:1:13 (Allele-1) | 138 | 997 | Z. mays subsp. Mexicana | Intron | |
| EXP-Zm.UbqM1:1:10 (Allele-1) | 139 | 1925 | Z. mays subsp. Mexicana | EXP: P-Zm.UbqM1-1:1:1 (SEQ ID NO: 42); L-Zm.UbqM1-1:1:1 (SEQ ID NO: 43); I-Zm.UbqM1-1:1:17 (SEQ ID NO: 140) | pMON131961 |
| I-Zm.UbqM1-1:1:17 (Allele-1) | 140 | 997 | Z. mays subsp. Mexicana | Intron | |
| EXP-Zm.UbqM1:1:7 (Allele-2) | 141 | 1974 | Z. mays subsp. Mexicana | EXP: P-Zm.UbqM1-1:1:4 (SEQ ID NO: 46); L-Zm.UbqM1-1:1:5 (SEQ ID NO: 47); I-Zm.UbqM1-1:1:14 (SEQ ID NO: 142) | pMON140882, PCR0145915, pMON129212 |
| I-Zm.UbqM1-1:1:14 (Allele-2) | 142 | 1010 | Z. mays subsp. Mexicana | Intron | |
| EXP-Zm.UbqM1:1:12 (Allele-2) | 143 | 1974 | Z. mays subsp. Mexicana | EXP: P-Zm.UbqM1-1:1:4 (SEQ ID NO: 46); L-Zm.UbqM1-1:1:5 (SEQ ID NO: 47); I-Zm.UbqM1-1:1:19 (SEQ ID NO: 144) | pMON131963 |
| I-Zm.UbqM1-1:1:19 (Allele-2) | 144 | 1010 | Z. mays subsp. Mexicana | Intron | |
| EXP-Zm.UbqM1:1:8 (Allele-3) | 145 | 2008 | Z. mays subsp. Mexicana | EXP: P-Zm.UbqM1-1:1:5 (SEQ ID NO: 50); L-Zm.UbqM1-1:1:4 (SEQ ID NO: 51); I-Zm.UbqM1-1:1:15 (SEQ ID NO: 146) | PCR0145916, pMON129211 |
| I-Zm.UbqM1-1:1:15 (Allele-3) | 146 | 1053 | Z. mays subsp. Mexicana | Intron | |
| EXP-Zm.UbqM1:1:9 (Allele-3) | 147 | 2008 | Z. mays subsp. Mexicana | EXP: P-Zm.UbqM1-1:1:5 (SEQ ID NO: 50); L-Zm.UbqM1-1:1:4 (SEQ ID NO: 51); I-Zm.UbqM1-1:1:16 (SEQ ID NO: 148) | |
| I-Zm.UbqM1-1:1:16 (Allele-3) | 148 | 1053 | Z. mays subsp. Mexicana | Intron | |
| EXP-Zm.UbqM1:1:11 (Allele-3) | 149 | 2008 | Z. mays subsp. Mexicana | EXP: P-Zm.UbqM1-1:1:5 (SEQ ID NO: 50); L-Zm.UbqM1-1:1:4 (SEQ ID NO: 51); I-Zm.UbqM1-1:1:18 (SEQ ID NO: 150) | pMON131962, pMON132047 |
| I-Zm.UbqM1-1:1:18 (Allele-3) | 150 | 1053 | Z. mays subsp. Mexicana | Intron | |
| EXP-Sb.Ubq4:1:2 | 151 | 1635 | S. bicolor | EXP: P-Sb.Ubq4-1:1:1 (SEQ ID NO: 56); L-Sb.Ubq4-1:1:1 (SEQ ID NO: 57); I-Sb.Ubq4-1:1:2 (SEQ ID NO: 152) | pMON140886, PCR0145921, pMON129219, pMON132932 |
| I-Sb.Ubq4-1:1:2 | 152 | 1080 | S. bicolor | Intron | |
| EXP-Sb.Ubq6:1:2 | 153 | 2067 | S. bicolor | EXP: P-Sb.Ubq6-1:1:1 (SEQ ID NO: 64); L-Sb.Ubq6-1:1:1 (SEQ ID NO: 57); I-Sb.Ubq6-1:1:2 (SEQ ID NO: 154) | pMON140887, PCR0145920, pMON129218, pMON132931 |
| I-Sb.Ubq6-1:1:2 | 154 | 1076 | S. bicolor | Intron | |
| EXP-Sb.Ubq6:1:3 | 155 | 2067 | S. bicolor | EXP: P-Sb.Ubq6-1:1:1 (SEQ ID NO: 64); L-Sb.Ubq6-1:1:1 (SEQ ID NO: 57); I-Sb.Ubq6-1:1:3 (SEQ ID NO: 1569) | pMON132931 |
| I-Sb.Ubq6-1:1:3 | 156 | 1076 | S. bicolor | Intron | |
| EXP-Sb.Ubq7:1:2 | 157 | 2003 | S. bicolor | EXP: P-Sb.Ubq7-1:1:1 (SEQ ID NO: 66); L-Sb.Ubq7-1:1:1 (SEQ ID NO: 67); I-Sb.Ubq7-1:1:A (SEQ ID NO: 158) | pMON132974 |
| I-Sb.Ubq7-1:1:2 | 158 | 1361 | S. bicolor | Intron | |
| EXP-SETit.Ubq1:1:E | 180 | 2625 | S. italica | EXP: P-SETit.Ubq1-1:1:4 (SEQ ID NO: 64); L-SETit.Ubq1-1:1:1 (SEQ ID NO: 71); I-SETit.Ubq1-1:1:5 (SEQ ID NO: 127) | |
| EXP-Zm.UbqM1:1:13 (Allele-3) | 181 | 2008 | Z. mays subsp. Mexicana | EXP: P-Zm.UbqM1-1:1:5 (SEQ ID NO: 50); L-Zm.UbqM1-1:1:4 (SEQ ID NO: 51); I-Zm.UbqM1-1:1:20 (SEQ ID NO: 182) | |
| I-Zm.UbqM1-1:1:20 (Allele-3) | 182 | 1053 | Z. mays subsp. Mexicana | Intron | |
| EXP-SETit.Ubq1:1:9 | 183 | 2625 | S. italica | EXP: P-SETit.Ubq1-1:1:4 (SEQ ID NO: 64); L-SETit.Ubq1-1:1:1 (SEQ ID NO: 71); I-SETit.Ubq1-1:1:2 (SEQ ID NO: 118) | |

As shown in Table 1, for example, the transcriptional regulatory EXP sequence designated EXP-ANDge.Ubq1:1:9 (SEQ ID NO: 1), with components isolated from *A. gerardii*, comprises a promoter element, P-ANDge.Ubq1-1:1:11 (SEQ ID NO: 2), operably linked 5' to a leader element, L-ANDge.Ubq1-1:1:2 (SEQ ID NO: 3), operably linked 5' to an intron element, I-ANDge.Ubq1-1:1:3 (SEQ ID NO: 4). Other EXP's are linked similarly, as outlined in Table 1.

As shown in Table 1, the sequence listing and FIGS. 1-7, variants of promoter sequences from the species *A. gerardii*, *E. ravennae*, *Z. mays* subsp. *mexicana*, *S. bicolor*, *C. lacryma-jobi*, *S. italica*, and *S. viridis* were engineered which comprise shorter promoter fragments of, for instance, P-ANDge.Ubq1-1:1:11 (SEQ ID NO:2), P-ERIra.Ubq1-1:1:10 (SEQ ID NO:19) or other respective promoters from other species, and for instance resulting in P-ANDge.Ubq1-1:1:9 (SEQ ID NO: 6), P-ERIra.Ubq1-1:1:9 (SEQ ID NO: 23), P-Cl.Ubq1-1:1:10 (SEQ ID NO: 96), P-SETit.Ubq1-1:1:2 (SEQ ID NO: 76) and P-Sv.Ubq1-1:1:2 (SEQ ID NO: 38), as well as other promoter fragments. P-SETit.Ubq1-1:1:4 (SEQ ID NO: 74) comprises a single nucleotide change relative to P-SETit.Ubq1-1:1:1 (SEQ ID NO: 70). Likewise, P-Sv.Ubq1-1:1:3 (SEQ ID NO: 40) comprises a single nucleotide change relative to P-Sv.Ubq1-1:1:4 (SEQ ID NO: 135).

In some instances, variants of specific introns were created by altering the last 3' nucleotides of each respective intron following the sequence 5'-AG-3' of the 3' intron splice junction. These intron variants are shown in Table 2 below.

TABLE 2

3' end sequence of intron variants.

| Annotation | SEQ ID NO: | Intron 3' end nucleotides immediately following 3' splice site AG |
|---|---|---|
| I-Cl.Ubq1-1:1:7 | 92 | GTG |
| I-Cl.Ubq1-1:1:6 | 94 | GTC |
| I-Cl.Ubq1-1:1:8 | 101 | GCG |
| I-Cl.Ubq1-1:1:9 | 103 | GAC |
| I-Cl.Ubq1-1:1:10 | 105 | ACC |
| I-Cl.Ubq1-1:1:11 | 107 | GGG |
| I-Cl.Ubq1-1:1:12 | 109 | GGT |
| I-Cl.Ubq1-1:1:13 | 111 | CGT |
| I-Cl.Ubq1-1:1:14 | 113 | TGT |
| I-SETit.Ubq1-1:1:2 | 118 | GTG |
| I-SETit.Ubq1-1:1:3 | 120 | GGT |
| I-SETit.Ubq1-1:1:4 | 122 | ACC |
| I-SETit.Ubq1-1:1:5 | 127 | GGC |
| I-Sv.Ubq1-1:1:2 | 129 | GTG |
| I-Sv.Ubq1-1:1:3 | 131 | GGT |
| I-Zm.UbqM1-1:1:13 (Allele-1) | 138 | GTC |
| I-Zm.UbqM1-1:1:17 (Allele-1) | 140 | GGT |
| I-Zm.UbqM1-1:1:14 (Allele-2) | 142 | GTC |
| I-Zm.UbqM1-1:1:19 (Allele-2) | 144 | GGT |
| I-Zm.UbqM1-1:1:15 (Allele-3) | 146 | GTC |
| I-Zm.UbqM1-1:1:18 (Allele-3) | 148 | GGT |
| I-Sb.Ubq6-1:1:2 | 154 | GTG |
| I-Sb.Ubq6-1:1:3 | 156 | GGT |
| I-Zm.UbqM1-1:1:20 (Allele-3) | 182 | CGG |

Also listed in Table 1 are three allelic variants isolated using the same primer sets designed for amplification of genomic DNA from *Z. mays* subsp. *mexicana*. Allelic variants of the EXP sequences are comprised of sequence that shares some identity within various regions of other sequences, but insertions, deletions and nucleotide mismatches may also be apparent within each promoter, leader and/or intron of each of the EXP sequences. The EXP sequence designated EXP-Zm.UbgM1:1:1 (SEQ ID NO: 41) represents a first allele (Allele-1) of the *Z. mays* subsp. *mexicana* Ubq1 gene transcriptional regulatory expression element group. The EXP sequences designated EXP-Zm.UbgM1:1:6 (SEQ ID NO: 137) and EXP-Zm.UbgM1:1:10 (SEQ ID NO: 139) represent a first allele (Allele-1), with the only difference between the two EXPs occurring in the last 3' nucleotides of each respective intron following the sequence 5'-AG-3' of the 3' intron splice junction. The EXP sequence designated EXP-Zm.UbgM1:1:4 (SEQ ID NO: 45) represents a second allele (Allele-2) of the *Z. mays* subsp. *mexicana* Ubq1 gene transcriptional regulatory expression element group. The EXP sequences designated EXP-Zm.UbgM1:1:7 (SEQ ID NO: 141) and EXP-Zm.UbgM1:1:12 (SEQ ID NO: 143) represent a second allele (Allele-2), with the only difference between the two EXPs occurring in the last 3' nucleotides of each respective intron following the sequence 5'-AG-3' of the 3' intron splice junction. The EXP sequences EXP-Zm.UbgM1:1:2 (SEQ ID NO: 49) and EXP-Zm.UbgM1:1:5 (SEQ ID NO: 53) represents a third allel (Allele-3) of the *Z. mays* subsp. *mexicana* Ubq1 gene transcriptional regulatory expression element group and comprise a single nucleotide difference at position 1034 within their respective introns (G for I-Zm.UbgM1-1:1:11, SEQ ID NO: 52 and T for I-Zm.UbgM1-1:1:12, SEQ ID NO: 54). The EXP sequences designated EXP-Zm.UbgM1:1:8 (SEQ ID NO: 145), EXP-Zm.UbgM1:1:9 (SEQ ID NO: 147), EXP-Zm.UbgM1:1:11 (SEQ ID NO: 149) and EXP-Zm.UbgM1:1:13 (SEQ ID NO: 181) also represent a third allele (Allele-3). The intron of EXP-Zm.UbgM1:1:9, I-Zm.UbgM1-1:1:16 (SEQ ID NO: 148) comprises a thymine residue at position 1034, while the introns of EXP-Zm.UbgM1:1:8, EXP-Zm.UbgM1:1:11 and EXP-Zm.UbgM1:1:13 (I-Zm.UbgM1-1:1:15, SEQ ID NO: 146; I-Zm.UbgM1-1:1:18, SEQ ID NO: 11 and; I-Zm.UbgM1-1:1:20, SEQ ID NO: 182) each comprise a guanine residue at position 1034. In addition, the last 3, 3' end nucleotides of EXP-Zm.UbgM1:1:8 (SEQ ID NO: 145) and EXP-Zm.UbgM1:1:9 (SEQ ID NO: 147) differ from those of EXP-Zm.UbgM1:1:11 (SEQ ID NO: 149) and EXP-Zm.UbgM1:1:13 (SEQ ID NO: 181).

Example 2: Analysis of Regulatory Elements Driving GUS in Corn Protoplasts

Corn leaf protoplasts were transformed with plant expression vectors containing an EXP sequence driving expression of the β-glucuronidase (GUS) transgene and compared to GUS expression in leaf protoplasts in which expression of GUS is driven by known constitutive promoters.

Expression of a transgene driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) was compared with expression from known constitutive promoters. The foregoing EXP sequences were cloned into plant expression vectors as shown in Table 3 below to yield vectors in which an EXP sequence is operably linked 5' to a β-glucuronidase (GUS) reporter that contained a processable intron (referred to as GUS-2, SEQ ID NO: 160) derived from the potato light-inducible tissue-specific ST-LS1 gene (GenBank Accession: X04753) or a contiguous GUS coding sequence (GUS-1, SEQ ID NOS: 159), which was operably linked 5' to a 3' UTR derived from the *A. tumefaciens* Nopaline synthase gene (T-AGRtu.nos-1:1:13, SEQ ID NO: 161) or the wheat Hsp17 gene (T-Ta.Hsp17-1:1:1, SEQ ID NO: 162).

TABLE 3

GUS plant expression plasmid construct and corresponding EXP sequence, GUS coding sequence and 3' UTR used for transformation of corn leaf protoplasts. "SEQ ID NO:" refers to given EXP sequence.

| Plasmid | EXP sequence | SEQ ID NO: | GUS | 3' UTR |
|---|---|---|---|---|
| pMON19469 | EXP-CaMV.35S-enh + Zm.DnaK:1:1 | 170 | GUS-1 | T-AGRtu.nos-1:1:13 |
| pMON65328 | EXP-CaMV.35S-enh + Ta.Lhcb1 + Os.Act1:1:1 | 163 | GUS-2 | T-Ta.Hsp17-1:1:1 |
| pMON25455 | EXP-Os.Act1:1:9 | 179 | GUS-1 | T-AGRtu.nos-1:1:13 |
| pMON122605 | EXP-Os.TubA-3:1:1 | 165 | GUS-1 | T-AGRtu.nos-1:1:13 |
| pMON136264 | EXP-ANDge.Ubq1:1:7 | 5 | GUS-1 | T-AGRtu.nos-1:1:13 |
| pMON136259 | EXP-ANDge.Ubq1:1:6 | 12 | GUS-1 | T-AGRtu.nos-1:1:13 |
| pMON136263 | EXP-ERIra.Ubq1:1:9 | 22 | GUS-1 | T-AGRtu.nos-1:1:13 |
| pMON136258 | EXP-ERIra.Ubq1:1:8 | 27 | GUS-1 | T-AGRtu.nos-1:1:13 |

Control plasmids (pMON19469, pMON65328, pMON25455 and pMON122605) used for comparison were constructed as described above and contain a known EXP sequence: EXP-CaMV.35S-enh+Zm.DnaK:1:1 (SEQ ID NO: 170), EXP-CaMV.35S-enh+Ta.Lhcb1+Os.Act1:1:1 (SEQ ID NO: 163), EXP-Os.Act1:1:9 (SEQ ID NO: 179), or EXP-Os.TubA-3:1:1 (SEQ ID NO: 165), respectively, operably linked 5' to a GUS coding sequence and 3' UTR. Three additional controls were provided to assess background GUS and luciferase expression: a no DNA control, an empty vector which is not designed for transgene expression, and an expression vector used to express green fluorescent protein (GFP).

Two plasmids, for use in co-transformation and normalization of data, were also constructed using methods known in the art. Each plasmid contained a specific luciferase coding sequence that was driven by a constitutive EXP sequence. The plant vector pMON19437 comprises a transgene cassette with a constitutive promoter operably linked 5' to an intron, (EXP-CaMV.35S-enh+Zm.DnaK:1:1, SEQ ID NO: 170), operably linked 5' to a firefly (*Photinus pyralis*) luciferase coding sequence (LUCIFERASE:1:3, SEQ ID NO: 166), operably linked 5' to a 3' UTR from the *Agrobacterium tumefaciens* nopaline synthase gene (T-AGRtu.nos-1:1:13, SEQ ID NO: 161). The plant vector pMON63934 comprises a transgene cassette with a constitutive EXP sequence (EXP-CaMV.35S-enh-Lhcb1, SEQ ID NO: 168), operably linked 5' to a sea pansy (*Renilla reniformis*) luciferase coding sequence (CR-Ren.hRenilla Lucife-0:0:1, SEQ ID NO: 167), operably linked 5' to a 3' UTR from the *Agrobacterium tumefaciens* nopaline synthase gene (T-AGRtu.nos-1:1:13, SEQ ID NO: 161).

Corn leaf protoplasts were transformed using a PEG-based transformation method, as is well known in the art. Protoplast cells were transformed with pMON19437 plasmid DNA, pMON63934 plasmid DNA, and an equimolar quantity of one of the plasmids presented in Table 3 and incubated overnight in total darkness. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, WI; see for example, Promega Notes Magazine, No: 57, 1996, p. 02). One or two transformations for each EXP sequence were performed and the mean expression values for each EXP sequence determined from several samples from each transformation experiment. Sample measurements were made using four replicates of each EXP sequence construct transformation, or alternatively, three replicates of each EXP sequence construct per one of two transformation experiments. The mean GUS and luciferase expression levels are provided in Table 4. In this table, the firefly luciferase values (e.g. from expression of pMON19437) are provided in the column labeled "FLuc" and the *Renilla* luciferase values are provided as in the column labeled "RLuc."

TABLE 4

Mean GUS and Luciferase activity in transformed corn leaf protoplast cells.

| Plasmid | EXP sequence | SEQ ID NO: | Gus | RLuc | FLuc |
|---|---|---|---|---|---|
| pMON19469 | EXP-CaMV.35S-enh + Zm.DnaK:1:1 | 170 | 789147 | 298899 | 36568 |
| pMON65328 | EXP-CaMV.35S-enh + Ta.Lhcb1 + Os.Act1:1:1 | 163 | 508327 | 158227 | 17193 |
| pMON25455 | EXP-Os.Act1:1:9 | 179 | 460579 | 183955 | 53813 |
| pMON122605 | EXP-Os.TubA-3:1:1 | 165 | 25082 | 25821 | 21004 |
| pMON136264 | EXP-ANDge.Ubq1:1:7 | 5 | 926083 | 101213 | 23704 |
| pMON136259 | EXP-ANDge.Ubq1:1:6 | 12 | 845274 | 193153 | 51479 |
| pMON136263 | EXP-ERIra.Ubq1:1:9 | 22 | 901985 | 132765 | 41313 |
| pMON136258 | EXP-ERIra.Ubq1:1:8 | 27 | 1011447 | 210635 | 66803 |

To compare the relative activity of each EXP sequence, GUS values were expressed as a ratio of GUS to luciferase activity and normalized with respect to the expression levels observed for the EXP sequence EXP-Os.TubA-3:1:1 (SEQ ID NO: 165). Table 5 below shows the GUS/RLuc ratios of expression normalized with respect to EXP-Os.TubA-3:1:1 expression in corn protoplasts.

As can be seen in Table 5, GUS expression, driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) was 4.51 to 9.42 fold higher than GUS expression driven by EXP-Os.TubA-3:1:1 (SEQ ID NO: 165). GUS expression driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) was also higher than that of EXP-CaMV.35S-enh+Zm.DnaK:1:1 (SEQ ID NO: 170), EXP-CaMV.35S-enh+Ta.Lhcb1+Os.Act1:1:1 (SEQ ID NO: 163), or EXP-Os-.Act1:1:9 (SEQ ID NO: 179).

ratio of GUS/FLuc values and is normalized with respect to EXP-Os.TubA-3:1:1 (SEQ ID NO: 165). Expression was 12.69 to 32.86 fold higher than GUS expression driven by EXP-Os.TubA-3:1:1 (SEQ ID NO: 165). GUS expression driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) was also higher in certain comparisons than that of EXP-CaMV.35S-enh+Zm.DnaK:1:1 (SEQ ID NO: 170), EXP-CaMV.35S-enh+Ta.Lhcb1+Os.Act1:1:1 (SEQ ID NO: 163), or EXP-Os.Act1:1:9 (SEQ ID NO: 179).

Example 3: Analysis of Regulatory Elements Driving GUS in Corn Protoplasts Using GUS Transgene Cassette Amplicons Corn leaf protoplasts were transformed with DNA amplicons derived from plant expression vectors containing an EXP sequence, driving expression of the β-glucuronidase

TABLE 5

GUS/RLuc fold expression as relative to EXP-Os.TubA-3:1:1 expression in corn leaf protoplast cells.

| Plasmid | EXP sequence | SEQ ID NO: | Gus/RLuc | Gus/RLuc Normalized with respect to EXP-Os.TubA-3:1:1 |
|---|---|---|---|---|
| pMON19469 | EXP-CaMV.35S-enh + Zm.DnaK:1:1 | 170 | 2.640000 | 2.72 |
| pMON65328 | EXP-CaMV.35S-enh + Ta.Lhcb1 + Os.Act1:1:1 | 163 | 3.210000 | 3.31 |
| pMON25455 | EXP-Os.Act1:1:9 | 179 | 2.500000 | 2.57 |
| pMON122605 | EXP-Os.TubA-3:1:1 | 165 | 0.971000 | 1.00 |
| pMON136264 | EXP-ANDge.Ubq1:1:7 | 5 | 9.150000 | 9.42 |
| pMON136259 | EXP-ANDge.Ubq1:1:6 | 12 | 4.380000 | 4.51 |
| pMON136263 | EXP-ERIra.Ubq1:1:9 | 22 | 6.790000 | 6.99 |
| pMON136258 | EXP-ERIra.Ubq1:1:8 | 27 | 4.800000 | 4.94 |

Table 6 below show GUS/FLuc ratios of expression normalized with respect to EXP-Os.TubA-3:1:1 expression in corn protoplasts.

TABLE 6

GUS/FLuc fold expression as relative to EXP-Os.TubA-3:1:1 expression in corn leaf protoplast cells.

| Plasmid | EXP sequence | SEQ ID NO: | Gus/FLuc | Normalized with respect to EXP-Os.TubA-3:1:1 |
|---|---|---|---|---|
| pMON19469 | EXP-CaMV.35S-enh + Zm.DnaK:1:1 | 170 | 21.600000 | 18.15 |
| pMON65328 | EXP-CaMV.35S-enh + Ta.Lhcb1 + Os.Act1:1:1 | 163 | 29.600000 | 24.87 |
| pMON25455 | EXP-Os.Act1:1:9 | 179 | 8.560000 | 7.19 |
| pMON122605 | EXP-Os.TubA-3:1:1 | 165 | 1.190000 | 1.00 |
| pMON136264 | EXP-ANDge.Ubq1:1:7 | 5 | 39.100000 | 32.86 |
| pMON136259 | EXP-ANDge.Ubq1:1:6 | 12 | 16.400000 | 13.78 |
| pMON136263 | EXP-ERIra.Ubq1:1:9 | 22 | 21.800000 | 18.32 |
| pMON136258 | EXP-ERIra.Ubq1:1:8 | 27 | 15.100000 | 12.69 |

As can be seen in Table 6, GUS expression, driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) demonstrated the same general trend when expressed as (GUS) transgene, and compared to leaf protoplast in which expression of GUS is driven by known constitutive promoters in a series of experiments presented below.

In a first set of experiments, corn protoplast cells, derived from leaf tissue were transformed as above with amplicons produced from amplification of GUS transgene cassettes comprising plant expression vectors to compare expression of a transgene (GUS) driven by one of EXP-ANDge.Ubq1:

1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:1:10 (SEQ ID NO: 134), EXP-Zm.UbgM1:1:6 (SEQ ID NO: 137), EXP-Zm.UbgM1:1:7 (SEQ ID NO: 141), EXP-Sb.Ubg4:1:2 (SEQ ID NO: 151), EXP-Sb.Ubg6:1:2 (SEQ ID NO: 153) and EXP-Cl.Ubq1:1:10 (SEQ ID NO: 98) with that of known constitutive promoters. Each EXP sequence comprising the amplification template from which the transgene cassette amplicon is produced was cloned using methods known in the art into a plant expression vector shown in Table 7 below under the heading of "Amplicon Template." The resulting plant expression vectors comprise a transgene cassette comprised of a EXP sequence, operably linked 5' to a coding sequence for β-glucuronidase (GUS) that either contains a processable intron ("GUS-2" as discussed in Example 2 above), or a contiguous GUS coding sequence ("GUS-1", as discussed above), operably linked 5' to a 3' UTR T-AGRtu.nos-1:1:13 or T-Ta.Hsp17-1:1:1, as also noted above. Amplicons were produced using methods known to those skilled in the art using the plasmid construct templates presented in Table 7 below. Briefly, a 5' oligo-nucleotide primer was designed to anneal to the promoter sequence and a 3' oligonucleotide primer, which anneals at the 3' end of the 3' UTR was used for amplification of each transgene cassette. Successive 5' deletions were introduced into the promoter sequences comprising the transgene cassettes, giving rise to different EXP sequences, by the use of different oligonucleotide primers which were designed to anneal at different positions within the promoter sequence comprising each amplicon template.

TABLE 7

GUS plant expression amplicons and corresponding plasmid construct amplicon templates, EXP sequence, GUS coding sequence and 3' UTR used for transformation of corn leaf protoplasts.

| Amplicon ID | Amplicon Template | EXP sequence | SEQ ID NO: | GUS Coding Sequence | 3' UTR |
|---|---|---|---|---|---|
| PCR0145942 | pMON25455 | EXP-Os.Act1:1:9 | 179 | GUS-1 | T-AGRtu.nos-1:1:13 |
| PCR0145941 | pMON33449 | P-CAMV.35S-ENH-1:1:102/ L-CAMV.35S-1:1:2 | 169 | GUS-1 | T-AGRtu.nos-1:1:13 |
| PCR0145943 | pMON65328 | EXP-CaMV.35S-enh + Ta.Lhcb1 + Os.Act1:1:1 | 163 | GUS-2 | T-Ta.Hsp17-1:1:1 |
| PCR0145944 | pMON81552 | EXP-CaMV.35S-enh + Zm.DnaK:1:1 | 170 | GUS-1 | T-AGRtu.nos-1:1:13 |
| PCR0145892 | pMON136264 | EXP-ANDge.Ubq1:1:7 | 5 | GUS-1 | T-AGRtu.nos-1:1:13 |
| PCR0145815 | pMON136264 | EXP-ANDge.Ubq1:1:10 | 10 | GUS-1 | T-AGRtu.nos-1:1:13 |
| PCR0145893 | pMON136259 | EXP-ANDge.Ubq1:1:6 | 12 | GUS-1 | T-AGRtu.nos-1:1:13 |
| PCR0145817 | pMON136264 | EXP-ANDge.Ubq1:1:11 | 14 | GUS-1 | T-AGRtu.nos-1:1:13 |
| PCR0145819 | pMON136264 | EXP-ANDge.Ubq1:1:12 | 16 | GUS-1 | T-AGRtu.nos-1:1:13 |
| PCR0145896 | pMON136263 | EXP-ERIra.Ubq1:1:9 | 22 | GUS-1 | T-AGRtu.nos-1:1:13 |
| PCR0145820 | pMON136263 | EXP-ERIra.Ubq1:1:10 | 25 | GUS-1 | T-AGRtu.nos-1:1:13 |
| PCR0145897 | pMON136258 | EXP-ERIra.Ubq1:1:8 | 27 | GUS-1 | T-AGRtu.nos-1:1:13 |
| PCR0145821 | pMON136263 | EXP-ERIra.Ubq1:1:11 | 29 | GUS-1 | T-AGRtu.nos-1:1:13 |
| PCR0145822 | pMON136263 | EXP-ERIra.Ubq1:1:12 | 31 | GUS-1 | T-AGRtu.nos-1:1:13 |
| PCR0145900 | pMON140877 | EXP-SETit.Ubq1:1:5 | 117 | GUS-1 | T-AGRtu.nos-1:1:13 |
| PCR0145928 | pMON140877 | EXP-SETit.Ubq1:1:7 | 123 | GUS-1 | T-AGRtu.nos-1:1:13 |
| PCR0145905 | pMON140877 | EXP-SETit.Ubq1:1:6 | 124 | GUS-1 | T-AGRtu.nos-1:1:13 |
| PCR0145909 | pMON140878 | EXP-Sv.Ubq1:1:7 | 128 | GUS-1 | T-AGRtu.nos-1:1:13 |
| PCR0145929 | pMON140878 | EXP-Sv.Ubq1:1:8 | 132 | GUS-1 | T-AGRtu.nos-1:1:13 |
| PCR0145911 | pMON140878 | EXP-Sv.Ubq1:1:10 | 134 | GUS-1 | T-AGRtu.nos-1:1:13 |
| PCR0145914 | pMON140881 | EXP-Zm.UbqM1:1:6 | 137 | GUS-1 | T-AGRtu.nos-1:1:13 |
| PCR0145915 | pMON140882 | EXP-Zm.UbqM1:1:7 | 141 | GUS-1 | T-AGRtu.nos-1:1:13 |
| PCR0145921 | pMON140886 | EXP-Sb.Ubq4:1:2 | 151 | GUS-1 | T-AGRtu.nos-1:1:13 |
| PCR0145920 | pMON140887 | EXP-Sb.Ubq6:1:2 | 153 | GUS-1 | T-AGRtu.nos-1:1:13 |
| PCR0145922 | pMON140889 | EXP-Cl.Ubq1:1:10 | 98 | GUS-1 | T-AGRtu.nos-1:1:13 |

Plasmid constructs listed as amplicon templates in Table 7 served as templates for amplification of transgene expression cassettes comprising the listed EXP sequences of Table 7. Control plasmids used to generate GUS transgene amplicons for comparison were constructed as previously described with known constitutive EXP sequences described in Example 2. Negative controls for determination of GUS and luciferase background, a no DNA control, and a control sample in which the two luciferase plasmids are used in transformation along with a plasmid DNA that does not express a coding sequence were also used. Plasmids pMON19437 and pMON63934, as discussed in Example 2, were also employed for co-transformation and normalization of data.

Corn leaf protoplasts were transformed using a PEG-based transformation method as described in Example 2, above. Table 8 below shows the average GUS and luciferase expression values determined for each transgene cassette.

TABLE 8

Mean GUS and Luciferase activity in transformed corn leaf protoplast cells.

| EXP sequence | SEQ ID NO: | GUS | RLuc | FLuc |
|---|---|---|---|---|
| EXP-Os.Act1:1:9 | 179 | 1540.3 | 105416.8 | 2671.8 |
| P-CAMV.35S-ENH-1:1:102/ L-CAMV.35S-1:1:2 | 169 | 10426.3 | 344088.6 | 8604.1 |
| EXP-CaMV.35S-enh + Ta.Lhcb 1 + Os.Act1:1:1 | 163 | 12530.8 | 137722.6 | 3067.1 |
| EXP-CaMV.35S-enh + Zm.DnaK:1:1 | 170 | 61036.1 | 208125.3 | 5787.6 |
| EXP-ANDge.Ubq1:1:7 | 5 | 59447.4 | 84667.6 | 2578.4 |
| EXP-ANDge.Ubq1:1:10 | 10 | 40123.3 | 76753.8 | 2419.8 |
| EXP-ANDge.Ubq1:1:6 | 12 | 42621.0 | 121751.3 | 3974.8 |
| EXP-ANDge.Ubq1:1:11 | 14 | 44358.5 | 87105.8 | 2687.1 |
| EXP-ANDge.Ubq1:1:12 | 16 | 48219.0 | 107762.1 | 3279.6 |
| EXP-ERIra.Ubq1:1:9 | 22 | 31253.0 | 171664.1 | 6476.1 |
| EXP-ERIra.Ubq1:1:10 | 25 | 7905.8 | 21235.6 | 462.4 |
| EXP-ERIra.Ubq1:1:8 | 27 | 39935.8 | 173766.6 | 5320.3 |
| EXP-ERIra.Ubq1:1:11 | 29 | 34141.3 | 111626.8 | 3377.6 |
| EXP-ERIra.Ubq1:1:12 | 31 | 11540.3 | 42362.1 | 1045.3 |
| EXP-SETit.Ubq1:1:5 | 117 | 20496.5 | 88695.8 | 2358.8 |
| EXP-SETit.Ubq1:1:7 | 123 | 75728.5 | 185223.8 | 4723.1 |
| EXP-SETit.Ubq1:1:6 | 124 | 44148.3 | 161216.3 | 4962.1 |
| EXP-Sv.Ubq1:1:7 | 128 | 15043.8 | 74670.6 | 1888.3 |
| EXP-Sv.Ubq1:1:8 | 132 | 31997.8 | 113787.1 | 3219.8 |
| EXP-Sv.Ubq1:1:10 | 134 | 38952.8 | 220208.6 | 7011.3 |
| EXP-Zm.UbqM1:1:6 | 137 | 30528.3 | 90113.1 | 2453.6 |
| EXP-Zm.UbqM1:1:7 | 141 | 34986.3 | 105724.7 | 2553.8 |
| EXP-Sb.Ubq4:1:2 | 151 | 9982.3 | 72593.8 | 2171.6 |
| EXP-Sb.Ubq6:1:2 | 153 | 33689.0 | 114709.6 | 3879.6 |
| EXP-Cl.Ubq1:1:10 | 98 | 50622.3 | 107084.3 | 2621.3 |

To compare the relative activity of each EXP sequence GUS values were expressed as a ratio of GUS to luciferase activity and normalized with respect to the expression levels observed for EXP-Os.Act1:1:1 and EXP-CaMV.35S-enh+Ta.Lhcb5+Os.Act1:1:1. Table 9 below shows the GUS/RLuc ratios of expression normalized with respect to EXP-Os.Act1:1:1 and EXP-CaMV.35S-enh+Ta.Lhcb1+Os-.Act1:1:1 driven expression in corn protoplasts. Table 10 below shows the GUS/FLuc ratios of expression normalized with respect to EXP-Os.Act1:1:1 and EXP-CaMV.35S-enh+Ta.Lhcb1+Os.Act1:1:1 driven expression in corn protoplasts.

TABLE 9

GUS/RLuc and GUS/FLuc ratios of expression normalized with respect to EXP-CaMV.35S-enh + Ta.Lhcb1 + Os.Act1:1:1 (SEQ ID NO: 163) in corn protoplasts.

| EXP sequence | SEQ ID NO: | GUS/RLuc Relative to EXP-CaMV.35S-enh + Ta.Lhcb1 + Os.Act1:1:1 | GUS/FLuc Relative to EXP-CaMV.35S-enh + Ta.Lhcb1 + Os.Act1:1:1 |
|---|---|---|---|
| EXP-Os.Act1:1:9 | 179 | 0.16 | 0.14 |
| P-CAMV.35S-ENH-1:1:102/ L-CAMV.35S-1:1:2 | 169 | 0.33 | 0.30 |
| EXP-CaMV.35S-enh + Ta.Lhcb1 + Os.Act1:1:1 | 163 | 1.00 | 1.00 |
| EXP-CaMV.35S-enh + Zm.DnaK:1:1 | 170 | 3.22 | 2.58 |
| EXP-ANDge.Ubq1:1:7 | 5 | 7.72 | 5.64 |
| EXP-ANDge.Ubq1:1:10 | 10 | 5.75 | 4.06 |
| EXP-ANDge.Ubq1:1:6 | 12 | 3.85 | 2.62 |
| EXP-ANDge.Ubq1:1:11 | 14 | 5.60 | 4.04 |
| EXP-ANDge.Ubq1:1:12 | 16 | 4.92 | 3.60 |
| EXP-ERIra.Ubq1:1:9 | 22 | 2.00 | 1.18 |
| EXP-ERIra.Ubq1:1:10 | 25 | 4.09 | 4.18 |
| EXP-ERIra.Ubq1:1:8 | 27 | 2.53 | 1.84 |
| EXP-ERIra.Ubq1:1:11 | 29 | 3.36 | 2.47 |
| EXP-ERIra.Ubq1:1:12 | 31 | 2.99 | 2.70 |
| EXP-SETit.Ubq1:1:5 | 117 | 2.54 | 2.13 |
| EXP-SETit.Ubq1:1:7 | 123 | 4.49 | 3.92 |
| EXP-SETit.Ubq1:1:6 | 124 | 3.01 | 2.18 |
| EXP-Sv.Ubq1:1:7 | 128 | 2.21 | 1.95 |
| EXP-Sv.Ubq1:1:8 | 132 | 3.09 | 2.43 |
| EXP-Sv.Ubq1:1:10 | 134 | 1.94 | 1.36 |
| EXP-Zm.UbqM1:1:6 | 137 | 3.72 | 3.05 |
| EXP-Zm.UbqM1:1:7 | 141 | 3.64 | 3.35 |
| EXP-Sb.Ubq4:1:2 | 151 | 1.51 | 1.13 |
| EXP-Sb.Ubq6:1:2 | 153 | 3.23 | 2.13 |
| EXP-Cl.Ubq1:1:10 | 98 | 5.20 | 4.73 |

TABLE 10

GUS/RLuc and GUS/FLuc ratios of expression normalized with respect to EXP-Os.Act1:1:9 (SEQ ID NO: 179) in corn leaf protoplasts.

| EXP sequence | SEQ ID NO: | GUS/RLuc Relative to EXP-Os.Act1:1:9 | GUS/FLuc Relative to EXP-Os.Act1:1:9 |
|---|---|---|---|
| EXP-Os.Act1:1:9 | 179 | 1.00 | 1.00 |
| P-CAMV.35S-ENH-1:1:102/ L-CAMV.35S-1:1:2 | 169 | 2.07 | 2.10 |
| EXP-CaMV.35S-enh + Ta.Lhcb1 + Os.Act1:1:1 | 163 | 6.23 | 7.09 |
| EXP-CaMV.35S-enh + Zm.DnaK:1:1 | 170 | 20.07 | 18.29 |
| EXP-ANDge.Ubq1:1:7 | 5 | 48.05 | 39.99 |
| EXP-ANDge.Ubq1:1:10 | 10 | 35.78 | 28.76 |
| EXP-ANDge.Ubq1:1:6 | 12 | 23.96 | 18.60 |
| EXP-ANDge.Ubq1:1:11 | 14 | 34.85 | 28.64 |
| EXP-ANDge.Ubq1:1:12 | 16 | 30.62 | 25.50 |
| EXP-ERIra.Ubq1:1:9 | 22 | 12.46 | 8.37 |
| EXP-ERIra.Ubq1:1:10 | 25 | 25.48 | 29.66 |
| EXP-ERIra.Ubq1:1:8 | 27 | 15.73 | 13.02 |
| EXP-ERIra.Ubq1:1:11 | 29 | 20.93 | 17.53 |
| EXP-ERIra.Ubq1:1:12 | 31 | 18.64 | 19.15 |
| EXP-SETit.Ubq1:1:5 | 117 | 15.82 | 15.07 |
| EXP-SETit.Ubq1:1:7 | 123 | 27.98 | 27.81 |
| EXP-SETit.Ubq1:1:6 | 124 | 18.74 | 15.43 |
| EXP-Sv.Ubq1:1:7 | 128 | 13.79 | 13.82 |
| EXP-Sv.Ubq1:1:8 | 132 | 19.25 | 17.24 |
| EXP-Sv.Ubq1:1:10 | 134 | 12.11 | 9.64 |
| EXP-Zm.UbqM1:1:6 | 137 | 23.19 | 21.58 |
| EXP-Zm.UbqM1:1:7 | 141 | 22.65 | 23.76 |
| EXP-Sb.Ubq4:1:2 | 151 | 9.41 | 7.97 |
| EXP-Sb.Ubq6:1:2 | 153 | 20.10 | 15.06 |
| EXP-Cl.Ubq1:1:10 | 98 | 32.35 | 33.50 |

As can be seen in Tables 9 and 10, nearly all of the EXP sequences were capable of driving GUS transgene expression in corn cells. Average GUS expression was higher for EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12

(SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:1:10 (SEQ ID NO: 134), EXP-Zm.UbgM1:1:6 (SEQ ID NO: 137), EXP-Zm.UbgM1:1:7 (SEQ ID NO: 141), EXP-Sb.Ubg4:1:2 (SEQ ID NO: 151), EXP-Sb.Ubg6:1:2 (SEQ ID NO: 153) and EXP-Cl.Ubq1:1:10 (SEQ ID NO: 98) when compared to GUS expression driven by EXP-Os.Act1:1:1 or EXP-CaMV.35S-enh+Ta.Lhcb1+Os.Act1:1:1.

In a second set of experiments, a GUS cassette amplicon comprising the EXP sequence EXP-Zm.UbgM1:1:8 (SEQ ID NO: 145) was compared to the control amplicons, PCR0145942 (EXP-Os.Act1:1:9, SEQ ID NO: 179) and PCR0145944 (EXP-CaMV.35S-enh+Zm.DnaK:1:1, SEQ ID NO: 170) with respect to GUS expression. GUS expression driven by the EXP sequence EXP-Zm.UbgM1:1:8 was higher than that of the two controls. Table 11 below shows the mean GUS and luciferase values determined for each amplicon. Table 12 below shows the GUS/RLuc and GUS/FLuc ratios of expression normalized with respect to EXP-Os.Act1:1:9 and EXP-CaMV.35S-enh+Zm.DnaK:1:1 driven expression in corn protoplasts.

TABLE 11

Mean GUS and Luciferase activity in transformed corn leaf protoplast cells.

| Amplicon | EXP sequence | SEQ ID NO: | GUS | RLuc | FLuc |
|---|---|---|---|---|---|
| PCR0145942 | EXP-Os.Act1:1:9 | 179 | 1512.25 | 190461 | 11333.8 |
| PCR0145944 | EXP-CaMV.35S-enh + Zm.DnaK:1:1 | 170 | 41176.5 | 330837 | 13885.8 |
| PCR0145916 | EXP-Zm.UbqM1:1:8 | 145 | 79581.5 | 330756 | 15262.5 |

TABLE 12

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in corn leaf protoplasts.

| EXP sequence | SEQ ID NO: | GUS/RLuc relative to EXP-Os.Act1:1:9 | GUS/FLuc relative to EXP-Os.Act1:1:9 | GUS/RLuc relative to EXP-CaMV.35S-enh + Zm.DnaK:1:1 | GUS/FLuc relative to EXP-CaMV.35S-enh + Zm.DnaK:1:1 |
|---|---|---|---|---|---|
| EXP-Os.Act1:1:9 | 179 | 1.00 | 1.00 | 0.06 | 0.04 |
| EXP-CaMV.35S-enh + Zm.DnaK:1:1 | 170 | 15.68 | 22.22 | 1.00 | 1.00 |
| EXP-Zm.UbqM1:1:8 | 145 | 30.30 | 39.08 | 1.93 | 1.76 |

In a third set of experiments, amplicon GUS transgene cassettes were made as described above and assayed for expression driven by the EXP sequences, EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116). The amplicons were comprised of an EXP sequence operably linked to the GUS-1 coding sequence which was operably linked to the T-AGRtu.nos-1:1:13 3' UTR. Expression was compared to the controls EXP-Os.Act1:1:9 (SEQ ID NO: 179) and EXP-CaMV.35S-enh+Zm.DnaK:1:1 (SEQ ID NO: 170). Table 13 below shows the mean GUS and luciferase values determined for each amplicon. Table 14 below shows the GUS/RLuc ratios of expression normalized with respect to EXP-Os.Act1:1:9 and EXP-CaMV.35S-enh+Zm.DnaK:1:1 driven expression in corn protoplasts.

TABLE 13

Mean GUS and Luciferase activity in transformed corn leaf protoplast cells.

| Amplicon ID | EXP sequence | SEQ ID NO: | GUS | RLuc |
|---|---|---|---|---|
| PCR0145942 | EXP-Os.Act1:1:9 | 179 | 9445.25 | 929755 |
| PCR0145944 | EXP-CaMV.35S-enh + Zm.DnaK:1:1 | 170 | 78591.25 | 445127 |
| PCR0146628 | EXP-ANDge.Ubq1:1:8 | 8 | 192056.75 | 972642 |
| PCR0145922 | EXP-Cl.Ubq1:1:10 | 98 | 175295.25 | 395563 |
| PCR0145945 | EXP-Cl.Ubq1:1:13 | 114 | 173674.5 | 402966 |
| PCR0145946 | EXP-Cl.Ubq1:1:14 | 115 | 185987.5 | 390052 |
| PCR0145947 | EXP-Cl.Ubq1:1:15 | 116 | 9435 | 320749 |

TABLE 14

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in corn leaf protoplasts.

| EXP sequence | SEQ ID NO: | GUS/RLuc relative to EXP-Os.Act1:1:9 | GUS/RLuc relative to EXP-CaMV.35S-enh + Zm.DnaK:1:1 |
|---|---|---|---|
| EXP-Os.Act1:1:9 | 179 | 1.00 | 0.06 |
| EXP-CaMV.35S-enh + Zm.DnaK:1:1 | 170 | 17.38 | 1.00 |
| EXP-ANDge.Ubq1:1:8 | 8 | 19.44 | 1.12 |
| EXP-Cl.Ubq1:1:10 | 98 | 43.62 | 2.51 |
| EXP-Cl.Ubq1:1:13 | 114 | 42.43 | 2.44 |

TABLE 14-continued

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in corn leaf protoplasts.

| EXP sequence | SEQ ID NO: | GUS/RLuc relative to EXP-Os.Act1:1:9 | GUS/RLuc relative to EXP-CaMV.35S-enh + Zm.DnaK:1:1 |
|---|---|---|---|
| EXP-Cl.Ubq1:1:14 | 115 | 46.94 | 2.70 |
| EXP-Cl.Ubq1:1:15 | 116 | 2.90 | 0.17 |

As can be seen in Table 14 above, the EXP sequences EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) are capable of driving transgene expression. Expression driven by EXP-ANDge.Ubq1:1:8 (SEQ ID NO: 8'), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) was higher than that of both controls. Expression driven by EXP-Cl.Ubq1:1:15 (SEQ ID NO: 116) was lower than EXP-CaMV.35S-enh+Zm.DnaK:1:1 (SEQ ID NO: 170) but higher than the control, EXP-Os.Act1:1:9 (SEQ ID NO: 179).

In a fourth set of experiments, amplicon GUS transgene cassettes were made as described above and assayed for expression driven by the EXP sequences, EXP-CR.Ubq1:1:10 (SEQ ID NO: 98), EXP-Cl.Ubq1:1:16 (SEQ ID NO: 93) and EXP-Cl.Ubq1:1:17 (SEQ ID NO: 97). Expression was compared to the controls EXP-s.Act1:1:9 (SEQ ID NO: 179) and EXP-CaMV.35-enh+Zm.DnaK:1:1 (SEQ ID NO: 170). Table 15 below shows the mean GUS and luciferase values determined for each amplicon. Table 16 below shows the GUS/RLuc and GUS/FLuc ratios of expression normalized with respect to EXP-Es.Act1:1:9 and EXP-CaMV.35S-enh+Zm.DnaK:1:1 driven expression in corn protoplasts.

TABLE 15

Mean GUS and Luciferase activity in transformed corn leaf protoplast cells.

| Amplicon ID | EXP sequence | SEQ ID NO: | GUS | RLuc | FLuc |
|---|---|---|---|---|---|
| PCR0145942 | EXP-Os.Act1:1:9 | 179 | 5333.5 | 171941.75 | 77817.88 |
| PCR0145944 | EXP-CaMV.35S-enh + Zm.DnaK:1:1 | 170 | 88517 | 177260.25 | 54207.38 |
| PCR0145922 | EXP-Cl.Ubq1:1:10 | 98 | 130125.75 | 194216 | 32055 |
| pMON146750 | EXP-Cl.Ubq1:1:16 | 93 | 134101.75 | 182317.5 | 32434.5 |
| pMON146751 | EXP-Cl.Ubq1:1:17 | 97 | 107122.5 | 151783.25 | 51354.38 |

TABLE 16

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in corn leaf protoplasts.

| Amplicon ID | EXP sequence | SEQ ID NO: | GUS/RLuc relative to EXP-Os.Act1:1:9 | GUS/FLuc relative to EXP-Os.Act1:1:9 | GUS/RLuc relative to EXP-CaMV.35S-enh + Zsm.DnaK:1:1 | GUS/FLuc relative to EXP-CaMV.35S-enh + Zm.DnaK:1:1 |
|---|---|---|---|---|---|---|
| PCR0145942 | EXP-Os.Act1:1:9 | 179 | 1.00 | 1.00 | 0.06 | 0.04 |
| PCR0145944 | EXP-CaMV.35S-enh + Zm.DnaK:1:1 | 170 | 16.10 | 23.83 | 1.00 | 1.00 |
| PCR0145922 | EXP-Cl.Ubq1:1:10 | 98 | 21.60 | 59.23 | 1.34 | 2.49 |
| pMON146750 | EXP-Cl.Ubq1:1:16 | 93 | 23.71 | 60.32 | 1.47 | 2.53 |
| pMON146751 | EXP-Cl.Ubq1:1:17 | 97 | 22.75 | 30.43 | 1.41 | 1.28 |

As can be seen in Table 16, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive transgene expression. Expression driven by each of the EXP sequences was higher than that of both controls.

In a fifth set of experiments, amplicon GUS transgene cassettes were made as described above assay expression driven by the EXP sequences, EXP-Zm.UbqM1:1:11 (SEQ ID NO: 149) and EXP-Cl.Ubq1:1:23 (SEQ ID NO: 108). Expression was compared to the controls EXP-Os.Act1:1:9 (SEQ ID NO: 179) and EXP-CaMV.351-enh+Ta.Lhcb1+Os.Act1:1:1 (SEQ ID NO: 163). Table 17 below shows the mean GUS and luciferase values determined for each amplicon. Table 18 below shows the GUS/RLuc ratios of expression normalized with respect to EXP-Os.Act1:1:9 and EXP-CaMV.351-enh+Ta.Lhcb1+Os.Act1:1:1 driven expression in corn protoplasts.

tory elements driving CP4 expression from amplicons in corn or wheat protoplasts may be similarly studied.

Example 4: Analysis of Regulatory Elements Driving GUS in Wheat Protoplasts Using GUS Transgene Cassette Amplicons Wheat leaf protoplasts were transformed with DNA amplicons derived from plant expression vectors containing an EXP sequence, driving expression of the β-glucuronidase (GUS) transgene, and compared to leaf protoplast in which expression of GUS was driven by known constitutive promoters.

Wheat protoplast cells derived from leaf tissue were transformed using methods known in the art with amplicons produced from amplification of GUS transgene cassettes comprising plant expression vectors to compare expression of a transgene (GUS) driven by the EXP sequences listed in

TABLE 17

Mean GUS and Luciferase activity in transformed corn leaf protoplast cells.

| Template | Amplicon | EXP sequence | SEQ ID NO: | GUS | RLuc |
|---|---|---|---|---|---|
| pMON65328 | PCR0145943 | EXP-CaMV.35S-enh + Ta.Lhcb1 + Os.Act1:1:1 | 163 | 70352.00 | 79028.75 |
| pMON25455 | PCR0145942 | EXP-Os.Act1:1:9 | 179 | 33155.25 | 92337.00 |
| pMON131962 | pMON131962 | EXP-Zm.UbqM1:1:11 | 149 | 18814.75 | 33663.00 |
| pMON132047 | pMON132047 | EXP-Cl.Ubq1:1:23 | 108 | 15387.50 | 40995.50 |

TABLE 18

GUS/RLuc ratios of expression normalized with respect to EXP-Os.Act1:1:9 (SEQ ID NO: 179) and EXP-CaMV.35S-enh + Ta.Lhcb1 + Os.Act1:1:1 (SEQ ID NO: 163) in corn leaf protoplasts.

| Amplicon | EXP sequence | SEQ ID NO: | GUS/RLuc relative to EXP-OS.Act1:1:9 | GUS/RLuc relative to EXP-CaMV.35S-enh + Ta.Lhcb1 + Os.Act1:1:1 |
|---|---|---|---|---|
| PCR0145943 | EXP-CaMV.35S-enh + Ta.Lhcb1 + Os.Act1:1:1 | 163 | 2.48 | 1.00 |
| PCR0145942 | EXP-Os.Act1:1:9 | 179 | 1.00 | 0.40 |
| pMON131962 | EXP-Zm.UbqM1:1:11 | 149 | 1.56 | 0.63 |
| pMON132047 | EXP-Cl.Ubq1:1:23 | 108 | 1.05 | 0.42 |

As can be seen in Table 18 above, the EXP sequences, EXP-Zm.UbgM1:1:11 (SEQ ID NO: 149) and EXP-Cl.Ubq1:1:23 (SEQ ID NO: 108) were able to drive GUS expression in corn leaf protoplasts. Expression was similar to that of the control, EXP-Os.Act1:1:9 (SEQ ID NO: 179) and lower than that of EXP-CaMV.35S-enh+Ta.Lhcb1+Os.Act1:1:1 (SEQ ID NO: 163).

The efficacy of regulatory elements driving GUS expression from amplicons can be similarly studied in sugarcane leaf protoplasts. For instance, sugarcane protoplasts may be transformed with DNA amplicons derived from plant expression vectors containing an EXP sequence, driving expression of the β-glucuronidase (GUS) transgene, and compared to leaf protoplast in which expression of GUS is driven by known constitutive promoters. Likewise, regulatory elements driving GUS expression from amplicons can be similarly studied in sugarcane leaf protoplasts. For instance, sugarcane protoplasts may be transformed with DNA amplicons derived from plant expression vectors containing an EXP sequence, driving expression of the β-glucuronidase (GUS) transgene, and compared to leaf protoplast in which expression of GUS is driven by known constitutive promoters. Likewise, regulatory elements driving GUS expression from amplicons can be similarly studied in sugarcane leaf protoplasts with that of known constitutive promoters with methodology as described in a previous example (Example 3), using the same GUS cassette amplicons as that used for assay in Corn in Example 3 above. Control GUS cassette amplicons and Luciferase plasmids used for wheat protoplast transformation were also the same as those presented in the previous example and provided in Table 7 above in Example 3. Likewise, negative controls were used for the determination of GUS and luciferase background, as described above. Wheat leaf protoplasts were transformed using a PEG-based transformation method, as described in Example 3 above. Table 19 lists mean GUS and LUC activity seen in transformed wheat leaf protoplast cells, and Table 20 shows normalized GUS/RLuc ratios of expression in wheat protoplasts.

TABLE 19

Mean GUS and Luciferase activity in transformed wheat leaf protoplast cells.

| EXP sequence | SEQ ID NO: | GUS | RLuc | GUS/RLuc |
|---|---|---|---|---|
| EXP-Os.Act1:1:9 | 179 | 2976.33 | 53334.8 | 0.0558047 |
| P-CAMV.35S-ENH-1:1:102/L-CAMV.35S-1:1:2 | 169 | 1431.33 | 55996.1 | 0.0255612 |
| EXP-CaMV.35S-enh + Ta.Lhcb1 + Os.Act1:1:1 | 163 | 29299.3 | 50717.4 | 0.5776973 |
| EXP-CaMV.35S-enh + Zm.DnaK:1:1 | 170 | 34294.3 | 63307.9 | 0.5417066 |
| EXP-ANDge.Ubq1:1:7 | 5 | 68444.3 | 60329.1 | 1.1345158 |
| EXP-ANDge.Ubq1:1:10 | 10 | 60606.3 | 60659.4 | 0.9991245 |
| EXP-ANDge.Ubq1:1:6 | 12 | 33386.3 | 56712.1 | 0.5886984 |
| EXP-ANDge.Ubq1:1:11 | 14 | 43237.3 | 48263.4 | 0.8958609 |
| EXP-ANDge.Ubq1:1:12 | 16 | 51712.7 | 64702.8 | 0.7992341 |
| EXP-ERIra.Ubq1:1:9 | 22 | 20998.3 | 60273.4 | 0.3483845 |
| EXP-ERIra.Ubq1:1:10 | 25 | 17268.3 | 25465.4 | 0.6781084 |
| EXP-ERIra.Ubq1:1:8 | 27 | 34635.7 | 59467.1 | 0.5824341 |
| EXP-ERIra.Ubq1:1:11 | 29 | 28979 | 56153.8 | 0.516065 |
| EXP-ERIra.Ubq1:1:12 | 31 | 41409.7 | 55152.4 | 0.7508221 |
| EXP-SETit.Ubq1:1:5 | 117 | 39427.7 | 57463.1 | 0.6861388 |
| EXP-SETit.Ubq1:1:7 | 123 | 108091 | 49330.4 | 2.191169 |
| EXP-SETit.Ubq1:1:6 | 124 | 58703 | 46110.1 | 1.2731047 |
| EXP-Sv.Ubq1:1:7 | 128 | 29330 | 43367.1 | 0.676319 |
| EXP-Sv.Ubq1:1:8 | 132 | 53359 | 40076.4 | 1.3314306 |
| EXP-Sv.Ubq1:1:10 | 134 | 49122.7 | 53180.8 | 0.9236922 |
| EXP-Zm.UbqM1:1:6 | 137 | 37268 | 54088.1 | 0.6890239 |
| EXP-Zm.UbqM1:1:7 | 141 | 51408 | 47297.4 | 1.0869087 |
| EXP-Sb.Ubq4:1:2 | 151 | 35660.3 | 62591.1 | 0.5697347 |
| EXP-Sb.Ubq6:1:2 | 153 | 27543 | 57826.4 | 0.4763046 |
| EXP-Cl.Ubq1:1:10 | 98 | 54493.3 | 41964.1 | 1.2985699 |

TABLE 20

GUS/RLuc ratios of expression normalized with respect to EXP-Os.Act1:1:9 (SEQ ID NO: 179) and EXP-CaMV.35S-enh + Ta.Lhcb1 + Os.Act1:1:1 (SEQ ID NO: 163) in wheat leaf protoplasts.

| EXP sequence | SEQ ID NO: | GUS/RLuc Relative to EXP-Os.Act1:1:9 | GUS/RLuc Relative to EXP-CaMV.35S-enh + Ta.Lhcb1 + Os.Act1:1:1 |
|---|---|---|---|
| EXP-Os.Act1:1:9 | 179 | 1.00 | 0.10 |
| P-CAMV.35S-ENH-1:1:102/L-CAMV.35S-1:1:2 | 169 | 0.46 | 0.04 |
| EXP-CaMV.35S-enh + Ta.Lhcb1 + Os.Act1:1:1 | 163 | 10.35 | 1.00 |
| EXP-CaMV.35S-enh + Zm.DnaK:1:1 | 170 | 9.71 | 0.94 |
| EXP-ANDge.Ubq1:1:7 | 5 | 20.33 | 1.96 |
| EXP-ANDge.Ubq1:1:10 | 10 | 17.90 | 1.73 |
| EXP-ANDge.Ubq1:1:6 | 12 | 10.55 | 1.02 |
| EXP-ANDge.Ubq1:1:11 | 14 | 16.05 | 1.55 |
| EXP-ANDge.Ubq1:1:12 | 16 | 14.32 | 1.38 |
| EXP-ERIra.Ubq1:1:9 | 22 | 6.24 | 0.60 |
| EXP-ERIra.Ubq1:1:10 | 25 | 12.15 | 1.17 |
| EXP-ERIra.Ubq1:1:8 | 27 | 10.44 | 1.01 |
| EXP-ERIra.Ubq1:1:11 | 29 | 9.25 | 0.89 |
| EXP-ERIra.Ubq1:1:12 | 31 | 13.45 | 1.30 |
| EXP-SETit.Ubq1:1:5 | 117 | 12.30 | 1.19 |
| EXP-SETit.Ubq1:1:7 | 123 | 39.26 | 3.79 |
| EXP-SETit.Ubq1:1:6 | 124 | 22.81 | 2.20 |
| EXP-Sv.Ubq1:1:7 | 128 | 12.12 | 1.17 |
| EXP-Sv.Ubq1:1:8 | 132 | 23.86 | 2.30 |
| EXP-Sv.Ubq1:1:10 | 134 | 16.55 | 1.60 |
| EXP-Zm.UbqM1:1:6 | 137 | 12.35 | 1.19 |
| EXP-Zm.UbqM1:1:7 | 141 | 19.48 | 1.88 |
| EXP-Sb.Ubq4:1:2 | 151 | 10.21 | 0.99 |
| EXP-Sb.Ubq6:1:2 | 153 | 8.54 | 0.82 |
| EXP-Cl.Ubq1:1:10 | 98 | 23.27 | 2.25 |

As can be seen in Table 20 above, nearly all of the EXP sequences were capable of driving GUS transgene expression in wheat cells. GUS transgene expression driven by EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:1:10 (SEQ ID NO: 134), EXP-Zm.UbqM1:1:6 (SEQ ID NO: 137), EXP-Zm.UbgM1:1:7 (SEQ ID NO: 141), EXP-Sb.Ubg4:1:2 (SEQ ID NO: 151), EXP-Sb.Ubg6:1:2 (SEQ ID NO: 153) and EXP-Cl.Ubq1:1:10 (SEQ ID NO: 98) was much higher than GUS expression driven by EXP-Os.Act1:1:9. GUS expression of the amplicons in wheat leaf protoplast cells relative to EXP-CaMV.35S-enh+Ta.Lhcb1+Os.Act1:1:1 was slightly different from the expression observed in corn protoplast cells. Each of EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:10 (SEQ ID NO: 25), EXP-ERIra.Ubq1:1:8 (SEQ ID NO: 27), EXP-ERIra.Ubq1:1:12 (SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:1:10 (SEQ ID NO: 134), EXP-Zm.UbgM1:1:6 (SEQ ID NO: 137), EXP-Zm.UbgM1:1:7 (SEQ ID NO: 141) and EXP-Cl.Ubq1:1:10 (SEQ ID NO: 98) demonstrated higher levels of GUS expression relative to EXP-CaMV.35S-enh+Ta.Lhcb1+Os.Act1:1:1. The EXP sequences EXP-ERIra.Ubq1:1:9 (SEQ ID NO: 22), EXP- ERIra.Ubq1:1:11 (SEQ ID NO: 29), EXP-Sb.Ubg4:1:2 (SEQ ID NO: 151) and EXP-Sb.Ubg6:1:2 (SEQ ID NO: 153) demonstrated lower levels of GUS expression relative to EXP-CaMV.35S-enh+Ta.Lhcb1+0s.Act1:1:1.

In a second set of experiments, amplicon GUS transgene cassettes were made as described above and assayed for expression driven by the EXP sequences, EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116). The amplicons were comprised of an EXP sequence operably linked to the GUS-1 coding sequence which was operably linked to the T-AGRtu.nos-1:1:13 3' UTR. Expression was compared to the controls EXP-Os.Act1:1:9 (SEQ ID NO: 179) and EXP-CaMV.35S-enh+Zm.DnaK:1:1 (SEQ ID NO: 170). Table 21 below shows the mean GUS and luciferase values determined for each amplicon. Table 22 below shows the GUS/RLuc ratios of expression normalized with respect to EXP-Os.Act1:1:9 and EXP-CaMV.35S-enh+Zm.DnaK:1:1 driven expression in corn protoplasts.

TABLE 21

Mean GUS and Luciferase activity in transformed wheat leaf protoplast cells.

| Amplicon ID | EXP sequence | SEQ ID NO: | GUS | RLuc |
|---|---|---|---|---|
| PCR0145942 | EXP-Os.Act1:1:9 | 179 | 1234 | 176970.5 |
| PCR0145944 | EXP-CaMV.35S-enh + Zm.DnaK:1:1 | 170 | 12883.5 | 119439 |
| PCR0146628 | EXP-ANDge.Ubq1:1:8 | 8 | 38353.3 | 171535.3 |
| PCR0145922 | EXP-Cl.Ubq1:1:10 | 98 | 34938 | 154245.8 |
| PCR0145945 | EXP-Cl.Ubq1:1:13 | 114 | 32121 | 122220.8 |
| PCR0145946 | EXP-Cl.Ubq1:1:14 | 115 | 56814 | 143318.3 |
| PCR0145947 | EXP-Cl.Ubq1:1:15 | 116 | 1890.5 | 167178.5 |

TABLE 22

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in wheat leaf protoplasts.

| EXP sequence | SEQ ID NO: | GUS/RLuc relative to EXP-Os.Act1:1:9 | GUS/RLuc relative to EXP-CaMV.35S-enh + Zm.DnaK:1:1 |
|---|---|---|---|
| EXP-Os.Act1:1:9 | 179 | 1.00 | 0.06 |
| EXP-CaMV.35S-enh + Zm.DnaK:1:1 | 170 | 15.47 | 1.00 |
| EXP-ANDge.Ubq1:1:8 | 8 | 32.07 | 2.07 |
| EXP-Cl.Ubq1:1:10 | 98 | 32.48 | 2.10 |
| EXP-Cl.Ubq1:1:13 | 114 | 37.69 | 2.44 |
| EXP-Cl.Ubq1:1:14 | 115 | 56.85 | 3.68 |
| EXP-Cl.Ubq1:1:15 | 116 | 1.62 | 0.10 |

As can be seen in Table 22 above, the EXP sequences EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) are capable of driving transgene expression. Expression driven by EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) was higher than that of both controls. Expression driven by EXP-Cl.Ubq1:1:15 (SEQ ID NO: 116) was lower than EXP-CaMV.35S-enh+Zm.DnaK:1:1 (SEQ ID NO: 170) but higher than the control, EXP-Os.Act1:1:9 (SEQ ID NO: 179).

In a third set of experiments, amplicon GUS transgene cassettes were made as described above to assay expression driven by the EXP sequences, EXP-Cl.Ubq1:1:10 (SEQ ID NO: 98), EXP-Co.Ubq1:1:16 (SEQ ID NO: 93) and EXP-Cl.Ubq1:1:17 (SEQ ID NO: 97). Expression was compared to the controls EXP-s.Act1:1:9 (SEQ ID NO: 179) and EXP-CaMV.35S-enh+Zm.DnaK:1:1 (SEQ ID NO: 170). Table 23 below shows the mean GUS and luciferase values determined for each amplicon. Table 24 below shows the GUS/RLuc and GUS/FLuc ratios of expression normalized with respect to EXP-1s.Act1:1:9 and EXP-CaMV.35-enh+Zm.DnaK: 1:1 driven expression in corn protoplasts.

TABLE 23

Mean GUS and Luciferase activity in transformed wheat leaf protoplast cells.

| Amplicon ID | EXP sequence | SEQ ID NO: | GUS | RLuc | FLuc |
|---|---|---|---|---|---|
| PCR0145942 | EXP-Os.Act1:1:9 | 179 | 478 | 46584.5 | 2709.75 |
| PCR0145944 | EXP-CaMV.35S-enh + Zm.DnaK:1:1 | 170 | 8178.5 | 43490.8 | 2927.25 |
| PCR0145922 | EXP-Cl.Ubq1:1:10 | 98 | 22068.3 | 47662.3 | 1289 |
| pMON146750 | EXP-Cl.Ubq1:1:16 | 93 | 34205 | 45064.5 | 1379.63 |
| pMON146751 | EXP-Cl.Ubq1:1:17 | 97 | 31758 | 45739.3 | 2820.75 |

TABLE 24

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in wheat leaf protoplasts.

| Amplicon ID | EXP sequence | SEQ ID NO: | GUS/RLuc relative to EXP-OsAct:1:9 | GUS/FLuc relative to EXP-Os.Act1:1:9 | GUS/RLuc relative to EXP-CaMV.35S-enh + Zm.DnaK:1:1 | GUS/FLuc relative to EXP-CaMV.35S-enh + Zm.DnaK:1:1 |
|---|---|---|---|---|---|---|
| PCR0145942 | EXP-Os.Act1:1:9 | 179 | 1.00 | 1.00 | 0.05 | 0.06 |
| PCR0145944 | EXP-CaMV.35S-enh + Zm.DnaK:1:1 | 170 | 18.33 | 15.84 | 1.00 | 1.00 |
| PCR0145922 | EXP-Cl.Ubq1:1:10 | 98 | 45.12 | 97.05 | 2.46 | 6.13 |
| pMON146750 | EXP-Cl.Ubq1:1:16 | 93 | 73.97 | 140.55 | 4.04 | 8.87 |
| pMON146751 | EXP-Cl.Ubq1:1:17 | 97 | 67.67 | 63.82 | 3.69 | 4.03 |

As can be seen in Table 24 above, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive transgene expression. Expression driven by each of the EXP sequences was higher than that of both controls.

In a fourth set of experiments, amplicon GUS transgene cassettes were made as described above to assay expression driven by the EXP sequences, EXP-Zm.UbqM1:1:11 (SEQ ID NO: 149) and EXP-Cl.Ubq1:1:23 (SEQ ID NO: 108). Expression was compared to the controls EXP-Os.Act1:1:9 (SEQ ID NO: 179) and EXP-CaMV.35S-enh+Ta.Lhcb1+Os.Act1:1:1 (SEQ ID NO: 163). Table 25 below shows the mean GUS and luciferase values determined for each amplicon. Table 26 below shows the GUS/RLuc ratios of expression normalized with respect to EXP-Os.Act1:1:9 and EXP-CaMV.35a-enh+Ta.Lhcb+Os.Act1:1:1 driven expression in corn protoplasts.

As can be seen in Table 26 above, the EXP sequences, EXP-Zm.UbqM1:1:11 (SEQ ID NO: 149) and EXP-Cl.Ubq1:1:23 (SEQ ID NO: 108) were able to drive GUS expression in wheat leaf protoplasts. Expression was similar to that of the control, EXP-Os.Act1:1:9 (SEQ ID NO: 179) and lower than that of EXP-CaMV.35S-enh+Ta.Lhcb1+Os.Act1:1:1 (SEQ ID NO: 163).

Example 5: Analysis of Regulatory Elements Driving GUS in Sugarcane Protoplasts Using GUS Transgene Cassette Amplicons Sugarcane leaf protoplasts were transformed with DNA amplicons derived from plant expression vectors containing an EXP sequence, driving expression of the β-glucuronidase (GUS) transgene, and compared to leaf protoplast in which expression of GUS was driven by known constitutive promoters.

TABLE 25

Mean GUS and Luciferase activity in transformed wheat leaf protoplast cells.

| Template | Amplicon ID | EXP sequence | SEQ ID NO: | GUS | RLuc |
|---|---|---|---|---|---|
| pMON65328 | PCR0145943 | EXP-CaMV.35S-enh + Ta.Lhcb1 + Os.Act1:1:1 | 163 | 67459.13 | 11682.00 |
| pMON25455 | PCR0145942 | EXP-Os.Act1:1:9 | 179 | 56618.33 | 16654.83 |
| pMON131962 | pMON131962 | EXP-Zm.UbqM1:1:11 | 149 | 53862.13 | 10313.75 |
| pMON132047 | pMON132047 | EXP-Cl.Ubq1:1:23 | 108 | 38869.38 | 12279.00 |

TABLE 26

GUS/RLuc ratios of expression normalized with respect to EXP-Os.Act1:1:9 (SEQ ID NO: 179) and EXP-CaMV.35S-enh + Ta.Lhcb1 + Os.Act1:1:1 (SEQ ID NO: 163) in wheat leaf protoplasts.

| Amplicon ID | EXP sequence | SEQ ID NO: | GUS/RLuc relative to EXP-Os.Act1:1:9 | GUS/RLuc relative to EXP-CaMV.35S-enh + Ta.Lhcb1 + Os.Act1:1:1 |
|---|---|---|---|---|
| PCR0145943 | EXP-CaMV.35S-enh + Ta.Lhcb1 + Os.Act1:1:1 | 163 | 1.70 | 1.00 |
| PCR0145942 | EXP-Os.Act1:1:9 | 179 | 1.00 | 0.59 |
| PMON131962 | EXP-Zm.UbqM1:1:11 | 149 | 1.54 | 0.90 |
| pMON132047 | EXP-Cl.Ubq1:1:23 | 108 | 0.93 | 0.55 |

Sugarcane protoplast cells derived from leaf tissue were transformed using a PEG-based transformation method, as described in Example 3 above with amplicons produced from amplification of GUS transgene cassettes comprising plant expression vectors to compare expression of a transgene (GUS) driven by one of EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) and presented in Table 27 below, with that of known constitutive promoters.

TABLE 27

GUS plant expression amplicons and corresponding plasmid construct amplicon template and EXP sequence.

| Amplicon ID | Amplicon Template | EXP sequence | SEQ ID NO: |
|---|---|---|---|
| PCR0145942 | pMON25455 | EXP-Os.Act1:1:9 | 179 |
| PCR0145944 | pMON81552 | EXP-CaMV.35S-enh + Zm.DnaK:1:1 | 170 |
| PCR0145892 | pMON136264 | EXP-ANDge.Ubq1:1:7 | 5 |
| PCR0145815 | pMON136264 | EXP-ANDge.Ubq1:1:10 | 10 |
| PCR0145893 | PMON136259 | EXP-ANDge.Ubq1:1:6 | 12 |
| PCR0145817 | pMON136264 | EXP-ANDge.Ubq1:1:11 | 14 |
| PCR0145819 | pMON136264 | EXP-ANDge.Ubq1:1:12 | 16 |
| PCR0145896 | PMON136263 | EXP-ERIra.Ubq1:1:9 | 22 |
| PCR0145820 | PMON136263 | EXP-ERIra.Ubq1:1:10 | 25 |
| PCR0145897 | PMON136258 | EXP-ERIra.Ubq1:1:8 | 27 |
| PCR0145821 | pMON136263 | EXP-ERIra.Ubq1:1:11 | 29 |
| PCR0145822 | pMON136263 | EXP-ERIra.Ubq1:1:12 | 31 |
| PCR0145922 | PMON140889 | EXP-Cl.Ubq1:1:10 | 98 |
| PCR0145945 | pMON140889 | EXP-Cl.Ubq1:1:13 | 114 |

TABLE 27-continued

GUS plant expression amplicons and corresponding plasmid construct amplicon template and EXP sequence.

| Amplicon ID | Amplicon Template | EXP sequence | SEQ ID NO: |
|---|---|---|---|
| PCR0145946 | pMON140889 | EXP-Cl.Ubq1:1:14 | 115 |
| PCR0145947 | PMON140889 | EXP-Cl.Ubq1:1:15 | 116 |

Control GUS cassette amplicons and Luciferase plasmids used for sugarcane protoplast transformation were also the same as those presented in Examples 2 through 4 and provided in Table 7 above in Example 3. Likewise, negative controls were used for the determination of GUS and luciferase background, as described above. Table 28 lists mean GUS and Luc activity seen in transformed sugarcane leaf protoplast cells, and Table 29 shows normalized GUS/RLuc ratios of expression in sugarcane leaf protoplasts.

TABLE 28

Mean GUS and Luciferase activity in transformed wheat leaf protoplast cells.

| EXP sequence | SEQ ID NO: | GUS | RLuc | FLuc |
|---|---|---|---|---|
| EXP-Os.Act1:1:9 | 179 | 6667.5 | 3024.5 | 1129.25 |
| EXP-CaMV.35S-enh + Zm.DnaK:1:1 | 170 | 14872.8 | 5171 | 2019.5 |
| EXP-ANDge.Ubq1:1:7 | 5 | 15225 | 4618.25 | 1775.75 |
| EXP-ANDge.Ubq1:1:10 | 10 | 17275.3 | 4333 | 1678 |
| EXP-ANDge.Ubq1:1:6 | 12 | 17236 | 5633.25 | 2240 |
| EXP-ANDge.Ubq1:1:11 | 14 | 22487.8 | 6898.25 | 2878 |
| EXP-ANDge.Ubq1:1:12 | 16 | 22145.3 | 6240.25 | 2676.5 |
| EXP-ERIra.Ubq1:1:9 | 22 | 16796.5 | 7759.75 | 3179 |
| EXP-ERIra.Ubq1:1:10 | 25 | 16267.5 | 5632.75 | 2436.75 |
| EXP-ERIra.Ubq1:1:8 | 27 | 25351 | 9019.5 | 4313.5 |
| EXP-ERIra.Ubq1:1:11 | 29 | 16652.3 | 3672.25 | 1534 |
| EXP-ERIra.Ubq1:1:12 | 31 | 12654.5 | 3256.75 | 1261.5 |
| EXP-Cl.Ubq1:1:10 | 98 | 22383.8 | 7097.5 | 3109.25 |
| EXP-Cl.Ubq1:1:13 | 114 | 14532.3 | 2786.5 | 1198.25 |
| EXP-Cl.Ubq1:1:14 | 115 | 19244.5 | 3455.25 | 1475 |
| EXP-Cl.Ubq1:1:15 | 116 | 6676.5 | 3870.25 | 1497.75 |

TABLE 29

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in sugarcane leaf protoplasts.

| EXP sequence | SEQ ID NO: | GUS/RLuc relative to EXP-Os.Act1:1:9 | GUS/FLuc relative to EXP-Os.Act1:1:9 | GUS/RLuc relative to EXP-CaMV.35S-enh + Zm.DnaK:1:1 | GUS/FLuc relative to EXP-CaMV.35S-enh + Zm.DnaK:1:1 |
|---|---|---|---|---|---|
| EXP-Os.Act1:1:9 | 179 | 1.00 | 1.00 | 0.77 | 0.80 |
| EXP-CaMV.35S-enh + Zm.DnaK:1:1 | 170 | 1.30 | 1.25 | 1.00 | 1.00 |
| EXP-ANDge.Ubq1:1:7 | 5 | 1.50 | 1.45 | 1.15 | 1.16 |
| EXP-ANDge.Ubq1:1:10 | 10 | 1.81 | 1.74 | 1.39 | 1.40 |
| EXP-ANDge.Ubq1:1:6 | 12 | 1.39 | 1.30 | 1.06 | 1.04 |
| EXP-ANDge.Ubq1:1:11 | 14 | 1.48 | 1.32 | 1.13 | 1.06 |
| EXP-ANDge.Ubq1:1:12 | 16 | 1.61 | 1.40 | 1.23 | 1.12 |
| EXP-ERIra.Ubq1:1:9 | 22 | 0.98 | 0.89 | 0.75 | 0.72 |
| EXP-ERIra.Ubq1:1:10 | 25 | 1.31 | 1.13 | 1.00 | 0.91 |
| EXP-ERIra.Ubq1:1:8 | 27 | 1.27 | 1.00 | 0.98 | 0.80 |
| EXP-ERIra.Ubq1:1:11 | 29 | 2.06 | 1.84 | 1.58 | 1.47 |
| EXP-ERIra.Ubq1:1:12 | 31 | 1.76 | 1.70 | 1.35 | 1.36 |
| EXP-Cl.Ubq1:1:10 | 98 | 1.43 | 1.22 | 1.10 | 0.98 |
| EXP-Cl.Ubq1:1:13 | 114 | 2.37 | 2.05 | 1.81 | 1.65 |
| EXP-Cl.Ubq1:1:14 | 115 | 2.53 | 2.21 | 1.94 | 1.77 |
| EXP-Cl.Ubq1:1:15 | 116 | 0.78 | 0.75 | 0.60 | 0.61 |

As can be seen in Table 29 above, the EXP sequences EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were all capable of driving transgene expression in sugarcane protoplasts. The EXP sequences, EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:10 (SEQ ID NO: 25), EXP-ERIra.Ubq1:1:8 (SEQ ID NO: 27), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) expressed GUS higher than EXP-CaMV.35S-enh+Zm.DnaK:1:1 (SEQ ID NO: 170) in this experiment.

Example 6: Analysis of Regulatory Elements Driving CP4 in Corn Protoplasts

This example illustrates the ability of EXP-Sv.Ubq1:1:7 (SEQ ID NO: 128), EXP-Sv.Ubq1:1:8 (SEQ ID NO: 132), EXP-Sv.Ubq1:1:9 (SEQ ID NO: 133), EXP-Zm.UbgM1:1:6 (SEQ ID NO: 137), EXP-Zm.UbgM1:1:8 (SEQ ID NO: 145), EXP-Zm.UbgM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sb.Ubg4:1:2 (SEQ ID NO: 151) and EXP-Sb.Ubg6:1:2 (SEQ ID NO: 153) in driving expression of glyphosate tolerance gene CP4 in corn protoplasts. These EXP sequences were cloned into plant binary transformation plasmid constructs using methods known in the art. The resulting plant expression vectors contained a right border region from *A. tumefaciens*, an ubiquitin EXP sequence operably linked 5' to a plastid targeted glyphosate tolerant EPSPS coding sequence (CP4, U.S. RE39247), operably linked 5' to the T-AGRtu.nos-1:1:13 3' UTR and a left border region from *A. tumefaciens* (B-AGRtu.left border). The resulting plasmid constructs were used to transform corn leaf protoplasts cells using methods known in the art.

Plasmid constructs listed in Table 30, with EXP sequences as defined in Table 1, were utilized. Three control plasmids (pMON30098, pMON42410, and pMON30167), with known constitutive regulatory elements driving either CP4 or GFP, were constructed and used to compare the relative CP4 expression levels driven by these EXP sequences with CP4 expression driven by known constitutive expression elements. Two other plasmids (pMON19437 and pMON63934) were also used as described above to evaluate transformation efficiency and viability. Each plasmid contains a specific luciferase coding sequence driven by a constitutive EXP sequence.

Corn leaf protoplasts were transformed using a PEG-based transformation method, as described in Example 2 above. Measurements of both CP4 and luciferase were conducted similarly to Example 2 above. The average levels of CP4 protein expression expressed as part per million (ppm) is shown in Table 30 below.

TABLE 30

Average CP4 protein expression in corn leaf protoplasts.

| Plasmid | EXP sequence | SEQ ID NO: | CP4 Average ppm | CP4 STDEV ppm |
|---|---|---|---|---|
| No DNA | No DNA | | 0 | 0 |
| pMON30098 | GFP | | 0 | 0 |
| pMON42410 | EXP-CaMV.35S-enh + Ta.Lhcb1 + Os.Act1:1:1 | 163 | 34.1 | 15.6 |
| pMON30167 | EXP-Os.Act1:1:1 | 164 | 40.4 | 11.6 |
| pMON129203 | EXP-Sv.Ubq1:1:7 | 128 | 45.2 | 6.2 |
| pMON129204 | EXP-Sv.Ubq1:1:8 | 132 | 101.9 | 13.8 |
| pMON129205 | EXP-Sv.Ubq1:1:9 | 133 | 71.1 | 8.7 |
| pMON129210 | EXP-Zm.UbqM1:1:6 | 137 | 137.1 | 14.8 |
| pMON129211 | EXP-Zm.UbqM1:1:8 | 145 | 136.5 | 12.3 |
| pMON129212 | EXP-Zm.UbqM1:1:7 | 141 | 170.2 | 18.1 |
| pMON129200 | EXP-SETit.Ubq1:1:5 | 117 | 44.3 | 9.5 |
| pMON129201 | EXP-SETit.Ubq1:1:7 | 123 | 105.1 | 8.4 |
| pMON129202 | EXP-SETit.Ubq1:1:6 | 124 | 124.9 | 33.7 |
| pMON129219 | EXP-Sb.Ubq4:1:2 | 151 | 14.3 | 1 |
| pMON129218 | EXP-Sb.Ubq6:1:2 | 153 | 75.7 | 8.9 |

As can be seen in Table 30, EXP-Sv.Ubq1:1:7 (SEQ ID NO: 128), EXP-Sv.Ubq1:1:8 (SEQ ID NO: 132), EXP-Sv.Ubq1:1:9 (SEQ ID NO: 133), EXP-Zm.UbqM1:1:6 (SEQ ID NO: 137), EXP-Zm.UbqM1:1:8 (SEQ ID NO: 145), EXP-Zm.UbqM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124) and EXP-Sb.Ubq6:1:2 (SEQ ID NO: 153) drove expression of the CP4 transgene at levels close to or higher than CP4 expression levels driven by EXP-CaMV.35S-enh+Ta.Lhcb1+Os.Act1:1:1 and EXP-Os.Act1:1:1. The EXP sequence, EXP-Sb.Ubg4:1:2 (SEQ ID NO: 151) demonstrated the ability to drive expression of CP4, but the level of expression was lower than that of the constitutive controls.

Similar data to that above may also be obtained from plants stably transformed with plasmid constructs described above, for instance, plants of progeny generation(s) $R_0$, $R_1$ or $F_1$ or later. Likewise, expression from other plasmid constructs may be studied. For instance, pMON141619, comprises the EXP sequence EXP-ANDge.Ubq1:1:8, while pMON142862 is comprised of the EXP sequence EXP-ERIra.Ubq1:1:8. These and other constructs may be analyzed in this manner.

Example 7: Analysis of Regulatory Elements Driving CP4 in Corn Protoplasts Using CP4 Transgene Cassette Amplicons This example illustrates the ability of EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO:

114), EXP-Cl.Ubq1:1:14 (SEQ ID NO: 115), EXP-Cl.Ubq1:1:15 (SEQ ID NO: 116), EXP-Cl.Ubq1:1:16 (SEQ ID NO: 93) and EXP-Cl.Ubq1:1:17 (SEQ ID NO: 97) in driving expression of glyphosate tolerance gene CP4 in corn protoplasts. These EXP sequences were cloned into plant binary transformation plasmid constructs. The resulting plant expression vectors were used as amplification templates to produce a transgene cassette amplicon comprised of an ubiquitin EXP sequence operably linked 5' to a plastid targeted glyphosate tolerant EPSPS coding sequence (CP4, U.S. Pat. No. RE39,247), operably linked 5' to the T-AGR-tu.nos-1:1:13 3' UTR and a left border region from *A. tumefaciens*. The resulting amplicons were used to transform corn leaf protoplasts cells.

Corn leaf protoplasts were transformed using a PEG-based transformation method, as described in Example 2 above. Measurements of both CP4 were conducted using an ELISA-based assay. The average levels of CP4 protein expression expressed as part per million (ppm) is shown in Tables 31 and 32 below.

In a first series of experiments, expression of CP4 driven by amplicons comprised of the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were assayed in transformed corn leaf protoplasts and compared to CP4 expression levels driven by the constitutive controls, EXP-CaMV.35S-enh+Zm.DnaK:1:1 (SEQ ID NO: 170) and EXP-Os.Act1:1:1 (SEQ ID NO: 164). The average levels of CP4 protein expression expressed as part per million (ppm) is shown in Tables 31 below.

TABLE 31

Average CP4 protein expression in corn leaf protoplasts.

| Amplicon Template | Amplicon ID | EXP sequence | SEQ ID NO: | CP4 ng/mg total protein Average | CP4 ng/mg total protein STDEV |
|---|---|---|---|---|---|
| | | no DNA | | 0.0 | 0.0 |
| pMON30098 | | GFP (negative control) | | 0.0 | 0.0 |
| pMON19469 | PCR24 | EXP-CaMV.35S-enh + Zm.DnaK:1:1 | 170 | 605.5 | 27.6 |
| pMON30167 | PCR25 | EXP-Os.Act1:1:1 | 164 | 50.6 | 14.2 |
| PMON140896 | PCR41 | EXP-ANDge.Ubq1:1:7 | 5 | 459.0 | 60.9 |
| pMON140917 | PCR42 | EXP-ANDge.Ubq1:1:8 | 8 | 258.2 | 38.4 |
| pMON140897 | PCR43 | EXP-ANDge.Ubq1:1:10 | 10 | 324.8 | 21.6 |
| pMON140898 | PCR44 | EXP-ANDge.Ubq1:1:6 | 12 | 394.9 | 66.4 |
| PMON140899 | PCR45 | EXP-ANDge.Ubq1:1:11 | 14 | 508.7 | 89.6 |
| pMON140900 | PCR46 | EXP-ANDge.Ubq1:1:12 | 16 | 329.3 | 14.5 |
| pMON140904 | PCR50 | EXP-ERIra.Ubq1:1:9 | 22 | 148.6 | 24.4 |
| pMON140905 | PCR51 | EXP-ERIra.Ubq1:1:10 | 25 | 215.8 | 22.6 |
| pMON140906 | PCR52 | EXP-ERIra.Ubq1:1:8 | 27 | 376.6 | 44.1 |
| pMON140907 | PCR53 | EXP-ERIra.Ubq1:1:11 | 29 | 459.9 | 104.7 |
| pMON140908 | PCR54 | EXP-ERIra.Ubq1:1:12 | 31 | 221.6 | 15.9 |
| pMON140913 | PCR19 | EXP-Cl.Ubq1:1:10 | 98 | 287.8 | 50.9 |
| pMON140914 | PCR20 | EXP-Cl.Ubq1:1:13 | 114 | 585.8 | 47.9 |
| pMON140915 | PCR21 | EXP-Cl.Ubq1:1:14 | 115 | 557.5 | 76.6 |
| pMON140916 | PCR22 | EXP-Cl.Ubq1:1:15 | 116 | 33.2 | 9.5 |

As can be seen in Table 31 above, the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were able to drive CP4 expression. All of the EXP sequences with the exception of one EXP-Cl.Ubq1:1:15 (SEQ ID NO: 116) drove CP4 expression levels at a much higher level than the constitutive control, EXP-Os.Act1:1:1 (SEQ ID NO: 164). Expression levels were lower than that of EXP-CaMV.35S-enh+Zm.DnaK:1:1 (SEQ ID NO: 170).

In a second series of experiments, expression of CP4 driven by amplicons comprised of the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were assayed in transformed corn leaf protoplasts and compared to CP4 expression levels driven by the constitutive control, EXP-Os.Act1:1:1 (SEQ ID NO: 164). The average levels of CP4 protein expression expressed as part per million (ppm) is shown in Tables 32 below.

TABLE 32

Average CP4 protein expression in corn leaf protoplasts.

| Amplicon Template | Amplicon ID | EXP sequence | SEQ ID NO: | Maize Leaf CP4 mg/total protein Avg | Maize Leaf CP4 mg/total protein StdDev |
|---|---|---|---|---|---|
| pMON30167 | PCR25 | EXP-Os.Act1:1:1 | 164 | 12.2 | 1.69 |
| pMON140913 | PCR19 | EXP-Cl.Ubq1:1:10 | 98 | 307.5 | 24.21 |
| pMON142748 | pMON142748 | EXP-Cl.Ubq1:1:16 | 93 | 245.95 | 30.14 |
| pMON142749 | pMON142749 | EXP-Cl.Ubq1:1:17 | 97 | 302.85 | 25.32 |

As can be seen in Table 32 above, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive CP4 expression. Expression levels driven by all three EXP sequences were higher than that of the constitutive control, EXP-Os.Act1:1:1 (SEQ ID NO: 164).

Example 8: Analysis of Regulatory Elements Driving CP4 in Wheat Protoplasts

This example illustrates the ability of EXP-Sv.Ubq1:1:7 (SEQ ID NO: 128), EXP-Sv.Ubq1:1:8 (SEQ ID NO: 132), EXP-Sv.Ubq1:1:9 (SEQ ID NO: 133), EXP-Zm.UbgM1:1:6 (SEQ ID NO: 137), EXP-Zm.UbgM1:1:8 (SEQ ID NO: 145), EXP-Zm.UbgM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sb.Ubg4:1:2 (SEQ ID NO: 151) and EXP-Sb.Ubg6:1:2 (SEQ ID NO: 153) to drive CP4 expression in wheat leaf protoplasts. These EXP sequences were cloned into plant binary transformation plasmid constructs using methods known in the art, and as described in Examples 2 and 5 above.

Three control plasmids (pMON30098, pMON42410, as previously described, and pMON43647 comprising a right border region from *Agrobacterium tumefaciens* with EXP-Os.Act1+CaMV.35S.2xA1-B3+Os.Act1:1:1 (SEQ ID NO: 138) operably linked 5' to a plastid targeted glyphosate tolerance coding sequence (CP4, U.S. RE39247), operably linked 5' to T-AGRtu.nos-1:1:13, and a left border region (B-AGRtu.left border) with known constitutive regulatory elements driving either CP4 or GFP were constructed as outlined in Example 5.

Wheat leaf protoplasts were transformed using a PEG-based transformation method as described in the previous examples with the exception that $1.5 \times 10^5$ protoplast cells per assay were used. Assays of luciferase and CP4 transgene expression were performed as described in Example 6 above. The mean CP4 expression levels determined by CP4 ELISA are presented in Table 34 below.

TABLE 34

Mean CP4 Protein Expression in Wheat Leaf Protoplast Cells.

| Plasmid | EXP sequence | SEQ ID NO: | CP4 Average ppm | CP4 STDEV ppm |
|---|---|---|---|---|
| No DNA | No DNA | | 0 | 0 |
| pMON30098 | GFP | | 0 | 0 |
| pMON43647 | EXP-Os.Act1 + CaMV.35S.2xA1-B3 + Os.Act1:1:1 | 172 | 656.2 | 124.5 |

TABLE 34-continued

Mean CP4 Protein Expression in Wheat Leaf Protoplast Cells.

| Plasmid | EXP sequence | SEQ ID NO: | CP4 Average ppm | CP4 STDEV ppm |
|---|---|---|---|---|
| pMON42410 | EXP-CaMV.35S-enh + Ta.Lhcb1 + Os.Act1:1:1 | 163 | 438.3 | 78.9 |
| pMON30167 | EXP-Os.Act1:1:1 | 164 | 583 | 107.4 |
| pMON129203 | EXP-Sv.Ubq1:1:7 | 128 | 156.9 | 25.1 |
| pMON129204 | EXP-Sv.Ubq1:1:8 | 132 | 39.5 | 7 |
| pMON129205 | EXP-Sv.Ubq1:1:9 | 133 | 154.5 | 56.5 |
| pMON129210 | EXP-Zm.UbqM1:1:6 | 137 | 1500 | 0 |
| pMON129211 | EXP-Zm.UbqM1:1:8 | 145 | 199.7 | 64.9 |
| pMON129212 | EXP-Zm.UbqM1:1:7 | 141 | 234.6 | 66.9 |
| pMON129200 | EXP-SETit.Ubq1:1:5 | 117 | 725.7 | 149.7 |
| pMON129201 | EXP-SETit.Ubq1:1:7 | 123 | 64.9 | 14.5 |
| pMON129202 | EXP-SETit.Ubq1:1:6 | 124 | 122.9 | 48.7 |
| pMON129219 | EXP-Sb.Ubq4:1:2 | 151 | 113.1 | 32.8 |

The total amount of CP4 expression in wheat protoplasts driven by the EXP sequences and the known constitutive EXP sequence EXP-CaMV.35S-enh+Ta.Lhcb1+Os.Act1:1:1 demonstrated different levels of CP4 expression in wheat protoplasts when compared to corn protoplasts.

Several EXP sequences drove CP4 expression at lower levels in wheat protoplasts than the known constitutive EXP sequences EXP-Os.Act1+CaMV.35S.2xA1-B3+Os.Act1:

1:1 and EXP-CaMV.35S-enh+Ta.Lhcb1+Os.Act1:1:1. Two EXP sequences, EXP-Zm.UbgM1:1:6 (SEQ ID NO: 137), and EXP-SETit.Ubq1:1:5 (SEQ ID NO: 117), provide higher levels of CP4 expression in wheat protoplasts than the known constitutive, EXP sequences in this assay. EXP-Zm.UbgM1:1:2 drove expression of CP4 at the highest level, with expression levels being 2.2 to 3.4 fold higher than EXP-Os.Act1+CaMV.35S.2xA1-B3+Os.Act1:1:1 and EXP-CaMV.35S-enh+Ta.Lhcb1+Os.Act1:1:1, respectively. All EXP sequences assayed demonstrated the capacity to drive expression of CP4 in wheat cells.

Example 9: Analysis of Regulatory Elements Driving CP4 in Wheat Protoplasts Using CP4 Transgene Cassette Amplicons This example illustrates the ability of EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115), EXP-Cl.Ubq1:1:15 (SEQ ID NO: 116), EXP-Cl.Ubq1:1:16 (SEQ ID NO: 93) and EXP-Cl.Ubq1:1:17 (SEQ ID NO: 97) in driving expression of glyphosate tolerance gene CP4 in wheat protoplasts. These EXP sequences were cloned into plant binary transformation plasmid constructs. The resulting plant expression vectors were used as amplification templates to produce a transgene cassette amplicon comprised of an ubiquitin EXP sequence operably linked 5' to a plastid targeted glyphosate tolerant EPSPS coding sequence (CP4, U.S. RE39247), operably linked 5' to the T-AGRtu.nos-1: 1:13 3' UTR and a left border region from A. tumefaciens. The resulting amplicons were used to transform corn leaf protoplasts cells.

Wheat leaf protoplasts were transformed using a PEG-based transformation method, as described in Example 2 above. Measurements of both CP4 were conducted using an ELISA-based assay. The average levels of CP4 protein expression expressed as part per million (ppm) is shown in Tables 35 and 36 below.

In a first series of experiments, expression of CP4 driven by amplicons comprised of the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were assayed in transformed wheat leaf protoplasts and compared to CP4 expression levels driven by the constitutive controls, EXP-CaMV.35S-enh+Zm.DnaK:1:1 (SEQ ID NO: 170) and EXP-Os.Act1:1:1 (SEQ ID NO: 164). The average levels of CP4 protein expression expressed as part per million (ppm) is shown in Tables 35 below.

TABLE 35

Average CP4 protein expression in wheat leaf protoplasts.

| Amplicon Template | Amplicon ID | EXP sequence | SEQ ID NO: | CP4 ng/mg total protein Average | CP4 ng/mg total protein STDEV |
|---|---|---|---|---|---|
| | | no DNA | | 0.00 | 0.00 |
| pMON30098 | | GFP (negative control) | | 0.00 | 0.00 |
| pMON19469 | PCR24 | EXP-CaMV.35S-enh + Zm.DnaK:1:1 | 170 | 76.11 | 18.65 |
| pMON30167 | PCR25 | EXP-Os.Act1:1:1 | 164 | 3.83 | 0.73 |
| pMON140896 | PCR41 | EXP-ANDge.Ubq1:1:7 | 5 | 103.46 | 16.31 |
| pMON140917 | PCR42 | EXP-ANDge.Ubq1:1:8 | 8 | 61.48 | 1.99 |
| pMON140897 | PCR43 | EXP-ANDge.Ubq1:1:10 | 10 | 62.65 | 4.58 |
| pMON140898 | PCR44 | EXP-ANDge.Ubq1:1:6 | 12 | 48.74 | 3.09 |
| pMON140899 | PCR45 | EXP-ANDge.Ubq1:1:11 | 14 | 54.91 | 3.50 |
| pMON140900 | PCR46 | EXP-ANDge.Ubq1:1:12 | 16 | 42.81 | 5.97 |
| pMON140904 | PCR50 | EXP-ERIra.Ubq1:1:9 | 22 | 31.26 | 1.69 |
| pMON140905 | PCR51 | EXP-ERIra.Ubq1:1:10 | 25 | 49.82 | 5.96 |
| pMON140906 | PCR52 | EXP-ERIra.Ubq1:1:8 | 27 | 37.43 | 4.52 |
| pMON140907 | PCR53 | EXP-ERIra.Ubq1:1:11 | 29 | 27.17 | 0.96 |
| pMON140908 | PCR54 | EXP-ERIra.Ubq1:1:12 | 31 | 17.41 | 4.13 |
| pMON140913 | PCR19 | EXP-Cl.Ubq1:1:10 | 98 | 66.66 | 13.45 |
| pMON140914 | PCR20 | EXP-Cl.Ubq1:1:13 | 114 | 79.42 | 10.74 |
| pMON140915 | PCR21 | EXP-Cl.Ubq1:1:14 | 115 | 75.53 | 9.32 |
| pMON140916 | PCR22 | EXP-Cl.Ubq1:1:15 | 116 | 0.00 | 0.00 |

As can be seen in Table 31 above, the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were able to drive CP4 expression. All of the EXP sequences with the exception of one EXP-Cl.Ubq1:1:15 (SEQ ID NO: 116) drove CP4 expression levels at a much higher level than the constitutive control, EXP-Os.Act1:1:1 (SEQ ID NO: 164). Expression levels were around the same level or lower than that of EXP-CaMV.35S-enh+Zm.DnaK:1:1 (SEQ ID NO: 170) for most of the EXP sequences.

In a second series of experiments, expression of CP4 driven by amplicons comprised of the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were assayed in transformed wheat leaf protoplasts and compared to CP4 expression levels driven by the constitutive control, EXP-Os.Act1:1:1 (SEQ ID NO: 164). The average levels of CP4 protein expression expressed as part per million (ppm) is shown in Tables 32 below.

EXP-Sv.Ubq1:1:9 (SEQ ID NO: 133), EXP-Zm.UbgM1:1:6 (SEQ ID NO: 137), EXP-Zm.UbgM1:1:8 (SEQ ID NO: 145), EXP-Zm.UbgM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sb.Ubg4:1:2 (SEQ ID NO: 151), EXP-Sb.Ubg6:1:2 (SEQ ID NO: 153) and EXP-Cl.Ubq1:1:10 (SEQ ID NO: 98) in driving expression of CP4 in sugar cane leaf protoplasts. The EXP sequences were cloned into plant binary transformation plasmid constructs. The resulting vectors contained a right border region from *Agrobacterium tumefaciens*, an ubiquitin EXP sequence operably linked 5' to a plastid targeted glyphosate tolerant EPSPS coding sequence (CP4, U.S. RE39247), operably linked 5' to the T-AGRtu.nos-1:1:13 (SEQ ID NO: 127) or T-CaMV.35S-1:1:1 (SEQ ID NO: 140) 3' UTR and a left border region from *A. tumefaciens* (B-AGRtu.left border). The resulting plasmid constructs were used to transform sugarcane leaf protoplasts cells using PEG transformation method.

Plasmid constructs pMON129203, pMON12904, pMON12905, pMON129210, pMON129211, pMON129212, pMON129200, pMON129201, pMON129202, pMON129219, and pMON129218 are as described in Table 12 above.

Three control plasmids (pMON30167 described above; pMON130803 also comprising EXP-Os.Act1:1:1 (SEQ ID NO: 164); and pMON132804 comprising EXP-P-CaMV.35S-enh-1:1:13/L-CaMV.35S-1:1:2/I-Os.Act1-1:1:

TABLE 36

Average CP4 protein expression in wheat leaf protoplasts.

| Amplicon Template | Amplicon ID | EXP sequence | SEQ ID NO: | Maize Leaf CP4 mg/total protein Avg | Maize Leaf CP4 mg/total protein StdDev |
|---|---|---|---|---|---|
| pMON30167 | PCR25 | EXP-Os.Act1:1:1 | 164 | 15.84 | 2.12 |
| pMON140913 | PCR19 | EXP-Cl.Ubq1:1:10 | 98 | 736.32 | 79.56 |
| pMON142748 | pMON142748 | EXP-Cl.Ubq1:1:16 | 93 | 593.72 | 80.22 |
| pMON142749 | pMON142749 | EXP-Cl.Ubq1:1:17 | 97 | 763.95 | 86.94 |

As can be seen in Table 36 above, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive CP4 expression. Expression levels driven by all three EXP sequences were higher than that of the constitutive control, EXP-Os.Act1:1:1 (SEQ ID NO: 164).

Example 10: Analysis of Regulatory Elements Driving CP4 in Sugarcane Protoplasts This example illustrates the ability of EXP-Sv.Ubq1:1:7 (SEQ ID NO: 128), EXP-Sv.Ubq1:1:8 (SEQ ID NO: 132), 19 (SEQ ID NO: 139), with known constitutive regulatory elements driving CP4 were constructed and used to compare the relative CP4 expression levels driven by the ubiquitin EXP sequences listed in Table 37 below.

Sugarcane leaf protoplasts were transformed using a PEG-based transformation method. The mean CP4 expression levels determined by CP4 ELISA are presented in Table 37 below.

TABLE 37

Mean CP4 Protein Expression in Sugarcane Leaf Protoplast Cells.

| | | | Experiment 1 | | Experiment 2 | |
|---|---|---|---|---|---|---|
| Plasmid Construct | EXP sequence | SEQ ID NO: | CP4 Average ppm | CP4 STDEV ppm | CP4 Average ppm | CP4 STDEV ppm |
| pMON132804 | EXP-P-CaMV.35S-enh-1:1:13/L-CaMV.35S-1:1:2/I-Os.Act1-1:1:19 | 173 | 557.97 | 194.05 | 283.63 | 95.8 |
| pMON30167 | EXP-Os.Act1:1:1 | 164 | 57.15 | 20.99 | 18.36 | 5.41 |
| pMON130803 | EXP-Os.Act1:1:1 | 164 | 34.26 | 1.61 | 16.57 | 3.71 |

TABLE 37-continued

Mean CP4 Protein Expression in Sugarcane Leaf Protoplast Cells.

| | | | Experiment 1 | | Experiment 2 | |
|---|---|---|---|---|---|---|
| Plasmid Construct | EXP sequence | SEQ ID NO: | CP4 Average ppm | CP4 STDEV ppm | CP4 Average ppm | CP4 STDEV ppm |
| pMON129203 | EXP-Sv.Ubq1:1:7 | 128 | 89.2 | 32.46 | 56.86 | 9.55 |
| pMON129204 | EXP-Sv.Ubq1:1:8 | 132 | 87.2 | 45.87 | 98.46 | 12.93 |
| pMON129205 | EXP-Sv.Ubq1:1:9 | 133 | 263.57 | 70.14 | 72.53 | 9.25 |
| pMON129210 | EXP-Zm.UbqM1:1:6 | 137 | 353.08 | 29.16 | 199.31 | 41.7 |
| pMON129211 | EXP-Zm.UbqM1:1:8 | 145 | 748.18 | 15.1 | 411.24 | 17.12 |
| pMON129212 | EXP-Zm.UbqM1:1:7 | 141 | 454.88 | 75.77 | 215.06 | 23.22 |
| pMON129200 | EXP-SETit.Ubq1:1:5 | 117 | 150.74 | 63.21 | 91.71 | 41.35 |
| pMON129201 | EXP-SETit.Ubq1:1:7 | 123 | 119.57 | 58.1 | 102.72 | 31.12 |
| pMON129202 | EXP-SETit.Ubq1:1:6 | 124 | 43.79 | 25.77 | 97.63 | 46.07 |
| pMON129219 | EXP-Sb.Ubq4:1:2 | 151 | 95.63 | 38.69 | | |
| pMON129218 | EXP-Sb.Ubq6:1:2 | 153 | 343.34 | 119.2 | 179.75 | 51.16 |
| pMON129221 | EXP-Cl.Ubq1:1:10 | 98 | 374.8 | 205.28 | 258.93 | 38.03 |

As can be seen in Table 37 above, the EXP sequences demonstrated the ability to drive expression CP4 expression in sugarcane protoplasts. The levels of expression were similar to or greater than that of CP4 expression driven by EXP-Os.Act1:1:1 (SEQ ID NO: 164). One EXP sequence, EXP-Zm.UbgM1:1:8 (SEQ ID NO: 145), demonstrated higher levels of expression when compared to EXP-P-CaMV.35S-enh-1:1:13/L-CaMV.35S-1:1:2/I-Os.Act1-1:1:19 (SEQ ID NO: 139) in sugarcane protoplasts.

Example 11: Analysis of Regulatory Elements Driving CP4 in Sugarcane Protoplasts Using CP4 Transgene Cassette Amplicons This example illustrates the ability of EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) in driving expression of the glyphosate tolerance gene CP4 in sugarcane protoplasts. These EXP sequences were cloned into plant binary transformation plasmid constructs. The resulting plant expression vectors were used as amplification templates to produce a transgene cassette amplicon comprised of an ubiquitin EXP sequence operably linked 5' to a plastid targeted glyphosate tolerant EPSPS coding sequence (CP4, U.S. RE39247), operably linked 5' to the T-AGRtu.nos-1:1:13 3' UTR and a left border region from A. tumefaciens. The resulting amplicons were used to transform sugarcane leaf protoplasts cells.

Sugarcane leaf protoplasts were transformed using a PEG-based transformation method, as described in Example 2 above. Measurements of both CP4 were conducted using an ELISA-based assay.

Expression of CP4 driven by amplicons comprised of the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were assayed in transformed wheat leaf protoplasts and compared to CP4 expression levels driven by the constitutive controls, EXP-CaMV.35S-enh+Zm.DnaK:1:1 (SEQ ID NO: 170) and EXP-Os.Act1:1:1 (SEQ ID NO: 164). The average levels of CP4 protein expression expressed as part per million (ppm) is shown in Table 38 below.

TABLE 38

Average CP4 protein expression in sugarcane leaf protoplasts.

| Amplicon Template | Amplicon ID | EXP sequence | SEQ ID NO: | CP4 ng/mg total protein Average | CP4 ng/mg total protein STDEV |
|---|---|---|---|---|---|
| pMON19469 | PCR24 | EXP-CaMV.35S-enh + Zm.DnaK:1:1 | 170 | 99.6 | 7.2 |
| pMON30167 | PCR25 | EXP-Os.Act1:1:1 | 164 | 0.0 | 0.0 |
| pMON140896 | PCR41 | EXP-ANDge.Ubq1:1:7 | 5 | 21.9 | 3.3 |
| pMON140917 | PCR42 | EXP-ANDge.Ubq1:1:8 | 8 | 15.4 | 1.9 |
| pMON140897 | PCR43 | EXP-ANDge.Ubq1:1:10 | 10 | 20.7 | 2.2 |
| pMON140898 | PCR44 | EXP-ANDge.Ubq1:1:6 | 12 | 21.8 | 2.8 |
| pMON140899 | PCR45 | EXP-ANDge.Ubq1:1:11 | 14 | 36.9 | 7.2 |
| pMON140900 | PCR46 | EXP-ANDge.Ubq1:1:12 | 16 | 51.7 | 5.6 |
| pMON140904 | PCR50 | EXP-ERIra.Ubq1:1:9 | 22 | 10.3 | 1.1 |

TABLE 38-continued

Average CP4 protein expression in sugarcane leaf protoplasts.

| Amplicon Template | Amplicon ID | EXP sequence | SEQ ID NO: | CP4 ng/mg total protein Average | CP4 ng/mg total protein STDEV |
|---|---|---|---|---|---|
| pMON140905 | PCR51 | EXP-ERIra.Ubq1:1:10 | 25 | 25.3 | 4.7 |
| pMON140906 | PCR52 | EXP-ERIra.Ubq1:1:8 | 27 | 29.9 | 4.6 |
| pMON140907 | PCR53 | EXP-ERIra.Ubq1:1:11 | 29 | 44.0 | 7.1 |
| pMON140908 | PCR54 | EXP-ERIra.Ubq1:1:12 | 31 | 37.0 | 5.4 |
| pMON140913 | PCR19 | EXP-Cl.Ubq1:1:10 | 98 | 19.2 | 1.3 |
| pMON140914 | PCR20 | EXP-Cl.Ubq1:1:13 | 114 | 20.5 | 2.1 |
| pMON140915 | PCR21 | EXP-Cl.Ubq1:1:14 | 115 | 23.2 | 1.6 |
| pMON140916 | PCR22 | EXP-Cl.Ubq1:1:15 | 116 | 0.0 | 0.0 |

As can be seen in Table 38 above, the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) were able to drive CP4 expression. EXP-Cl.Ubq1:1:15 (SEQ ID NO: 116) did not appear to express CP4 expression in this assay.

Example 12: Analysis of Regulatory Elements Driving GUS in Transgenic Corn

Corn plants were transformed with plant expression vectors containing a EXP sequences driving expression of the β-glucuronidase (GUS) transgene, and the resulting plants were analyzed for GUS protein expression. The ubiquitin EXP sequences were cloned into plant binary transformation plasmid constructs using methods known in the art.

The resulting plant expression vectors contain a right border region from A. tumefaciens, a first transgene cassette to assay the EXP sequence operably linked to a coding sequence for β-glucuronidase (GUS) that possesses the processable intron GUS-2, described above, operably linked 5' to the 3' UTR from the rice lipid transfer protein gene (T-Os.LTP-1:1:1, SEQ ID NO: 141); a second transgene selection cassette used for selection of transformed plant cells that confers resistance to the herbicide glyphosate (driven by the rice Actin 1 promoter), and a left border region from A. tumefaciens. The resulting plasmids were used to transform corn plants. Table 39 lists the plasmid designations, the EXP sequences and the SEQ ID NOs, which are also described in Table 1.

TABLE 39

Binary plant transformation plasmids and the associated EXP sequences.

| Plasmid Construct | EXP sequence | SEQ ID NO: | Data |
|---|---|---|---|
| pMON142865 | EXP-ANDge.Ubq1:1:8 | 8 | $R_0$ and $R_1$ |
| pMON142864 | EXP-ERIra.Ubq1:1:8 | 27 | $R_0$ and $R_1$ |
| pMON142729 | EXP-Cl.Ubq1:1:12 | 90 | $R_0$ |
| pMON142730 | EXP-Cl.Ubq1:1:11 | 95 | $R_0$ |
| pMON132047 | EXP-Cl.Ubq1:1:23 | 108 | $R_0$ |

TABLE 39-continued

Binary plant transformation plasmids and the associated EXP sequences.

| Plasmid Construct | EXP sequence | SEQ ID NO: | Data |
|---|---|---|---|
| pMON132037 | EXP-SETit.Ubq1:1:10 | 119 | $R_0$ and $F_1$ |
| pMON131957 | EXP-SETit.Ubq1:1:11 | 125 | $F_1$ |
| pMON131958 | EXP-Sv.Ubq1:1:11 | 130 | $R_0$ and $F_1$ |
| pMON131959 | EXP-Sv.Ubq1:1:12 | 136 | $R_0$ |
| pMON131961 | EXP-Zm.UbqM1:1:10 | 139 | $R_0$ |
| pMON131963 | EXP-Zm.UbqM1:1:12 | 143 | $R_0$ |
| pMON131962 | EXP-Zm.UbqM1:1:11 | 149 | $R_0$ |
| pMON132932 | EXP-Sb.Ubq4:1:2 | 151 | $R_0$ |
| pMON132931 | EXP-Sb.Ubq6:1:3 | 155 | $R_0$ |
| pMON132974 | EXP-Sb.Ubq7:1:2 | 157 | $R_0$ and $F_1$ |

Plants were transformed using Agrobacterium-mediated transformations, for instance as described in U.S. Patent Application Publication 20090138985.

Histochemical GUS analysis was used for qualitative expression analysis of transformed plants. Whole tissue sections were incubated with GUS staining solution X-Gluc (5-bromo-4-chloro-3-indolyl-b-glucuronide) (1 milligram/milliliter) for an appropriate length of time, rinsed, and visually inspected for blue coloration. GUS activity was qualitatively determined by direct visual inspection or inspection under a microscope using selected plant organs and tissues. The $R_0$ plants are inspected for expression in the roots and leaves as well as the anther, silk and developing seed and embryo 21 days after pollination (21 DAP).

For quantitative analysis, total protein was extracted from selected tissues of transformed corn plants. One microgram of total protein was used with the fluorogenic substrate 4-methyleumbelliferyl-β-D-glucuronide (MUG) in a total reaction volume of 50 microliters. The reaction product, 4-methylumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 (Horiba; Kyoto, Japan) with Micromax Reader, with slit width set at excitation 2 nm and emission 3 nm.

The average $R_0$ GUS expression observed for each transformation is presented in Tables 40 and 41 below. The $R_0$ GUS assay performed on transformants transformed with pMON131957 (EXP-SETit.Ubq1:1:11, SEQ ID NO: 125) did not pass quality standards. These transformants were assayed at F1 generation and are presented further below in this example.

TABLE 40

Average R₀ GUS expression in root and leaf tissue.

| EXP sequence | SEQ ID NO: | V3 Root | V4 Root | V7 Root | VT Moot | V3 Leaf | V4 Leaf | V7 Leaf | VT Leaf |
|---|---|---|---|---|---|---|---|---|---|
| EXP-ANDge.Ubq1:1:8 | 8 | nd | 255 | 199 | 70 | nd | 638 | 168 | 130 |
| EXP-ERIra.Ubq1:1:8 | 27 | nd | 477 | 246 | 62 | nd | 888 | 305 | 242 |
| EXP-Cl.Ubq1:1:12 | 90 | nd | 27 | 147 | 52 | nd | 75 | 189 | 199 |
| EXP-Cl.Ubq1:1:11 | 95 | nd | 28 | 77 | 50 | nd | 101 | 177 | 223 |
| EXP-Cl.Ubq1:1:23 | 108 | 0 | nd | 75 | 34 | 201 | nd | 194 | 200 |
| EXP-SETit.Ubq1:1:10 | 119 | 0 | nd | 29 | 57 | 58 | nd | 37 | 46 |
| EXP-Sv.Ubq1:1:11 | 130 | nd | nd | nd | 9 | 20 | nd | 55 | 29 |
| EXP-Sv.Ubq1:1:12 | 136 | 63 | nd | 0 | 28 | 184 | nd | 27 | 16 |
| EXP-Zm.UbqM1:1:10 | 139 | 0 | nd | 237 | 18 | 221 | nd | 272 | 272 |
| EXP-Zm.UbqM1:1:12 | 143 | 0 | nd | 21 | 43 | 234 | nd | 231 | 196 |
| EXP-Zm.UbqM1:1:11 | 149 | 124 | nd | 103 | 112 | 311 | nd | 369 | 297 |
| EXP-Sb.Ubq4:1:2 | 151 | 125 | nd | 0 | 95 | 233 | nd | 150 | 88 |
| EXP-Sb.Ubq6:1:3 | 155 | 154 | nd | 13 | 128 | 53 | nd | 39 | 55 |
| EXP-Sb.Ubq7:1:2 | 157 | 37 | nd | 22 | 18 | 165 | nd | 89 | 177 |

TABLE 41

Average R₀ GUS expression in corn reproductive organs (anther, silk) and developing seed (embryo and endosperm).

| EXP sequence | SEQ ID NO: | VT Anther | VT/R1 Silk | 21 DAP Embryo | 21 DAP Endosperm |
|---|---|---|---|---|---|
| EXP-ANDge.Ubq1:1:8 | 8 | 247 | 256 | 24 | 54 |
| EXP-ERIra.Ubq1:1:8 | 27 | 246 | 237 | 36 | 61 |
| EXP-Cl.Ubq1:1:12 | 90 | 420 | 121 | 26 | 220 |
| EXP-Cl.Ubq1:1:11 | 95 | 326 | 227 | 41 | 221 |
| EXP-Cl.Ubq1:1:23 | 108 | 598 | 416 | 212 | 234 |
| EXP-SETit.Ubq1:1:10 | 119 | 132 | 85 | 50 | 63 |
| EXP-Sv.Ubq1:1:11 | 130 | 217 | 3 | 45 | 92 |
| EXP-Sv.Ubq1:1:12 | 136 | 120 | 21 | 49 | 112 |
| EXP-Zm.UbqM1:1:10 | 139 | 261 | 506 | 403 | 376 |
| EXP-Zm.UbqM1:1:12 | 143 | 775 | 362 | 253 | 247 |
| EXP-Zm.UbqM1:1:11 | 149 | 551 | 452 | 234 | 302 |
| EXP-Sb.Ubq4:1:2 | 151 | 213 | 0 | 25 | 79 |
| EXP-Sb.Ubq6:1:3 | 155 | 295 | 87 | 51 | 61 |
| EXP-Sb.Ubq7:1:2 | 157 | 423 | 229 | 274 | 90 |

In R₀ corn plants, GUS expression levels in the leaf and root differed amongst the ubiquitin EXP sequences. While all of the EXP sequences demonstrated the ability to drive GUS transgene expression in stably transformed plants, each EXP sequence demonstrated a unique pattern of expression relative to the others. For example, high levels of GUS expression were observed in early stages of root development (V4 and V7) for EXP-ANDge.Ubq1:1:8 (SEQ ID NO: 8) and EXP-ERIra.Ubq1:1:8 (SEQ ID NO: 27) and declined by VT stage. Root expression driven by EXP-Zm.UbgM1:1:10 (SEQ ID NO: 139) demonstrated no expression at V3 but was high at V7 and then dropped by VT stage. Root expression driven by EXP-Zm.UbgM1:1:11 (SEQ ID NO: 149) was maintained to a similar level throughout development from stages V3, V7 through VT. Root expression was observed to increase from early development (V3/V4) to V7 stage and then drop from V7 to V8 stage in plants transformed with EXP-Cl.Ubq1:1:12 (SEQ ID NO: 90), EXP-Cl.Ubq1:1:11 (SEQ ID NO: 95) and EXP-Cl.Ubq1:1:23 (SEQ ID NO: 108). GUS expression levels showed dramatic differences in leaf tissue as well. The highest levels of leaf expression were conferred in early development (V3/V4) with EXP-ANDge.Ubq1:1:8 (SEQ ID NO: 8) and EXP-ERIra.Ubq1:1:8 (SEQ ID NO: 27) which decline at V7 through VT stage. GUS expression is retained from V3 through VT stage using EXP-Zm.UbgM1:1:10 (SEQ ID NO: 139), EXP-Zm.UbgM1:1:11 (SEQ ID NO: 149), EXP-Zm.UbgM1:1:12 (SEQ ID NO: 143) and EXP-Cl.Ubq1:1:23 (SEQ ID NO: 108); and to a lower extent using EXP-SETit.Ubq1:1:10 (SEQ ID NO: 119) and EXP-Sb.Ubg6:1:3 (SEQ ID NO: 155). Expression in the leaf increased from V3 to V7 to VT stage using EXP-Cl.Ubq1:1:12 (SEQ ID NO: 90), EXP-Cl.Ubq1:1:11 (SEQ ID NO: 95) and EXP-Cl.Ubq1:1:23 (SEQ ID NO: 108) while expression declined from V3 to VT stage using EXP-Sv.Ubq1:1:12 (SEQ ID NO: 136) and EXP-Sb.Ubg4:1:2 (SEQ ID NO: 151).

Likewise, with respect to reproductive tissue (anther and silk) and developing seed (21DAP embryo and endosperm) different patterns of expression were observed unique to each EXP sequence. For example, High levels of expression were observed in anther and silk as well as the developing seed using EXP-Zm.UbgM1:1:10 (SEQ ID NO: 139), EXP-Zm.UbgM1:1:11 (SEQ ID NO: 149), EXP-Zm.UbgM1:1:12 (SEQ ID NO: 143) and EXP-Cl.Ubq1:1:23 (SEQ ID NO: 108). Expression was high in the anther and silk but low in the developing seed using EXP-ANDge.Ubq1:1:8 (SEQ ID NO: 8) and EXP-ERIra.Ubq1:1:8 (SEQ ID NO: 27). Expression driven by EXP-Sb.Ubg7:1:2 (SEQ ID NO: 157) was high in reproductive tissue and high in the developing embryo but was lower in the developing endosperm. The EXP sequence, EXP-Sb.Ubg4:1:2 (SEQ ID NO: 151) only demonstrated expression in the anther but not in the silk and expressed much lower in the developing seed. EXP-Sv.Ubq1:1:11 (SEQ ID NO: 130) demonstrated a similar pattern as EXP-Sb.Ubg4:1:2 (SEQ ID NO: 151) with respect to reproductive tissue and developing seed, but whereas EXP-Sb.Ubg4:1:2 (SEQ ID NO: 151) showed expression in root and leaf tissues, EXP-Sv.Ubq1:1:11 (SEQ ID NO: 130) expressed much lower in these same tissues.

R₀ generation transformants, selected for single copy insertions were crossed with a non-transgenic LH244 line (resulting in F₁) or were self-pollinated (resulting in R₁) in order to produce an F₁ or R₁ population of seeds. In either case, heterozygous F₁ or R₁ plants were selected for study. GUS expression levels were measured in selected tissues over the course of development as previously described. The F₁ or R₁ tissues used for this study included: imbibed seed embryo, imbibed seed endosperm, root and coleoptide at 4 days after germination (DAG); leaf and root at V3 stage; root and mature leaf at V8 stage; root, mature leaves, VT stage (at tasseling, prior to reproduction) anther, pollen, leaf and senescing leaf; R1 cob, silk, root and internode; kernel 12 days after pollination (DAP) and; embryo and endosperm 21 and 38 DAP. Selected tissue samples were also analyzed for F₁ plants exposed to conditions of drought and cold stress for transformants comprising pMON132037 (EXP-SETit.Ubq1:1:10, SEQ ID NO: 119), pMON131957 (EXP-SETit.Ubq1:1:11, SEQ ID NO: 125), pMON131958 (EXP-Sv.Ubq1:1:11, SEQ ID NO: 130) and pMON132974 (EXP-Sb.Ubg7:1:2, SEQ ID NO: 157). V3 root and leaf tissue was sampled after cold and drought exposure.

Drought stress was induced in $F_1$, V3 plants transformed with pMON132037 (EXP-SETit.Ubq1:1:10, SEQ ID NO: 119), pMON131957 (EXP-SETit.Ubq1:1:11, SEQ ID NO: 125), pMON131958 (EXP-Sv.Ubq1:1:11, SEQ ID NO: 130) and pMON132974 (EXP-Sb.Ubg7:1:2, SEQ ID NO: 157) by withholding watering for 4 days allowing the water content to be reduced by at least 50% of the original water content of the fully watered plant. The drought protocol was comprised essentially of the following steps. V3 stage plants were deprived of water. As a corn plant experiences drought, the shape of the leaf will change from the usual healthy and unfolded appearance to a leaf demonstrating folding at the mid-rib vascular bundle and appearing V-shaped when viewed from the leaf tip to the stem. This change in morphology usually began to occur by about 2 days after the cessation of watering and was shown in earlier experiments to be associated with water loss of around 50% as measured by weight of pots prior to cessation of watering and weight of pots when the leaf curl morphology was observed in un-watered plants. Plants were considered to be under drought conditions, when the leaves showed wilting as evidenced by an inward curling (V-shape) of the leaf. This level of stress is considered to be a form of sub-lethal stress. Once each plant demonstrated drought induction as defined above, the plant was destroyed to acquire both root and leaf samples.

In addition to drought, $F_1$ V3 stage plants transformed with pMON132037 (EXP-SETit.Ubq1:1:10, SEQ ID NO: 119), pMON131957 (EXP-SETit.Ubq1:1:11, SEQ ID NO: 125), pMON131958 (EXP-Sv.Ubq1:1:11, SEQ ID NO: 130) and pMON132974 (EXP-Sb.Ubg7:1:2, SEQ ID NO: 157) were also exposed to conditions of cold to determine if the regulatory elements demonstrated cold-induced expression of GUS. Whole plants were assayed for induction of GUS expression under cold stress at V3 stage. V3 stage corn plants were exposed to a temperature of 12° C. in a growth chamber for 24 hours. Plants in the growth chamber were grown under a white light fluence of 800 micro moles per meter squared per second with a light cycle of ten hours of white light and fourteen hours of darkness. After cold exposure, leaf and root tissues were sampled for quantitative GUS expression.

GUS expression was measured as described above. The average $F_1$ GUS expression determined for each tissue sample is presented in Tables 42 and 43 below.

TABLE 42

Average $F_1$ GUS expression in plants transformed with pMON142864 and pMON142865.

| Organ | pMON142864 | pMON142865 |
|---|---|---|
| V3 Leaf | 86 | 74 |
| V3 Root | 41 | 52 |
| V8 Leaf | 109 | 123 |
| V8 Root | 241 | 252 |
| VT Flower, anthers | 168 | 208 |
| VT Leaf | 158 | 104 |
| R1 Cob | 171 | 224 |
| R1 silk | 314 | 274 |
| R1 Root | 721 | 308 |
| R1 internode | 428 | 364 |
| R2 Seed-12DAP | 109 | 72 |
| R3 Seed-21DAP-Embryo | 45 | 32 |
| R3 Seed-21DAP-Endosperm | 175 | 196 |
| R5 Seed-38DAP-Embryo | 163 | 58 |
| R5 Seed-38DAP-Endosperm | 90 | 69 |

TABLE 43

Average $F_1$ GUS expression in plants transformed with pMON132037, pMON131957, pMON131958 and pMON132974.

| Organ | pMON132037 | pMON131957 | pMON131958 | pMON132974 |
|---|---|---|---|---|
| Imbibed Seed Embryo | 536 | 285 | 288 | 1190 |
| Imbibed Seed Endosperm | 95 | 71 | 73 | 316 |
| Coleoptile-4 DAG | 218 | 60 | 143 | 136 |
| Root-4 DAG | 74 | 33 | 101 | 48 |
| V3 Leaf | 104 | 120 | 66 | 52 |
| V3 Root | 74 | 71 | 81 | 194 |
| V3 Leaf-cold | 73 | 15 | 72 | N/A |
| V3 Root-cold | 113 | 44 | 89 | 49 |
| V3 Leaf-drought | 97 | 344 | 103 | 157 |
| V3 Root-drought | 205 | 153 | 129 | 236 |
| V8 Leaf | 185 | 142 | 77 | 282 |
| V8 Root | 33 | 16 | 61 | 28 |
| VT Flower-anthers | 968 | 625 | 619 | 888 |
| VT Leaf | 138 | 89 | 132 | 268 |
| VT Leaf-senescing | 121 | 100 | 156 | 345 |

TABLE 43-continued

Average F$_1$ GUS expression in plants transformed with pMON132037, pMON131957, pMON131958 and pMON132974.

| Organ | pMON132037 | pMON131957 | pMON131958 | pMON132974 |
|---|---|---|---|---|
| VT Pollen | 610 | 1119 | 332 | 4249 |
| R1 Cob | 291 | 70 | 168 | 127 |
| R1 silk | 164 | 124 | 167 | 101 |
| R1 Root | 36 | 39 | 39 | 21 |
| R1 internode | 255 | 89 | 232 | 141 |
| R2 Seed-12DAP | 138 | 170 | 165 | 169 |
| R3 Seed-21 DAP-Embryo | 94 | 97 | 489 | 389 |
| R3 Seed-21 DAP-Endosperm | 57 | 118 | 52 | 217 |
| R5 Seed-38 DAP-Embryo | 600 | 147 | 377 | 527 |
| R5 Seed-38 DAP-Endosperm | 58 | 36 | 57 | 106 |

In F$_1$ corn plants, GUS expression levels in the various tissues sampled differed amongst the ubiquitin EXP sequences. While all of the EXP sequences demonstrated the ability to drive GUS transgene expression in stably transformed F$_1$ corn plants, each EXP sequence demonstrated a unique pattern of expression relative to the others. For example, R1 root expression is about twice that for EXP-ERIra.Ubq1:1:8 (SEQ ID NO: 27) than EXP-ANDge.Ubq1:1:8 (SEQ ID NO: 8). GUS expression in the developing seed embryo at 38 DAP is almost three fold higher for EXP-ERIra.Ubq1:1:8 (SEQ ID NO: 27) than EXP-ANDge.Ubq1:1:8 (SEQ ID NO: 8). In contrast leaf and root expression at V3 and V8 stage is about the same for EXP-ERIra.Ubq1:1:8 (SEQ ID NO: 27) than EXP-ANDge.Ubq1:1:8 (SEQ ID NO: 8).

The F$_1$ GUS expression in imbided seeds (embryo and endosperm tissues) was much higher in plants transformed with EXP-Sb.Ubg7:1:2 (SEQ ID NO: 157) than in those transformed with EXP-SETit.Ubq1:1:10 (SEQ ID NO: 119), EXP-SETit.Ubq1:1:11 (SEQ ID NO: 125) and EXP-Sv.Ubq1:1:11 (SEQ ID NO: 130). Drought caused an increase in V3 root expression in plants transformed with EXP-SETit.Ubq1:1:10 (SEQ ID NO: 119), EXP-SETit.Ubq1:1:11 (SEQ ID NO: 125), EXP-Sv.Ubq1:1:11 (SEQ ID NO: 130) and EXP-Sb.Ubq7:1:2 (SEQ ID NO: 157), but only increased leaf expression in plants transformed with EXP-SETit.Ubq1:1:11 (SEQ ID NO: 125), EXP-Sv.Ubq1:1:11 (SEQ ID NO: 130) and EXP-Sb.Ubq7:1:2 (SEQ ID NO: 157). The drought enhanced V3 expression was greatest using EXP-SETit.Ubq1:1:11 (SEQ ID NO: 125). Pollen expression was also much higher in plants transformed with EXP-Sb.Ubg7:1:2 (SEQ ID NO: 157) than in those transformed with EXP-SETit.Ubq1:1:10 (SEQ ID NO: 119), EXP-SETit.Ubq1:1:11 (SEQ ID NO: 125) and EXP-Sv.Ubq1:1:11 (SEQ ID NO: 130). Expression in the R1 internode was greatest with EXP-SETit.Ubq1:1:10 (SEQ ID NO: 119) and EXP-Sv.Ubq1:1:11 (SEQ ID NO: 130) and least in plants transformed with EXP-SETit.Ubq1:1:11 (SEQ ID NO: 125).

Each EXP sequence demonstrated the ability to drive transgene expression in stably transformed corn plants. However, each EXP sequence had a pattern of expression for each tissue that was unique and offers an opportunity to select the EXP sequence which will best provide expression of a specific transgene depending upon the tissue expression strategy needed to achieve the desired results. This example demonstrates EXP sequences isolated from homologous genes do not necessarily behave equivalently in the transformed plant and that expression can only be determined through empirical investigation of the properties for each EXP sequence and cannot be predicted based upon the gene homology from which the promoter was derived.

Example 13: Analysis of Regulatory Elements Driving CP4 in Transgenic Corn

Corn plants were transformed with plant expression vectors containing EXP sequences driving expression of the CP4 transgene, and the resulting plants were analyzed for CP4 protein expression.

The EXP sequences EXP-ANDge.Ubq1:1:8 (SEQ ID NO: 8), EXP-ERIra.Ubq1:1:8 (SEQ ID NO: 27), EXP-Cl.Ubq1:1:10 (SEQ ID NO: 98), EXP-Sv.Ubq1:1:9 (SEQ ID NO: 133) and EXP-Zm.UbgM1:1:7 (SEQ ID NO: 141) were cloned into plant binary transformation plasmid constructs. The resulting vectors contained a right border region from *Agrobacterium tumefaciens*, an ubiquitin EXP sequence operably linked 5' to a plastid targeted glyphosate tolerant EPSPS coding sequence (CP4, U.S. RE39247), operably linked 5' to the T-AGRtu.nos-1:1:13 (SEQ ID NO: 127) 3' UTR and a left border region from *A. tumefaciens*. Table 44 below shows the plasmid constructs used to transform corn and the corresponding EXP sequences.

TABLE 44

CP4 plasmid constructs and corresponding EXP sequences used to transform corn.

| Plasmid Construct | EXP sequence | SEQ ID NO: | Data |
|---|---|---|---|
| pMON141619 | EXP-ANDge.Ubq1:1:8 | 8 | R$_0$ and F$_1$ |
| pMON142862 | EXP-ERIra.Ubq1:1:8 | 27 | R$_0$ and F$_1$ |
| pMON129221 | EXP-Cl.Ubq1:1:10 | 98 | R$_0$ and F$_1$ |
| pMON129205 | EXP-Sv.Ubq1:1:9 | 133 | R$_0$ and F$_1$ |
| pMON129212 | EXP-Zm.UbqM1:1:7 | 141 | R$_0$ |

The resulting plasmids were used to transform corn plants. Transformed plants were selected for one or two copies of the inserted T-DNA and grown in the greenhouse.

Selected tissues were sampled from the $R_0$ transformed plants at specific stages of development and CP4 protein levels were measured in those tissues using an CP4 ELISA assay. The average CP4 expression observed for each transformation is presented in Tables 45 and 46 below and graphically in FIG. 7.

cassette were selected for analysis of CP4 expression. Seed was grown in the greenhouse and two groups of plants were produced, one group was sprayed with glyphosate while the other was left unsprayed. Expression of CP4 was analyzed in selected tissues using a standard ELISA based assay. The average CP4 expression is shown in Tables 47 and 48 below.

TABLE 45

Average leaf and root CP4 expression in $R_0$ transformed corn plants.

| EXP sequence | SEQ ID NO: | V4 Leaf | V7 Leaf | VT Leaf | V4 Root | V7 Root | VT Root |
|---|---|---|---|---|---|---|---|
| EXP-ANDge.Ubq1:1:8 | 8 | 20.90 | 18.53 | 25.49 | 11.50 | 26.54 | 17.20 |
| EXP-ERIra.Ubq1:1:8 | 27 | 19.92 | 16.60 | 25.58 | 9.92 | 26.31 | 13.33 |
| EXP-Cl.Ubq1:1:10 | 98 | 10.70 | 12.49 | 17.42 | 7.56 | 13.95 | 6.68 |
| EXP-Sv.Ubq1:1:9 | 133 | 3.72 | 4.34 | 4.48 | 2.90 | 6.99 | 2.78 |
| EXP-Zm.UbqM1:1:7 | 141 | 13.42 | 21.89 | 38.78 | 9.56 | 16.69 | 11.15 |

TABLE 46

Average CP4 expression in reproductive tissue and developing seed in $R_0$ transformed corn plants.

| EXP sequence | SEQ ID NO: | VT Tassel | R1 Silk | R3 Embryo | R3 Endosperm |
|---|---|---|---|---|---|
| EXP-ANDge.Ubq1:1:8 | 8 | 24.14 | 5.55 | 7.29 | 4.91 |
| EXP-ERIra.Ubq1:1:8 | 27 | 19.20 | 10.27 | 12.60 | 4.70 |
| EXP-Cl.Ubq1:1:10 | 98 | 18.70 | 16.21 | 8.26 | 8.82 |
| EXP-Sv.Ubq1:1:9 | 133 | 7.10 | 4.72 | 3.13 | 1.74 |
| EXP-Zm.UbqM1:1:7 | 141 | 67.25 | 11.21 | 7.85 | 10.69 |

As can be seen in Tables 45 and 46, each of the EXP sequences EXP-ANDge.Ubq1:1:8 (SEQ ID NO: 8), EXP-ERIra.Ubq1:1:8 (SEQ ID NO: 27), EXP-Cl.Ubq1:1:10 (SEQ ID NO: 98), EXP-Sv.Ubq1:1:9 (SEQ ID NO: 133) and EXP-Zm.UbgM1:1:7 (SEQ ID NO: 141) was able to drive CP4 expression in all tissues sampled from the $R_0$ transformed plants. Higher expression of CP4 in the root and leaf of transformants comprising EXP-ANDge.Ubq1:1:8 (SEQ ID NO: 8) and EXP-ERIra.Ubq1:1:8 (SEQ ID NO: 27) driving CP4 than EXP-Cl.Ubq1:1:10 (SEQ ID NO: 98) driving CP4 may be related to the level of vegetative tolerance to glyphosate application as observed for these populations of transformants (see Example 14 below).

Each EXP sequence exhibited a unique expression pattern with respect to the level of expression for each tissue sampled. For example, while CP4 expression in leaf, root and tassel were similar for the EXP sequences, EXP-ANDge.Ubq1:1:8 (SEQ ID NO: 8) and EXP-ERIra.Ubq1:1:8 (SEQ ID NO: 27), expression in silk using EXP-ANDge.Ubq1:1:8 (SEQ ID NO: 8) was half that of expression driven by ERIra.Ubq1:1:8 (SEQ ID NO: 21). This might be advantageous for expression of transgenes in which constitutive expression is desired but less expression in silk tissue would be preferred. The EXP sequences demonstrate unique patterns of CP4 constitutive expression in $R_0$ transformed corn plants.

The $R_0$ transformed corn plants were crossed with a non-transgenic LH244 variety to produce $F_1$ seed. The resulting $F_1$ generation seed was analyzed for segregation of the transgene cassette and plants heterozygous for the CP4

TABLE 47

Average CP4 expression in $F_1$ transformed corn plants.

| Organ | pMON141619 | pMON142862 | pMON129221 |
|---|---|---|---|
| V4 Leaf | 11.50 | 13.51 | 7.68 |
| V4 Root | 12.48 | 12.60 | 10.29 |
| V7 Leaf | 16.59 | 20.21 | 12.01 |
| V7 Root | 11.00 | 13.62 | 8.15 |
| VT Leaf | 39.88 | 44.85 | 29.42 |
| VT Root | 17.43 | 21.83 | 13.43 |
| VT Flower, anthers | 52.74 | 55.72 | 53.62 |
| R1 Silk | 16.01 | 23.81 | 14.42 |
| R3 Seed-21 DAP-Embryo | 33.29 | 57.96 | 51.64 |
| R3 Seed-21 DAP-Endosperm | 2.99 | 3.20 | 6.44 |

As can be seen in Table 47 above, CP4 expression in leaf and root was higher in $F_1$ transformants transformed with pMON141619 (EXP-ANDge.Ubq1:1:8, SEQ ID NO: 5) and pMON142862 (EXP-ERIra.Ubq1:1:8, SEQ ID NO: 27) than in those transformed with pMON129221 (EXP-Cl.Ubq1:1:10, SEQ ID NO: 98). Expression in the anther tissue was similar for all three EXP sequences while expression in the silk was highest using EXP-ERIra.Ubq1:1:8 (SEQ ID NO: 27). Expression in the developing embryo (21 DAP) was highest in transformants comprising EXP-ERIra.Ubq1:1:8 (SEQ ID NO: 27) and EXP-Cl.Ubq1:1:10 (SEQ ID NO: 98) driving CP4. Expression in the developing endosperm was higher in transformants comprising EXP-Cl.Ubq1:1:10 (SEQ ID NO: 98) driving CP4.

TABLE 48

Average CP4 expression in $F_1$ transformed corn plants.

| Organ | pMON129205 |
|---|---|
| V4 Leaf | 1.73 |
| V4 Root | 2.44 |
| V7 Leaf | 2.84 |
| V7 Root | 1.51 |
| VT Leaf | 3.29 |
| VT Root | 2.63 |
| VT Flower, anthers | 7.52 |
| R1 Silk | 1.99 |
| R3 Seed-21 DAP-Embryo | 3.40 |
| R3 Seed-21 DAP-Endosperm | 1.79 |

As can be seen in Tables 47-48 above, CP4 expression was lower in all tissues of $F_1$ transformants transformed with pMON129205 (EXP-Sv.Ubq1:1:9, SEQ ID NO: 133) than those transformed with pMON141619 (EXP-ANDge.Ubq1:1:8, SEQ ID NO: 8), pMON142862 (EXP-ERIra.Ubq1:1:8, SEQ ID NO: 27) and pMON129221 (EXP-Cl.Ubq1:1:10, SEQ ID NO: 98).

The unique patterns of expression conferred by each of the EXP sequences assayed provide an opportunity to produce a transgenic plant in which expression can be fine-tuned to make small adjustments in transgene expression for optimal performance or effectiveness. In addition, empirical testing of these EXP sequences driving different transgene expression may produce results in which one particular EXP sequence is most suitable for expression of a specific transgene or class of transgenes while another EXP sequence is found to be best for a different transgene or class of transgenes.

Example 14: Analysis of Vegetative Glyphosate Tolerance in $R_0$ Transgenic Corn Plants Corn plants were transformed with plant expression vectors containing EXP sequences driving expression of the CP4 transgene, and the resulting plants were assessed for vegetative and reproductive tolerance to glyphosate application.

$F_1$ transformed corn plants described in Example 13 above transformed with pMON141619, pMON142862, pMON129221, pMON129205 and pMON129212 and comprised of the EXP sequences EXP-ANDge.Ubq1:1:8 (SEQ ID NO: 8), EXP-ERIra.Ubq1:1:8 (SEQ ID NO: 27), EXP-Cl.Ubq1:1:10 (SEQ ID NO: 98), EXP-Sv.Ubq1:1:9 (SEQ ID NO: 133) and EXP-Zm.UbgM1:1:7 (SEQ ID NO: 141), respectively driving CP4 were assessed for both vegetative and reproductive tolerance when sprayed with glyphosate. Ten $F_1$ plants for each event were divided into two groups, the first group consisting of five plants that received glyphosate spray and V4 and V8 stage of development; and a second group of five plants that were left unsprayed (i.e. control). Glyphosate was applied by broadcast foliar spray application using Roundup WeatherMax® at an application rate of 1.5 a.e./acre (a.e. acid equivalent). After seven to ten days, the leaves of each plant were assessed for damage. Vegetative tolerance (Veg Tol in Table 49) was assessed comparing the unsprayed and sprayed plants for each event and a damage rating scale was used to provide a final rating for vegetative tolerance (T=tolerant, NT=not tolerant). In addition seed set was assayed for all of the plants in each event. Seed set measures between control plants and sprayed plants was compared and an assignment of reproductive tolerance (Repro Tol in Table 49) was given for each event based upon the percent seed set of sprayed plants relative to the controls (T=tolerant, NT=not tolerant). Table 49 below shows the vegetative and reproductive tolerance ratings for each event sprayed at V4 and V8 stage. The letter "T" denotes tolerant and "NT" denotes not tolerant.

TABLE 49

Leaf damage ratings of individual transformed corn events at V4 and V8 stage.

| Plasmid Construct | EXP sequence | SEQ ID NO: | Event | Veg Tol V4 | Veg Tol V8 | Repro Tol |
|---|---|---|---|---|---|---|
| pMON141619 | EXP-ANDge.Ubq1:1:8 | 8 | Event 1 | T | T | NT |
| | | | Event 2 | T | T | T |
| | | | Event 3 | T | T | NT |
| | | | Event 4 | T | T | NT |
| | | | Event 5 | T | T | T |
| | | | Event 6 | T | T | NT |
| | | | Event 7 | T | T | T |
| | | | Event 8 | T | T | T |
| | | | Event 9 | T | T | NT |
| pMON142862 | EXP-ERIra.Ubq1:1:8 | 27 | Event 1 | T | T | T |
| | | | Event 2 | T | T | NT |
| | | | Event 3 | T | T | T |
| | | | Event 4 | T | T | T |
| | | | Event 5 | T | T | NT |
| | | | Event 6 | T | T | T |
| | | | Event 7 | T | T | NT |
| | | | Event 8 | T | T | T |
| | | | Event 9 | T | T | T |
| pMON129221 | EXP-Cl.Ubq1:1:10 | 98 | Event 1 | T | T | NT |
| | | | Event 2 | T | T | NT |
| | | | Event 3 | NT | NT | T |
| | | | Event 4 | NT | NT | T |
| | | | Event 5 | T | T | NT |
| | | | Event 6 | NT | NT | T |
| | | | Event 7 | T | T | T |
| pMON129205 | EXP-Sv.Ubq1:1:9 | 133 | Event 1 | NT | NT | |
| | | | Event 2 | NT | NT | NT |
| | | | Event 3 | T | T | NT |
| | | | Event 4 | NT | NT | |
| | | | Event 5 | NT | NT | NT |
| | | | Event 6 | NT | NT | NT |
| | | | Event 7 | NT | NT | NT |
| pMON129212 | EXP-Zm.UbqM1:1:7 | 141 | Event 1 | T | T | |
| | | | Event 2 | T | T | |
| | | | Event 3 | T | T | |
| | | | Event 4 | T | T | |
| | | | Event 5 | T | T | |
| | | | Event 6 | T | T | |

TABLE 49-continued

Leaf damage ratings of individual transformed corn events at V4 and V8 stage.

| Plasmid Construct | EXP sequence | SEQ ID NO: | Event | Veg Tol V4 | Veg Tol V8 | Repro Tol |
|---|---|---|---|---|---|---|
| | | | Event 7 | T | T | |
| | | | Event 8 | T | T | |
| | | | Event 9 | T | T | |
| | | | Event 10 | T | T | |

From Table 49 above, all transformed events assayed comprising CP4 transgene cassettes comprising the EXP sequences EXP-ANDge.Ubq1:1:8 (SEQ ID NO: 8), EXP-ERIra.Ubq1:1:8 (SEQ ID NO: 27) and EXP-Zm.UbgM1:1:7 (SEQ ID NO: 141) demonstrated full vegetative tolerance based upon damage ratings that did not exceed a score of ten. Four events of nine comprising EXP-ANDge.Ubq1:1:8 (SEQ ID NO: 8) and six events of nine comprising EXP-ERIra.Ubq1:1:8 (SEQ ID NO: 27) were both vegetatively and reproductively tolerant to glyphosate application. In contrast, events comprising EXP-Cl.Ubq1:1:10 (SEQ ID NO: 98) were either vegetatively tolerant or reproductively tolerant but not both. Only one event comprising EXP-Sv.Ubq1:1:9 (SEQ ID NO: 133) demonstrated vegetative tolerance and none of the events tested were reproductive tolerant. All events comprising EXP-Zm.UbgM1:1:7 (SEQ ID NO: 141) demonstrated vegetative tolerance but and assessment of reproductive tolerance is still in progress.

Example 15: Analysis of Expression Using Different 3' End Intron/Exon Splice Junction Sequences Corn and Wheat leaf protoplast cells were transformed with plant expression constructs comprising EXP sequences driving GUS expression that comprise the same promoter and leader but have different 3' end nucleotides following the intron/exon splice junction sequence, 5'-AG-3' to see if expression is affected by the slight change in sequence. Expression was also compared to that of two constitutive control plasmids.

Plant expression constructs are built comprising a GUS expression cassette. The resulting vectors are comprised of the *Coix lacryma-jobi* ubiquitin promoter, P-Cl.Ubq1-1:1:1 (SEQ ID NO: 80) operably linked 5' to the leader sequence, L-C.Ubq1-1:1:1 (SEQ ID NO: 81), operably linked 5' to an intron element shown in Table 50 below which each comprise different nucleotides at the very 3' end just after the intron/exon splice junction 5'-AG-3' sequence, operably linked 5' to a GUS coding sequence which is operably linked 5' to T-AGRtu.nos-1:1:13 (SEQ ID NO: 127) 3' UTR. Table 50 below shows the plant expression constructs and the corresponding 3' end sequence.

TABLE 50

Plant expression constructs, introns and 3' end sequence following the intron/exon splice junction sequence 5'-AG-3'.

| Plasmid construct | EXP sequence | SEQ ID NO: | Intron Variant | Intron 3' end nucleotides immediately following 3' splice site AG |
|---|---|---|---|---|
| pMON140889 | EXP-Cl.Ubq1:1:10 | 98 | I-Cl.Ubq1-1:1:6 (SEQ ID NO: 94) | GTC |
| pMON146795 | EXP-Cl.Ubq1:1:18 | 99 | I-Cl.Ubq1-1:1:7 (SEQ ID NO: 92) | GTG |
| pMON146796 | EXP-Cl.Ubq1:1:19 | 100 | I-Cl.Ubq1-1:1:8 (SEQ ID NO: 101) | GCG |
| pMON146797 | EXP-Cl.Ubq1:1:20 | 102 | I-Cl.Ubq1-1:1:9 (SEQ ID NO: 103) | GAC |
| pMON146798 | EXP-Cl.Ubq1:1:21 | 104 | I-Cl.Ubq1-1:1:10 (SEQ ID NO: 105) | ACC |
| pMON146799 | EXP-Cl.Ubq1:1:22 | 106 | I-Cl.Ubq1-1:1:11 (SEQ ID NO: 107) | GGG |
| pMON146800 | EXP-Cl.Ubq1:1:23 | 108 | I-Cl.Ubq1-1:1:12 (SEQ ID NO: 109) | GGT |
| pMON146801 | EXP-Cl.Ubq1:1:24 | 110 | I-Cl.Ubq1-1:1:13 (SEQ ID NO: 111) | CGT |
| pMON146802 | EXP-Cl.Ubq1:1:25 | 112 | I-Cl.Ubq1-1:1:14 (SEQ ID NO: 113) | TGT |
| pMON25455 | EXP-Os.Act1:1:9 | 179 | | Constitutive Control |
| pMON65328 | EXP-CaMV.35S-enh + Ta.Lhcb1 + Os.Act1:1:1 | 163 | | Constitutive Control |

Corn and Wheat protoplasts were transformed as previously described and assayed for GUS and luciferase expression. Table 51 below shows the average GUS and RLuc values for both corn and wheat protoplast expression.

TABLE 51

Average GUS and RLuc values for corn and wheat protoplast cells.

| EXP sequence | Intron 3' end nucleotides immed. following 3' splice site AG | Corn | | | Wheat | | |
|---|---|---|---|---|---|---|---|
| | | Average GUS | Average RLuc | GUS/ RLuc | Ave. GUS | Ave. RLuc | GUS/ RLuc |
| EXP-Cl.Ubq1:1:10 | GTC | 140343.0 | 93870.75 | 1.50 | 40906.25 | 17381.75 | 2.35 |
| EXP-Cl.Ubq1:1:18 | GTG | 143106.25 | 60565.25 | 2.36 | 56709.00 | 17898.75 | 3.17 |
| EXP-Cl.Ubq1:1:19 | GCG | 136326.83 | 88589.75 | 1.54 | 43211.00 | 17352.50 | 2.49 |
| EXP-Cl.Ubq1:1:20 | GAC | 138110.83 | 104751.42 | 1.32 | 31711.50 | 17953.75 | 1.77 |
| EXP-Cl.Ubq1:1:21 | ACC | 137906.75 | 72519.50 | 1.90 | 54164.17 | 17772.83 | 3.05 |
| EXP-Cl.Ubq1:1:22 | GGG | 137306.83 | 92643.42 | 1.48 | 55198.25 | 14476.75 | 3.81 |
| EXP-Cl.Ubq1:1:23 | GGT | 144085.50 | 64351.25 | 2.24 | 43008.83 | 13911.50 | 3.09 |
| EXP-Cl.Ubq1:1:24 | CGT | 142061.50 | 65884.00 | 2.16 | 51210.50 | 15041.00 | 3.40 |
| EXP-Cl.Ubq1:1:25 | TGT | 140353.00 | 61249.50 | 2.29 | 49577.75 | 15348.25 | 3.23 |
| EXP-Os.Act1:1:9 | Constitutive Control | 37665.25 | 65835.50 | 0.57 | 10830.25 | 17716.50 | 0.61 |
| EXP-CaMV.35S-enh + Ta.Lhcb1 + Os.Act1:1:1 | Constitutive Control | 49833.75 | 41268.75 | 1.21 | 15598.83 | 14877.50 | 1.05 |

The GUS/RLuc values for each *Coix lacryma-jobi* ubiquitin EXP sequence from Table 46 above were used to normalize the expression relative to the two constitutive controls EXP-Os.Act1:1:9 (SEQ ID NO: 179) and EXP-CaMV.35S-enh+Ta.Lhcb1+Os.Act1:1:1 (SEQ ID NO: 163) and are presented in Table 52 below.

TABLE 52

Normalized expression values of the *Coix lacryma-jobi* ubiquitin EXP sequences relative to EXP-Os.Act1:1:9 (SEQ ID NO: 179) and EXP-CaMV.35S-enh + Ta.Lhcb1 + Os.Act1:1:1 (SEQ ID NO: 163).

| EXP sequence | Intron 3' end nucleotides immediately following 3' splice site AG | Corn | | Wheat | |
|---|---|---|---|---|---|
| | | GUS/RLuc Normalized with respect to EXP-Os.Act1:1:9 | GUS/RLuc Normalized with respect to EXP-CaMV.35S-enh + Ta.Lhcb1 + Os.Act1:1:1 | GUS/Rluc Normalized with respect to EXP-Os.Act1:1:9 | GUS/Rluc Normalized with respect to EXP-CaMV.35S-enh + Ta.Lhcb1 + Os.Act1:1:1 |
| EXP-Cl.Ubq1:1:10 | GTC | 2.61 | 1.24 | 3.85 | 2.24 |
| EXP-Cl.Ubq1:1:18 | GTG | 4.13 | 1.96 | 5.18 | 3.02 |
| EXP-Cl.Ubq1:1:19 | GCG | 2.69 | 1.27 | 4.07 | 2.38 |
| EXP-Cl.Ubq1:1:20 | GAC | 2.30 | 1.09 | 2.89 | 1.68 |
| EXP-Cl.Ubq1:1:21 | ACC | 3.32 | 1.57 | 4.99 | 2.91 |
| EXP-Cl.Ubq1:1:22 | GGG | 2.59 | 1.23 | 6.24 | 3.64 |
| EXP-Cl.Ubq1:1:23 | GGT | 3.91 | 1.85 | 5.06 | 2.95 |
| EXP-Cl.Ubq1:1:24 | CGT | 3.77 | 1.79 | 5.57 | 3.25 |
| EXP-Cl.Ubq1:1:25 | TGT | 4.01 | 1.90 | 5.28 | 3.08 |
| EXP-Os.Act1:1:9 | Constitutive Control | 1.00 | 0.47 | 1.00 | 0.58 |
| EXP-CaMV.35S-enh + Ta.Lhcb1 + Os.Act1:1:1 | Constitutive Control | 2.11 | 1.00 | 1.72 | 1.00 |

As is shown in Table 52 above, each of the *Coix lacryma-jobi* ubiquitin EXP sequences provided expression that was greater than either constitutive control in both corn and wheat. Expression in corn protoplasts was relatively similar for all of the *Coix* ubiquitin EXP sequences. Expression in wheat was a little more variable. The use of different 3' end nucleotides following the intron/exon splice junction sequence, 5'-AG-3' did not appear to dramatically affect expression of GUS with the exception of GUS driven by EXP-Cl.Ubq1:1:20 (SEQ ID NO: 102). EXP-Cl.Ubq1:1:20 comprises the 3' end nucleotide sequences, 5'-GAC-3' following the intron/exon splice junction 5'-AG-3' sequence and caused expression to drop slightly relative to the other *Coix* ubiquitin EXP sequences. Assessment of the resulting spliced messenger RNA showed that approximately 10% of the mRNA expressed using EXP-Cl.Ubq1:1:20 (SEQ ID NO: 102) to drive GUS expression was improperly spliced. The mRNA resulting from GUS expression using the other *Coix* ubiquitin EXP sequences appeared to process properly. This experiment provides evidence that any of the 3' end nucleotides for any of the intron variants presented in Table 2 of Example 1 with the exception of the 3' end sequence 5'-GAC-3' which is found associated only with the intron element, I-Cl.Ubq1-1:1:9 (SEQ ID NO: 103) should be suitable for use in transgene expression cassettes without significant loss of activity and processing.

Example 16: Enhancers Derived from the Regulatory Elements

Enhancers are derived from the promoter elements provided herein, such as those presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135. The enhancer element may be comprised of one or more cis regulatory elements that, when operably linked 5' or 3' to a promoter element, or operably linked 5' or 3' to additional enhancer elements that are operably linked to a promoter, can enhance or modulate expression of a transgene, or provide expression of a transgene in a specific cell type or plant organ or at a particular time point in development or circadian rhythm. Enhancers are made by removing the TATA box or functionally similar elements and any downstream sequence from the promoters that allow transcription to be initiated from the promoters provided herein as described above, including fragments thereof, in which the TATA box or functionally similar elements and sequence downstream of the TATA box are removed. The enhancer element, E-Cl.Ubq1-1:1:1 (SEQ ID NO: 89) which is derived from the promoter element, P-Cl.Ubq1-1:1:1 is provided herein to demonstrate enhancers derived from a promoter element.

Enhancer elements may be derived from the promoter elements provided herein and cloned using methods known in the art to be operably linked 5' or 3' to a promoter element, or operably linked 5' or 3' to additional enhancer elements that are operably linked to a promoter. Alternatively, enhancer elements are cloned, using methods known in the art, to be operably linked to one or more copies of the enhancer element which are operably linked 5' or 3' to a promoter element, or operably linked 5' or 3' to additional enhancer elements that are operably linked to a promoter. Enhancer elements can also be cloned to be operably linked 5' or 3' to a promoter element derived from a different genus organism, or operably linked 5' or 3' to additional enhancer elements derived from other genus organisms or the same genus organism that are operably linked to a promoter derived from either the same or different genus organism, resulting in a chimeric regulatory element. A GUS expression plant transformation vector is constructed using methods known in the art similar to the constructs described in the previous examples in which the resulting plant expression vectors contain a right border region from *A. tumefaciens*, a first transgene cassette to test the regulatory or a chimeric regulatory element comprised of, a regulatory or chimeric regulatory element, operably linked to an intron derived from the HSP70 heat shock protein of *Z. mays* (I-Zm.DnaK-1:1:1 SEQ ID NO: 144) or any of the introns presented herein or any other intron, operably linked to a coding sequence for β-glucuronidase (GUS) that either possesses a processable intron (GUS-2, SEQ ID NO: 160) or no intron (GUS-1, SEQ ID NO: 159), operably linked to the Nopaline synthase 3' UTR from *A. tumefaciens* (T-AGRtu.nos-1:1:13, SEQ ID NO: 161) or the 3' UTR from the rice lipid transfer protein gene (T-Os.LTP-1:1:1, SEQ ID NO: 175); a second transgene selection cassette used for selection of transformed plant cells that confers resistance to the herbicide glyphosate (driven by the rice Actin 1 promoter), or alternatively, the antibiotic kanamycin (driven by the rice Actin 1 promoter) and a left border region from *A. tumefaciens*. The resulting plasmids are used to transform corn plants or other genus plants by the methods described above or by other *Agrobacterium*-mediated or particle bombardment methods known in the art. Alternatively, protoplast cells derived from corn or other genus plants are transformed using methods known in the art to perform transient assays GUS expression driven by the regulatory element comprising one or more enhancers is evaluated in stable or transient plant assays to determine the effects of the enhancer element on expression of a transgene. Modifications to one or more enhancer elements or duplication of one or more enhancer elements is performed based upon empirical experimentation and the resulting gene expression regulation that is observed using each regulatory element composition. Altering the relative positions of one or more enhancers in the resulting regulatory or chimeric regulatory element may affect the transcriptional activity or specificity of the regulatory or chimeric regulatory element and is determined empirically to identify the best enhancers for the desired transgene expression profile within the corn plant or other genus plant.

Example 17: Analysis of Intron Enhancement of GUS Activity Using Plant Derived Protoplasts An intron is selected based upon experimentation and comparison with an intronless expression vector control to empirically select an intron and configuration within the vector T-DNA element arrangement for optimal expression of a transgene. For example, in the expression of an herbicide resistance gene, such as CP4 which confers tolerance to glyphosate, it is desirable to have transgene expression within the reproductive tissues as well as the vegetative tissues, to prevent the loss of yield when applying the herbicide. An intron in this instance would be selected upon its ability when operably linked to a constitutive promoter, to enhance expression of the herbicide resistance conferring transgene, particularly within the reproductive cells and tissues of the transgenic plant and thus providing both vegetative and reproductive tolerance to the transgenic plant, when sprayed with the herbicide. In most ubiquitin genes, the 5' UTR is comprised of a leader, which has an intron sequence embedded within it. The expression elements derived from such genes are therefore assayed using the entire 5' UTR comprising the promoter, leader, and intron. To achieve different expression profiles or to modulate the level of transgene expression, the intron from such an expression element may be removed or substituted with a heterologous intron.

Introns presented herein as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 are identified using genomic DNA contigs in comparison to expressed sequence tag clusters or cDNA contigs to identify exon and intron sequences within the genomic DNA. In addition, 5' UTR or leader sequences are also used to define the intron/exon splice junction of one or more introns under conditions when the gene sequence encodes a leader sequence that is interrupted by one or more introns. Introns are cloned using methods known in the art into a plant transformation vector to be operably linked 3' to a transcriptional regulatory element and leader fragment and operably linked 5' to either a second leader fragment or to coding sequences, for instance as depicted in the two transgene cassettes presented in FIG. 1.

Thus, for instance, a first possible transgene cassette (Transgene Cassette Configuration 1 in FIG. 8) is comprised of a promoter or chimeric promoter element [A], operably linked 5' to a leader element [B], operably linked 5' to a test intron element [C], operably linked to a coding region [D], which is operably linked to a 3' UTR element [E]. Alternatively, a second possible transgene cassette (Transgene Cassette Configuration 2 in FIG. 8) is comprised of a promoter or chimeric promoter element [F], operably linked 5' to a first leader element or first leader element fragment [G], operably linked 5' to a test intron element [H], operably linked 5' to a second leader element or first leader element second fragment [I], operably linked to a coding region [J], which is operably linked to a 3' UTR element [K]. Further, a third possible transgene cassette (Transgene Cassette Configuration 3 in FIG. 8) is comprised of a promoter or chimeric promoter element [L], operably linked 5' to a leader element [M], operably linked 5' to a first fragment of the coding sequence element [N], operably linked 5' to an intron element [O] element, operably linked 5' to a second fragment of the coding sequence element [P], which is operably linked to a 3' UTR element [Q]. Transgene Cassette Configuration 3 is designed to allow splicing of the intron in such a manner as to produce a complete open reading frame without a frame shift between the first and second fragment of the coding sequence.

The first 6 nucleotides on the 5' end and the last 6 nucleotides on the 3' end of the introns presented as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 represent nucleotides before and after the intron/exon splice junction, respectively. These short 6 nucleotide sequences, for example, can be modified by having additional sequence appended (i.e. native or artificial) to facilitate cloning of the intron into a plant transformation vector, so long as the first and second nucleotides from the 5' end (GT) and the fourth and fifth nucleotide from the 3' end (AG) of SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 are preserved, thus preserving the intron/exon splice junction of the intron. As discussed above, it may be preferable to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The sequence around the 5' or 3' end splice junction sites of the intron can thus be modified.

The introns are assayed for an enhancement effect through the ability to enhance expression in transient assay or stable plant assay. For transient assay of intron enhancement, a base plant vector is constructed using methods known in the art. The intron is cloned into a base plant vector which comprises an expression cassette comprised of a constitutive promoter such as the Cauliflower mosaic virus promoter, P-CaMV.35S-enh-1:1:9 (SEQ ID NO: 176), operably linked 5' to a leader element, L-CaMV.35S-1:1:15 (SEQ ID NO: 177 (acacgctg)), operably linked 5' to a test intron element (e.g. one of SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182), operably linked to a coding sequence for β-glucuronidase (GUS) that either possesses a processable intron (GUS-2, SEQ ID NO: 160) or no intron (GUS-1, SEQ ID NO: 159), operably linked to the Nopaline synthase 3' UTR from *A. tumefaciens* (T-AGRtu.nos-1:1:13, SEQ ID NO: 161). Protoplast cells derived from corn or other genus plant tissue are transformed with the base plant vector and luciferase control vectors as described previously in Example 2 above and assayed for activity. To compare the relative ability of the intron to enhance expression, GUS values are expressed as a ratio of GUS to luciferase activity and compared with those levels imparted by a construct comprising the constitutive promoter operably linked to a known intron standard such as that as the intron derived from the HSP70 heat shock protein of *Zea mays*, I-Zm.DnaK-1:1:1 (SEQ ID NO: 178) as well as a construct comprising the constitutive promoter but without an intron operably linked to the promoter.

For stable plant assay of the introns presented as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182, a GUS expression plant transformation vector is constructed similar to the constructs described in the previous examples in which the resulting plant expression vectors contains a right border region from *A. tumefaciens*, a first transgene cassette to test the intron comprised of a constitutive promoter such as the Cauliflower mosaic virus promoter, P-CaMV.35S-enh-1:1:9 (SEQ ID NO: 176), operably linked 5' to a leader element, L-CaMV.35S-1:1:15 (SEQ ID NO: 177 (acacgctg)), operably linked 5' to a test intron element provided herein, operably linked to a coding sequence for β-glucuronidase (GUS) that either possesses a processable intron (GUS-2, SEQ ID NO: 160) or no intron (GUS-1, SEQ ID NO: 158), operably linked to the Nopaline synthase 3' UTR from *A. tumefaciens* (T-AGRtu.nos-1:1:13, SEQ ID NO: 161); a second transgene selection cassette used for selection of transformed plant cells that confers resistance to glyphosate (driven by the rice Actin 1 promoter), or alternatively, the antibiotic kanamycin (driven by the rice Actin 1 promoter) and a left border region from *A. tumefaciens*. The resulting plasmids are used to transform corn plants or other genus plants by the methods described above or by *Agrobacterium*-mediated methods known in the art. Single-copy or low copy number transformants are selected for comparison to single-copy or low copy number transformed plants, transformed with a plant transformation vector identical to the test vector but without the test intron to determine if the test intron provides an intron mediated enhancement effect.

Any of the introns presented as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 can be modified in a number of ways, such as deleting fragments within the intron sequence, which may reduce expression or duplication of fragments with the intron that may enhance expression. In addition, sequences within the intron that may affect the specificity of expression to either particular cells types or tissues and organs can be duplicated or altered or deleted to affect expression and patterns of expression of the transgene. In addition, the introns provided herein can be modified to remove any potential start codons (ATG) that may cause unintentional transcripts from being expressed from improperly spliced introns as different, longer or truncated proteins. Once the intron has been empirically tested, or it has been altered based upon experimentation, the intron is used to enhance expression of a transgene in stably transformed plants that can be of any genus monocot or dicot plant, so long as the intron provides enhancement of the transgene. The intron can also be used to enhance expression in other organisms, such as algae, fungi or animal cells, so long as the intron provides enhancement or attenuation or specificity of expression of the transgene to which it is operably linked.

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A DNA molecule comprising a DNA sequence selected from the group consisting of:
   a) a sequence with at least 99 percent sequence identity to the full length of SEQ ID NO:46 or 141, wherein said sequence has promoter activity; and
   b) a sequence comprising SEQ ID NO:46 or 141;
   wherein said sequence is operably linked to a heterologous transcribable polynucleotide molecule.

2. The DNA molecule of claim 1, wherein the heterologous transcribable polynucleotide molecule comprises a gene of agronomic interest.

3. The DNA molecule of claim 2, wherein the gene of agronomic interest confers herbicide tolerance in plants.

4. The DNA molecule of claim 2, wherein the gene of agronomic interest confers pest resistance in plants.

5. A transgenic plant cell comprising the DNA molecule of claim 1.

6. The transgenic plant cell of claim 5, wherein said transgenic plant cell is a monocotyledonous plant cell.

7. The transgenic plant cell of claim 5, wherein said transgenic plant cell is a dicotyledonous plant cell.

8. A transgenic plant, or part thereof, comprising the DNA molecule of claim 1.

9. A progeny plant of the transgenic plant of claim 8, or a part thereof, wherein the progeny plant or part thereof comprises said DNA molecule.

10. A transgenic seed, wherein the seed comprises the DNA molecule of claim 1.

11. A method of producing a commodity product comprising obtaining a transgenic plant or part thereof according to claim 8 and producing the commodity product therefrom.

12. The method of claim 11, wherein the commodity product is selected from the group consisting of protein concentrate, protein isolate, grain, starch, seeds, meal, flour, biomass, or seed oil.

13. A commodity product comprising the DNA molecule of claim 1.

14. The commodity product of claim 13, wherein the commodity product is selected from the group consisting of protein concentrate, protein isolate, grain, starch, seeds, meal, flour, biomass, or seed oil.

15. A method of expressing a transcribable polynucleotide molecule comprising obtaining a transgenic plant according to claim 8 and cultivating said plant, wherein the transcribable polynucleotide is expressed.

16. The DNA molecule of claim 1, wherein said DNA molecule comprises a sequence with at least 99 percent sequence identity to the full length of SEQ ID NO: 46 and has promoter activity.

17. The DNA molecule of claim 1, wherein said DNA molecule comprises a sequence with at least 99 percent sequence identity to the full length of SEQ ID NO: 141 and has promoter activity.

18. The DNA molecule of claim 1, wherein said DNA molecule comprises a sequence comprising SEQ ID NO: 46.

19. The DNA molecule of claim 1, wherein said DNA molecule comprises a sequence comprising SEQ ID NO: 141.

* * * * *

SEQUENCE LISTING

```
Sequence total quantity: 183
SEQ ID NO: 1              moltype = DNA   length = 3741
FEATURE                   Location/Qualifiers
source                    1..3741
                          mol_type = other DNA
                          organism = Andropogon gerardii
SEQUENCE: 1
agcagactcg cattatcgat ggaggggtgg gtttagaacc ctgaaaactg gtactgtttc   60
gaactgaaaa acactgtagc acttttcgtt tgtttgtggt aaatattatc ttactatggt  120
ctaactaggc tcaaaagaat cgtctcgcaa tgtacatcta aattatgcaa ttagttattt  180
tgtttacctg catttcatac tccgagcatg cgtcttttgg tacatttaat gcttcgatgt  240
gatgggaatt ttaaaaattt tggagaaaag ttggtttcta aacacccccg aggacgaaat  300
tggattcggt ctttgacgcg gatgcagcaa ctgcagtgcg caggatacca tcttagccgt  360
tgcgtcgaag ttcgctttgc taacgttttg agaaaattaa accagctttg accaacgtga  420
gacgagcgcc ttacgtggca gtgtaatgga accgggcacg gcaagtttga cgctgtagtg  480
ttagccggtc tcgttacgtt tggcacaact tagttgaatc cggcttccgg caaactatat  540
ggcaagttag acccaagtgt gagccggcca ccgcaagtta ttgggacatt atacgtagga  600
agcaagtgta taataagaat atgagataat gtaagcagct atatgaatca tcacgtcata  660
tttatgttaa gatgaagagg atagaataaa cggtatgtaa atttatagcg agtgatagac  720
gggcacaagg cctcctagct atttccataa atcggatttt gtaagaacaa aaaagaggac  780
ttattataag agaatgtggt aagtaagtat actctctccg tttcaaatta taagttgttt  840
tgatttttttt ggtacatcta ttttactatg cattagatat aataatgtgt ctagatacat  900
aacaaaatgg atgaatcaaa aaagtcaaag tgatttacaa tttggaacgg agagagtaag  960
ttcaagccgt caaggcactt ctatgcaacc acagtcaact tgaatgccgc ttgagtgcct 1020
tctcaagttt ttttttcttg caaaaatcat ttctttttt taaaaaagt ataatttgga 1080
tcgtgcaaat ttctctctag gtgtgtgtgt gactgtgtga gtaacaattt ctctagttgt 1140
gcgcgactgc tgcttacttt ggagattaca atatctttct aaaatgcttc gattacttat 1200
ttataaaccg tctctaaggc caattgctca agattcattc aacaattgaa acgtctcaca 1260
tgattaaatc atataaagtt tctaagtctt gtttgacaag attttttttag attttcatct 1320
aaattggatg aaactatcaa acactaattt taaaaaatat aagagaagct ccggagataa 1380
aaggtcgtct atgttattat aagagtaaag tcgtctattc tcttcgtccc aacatatata 1440
attctaagca tgaattgctt tcttttttgga caaaaggagc atgccacaac acaagaatga 1500
tgtcaccgtc atgcttggat cctttatgg taaagcttca ccttctataa tctaacaata 1560
gagaaatcag ggaaaaatca tgttttggtt gttttttattt ctaacctcca caataacttt 1620
ggtttaccat tttttgtttg attttagttt tagagaagcg tttataacag gacctaaaat 1680
ctttttttcag tacacagtac aacgcagacg ctcatacacg cacgcacact cacctctatg 1740
aacacacgta agaaaaccct acaccttgag caccttcgaa ggactgagcg ggtaaatata 1800
gagattctcg aagtcactat tagcgcctcg ttgtcaacgg gaatgtcgct taccacttaa 1860
agcataacgc cgagaaatcc cgtaataaat ccagtaaaat acgagcaccc gtgccaagtt 1920
gaatatttga acccgagtgg gtagattcca ccgcaaagga cctaaccaga tcatttcgca 1980
aacaggaact aaaatcggta gagagcccag acaaaagcct ttcctaagag ccactccagt 2040
ggaagcccct actttaggta taaatgcaa tactagtggg gctcctaaat aaacttctat 2100
ttttcatggc cttctaaaat tcactcccaa acccctagct atagaagtct cttatccatc 2160
ctctaaataa aaatgggagt ctatttttatt tcaccagagt tgatcgtaaa tttagtctct 2220
caaattttat aagttgaggg tagaggatga ctggagttgc tctaaacgga cctatcttca 2280
agtgacctca gtgagcccgt ttaacggcgt cgacaagttt aatctaacgg acaccaacca 2340
gagaagagaa ccaccgccag cgccgagcca agcgacgttg acatcttggc gcggcacggc 2400
atctccctgg cgtctggccc cctctcgaga cttccgctcc acctccacc ggtggcggtt 2460
tccaagtccg ttccgcctcc tctcacacgg cacgaaaccg tgacgggcac cggcagcacg 2520
gggggattcc ttttcccaccg ctccttccct ttcccttcct ctcccgccgc tataaatagc 2580
cagcccccatc cccagcttct ttccccaacc tcatcttctc tcgtgttgtt cggcacaacc 2640
cgatcgatcc ccaactcccct cgtcgtctct cctcgcgagc ctcgtcgatc cccgcttca 2700
```

-continued

```
aggtacggcg atcgattatc ttccctctct ctaccttctc tctcttatag ggcctgctag  2760
ctctgttcct gtttttccat ggctgcgagg tacaatagat cggcgatcca tggttagggc  2820
ctgctagttg tgttcctgtt tttccatggc tgcgaggcac aatagatctg atggcgttat  2880
gatggttaac ttgtcatact cttgcgatct atggtcccct taggagttta ggacatctat  2940
ttaatttcgg atagttcgag atctgtgatc catggttagt accctaggca gtggggttag  3000
atccgtgctg ttatggttcg tagatggatt ctgattgctc agtaactggg aatcctggga  3060
tggttctagc tggttcgcag ataagatcga tttcatgata tgctatatct tgtttggttg  3120
ccgtggttcc gttaaatctg tctgttatga tcttagtctt tgataaggtt cggtcgtgct  3180
agctacgtcc tgtgcagcac ttaattgtca ggtcataatt tttagcatgc cttttttta   3240
ttggtttggt tttgtctgac tgggctgtag atagtttcaa tctttgtctg actgggctgt  3300
agatagtttc aatctacctg tcggtttatt ttattaaatt tggatctgta tgtgtgtcat  3360
atatcttcat cttttagata tatcgatagg tttatatgtt gctgtcggtt ttttactgtt  3420
cctttatgag atatattcat gcttagatac atgaaacaac gtgctgttac agtttaaatag 3480
ttcttgttta tctaataaac aaataaggat aggtatatgc tgcagttagt tttactggta  3540
ctttttttga catgaaccta cggcttaata attagtcttc atcaaataaa agcatatttt  3600
tttaattatt tcgatatact tgaatgatgt catatgcagc atctgtgtga attttttggcc 3660
ctgtcttcat atgctgttta tttgtttggg actgtttctt tggttgataa ctcatcctgt  3720
tgtttggtga tccttttgca g                                            3741

SEQ ID NO: 2           moltype = DNA  length = 2603
FEATURE                Location/Qualifiers
source                 1..2603
                       mol_type = other DNA
                       organism = Andropogon gerardii
SEQUENCE: 2
agcagactcg cattatcgat ggaggggtgg gtttagaacc ctgaaaactg gtactgtttc   60
gaactgaaaa acactgtagc acttttcgtt tgtttgtggt aaatattatc ttactatggt   120
ctaactaggc tcaaaagaat cgtctcgcaa tgtacatcta aattatgcaa ttagttattt   180
tgtttacctg catttcatac tccgagcatg cgtcttttgg tacatttaat gcttcgatgt   240
gatgggaatt ttaaaaattt tggagaaaag ttggttctca aacacccccg aggacgaaat   300
tggattcggt ctttgacgcg gatgcagcaa ctgcagtgcg caggatacca tcttagccgt   360
tgcgtcgaag ttcgctttgc taacgttttg agaaaattaa accagctttg accaacgtga   420
gacgagcgcc ttacgtggca gtgtaatgga accgggcacg gcaagtttga cgctgtagtg   480
ttagccggtc tcgttacgtt tggcacaact tagttgatac cggcttccgg caaactatat   540
ggcaagttag acccaagtgt gagccggcca ccgcaagtta ttgggacatt atacgtagga   600
agcaagtgta taataagaat atgagataat gtaagcagct atatgaatca tcacgtcata   660
tttatgttaa gatgaagagg atagaataaa cggtatgtaa atttatagcg agtgatagac   720
gggcacaagg cctcctagct atttccataa atcggatttt gtaagaacaa aaaagaggac   780
ttattataag agaatgtggt aagtaagtat actctctccg tttcaaatta taagttgttt   840
tgattttttt ggtacatcta ttttactatg cattagatat aataatgtgt ctagatacat   900
aacaaaatgg atgaatcaaa aaagtcaaag tgatttacaa tttggaacgg agagagtaag   960
ttcaagccgt caaggcactt ctatgcaacc acagtcaact tgaatgccgc ttgagtgcct   1020
tctcaagttt ttttttcttg caaaaatcat ttcttttttt taaaaaaagt ataatttgga   1080
tcgtgcaaat ttctctctag gtgtgtgtgt gactgtgtga gtaacaattt ctctagttgt   1140
gcgcgactgc tgcttacttt ggagattaca atatctttct aaaatgcttc gattacttat   1200
ttataaaccg tctctaaggc caattgctca agattcattc aacaattgaa acgtctcaca   1260
tgattaaatc atataaagtt tctaagtctt gtttgacaag atttttttag attttcatct   1320
aaattggatg aaactatcaa acactaattt taaaaatat aagagaagct ccggagataa   1380
aaggtcgtct atgttattat aagagtaaag tcgtctattc tcttcgtccc aacatatata   1440
attctaagca tgaattgctt tcttttttgga caaaaggagc atgccacaac acaagaatga   1500
tgtcaccgtc atgcttggat cctttatgg taaagcttca ccttctataa tctaacaata   1560
gagaaatcag ggaaaaatca tgttttggtt gtttttattt ctaacctcca caataactttt  1620
ggtttaccat ttttttgtttg attttagttt tagagaagcg tttataacag gacctaaaat   1680
cttttttttcag tacacagtac aacgcagacg ctcatacacg cacgcacact cacctctatg   1740
aacacagta agaaaaccct acaccttgag caccttcgaa ggactgagcc ggtaaatata   1800
gagattctcg aagtcactat tagcgcctcc ttgtcaacgg gaatgtcgct taccacttaa   1860
agcataacgc cgagaaatcc cgtaataaat ccagtaaaat acgagcaccc gtgccaagtt   1920
gaatatttga acccgagtgg gtagattcca ccgcaaagga cctaaccaga tcatttcgca   1980
aacaggaact aaaatcggta gagagcccag acaaaagcct ttcctaagag ccactccagt   2040
ggaagcccct actttaggta taaaatgcaa tactagtggg gctccaaat aaacttctat    2100
ttttcatggc cttctaaaat tcactcccaa accctagct atagaagtct cttatccatc    2160
ctctaaataa aaatgggagt ctatttatt tcaccagagt tgatcgtaaa tttagtctct    2220
caaattttat aagttgaggg tagaggatga ctggagttgc tctaaacgga cctatcttca   2280
agtgacctca gtgagcccgt ttaacggcgt tgcagttttt aatcaacgg acaccaacca   2340
gagaagagaa ccaccgccag cgccgagcca agcgacgttg acatcttggc gcggcacggc   2400
atctccctgg cgtctggccc cctctcgaga cttccgctcc acctccacc ggtggcggtt    2460
tccaagtccg ttccgcctcc tctcacacg cacgaaaccg tgacgggcac cggcagcacg    2520
gggggattcc tttcccaccg ctccttccct ttcccttcct ctcccgccgc tataaatagc   2580
cagcccatc cccagcttct ttc                                            2603

SEQ ID NO: 3           moltype = DNA  length = 99
FEATURE                Location/Qualifiers
source                 1..99
                       mol_type = other DNA
                       organism = Andropogon gerardii
SEQUENCE: 3
cccaacctca tcttctctcg tgttgttcgg cacaacccga tcgatcccca actccctcgt   60
cgtctctcct cgcgagcctc gtcgatcccc gcttcaag                            99
```

```
SEQ ID NO: 4            moltype = DNA   length = 1039
FEATURE                 Location/Qualifiers
source                  1..1039
                        mol_type = other DNA
                        organism = Andropogon gerardii
SEQUENCE: 4
gtacggcgat cgattatctt ccctctctct accttctctc tcttataggg cctgctagct   60
ctgttcctgt ttttccatgg ctgcgaggta caatagatcg gcgatccatg gttagggcct  120
gctagttgtg ttcctgtttt tccatggctg cgaggcacaa tagatctgat ggcgttatga  180
tggttaactt gtcatactct tgcgatctat ggtccctta ggagtttagg acatctattt   240
aatttcggat agttcgagat ctgtgatcca tggttagtac cctaggcagt ggggttagat  300
ccgtgctgtt atggttcgta gatggattct gattgctcag taactgggaa tcctgggatg  360
gttctagctg gttcgcagat aagatcgatt tcatgatatg ctatatcttg tttggttgcc  420
gtggttccgt taaatctgtc tgttatgatc ttagtctttg ataaggttcg gtcgtgctag  480
ctacgtcctg tgcagcactt aattgtcagg tcataatttt tagcatgcct ttttttttatt  540
ggtttggttt tgtctgactg ggctgtagat agtttcaatc tttgtctgac tgggctgtag  600
atagtttcaa tctacctgtc ggtttatttt attaaatttg gatctgtatg tgtgtcatat  660
atcttcatct tttagatata tcgataggtt tatatgttgc gtcggtttt ttactgttcc    720
tttatgagat atattcatgc ttagatacat gaaacaacgt gctgttacag tttaatagtt  780
cttgtttatc taataaacaa ataaggatag gtatatgctg cagttagttt tactggtact  840
ttttttgaca tgaacctacg gcttaataat tagtcttcat caaataaaaa gcatattttt  900
taattatttc gatatacttg aatgatgtca tatgcagcat ctgtgtgaat ttttggccct  960
gtcttcatat gctgtttatt tgtttgggac tgtttctttg gttgataact catcctgttg 1020
tttggtgatc cttttgcag                                               1039

SEQ ID NO: 5            moltype = DNA   length = 3255
FEATURE                 Location/Qualifiers
source                  1..3255
                        mol_type = other DNA
                        organism = Andropogon gerardii
SEQUENCE: 5
ctcgttacgt ttggcacaac ttagttgaat ccggcttccg gcaaactata tggcaagtta   60
gacccaagtg tgagccggcc accgcaagtt attgggacat tatacgtagg aagcaagtgt  120
ataataagaa tatgagataa tgtaagcagc tatatgaatc atcacgtcat atttatgtta  180
agatgaagag gatagaataa acggtatgta aatttatagc gagtgataga cgggcacaag  240
gcctcctagc tatttccata aatcggattt tgtaagaaca aaaaagagga cttattataa  300
gagaatgtgg taagtaagta tactctctcc gtttcaaatt ataagttgtt ttgattttt   360
tggtacatct attttactat gcattagata taataatgtg tctagataca taacaaaatg  420
gatgaatcaa aaaagtcaaa gtgatttaca atttggaacg gagagagtaa gttcaagccg  480
tcaaggcact tctatgcaac cacagtcaac ttgaatgccg cttgagtgcc ttctcaagtt  540
tttttttctt gcaaaaatca tttctttttt ttaaaaaag tataatttgg atcgtgcaaa   600
tttctctcta ggtgtgtgtg tgactgtgtg agtaacaatt tctctagttg tgcgcgactg  660
ctgcttactt tggagattac aatatctttc taaaatgctt cgattactta tttataaacc  720
gtctctaagg ccaattgctc aagattcatt caacaattga aacgtctcac atgattaaat  780
catataaagt ttcaagtctt tgtttgacaa gattttttta gattttcatc taaattggat  840
gaaactatca aacactaatt ttaaaaaata taagagaagc tccggagata aaggtcgtc   900
tatgttatta taagagtaaa gtcgtctatt ctcttcgtcc caacatatat aattctaagc  960
atgaattgct ttcttttggg acaaaaggag catgccacaa cacaagaatg atgtcaccgt 1020
catgcttgga tccttttatg gtaaagcttc accttctata atctaacaat agagaaatca 1080
gggaaaaatc atgttttggt tgtttttatt tctaacctcc acaataactt tggtttacca 1140
ttttttgttt gattttagtt ttagagaagc gtttataaca ggacctaaaa tctttttca  1200
gtacacagta caacgcagac gctcatacac gcacgcacac tcacctctat gaacacacgt 1260
aagaaaaccc tacaccttga gcaccttcga aggactgagc cggtaaatat agagattctc 1320
gaagtcacta ttagcgcctc gttgtcaacg ggaatgtcgc ttaccactta aagcataacg 1380
ccgagaaatc ccgtaataaa tccagtaaaa tacgagcacc cgtgccaagt tgaatatttg 1440
aacccgagtg ggtagattcc accgcaaagg acctaaccag atcatttcgc aaacaggaac 1500
taaaatcggt agagagccca gacaaaagcc tttcctaaga gccactccag tggaagcccc 1560
tactttaggt ataaaatgca atactagtgg ggctcctaaa taaacttcta tttttcatgg 1620
cctctcaaaa ttcactccca aaccctagc tatagaagtc tcttatccat cctctaaata  1680
aaaatgggag tctatttat ttcaccagag ttgatcgtaa atttagtctc tcaaattta   1740
taagttgagg gtagaggatg actggagttg ctctaaacgg acctatcttc aagtgacctc 1800
agtgagcccg tttaacggcg tcgacaagtt taatctaacg gacaccaacc agagaagaga 1860
accaccgcca gcgccgagcc aagcgacgtt gacatcttgg cgcggcacgg catctccctg 1920
gcgtcgtcgcc ccctcctgag acttccgctc cacctcccac ggctcgtggc ttccaagtcc 1980
gttccgcctc ctctcacacg gcacgaaacc gtgacgggca ccggcagcac gggggattc   2040
ctttcccacc gctccttccc ttttccttcc tctcccgccg ctataaatag ccagcccat   2100
ccccagcttc ttttcccaac ctcatcttct ctcgtgttgt tcggcacaac ccgatcgatc 2160
cccaactccc tcgtcgtctc tcctcgcgag cctcgtcgat ccccgccttc aaggtacggc 2220
gatcgattat cttccctctc tctaccttct ctctcttata gggcttgcta gctctgttc  2280
tgttttccca tggctgcgag gtacaataga tcgcgatcc atggttaggg cctgctagtt 2340
gtgttcctgt ttttccatgg ctgcgaggca atagatct gatggcgtta tgatggttaa   2400
cttgtcatac tcttgcgatc tatggtccct taggagttt aggacatcta tttaatttcg  2460
gatagttcga gatctgtgat ccatggttag taccctaggc agtggggtta gatccgtgct 2520
gttatggttc gtagatggat tctgattgct cagtaactgg gaatcctggg atggttctag 2580
ctggttcgca gataagatcg atttcatgat atgctatatc ttgtttggtt gccgtggttc 2640
cgttaaatct gtctgttatg atcttagtct tgataaggt tcggtcgtgc tagctacgtc  2700
ctgtgcagca cttaattgtc aggtcataat ttttagcatg cctttttttt attggtttgg 2760
ttttgtctga ctgggctgta gatagtttca atctttgtct gactgggctg tagatagttt 2820
caatctacct gtcggtttat tttattaaat ttggatctgt atgtgtgtca tatatcttca 2880
```

```
tcttttagat atatcgatag gtttatatgt tgctgtcggt tttttactgt tcctttatga  2940
gatatattca tgcttagata catgaaacaa cgtgctgtta cagttttaata gttcttgttt  3000
atctaataaa caaataagga taggtatatg ctgcagttag ttttactggt acttttttg   3060
acatgaacct acggcttaat aattagtctt catcaaataa aaagcatatt ttttaattat  3120
ttcgatatac ttgaatgatg tcatatgcag catctgtgtg aatttttggc cctgtcttca  3180
tatgctgttt atttgtttgg gactgtttct ttggttgata actcatcctg ttgtttggtg  3240
atccttttgc aggtg                                                    3255

SEQ ID NO: 6           moltype = DNA  length = 2114
FEATURE                Location/Qualifiers
source                 1..2114
                       mol_type = other DNA
                       organism = Andropogon gerardii
SEQUENCE: 6
ctcgttacgt ttggcacaac ttagttgaat ccggcttccg gcaaactata tggcaagtta    60
gacccaagtg tgagccggcc accgcaagtt attgggacat tatacgtagg aagcaagtgt   120
ataataagaa tatgagataa tgtaagcagc tatatgaatc atcacgtcat attatgtta   180
agatgaagag gataagataa acggtatgta aatttatagc gagtgataga cgggcacaag   240
gcctcctagc tatttccata aatcggattt tgtaagaaca aaaaagagga cttattataa   300
gagaatgtgg taagtaagta tactctctcc gtttcaaatt ataagttgtt ttgatttttt   360
tggtacatct atttactat gcattagata taataatgtg tctagataca taacaaaatg   420
gatgaatcaa aaaagtcaaa gtgatttaca atttggaacg gagagagtaa gttcaagccg   480
tcaaggcact tctatgcaac cacagtcaac ttgaatgccg cttgagtgcc ttctcaagtt   540
ttttttttctt gcaaaaatca ttttctttttt ttaaaaaaag tataatttgg atcgtgcaaa  600
tttctctcta ggtgtgtgtg tgactgtgtg agtaacaatt tctctagttg tgcgcgactg   660
ctgcttactt tggagattac aatatctttc taaaatgctt cgattactta tttataaacc   720
gtctctaagg ccaattgctc aagattcatt caacaattga aacgtctcac atgattaat   780
catataaagt ttcaagtct tgtttgacaa gattttttta gatttcatc taaattggat   840
gaaactatca aacactaatt ttaaaaaata taagagaagc tccggagata aaggtcgtc   900
tatgttatta taagagtaaa gtcgtctatt ctcttcgtcc caacatatat aattctaagc   960
atgaattgct ttcttttgg acaaaaggag catgccacaa cacaagaatg atgtcaccgt  1020
catgcttgga tccttttatg gtaaagcttc accttctata atctaacaat agagaaatca  1080
gggaaaaatc atgttttggt tgtttttatt tctaacctcc acaataactt tggtttacca  1140
tttttgttt gatttagtt ttagagaagc gtttataaca ggacctaaaa tcttttttca  1200
gtacacagta caacgcagac gctcatacac gcacgcacac tcacctctat gaacacacgt  1260
aagaaaaccc tacaccttga gcaccttcga aggactgagc cggtaaatat agagattctc  1320
gaagtcacta ttagcgcctc gttgtcaacg ggaatgtcgc ttaccactta aagcataacg  1380
ccgagaaatc ccgtaataaa tccagtaaaa tacgagcacc cgtgccaagt tgaatatttg  1440
aacccgagtg ggtagattcc accgcaaagg acctaaccag atcatttcgc aaacaggaac  1500
taaaatcggt agagagccca gacaaaagcc tttcctaaga gccactccag tggaagcccc  1560
tactttaggt ataaaatgca atactagtgg ggctcctaaa taaacttcta ttttcatgg  1620
ccttctaaaa ttcactccca aacccctagc tatagaagtc tcttatccat cctctaaata  1680
aaaatgggag tctatttat ttcaccagag ttgatcgtaa atttagtctc tcaaattta  1740
taagttgagg gtagaggatg actggagttg ctctaaacgg acctatcttc aagtgacctc  1800
agtgagcccg tttaacggcg tcgacaagtt taatctaacg gacaccaacc agagaagaga  1860
accaccgcca gcgccgagcc aagcgacgtt gacatcttgg cgcggcacgg catctccctg  1920
gcgtcgtgcc ccctctcgag acttccgctc cacctcccac ccggtggcggt ttccaagtcc  1980
gttccgcctc ctctcacacg gcacgaaacc gtgacgggca ccggcagcac gggggggattc  2040
ctttcccacc gctccttccc tttcccttcc tctcccgccg ctataaatag ccagcccat   2100
ccccagcttc tttc                                                    2114

SEQ ID NO: 7           moltype = DNA  length = 1042
FEATURE                Location/Qualifiers
source                 1..1042
                       mol_type = other DNA
                       organism = Andropogon gerardii
SEQUENCE: 7
gtacggcgat cgattatctt ccctctctct accttctctc tcttataggg cctgctagct    60
ctgttcctgt ttttccatgg ctgcgaggta caatagatcg gcgatccatg gttagggcct   120
gctagttgtg ttcctgtttt tccatggctg cgaggcacaa tagatctgat ggcgttatga   180
tggttaactt gtcatactct tgcgatctat ggtccctta ggagtttagg acatctattt    240
aatttcggat agttcgagat ctgtgatcca tggttagtac cctaggcagt ggggttagat   300
ccgtgctgtt atggttcgta gatggattct gattgctcag taactgggaa tcctgggatg   360
gttctagctg gttcgcagat aagatcgatt tcatgatatg ctatatcttg tttggttgcc   420
gtggttccgt taaatctgtc tgttatgatc ttagtctttg ataaggttcg gtcgtgctag   480
ctacgtcctg tgcagcactt aattgtcagg tcataattt tagcatgcct ttttttttatt   540
ggtttggttt tgtctgactg ggctgtagat agtttcaatc tttgtctgac tgggctgtag   600
atagtttcaa tctacctgtc ggtttatttt attaaatttg gatctgtatg tgtgtcatat   660
atcttcatct tttagatata tcgataggtt tatatgttgc tgtcggtttt tactgttcct   720
tttatgagat atattcatgc ttagatacat gaaacaacgt gctgttacag tttaatagtt   780
cttgtttatc taataaacaa ataaggatag gtatatgctg cagttagttt tactggtact   840
ttttttgaca tgaacctacg gcttaataat tagtcttcat caaataaaaa gcatattttt   900
taattattc gatatacttg aatgatgtca tatgcagcat ctgtgtgaat ttttggccct   960
gtcttcatat gctgttatt tgtttgggac tgtttctttg gttgataact catcctgttg  1020
tttggtgatc ctttgcagg tg                                            1042

SEQ ID NO: 8           moltype = DNA  length = 2785
FEATURE                Location/Qualifiers
source                 1..2785
```

```
                        mol_type = other DNA
                        organism = Andropogon gerardii
SEQUENCE: 8
gttcaagccg tcaaggcact tctatgcaac cacagtcaac ttgaatgccg cttgagtgcc      60
ttctcaagtt ttttttttctt gcaaaaatca tttcttttt ttaaaaaaag tataatttgg     120
atcgtgcaaa tttctctcta ggtgtgtgtg tgactgtgtg agtaacaatt tctctagttg     180
tgcgcgactg ctgcttactt tggagattac aatatctttc taaatgctt cgattactta     240
tttataaacc gtctctaagg ccaattgctc aagattcatt caacaattga aacgtctcac     300
atgattaaat catataaagt ttctaagtct tgtttgacaa gatttttta gattttcatc      360
taaattggat gaaactatca aacactaatt ttaaaaaata taagagaagc tccggagata     420
aaaggtcgtc tatgttatta taagagtaaa gtcgtctatt ctcttcgtcc caacatatat    480
aattctaagc atgaattgct ttcttttgg acaaaaggag catgccacaa cacaagaatg     540
atgtcaccgt catgcttgga tccttttatg gtaaagcttc accttctata atctaacaat    600
agagaaatca gggaaaaatc atgttttggt tgtttttatt tctaacctcc acaataactt    660
tggtttacca tttttgttt gattttagtt ttagagaagc gtttataaca ggacctaaaa     720
tcttttttca gtacacagta caacgcgaga gctcatacac gcacgcacac tcacctctat    780
gaacacacgt aagaaaaccc tacaccttga gcaccttcga aggactgagc cggtaaatat    840
agagattctc gaagtcacta ttagcgcctc gttgtcaacg ggaatgtcgc ttaccactta    900
aagcataacg ccgagaaatc ccgtaataaa tccagtaaaa tacgagcacc cgtgccaagt    960
tgaatatttg aacccgagtg ggtagattcc accgcaaagg acctaaccag atcatttcgc   1020
aaacaggaac taaaatcggt agagagccca gacaaaagcc tttcctaaga gccactccag   1080
tggaagcccc tactttaggt ataaaatgca atactagtgg ggctcctaaa taaacttcta   1140
tttttcatgg ccttctaaaa ttcactccca aaccctagc tatagaagtc tcttatccat    1200
cctctaaata aaaatgggag tctattttat ttcaccagag ttgatcgtaa atttagtctc   1260
tcaaatttta taagttgagg gtagaggatg actggagttg ctctaaacgg acctatcttc   1320
aagtgacctc agtgagcccg tttaacggcg tcgacaaggt taatctaacg gacaccaacc   1380
agagaagaga accaccgcca gcgccgagcc aagcgacgtt gacatcttgg cgcggcacgg   1440
catctccctg gcgtctggcc ccctctcgag acttccgctc cacctcccac cggtggcggt   1500
ttccaagtcc gttccgcctc ctctcacacg gcacgaaacc gtgacgggca ccggcagcac   1560
gggggattc ctttcccacc gctccttccc tttcccttcc tctcccgccg ctaaaatag    1620
ccagccccat ccccagcttc ttttcccaac ctcatcttct ctcgtgttgt tcggcacaac   1680
ccgatcgatc cccaactccc tcgtcgtctc tcctcgcgag cctcgtcgat ccccccgcttc  1740
aaggtacggc gatcgattat cttccctctc tctaccttct ctctcttata gggcctgcta   1800
gctctgttcc tgtttttcca tggctgcgag gtacaataga tcggcgatcc atggttaggg   1860
cctgctagtt gtgttcctgt ttttccatgg ctgcgaggca caatagatct gatggcgtta   1920
tgatggttaa cttgtcatac tcttgcgatc tatggtccct ttaggagttt aggacatcta   1980
tttaatttcg gatagttcga gatctgtgat ccatggttag taccctaggc agtggggtta   2040
gatccgtgct gttatggttc gtagatggat tctgattgct cagtaactgg gaatcctggg   2100
atggttctag ctggttcgca gataagatcg atttcatgat atgctatatc ttgtttggtt   2160
gccgtggttc cgttaaatct gtctgttatg atcttagtct ttgataaggt tcggtcgtgc   2220
tagctacgtc ctgtgcagca cttaattgtc aggtcataat ttttagcatg ccttttttt    2280
attggtttgg ttttgtctga ctgggctgta gatagtttca atctttgtct gactgggctg   2340
tagatagttt caatctacct gtcggtttat tttattaaat ttggatctgt atgtgtgtca   2400
tatatcttca tcttttagat atatcgatag gtttatatgt tgctgtcggt tttttactgt   2460
tcctttatga gatatattca tgcttagata catgaaacaa cgtgctgtta cagtttaata   2520
gttcttgttt atctaataaa caaataagga taggtatatg ctgcagttag ttttactggt   2580
acttttttg acatgaacct acggcttaat aattagtctt catcaaataa aaagcatatt   2640
ttttaattat ttcgatatac ttgaatgatg tcatatgcag catctgtgtg aattttttggc  2700
cctgtcttca tatgctgttt attttgtttgg gactgtttct ttggttgata actcatcctg   2760
ttgtttggtg atccttttgc aggtg                                          2785

SEQ ID NO: 9             moltype = DNA   length = 1644
FEATURE                  Location/Qualifiers
source                   1..1644
                        mol_type = other DNA
                        organism = Andropogon gerardii
SEQUENCE: 9
gttcaagccg tcaaggcact tctatgcaac cacagtcaac ttgaatgccg cttgagtgcc      60
ttctcaagtt ttttttttctt gcaaaaatca tttcttttt ttaaaaaaag tataatttgg     120
atcgtgcaaa tttctctcta ggtgtgtgtg tgactgtgtg agtaacaatt tctctagttg     180
tgcgcgactg ctgcttactt tggagattac aatatctttc taaatgctt cgattactta     240
tttataaacc gtctctaagg ccaattgctc aagattcatt caacaattga aacgtctcac     300
atgattaaat catataaagt ttctaagtct tgtttgacaa gatttttta gattttcatc     360
taaattggat gaaactatca aacactaatt ttaaaaaata taagagaagc tccggagata    420
aaaggtcgtc tatgttatta taagagtaaa gtcgtctatt ctcttcgtcc caacatatat   480
aattctaagc atgaattgct ttcttttgg acaaaaggag catgccacaa cacaagaatg    540
atgtcaccgt catgcttgga tccttttatg gtaaagcttc accttctata atctaacaat   600
agagaaatca gggaaaaatc atgttttggt tgtttttatt tctaacctcc acaataactt   660
tggtttacca tttttgttt gattttagtt ttagagaagc gtttataaca ggacctaaaa   720
tcttttttca gtacacagta caacgcgaga gctcatacac gcacgcacac tcacctctat   780
gaacacacgt aagaaaaccc tacaccttga gcaccttcga aggactgagc cggtaaatat   840
agagattctc gaagtcacta ttagcgcctc gttgtcaacg ggaatgtcgc ttaccactta   900
aagcataacg ccgagaaatc ccgtaataaa tccagtaaaa tacgagcacc cgtgccaagt   960
tgaatatttg aacccgagtg ggtagattcc accgcaaagg acctaaccag atcatttcgc  1020
aaacaggaac taaaatcggt agagagccca gacaaaagcc tttcctaaga gccactccag  1080
tggaagcccc tactttaggt ataaaatgca atactagtgg ggctcctaaa taaacttcta  1140
tttttcatgg ccttctaaaa ttcactccca aaccctagc tatagaagtc tcttatccat  1200
cctctaaata aaaatgggag tctattttat ttcaccagag ttgatcgtaa atttagtctc  1260
tcaaatttta taagttgagg gtagaggatg actggagttg ctctaaacgg acctatcttc  1320
```

```
aagtgacctc agtgagcccg tttaacggcg tcgacaagtt taatctaacg gacaccaacc   1380
agagaagaga accaccgcca gcgccgagcc aagcgacgtt gacatcttgg cgcggcacgg   1440
catctccctg gcgtctggcc ccctctcgag acttccgctc cacctccac cggtggcggt    1500
ttccaagtcc gttccgcctc ctctcacacg gcacgaaacc gtgacgggca ccggcagcac   1560
gggggattc ctttcccacc gctccttccc tttcccttcc tctcccgccg ctataaatag    1620
ccagcccat ccccagcttc tttc                                           1644
```

```
SEQ ID NO: 10           moltype = DNA   length = 2613
FEATURE                 Location/Qualifiers
source                  1..2613
                        mol_type = other DNA
                        organism = Andropogon gerardii
SEQUENCE: 10
tctagttgtg cgcgactgct gcttactttg gagattacaa tatctttcta aaatgcttcg   60
attacttatt tataaaccgt ctctaaggcc aattgctcaa gattcattca acaattgaaa   120
cgtctcacat gattaaatca tataaagttt ctaagtcttg tttgacaaga tttttttaga   180
ttttcatcta aattggatga aactatcaaa cactaatttt aaaaaatata agagaagctc   240
cggagataaa aggtcgtcta tgttattata agagtaaagt cgtctattct cttcgtccca   300
acatatataa ttctaagcat gaattgcttt ctttttggac aaaaggagca tgccacaaca   360
caagaatgat gtcaccgtca tgcttggatc cttttatggt aaagcttcac cttctataat   420
ctaacaatag agaaatcagg gaaaaatcat gttttggttg ttttttattc taacctccac   480
aataactttg gtttaccatt ttttgtttga ttttagtttt agagaagcgt ttataacagg   540
acctaaaatc tttttttcagt acacagtaca acgcagacgc tcatacacgc acgcacactc   600
acctctatga acacacgtaa gaaaaccta caccttgagc accttcgaag gactgagccg    660
gtaaatatag agattctcga agtcactatt agcgcctcgt tgtcaacggg aatgtcgctt   720
accacttaaa gcataacgcc gagaaatccc gtaataaatc cagtaaaata cgagcacccg   780
tgccaagttg aatatttgaa cccgagtggg tagattccac cgcaaaggac ctaaccagat   840
catttcgcaa acaggaacta aaatcggtag agagcccaga caaaagcctt tcctaagagc   900
cactccagtg gaagcccta ctttaggtat aaaatgcaat actagtgggg ctcctaaata    960
aacttctatt tttcatggcc ttctaaaatt cactcccaaa cccctacgta tagaagtctc   1020
ttatccatcc tctaaataaa aatgggagtc tattttattt caccagagtt gatcgtaaat   1080
ttagtctctc aaattttata agttgagggt agaggatgac tggagttgct ctaaacggac   1140
ctatcttcaa gtgacctcag tgagcccgtt taacggcgtc gacaagttta atctaacgga   1200
caccaaccag agaagagaac caccgccagc gccgagcgaa gcgacgttga catcttgcg    1260
cggcacggca tctccctggc gtctggcccc ctctcgagac ttccgctcca cctcccaccg   1320
gtggcggttt ccaagtccgt tccgcctcct ctcacacggc acgaaaccgt gacgggcacc   1380
ggcagcacgg ggggattcct ttcccaccgc tccttccctt tccttcctc tcccgccgct    1440
ataaaatagcc agccccatcc ccagcttctt tcccaacct catcttctct cgtgttgttc   1500
ggcacaaccc gatcgatccc caactccctc gtcgtctctc ctcgcgagcc tcgtcgatcc   1560
cccgcttcaa ggtacggcga tcgattatct tccctctctc taccttctct ctcttatagg   1620
gcctgctagc tctgttcctg ttttccatg gctgcgaggt acaatagatc ggcgatccat     1680
ggttagggcc tgctagttgt gttcctgttt tccatggct gcgaggcaca atagatctga    1740
tggcgttatg atggttaact tgtcatactc ttgcgatcta tgtccctt aggagtttga     1800
gacatctatt taatttcgga tagttcgaga tctgtgatcc atggttagta ccctaggcag   1860
tggggttaga tccgtgctgt tatggttcgt agatggattc tgattgctca gtaactggga   1920
atcctgggat ggttctagct ggttcgcaga taagatcgat ttcatgatat gctatatctt   1980
gtttggttgc cgtggttccg ttaaatctgt ctgttatgat cttagtcttt gataaggttc   2040
ggtcgtgcta gctacgtcct gtgcagcact taattgtcag gtcataattt ttagcatgcc   2100
ttttttttat tggtttggtt ttgtctgact gggctgtaga tagtttcaat cttttgtctga  2160
ctgggctgta gatagtttca atctaccgtg cggtttattt tattaaattt ggatctgtat   2220
gtgtgtcata tatcttcatc tttagatat atcgatagt ttatatgttg ctcgtcggtt     2280
tttactgttc ctttatgaga tatattcatg cttagataca tgaacaacg tgctgttaca    2340
gtttaatagt tcttgtttat ctaataaaca aataaggata ggtatatgct gcagttagtt   2400
ttactggtac ttttttttgac atgaacctac ggcttaataa ttagtcttca tcaaataaaa   2460
agcatatttt ttaattattt cgatatactt gaatgatgtc atatgcagca tctgtgtgaa   2520
tttttggccc tgtcttcata tgctgtttat ttgtttggga ctgtttctttt ggttgataac   2580
tcatcctgtt gtttggtgat ccttttgcag gtg                                2613
```

```
SEQ ID NO: 11           moltype = DNA   length = 1472
FEATURE                 Location/Qualifiers
source                  1..1472
                        mol_type = other DNA
                        organism = Andropogon gerardii
SEQUENCE: 11
tctagttgtg cgcgactgct gcttactttg gagattacaa tatctttcta aaatgcttcg   60
attacttatt tataaaccgt ctctaaggcc aattgctcaa gattcattca acaattgaaa   120
cgtctcacat gattaaatca tataaagttt ctaagtcttg tttgacaaga tttttttaga   180
ttttcatcta aattggatga aactatcaaa cactaatttt aaaaaatata agagaagctc   240
cggagataaa aggtcgtcta tgttattata agagtaaagt cgtctattct cttcgtccca   300
acatatataa ttctaagcat gaattgcttt ctttttggac aaaaggagca tgccacaaca   360
caagaatgat gtcaccgtca tgcttggatc cttttatggt aaagcttcac cttctataat   420
ctaacaatag agaaatcagg gaaaaatcat gttttggttg ttttttattc taacctccac   480
aataactttg gtttaccatt ttttgtttga ttttagtttt agagaagcgt ttataacagg   540
acctaaaatc tttttttcagt acacagtaca acgcagacgc tcatacacgc acgcacactc   600
acctctatga acacacgtaa gaaaaccta caccttgagc accttcgaag gactgagccg    660
gtaaatatag agattctcga agtcactatt agcgcctcgt tgtcaacggg aatgtcgctt   720
accacttaaa gcataacgcc gagaaatccc gtaataaatc cagtaaaata cgagcacccg   780
tgccaagttg aatatttgaa cccgagtggg tagattccac cgcaaaggac ctaaccagat   840
catttcgcaa acaggaacta aaatcggtag agagcccaga caaaagcctt tcctaagagc   900
```

```
cactccagtg gaagcccta ctttaggtat aaaatgcaat actagtgggg ctcctaaata    960
aacttctatt tttcatggcc ttctaaaatt cactcccaaa cccctagcta tagaagtctc   1020
ttatccatcc tctaaataaa aatgggagtc tattttattt caccagagtt gatcgtaaat   1080
ttagtctctc aaattttata agttgagggt agaggatgac tggagttgct ctaaacggac   1140
ctatcttcaa gtgacctcag tgagcccgtt taacggcgtc gacaagttta atctaacgga   1200
caccaaccag agaagagaac caccgccagc gccgagccaa gcgacgttga catcttggcg   1260
cggcacggca tctccctggc gtctggcccc ctctcgagac ttccgctcca cctcccaccg   1320
gtggcggttt ccaagtccgt tccgcctcct ctcacacggc acgaaccgt gacgggcacc   1380
ggcagcacgg ggggattcct ttcccaccgc tccttccctt tcccttcctc tcccgccgct   1440
ataaatagcc agccccatcc ccagcttctt tc                                 1472

SEQ ID NO: 12           moltype = DNA   length = 2255
FEATURE                 Location/Qualifiers
source                  1..2255
                        mol_type = other DNA
                        organism = Andropogon gerardii
SEQUENCE: 12
cacaagaatg atgtcaccgt catgcttgga tcctttatg gtaaagcttc accttctata   60
atctaacaat agagaaatca gggaaaaatc atgttttggt tgtttttatt tctaacctcc  120
acaataactt tggtttacca ttttttgttt gattttagtt ttagagaagc gtttataaca  180
ggacctaaaa tctttttttca gtacacagta caacgcagac gctcatacac gcacgcacac  240
tcacctctat gaacacacgt aagaaaaccc tacaccttga gcaccttcga aggactgagc  300
cggtaaatat agagattctc gaagtcacta ttagcgcctc gttgtcaacg ggaatgtcgc  360
ttaccactta aagcataacg ccgagaaatc ccgtaataaa tccagtaaaa tacgagcacc  420
cgtgccaagt tgaatatttg aacccgagtg ggtagattcc accgcaaagg acctaaccag  480
atcatttcgc aaacaggaac taaaatcggt agagagcccca gacaaagcc tttcctaaga  540
gccactccag tggaagcccc tactttaggt ataaaatgca atactagtgg ggctcctaaa  600
taaacttcta ttttttcatgg ccttctaaaa ttcactccca aaccctagc tatagaagtc  660
tcttatccat cctctaaata aaaatgggag tctattttat ttcaccagag ttgatcgtaa  720
atttagtctc tcaaatttta taagttgagg gtagaggatg actggagttg ctctaaacgg  780
acctatcttc aagtgacctc agtgagcccg tttaacggcg tcgacaagtt taatctaacg  840
gacaccaacc agaagagaga accaccgcca gcgccgagcc aagcgacgtt gacatcttgg  900
cgcggcacgg catctccctg gcgtctggcc cctctcgag acttccgctc cacctcccac  960
cggtggcggt ttccaagtcc gttccgcctc ctctcacacg gcacgaaacc gtgacgggca  1020
ccggcagcac ggggggattc ctttcccacc gctccttcc tttccttcc tctcccgccg  1080
ctataaatag ccagccccat ccccagcttc ttttcccaac ctcatcttct ctcgtgttgt  1140
tcggcacaac ccgatcgatc cccaactccc tcgtcgtctc tcctcgcgag cctcgtcgat  1200
cccccgcttc aaggtacggc gatcgattat cttccctgcg tctaccttct ctctcttata  1260
gggcctgcta gctctgttcc tgttttttcca tggctgcgag gtacaataga tcggcgatcc  1320
atggttaggg cctgctagtt gtgttcctgt ttttccatgg ctgcgaggca caatagatct  1380
gatggcgtta tgatggttaa cttgtcatac tcttgcgatc tatggtccct ttaggagttt  1440
aggacatcta tttaatttcg gatagttcga gatctgtgat ccatggttag taccctaggc  1500
agtggggtta gatccgtgct gttatggttc gtagatgat tctgattgct cagtaactgg  1560
gaatcctggg atggttctag ctggttcgca gataagatcg atttcatgat atgctatatc  1620
ttgtttggtt gccgtggttc cgttaaatct gtctgttatg atcttagtct ttgataaggt  1680
tcggtcgtgc tagctacgtc ctgtgcagca cttaattgtc aggtcataat ttttagcatg  1740
cctttttttt attggtttgg ttttgtctga ctgggctaga gatagtttca atctttgtct  1800
gactgggctg tagatagttt caatctacct gtcggtttat tttattaaat ttggatctgt  1860
atgtgtgtca tatatcttca tcttttagat atatcgatag gtttatatgt tgctgtcggt  1920
tttttactgt tccttttatga gatatattca tgcttagata catgaaacaa cgtgctgtta  1980
cagtttaata gttcttgttt atctaataaa caaatagggta taggtatatg ctgcagttag  2040
ttttactggt actttttttg acatgaacct acgcttaat aattagtctt catcaaataa  2100
aaagcatatt ttttaattat ttcgatatac ttgaatgatg tcatatgcag catctgtgtg  2160
aattttggc cctgtcttca tatgctgttt atttgttttgg gactgtttct ttggttgata  2220
actcatcctg ttgtttggtg atccttttgc aggtg                              2255

SEQ ID NO: 13           moltype = DNA   length = 1114
FEATURE                 Location/Qualifiers
source                  1..1114
                        mol_type = other DNA
                        organism = Andropogon gerardii
SEQUENCE: 13
cacaagaatg atgtcaccgt catgcttgga tcctttatg gtaaagcttc accttctata   60
atctaacaat agagaaatca gggaaaaatc atgttttggt tgtttttatt tctaacctcc  120
acaataactt tggtttacca ttttttgttt gattttagtt ttagagaagc gtttataaca  180
ggacctaaaa tctttttttca gtacacagta caacgcagac gctcatacac gcacgcacac  240
tcacctctat gaacacacgt aagaaaaccc tacaccttga gcaccttcga aggactgagc  300
cggtaaatat agagattctc gaagtcacta ttagcgcctc gttgtcaacg ggaatgtcgc  360
ttaccactta aagcataacg ccgagaaatc ccgtaataaa tccagtaaaa tacgagcacc  420
cgtgccaagt tgaatatttg aacccgagtg ggtagattcc accgcaaagg acctaaccag  480
atcatttcgc aaacaggaac taaaatcggt agagagccca gacaaagcc tttcctaaga  540
gccactccag tggaagcccc tactttaggt ataaaatgca atactagtgg ggctcctaaa  600
taaacttcta ttttttcatgg ccttctaaaa ttcactccca aaccctagc tatagaagtc  660
tcttatccat cctctaaata aaaatgggag tctattttat ttcaccagag ttgatcgtaa  720
atttagtctc tcaaatttta taagttgagg gtagaggatg actggagttg ctctaaacgg  780
acctatcttc aagtgacctc agtgagcccg tttaacggcg tcgacaagtt taatctaacg  840
gacaccaacc agaagagaga accaccgcca gcgccgagcc aagcgacgtt gacatcttgg  900
cgcggcacgg catctccctg gcgtctggcc cctctcgag acttccgctc cacctcccac  960
cggtggcggt ttccaagtcc gttccgcctc ctctcacacg gcacgaaacc gtgacgggca 1020
```

```
ccggcagcac ggggggattc ctttcccacc gctccttccc tttcccttcc tctcccgccg 1080
ctataaatag ccagccccat ccccagcttc tttc                              1114

SEQ ID NO: 14           moltype = DNA  length = 1912
FEATURE                 Location/Qualifiers
source                  1..1912
                        mol_type = other DNA
                        organism = Andropogon gerardii
SEQUENCE: 14
gtcaacggga atgtcgctta ccacttaaag cataacgccg agaaatcccg taataaatcc  60
agtaaaatac gagcacccgt gccaagttga atatttgaac ccgagtgggt agattccacc  120
gcaaaggacc taaccagatc atttcgcaaa caggaactaa aatcggtaga gagcccagac  180
aaaagccttt cctaagagcc actccagtgg aagcccctac tttaggtata aaatgcaata  240
ctagtggggc tcctaaataa acttctattt ttcatggcct tctaaaattc actcccaaac  300
ccctagctat agaagtctct tatccatcct ctaaataaaa atgggagtct attttatttc  360
accagagttg atcgtaaatt tagtctctca aattttataa gttgagggta gaggatgact  420
ggagttgctc taaacggacc tatcttcaag tgacctcagt gagcccgttt aacggcgtcg  480
acaagtttaa tctaacggac accaaccaga gaagagaacc accgccagcg ccgagccaag  540
cgacgttgac atcttggcgc ggcacggcat ctccctggcg tctggccccc tctcgagact  600
tccgctccac ctcccaccgg tggcggtttc caagtccgtt ccgcctcctc tcacacggca  660
cgaaaccgtg acgggcaccg gcagcacggg gggattcctt tccaccgct ccttcccttt  720
cccttcctct cccgccgcta taaatagcca gccccatcc cagcttcttt ccccaacctc  780
atcttctctc gtgttgttcg gcacaacccg atcgatcccc aactccctcg tcgtctctc  840
tcgcgagcct cgtcgatccc ccgcttcaag gtacggcgat cgattatctt ccctctctct  900
accttctctc tcttataggg cctgctagct ctgttcctgt ttttcatgg ctgcgaggta  960
caatagatcg gcgatccatg gttagggcct gctagttgta ttcctgtttt tccatggctg  1020
cgaggcacaa tagatctgat ggcgttatga tggttaactt gtcatactct tgcgatctat  1080
ggtccctttta ggagtttagg acatctattt aatttcggat agttcgagat ctgtgatcca  1140
tggttagtac cctaggcagt ggggttagat ccgtgctgtt atggttcgta gatggattct  1200
gattgctcag taactgggaa tcctgggatg gttctagctg gttcgcagat aagatcgatt  1260
tcatgatatg ctatatcttg ttttggttgcc gtggttccgt taaatctgtc tgttatgatc  1320
ttagtctttg ataaggttcg gtcgtgctag ctacgtcctg tgcagcactt aattgtcagg  1380
tcataatttt tagcatgcct ttttttttatt ggtttggttt tgtctgactg ggctgtagat  1440
agtttcaatc tttgtctgac tgggctgtag atagtttcaa tctacctgtc ggttatttt  1500
attaaatttg gatctgtatg tgtgtcatat atcttcatct tttagatata tcgataggtt  1560
tatatgttgc tgtcggtttt ttactgttcc tttatgagat atattcatgc ttagatacat  1620
gaaacaacgt gctgttacag tttaaatagtt cttgtttatc taataaacaa ataaggatag  1680
gtatatgctg cagttagttt tactggtact tttttttgaca tgaacctacg gcttaataat  1740
tagtcttcat caaataaaaa gcatatttt taattacttt gatatacttg aatgatgtca  1800
tatgcagcat ctgtgtgaat ttttggccct gtcttcatat gctgtttatt tgtttgggac  1860
tgtttctttg gttgataact catcctgttg tttggtgatc cttttgcagg tg           1912

SEQ ID NO: 15           moltype = DNA  length = 771
FEATURE                 Location/Qualifiers
source                  1..771
                        mol_type = other DNA
                        organism = Andropogon gerardii
SEQUENCE: 15
gtcaacggga atgtcgctta ccacttaaag cataacgccg agaaatcccg taataaatcc  60
agtaaaatac gagcacccgt gccaagttga atatttgaac ccgagtgggt agattccacc  120
gcaaaggacc taaccagatc atttcgcaaa caggaactaa aatcggtaga gagcccagac  180
aaaagccttt cctaagagcc actccagtgg aagcccctac tttaggtata aaatgcaata  240
ctagtggggc tcctaaataa acttctattt ttcatggcct tctaaaattc actcccaaac  300
ccctagctat agaagtctct tatccatcct ctaaataaaa atgggagtct attttatttc  360
accagagttg atcgtaaatt tagtctctca aattttataa gttgagggta gaggatgact  420
ggagttgctc taaacggacc tatcttcaag tgacctcagt gagcccgttt aacggcgtcg  480
acaagtttaa tctaacggac accaaccaga gaagagaacc accgccagcg ccgagccaag  540
cgacgttgac atcttggcgc ggcacggcat ctccctggcg tctggccccc tctcgagact  600
tccgctccac ctcccaccgg tggcggtttc caagtccgtt ccgcctcctc tcacacggca  660
cgaaaccgtg acgggcaccg gcagcacggg gggattcctt tccaccgct ccttcccttt  720
cccttcctct cccgccgcta taatagcca gccccatcc cagcttcttt c             771

SEQ ID NO: 16           moltype = DNA  length = 1623
FEATURE                 Location/Qualifiers
source                  1..1623
                        mol_type = other DNA
                        organism = Andropogon gerardii
SEQUENCE: 16
cactcccaaa ccctagcta tagaagtctc ttatccatcc tctaaataaa atgggagtc   60
tattttattt caccagagtt gatcgtaaat ttagtctctc aaattttata agttgagggt  120
agaggatgac tggagttgct ctaaacggac ctatcttcaa gtgacctcag tgagcccgtt  180
taacggcgtc gacaagttta atctaacgga caccaaccag agaagagaac caccgccagc  240
gccgagccaa gcgacgttga catcttggcg cggcacggca tctccctggc gtctggcccc  300
ctctcgagac ttccgctcca cctcccaccg gtggcggttt ccaagtccgt tccgcctcct  360
ctcacacggc acgaaaccgt gacgggcacc ggcagcacgg ggggattcct ttccaccgc  420
tccttccctt tcccttcctc tcccgccgct ataatagcc agcccatcc cagcttctt   480
tccccaacct catcttctct cgtgttgttc ggcacaaccc gatcgatccc caactccctc  540
gtcgtctctc ctcgcgagcc tcgtcgatcc cccgcttcaa ggtacggcga tcgattatct  600
tccctctctc taccttctct ctcttatagg gcctgctagc tctgttcctg ttttccatg  660
```

```
gctgcgaggt acaatagatc ggcgatccat ggttagggcc tgctagttgt gttcctgttt   720
ttccatggct gcgaggcaca atagatctga tggcgttatg atggttaact tgtcatactc   780
ttgcgatcta tggtcccttt aggagtttag gacatctatt taatttcgga tagttcgaga   840
tctgtgatcc atggttagta ccctaggcag tggggttaga tccgtgctgt tatggttcgt   900
agatggattc tgattgctca gtaactggga atcctggcag ggttctagct ggttcgcaga   960
taagatcgat ttcatgatat gctatatctt gtttggttgc cgtggttccg ttaaatctgt  1020
ctgttatgat cttagtcttt gataaggttc ggtcgtgcta gctacgtcct gtgcagcact  1080
taattgtcag gtcataattt ttagcatgcc tttttttat tggtttggtt ttgtctgact   1140
gggctgtaga tagtttcaat cttttgtctga ctgggctgta gatagtttca atctacctgt  1200
cggtttattt tattaaattt ggatctgtat gtgtgtcata tatcttcatc ttttagatat   1260
atcgataggt ttatatgttg ctgtcggttt tttactgttc ctttatgaga tatattcatg   1320
cttagataca tgaaacaacg tgctgttaca gtttaatagt tcttgtttat ctaataaaca   1380
aataaggata ggtatatgct gcagttagtt ttactggtac tttttttgac atgaacctac   1440
ggcttaataa ttagtcttca tcaaataaaa agcatatttt ttaattattt cgatatactt   1500
gaatgatgtc atatgcagca tctgtgtgaa ttttttggccc tgtcttcata tgctgtttat   1560
ttgtttggga ctgtttcttt ggttgataac tcatcctgtt gtttggtgat cctttttgcag  1620
gtg                                                                 1623

SEQ ID NO: 17           moltype = DNA   length = 482
FEATURE                 Location/Qualifiers
source                  1..482
                        mol_type = other DNA
                        organism = Andropogon gerardii
SEQUENCE: 17
cactcccaaa ccctagcta tagaagtctc ttatccatcc tctaaataaa aatgggagtc    60
tattttattt caccagagtt gatcgtaaat ttagtctctc aaattttata agttgagggt   120
agaggatgac tggagttgct ctaaacggaa ctatcttcaa gtgacctcag tgagcccgtt   180
taacggcgtc gacaagttta atctaacgga caccaaccag agaagagaac caccgccagc   240
gccgagccaa gcgacgttga catcttggcg cggcacggca tctccctggc gtctggcccc   300
ctctcgagac ttccgctcca cctcccaccg gtggcggttt ccaagtccgt tccgcctcct   360
ctcacacggc acgaaaccgt gacgggcacc ggcacgacgg ggggattcct ttcccaccgc   420
tccttcccttt tcccttcctc tcccgccgct ataaatagcc agccccatcc ccagcttctt   480
tc                                                                  482

SEQ ID NO: 18           moltype = DNA   length = 3483
FEATURE                 Location/Qualifiers
source                  1..3483
                        mol_type = other DNA
                        organism = Tripidium ravennae
                        sub_species = ravennae
SEQUENCE: 18
gtggccagct tttgttctag ttcaacggcc ccggccttcc gggcacctaa taccctaatt    60
aatctattgc agctaacctc aaaagaaatg catttgcagt tgtctgtccc aatcaatcta   120
ctagcagact tacattatag atggaggaaa ttaaattcag cctttgacgt ggatgcaaca   180
actgcactgc acaggatacc atcttagccg ttgtgtcaaa gtttgctttg ctaaacgttt   240
tgagaaaacc agctttgacc aacgcgagat gagcgcctta cgtttggcac aatgtaatgt   300
aatccggcac ggcaagttag actctcgtagt gttagccggc ctcttttacgt ttggcatagt   360
ttaattgaat ccggcatggc aagttagacc gtagtgtgag ccggccaacg caagttatta   420
tgacatatgt ataagagcaa gtgtattgtc acgtgatatt tatgttgaga tgaagaagag   480
aaaataaaca gcctgcaaat ttatagcgag tgatagatgg gcacaaggct tcctatttct   540
taaatcagac tttgtaagaa caaaaaaagg acttataaga gaatgggaa aaccatatat   600
caatggtgta gtatgttagt atgcattaag atctgactat tatatgagtg agttgttaaa   660
ttcatttttag gtgacatggc ccggttaaat tattagccat accctaacag ctctaaaaaa   720
gatatattcg ttgaggcact tttatgcaac cacatagtca acttgaatgc cgcttgagtg   780
ttctcaaag ttttttttct tgcaaattac gcttttttaa gaaagtataa tttggatcgt   840
gcgatttttt ttctctaggt gtgcgtgact gtgtgagtga caattttgga tctcagaaag   900
gtaataaaag aataatactg ctgcctactt tgaggattac aatatctttc tctaaaatgt   960
tttggtttgt tatttaaacc gtctttaagg ccaattgctc aagattcatt caacaattga  1020
aacgtctcac atgattaaat catataaggt tgctaaggtc ttgtttgaca aggttttttt  1080
tgtggaaatt tcatctaaat ttttgagtga aactatcaaa tactaattta aaaaggcaa   1140
atttgctgg aggacactgc agaaacgtgt aattggccgg cacaaaccgc caaacgagga   1200
atttgcccag taccattata aattcatgat aaattcatgg ttgtttgcca gtggggctag   1260
ggttcctcgc gtatggtgcg gaatgtggtt tggttcgacc aactcgaact caatccgatc   1320
caaaggggca tcaatagtca tttttagaaag tttctctcc ccgagcagtg gaaatgatta   1380
ttctattttgg cgcgatgtcc accggcaaac aaccacgaat ttgtaatggt actaggcaaa  1440
ttctccgttt ggcggtgtgt gccggccaat tacacgtttt tgcggtgtcc tccgacaaaa  1500
tttgcctttt aaaacaatt ttataagaga agctccggag ataaaaggcc gtcaatgtta   1560
caagagtgaa gtcgtctact ccctccatcc caaaaaattg aattctaagt atgagttgta   1620
ttattatttt tggacaaaag gagtataccca caagaatgat atcatcgtca tgcttagatc   1680
ctttttagta aagcttgagc ttctctaaaa gtagagaaat tagaaaaaaaa tcacgttttt   1740
gtggtcttga tttctagcct ccacaaaatc tttggtttta catttttttgt ttgatttgg   1800
tttcagaagt ccttatttat atgtgctagt ttggcagcac ttaaaatcgt tagagagagc   1860
ctaaacaaaa gccttttcaa aacgaccttg agccagattg gttgatggcc aaaatttgat   1920
tgtcaaaact taggcaagcc aagattttag cagctatttg gtttggtacc aaaatttgcc   1980
aatgatctgt tcttttgcct tttcaaccgg tttatcagcc gtacttcagc ttattctctc   2040
tcacagaaca ctattgaatc agccgaaaag ccaccgcaga acaggaccag tatctccaca   2100
atggcatgcc aaaatatactc accgtcagtg agcccgttta acggcgtcga caagtctaac   2160
ggccaccaac cagcgaacca ccagcgtcaa gctagccaag cgaagcagac ggccgagacg   2220
ttgacacctt ggcgcgggca tctctctggc ccctctcga gagttccgct ccacctccac   2280
```

```
tggtggcggt ttccaagtcc gttccgcctc ctgctcctcc tcacacggca cgaaaccgtc    2340
acggcaccgg cagcacgggg gattcctttc ccaccgctcc ttcccttttcc cttcctcgcc    2400
cgccgtttta aatagccagc cccatcccca gcttctctcc ccgtacggcg atcatcctcc    2460
ctttctctac cttctcttct ctagactagg tcggcgatcc atggttaggg cctgctagtt    2520
ctgttcctgt ttttccgtgg ctgcgaggta caatagatcg gatggcgtta tgatggttaa    2580
cttgtcatac tcctgcggtg tgcggtctat agtgctttta ggacatcaat ttgacctggc    2640
tcgttcgaga tcggcgatcc atggttagga ccctaggcgg tggagtcggg ttagatccgc    2700
gctgtttgtg ttagtagatg gatgcgacct ttacttcaga cacgttctga ttgttaactt    2760
gtcagcacct gggagtcctg ggatggttct agctggttcg tgatgagat cgatttcatg    2820
atctgctgta tcttgtttcg ttaggttcct tttaatctat ccgtggtatt atgctaacct    2880
atgatatggt tcgatcgtgc tagctacgtc ctgtgtcata attttagca tgcccttttt    2940
tgtttggttt tgtctgattg ggctgtagat cagagtatac tgtttcaaac tacctactgg    3000
atatatttat taaatttgaa tctgtatgtg tgtcacatat atcttcataa ttaaaatgga    3060
tggaaagata tatggatagg tacatgtgtt gctgtgggtt ttactggtac tttgttagat    3120
atacatgctt agatacatga agcaacatga tgttacagtt caataattct tgtttaccta    3180
ataaacaaat aaggataggt gtatgttgct gtggggttttg ctggtacttt gttagatata    3240
tatgcttaga tatatgaagc aacatcctgc tacggtttaa taattattgt ttatatctaa    3300
tagacaagcc tgcttttttaa ttattttgat atacttggat gatggcatac agcagctatg    3360
tgtggatttt taaatacccca gcatcatgag catgcatgac cctgcctag tatgctgttt    3420
atttgcttga gacttctttt tttgttggta ctcacctttt gtagtttggt gactcttctg    3480
cag                                                                    3483

SEQ ID NO: 19           moltype = DNA   length = 2536
FEATURE                 Location/Qualifiers
source                  1..2536
                        mol_type = other DNA
                        organism = Tripidium ravennae
                        sub_species = ravennae
SEQUENCE: 19
gtggccagct tttgttctag ttcaacggcc ccggccttcc gggcacctaa taccctaatt     60
aatctattgc agctaacctc aaaagaaatg catttgcagt tgtctgtccc aatcaatcta    120
ctagcagact tacattatag atggaggaaa ttaaattcag cctttgacgt ggatgcaaca    180
actgcactgc acaggatacc atcttagccg ttgtgtcaaa gtttgctttg ctaaacgttt    240
tgagaaaacc agctttgacc aacgcgagat gagcgcctta cgttggcacc aatgtaatgt    300
aatccggcac ggcaagttag actctgtagt gttagccggc ctctttacgt ttggcatagt    360
ttaattgaat ccggcatggc aagttagacc gtagtgtgag ccggccaacg caagttatta    420
tgacatatgt ataagagcaa gtgtattgtc acgtgatatt tatgttgaga tgaagaagag    480
aaaataaaca gcctgcaaat ttatagcgag tgatagatgg gcacaaggct tcctatttct    540
taaatcagac tttgtaagaa caaaaaaagg acttataaga gaatgggata aaccatatat    600
caatggtgta gtatgttagt atgcattaag atctgactat tatatgagtg agttgttaaa    660
ttcattttag gtgacatggc ccggttaaat tattagccat acccctaacag ctctaaaaaa    720
gatatattcg ttgaggcact tttatgcaac cacatagtca acttgaatgc cgcttgagtg    780
cgttctcaag tttttttttct tgcaaattac gcttttttta gaaagtataa tttggatcgt    840
gcgattttttt ttctctaggt gtgcgtgact gtgtgagtaa caattttgga tctcagaaag    900
gtaataaaag aataatactg ctgcctactt tgaggattac aatatctttc tctaaaatgt    960
tttggtttgt tatttaaacc gtctttaagg ccaattgctc aagattcatt caacaattga   1020
aacgtctcac atgattaaat catataaggt tgctaaggtc ttgttttgaca aggttttttt   1080
tgtgaaaatt tcatctaaat ttttgagtga aactatcaaa tactaattta aaaaaggcaa   1140
attttgctgg aggacactgc agaaacgtgt aattggccgg cacaaccgc caaacggaga   1200
atttgcccag taccattata aattcatgat aaattcatgg ttgtttgcca gtggggctag   1260
ggttcctcgc gtatggtgcg gaatgtggtt tggttcgacc aactcgaact caatccgatc   1320
caaagggggca tcaatagtca ttttagaaag tttctctctc ccgagcagtg gaaatgatta   1380
ttctattttgg cgcgatgtcc accggcaaac aaccacgaat ttgtaatggt actaggcaaa   1440
ttctccgttt ggcggtgtgt gccggccaat tacacgtttt tgcggtgtcc tccgacaaaa   1500
tttgcctttt aaaaacaatt ttataagaga agctccggag ataaaaggcc gtcaatgtta   1560
caagagtgaa gtcgtctact ccctccatcc caaaaaatgt aattctaagt atgagttgta   1620
ttattattttt tggacaaaag gagtatacca caagaatgat atcatcgtca tgcttagatc   1680
cttttttagta aagcttgagc ttctctaaaa gtagagaaat tagaaaaaaaa tcacgttttt   1740
gtggtcttga tttctagcct ccacaaaatc tttggttttta catttttttgt ttgattttgg   1800
tttcagaagt ccttatttat atgtgctagt ttggcagcac ttaaaatcgt tagagagagc   1860
ctaaacaaaa gccttttcaa aacgaccttg agccagattg gttgatggcc aaaatttgat   1920
tgtcaaaact taggcaagcc aagattttag cagctatttg gtttggtacc aaaatttgcc   1980
aatgatctgt tcttttgcct tttcaaccgg tttatcagcc gtacttcagc ttattctctc   2040
tcacagaaca ctattgaatc agccgaaaag ccaccgacaa acaggaccag tatctcacaa   2100
atggcatgcc aaatatactc accgtcagtg agcccgttta acggcgtcga caagtctaac   2160
ggccaccaac cagcgaacca ccagcgtcaa gctagccaag cgaagcagac ggccgagacg   2220
ttgacacctt ggcgcgggca tctctctggc ccctctcga gagttccgct ccacctccac   2280
tggtggcggt ttccaagtcc gttccgcctc ctgctcctcc tcacacggca cgaaaccgtc   2340
acggcaccgg cagcacgggg gattcctttc ccaccgctcc ttcccttttcc cttcctcgcc   2400
cgccgtttta aatagccagc cccatcccca gcttctctcc caacctcag cttctctcgt   2460
tgttcggagc gcacacacaa cccgatcccc aatcccctcg tctctcctcg cgagcctcgt   2520
cgatccccgc ttcaag                                                     2536

SEQ ID NO: 20           moltype = DNA   length = 94
FEATURE                 Location/Qualifiers
source                  1..94
                        mol_type = other DNA
                        organism = Tripidium ravennae
                        sub_species = ravennae
```

-continued

```
SEQUENCE: 20
aacctcagct tctctcgttg ttcggagcgc acacacaacc cgatcccaa tccctcgtc    60
tctcctcgcg agcctcgtcg atcccgctt caag                                94

SEQ ID NO: 21          moltype = DNA   length = 1041
FEATURE                Location/Qualifiers
source                 1..1041
                       mol_type = other DNA
                       organism = Tripidium ravennae
                       sub_species = ravennae
SEQUENCE: 21
gtacggcgat catcctccct ttctctacct tctcttctct agactaggtc ggcgatccat    60
ggttagggcc tgctagttct gttcctgttt ttccgtggct gcgaggtaca atagatctga   120
tggcgttatg atggttaact tgtcatactc ctgcggtgtg cggtctatag tgcttttagg   180
acatcaattt gacctggctc gttcgagatc ggcgatccat ggttaggacc ctaggcggtg   240
gagtcggtt agatccgcgc tgtttgtgtt agtagatgga tgcgaccttt acttcagaca    300
cgttctgatt gttaacttgt cagcacctgg gagtcctggg atggttctag ctggttcgca   360
gatgagatcg atttcatgat tgctgtatc ttgtttcgtt aggttcctt taatctatcc    420
gtggtattat gctaacctat gatatggttc gatcgtgcta gctacgtcct gtgtcataat   480
ttttagcatg cccttttttg tttggttttg tctgattggg ctgtagatca gagtatactg   540
tttcaaaacta cctactggat atatttatta aatttgaatc tgtatgtgtg tcacatatat  600
cttcataatt aaaatggatg gaaagatata tggatagta catgtgttgc tgtggggttt    660
actggtactt tgttagatat acatgcttag atacatgaag caacatgatg ttacagttca   720
ataattcttg tttacctaat aaacaaataa ggataggtgt atgttgctgt gggtttgct   780
ggtactttgt tagatatata tgcttagata tatgaagcaa catcctgcta cggtttaata   840
attattgttt atatctaata gacaagcctg cttttaatt attttgatat acttggatga   900
tggcatacag cagctatgtg tggatttta aatacccagc atcatgagca tgcatgaccc    960
tgccttagta tgctgtttat ttgcttgaga cttcttttt tgttggtact caccttttgt    1020
agtttggtga ctcttctgca g                                            1041

SEQ ID NO: 22          moltype = DNA   length = 3152
FEATURE                Location/Qualifiers
source                 1..3152
                       mol_type = other DNA
                       organism = Tripidium ravennae
                       sub_species = ravennae
SEQUENCE: 22
gtataagagc aagtgtattg tcacgtgata tttatgttga gatgaagaag agaaaataaa    60
cagcctgcaa atttatagcg agtgatagat gggcacaagg cttcctattt cttaaatcag   120
actttgtaag aacaaaaaaa ggacttataa gagaatggga taaaccatat atcaatggtg   180
tagtatgtta gtatgcatta agatctgact attatatgag tgagttgtta aattcatttt   240
aggtgacatg gcccggttaa attattagcc ataccctaac agctctaaaa aagatatatt   300
cgttgaggca cttttatgca accacatagt caacttgagt gccgcttgag tgcgttctca   360
agtttttttt cttgcaaatt acgcttttt aagaaagtat aatttggatc gtgcgatttt   420
ttttctctag gtgtgcgtga ctgtgtgagt aacaattttg gatctcagaa aggtaataaa   480
agaataatac tgctgcctac tttgaggatt acaatatctt tctctaaaat gttttggttt   540
gttatttaaa ccgtctttaa ggccaattgc tcaagattca ttcaacaatt gaaacgtctc   600
acatgattaa atcatataag gttgctaagg tcttgtttga caaggttttt tttgtggaaa   660
tttcatctaa atttttgagt gaaactatca aatactaatt taaaaaaggc aaattttgct   720
ggaggacact gcagaaacgt gtaattggcc ggcacaaacc gccaaacgga gaatttgccc   780
agtaccatta taaattcatg ataaattcat ggttgtttgc cagtggggct agggttcctc   840
gcgtatggtg cggaatgtgg tttggttcga ccaactcgaa ctcaatccga tccaaagggg   900
catcaatagt catttagaa agtttctctc tcccgagcag tggaaatgat tattctattt   960
ggcgcgatgt ccaccggcaa acaaccacga atttgtaatg gtactaggca aattctccgt  1020
ttggcggtgt gtgccggcca attacacgtt tttgcggtgt cctccgacaa aatttgcctt  1080
ttaaaaacaa ttttataaga gaagctccgg agataaaagg ccgtcaatgt tacaagagtg  1140
aagtcgtcta ctccctccat cccaaaaaat gtaattctaa gtatgagttg tattattatt  1200
tttgacaaa aggagtatac cacaagaatg atatcatcgt catgcttaga tcctttttag   1260
taaagcttga gcttctctaa aagtagagaa attagaaaaa aatcacgttt ttgtggtctt  1320
gatttctagc ctccacaaaa tctttggttt tacattttt gtttgatttt ggtttcagaa   1380
gtccttattt atatgtgcta gtttggcagc acttaaaatc gttagagaga gcctaaacaa   1440
aagccttttc aaaacgacct tgagccagat tggttgatgg ccaaaatttg attgtcaaaa   1500
cttaggcaag ccaagatttt agcagctatt tggtttggta ccaaaatttg ccaatgatct   1560
gttcttttgc cttttcaacc ggtttatcag ccgtacttca gcttattctc tctcacagaa   1620
cactattgaa tcagccgaaa agccaccgca gaacaggacc agtatctcac aaatggcatg   1680
ccaaatatac tcaccgtcag tgagcccgtt aacggcgtc gacaagtcta acggccacca   1740
accagcgaac caccagcgtc aagctagcca agcgaagcag acggccgaga cgttgacacc   1800
ttggcgcggg catctctctg gccccctctc gagagttccg ctccacctcc actggtggcg   1860
gtttccaagt ccgttccgcc tcctgctcct cctcacacgg cacgaaaccg tcacggcacc   1920
ggcagcacgg gggattcctt tcccaccgct cctcctttt ccttcctcg cccgccgttt    1980
taaatagcca gccccatccc cagcttctct ccccaacctc agcttctctc gttgttcgga   2040
gcgcacacac aacccgatcc ccaatcccct cgtctctcct cgcgagcctc gtcgatcccc   2100
gcttcaaggt acggcgatca tcctcccttt ctctaccttc tcttctctag actaggtcgg   2160
cgatccatgg ttagggcctg ctagttctgt tcctgttttc cgtggctgcg aggtacaag   2220
agatctgatg gcgttatgat ggttaacttg tcatactcct gcggtgtgcg gtctatagtg   2280
cttttaggac atcaatttga cctggctcgt tcgagatcgg cgatccatgg ttaggaccct   2340
aggcggtgga gtcgggttag atccgcgctg tttgtgttag tagatggatg cgaccttac   2400
ttcagacacg ttctgattgt taacttgtca gcacctggga gtcctgggat ggttctagct   2460
ggttcgcaga tgagatcgat ttcatgatct gctgtatctt gtttcgttag gttcctttta  2520
```

```
atctatccgt ggtattatgc taacctatga tatggttcga tcgtgctagc tacgtcctgt    2580
gtcataattt ttagcatgcc ctttttgtt tggttttgtc tgattgggct gtagatcaga     2640
gtatactgtt tcaaactacc tactggatat atttattaaa tttgaatctg tatgtgtgtc    2700
acatatatct tcataattaa aatggatgga aagatatatg gataggtaca tgtgttgctg    2760
tgggttttac tggtactttg ttagatatac atgcttagat acatgaagca acatgatgtt    2820
acagttcaat aattcttgtt tacctaataa acaaataagg ataggtgtat gttgctgtgg    2880
gttttgctgg tactttgtta gatatatatg cttagatata tgaagcaaca tcctgctacg    2940
gtttaataat tattgtttat atctaataga caagcctgct tttttaattat tttgatatac    3000
ttggatgatg gcatacagca gctatgtgtg gattttttaaa tacccagcat catgagcatg    3060
catgacccctg ccttagtatg ctgtttattt gcttgagact tctttttttg ttggtactca    3120
ccttttgtag tttggtgact cttctgcagg tg                                  3152

SEQ ID NO: 23           moltype = DNA  length = 2014
FEATURE                 Location/Qualifiers
source                  1..2014
                        mol_type = other DNA
                        organism = Tripidium ravennae
                        sub_species = ravennae
SEQUENCE: 23
gtataagagc aagtgtattg tcacgtgata tttatgttga gatgaagaag agaaaataaa    60
cagcctgcaa atttatagcg agtgatagat gggcacaagg cttcctattt cttaaatcag    120
actttgtaag aacaaaaaaa ggacttataa gagaatggata taaaccatat atcaatggtg    180
tagtatgtta gtatgcatta agatctgact attatatgag tgagttgtta aattcatttt    240
aggtgacatg gcccggttaa attattagcc ataccctaac agctctaaaa aagatatatt    300
cgttgaggca ctttatgca accacatagt caacttgaat gccgcttgag tgcgttctca     360
agtttttttt cttgcaaatt acgctttttt aagaaagtat aatttggatc gtgcgattt     420
ttttctctag gtgtgcgtga ctgtgtgagt aacaattttg gatctcagaa aggtaataaa    480
agaataaatac tgctgcctac tttgaggatt acaatatctt tctctaaaat gttttggttt    540
gttatttaaa ccgtctttaa ggccaattgc tcaagattca ttcaacaatt gaaacgtctc    600
acatgattaa atcatataag gttgctaagg tcttgtttga caaggttttt tttgtggaaa    660
tttcatctaa attttgagt gaaactatca aatactaatt taaaaaaggc aaattttgct    720
ggaggacact gcagaaacgt gtaattggcc ggcacaaacc gccaaacgga gaatttgccc    780
agtaccatta taaattcatg ataaattcat ggttgtttgc cagtggggct agggttcctc    840
gcgtatggtg cggaatgtgg tttggttcga ccaactcgaa ctcaatccga tccaaagggg    900
catcaatagt catttagaa agtttctctc tcccgacgag tggaaatgat tattctattt    960
ggcgcgatgt ccaccggcaa acaaccacga atttgtaatg gtactaggca aattctccgt    1020
ttggcggtgt gtgccggcca attacacgtt tttgcggtgt cctccgacaa aatttgcctt    1080
ttaaaaacaa ttttataaga gaagctccgg agataaaagg ccgtcaatgt tacaagagtg    1140
aagtcgtcta ctccctccat cccaaaaaat gtaattctaa gtatgagttg tattattatt    1200
tttgacaaaa aggagtatac cacaagaatg atatcatcgt catgcttaga tccttttttag    1260
taaagcttga gcttctctaa aagtagagaa attagaaaaa aatcacgttt ttgtggtctt    1320
gatttctagc ctccacaaaa tctttggttt tacatttttt gtttgatttt ggtttcagaa    1380
gtccttattt atatgtgcta gtttggcagc acttaaaatc gttagagaga gcctaaacaa    1440
aagccttttc aaaacgacct tgagccagat tggttgatgg ccaaaatttg attgtcaaaa    1500
cttaggcaag ccaagatttt agcagctatt tggtttggta ccaaaatttg ccaatgatct    1560
gttctttttgc cttttcaacc ggtttatcag ccgtacttca gcttattctc tctcacagaa    1620
cactattgaa tcagccgaaa agccaccgca gaacaggacc agtatctcac aaatggcatg    1680
ccaaatatac tcaccgtcag tgagcccgtt taacggcgtc gacaagtcta acggccacca    1740
accagcgaac caccagcgtc aagctagcca agcgaagcag acggccgaga cgttgacacc    1800
ttggcgcggg catctctctg gccccctctc gagagttccg ctccacctcc actggtggcg    1860
gtttccaagt ccgttccgcc tcctgctcct cctcacacgg cacgaaaccg tcacggcacc    1920
ggcagcacgg gggattcctt tcccaccgct ccttcccttt cccttcctcg cccgccgttt    1980
taaatagcca gccccatccc cagcttctct cccc                                2014

SEQ ID NO: 24           moltype = DNA  length = 1044
FEATURE                 Location/Qualifiers
source                  1..1044
                        mol_type = other DNA
                        organism = Tripidium ravennae
                        sub_species = ravennae
SEQUENCE: 24
gtacggcgat catcctccct ttctctacct tctcttctct agactaggtc ggcgatccat    60
ggttagggcc tgctagttct gttcctgttt ttccgtggct gcgaggtaca atagatcga    120
tggcgttatg atggttaact tgtcatactc ctgcggtgtg cggtctatag cggttctagg    180
acatcaattt gacctggctc gttcgagatc ggcgatccat ggttaggacc ctaggcggtg    240
gagtcgggtt agatccgcgc tgtttgtgtt agtagatgga tgcgacctttt acttcagaca    300
cgttctgatt gttaacttgt cagcacctgg gagtcctggg atggtctag ctggttcgca     360
gatgagatcg atttcatgat ctgctgtatc ttgtttcgtt aggttcctts taatctatcc    420
gtggtattat gctaacctat gatatggttc gatcgtgcta gctacgtcct gtgtcataat    480
ttttagcatg ccctttttgg tttggtttg tctgattggg ctgtagatca gagtatactg    540
tttcaaacta cctactggat atatttatta aatttgaatc tgtatgtgtg tcacatatat    600
cttcataatt aaaatggatg gaaagatata tggataggta catgtgttgc tgtgggtttt    660
actggtactt tgtagatat acatgcttag atacatgaag caacatgatg ttacagttca    720
ataattcttg tttacctaat aaacaaataa ggataggtgt atgttgctgt ggtttgct    780
ggtactttgt tagatatata tgcttagata tatgaagcaa catcctgcta cggtttaata    840
attattgttt atatctaata gacaagcctg ctttttaatt atttttgatat acttggatga    900
tggcatacag cagctatgtg tggatttta aatacccagc atcatgagca tgcatgaccc    960
tgccttagta tgctgtttat ttgcttgaga cttcttttttt tgttggtact caccttttgt    1020
agtttggtga ctcttctgca ggtg                                           1044
```

| SEQ ID NO: 25 | moltype = DNA   length = 2663 |
| --- | --- |
| FEATURE | Location/Qualifiers |
| source | 1..2663 |
| | mol_type = other DNA |
| | organism = Tripidium ravennae |
| | sub_species = ravennae |

SEQUENCE: 25

```
ctgctgccta ctttgaggat tacaatatct ttctctaaaa tgttttggtt tgttatttaa   60
accgtcttta aggccaattg ctcaagattc attcaacaat tgaaacgtct cacatgatta  120
aatcatataa ggttgctaag gtcttgtttg acaaggtttt ttttgtggaa atttcatcta  180
aattttgag  tgaaactatc aaatactaat ttaaaaaagg caaattttgc tggaggacac  240
tgcagaaacg tgtaattggc cggcacaaac cgccaaacgg agaatttgcc cagtaccatt  300
ataaattcat gataaattca tggttgtttg ccagtggttc tagggttcct cgcgtatggt  360
gcggaatgtg gtttggttcg accaactcga actcaatccg atccaaaggg gcatcaatag  420
tcatttaga  aagtttctct ctcccgagca gtggaaatga ttattctatt tggcgcgatg  480
tccaccggca aacaaccacg aatttgtaat ggtactaggc aaattctccg tttggcggtg  540
tgtgccggcc aattacacgt ttttgcggtg tcctccgaca aaatttgcct tttaaaaaca  600
atttataag  agaagctccg gagataaaag gccgtcaatg ttacaagagt gaagtcgtct  660
actccctcca tcccaaaaaa tgtaattcta agtatgagtt gtattattat ttttggacaa  720
aaggagtata ccacaagaat gatatcatcg tcatgcttag atcctttta  gtaaagcttg  780
agcttctcta aaagtagaga aattagaaaa aaatcacgtt tttgtggtct tgatttctag  840
cctccacaaa atctttggtt ttacatttt  tgtttgattt tggttcaga  agtccttatt  900
tatatgtgct agtttggcag cacttaaaat cgttagagag agcctaaaca aaagcctttt  960
caaaacgacc ttgagccaga ttggttgatg gccaaaattt gattgtcaaa acttaggcaa 1020
gccaagattt tagcagctat ttggtttggt accaaaattt gccaatgatc tgttctttg  1080
ccttttcaac cggtttatca gccgtacttc agcttattct ctctcacaga acactattga 1140
atcagccgaa aagccaccgc agaacaggac cagtatctca caaatggcat gccaaatata 1200
ctcaccgtca gtgagcccgt taacggcgt  cgacaagtct aacggccacc aaccagcgaa 1260
ccaccagcgt caagctagcc aagcgaagca gacggccgaa acgttgacac cttggcgcgg 1320
gcatctctct ggccccctct cgagagttcc gctccacctc cactggtggc ggtttcaag  1380
tccgttccgc ctcctgctcc tcctcacacg gcacgaaacc gtcacggcac cggcagcacg 1440
ggggattcct ttcccaccgc tccttccctt tccttcctc  gcccgccgtt taaatagcc  1500
agcccatcc  ccagcttctc tccccaacct cagcttctct cgttgttcgg agcgcacaca 1560
caacccgatc cccaatcccc tcgtctctcc tcgcgagcct cgtcgatccc gcttcaagg  1620
tacggcgatc atcctccctt tctctacctt ctcttctcta gactaggtcg gcgatccatg 1680
gttagggcct gctagttctg ttcctgtttt tccgtggctg cgaggtacaa tagatctgat 1740
ggcgttatga tggttaactt gtcatactcc tgcggtgtgc ggtctatagt gcttttagga 1800
catcaattg  acctggctcg ttcgagatcg gcgatccatg gttaggaccc taggcggtgg 1860
agtcgggtta gatccgcgct gtttgtgtta gtagatggat gcgacccttta cttcagacac 1920
gttctgattg ttaacttgtc agcacctggg agtcctggga tggttctagc tggttcgcag 1980
atgagatcga tttcatgatc tgctgtatct tgtttcgtta ggttcctttt aatctatccg 2040
tggtattatg ctaacctatg atatggttcg atcgtgctag ctgctcctg  tgtcataatt 2100
tttagcatgc cctttttgt  ttggttttgt ctgattgggc tgtagatcag agtatactgt 2160
ttcaaactac ctactggata tatttattaa atttgaatct gtatgtgtgt cacatatatc 2220
ttcataatta aaatggatgg aaagatatat ggataggtac atgtgttgct gtgggtttta 2280
ctggtacttt gttagatata catgcttaga tacatgaaga aacatgatgt tacagttcaa 2340
taattcttgt ttacctaata aacaaataag gataggtgta tgttgctgtg ggttttgctg 2400
gtactttgtt agatatatat gcttagatat atgaagcaac atcctgctac ggtttaataa 2460
ttattgttta tatctaatag acaagcctgc ttttaatta  ttttgatata cttggatgat 2520
ggcatacagc agctatgtgt ggatttttaa atacccagca tcatgagcat gcatgaccct 2580
gccttagtat gctgtttatt tgcttgagac ttcttttttt gttggtactc accttttgta 2640
gtttggtgac tcttctgcag gtg                                         2663
```

| SEQ ID NO: 26 | moltype = DNA   length = 1525 |
| --- | --- |
| FEATURE | Location/Qualifiers |
| source | 1..1525 |
| | mol_type = other DNA |
| | organism = Tripidium ravennae |
| | sub_species = ravennae |

SEQUENCE: 26

```
ctgctgccta ctttgaggat tacaatatct ttctctaaaa tgttttggtt tgttatttaa   60
accgtcttta aggccaattg ctcaagattc attcaacaat tgaaacgtct cacatgatta  120
aatcatataa ggttgctaag gtcttgtttg acaaggtttt ttttgtggaa atttcatcta  180
aattttgag  tgaaactatc aaatactaat ttaaaaaagg caaattttgc tggaggacac  240
tgcagaaacg tgtaattggc cggcacaaac cgccaaacgg agaatttgcc cagtaccatt  300
ataaattcat gataaattca tggttgtttg ccagtgggc  tagggttcct cgcgtatggt  360
gcggaatgtg gtttggttcg accaactcga actcaatccg atccaaaggg gcatcaatag  420
tcatttaga  aagtttctct ctcccgagca gtggaaatga ttattctatt tggcgcgatg  480
tccaccggca aacaaccacg aatttgtaat ggtactaggc aaattctccg tttggcggtg  540
tgtgccggcc aattacacgt ttttgcggtg tcctccgaca aaatttgcct tttaaaaaca  600
atttataag  agaagctccg gagataaaag gccgtcaatg ttacaagagt gaagtcgtct  660
actccctcca tcccaaaaaa tgtaattcta agtatgagtt gtattattat ttttggacaa  720
aaggagtata ccacaagaat gatatcatcg tcatgcttag atcctttta  gtaaagcttg  780
agcttctcta aaagtagaga aattagaaaa aaatcacgtt tttgtggtct tgatttctag  840
cctccacaaa atctttggtt ttacatttt  tgtttgattt tggttcaga  agtccttatt  900
tatatgtgct agtttggcag cacttaaaat cgttagagag agcctaaaca aaagcctttt  960
caaaacgacc ttgagccaga ttggttgatg gccaaaattt gattgtcaaa acttaggcaa 1020
gccaagattt tagcagctat ttggtttggt accaaaattt gccaatgatc tgttctttg  1080
```

```
cctttttcaac cggtttatca gccgtacttc agcttattct ctctcacaga acactattga 1140
atcagccgaa aagccaccgc agaacaggac cagtatctca caaatggcat gccaaatata 1200
ctcaccgtca gtgagcccgt ttaacggcgt cgacaagtct aacggccacc aaccagcgaa 1260
ccaccagcgt caagctagcc aagcgaagca gacggccgag acgttgacac cttggcgcgg 1320
gcatctctct ggcccctct cgagagttcc gctccacctcc cactggtggc ggtttccaag 1380
tccgttccgc ctcctgctcc tccttcacacg gcacgaaacc gtcacggcac cggcagcacg 1440
ggggattcct ttcccaccgc tccttcccctt tccttcctc gcccgccgtt ttaaatagcc 1500
agccccatcc ccagcttctc tcccc                                      1525

SEQ ID NO: 27         moltype = DNA  length = 2182
FEATURE               Location/Qualifiers
source                1..2182
                      mol_type = other DNA
                      organism = Tripidium ravennae
                      sub_species = ravennae
SEQUENCE: 27
ccaccggcaa acaaccacga atttgtaatg gtactaggca aattctccgt ttggcggtgt  60
gtgccggcca attacacgtt tttgcggtgt cctccgacaa aatttgcctt ttaaaaacaa 120
ttttataaga gaagctccgg agataaaagg ccgtcaatgt tacaagagtg aagtcgtcta 180
ctccctccat cccaaaaaat gtaattctaa gtatgagttg tattattatt tttgacaaa  240
aggagtatac cacaagaatg atatcatcgt catgcttaga tcctttttag taaagcttga 300
gcttctctaa aagtagagaa attagaaaaa aatcacgttt ttgtggtctt gatttctagc 360
ctccacaaaa tctttggttt tacattttt gtttgatttt ggtttcagaa gtccttattt  420
atatgtgcta gtttggcagc acttaaaatc gttagagaga gcctaaacaa aagccttttc 480
aaaacgacct tgagccagat tggttgatgg ccaaaatttg attgtcaaaa cttaggcaag 540
ccaagatttt agcagctatt tggtttggta ccaaaatttg ccaatgatct gttcttttgc 600
cttttcaacc ggtttatcag ccgtacttca gcttattctc tctcacagaa cactattgaa 660
tcagccgaaa agccaccgca gaacaggacc agtatctcac aaatggcatg ccaaatatac 720
tcaccgtcag tgagcccgtt taacggcgtc gacaagtcta acggccacca accagcgaac 780
caccagcgtc aagctagcca agcgaagcag acggccgaga cgttgacacc ttggcgcggg 840
catctctctg gcccctctc gagagttccg ctccacctcc actggtggcg gtttccaagt 900
ccgttccgcc tcctgctcct cctcacacg cacgaaaccg tcacggcacc ggcagcacgg 960
gggattcctt tcccaccgct ccttcccttt ccttcctcg cccgccgttt taaatagcca 1020
gccccatccc cagcttctct cccaaacctc agcttctcgc gttgttcgga gcgcacacac 1080
aacccgatcc ccaatcccct cgtctctcct cgcgagcctc gtcgatcccc gcttcaaggt 1140
acggcgatca tcctccctttt ctctaccttc tcttctctag actaggtcgg cgatccatgg 1200
ttagggcctg ctagttctgt tcctgttttt ccgtggctgc gaggtacaat agatctgatg 1260
gcgttatgat ggttaacttg tcatactcct gcggtgtgcg gtctatagtg cttttaggac 1320
atcaatttga cctggctcgt tcgagatcgg cgatccatgg ttagggccct aggcggtgga 1380
gtcgggttag atccgcgctg tttgtgttag tagatggatg cgacctttac ttcagacacg 1440
ttctgattgt taacttgtca gcacctggga gtcctgggat ggttctagct ggttcgcaga 1500
tgagatcgat ttcatgatct gctgtatctt gtttcgttag gttccttttta atctatccgt 1560
ggtattatgc taacctatga tatgtttcga tcgtgctagc tacgtcctgt gtcataattt 1620
ttagcatgcc cttttttgtt tggttttgtc tgattgggct gtagatcaga gtatactgtt 1680
tcaaactacc tactggatat atttattaaa tttgaatctg tatgtgtgtc acatatatct 1740
tcataattaa aatggatgga aagatatatg gataggtaca tgtgttgctg tgggttttac 1800
tggtactttg ttagatatac atgcttagat acatgaagca acgatgatgtt acagttcaat 1860
aattcttgtt tacctaataa acaaataagg ataggtgtat gttgctgtgg gttttgctgg 1920
tactttgtta gatatatatg cttagatata tgaagcaaca tcctgctacg gtttaataat 1980
tattgtttat atctaataga caagcctgct ttttaattat tttgatatac ttggatgatg 2040
gcatacagca gctatgtgtg gatttttaaa tacccagcat catgagcatg catgaccctg 2100
ccttagtatg ctgttttatt gcttgagact tctttttttg ttggtactca ccttttgtag 2160
tttggtgact cttctgcagg tg                                         2182

SEQ ID NO: 28         moltype = DNA  length = 1044
FEATURE               Location/Qualifiers
source                1..1044
                      mol_type = other DNA
                      organism = Tripidium ravennae
                      sub_species = ravennae
SEQUENCE: 28
ccaccggcaa acaaccacga atttgtaatg gtactaggca aattctccgt ttggcggtgt  60
gtgccggcca attacacgtt tttgcggtgt cctccgacaa aatttgcctt ttaaaaacaa 120
ttttataaga gaagctccgg agataaaagg ccgtcaatgt tacaagagtg aagtcgtcta 180
ctccctccat cccaaaaaat gtaattctaa gtatgagttg tattattatt tttgacaaa  240
aggagtatac cacaagaatg atatcatcgt catgcttaga tcctttttag taaagcttga 300
gcttctctaa aagtagagaa attagaaaaa aatcacgttt ttgtggtctt gatttctagc 360
ctccacaaaa tctttggttt tacattttt gtttgatttt ggtttcagaa gtccttattt  420
atatgtgcta gtttggcagc acttaaaatc gttagagaga gcctaaacaa aagccttttc 480
aaaacgacct tgagccagat tggttgatgg ccaaaatttg attgtcaaaa cttaggcaag 540
ccaagatttt agcagctatt tggtttggta ccaaaatttg ccaatgatct gttcttttgc 600
cttttcaacc ggtttatcag ccgtacttca gcttattctc tctcacagaa cactattgaa 660
tcagccgaaa agccaccgca gaacaggacc agtatctcac aaatggcatg ccaaatatac 720
tcaccgtcag tgagcccgtt taacggcgtc gacaagtcta acggccacca accagcgaac 780
caccagcgtc aagctagcca agcgaagcag acggccgaga cgttgacacc ttggcgcggg 840
catctctctg gcccctctc gagagttccg ctccacctcc actggtggcg gtttccaagt 900
ccgttccgcc tcctgctcct cctcacacg cacgaaaccg tcacggcacc ggcagcacgg 960
gggattcctt tcccaccgct ccttcccttt ccttcctcg cccgccgttt taaatagcca 1020
gccccatccc cagcttctct cccc                                       1044
```

| SEQ ID NO: 29 | moltype = DNA length = 1934 |
|---|---|
| FEATURE | Location/Qualifiers |
| source | 1..1934 |
| | mol_type = other DNA |
| | organism = Tripidium ravennae |
| | sub_species = ravennae |

SEQUENCE: 29

```
accacaagaa tgatatcatc gtcatgctta gatccttttt agtaaagctt gagcttctct   60
aaaagtagag aaattagaaa aaaatcacgt ttttgtggtc ttgatttcta gcctccacaa  120
aatctttggt tttacatttt ttgtttgatt ttggtttcag aagtccttat ttatatgtgc  180
tagtttggca gcacttaaaa tcgttagaga gagcctaaac aaaagccttt tcaaaacgac  240
cttgagccag attggttgat ggccaaaatt tgattgtcaa aacttaggca agccaagatt  300
ttagcagcta tttggtttgg taccaaaatt tgccaatgat ctgttctttt gccttttcaa  360
ccggtttatc agccgtactt cagcttattc tctctcacag aacactattg aatcagccga  420
aaagccaccg cagaacagga ccagtatctc acaaatggca tgccaaatat actcaccgtc  480
agtgagcccg tttaacggcg tcgacaagtc taacggccac caaccagcga accaccagcg  540
tcaagctagc caagcgaagc agacggccga gacgttgaca ccttggcgcg ggcatctctc  600
tggcccccctc tcgagagttc cgctccacct ccactggtgg cggtttccaa gtccgttccg  660
cctcctgctc ctcctcacac ggcacgaaac cgtcacggca ccggcagcac ggggggattcc  720
tttcccaccg ctccttccct ttcccttcct cgcccgccgt tttaaatagc cagcccccatc  780
cccagcttct ctccccaacc tcagctctc tcgttgttcg gagcgcacac acaacccgat  840
ccccaatccc ctcgtctctc ctcgcgagcc tcgtcgatcc ccgcttcaag gtacggcgat  900
catcctcccct ttctctacct tctcttctct agactaggtc ggcgatccat ggttagggcc  960
tgctagttct gttcctgttt ttccgtggct gcgaggtaca atagatctga tggcgttatg 1020
atggttaact tgtcatactc ctgcggtgtg cggtctatag ttgttttagg acatcaattt 1080
gacctggctc gttcgagatc ggcgatccat ggttaggacc ctaggcgtg gagtcggggt 1140
agatccgcgc tgtttgtgtt agtagatgga tgcgaccttt acttcagaca cgttctgatt 1200
gttaacttgt cagcacctgg gagtcctggg atggttctag ctggttcgca gatgagatcg 1260
atttcatgat ctgctgtatc tgtttcgtt aggttcctt taatctatcc gtggtattat 1320
gctaacctat gatatggttc gatcgtgcta gctacgtcct gtgtcataat ttttagcatg 1380
ccctttttttg tttggttttg tctgattggg ctgtagatca gagtatactg tttcaaacta 1440
cctactggat atatttatta aatttgaatc tgtatgtgtg tcatatatat cttcataatt 1500
aaaatggatg gaaagatata tggataggta catgtgttgc tgtgggtttt actggtactt 1560
tgttagatat acatgcttag atacatgaag caacatgatg ttacagttca ataattcttg 1620
tttacctaat aaacaaataa ggataggtgt atgttgctgt gggttttgct ggtactttgt 1680
tagatatata tgcttagata tatgaagcaa catcctgcta cggtttaata attattgttt 1740
atatctaata gacaagcctg cttttttaatt attttgatat acttggatga tggcatacag 1800
cagctatgtg tggatttta aatacccagc atcatgagca tgcatgaccc tgccttagta 1860
tgctgtttat ttgcttgaga cttctttttt tgttggtact caccttttgt agtttggtga 1920
ctcttctgca ggtg                                                  1934
```

| SEQ ID NO: 30 | moltype = DNA length = 796 |
|---|---|
| FEATURE | Location/Qualifiers |
| source | 1..796 |
| | mol_type = other DNA |
| | organism = Tripidium ravennae |
| | sub_species = ravennae |

SEQUENCE: 30

```
accacaagaa tgatatcatc gtcatgctta gatccttttt agtaaagctt gagcttctct   60
aaaagtagag aaattagaaa aaaatcacgt ttttgtggtc ttgatttcta gcctccacaa  120
aatctttggt tttacatttt ttgtttgatt ttggtttcag aagtccttat ttatatgtgc  180
tagtttggca gcacttaaaa tcgttagaga gagcctaaac aaaagccttt tcaaaacgac  240
cttgagccag attggttgat ggccaaaatt tgattgtcaa aacttaggca agccaagatt  300
ttagcagcta tttggtttgg taccaaaatt tgccaatgat ctgttctttt gccttttcaa  360
ccggtttatc agccgtactt cagcttattc tctctcacag aacactattg aatcagccga  420
aaagccaccg cagaacagga ccagtatctc acaaatggca tgccaaatat actcaccgtc  480
agtgagcccg tttaacggcg tcgacaagtc taacggccac caaccagcga accaccagcg  540
tcaagctagc caagcgaagc agacggccga cgttgaca ccttggcgcg ggcatctctc  600
tggcccccctc tcgagagttc cgctccacct ccactggtgg cggtttccaa gtccgttccg  660
cctcctgctc ctcctcacac ggcacgaaac cgtcacggca ccggcagcac ggggggattcc  720
tttcccaccg ctccttccct ttcccttcct cgcccgccgt tttaaatagc cagcccccatc  780
cccagcttct ctcccc                                                  796
```

| SEQ ID NO: 31 | moltype = DNA length = 1649 |
|---|---|
| FEATURE | Location/Qualifiers |
| source | 1..1649 |
| | mol_type = other DNA |
| | organism = Tripidium ravennae |
| | sub_species = ravennae |

SEQUENCE: 31

```
aggcaagcca agatttttagc agctatttgg tttggtacca aaatttgcca atgatctgtt   60
cttttgcctt ttcaaccggt ttatcagccg tacttcagct tattctctct cacagaaacac  120
tattgaatca gccgaaaagc caccgcagaa caggaccagt atctcacaaa tggcatgcca  180
aatatactca ccgtcagtga gcccgtttaa cggcgtcgac aagtctaacg gccaccaacc  240
agcgaaccac cagcgtcaag ctagccaagc gaagcagacg gccgagacgt tgacaccttg  300
gcgcgggcat ctctctggcc cctctcgag agttccgctc cacctccact ggtggcggtt  360
tccaagtccg ttccgcctcc tgctcctcct cacacggcac gaaaccgtca cggcaccggc  420
agcacggggg attcctttcc caccgctcct tcccttccc ttcctcgccc gccgttttaa  480
```

```
atagccagcc ccatcccag cttctctccc caacctcagc ttctctcgtt gttcggagcg    540
cacacacaac ccgatcccca atccctcgt ctctcctcgc gagcctcgtc gatcccgct     600
tcaaggtacg gcgatcatcc tcccttctc taccttctct tctctagact aggtcggcga    660
tccatggtta gggcctgcta gttctgttcc tgtttttccg tggctgcgag gtacaataga   720
tctgatggcg ttatgatggt taacttgtca tactcctgca gtgtgcggtc tatagtgctt   780
ttaggacatc aatttgacct ggctcgttca agatcggcga tccatggtta ggaccctagg   840
cggtggagtc gggttagatc cgcgctgttt gtgttagtag atggatgcga cctttacttc   900
agacacgttc tgattgttaa cttgtcagca cctgggagtc ctgggatggt tctagctggt   960
tcgcagatga gatcgatttc atgatctgct gtatcttgtt tcgttaggtt ccttttaatc  1020
tatccgtggt attatgctaa cctatgatat ggttcgatcg tgctagctac gtcctgtgtc  1080
ataattttta gcatgccctt ttttgttggt tttgtctga ttgggctgta gatcagagta   1140
tactgtttca aactacctac tggatatatt tattaaattt gaatctgtat gtgtgtcaca  1200
tatatcttca taattaaaat ggatggaaag atatatggat aggtacatgt gttgctgtgg  1260
gttttactgg tactttgtta gatatacatg cttagataca tgaagcaaca tgatgttaca  1320
gttcaataat tcttgtttac ctaataaaca aataaggata ggtgtatgtt gctgtgggtt  1380
ttgctggtac tttgttagat atatatgctt agatatatga agcaacatcc tgctacggtt  1440
taataattat tgtttatatc taatagacaa gcctgctttt taattatttt gatatacttg  1500
gatgatggca tacagcagct atgtgtggat ttttaaatac ccagcatcat gagcatgcat  1560
gaccctgcct tagtatgctg tttatttgct tgagacttct ttttttgttg gtactcacct  1620
tttgtagttt ggtgactctt ctgcaggtg                                    1649

SEQ ID NO: 32          moltype = DNA  length = 511
FEATURE                Location/Qualifiers
source                 1..511
                       mol_type = other DNA
                       organism = Tripidium ravennae
                       sub_species = ravennae
SEQUENCE: 32
aggcaagcca agatttagc agctatttgg tttggtacca aaatttgcca atgatctgtt    60
cttttgcctt ttcaaccggt ttatcagccg tacttcagct tattctctct cacagaacac   120
tattgaatca gccgaaaagc caccgcagaa caggaccagt atatctcacaa tggcatgcca  180
aatatactca ccgtcagtga gcccgtttaa cggcgtcgac aagtctaacg gccaccaacc   240
agcgaaccac cagcgtcaag ctagccaagc gaagcagacg gccagacgt tgacaccttg    300
gcgcgggcat ctctctggcc ccctctcgag agttccgctc cacctccact ggtggcggtt   360
tccaagtccg ttccgcctcc tgctcctcct cacacggcac gaaaccgtca cggcaccggc   420
agcacggggg attcctttcc caccgctcct tcccttccc ttcctcgccc gccgttttaa    480
atagccagcc ccatcccag cttctctccc c                                  511

SEQ ID NO: 33          moltype = DNA  length = 2631
FEATURE                Location/Qualifiers
source                 1..2631
                       mol_type = other DNA
                       organism = Setaria viridis
SEQUENCE: 33
actgccgcga cacgcctcac tggcgggagg gctccgagcg ctctctcccc ggcggccggc    60
ggagcagcga tctggattgg agagaataga ggaaagagag ggaaaggag agagatagcg    120
caaagagctg aaaagataag gttgtgcggg ctgtggtgat tagaggacca ctaatccctc   180
catctcctaa tgacgcggtg cccaagacca gtgccgcggc acaccagcgt ctaagtgaac   240
ttccgctaac cttccggtca ttgcgcctga aagatgtcat gtggcgaggc ccccctctca   300
gtagattgcc aactgcctac cgtgccactc ttccatgcat gattgctccc gtctatcccg   360
tttctcacaa cagatagaca acagtaagca tcactaaagc aagcatgtgt agaaccttaa   420
aaaaaggctt atactaccag tatactatca accagcatgc cgtttttgaa gtatccagga   480
ttagaagctt ctactgcgct tttatattat agctgtggac ctgtggtaac ctttctcttt   540
tggcgcttgc ttaatctcgg ccgtgctggt ccatgcttag gcactaggca gagatagagc   600
cggggtgaa tggggctaaa gctcagctgc tcgagggcg gtgggctggt ttccactagc    660
ctacagctgt gccacgtgcg gccgcgcaag ccgaagcaag cacgctgagc cgttggacag   720
cttgtcataa tgccattacg tggattacag gtaactggcc ctgtaactac tcgttcggcc   780
atcatcaaac gacgacgtcc gctaggcgac gacacgggta atgcacgcag ccacccaggc   840
gcgcgcgcta gcggagcacg gtcaggtgac acgggcgtgc tgacgcttcc gagttgaagg   900
ggttaacgcc agaaacagtg tttggccagg gtatgaacat aacaaaaaat attcacacga   960
aagaatggaa gtatgcagct gctactgtgt aaatgccaag caggaaactc acgcccgcta  1020
acatccaacg gccaacagct cgacgtgccg gtcagcagag acatcggaac actggtgatt  1080
ggtggagccg gcagtatgcg ccccagcacg gccgaggtgg tggtggcccg tggccctgct  1140
gtctgcgcgg ctcgggacaa cttgaaactg gccaccgtc tcgtcgcaac tcgcaacccg   1200
ttggcggaag aaaggaatgg ctcgtagggg cccgggtaga atccaagaat gttgcgctgg   1260
gcttcgattc acataacatg ggcctgaagc tctaaaacga cggcccggtc accgggcgat   1320
ggaaagagac cggatcctcc tcgtgaattc tggaaggcca cacgagagcg acccaccacc   1380
gacgcggagg agtcgtgcgt ggtccaacac ggccggcggg ctgggctgcg accttaacca  1440
gcaaggcacc ccacgacccg cctcgccctc gaggcataaa taccctccca tcccgttgcg  1500
gcaagactca gatcagattc cgatcccag ttcttcccca atcaccttgt ggtctctcgt    1560
gtcgcggttc ccaggacgc ctccggctcg tcgctcgaca gcgatctccg ccccagcaag    1620
gtatagattc agttccttgc tccgatccca atctggttga gatgttgctc cgatgcgact   1680
tgattatgtc atatatctgc ggtttgcacc gatctgaagc ctagggtttc tcgagcgacc   1740
cagttgtttg caatttgcga tttgctcgtt tgttgcgcat gctagtttat gtttggagta   1800
atcgaggatt tgtatgcggc gtcggcgcta cctgctaat cacgccatgt gacgcggtta    1860
cttgcagagg ctgggttagt gggttctgtt atgtcgtgat ctaagaatct agattaggct   1920
cagtcgttct tgctgtcgac tagtttgttt tgatatccat gtagtacaag ttacttaaaa   1980
tttaggtcca atatattttg catgcttttg gcctgttatt cttgccaaca agttgtcctg   2040
gtaaaaagta gatgtgaaag tcacgtattg ggacaaattg atggttaagt gctatagttc   2100
```

```
tatagttctg tgatacatct atctgatttt ttttggtcta ttggtgccta acttatctga    2160
aaatcatgga acatgaggct agtttgatca tggtttagtt cattgtgatt aataatgtat    2220
gatttagtag ctattttggt gatcgtgtca ttttatttgt gaatggaatc attgtatgta    2280
aatgaagcta gttcagggt tatgatgtag ctggctttgt attctaaagg ctgctattat     2340
tcatccatcg atttcaccta tatgtaatcc agagctttcg atgtgaaatt tgtctgatcc    2400
ttcactagga aggacagaac attgttaata ttttggcaca tctgtcttat tctcatcctt    2460
tgtttgaaca tgttagcctg ttcaaacaga tactgttgta atgtcctagt tatataggta    2520
catatgtgtt ctctattgag tttatggact tttgtgtgtg aagttatatt tcattttgct   2580
caaaactcat gtttgcaagc tttctgacat tattctattg ttctgaaaca g            2631

SEQ ID NO: 34            moltype = DNA   length = 1493
FEATURE                  Location/Qualifiers
source                   1..1493
                         mol_type = other DNA
                         organism = Setaria viridis
SEQUENCE: 34
actgccgcga cacgcctcac tggcgggagg gctccgagcg ctctctcccc ggcggccggc    60
ggagcagcga tctggattgg agagaataga ggaaagagag ggaaaaggag agagatagcg    120
caaagagctg aaaagataag gttgtgcggg ctgtggtgat tagaggacca ctaatccctc    180
catctcctaa tgacgcggtg cccaagacca gtgccgcggc acaccagcgt ctaagtgaac    240
ttccgctaac cttccggtca ttgcgcctga agatgtcat gtggcgaggc ccccctctca     300
gtagattgcc aactgcctac cgtgccactc ttccatgcat gattgctccc gtctatcccg    360
tttctcacaa cagatagaca acagtaagca tcactaaagc aagcatgtgt agaaccttaa    420
aaaaaggctt atactaccag tatactatca accagcatgc cgttttgaa gtatccagga     480
ttagaagctt ctactgcgct tttatattat agctgtggac ctgtggtaac cttctcttt     540
tggcgcttgc ttaatctcgg ccgtgctggt ccatgcttag gactaggca gagatagagc     600
cgggggtgaa tggggctaaa gctcagctgc tcgaggggcc gtgggctggt ttccactagc    660
ctacagctgt gccacgtgcg gccgcgcaag ccgaagcaag cacgctgagc cgttggacag    720
cttgtcataa tgccattacg tggattacag gtaactggcc ctgtaactac tcgttcggcc    780
atcatcaaac gacgacgtcc gctaggcaac gacacgcag atgcacgcag ccacccaggc    840
gcgcgcgcta gcggagcacg gtcaggtgac acgggcgtcg tgacgcttcc gagttgaagg    900
ggttaacgcc agaaacagtg tttggccagg gtatgaacat aacaaaaaat attcacacga    960
aagaatggaa gtatggagct gctactgtgt aaatgccaag caggaaactc acgcccgcta    1020
acatccaacg gccaacagct cgacgtgccg gtcagcagag acatcggaac actggtgatt    1080
ggtggagccg gcagtatgcg cccccagcacg gccgaggtgg tggtggcccg tggccctgct   1140
gtctgcgcgg ctcgggacaa cttgaaactg ggccaccgcc tcgtcgcaac tcgcaacccg    1200
ttggcggaag aaaggaatgg ctcgtagggg cccgggtaga atccaagaat gttgcgctgg    1260
gcttcgattc acataaacatg ggcctgaagc tctaaaacga cggcccggtc accgggcgat   1320
ggaaagagac cggatcctcc tcgtgaattc tggaaggcca cacgagagcg acccaccacc    1380
gacgcggagg agtcgtgcgt ggtccaaac ggccggcggg ctgggctgcg accttaacca     1440
gcaaggcacg ccacgacccg cctcgccctc gaggcataaa taccctccca tcc           1493

SEQ ID NO: 35            moltype = DNA   length = 127
FEATURE                  Location/Qualifiers
source                   1..127
                         mol_type = other DNA
                         organism = Setaria viridis
SEQUENCE: 35
cgttgccgca agactcagat cagattccga tccccagttc ttccccaatc accttgtggt    60
ctctcgtgtc gcggttccca gggacgcctc cggctcgtcg ctcgacagcg atctccgccc    120
cagcaag                                                              127

SEQ ID NO: 36            moltype = DNA   length = 1011
FEATURE                  Location/Qualifiers
source                   1..1011
                         mol_type = other DNA
                         organism = Setaria viridis
SEQUENCE: 36
gtatagattc agttccttgc tccgatccca atctggttga gatgttgctc cgatgcgact    60
tgattatgtc atatatctgc ggtttgcacc gatctgaagc ctaggggttc tcgagcgacc    120
cagttgtttg caatttgcga tttgctcgtt tgttgcgcat cgtagtttat gtttggagta    180
atcgaggatt tgtatgcggc gtcggcgcta cctgcttaat cacgccatgt gacgcggtta    240
cttgcagagg ctggggttagt gggttctgtt atgtcgtgat ctaagaatct agattaggct   300
cagtcgttct tgctgtcgac tagtttgttt tgatatccat tgtatacaag ttacttaaaa    360
tttaggtcca atatattttg catgcttttg gcctgttatt cttgccaaca agttgtcctg    420
gtaaaaagta gatgtgaaag tcacgtattg ggacaaattg atggttaagt gctatagttc    480
tatagttctg tgatacatct atctgatttt ttttggtcta ttggtgccta acttatctga    540
aaatcatgga acatgaggct agtttgatca tggtttagtt cattgtgatt aataatgtat    600
gatttagtag ctattttggt gatcgtgtca ttttatttgt gaatggaatc attgtatgta    660
aatgaagcta gttcagggt tatgatgtag ctggctttgt attctaaagg ctgctattat     720
tcatccatcg atttcaccta tatgtaatcc agagctttcg atgtgaaatt tgtctgatcc    780
ttcactagga aggacagaac attgttaata ttttggcaca tctgtcttat tctcatcctt    840
tgtttgaaca tgttagcctg ttcaaacaga tactgttgta atgtcctagt tatataggta    900
catatgtgtt ctctattgag tttatggact tttgtgtgtg aagttatatt tcattttgct   960
caaaactcat gtttgcaagc tttctgacat tattctattg ttctgaaaca g             1011

SEQ ID NO: 37            moltype = DNA   length = 2173
FEATURE                  Location/Qualifiers
source                   1..2173
```

```
                        mol_type = other DNA
                        organism = Setaria viridis
SEQUENCE: 37
gccgtttttg aagtatccag gattagaagc ttctactgcg cttttatatt atagctgtgg   60
acctgtggta acctttctct tttggcgctt gcttaatctc ggccgtgctg gtccatgctt  120
aggcactagg cagagataga gccggggtg aatggggcta aagctcagct gctcgagggg   180
ccgtgggctg gtttccacta gcctacagct gtgccacgtg cggccgcgca agccgaagca  240
agcacgctga gccgttggac agcttgtcat aatgccatta cgtggattac aggtaactgg  300
ccctgtaact actcgttcgg ccatcatcaa acgacgacgt ccgctaggcg acgacacggg  360
taatgcacgc agccacccag gcgcgcgcgc tagcggagca cggtcaggtg acacgggcgt  420
cgtgacgctt ccgagttgaa ggggttaacg ccagaaacag tgtttggcca gggtatgaac  480
ataacaaaaa atattcacac gaaagaatgg aagtatggag ctgctactgt gtaaatgcca  540
agcaggaaac tcacgcccgc taacatccaa cggccaacag ctcgacgtgc cggtcagcag  600
agacatcgga acactggtga ttggtggagc cggcagtatg cgcccagca cggccgaggt   660
ggtggtggcc cgtggccctg ctgtctcgcg ggctcgggac aacttgaaac tgggccaccg  720
cctcgtcgca actcgcaacc cgttggcgga agaaaggaat ggctcgtagg ggcccgggta  780
gaatccaaga atgttgcgct gggcttcgat tcacataaca tgggcctgaa gctctaaaac  840
gacggcccgg tcaccgggcg atggaaagag accggatcct cctcgtgaat tctgaaggc   900
cacacgagag cgaccaccca ccgacgcgga ggagtcgtgc gtggtccaac acggccggcg  960
ggctgggctg cgaccttaac cagcaaggca cgccacgacc cgcctcgccc tcgaggcata 1020
aatacccctcc catcccgttg ccgcaagact cagatcagat tccgatcccc agttcttccc 1080
caatcacctt gtggtctctc gtgtcgcggt tcccagggac gctccggct cgtcgctcga  1140
cagcgatctc cgcccagca aggtatagat tcagttcctt gctccgatcc caatctggtt  1200
gagatgttgc tccgatgcga cttgattatg tcatatatct gcggtttgca ccgatctgaa  1260
gcctaggggt tctcgagcga cccagttgtt tgcaatttgc gatttgctcg tttgttgcgc  1320
atcgtagttt atgttggag taatcgagga tttgtatgcg cgtcggcgc tacctgctta   1380
atcacgccat gtgacgcggt tacttgcaga ggctgggtta gtgggttctg ttatgtcgtg  1440
atctaagaat ctagattagg ctcagtcgtt cttgctgtcg actagtttgt tttgatatcc  1500
atgtagtaca agttacttaa aattaggtc caatatattt tgcatgcttt tggcctgtta  1560
ttcttgccaa caagttgtcc tggtaaaaag tagatgtgaa agtcacgtat tgggacaaat  1620
tgatggttaa gtgctatagt tctatagttc tgtgatacat ctatctgatt ttttttggtc  1680
tattggtgcc taacttatct gaaaatcatg gaacatgagg ctagtttgat catgggtttag 1740
ttcattgtga ttaataatgt atgatttagt agctattttg gtgatcgtgt cattttattt  1800
gtgaatggaa tcattgtatg taaatgaagc tagttcaggg gttatgatgt agctggcttt  1860
gtattctaaa ggctgctatt attcatccat cgatttcacc tatatgtaat ccagagcttt  1920
cgatgtgaaa tttgtctgat ccttcactag gaaggacaga acattgttaa tattttggca  1980
catctgtctt attctcatcc tttgtttgaa catgttagcc tgttcaaaca gatactgttg  2040
taatgtccta gttatatagg tacatatgtg ttctctattg agtttatgga cttttgtgtg  2100
tgaagttata tttcattttg ctcaaaactc atgtttgcaa gctttctgac attattctat  2160
tgttctgaaa cag                                                     2173

SEQ ID NO: 38          moltype = DNA  length = 1035
FEATURE                Location/Qualifiers
source                 1..1035
                        mol_type = other DNA
                        organism = Setaria viridis
SEQUENCE: 38
gccgtttttg aagtatccag gattagaagc ttctactgcg cttttatatt atagctgtgg   60
acctgtggta acctttctct tttggcgctt gcttaatctc ggccgtgctg gtccatgctt  120
aggcactagg cagagataga gccggggtg aatggggcta aagctcagct gctcgagggg   180
ccgtgggctg gtttccacta gcctacagct gtgccacgtg cggccgcgca agccgaagca  240
agcacgctga gccgttggac agcttgtcat aatgccatta cgtggattac aggtaactgg  300
ccctgtaact actcgttcgg ccatcatcaa acgacgacgt ccgctaggcg acgacacggg  360
taatgcacgc agccacccag gcgcgcgcgc tagcggagca cggtcaggtg acacgggcgt  420
cgtgacgctt ccgagttgaa ggggttaacg ccagaaacag tgtttggcca gggtatgaac  480
ataacaaaaa atattcacac gaaagaatgg aagtatggag ctgctactgt gtaaatgcca  540
agcaggaaac tcacgcccgc taacatccaa cggccaacag ctcgacgtgc cggtcagcag  600
agacatcgga acactggtga ttggtggagc cggcagtatg cgcccagca cggccgaggt   660
ggtggtggcc cgtggccctg ctgtctcgcg ggctcgggac aacttgaaac tgggccaccg  720
cctcgtcgca actcgcaacc cgttggcgga agaaaggaat ggctcgtagg ggcccgggta  780
gaatccaaga atgttgcgct gggcttcgat tcacataaca tgggcctgaa gctctaaaac  840
gacggcccgg tcaccgggcg atggaaagag accggatcct cctcgtgaat tctgaaggc   900
cacacgagag cgaccaccca ccgacgcgga ggagtcgtgc gtggtccaac acggccggcg  960
ggctgggctg cgaccttaac cagcaaggca cgccacgacc cgcctcgccc tcgaggcata 1020
aatacccctcc catcc                                                  1035

SEQ ID NO: 39          moltype = DNA  length = 1819
FEATURE                Location/Qualifiers
source                 1..1819
                        mol_type = other DNA
                        organism = Setaria viridis
SEQUENCE: 39
cacgggtaat gcacgcagcc acccaggcgc gcgcgctagc ggagcacggt caggtgacac   60
gggcgtcgtg acgcttccga gttgaagggg ttaacgccag aaacagtgtt tggccagggt  120
atgaacataa caaaaatat tcacacgaaa gaatgaagt atggagctgc tactgtgtaa   180
atgccaagca ggaaactcac gcccgctaac atccaacggc caacagctcg acgtgccggt  240
cagcagagac atcggaacac tggtgattgg tggagccggc agtatgcgcc ccagcacggc  300
cgaggtggtg gtggccgtg gccctgctgt ctgcgcggct cgggacaact tgaaactggg   360
ccaccgcctc gtcgcaactc gcaacccgtt ggcggaagaa aggaatggct cgtagggggcc  420
```

```
cgggtagaat ccaagaatgt tgcgctgggc ttcgattcac ataacatggg cctgaagctc    480
taaaacgacg gcccggtcac cgggcgatgg aaagagaccg gatcctcctt gtgaattctg    540
gaaggccaca cgagagcgac ccaccaccga cgcggaggag tcgtgcgtgg tccaacacgg    600
ccggcgggct gggctgcgac cttaaccagc aaggcacgcc acgacccgcc tcgccctcga    660
ggcataaata ccctcccatc ccgttgccgc aagactcaga tcagattccg atccccagtt    720
cttccccaat caccttgtgg tctctcgtgt cgcggttccc agggacgcct ccggctcgtc    780
gctcgacagc gatctccgcc ccagcaaggt atagattcag ttccttgctc cgatcccaat    840
ctggttgaga tgttgctccg atgcgacttg attatgtcat atatctgcgg tttgcaccga    900
tctgaagcct aggggtttctc gagcgaccca gttgtttgca atttgcgatt tgctcgtttg    960
ttgcgcatcg tagtttatgt ttggagtaat cgaggatttg tatgcggcgt cggcgctacc    1020
tgcttaatca cgccatgtga cgcggttact tgcagaggct gggttagtgg gttctgttat    1080
gtcgtgatct aagaatctag attaggctca gtcgttcttg ctgtcgacta gtttgttttg    1140
atatccatgt agtacaagtt acttaaaatt taggtccaat atattttgca tgcttttggc    1200
ctgttattct tgccaacaag ttgtcctggt aaaaagtaga tgtgaaagtc acgtattggg    1260
acaaattgat ggttaagtgc tatagttcta tagttctgtg atacatctat ctgatttttt    1320
ttggtctatt ggtgcctaac ttatctgaaa atcatggaac atgaggctag tttgatcatg    1380
gtttagttca ttgtgattaa taatgtatga tttagtagct attttggtga tcgtgtcatt    1440
ttatttgtga atggaatcat tgtatgtaaa tgaagctagt tcaggggtta tgatgtagct    1500
ggctttgtat tctaaaggct gctattattc atccatcgat ttcacctata tgtaatccag    1560
agctttcgat gtgaaatttg tctgatcctt cactaggaag gacagaacat tgttaatatt    1620
ttggcacatc tgtcttattc tcatcctttg tttgaacatg ttagcctgtt caaacagata    1680
ctgttgtaat gtcctagtta taggtacata tatgtgttct ctattgagtt tatggacttt    1740
tgtgtgtgaa gttatatttc attttgctca aaactcatgt ttgcaagctt tctgacatta    1800
ttctattgtt ctgaaacag                                                 1819

SEQ ID NO: 40          moltype = DNA   length = 681
FEATURE                Location/Qualifiers
source                 1..681
                       mol_type = other DNA
                       organism = Setaria viridis
SEQUENCE: 40
cacgggtaat gcacgcagcc acccaggcgc gcgcgctagc ggagcacggt caggtgacac    60
gggcgtcgtg acgcttccga gttgaagggg ttaacgccag aaacagtgtt tggccagggt    120
atgaacataa caaaaaatat tcacacgaaa gaatggaagt atggagctgc tactgtgtaa    180
atgccaagca ggaaactcac gcccgctaac atccaacggc caacagctcg acgtgccggt    240
cagcagagac atcggaacac tggtgattgg tggagccggc agtatgcgcc ccagcacggc    300
cgaggtggtg gtgccccgtg gccctgctgt ctgcgcggct cgggacaact tgaaactggg    360
ccaccgcctc gtcgcaactc gcaacccgtt ggcggaagaa aggaatggct cgtaggggcc    420
cgggtagaat ccaagaatgt tgcgctgggc ttcgattcac ataacatggg cctgaagctc    480
taaaacgacg gcccggtcac cgggcgatgg aaagagaccg gatcctcctt gtgaattctg    540
gaaggccaca cgagagcgac ccaccaccga cgcggaggag tcgtgcgtgg tccaacacgg    600
ccggcgggct gggctgcgac cttaaccagc aaggcacgcc acgacccgcc tcgccctcga    660
ggcataaata ccctcccatc c                                              681

SEQ ID NO: 41          moltype = DNA   length = 1922
FEATURE                Location/Qualifiers
source                 1..1922
                       mol_type = other DNA
                       organism = Zea mays
                       sub_species = Mexicana
SEQUENCE: 41
gtcgtgcccc tctctagaga taatgagcat tgcatgtcta agttataaaa aattaccaca    60
tatttttttt tgtcacactt gtgtttgaag tgcagtttat ctatctctat acatatattt    120
aaacttcact atatgaataa tatagtctat agtattaaaa taatatcaat gttttagatg    180
attatataac tgaactgcta gacatggtct aaaggacaac cgagtgtttt gacaacatga    240
ctctacagtt ttatctttttt agtgtgcatg tgttcttttt actttgcaa atagcttcac    300
ctatataata cttcatccat tttattagta catccattta ctaaattttt agtacatcta    360
ttttattcta ttttagcctc taaattaaga aaacttaaac tctatttttag ttttttattt    420
aataatttag atataaaata gaataaaata aagtgactaa aaaataacta aataccttt    480
aagaaataaa aaaactaagg aaccattttt cttgttccga gtagataatg acagcctgtt    540
caacgccgtc gacgagtcta acggacacca accagcgaac cagcagcgtc gcgtcgggcc    600
aagcgaagca gacggcacgg catctctgta gctgcctctg gacccctctc gagagttccg    660
ctccaccgtt ggacttgctc cgctgtcggc atccagaaat tgcgtggcgg agcggcagac    720
gtgagccggc acggacaggcg gcctcctctc acggacgtacgg ggattccttc    780
cccaccgctc cttcgctttc ccttcctcgc ccgccgtaat aaatagaccc cctccacacc    840
ctctttcccc aacctcgtgt tcgttcggag cgcgcacaca cacaaccaga tctccccaa    900
atccaccccgt cggcacctcc gcttcaaggt acgccgctca tcctcctccc ccccctctct    960
ctaccttctc tagatcggcg tttcggtcca tggttagggc ccggtagttc tacttctgtt    1020
catgttttgtg ttagatccgt gtttgtgtta gatccgtgct ctagatttgc gtacacggat    1080
gcgacctgta catcagacat gttctgattg ctaacttgcc agtgtttctc tttggggaat    1140
cctgggatgg ctctagccgt tccgcagacg ggatcgattt catgaatttt ttttgtttcg    1200
ttgcataggg tttggtttgc ccttttcctt tatttcaata tatgccgtgc acttgtttgt    1260
cgggtcatct tttcatgttt tttttggctt ggttgtgatg atgtggtctg gttgggcggt    1320
cgttctagat cggagtagaa tactgtttca aactgtttta tggatttatt aaaggatctg    1380
tatgtatgtg ccatacatct tcatagttac gagttgtaaga tgatggatgg aaatatcgat    1440
ctaggatagg tatacatgtt gatgcgggtt ttactgatgc atatacagag atgcttttttt    1500
ttcgcttggt tgtgatgatg tggtctgtc gggcggtcgt tctagatcgg agtagaatac    1560
tgtttcaaac tacctggtgg atttattaat tttggatctg tatgtgtgtc acacatcttc    1620
atagttacga gtttaagatc gatggaaata tcgatctagg ataggtatac atgttgatgt    1680
```

```
gggttttact gatgcatata catggcatat gcagcatcta ttcatatgct ctaaccttga   1740
gtacctatct attataataa acaagtatgt tttataatta ttttgatctt gatatacttg   1800
gatgatggca tatgcagcag ctatatgtgg atttttttag ccctgccttc atacgctatt   1860
tatttgcttg gtactgtttc ttttgtcgat gctcaccctg ttgtttggtg atacttctgc   1920
ag                                                                 1922

SEQ ID NO: 42           moltype = DNA   length = 850
FEATURE                 Location/Qualifiers
source                  1..850
                        mol_type = other DNA
                        organism = Zea mays
                        sub_species = Mexicana
SEQUENCE: 42
gtcgtgcccc tctctagaga taatgagcat tgcatgtcta agttataaaa aattaccaca    60
tatttttttt tgtcacactt gtgtttgaag tgcagtttat ctatctctat acatatattt   120
aaacttcact atatgaataa tatagtctat agtattaaaa taatatcaat gttttagatg   180
attatataac tgaactgcta gacatggtct aaaggacaac cgagtatttt gacaacatga   240
ctctacagtt ttatctttt agtgtgcatg tgttctttt acttttgcaa atagcttcac    300
ctatataata cttcatccat tttattagta catccattta ctaaatttt agtacatcta    360
ttttattcta ttttagcctc taaattaaga aaacttaaac tctatttag tttttttattt    420
aataatttag atataaaata gaataaaata aagtgactaa aaaataacta aatacctttt    480
aagaaataaa aaaactaagg aaccattttt cttgttccga tgtagataatg acagcctgtt   540
caacgccgtc gacgagtcta acggacacca accagcgaac cagcagcgtc gcgtcgggcc    600
aagcgaagca gacggcacgg catctctgta gctgcctctg gacccctctc gagagttccg    660
ctccaccgtt ggacttgctc cgctgtcggc atccagaaat tgcgtggcgg agcggcagac    720
gtgagccggc acggcaggcg gcctcctctc acggcaccgg cagctacggg ggattccttt    780
cccaccgctc cttcgctttc ccttcctcgc ccgccgtaat aaatagaccc cctccacacc    840
ctctttcccc                                                          850

SEQ ID NO: 43           moltype = DNA   length = 78
FEATURE                 Location/Qualifiers
source                  1..78
                        mol_type = other DNA
                        organism = Zea mays
                        sub_species = Mexicana
SEQUENCE: 43
aacctcgtgt tcgttcggag cgcgcacaca cacaaccaga tctcccccaa atccacccgt    60
cggcaccctcc gcttcaag                                                78

SEQ ID NO: 44           moltype = DNA   length = 994
FEATURE                 Location/Qualifiers
source                  1..994
                        mol_type = other DNA
                        organism = Zea mays
                        sub_species = Mexicana
SEQUENCE: 44
gtacgccgct catcctcctc ccccccctct ctctaccttc tctagatcgg cgtttcggtc    60
catggttagg gcccggtagt tctacttctg ttcatgtttg tgttagatcc gtgtttgtgt   120
tagatccgtg ctgctagatt tcgtacacgg atgcgacctg tacatcagac atgttctgat   180
tgctaacttg ccagtgtttc tctttgggga atcctgggat ggctctagcc gttccgcaga   240
cgggatcgat ttcatgaatt ttttttgttt cgttgcatga ggtttggttt gccctttcc    300
tttatttcaa tatatgccgt gcacttgttt gtcgggtcat ctttttcatgt ttttttttggc   360
ttggttgtga tgatgtggtc tggttgggcg gtcgttctag atcggagtag aatactgttt    420
caaactacct ggtggattta ttaaaggatc tgtatgtatg tgccatacat cttcatagtt    480
acgagtttaa gatgatggat ggaaatatcg atctaggata ggtatacatg ttgatgcggg    540
ttttactgat gcatatacag agatgcttt ttttcgcttg gttgtgatga tgtggtctgg    600
tcggccggtc gttctagatc ggagtagaat actgttcaa actacctggt ggatttatta    660
attttggatc tgtatgtgtg tcatacatct tcatagttac gagtttaaga tcgatggaaa    720
tatcgatcta ggataggtat acatgttgat gtgggttta ctgatgcata tacatggcat    780
atgcagcatc tattcatatg ctctaacctt gagtacctat ctattataat aaacaagtat    840
gtttataat tattttgatc ttgatatact tggatgatgg catatgcagc agctatatgt    900
ggatttttt agccctgcct tcatacgcta tttatttgct tggtactgtt tcttttgtcg    960
atgctcaccc tgttgtttgg tgatacttct gcag                               994

SEQ ID NO: 45           moltype = DNA   length = 1971
FEATURE                 Location/Qualifiers
source                  1..1971
                        mol_type = other DNA
                        organism = Zea mays
                        sub_species = Mexicana
SEQUENCE: 45
gtcgtgcccc tctctagaga taaagagcat tgcatgtcta agttataaaa aattaccaca    60
tatttttttt gtcacacttg tttgaagtgc agtttatcta tctttataca tatatttaaa   120
ctttactcta cgaataatat aatctatagt actacaatga tatcagtgtt ttagagaatc   180
atataaatga acagttagac atggtctaaa ggacaattga gtattttgac aacaggactc   240
tacagtttta tcttttagt gtgcatgtgt tctccttttt ttttgcaaa tagcttcacc     300
tatataatac ttcatccatt ttattagtac atccatttag gtttagggt taatggtttt    360
tatagactaa tttttttagt acatctattt tattctattt tagcctctaa attaagaaaa    420
ctaaaactct atttttagttt ttatttaa taatttgat ataaaataga ataaatataaa    480
```

```
gtgactaaaa attaaacaaa tacccttaa gaaattaaaa aaactaagga aacatttttc   540
ttgtttcgag tagataatgc cagcctgtta aacgccgtcg acgagtctaa cggacaccaa   600
ccagcgaacc agcagcgtcg cgtcgggcca agcgaagcag acggcacggc atctctgtcg   660
ctgcctctgg accoctctcg agagttccgc tccaccgttg gacttgctcc gctgtcggca   720
tccagaaatt gcgtggcgga gcggcagacg tgagccggca cggcaggcgg cctcctcctc   780
ctctcacggc accggcagct acggggatt cctttcccac cgctccttcg ctttcccttc    840
ctcgcccgcc gtaataaata gacaccccct ccacaccttc tttccccaac ctcgtgttgt    900
tcggagcgca cacacacaca accagatctc ccccaaatcc acccgtcggc acctccgctt    960
caaggtacgc cgctcatcct ccccccccc tctctacctt ctctagatcg gcgttccggt   1020
ccatggttag ggcccggtag ttctacttct gttcatgttt gtgttagatc cgtgttttgtg  1080
ttagatccgt gctgctagcg ttcgtacacg gatgcgacct gtacgtcaga cacgttctga   1140
ttgctaactt gccagtgttt ctctttgggg aatcctggga tggctctagc cgttccgcag   1200
acgggatcga tttcatgatt tttttgttt cgttgcatag ggtttggttt gcccttttcc    1260
ttttattcaa tatatgccgt gcacttgttt gtcgggtcat cttttttttgt ttttttttgt   1320
cttggttgtg atgatgcggt ctggttgggc ggtcgttcta gatcggagaa gaattctgtt   1380
tcaaactacc tggtggattt attaattttg gatctgtatg tgtgtgccat acatatttcat  1440
agttacgaat tgaagatgat ggatggaaat atcgatctag gataggtata catgttgatg   1500
cgggttttac tgatgcatat acagagatgc ttttgttcg cttggttgtg atgatgtggt   1560
ctggttgggc ggtcgttcat tcgttctaga tcggagtaga atactgtttc aaactacctg   1620
gtgtatttat taattttgga actgtatgtg tgtgtcatac atcttcatag ttacgagttt   1680
aagatggatg gaaatatcga tctaggatag gtatacatgt tgatgtgggt tttactgatg   1740
catatacatg atggcatatg cagcatctat tcatatgctc taaccttgag tacctatcta   1800
ttataataaa caagtatgtt ttataattat tttgatcttg atatacttgg atgatggcat   1860
atgcagcagc tatatgtgga ttttttttagc cctgccttca tacgctattt attttgcttgg  1920
tactgtttct tttgtcgatg ctcaccctgt tgttggtga tacttctgca g              1971

SEQ ID NO: 46           moltype = DNA  length = 887
FEATURE                 Location/Qualifiers
source                  1..887
                        mol_type = other DNA
                        organism = Zea mays
                        sub_species = Mexicana
SEQUENCE: 46
gtcgtgcccc tctctagaga taaagagcat tgcatgtcta agttataaaa aattaccaca    60
tatttttttt gtcacacttg tttgaagtgc agtttatcta tctttataca tatatttaaa  120
ctttactcta cgaataatat aatctatagt actacaataa tatcagtgtt ttagagaatc  180
atataaatga acagttagac atggtctaaa ggacaattga gtattttgac aacaggactc  240
tacagtttta tcttttttagt gtgcatgtgt tctccttttt tttttgcaaa tagcttcacc  300
tatataatac ttcatccatt ttattagtac atccatttag ggtttagggt taatggtttt  360
tatagactaa tttttttagt acatctattt tattctattt tagcctctaa attaagaaaa  420
ctaaaactct attttagttt ttttattaa taatttagat ataaaataga ataaaataaa   480
gtgactaaaa attaaacaaa tacccttaa gaaattaaaa aaactaagga aacatttttc    540
ttgtttcgag tagataatgc cagcctgtta aacgccgtcg acgagtctaa cggacaccaa   600
ccagcgaacc agcagcgtcg cgtcgggcca agcgaagcag acggcacggc atctctgtcg   660
ctgcctctgg accoctctcg agagttccgc tccaccgttg gacttgctcc gctgtcggca   720
tccagaaatt gcgtggcgga gcggcagacg tgagccggca cggcaggcgg cctcctcctc   780
ctctcacggc accggcagct acggggatt cctttcccac cgctccttcg ctttcccttc    840
ctcgcccgcc gtaataaata gacaccccct ccacaccttc tttccc                   887

SEQ ID NO: 47           moltype = DNA  length = 77
FEATURE                 Location/Qualifiers
source                  1..77
                        mol_type = other DNA
                        organism = Zea mays
                        sub_species = Mexicana
SEQUENCE: 47
aacctcgtgt tgttcggagc gcacacacac acaaccagat ctcccccaaa tccacccgtc    60
ggcacctccg cttcaag                                                   77

SEQ ID NO: 48           moltype = DNA  length = 1007
FEATURE                 Location/Qualifiers
source                  1..1007
                        mol_type = other DNA
                        organism = Zea mays
                        sub_species = Mexicana
SEQUENCE: 48
gtacgccgct catcctcccc cccctctc taccttctct agatcggcgt tccggtccat    60
ggttagggcc cggtagttct acttctgttc atgtttgtgt tagatccgtg tttgtgttag   120
atccgtgctg ctagcgtacg gatgcgacct gtcagacacg ttctgattgc              180
taacttgcca gtgtttctct tgggaatc ctgggatggc tctagccgtt ccgcagacg      240
gatcgatttc atgatttttt ttgtttcgtt gcatagggtt tggttgccc ttttcctta     300
tttcaatata tgccgtgcac ttgtttgtcg ggtcatcttt tcatgctttt ttttgtcttg   360
gttgtgatga tgtggtctgg ttgggcggtc gttcagatc ggagaagaat tctgtttcaa    420
actacctggt ggatttatta ttttggatc tgtatgtgcc atacat attcatagtt         480
acgaattgaa gatgatggat ggaaatatcg atctaggata ggtatacatg ttgatgcggg   540
ttttactgat gcatatacag agatgcttcg tgttcgcttg gttgtgatga tgtggtctgg   600
ttgggcggtc gttcattcgt tctagatcgg agtagaatac tgtttcaaac tacctggtgt   660
atttattaat tttggaactg tatgtgtgtg tcatacatct tcatagttac gagtttaaga   720
tggatggaaa tatcgatcta ggataggtat acatgttgat gtgggtttta ctgatgcata   780
```

```
tacatgatgg catatgcagc atctattcat atgctctaac cttgagtacc tatctattat    840
aataaacaag tatgttttat aattattttg atcttgatat acttggatga tggcatatgc    900
agcagctata tgtggatttt tttagccctg ccttcatacg ctatttattt gcttggtact    960
gtttcttttg tcgatgctca ccctgttgtt tggtgatact tctgcag                 1007

SEQ ID NO: 49            moltype = DNA   length = 2005
FEATURE                  Location/Qualifiers
source                   1..2005
                         mol_type = other DNA
                         organism = Zea mays
                         sub_species = Mexicana
SEQUENCE: 49
gtcgtgcccc tctctagaga taaagagcat tgcatgtcta aagtataaaa aattaccaca     60
tatttttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tatttgaca atctacagtt    240
ttatcttttt agtgtgcatg tgatctctct gttttttttg caaatagctt gacctatata    300
atacttcatc cattttatta gtacatccat ttaggattta gggttgatgg tttctataga    360
ctaattttta gtacatccat tttattcttt ttagtctcta aatttttaa aactaaaact    420
ctattttagt tttttattta ataatttaga tataaaatga aataaaataa attgactaca    480
aataaaacaa atacccttta agaaataaaa aaactaagca aacattttc ttgtttcgag    540
tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
acccctctcg agagttccgc tccaccgttg gacttgctcc gctgtcggca tccagaaatt    720
gcgtggcgga gcggcagacg tgaggcggca cggcaggcgg cctcttcctc ctctcacggc    780
accggcagct acggggggatt cctttcccac cgctccttcg ctttcccttc ctcgcccgcc    840
gtaataaaata gacacccccct ccacaccctc tttccccaac ctcgtgttcg ttcggagcgc    900
acacacacgc aaccagatct cccccaaatc cagccgtcgg cacctccgct tcaaggtacg    960
ccgctcatcc tccccccccc cctctctcta ccttctctag atcggcgatc cggtccatgg   1020
ttagggcccg gtagttctac ttctgttcat gtttgtgtta gagcaaacat gttcatgttc   1080
atgtttgtga tgatgtggtc tggttgggcg gtcgttctag atcggagtag gatactgttt   1140
caagctacct ggtggattta ttaattttgt atctgtatgt gtgtgccata catcttcata   1200
gttacgagtt aagatgatg gatggaaata tcgatctagg ataggtatac atgttgatgc   1260
gggttttact gatgcatata cagagatgct ttttttctcg cttggttgtg atgatatggt   1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
atttattaaa ggatctgtat gtatgtgcct acatcttcat agttacgagt ttaagatgat   1500
ggatggaaat atcgatctag gataggtata catgttgatg cgggttttac tgatgcatat   1560
acagagatgc ttttttttcgc ttggttgtga tgatggcg tggttggcg gtcgttctag   1620
atcggagtag aatactgttt caaactacct ggtggattta ttaattttgt atctttatgt   1680
gtgtgccata catcttcata gttacgagtt aagatgatg gatggaaata ttgatctagg   1740
ataggtatac atgttgatgt gggttttact gatgcatata catgatggca tatgcggcat   1800
ctattcatat gctctaacct tgagtaccta tctattataa taaacaagta tgttttataa   1860
ttattttgat cttgatatac ttggatgatg gcatatgcag cagctatatg tggatttttt   1920
agccctgcct tcatacgcta tttattgct tggtactgtt tcttttgtcc gatgctcacc   1980
ctgttgttgg gtgatacttc tgcag                                         2005

SEQ ID NO: 50            moltype = DNA   length = 877
FEATURE                  Location/Qualifiers
source                   1..877
                         mol_type = other DNA
                         organism = Zea mays
                         sub_species = Mexicana
SEQUENCE: 50
gtcgtgcccc tctctagaga taaagagcat tgcatgtcta aagtataaaa aattaccaca     60
tatttttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tatttgaca atctacagtt    240
ttatcttttt agtgtgcatg tgatctctct gttttttttg caaatagctt gacctatata    300
atacttcatc cattttatta gtacatccat ttaggattta gggttgatgg tttctataga    360
ctaattttta gtacatccat tttattcttt ttagtctcta aatttttaa aactaaaact    420
ctattttagt tttttattta ataatttaga tataaaatga aataaaataa attgactaca    480
aataaaacaa atacccttta agaaataaaa aaactaagca aacattttc ttgtttcgag    540
tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
acccctctcg agagttccgc tccaccgttg gacttgctcc gctgtcggca tccagaaatt    720
gcgtggcgga gcggcagacg tgaggcggca cggcaggcgg cctcttcctc ctctcacggc    780
accggcagct acggggggatt cctttcccac cgctccttcg ctttcccttc ctcgcccgcc    840
gtaataaaata gacacccccct ccacaccctc tttcccc                            877

SEQ ID NO: 51            moltype = DNA   length = 78
FEATURE                  Location/Qualifiers
source                   1..78
                         mol_type = other DNA
                         organism = Zea mays
                         sub_species = Mexicana
SEQUENCE: 51
aacctcgtgt tcgttcggag cgcacacaca cgcaaccaga tctcccccaa atccagccgt     60
cggcacctcc gcttcaag                                                   78
```

SEQ ID NO: 52           moltype = DNA  length = 1050
FEATURE                 Location/Qualifiers
source                  1..1050
                        mol_type = other DNA
                        organism = Zea mays
                        sub_species = Mexicana
SEQUENCE: 52
gtacgccgct catcctcccc cccccctct ctctaccttc tctagatcgg cgatccggtc    60
catggttagg gcccggtagt tctacttctg ttcatgtttg tgttagagca aacatgttca   120
tgttcatgtt tgtgatgatg tggtctggtt gggcggtcgt tctagatcgg agtaggatac   180
tgtttcaagc tacctggtgg atttattaat tttgtatctg tatgtgtgtg ccatacatct   240
tcatagttac gagtttaaga tgatggatgg aaatatcgat ctaggatagg tatacatgtt   300
gatgcgggtt ttactgatgc atatacagag atgcttttt tctcgcttgg ttgtgatgat    360
atggtctggt tgggcggtcg ttctagatcg gagtagaata ctgtttcaaa ctacctggtg   420
gatttattaa aggataaagg gtcgttctag atcggagtag aatactgttt caaactacct   480
ggtggattta ttaaaggatc tgtatgtatg tgcctcacatc ttcatagtta cgagtttaag  540
atgatggatg gaaatatcga tctaggatag gtatacatgt tgatgcgggt tttactgatg   600
catatacaga gatgcttttt ttcgcttggt tgtgatgatg tggtctggtt gggcggtcgt   660
tctagatcgg agtagaatac tgtttcaaac tacctggtgg atttattaat tttgtatctt   720
tatgtgtgtg ccatacatct tcatagttac gagtttaaga tgatggatgg aaatattgat   780
ctaggatagg tatacatgtt gatgtgggtt ttactgatca atatacatga tggcatatgc   840
ggcatctatt catatgctct aaccttgagt acctatctat tataataaac aagtatgttt   900
tataattatt ttgatcttga tatacttgga tgatggcata tgcagcagct atatgtggat   960
tttttagccc tgccttcata cgctatttat ttgcttggta ctgtttcttt tgtccgatgc   1020
tcaccctgtt gttgggtgat acttctgcag                                    1050

SEQ ID NO: 53           moltype = DNA  length = 2005
FEATURE                 Location/Qualifiers
source                  1..2005
                        mol_type = other DNA
                        organism = Zea mays
                        sub_species = Mexicana
SEQUENCE: 53
gtcgtgcccc tctctagaga taaagagcat tgcatgtcta aagtatataaa aattaccaca    60
tattttttg tcacacttat ttgaagtgta gtttatctat ctctatacat atatttaaac   120
ttcactctac aaataatata gtctataata ctaaaataat attagtgttt tagaggatca   180
tataaataaa ctgctagaca tggtctaaag gataattgaa tatttttgaca atctacagtt   240
ttatctttttt agtgtgcatg tgatctctct gtttttttttg caaatagctt gacctatata  300
atacttcatc cattttatta gtacatccat ttaggatttta gggttgatgg tttcatataga  360
ctaatttta gtacatccat tttattcttt ttagtctcta aatttttttaa aactaaaaact  420
ctatttttagt tttttattta ataatttaga tataaaatga aataaaaataa attgactaca   480
aataaaacaa ataccctta agaaatttaaaa aaactaagca aacatttttc ttgtttcgaa   540
tagataatga caggctgttc aacgccgtcg acgagtctaa cggacaccaa ccagcgaacc   600
agcagcgtcg cgtcgggcca agcgaagcag acggcacggc atctctgtag ctgcctctgg   660
accccctctg agagttccgc tccaccgttg gacttgctcc gctgtcggca tccagaaatt   720
gcgtgcggga gcggcagacg tgaggcggca cggcacgggg cctcttcctc ctctcacggc   780
accggcagct acgggggatt cctttcccac cgctccttcg cttttccctc ctcgcccgcc   840
gtaataaaata gacaccccct ccacaccctc tttcccaaac ctcgtgttcg ttcggagcgc   900
acacacgcc aaccagatct ccccccaaatc cagccgtcgg cacctccgct tcaaggtacg    960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatggtc tggttgggcg tcgttctag atcggagtag gatactgttt    1140
caagctacct ggtggattta ttaatttttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc tttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa aaacaagta tgttttataa    1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg tgatacttc tgcag                                         2005

SEQ ID NO: 54           moltype = DNA  length = 1050
FEATURE                 Location/Qualifiers
source                  1..1050
                        mol_type = other DNA
                        organism = Zea mays
                        sub_species = Mexicana
SEQUENCE: 54
gtacgccgct catcctcccc cccccctct ctctaccttc tctagatcgg cgatccggtc    60
catggttagg gcccggtagt tctacttctg ttcatgtttg tgttagagca aacatgttca   120
tgttcatgtt tgtgatgatg tggtctggtt gggcggtcgt tctagatcgg agtaggatac   180

```
tgtttcaagc tacctggtgg atttattaat tttgtatctg tatgtgtgtg ccatacatct    240
tcatagttac gagtttaaga tgatggatgg aaatatcgat ctaggatagg tatacatgtt    300
gatgcgggtt ttactgatgc atatacagag atgcttttt tctcgcttgg ttgtgatgat    360
atggtctggt tgggcggtcg ttctagatcg gagtagaata ctgtttcaaa ctacctggtg    420
gatttattaa aggataaagg gtcgttctag atcggagtag aatactgttt caaactacct    480
ggtggattta ttaaaggatc tgtatgtatg tgcctacatc ttcatagtta cgagtttaag    540
atgatggatg gaaatatcga tctaggatag gtatacatgt tgatgcgggt ttactgatg    600
catatacaga gatgcttttt ttcgcttggt tgtgatgatg tggtctggtt gggcggtcgt    660
tctagatcgg agtagaatac tgtttcaaac tacctggtgg atttattaat tttgtatctt    720
tatgtgtgtg ccatacatct tcatagttac gagtttaaga tgatggatgg aaatattgat    780
ctaggatagg tatacatgtt gatgtgggtt ttactgatgc atatacatga tggcatatgc    840
ggcatctatt catatgctct aaccttgagt acctatctat tataataaac aagtatgttt    900
tataattatt ttgatcttga tacttggat tgatggcata tgcagcagct atatgtggat    960
tttttagccc tgccttcata cgctatttat ttgcttggta ctgtttcttt tgtccgatgc    1020
tcaccctgtt gtttggtgat acttctgcag                                     1050

SEQ ID NO: 55          moltype = DNA  length = 1632
FEATURE                Location/Qualifiers
source                 1..1632
                       mol_type = other DNA
                       organism = Sorghum bicolor
SEQUENCE: 55
ccaagtccaa atgtcaattc ccttgaagat gatctatttt tatctttgc attttgttat     60
ggaagtttgc aaatagcaac aaatgctaag tcaatttgcc aaagtctttg gagatgctct   120
tagtctataa ttgaacaata tttgtaaaat acaaaaaaaa atagtactat ttttatttta   180
aaaaatttt ggaagtaaac aaggccgagg atggggaaac ggaagtccaa cacgtcgttt   240
tctaagttgg gctcaaaagc ccatcacgga actgacctgc tatgggtcgg aggagagcgc   300
gtccagatgg ttccagaggc tggtggtggt gggccaaacg cggaactccg ccaccgccac   360
ggcctcgtgc gcaagcgcag cgcgttgccg tgagccgtga cgtaaccctc cgttgcccac   420
gataaaagct ccaccccga ccccggcccc ccgatttccc ctaccgacca gtctcccccg   480
gatcgcaatc gcgaattcgt cgcaccatcg gcacgcagac gaacgaagca aggctctccc   540
catcggctcg tcaaggtatg cgttcccctag atttgttccc ttcctctctc ggtttgtcta   600
tatatatgca tgtatggtcg attcccgatc tgtcgattc tcggtttcgc cttccgtacg   660
aagattcgtt tagattgttc agattgttctg ttgtgttacc agattgatcg gatcaacttg   720
atccagttat cttcgctcct ccgattagat ccgtttctat ttcagtatat atatactagt   780
atagtatcta gggttcacac tgttgaccga ctggttactt ggaattgatc cgtgctgagt   840
tcagttgttg ccgtccataa aggcccgtgc tattgtctgt tctgaaacga atcctgtag   900
atttcttagg gttagtgttc aattcatcaa aaggttgatt agtgaattat caaatttgag   960
agggttaaat cattctcatc atgttgtctc gaatgtaatc ccaaagatat tatagactgt  1020
gtttcgattt gatggattga tttgtgtatc atctaaatca acaaggctaa gtcatcagtt  1080
catagaatca tgtttaggtt tccgttcaat agactagttt tatcaatata taaaattata  1140
agaagggtag ggtaaatcac gttgcctcaa atgccatcct gtatggtttg gtttcaattc  1200
aattagtttg gttgattagg gtatgctctg gattaagatg gttaaatctt ccctagcatc  1260
ttccctgcct atccttactt gatccgtttc ggatatgttg gaagtacagc gagcttattt  1320
catgttgata gtgacccctt tcagattata ctattgaata ttgtatgttt gccacttctg  1380
tatgttgaat tatcctgcta aattagcaat ggaattagca tattggcaat ggtatgcat   1440
ggacctaatc aggacggatg tggttatgtt agtttcaatt cattgtcaat tcattgttca  1500
cctgcgttag atatatatga tgattttac gtgtagttca tagttcttga gttttggatc  1560
tttcttatct gatatatgct ttcctgtgcc tgtgctttat tgtgtcttac catgcgattt  1620
ttgtctatgc ag                                                      1632

SEQ ID NO: 56          moltype = DNA  length = 401
FEATURE                Location/Qualifiers
source                 1..401
                       mol_type = other DNA
                       organism = Sorghum bicolor
SEQUENCE: 56
ccaagtccaa atgtcaattc ccttgaagat gatctatttt tatctttgc attttgttat     60
ggaagtttgc aaatagcaac aaatgctaag tcaatttgcc aaagtctttg gagatgctct   120
tagtctataa ttgaacaata tttgtaaaat acaaaaaaaa atagtactat ttttatttta   180
aaaaatttt ggaagtaaac aaggccgagg atggggaaac ggaagtccaa cacgtcgttt   240
tctaagttgg gctcaaaagc ccatcacgga actgacctgc tatgggtcgg aggagagcgc   300
gtccagatgg ttccagaggc tggtggtggt gggccaaacg cggaactccg ccaccgccac   360
ggcctcgtgc gcaagcgcag cgcgttgccg tgagccgtga c                      401

SEQ ID NO: 57          moltype = DNA  length = 154
FEATURE                Location/Qualifiers
source                 1..154
                       mol_type = other DNA
                       organism = Sorghum bicolor
SEQUENCE: 57
gtaaccctcc gttgcccacg ataaaagctc caccccgac cccggcccc cgatttcccc      60
tacgaccag tctcccccg atcgcaatcg cgaattcgtc gcaccatcgg cacgcagacg    120
aacgaagcaa ggctctcccc atcggctcgt caag                              154

SEQ ID NO: 58          moltype = DNA  length = 1077
FEATURE                Location/Qualifiers
source                 1..1077
                       mol_type = other DNA
```

```
                          organism = Sorghum bicolor
SEQUENCE: 58
gtatgcgttc cctagatttg ttcccttcct ctctcggttt gtctatatat atgcatgtat    60
ggtcgattcc cgatctcgtc gattctcggt ttcgccttcc gtacgaagat tcgtttagat   120
tgttcatatg ttctgttgtg ttaccagatt gatcggatca acttgatcca gttatcttcg   180
ctcctccgat tagatccgtt tctatttcag tatatatata ctagtatagt atctagggtt   240
cacactgttg accgactggt tacttggaat tgatccgtgc tgagttcagt tgttgccgtc   300
cataaaggcc cgtgctattg tctgttctga aacgaaatcc tgtagatttc ttagggttag   360
tgttcaattc atcaaaaggt tgattagtga attatcaaat ttgagagggt taaatcattc   420
tcatcatgtt gtctcgaatg taatcccaaa gatattatag actgtgtttc gatttgatgt   480
attgatttgt gtatcatcta aatcaacaag gctaagtcat cagttcatag aatcatgttt   540
aggtttccgt tcaatagact agttttatca atatataaaa ttataagaag ggtagggtaa   600
atcacgttgc ctcaaatgcc atcctgtatg gtttggtttc aattcaatta gtttggttga   660
ttagggtatg ctctggatta agatggttaa atcttcccta gcatcttccc tgcctatcct   720
tacttgatcc gtttcggata tgttggaagt acagcgagct tatttcatgt tgatagtgac   780
ccctttcaga ttatactatt gaatattgta tgtttgccac ttctgtatgt tgaattatcc   840
tgctaaatta gcaatggaat tagcatattg gcaattggta tgcatggacc taatcaggac   900
ggatgtggtt atgttagttc caattcattg tcaattcatt gttcacctgc gttagatata   960
tatgatgatt tttacgtgta gttcatagtt cttgagtttt ggatcttttct tatctgtatat  1020
atgctttcct gtgcctgtgc tttattgtgt cttaccatgc gatttttgtc tatgcag      1077

SEQ ID NO: 59            moltype = DNA   length = 2000
FEATURE                  Location/Qualifiers
source                   1..2000
                          mol_type = other DNA
                          organism = Sorghum bicolor
SEQUENCE: 59
cactagctgc gcatgataaa gccacaagcc aaaattaatt attatgggtg agaataaata    60
cgtaccagca ccggccatag aaaaagtaca ttattaaagg tctaatttgg aaacagtctg   120
aaaacgacgt gcgctgcaga ggtaaatgta attttcggca ctaaaaccat tatcaactaa   180
ttcattcaat aacagttatt tagaaaatgt atagctcgct ctaaaaaaac agtttagaaa   240
aacagtcaaa ataattcgac caacaaacag ttaataaggt tcattaaata tataatgcac   300
ggtgctattt gatcttttaa aggaaaaaga ggaatagtcg tgggcgccag gcgggaattg   360
gggcgcggga gtctgccgga cgacgcgttc cgtccgaacg gccggacccg acgaggcccc   420
cccgccgccc cacgtcgcag aaccgtccgt gggtggtaat ctggccgggt acaccagccg   480
tcccctttggg cggcctcaca gcactgggct cacacgtgag ttttgttctg ggcttcggat   540
cgcaccatat gggcctcggc atcagaaaga cggggcccgt ctgggataga agagacagga   600
acctcctcgt ggattccaga agccagccac gagcgaccac cgacgcggag gatactcgtc   660
gtccaagtcc aacacggcgg gcgggcgggc ggacggcggg gctgggctaa ctgcctaacc   720
ttaacctcca aggcacgcca aggcccgctt ctcccacccg acataaatat ccccccatcc   780
aggcaaggcg cagagcctca gaccagattc cgatcaatca cccataagct cccccccaaat   840
ctgttcctcg tctcccgtct cgcggtttcc tacttccctc ggacgcctcc ggcaagtcgc   900
tcgaccgcgc gattccgccc gctcaaggta tcaactcgct tcaccactcc aatctacgtc   960
tgatttagat gttacttcca tctatgtcta atttagatgt tactccgatg cgattcggatt  1020
atgtttatgc ggtttgcact gctctggaaa ctggaatcta gggtttcgag tgatttgatc  1080
gatcgcgatc tgtgatttcg ttgcgccttg tgtatgcttg gagtgatcta ggcttgtata  1140
tgcggcatcg cgatctgacg cggttgcttt gtagaggctg ggggtctagg ctgtgatttt  1200
agaatcaaat aaagctgttc cttaccgtag atgtttccta catgttctgt ccagtactcc  1260
agtgctatat tcacattgtt tgaggcttga gttttgtcga tcagtggtca tgagaaaaat  1320
atatctcatg attttagagg cacctattgg gaaaggtaga tggttccgtt ttacatgttt  1380
tatagacctt ggtggcatgc tcctttgttc tatgggtgct ttattttcct gaataacagt  1440
aatgcgagac tggtctatgg gtgctttgac cagtaatgcg agactagtta tttgatcatg  1500
gtgcagttcc tagtgattac gaacaacaat ttggtagctc agttcattca gcattggttt  1560
ctacgatcct tatcatttta cttctgaatg aaatttattta tttaagatat tacagtgcaa  1620
taaactgctg tataatatca gtaacaaact gctattacta gtaaatgcct agattcataa  1680
taattcatta ttctacttga aaatgatctt aggccttttt atgcggtcct acgcatcctt  1740
ccacaggact tgctgtttgt ttgttttttg taatccctcg ctgggacgca gaatggttca  1800
tctgtgctaa taattttttt gcatatataa gtttatagtt ctcattattc atgtggctat  1860
ggtagcctgt aaaatctatt gtaataacat attagtcagc catacatctg ttccaacttg  1920
ctcaattgca aatcatatct ccacttaaag cacatgtttg caagctttct gacaagtttc  1980
tttgtgtttg attgaaacag                                              2000

SEQ ID NO: 60            moltype = DNA   length = 791
FEATURE                  Location/Qualifiers
source                   1..791
                          mol_type = other DNA
                          organism = Sorghum bicolor
SEQUENCE: 60
cactagctgc gcatgataaa gccacaagcc aaaattaatt attatgggtg agaataaata    60
cgtaccagca ccggccatag aaaaagtaca ttattaaagg tctaatttgg aaacagtctg   120
aaaacgacgt gcgctgcaga ggtaaatgta attttcggca ctaaaaccat tatcaactaa   180
ttcattcaat aacagttatt tagaaaatgt atagctcgct ctaaaaaaac agtttagaaa   240
aacagtcaaa ataattcgac caacaaacag ttaataaggt tcattaaata tataatgcac   300
ggtgctattt gatcttttaa aggaaaaaga ggaatagtcg tgggcgccag gcgggaattg   360
gggcgcggga gtctgccgga cgacgcgttc cgtccgaacg gccggacccg acgaggcccc   420
cccgccgccc cacgtcgcag aaccgtccgt gggtggtaat ctggccgggt acaccagccg   480
tcccctttggg cggcctcaca gcactgggct cacacgtgag ttttgttctg ggcttcggat   540
cgcaccatat gggcctcggc atcagaaaga cggggcccgt ctgggataga agagacagga   600
acctcctcgt ggattccaga agccagccac gagcgaccac cgacgcggag gatactcgtc   660
```

```
gtccaagtcc aacacggcgg gcgggcgggc ggacgcgtgg gctgggctaa ctgcctaacc    720
ttaacctcca aggcacgcca aggcccgctt ctcccacccg acataaatat ccccccatcc    780
aggcaaggcg c                                                         791

SEQ ID NO: 61          moltype = DNA   length = 136
FEATURE                Location/Qualifiers
source                 1..136
                       mol_type = other DNA
                       organism = Sorghum bicolor
SEQUENCE: 61
agagcctcag accagattcc gatcaatcac ccataagctc cccccaaatc tgttcctcgt    60
ctcccgtctc gcggtttcct acttccctcg gacgcctccg gcaagtcgct cgaccgcgcg    120
attccgcccg ctcaag                                                    136

SEQ ID NO: 62          moltype = DNA   length = 1073
FEATURE                Location/Qualifiers
source                 1..1073
                       mol_type = other DNA
                       organism = Sorghum bicolor
SEQUENCE: 62
gtatcaactc ggttcaccac tccaatctac gtctgattta gatgttactt ccatctatgt    60
ctaatttaga tgttactccg atgcgattgt attatgttta tgcgtttgc actgctctgg     120
aaactggaat ctagggtttc gagtgatttg atcgatcgcg atctgtgatt tcgttgcgcc    180
ttgtgtatgc ttggagtgat ctaggcttgt atatgcggca tcgcgatctg acgcggttgc    240
tttgtagagg ctgggggtct aggctgtgat tttagaatca aataaagctg ttccttaccg    300
tagatgtttc ctacatgttc tgtccagtac tccagtgcta tattcacatt gtttgaggct    360
tgagttttgt cgatcagtgg tcatgagaaa aatatatctc atgattttag aggcacctat    420
tgggaaaggt agatggttcc gttttacatg ttttatagac cttgtggcat ggctcctttg    480
ttctatgggt gctttatttt cctgaataac agtaatgcga gactggtcta tgggtgcttt    540
gaccagtaat gcgagactag ttatttgatc atggtgcagt tcctagtgat tacgaacaac    600
aatttggtag ctcagttcat tcagcattgg tttctacgat ccttatcatt ttacttctga    660
atgaatttat ttatttaaga tattacagtg caataaactg ctgtataata tcagtaacaa    720
actgctatta ctagtaaatg cctagattca taataattca ttattctact tgaaaatgat    780
cttaggcctt tttatgcggt cctacgcatc tttccacagg acttgctgtt tgtttgtttt    840
ttgtaatccc tcgctgggac gcagaatggt tcatctgtgc taataatttt tttgcatata    900
taagttttata gttctcatta ttcatgtggc tatggtagcc tgtaaaatct attgtaataa    960
catattagtc agccatacat ctgttccaac ttgctcaatt gcaaatcata tctccactta    1020
aagcacatgt ttgcaagctt tctgacaagt ttctttgtgt ttgattgaaa cag           1073

SEQ ID NO: 63          moltype = DNA   length = 2064
FEATURE                Location/Qualifiers
source                 1..2064
                       mol_type = other DNA
                       organism = Sorghum bicolor
SEQUENCE: 63
cattaaaagt cattatgtgc atgcgtcgta actaacatgg atatgttgct gcactatctc    60
ctcgcactag ctgcgcatga taaagccaca agccaaaatt aattattatg ggtgagaata    120
aatacgtacc agcaccggcc atagaaaaag tacattatta aaggtctaat ttggaaacag    180
tctgaaaacg acgtgcgctg cagaggtaaa tgtaattttc ggcactaaaa ccattatcaa    240
ctaattcatt caataacagt tatttagaaa atgtatagct cgctctaaaa aaacagttta    300
gaaaaacagt caaaataatt cgaccaacaa acagttaata aggttcatta aatatataat    360
gcacggtgct atttgatctt ttaaaggaaa aagaggaata gtcgtgggcg ccaggcggga    420
attggggcgc gggagtctgc cggacgacgc gttccgtccg aacggccgga cccgacgagg    480
ccccccccgcc gccccacgtc gcagaaccgt ccgtgggtgg taatctggcc gggtacacca    540
gccgtccccct tgggcggcct cacagcactg ggctcacacg tgagttttgt tctgggcttc    600
ggatcgcacc atatgggcct cggcatcaga aagacgggggc ccgtctggga tagaagagac    660
aggaacctcc tcgtggattc cagaagccag ccacgagcga ccaccgacgc ggaggatact    720
cgtcgtccaa gtccaacacg gcgggcgggc gggcggacgc gtgggctggg ctaactgcct    780
aaccttaacc tccaaggcac gccaaaggcc cgcttctctca cccgacataa atatcccccc    840
atccaggcaa ggcgcagagc ctcagaccag attccgatca atcacccata agctccccc    900
aaatctgttc ctcgtctccc gtctcgcggt ttcctacttc cctcggacgc ctccggcaag    960
tcgctcgacc gcgcgattcc gcccgctcaa ggtatcaact cggttcacca ctccaatcta    1020
cgtctgattt agatgttact tccatctatg tctaatttag atgttactcc gatgcgattg    1080
tattatgttt atgcggttt gcactgctctg gaaactggaa tctagggttt cgagtgattt    1140
gatcgatcgc gatctgtgat tcgttgcgc cttgtgtatg cttggagtga tctaggcttg    1200
tatatgcggc atcgcgatct gacgcggttg ctttgtagag ctgggggtc taggctgtga    1260
ttttagaatc aaataaagct gttccttacc gtagatgttt cctacatgtt ctgtccagta    1320
ctccagtgct atattcacat tgtttgaggc ttgagttttg tcgatcagtg gtcatgagaa    1380
aaatatatct catgatttta gaggcaccta ttgggaaagg tagatggttc cgtttttact    1440
gttttataga ccttgtggca tggctccttt gttctatggg tgctttattt tcctgaataa    1500
cagtaatgcg agactggtct atgggtgctt tgaccagtaa tgcgagacta gttatttgat    1560
catggtgcag ttcctagtga ttacgaacaa caattttggta gctcagttca ttcagcattg    1620
gtttctacga tccttatcat tttacttctg aatgaattta tttatttaag atattacagt    1680
gcaataaact gctgtataat actagtaaat gcctagattc ataataattc attattctac    1740
ttgaaaatga tcttaggcct ttttatgcgg tcctacgcat ccttccacag gacttgctgt    1800
ttgtttgttt tttgtaatcc ctcgctggga cgcagaatgg ttcatctgtg ctaataattt    1860
ttttgcatat ataagtttat agttctcatt attcatgtgg ctatggtagc ctgtaaaatc    1920
tattgtaata acatattagt cagccataca tctgttccaa                          1980
cttgctcaat tgcaaatcat atctccactt aaagcacatg tttgcaagct ttctgacaag    2040
```

```
tttctttgtg tttgattgaa acag                                              2064

SEQ ID NO: 64           moltype = DNA  length = 855
FEATURE                 Location/Qualifiers
source                  1..855
                        mol_type = other DNA
                        organism = Sorghum bicolor
SEQUENCE: 64
cattaaaagt cattatgtgc atgcgtcgta actaacatgg atatgttgct gcactatctc        60
ctcgcactag ctgcgcatga taaagccaca agccaaaatt aattattatg ggtgagaata       120
aatacgtacc agcaccggcc atagaaaaag tacattatta aaggtctaat ttggaaacag       180
tctgaaaacg acgtgcgctg cagaggtaaa tgtaattttc ggcactaaaa ccattatcaa       240
ctaattcatt caataacagt tatttagaaa atgtatagct cgctctaaaa aaacagttta       300
gaaaaacagt caaaataatt cgaccaacaa acagttaata aggttcatta aatatataat       360
gcacggtgct atttgatctt ttaaaggaaa aagaggaata gtcgtgggcg ccaggcggga       420
attggggcgc gggagtctgc cggacgacgc gttccgtccg aacggccgga cccgacgagg       480
ccccccccgcc gccccacgtc gcagaaccgt ccgtgggtgg taatctggcc gggtacacca       540
gccgtcccct tgggcggcct cacagcactg ggctcacacg tgagttttgt tctgggcttc       600
ggatcgcacc atatgggcct cggcatcaga aagacgggc ccgtctggga tagaagagac        660
aggaacctcc tcgtggattc cagaagccag ccacgagcga ccaccgacgc ggaggatact       720
cgtcgtccaa gtcaacacg gcgggcgggc gggcggacgc gtgggctggg ctaactgcct        780
aaccttaacc tccaaggcac gccaaggccc gcttctccca cccgacataa atatccccc        840
atccaggcaa ggcgc                                                        855

SEQ ID NO: 65           moltype = DNA  length = 2000
FEATURE                 Location/Qualifiers
source                  1..2000
                        mol_type = other DNA
                        organism = Sorghum bicolor
SEQUENCE: 65
agaagtaaaa aaaagttcg tttcagaatc ataaaggtaa gttaaaaaaa gaccatacaa         60
aaaagaggta tttaatgata aactataatc cagaatttgt taggatagta tataagaata       120
agaccttgtt tagtttcaaa aaaatttgca aaatttttcca gattcctcgt cacatcaaat      180
ctttagaggt atgcatggag tattaaatat agacaagacc taaataagaa aacatgaaat       240
gttcacgaaa aaaatcaagc caatgcatga tcgaagcaaa cggtatagta acggtgttaa       300
cctgatccat tgatctttgt aatctttaac ggccacctac cgcgggcagc aaacggcgtc       360
cccctcctcg atatctccgc ggcggcctct ggcttttttcc gcggaattgc gcggtgggga     420
cggattccac gagaccgcaa cgcaaccgcc tctcgccgct gggccccaca ccgctcggtg       480
ccgtagccg tagcctcacg ggattctttc tccctcctcc ccgtgtata aattggcttc        540
atccctccc tgcctcatcc atccaaatcc cactccccaa tcccatcccg tcggagaaat       600
tcatcgaagc gaagcgaagc gaatcctccc gatcctctca aggtacgcga gttttcgaat       660
cccctccaga cccctcgtat gctttccctg ttcgttttcg tcgtagcgtt tgattaggta       720
tgctttccct gttcgtgttc gtcgtagggt tcgattaggt cgtgtgaggc catggcctgc       780
tgtgataaat ttatttgttg ttatatcgga tctgtagtcg atttgggggt cgtggtgtag       840
atccgcgggc tgtgatgaag ttatttggtg tgattgtgct cgcgtgattc tgcgcgttga       900
gctcgagtag atctgatggt tggacgaccg attggttcgt tggctggctg cgctaaggtt       960
gggctgggct catgttgcgt tcgctgttgc gcgtgattcc gcggatggac ttgcgcttga      1020
ttgccgccag atcacgttac gattatgtga tttcgtttgg aacttttttag atttgtagct     1080
tctgcttatt atatgacaga tgcgcctact gctcatatgc ctgtggtaaa taatggatgg      1140
ctgtgggtca aactagttga ttgtcgagtc atgtatcata tacaggtgta tagacttgcg      1200
tctaattgtt tgcatgttgc agttatatga tttgttttag attgttttgt ccactcatct      1260
aggctgtaaa agggacacta cttattagct tgttgtttaa tcttttttatt agtagattat     1320
attggtaatg ttttactaat tattattatg ttatatgtga cttctgctca tgcctgatta      1380
taatcataga tcactgtagt tgattgttga atcatgtgtc aaatacccgt atacataaca      1440
ctacacattt gcttagttgt ttcctttaact catgcaaatt gaacaccatg tatgatttgc     1500
atggtgctgt aatgttaaat actacagtcc tgttggtact tgtttagtaa gaatctgctt      1560
catacaacta tatgctatgc ctgatgataa tcatatatct ttgtgtaatt aataattagt      1620
tgactgttga ataatgtatc gagtacatac catggcacaa ttgcttagtc acttccttaa      1680
ccatgcatat tgaactgacc ccttcatgtt ctgctgaatt gttctattct gattagacca      1740
tacatcatgt attgcaatct ttatttgcaa ttgtaatgta atggttcggt tctcaaatgt      1800
taaatgctat agttgtgcta ctttctaatg ttaaatgcta tagctgtgct acttgtaaga      1860
tctgcttcat agtttagtta aattaggatg atgagctttg atgctgtaac tttgtttgat      1920
tatgttcata gttgatcagt ttttgttaga ctcacagtaa cttatggtct cactcttctt      1980
ctggtctttg atgtttgcag                                                  2000

SEQ ID NO: 66           moltype = DNA  length = 565
FEATURE                 Location/Qualifiers
source                  1..565
                        mol_type = other DNA
                        organism = Sorghum bicolor
SEQUENCE: 66
agaagtaaaa aaaagttcg tttcagaatc ataaaggtaa gttaaaaaaa gaccatacaa         60
aaaagaggta tttaatgata aactataatc cagaatttgt taggatagta tataagaata       120
agaccttgtt tagtttcaaa aaaatttgca aaatttttcca gattcctcgt cacatcaaat      180
ctttagaggt atgcatggag tattaaatat agacaagacc taaataagaa aacatgaaat       240
gttcacgaaa aaaatcaagc caatgcatga tcgaagcaaa cggtatagta acggtgttaa       300
cctgatccat tgatctttgt aatctttaac ggccacctac cgcgggcagc aaacggcgtc       360
cccctcctcg atatctccgc ggcggcctct ggcttttttcc gcggaattgc gcggtgggga     420
cggattccac gagaccgcaa cgcaaccgcc tctcgccgct gggccccaca ccgctcggtg       480
```

```
ccgtagcccg tagcctcacg ggattctttc tccctcctcc cccgtgtata aattggcttc    540
atcccctccc tgcctcatcc atcca                                          565

SEQ ID NO: 67           moltype = DNA  length = 77
FEATURE                 Location/Qualifiers
source                  1..77
                        mol_type = other DNA
                        organism = Sorghum bicolor
SEQUENCE: 67
aatcccactc cccaatccca tcccgtcgga gaaattcatc gaagcgaagc gaagcgaatc     60
ctcccgatcc tctcaag                                                    77

SEQ ID NO: 68           moltype = DNA  length = 1358
FEATURE                 Location/Qualifiers
source                  1..1358
                        mol_type = other DNA
                        organism = Sorghum bicolor
SEQUENCE: 68
gtacgcgagt tttcgaatcc cctccagacc cctcgtatgc tttccctgtt cgttttcgtc     60
gtagcgtttg attaggtatg cttccctgt tcgtgttcgt cgtagggttc gattaggtcg    120
tgtgaggcca tggcctgctg tgataaattt atttgttgtt atatcggatc tgtagtcgat    180
ttgggggtcg tggtgtagat ccgcgggctg tgatgaagtt atttggtgtg attgtgctcg    240
cgtgattctg cgcgttgagc tcgagtagat ctgatggttg gacgaccgat tggttcgttg    300
gctggctgcg ctaaggttgg gctgggctca tgttgcgttc gctgttgcgc gtgattccgc    360
ggatggactt gcgcttgatt gccgccagat cacgttacga ttatgtgatt tcgtttggaa    420
cttttttagat ttgtagcttc tgcttattat atgacagatg cgcctactgc tcatatgcct    480
gtggtaaaata atggatggct gtgggtcaaa ctagttgatt gtcgagtcat gtatcatata    540
caggtgtata gacttgcgtc taattgtttg catgttgcag ttatatgatt tgttttagat    600
tgtttgttcc actcatctag gctgtaaaag ggacactact tattagcttg ttgtttaatc    660
ttttttattag tagattatat tggtaatgtt ttactaatta ttattatgtt atatgtgact    720
tctgctcatg cctgattata atcatagatc actgtagttg attgttgaat catgtgtcaa    780
ataccgtat acataacact acacatttgc ttagttgttt ccttaactca tgcaaattga     840
acaccatgta tgatttgcat ggtgctgtaa tgttaaatac tacagtcctg ttggtacttg    900
tttagtaaga atctgcttca tacaactata tgctatgcct gatgataatc atatatcttt    960
gtgtaattaa taattagttg actgttgaat aatgtatcga gtacatacca tggcacaatt   1020
gcttagtcac ttccttaacc atgcatattg aactgaccccc ttcatgttct gctgaattgt   1080
tctattctga ttagaccata catcatgtat tgcaatcttt attgcaatt gtaatgtaat    1140
ggttcggttc tcaaatgtta aatgcatag ttgtgctact ttctaatgtt aaatgctata    1200
gctgtgctac ttgtaagatc tgcttcatag tttagttaaa ttaggatgat gagctttgat   1260
gctgtaactt tgtttgatta tgttcatagt tgatcagttt ttgttagact cacagtaact   1320
tatggtctca ctcttcttct ggtctttgat gtttgcag                            1358

SEQ ID NO: 69           moltype = DNA  length = 2622
FEATURE                 Location/Qualifiers
source                  1..2622
                        mol_type = other DNA
                        organism = Setaria italica
SEQUENCE: 69
actgccgcga cacgcctcac tggcgggagg gctccgagcg ctctctcccc ggcggccggc     60
ggagcagcga tctggattgg agagaataga ggaaagagag ggaaaaggag agagatagcg    120
caaagagctg aaaagataag gttgtgcggg ctgtggtgat tagaggacca ctaatccctc    180
catctcctaa tgacgcggtg cccaagacca gtgccgcggc acaccagcgt ctaagtgaac    240
ttccgctaac cttccggtca ttgcgcctga aagatgtcat gtggcgaggc cccctctca    300
gtagattgcc aactgcctac cgtgccactc ttccatgcat gattgctccc gtctatcccg    360
tttctcacaa cagatagaca acagtaagca tcactaaagc aagcatgtgt agaaccttaa    420
aaaaaggctt atactaccag tatactatca accagcatgc cgttttttgaa gtatccagga    480
ttagaagctt ctactgcgct tttatattat agctgtggac ctgtggtaac cttttctcttt   540
tggcgcttgc ttaatctcgg ccgtgctggt ccatgcttag gcactaggca gagatagagc    600
cggggggtgaa tgggggctaaa gctcagctgc tcgaggggcc gtgggctggt ttccactagc    660
ctacagctgt gccacgtgcg gccgcgcaag ccgaagcaag cacgctgagc cgttggacag    720
cttgtcataa tgccattacg tggattacac gtaactggcc ctgtaactac tcgttcggcc    780
atcatcaaac gacgacgtcc gctaggcgac gacacgggta atgcacgcag ccacccaggc    840
gcgcgcgcta gcggagcacg tcaggtgac acgggcgtcg tgacgcttcc gagttgaagg    900
ggttaacgcc agaaacagtg tttggccagg tgatgaacat aacaaaaaat attcacacga    960
aagaatggaa gtatgagct gctactgtgt aaatgccaag caggaaactc acgcccgcta   1020
acatccaacg gccaacagct cgacgtgccg gtcagcagag catcggaaca ctggtgattg   1080
gtggagccgg cagtatgcgc cccagcacgg ccgaggtggt ggtggcccgt ggccctgctg   1140
tctgcgcggc tcgggacaac ttgaaactgg gccaccgcct cgtcgcaact cgcaaccgt    1200
tggcgaagaa aaggaatggc tcgtaggggc ccgggtgaaa tcgaagaatg ttgcgctggt   1260
cttcgattca cataacatgg gcctgaagct ctaaaacgac ggcccggtcg ccgcgcgatg   1320
gaaagagacc ggatcctcct cgtgaattct ggaaggccac acgagagcga cccaccaccg   1380
acgcggagga gtcgtgcgtg gtccaacacg gccggcggg tgggctgcga ccttaaccag    1440
caaggcacgc cacgacccgc cccgcccctcg aggcataaat accctcccat cccgttgccg   1500
caagactcag atcagattcc gatcccccagt tcttccccaa tcaccttgtg gtctcgtg    1560
tcgcggttcc caggggacgcc tccggctcgt cgctcgacag cgatctcgc cccagcaagg   1620
tatagattca gttccttgct ccgatcccaa tctggttgag atgttgctcc gatgcgactt   1680
gattatgtca tatatctgcg gttttgcaccg atctgaagcc tagggttctt cgagcgaccc   1740
agttattgc aatttgcgat tgctcgtttt gttgcgcagc gtagtttatg tttggagtaa    1800
tcgaggattt gtatgcggcg tcggcgctac ctgcttaatc acgccatgtg acgcggttac   1860
```

```
ttgcagaggc tgggttctgt tatgtcgtga tctaagaatc tagattaggc tcagtcgttc   1920
ttgctgtcga ctagtttgtt ttgatatcca tgtagtacaa gttacttaaa atttaggtcc   1980
aatatatttt gcatgctttt ggcctgttat tcttgccaac aagttgtcct ggtaaaaagt   2040
agatgtgaaa gtcacgtatt gggacaaatt gatggtttag tgctatagtt ctatagttct   2100
gtgatacatc tatctgattt tttttggtct attggtgcct aacttatctg aaaatcatgg   2160
aacatgaggc tagtttgatc atggtttagt tcattgtgat taataatgta tgatttagta   2220
gctattttgg tgatcgtgtc atttttatttg tgaatggaat cattgtatgt aaatgaagct   2280
agttcagggg ttacgatgta gctggctttg tattctaaag ctgctatta ttcatccatc    2340
gatttcacct atatgtaatc cagagctttt gatgtgaaat ttgtctgatc cttcactagg   2400
aaggacagaa cattgttaat attttggcac atctgtctta ttctcatcct ttgtttgaac   2460
atgttagcct gttcaaacag atactgttgt aatgtcctag ttatataggt acatatgtgt   2520
tctctattga gtttatggac ttttgtgtgt gaagttatat ttcattttgc tcaaaactca   2580
tgtttgcaag ctttctgaca ttattctatt gttctgaaac ag                      2622

SEQ ID NO: 70           moltype = DNA   length = 1492
FEATURE                 Location/Qualifiers
source                  1..1492
                        mol_type = other DNA
                        organism = Setaria italica
SEQUENCE: 70
actgccgcga cacgcctcac tggcgggagg gctccgagcg ctctctcccc ggcggccggc   60
ggagcagctga tctggattgg agagaataga ggaaaagag ggaaaaggag agagatagcg    120
caaagagctg aaaagataag gttgtgcggg ctgtggtgat tagaggacca ctaatccctc   180
catctcctaa tgacgcggtg cccaagacca gtgccgcggc acaccagcgt ctaagtgaac   240
ttccgctaac cttccggtca ttgcgcctga agatgtcat gtggcgaggc ccccctctca    300
gtagattgcc aactgcctac cgtgccactc ttccatgcat gattgctcct gtctatcccg   360
tttctcacaa cagatagaca acagtaagca tcactaaagt aagcatgtgt agaaccttaa   420
aaaaaggctt atactaccag tatactatca accagcatgc cgtttttgaa gtatccagga   480
ttagaagctt ctactgcgct tttatattat agctgtggac ctgtggtaac cttctctctt   540
tggcgcttgc ttaatctcgg ccgtgctggt ccatgcttag gacataggca gagatagac   600
cgggggtgaa tggggctaaa gctcagctgc tcgaggggcc gtgggctggt ttccactagc    660
ctacagctgt gccacgtgcg gccgcgcaag ccgaagcaag cacgctgagc cgttggacag   720
cttgtcataa tgccattacg tggattacac gtaactggcc ctgtaactac tcgttcggcc   780
atcatcaaac gacgacgtcc gctaggcgac gacagggta atgcacgcag ccaccaggc    840
gcgcgcgcta gcggagcacg gtcaggtgac acgggcgtcg tgacgcttcc gagttgaagg    900
ggttaacgcc agaaacagtg tttggccagg gtatgaacat aacaaaaaat attcacacga   960
aagaatggaa gtatggagct gctactgtgt aaatgccaag caggaaactc acgcccgcta   1020
acatccaacg gccaacagct cgacgtgccg gtcagcagag catcggaaca ctggtgattg    1080
gtgggaccgg cagtatgcgc cccagcacgg cgaggtggt ggtggcccgt ggccctgctg    1140
tctgcgcggc tcgggacaac ttgaaactgg gccaccgcct cgtcgcaact cgcaaccgt    1200
tggcggaaga aaggaatggc tcgtaggggc ccgggtagaa tcgaagaatg ttgcgctggg   1260
cttcgattca cataacatgg gcctgaagct ctaaaacgag gcccggtcg ccgcgcgatg    1320
gaaagagacc ggatcctcct cgtgaattct ggaaggccac acgagagcga cccaccaccg   1380
acgcggagga gtcgtgcgtg gtccaacacg gccggcgggc tgggctgcga ccttaaccag   1440
caaggcacgc cacgacccgc cccgccctcg aggcataaat accctcccat cc            1492

SEQ ID NO: 71           moltype = DNA   length = 127
FEATURE                 Location/Qualifiers
source                  1..127
                        mol_type = other DNA
                        organism = Setaria italica
SEQUENCE: 71
cgttgccgca agactcagat cagattccga tccccagttc ttccccaatc accttgtggt   60
ctctcgtgtc gcggttccca gggacgcctc cggctcgtcg ctcgacagcg atctccgccc   120
cagcaag                                                              127

SEQ ID NO: 72           moltype = DNA   length = 1003
FEATURE                 Location/Qualifiers
source                  1..1003
                        mol_type = other DNA
                        organism = Setaria italica
SEQUENCE: 72
gtatagattc agttccttgc tccgatccca atctggttga gatgttgctc cgatgcgact   60
tgattatgtc atatatctgc ggtttgcacc gatctgaagc ctaggggttc tcgacgacc    120
cagtatttg caatttgcga tttgctcgtt tgttgcgcag cgtagtttat gtttggagta   180
atcgaggatt tgtatgcggc gtcggcgcta cctgcttaat cacgccatgt gacgcggtta   240
cttgcagagg ctgggttctg ttatgtcgtg atctaagaat ctagattagg ctcagtcgtt   300
cttgctgtcg actagtttgt tttgatatcc atgtagtaca agttacttaa aatttaggtc   360
caatatattt tgcatgcttt tggcctgtta ttcttgccaa caagttgtcc tggtaaaaag   420
tagatgtgaa agtcacgtat tgggacaaat tgatggttta gtgctatagt tctatagttc   480
tgtgatacat ctatctgatt ttttttggtc tattggtgcc taacttatct gaaaatcatg   540
gaacatgagg ctagtttgat catggtttag ttcattgtga ttaataatgt atgatttagt   600
agctattttg gtgatcgtgt catttttattt gtgaatggaa tcattgtatg taaatgaagc   660
tagttcaggg gttacgatgt agctggcttt gtattctaaa gctgctatt attcatccat    720
cgatttcacc tatatgtaat ccagagcttt tgatgtgaaa tttgtctgat ccttcactag   780
gaaggacaga acattgttaa tattttggca catctgtctt attctcatcc tttgtttgaa   840
catgttagcc tgttcaaaca gatactgttg taatgtccta gttatatagg tacatatgtg   900
ttctctattg agtttatgga cttttgtgtg tgaagttata tttcattttg ctcaaaactc    960
atgtttgcaa gctttctgac attattctat tgttctgaaa cag                      1003
```

| SEQ ID NO: 73 | moltype = DNA  length = 2622 |
| --- | --- |
| FEATURE | Location/Qualifiers |
| source | 1..2622 |
| | mol_type = other DNA |
| | organism = Setaria italica |

SEQUENCE: 73

```
actgccgcga cacgcctcac tggcgggagg gctccgagcg ctctctcccc ggcggccggc   60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcggc acaccagcgt ctaagtgaac  240
ttccgctaac cttccggtca ttgcgcctga aagatgtcat gtggcgaggc cccctctca   300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagcatgc cgtttttgaa gtatccagga  480
ttagaagctt ctactgcgct tttatattat agctgtggac ccgtggtaac ctttctcttt  540
tggcgcttgc ttaatctcgg ccgtgctggt ccatgcttag gcactaggca gagatagagc  600
cggggtgaa tggggctaaa gctcagctgc tcgaggggcc gtgggctggt ttccactagc   660
ctacagctgt gccacgtgcg gccgcgcaag ccgaagcaag cacgctgagc cgttggacag  720
cttgtcataa tgccattacg tggattacac gtaactggcc ctgtaactac tcgttcggcc  780
atcatcaaac gacgacgtcc gctaggcgac gacacgggta atgcacgcag ccacccaggc  840
gcgcgcgcta gcggagcacg gtcaggtgac acgggcgtcg tgacgcttcc gagttgaagg  900
ggttaacgcc agaaacagtg tttggccagg gtatgaacat aacaaaaaat attcacacga  960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaaccgt  1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga ccaccaccg  1380
acgcggagga gtcgtgcgtg gtccaacacg gccggcgggc tgggctgcga ccttaaccag 1440
caaggcacgc cacgacccgc cccgccctcg aggcataaat accctcccat cccgttgccg 1500
caagactcag atcagattcc gatcccagt tcttccccaa tcaccttgtg gtctctcgtg  1560
tcgcggttcc cagggacgcc tccggctcgt cgctcagcac cgatctccgc cccagcaagg 1620
tatagattca gttccttgct ccgatcccaa tctggttgag atgttgctcc gatgcgactt 1680
gattatgtca tatatctgcg gtttgcaccg atctgaagcc tagggtttct cgagcgaccc 1740
agttatttgc aatttgcgat ttgctcgttt gttgcgcagc gtagtttatg tttggagtaa 1800
tcgaggattt gtatgcggcg tcggcgctac ctgcttaatc acgccatgtg acgcggttac 1860
ttgcagaggc tgggttctgt tatgtcgtga tctaagaatc tagattaggc tcagtcgttc 1920
ttgctgtcga ctagtttgtt ttgatatcca tgtagtacaa gttacttaaa atttaggtcc 1980
aatatatttt gcatgctttt ggcctgttat tcttgccaac aagttgtcct ggtaaaaagt 2040
agatgtgaaa gtcacgtatt gggacaaatt gatggtttag tgctataagtt ctatagttct 2100
gtgatacatc tatctgattt tttttggtct attggtgcct aacttatctg aaaatcatgg 2160
aacatgaggc tagtttgatc atggtttagt tcattgtgat taataatgta tgatttagta  2220
gctatttgg tgatcgtgtc attttatttg tgaatggaat cattgtatgt aaatgaagct  2280
agttcagggg ttacgatgta gctggctttg tattctaaag gctgctatta ttcatccatc  2340
gatttcacct atatgtaatc cagagctttt gatgtgaaat ttgtctgatc cttcactagg  2400
aaggacagaa cattgttaat attttggcac atctgtctta ttctcatcct ttgttgaac   2460
atgttagcct gttcaaacag atactgttgt aatgtcctag ttataggt acatatgtgt    2520
tctctattga gtttatggac ttttgtgtgt gaagttatat ttcattttgc tcaaaactca  2580
tgtttgcaag ctttctgaca ttattctatt gttctgaaac ag                     2622
```

| SEQ ID NO: 74 | moltype = DNA  length = 1492 |
| --- | --- |
| FEATURE | Location/Qualifiers |
| source | 1..1492 |
| | mol_type = other DNA |
| | organism = Setaria italica |

SEQUENCE: 74

```
actgccgcga cacgcctcac tggcgggagg gctccgagcg ctctctcccc ggcggccggc   60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcggc acaccagcgt ctaagtgaac  240
ttccgctaac cttccggtca ttgcgcctga aagatgtcat gtggcgaggc cccctctca   300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagcatgc cgtttttgaa gtatccagga  480
ttagaagctt ctactgcgct tttatattat agctgtggac ccgtggtaac ctttctcttt  540
tggcgcttgc ttaatctcgg ccgtgctggt ccatgcttag gcactaggca gagatagagc  600
cggggtgaa tggggctaaa gctcagctgc tcgaggggcc gtgggctggt ttccactagc   660
ctacagctgt gccacgtgcg gccgcgcaag ccgaagcaag cacgctgagc cgttggacag  720
cttgtcataa tgccattacg tggattacac gtaactggcc ctgtaactac tcgttcggcc  780
atcatcaaac gacgacgtcc gctaggcgac gacacgggta atgcacgcag ccacccaggc  840
gcgcgcgcta gcggagcacg gtcaggtgac acgggcgtcg tgacgcttcc gagttgaagg  900
ggttaacgcc agaaacagtg tttggccagg gtatgaacat aacaaaaaat attcacacga  960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaaccgt  1200
tggcggaaga aaggaatggc tcgtaggggc ccgggtagaa tcgaagaatg ttgcgctggg 1260
```

```
cttcgattca cataacatgg gcctgaagct ctaaaacgac ggcccggtcg ccgcgcgatg   1320
gaaagagacc ggatcctcct cgtgaattct ggaaggccac acgagagcga cccaccaccg   1380
acgcggagga gtcgtgcgtg gtccaacacg gccggcgggc tgggctgcga ccttaaccag   1440
caaggcacgc cacgacccgc cccgccctcg aggcataaat accctcccat cc           1492

SEQ ID NO: 75              moltype = DNA   length = 2164
FEATURE                    Location/Qualifiers
source                     1..2164
                           mol_type = other DNA
                           organism = Setaria italica
SEQUENCE: 75
gccgttttttg aagtatccag gattagaagc ttctactgcg cttttatatt atagctgtgg   60
acctgtggta acctttctct tttggcgctt gcttaatctc ggccgtgctg gtccatgctt   120
aggcactagg cagagataga gccggggggtg aatgggggcta aagctcagct gctcgagggg   180
ccgtgggctg gtttccacta gcctacagct gtgccacgtg cggccgcgca agccgaagca   240
agcacgctga gccgttggac agcttgtcat aatgccatta cgtggattac acgtaactgg   300
ccctgtaact actcgttcgg ccatcatcaa acgacgacgt ccgctaggcg acgacacggg   360
taatgcacgc agccacccag gcgcgcgcgc tagcggagca cggtcaggtg acacgggcgt   420
cgtgacgctt ccgagttgaa ggggttaacg ccagaaacag tgtttggcca gggtatgaac   480
ataacaaaaa atattcacac gaaagaatgg aagtatggag ctgctactgt gtaaatgcca   540
agcaggaaac tcacgcccgc taacatccaa cggccaacag ctcgacgtgc cggtcagcag   600
agcatcggaa cactggtgat tggtggagcc ggcagtatgc gccccagcac ggccgaggtg   660
gtggtggccc gtggccctgc tgtctgcgcg gctcgggaca acttgaaact gggccaccgc   720
ctcgtcgcaa ctcgcaaccc gttggcggaa gaaaggaatg gctcgtaggg gcccgggtag   780
aatcgaagaa tgttgcgctg ggcttcgatt cacataacat gggcctgaag ctctaaaacg   840
acggcccggt cgccgcgcga tggaaagaga ccggatcctc ctcgtgaatt ctggaaggcc   900
acacgagagc gacccaccac cgacgcggag gagtcgtgcg tggtccaaca cggccggcgg   960
gctgggctgc gaccttaacc agcaaggcac gccacgaccc gccccgccct cgaggcataa   1020
ataccctccc atcccgttgc cgcaagactc agatcagatt ccgatcccca gttcttcccc   1080
aatcaccttg tggtctctcg tgtcgcggtt cccagggacg cctccggctc gtcgctcgac   1140
agcgatctcc gccccagcaa ggtatagatt cagttccttg ctccgatccc aatctggttg   1200
agatgttgct ccgatcgcgac ttgattatgt catatatctg cggtttgcac cgatctgaag   1260
cctaggggttta ctcgagcgac ccagttattt gcaatttgcg atttgctcgt tgttgcgca   1320
gcgtagttta tgtttggagt aatcgaggat ttgtatgcgg cgtcggcgct acctgcttaa   1380
tcacgccata tgacgcggtt acttgcagag gctgggtct gttatgtcgt gatctaagaa   1440
tctagattag gctcagtcgt tcttgctgtc gactagtttg ttttgatatc catgtagtac   1500
aagttactta aaatttaggt ccaatatatt ttgcatgctt ttggcctgtt attcttgcca   1560
acaagttgtc ctggtaaaaa gtagatgtga aagtcacgta ttgggacaaa ttgatggttt   1620
agtgctatag ttctatagtt ctgtgataca tctatctgat ttttttttggt ctattggtgc   1680
ctaacttatc tgaaaatcat ggaacatgag gctagtttga tcatggttta gttcattgtg   1740
attaataatg tatgatttag tagctatttt ggtgatcgtg tcatttattt tgtgaatgga   1800
atcattgtat gtaaatgaag ctagttcagg ggttacgatg tagctggctt tgtattctaa   1860
aggctgctat tattcatcca tcgatttcac ctatatgtaa tccagagctt ttgatgtgaa   1920
atttgtctga tccttcacta ggaaggacag aacattgtta atattttggc acatctgtct   1980
tattctcatc ctttgtttga acatgttagc ctgttcaaac agatactgtt gtaatgtcct   2040
agttatatag gtacatatgt gttctctatt gagtttatgg acttttgtgt gtgaagttat   2100
atttcatttt gctcaaaact catgtttgca agctttctga cattattcta ttgttctgaa   2160
acag                                                               2164

SEQ ID NO: 76              moltype = DNA   length = 1034
FEATURE                    Location/Qualifiers
source                     1..1034
                           mol_type = other DNA
                           organism = Setaria italica
SEQUENCE: 76
gccgttttttg aagtatccag gattagaagc ttctactgcg cttttatatt atagctgtgg   60
acctgtggta acctttctct tttggcgctt gcttaatctc ggccgtgctg gtccatgctt   120
aggcactagg cagagataga gccggggggtg aatgggggcta aagctcagct gctcgagggg   180
ccgtgggctg gtttccacta gcctacagct gtgccacgtg cggccgcgca agccgaagca   240
agcacgctga gccgttggac agcttgtcat aatgccatta cgtggattac acgtaactgg   300
ccctgtaact actcgttcgg ccatcatcaa acgacgacgt ccgctaggcg acgacacggg   360
taatgcacgc agccacccag gcgcgcgcgc tagcggagca cggtcaggtg acacgggcgt   420
cgtgacgctt ccgagttgaa ggggttaacg ccagaaacag tgtttggcca gggtatgaac   480
ataacaaaaa atattcacac gaaagaatgg aagtatggag ctgctactgt gtaaatgcca   540
agcaggaaac tcacgcccgc taacatccaa cggccaacag ctcgacgtgc cggtcagcag   600
agcatcggaa cactggtgat tggtggagcc ggcagtatgc gccccagcac ggccgaggtg   660
gtggtggccc gtggccctgc tgtctgcgcg gctcgggaca acttgaaact gggccaccgc   720
ctcgtcgcaa ctcgcaaccc gttggcggaa gaaaggaatg gctcgtaggg gcccgggtag   780
aatcgaagaa tgttgcgctg ggcttcgatt cacataacat gggcctgaag ctctaaaacg   840
acggcccggt cgccgcgcga tggaaagaga ccggatcctc ctcgtgaatt ctggaaggcc   900
acacgagagc gacccaccac cgacgcggag gagtcgtgcg tggtccaaca cggccggcgg   960
gctgggctgc gaccttaacc agcaaggcac gccacgaccc gccccgccct cgaggcataa   1020
ataccctccc atcc                                                    1034

SEQ ID NO: 77              moltype = DNA   length = 1810
FEATURE                    Location/Qualifiers
source                     1..1810
                           mol_type = other DNA
                           organism = Setaria italica
```

```
SEQUENCE: 77
cacgggtaat gcacgcagcc acccaggcgc gcgcgctagc ggagcacggt caggtgacac    60
gggcgtcgtg acgcttccga gttgaagggg ttaacgccag aaacagtgtt tggccagggt   120
atgaacataa caaaaaatat tcacacgaaa gaatggaagt atggagctgc tactgtgtaa   180
atgccaagca ggaaactcac gcccgctaac atccaacggc caacagctcg acgtgccggt   240
cagcagagca tcggaacact ggtgattggt ggagccggca gtatgcgccc agcacggcc    300
gaggtggtgg tggcccgtgg ccctgctgtc tgccgcggctc gggacaactt gaaactgggc   360
caccgcctcg tcgcaactcg caacccgttg gcggaagaaa ggaatggctc gtaggggccc   420
gggtagaatc gaagaatgtt gcgctgggct tcgattcaca taacatgggc ctgaagctct   480
aaaacgacgg cccggtcgcc gcgcgatgga aagagaccgg atcctcctcg tgaattctga   540
aaggccacac gagagcgacc caccaccgac gcggaggagt cgtgcgtggt ccaacacggc   600
cggcgggctg ggctgcgacc ttaaccagca aggcacgcca cgacccgccc cgccctcgag   660
gcataaatac cctcccatcc cgttgccgca agactcagat cagattccga tccccagttc   720
ttccccaatc accttgtggt ctctcgtgtc gcggttccca gggacgcctc cggctcgtgc   780
ctcgacagcg atctccgccc cagcaaggta tagattcagt tccttgctcc gatcccaatc   840
tggttgagat gttgctccga tgcgacttga ttatgtcata tatctgcggt ttgcaccgat   900
ctgaagccta gggtttctcg agcgaccccag ttatttgcaa tttgcgattt gctcgtttgt   960
tgcgcagcgt agtttatgtt tggagtaatc gaggatttgt atgcggcgtc ggcgctacct  1020
gcttaatcac gccatgtgac gcggttactt gcagaggctg ggttctgtta tgtcgtgatc  1080
taagaatcta gattaggctc agtcgttctt gctgtcgact agtttgtttt gatatccatg  1140
tagtacaagt tacttaaaat ttaggtccaa tatatttttgc atgcttttgg cctgttattc  1200
ttgccaacaa gttgtcctgg taaaaagtag atgtgaaagt cacgtattgg gacaaattga  1260
tggtttagtg ctatagttct atagttctgt gatacatcta tctgattttt tttggtctat  1320
tggtgcctaa cttatctgaa aatcatggaa catgaggcta gtttgatcat ggtttagttc  1380
attgtgatta ataatgtatg atttagtagc tattttggtg atcgtgtcat tttatttgtg  1440
aatggaatca ttgtatgtaa atgaagctag tttcagggtt acgatgtgagc tggcttttga  1500
ttctaaaggc tgctattatt catccatcga tttcacctat atgtaatcca gagcttttga  1560
tgtgaaattt gtctgatcct tcactaggaa ggacagaaca ttgttaatat tttggcacat  1620
ctgtcttatt ctcatccttt gtttgaacat gttagcctgt tcaaacagat actgttgtaa  1680
tgtcctagtt atataggtac atatgtgttc tctattgagt ttatgactt ttgtgtgtga  1740
agttatattt cattttgctc aaaactcatg tttgcaagct ttctgacatt attctattgt  1800
tctgaaacag                                                         1810

SEQ ID NO: 78          moltype = DNA   length = 680
FEATURE                Location/Qualifiers
source                 1..680
                       mol_type = other DNA
                       organism = Setaria italica
SEQUENCE: 78
cacgggtaat gcacgcagcc acccaggcgc gcgcgctagc ggagcacggt caggtgacac    60
gggcgtcgtg acgcttccga gttgaagggg ttaacgccag aaacagtgtt tggccagggt   120
atgaacataa caaaaaatat tcacacgaaa gaatggaagt atggagctgc tactgtgtaa   180
atgccaagca ggaaactcac gcccgctaac atccaacggc caacagctcg acgtgccggt   240
cagcagagca tcggaacact ggtgattggt ggagccggca gtatgcgccc agcacggcc    300
gaggtggtgg tggcccgtgg ccctgctgtc tgccgcggctc gggacaactt gaaactgggc   360
caccgcctcg tcgcaactcg caacccgttg gcggaagaaa ggaatggctc gtaggggccc   420
gggtagaatc gaagaatgtt gcgctgggct tcgattcaca taacatgggc ctgaagctct   480
aaaacgacgg cccggtcgcc gcgcgatgga aagagaccgg atcctcctcg tgaattctga   540
aaggccacac gagagcgacc caccaccgac gcggaggagt cgtgcgtggt ccaacacggc   600
cggcgggctg ggctgcgacc ttaaccagca aggcacgcca cgacccgccc cgccctcgag   660
gcataaatac cctcccatcc                                               680

SEQ ID NO: 79          moltype = DNA   length = 1940
FEATURE                Location/Qualifiers
source                 1..1940
                       mol_type = other DNA
                       organism = Coix lacryma-jobi
SEQUENCE: 79
agcagactcg cattatcgat ggagctctac caaactggcc ctaggcatta acctaccatg    60
gatcacatcg taaaaaaaaa accctaccat ggatcctatc tgttttcttt ttgccctgaa   120
agagtgaagt catcatcata tttaccatgg cgcgcgtagg agcgcttcgt cgaagaccca   180
tagggggggcg gtactcgcac cgtggttgtt tcctgttatg taatatcgga tggggggagca   240
gtcggctagg ttggtcccat cggtactggt cgtcccctag tgcgctagat gcgcgatgtt   300
tgtcctcaaa aactctttc ttcttaataa caatcatacg caaattttt gcgtattcga   360
gaaaaaaga agattctatc tgtttttttt ttgaaatggc tccaatttat aggaggagc   420
cgtttaacgg cgtcgacaaa tctaacggac accaaccagc gaatgagcga acccaccagc   480
gccaagctag ccaagcgaag cagacggccg agacgctgac accccttgcct tggcgcggca   540
tctccgtcgc tggctcgctg gctctggccc cttcgcgaga gttccggtcc acctccacct   600
gtgtcggttt ccaactccgt tccgccttcg cgtgggactt gttccgttca tccgttgcgg   660
gcatccggaa attgcgtggc gtagagcacg ggggcctcct ctcacacggc acggaaccgt   720
cacgagctca cggcacggcc agcacggcgg ggattccttc cccaccaccg ctccttccct   780
ttcccttcct cgcccgccat cataaatagc cacccctccc agcttccttc gccacatcct   840
ctcatcatct tctctcgtgt agcacgcgca gcccgatccc caatccctc tcctcgcgag   900
cctcgtcgat ccctcgcttc aaggtatggc tctctctctc tctttacctt   960
atctagatcg gcgatccatg gttagggcct gctagttctc cgttcgtgtt tgtcgatggc  1020
tgtgaggcac aatagatccg tcggcgttat gatggttagc ctgtcatgct cttgcgatct  1080
gtggttcctt taggaaaggc attaatttaa tccctgatgg ttcagatcg gtgatccatg  1140
gttagtaccc taagctgtgg agtcgggttt agatccgcgc tgttcgtagg cgatctgttc  1200
tgattgttaa cttgtcagta cctgcgaatc ctcggtggtt ctagctggtt cggagatcag  1260
```

```
atcgattcca ttatctgcta tacatcttgt ttcgttgcct aggctccgtt taatctatcc    1320
atcgtatgat gttagccttt gatatgattc gatcgtgcta gctatgtcct gtggacttaa    1380
ttgtcaggtc ctaatttta  ggaagactgt tccaaaccat ctgctggatt tattaaattt    1440
ggatctggat gtgtcacata caccttcata attaaaatgg atggaaatat ctcttatctt    1500
ttagatatgg ataggcattt atatgatgct gtgagtttta ctagtacttt cttagaaatat   1560
atgtactttt ttagacggaa tattgatatg tatacatgtg tagatacatg aagcaacatg    1620
ctgctgtagt ctaataattc ctgttcatct aataatcaag tatgtatatg ttctgtgtgt    1680
tttattggta tttgattaga tatatacatg cttagataca tacatgaagc agcatgctgc    1740
tacagtttaa tcattattgt ttatccaata aacaaacatg cttttttaatt tatcttgata   1800
tgcttggatg acggaatatg cagagatttt aagtacccag catcatgagc atgcatgacc    1860
ctgcgttagt atgctgttta tttgcttgag actctttctt ttgtagatac tcaccctgtt    1920
ttctggtgat cctactgcag                                                1940

SEQ ID NO: 80          moltype = DNA   length = 837
FEATURE                Location/Qualifiers
source                 1..837
                       mol_type = other DNA
                       organism = Coix lacryma-jobi
SEQUENCE: 80
agcagactcg cattatcgat ggagctctac caaactggcc ctaggcatta acctaccatg     60
gatcacatcg taaaaaaaaa accctaccat ggatcctatc tgttttcttt ttgccctgaa    120
agagtgaagt catcatcata tttaccatgg cgcgcgtagg agcgcttcgt cgaagaccca    180
tagggggggcg gtactcgcac cgtggttgtt tcctgttatg taatatcgga tgggggagca   240
gtcggctagg ttggtcccat cggtactggt cgtcccctag tgcgctagat gcgcgatgtt    300
tgtcctcaaa aactctttc  ttcttaataa caatcatacg caaatttttt gcgtattcga    360
gaaaaaaaga agattctatc tgtttttttt ttgaaatggc tccaatttat aggaggagcc    420
cgtttaacgg cgtcgacaaa tctaacggac accaaccagc gaatgagcga acccaccagc    480
gccaagctag ccaagcgaag cagacggccg agacgctgac acccttgcct tggcgcggca    540
tctccgtcgc tggctcgctg gctctggccc cttcgcgaga gttccggtcc acctccacct    600
gtgtcggttt ccaactccgt tccgccttcg cgtgggactt gttccgttca tccgttggcg    660
gcatccggaa attgcgtggc gtagagcacg gggccctcct ctcacacggc acggaaccgt    720
cacgagctca cggcaccggc agcacggcgg ggattccttc cccaccaccg ctccttccct    780
ttcccttcct cgcccgccat cataaatagc cacccctccc agcttccttc gccacat       837

SEQ ID NO: 81          moltype = DNA   length = 86
FEATURE                Location/Qualifiers
source                 1..86
                       mol_type = other DNA
                       organism = Coix lacryma-jobi
SEQUENCE: 81
cctctcatca tcttctctcg tgtagcacgc gcagcccgat ccccaatccc ctctcctcgc     60
gagcctcgtc gatccctcgc ttcaag                                          86

SEQ ID NO: 82          moltype = DNA   length = 1017
FEATURE                Location/Qualifiers
source                 1..1017
                       mol_type = other DNA
                       organism = Coix lacryma-jobi
SEQUENCE: 82
gtatggctat cgtccttcct ctctctctct ttacccttatc tagatcggcg atccatggtt     60
agggcctgct agttctccgt tcgtgtttgt cgatggctgt gaggcacaat agatccgtcg    120
gcgttatgat ggttagcctg tcatgctctt gcgatctgtg gttcctttag gaaaggcatt    180
aatttaatcc ctgatggttc gagatcggtg atccatggtt agtacccgtaa gctgtggagt   240
cgggtttaga tccgcgctgt tcgtaggcga tctgttctga ttgttaactt gtcagtacct    300
gcgaatcctc ggtggttcta gctggttcgg agatcagatc gattccatta tctgctatac    360
atcttgtttc gttgcctagg ctccgtttaa tctatccatc gtatgatgtt agcctttgat    420
atgattcgat cgtgctagct atgtcctgtg gacttaattg tcaggtccta attttaggaa    480
agactgttcc aaaccatctg ctggatttat taaatttgga tctggatgtg tcacatacac    540
cttcataatt aaaatggatg gaaatatctc ttatcttta  gatatggata ggcatttata    600
tgatgctgtg agttttacta gtactttctt agaatatatg tacttttta  gacggaatat    660
tgatatgtat acatgtgtag acatgaag   caacatgctg ctgtagtcta ataattcctg    720
ttcatctaat aatcaagtat gtatatgttc tgtgtgtttt attggtattt gattagatat    780
atacatgctt agatacatac atgaagcagc atgctgctac agtttaatca ttattgttta    840
tccaataaac aaacatgctt tttaattat  cttgatatgc ttggatgacg gaatatgcag    900
agattttaag tacccagcat catgagcatg catgaccctg cgttagtatg ctgtttatttt   960
gcttgagact ctttcttttg tagatactca ccctgttttc tggtgatcct actgcag      1017

SEQ ID NO: 83          moltype = DNA   length = 1845
FEATURE                Location/Qualifiers
source                 1..1845
                       mol_type = other DNA
                       organism = Coix lacryma-jobi
SEQUENCE: 83
ctatctgttt tcttttttgcc ctgaaagagt gaagtcatca tcatatttac catggcgcgc    60
gtaggagcgc ttcgtcgaag acccataggg gggcggtact cgcaccgtgg ttgtttcctg   120
ttatgtaata tcggatgggg gagcagtcgg ctaggttggt cccatcggta ctggtcgtcc   180
cctagtgcgc tagatgcgcg atgtttgtcc tcaaaaactc ttttcttctt aataacaatc   240
atacgcaaat ttttgcgta  ttcgagaaaa aaagaagatt ctatctgttt tttttttgaa   300
atggctccaa tttataggag gagcccgttt aacggcgtcg acaaatctaa cggacaccaa   360
```

```
ccagcgaatg agcgaaccca ccagcgccaa gctagccaag cgaagcagac ggccgagacg    420
ctgacaccct tgccttggcg cggcatctcc gtcgctggct cgctggctct ggccccttcg    480
cgagagttcc ggtccacctc cacctgtgtc ggtttccaac tccgttccgc cttcgcgtgg    540
gacttgttcc gttcatccgt tggcggcatc cggaaattgc gtggcgtaga gcacggggcc    600
ctcctctcac acggcacgga accgtcacga gctcacggca ccggcagcac ggcggggatt    660
ccttccccac caccgctcct tccctttccc ttcctcgccc gccatcataa atagccaccc    720
ctcccagctt ccttcgccac atcctctcat catcttctct cgtgtagcac gcgcagcccg    780
atccccaatc ccctctcctc gcgagcctcg tcgatccctc gcttcaaggt atggctatcg    840
tccttcctct ctctctcttt accttatcta gatcggcgat ccatggttag ggcctgctag    900
ttctccgttc gtgtttgtcg atggctgtga ggcacaatag atccgtcggc gttatgatgg    960
ttagcctgtc atgctcttgc gatctgtggt tcctttagga aaggcattaa tttaatccct   1020
gatggttcga gatcggtgat ccatggttag taccctaagc tgtggagtcg ggtttagatc   1080
cgcgctgttc gtaggcgatc tgttctgatt gttaacttgt cagtacctgc gaatcctcgg   1140
tggttctagc tggttcggag atcagatcga ttccattatc tgctatacat cttgtttcgt   1200
tgcctaggct ccgtttaatc tatccatcgt atgatgttag cctttgatat gattcgatcg   1260
tgctagctat gtcctgtgga cttaattgtc aggtcctaat ttttaggaag actgttccaa   1320
accatctgct ggatttatta aatttggatc tggatgtgtc acatacacct tcataattaa   1380
aatggatgga aatatctctt atcttttaga tatggataggg catttatatg atgctgtgag   1440
ttttactagt actttcttag aatatatgta cttttttaga cggaatattg atatgtatac   1500
atgtgtagat acatgaagca acatgctgct gtagtctaat aattcctgtt catctaataa   1560
tcaagtatgt atatgttctg tgtgttttat tggtatttga ttagatatat acatgcttag   1620
atacatacat gaagcagcat gctgctacag tttaatcatt attgtttatc caataaacaa   1680
acatgctttt taatttatct tgatatgctt ggatgacgaa atatgcagag attttaagta   1740
cccagcatca tgagcatgca tgaccctgcg ttagtatgct gtttatttgc ttgagactct   1800
ttcttttgta gatactcacc ctgttttctg gtgatcctac tgcag                   1845

SEQ ID NO: 84           moltype = DNA  length = 742
FEATURE                 Location/Qualifiers
source                  1..742
                        mol_type = other DNA
                        organism = Coix lacryma-jobi
SEQUENCE: 84
ctatctgttt tcttttgcc ctgaaagagt gaagtcatca tcatatttac catggcgcgc     60
gtaggagcgc ttcgtcgaag acccataggg gggcggtact cgcaccgtgg ttgtttcctg    120
ttatgtaata tcggatgggg gagcagtcgg ctaggttggt cccatccgta ctgtgtcgtc    180
cctagtgcgc tagatgcgcg atgtttgtcc tcaaaaactc ttttcttctt aataacaatc    240
atacgcaaat tttttgcgta ttcgagaaaa aagaagatt ctatctgttt ttttttgaa     300
atggctccaa tttataggag gagcccgttt aacggcgtcg acaaatctaa cggacaccaa    360
ccagcgaatg agcgaaccca ccagcgccaa gctagccaag cgaagcagac ggccgagacg    420
ctgacaccct tgccttggcg cggcatctcc gtcgctggct cgctggctct ggccccttcg    480
cgagagttcc ggtccacctc cacctgtgtc ggtttccaac tccgttccgc cttcgcgtgg    540
gacttgttcc gttcatccgt tggcggcatc cggaaattgc gtggcgtaga gcacggggcc    600
ctcctctcac acggcacgga accgtcacga gctcacggca ccggcagcac ggcggggatt    660
ccttccccac caccgctcct tccctttccc ttcctcgccc gccatcataa atagccaccc    720
ctcccagctt ccttcgccac at                                             742

SEQ ID NO: 85           moltype = DNA  length = 1504
FEATURE                 Location/Qualifiers
source                  1..1504
                        mol_type = other DNA
                        organism = Coix lacryma-jobi
SEQUENCE: 85
caaatctaac ggacaccaac cagcgaatga gcgaacccac cagcgccaag ctagccaagc     60
gaagcagacg gccgagacgc tgacaccctt gccttggcgc ggcatctccg tcgctggctc    120
gctggctctg gccccttcgc gagagttccg gtccacctcc acctgtgtcg gtttccaact    180
ccgttccgcc ttcgcgtggg acttgttccg ttcatccgtt ggcggcatcc ggaaattgcg    240
tggcgtagag cacggggccc tcctctcaca cggcacggaa ccgtcacgag ctcacggcac    300
cggcagcacg gcggggattc cttccccacc accgctcctt ccctttccct tcctcgcccg    360
ccatcataaa tagccacccc tcccagcttc cttcgccaca tcctctcatc atcttctctc    420
gtgtagcacg cgcagcccga tccccaatcc cctctcctcg cgagcctcgt cgatccctcg    480
cttcaaggta tggctatcgt ccttcctctc tctctcttta ccttatctag atcggcgatc    540
catggttagg gcctgctagt tctccgttcg tgtttgtcga tggctgtgag gcacaataga    600
tccgtcggcg ttatgatggt tagcctgtca tgctcttgcg atctgtggtt cctttaggaa    660
aggcattaat ttaatccctg atggttcgag atcggtgatc catggttagt accctaagct    720
gtggagtcgg gtttagatcc gcgctgttcg taggcgatct gttctgattg ttaacttgtc    780
agtacctgcg aatcctcggt ggttctagct ggttcggaga tcagatcgat tccattatct    840
gctatacatc ttgtttcgtt gcctaggctc cgtttaatct atccatcgta tgatgttagc    900
ctttgatatg attcgatcgt gctagctatg tcctgtggac ttaattgtca ggtcctaatt    960
tttaggaaga ctgttccaaa ccatctgctg gatttattaa atttggatct ggatgtgtca   1020
catacacctt cataattaaa atggatggaa atatctctta tcttttagat atggataggg   1080
atttatatga tgctgtgagt tttactagta ctttcttaga atatatgtac ttttttagac   1140
ggaatattga tatgtataca tgtgtagata catgaagcaa catgctgctg tagtctaata   1200
attcctgttc atctaataat caagtatgta tatgttctgt gtgttttatt ggtatttgat   1260
tagatatata catgcttaga tacatacatg aagcagcatg ctgctacagt ttaatcatta   1320
ttgtttatcc aataaacaaa catgctttt aatttatctt gatatgcttg gatgacgaa    1380
tatgcagaga ttttaagtac ccagcatcat gagcatgcat gaccctgcgt tagtatgctg   1440
tttatttgct tgagactctt tcttttgtag atactcaccc tgttttctgg tgatcctact   1500
gcag                                                                1504
```

| SEQ ID NO: 86 | moltype = DNA   length = 401 |
|---|---|
| FEATURE | Location/Qualifiers |
| source | 1..401 |
| | mol_type = other DNA |
| | organism = Coix lacryma-jobi |

SEQUENCE: 86

| | | | | | | |
|---|---|---|---|---|---|---|
| caaatctaac | ggacaccaac | cagcgaatga | gcgaacccac | cagcgccaag | ctagccaagc | 60 |
| gaagcagacg | gccgagacgc | tgacacccct | gccttggcgc | ggcatctccg | tcgctggctc | 120 |
| gctggctctg | gccccttcgc | gagagttccg | gtccacctcc | acctgtgtcg | gtttccaact | 180 |
| ccgttccgcc | ttcgcgtggg | acttgttccg | ttcatccgtt | ggcggcatcc | ggaaattgcg | 240 |
| tggcgtagag | cacggggccc | tcctctcaca | cggcacggaa | ccgtcacgag | ctcacggcac | 300 |
| cggcagcacg | gcggggattc | cttccccacc | accgctcctt | ccctttccct | tcctcgcccg | 360 |
| ccatcataaa | tagccacccc | tcccagcttc | cttcgccaca | t | | 401 |

| SEQ ID NO: 87 | moltype = DNA   length = 1157 |
|---|---|
| FEATURE | Location/Qualifiers |
| source | 1..1157 |
| | mol_type = other DNA |
| | organism = Coix lacryma-jobi |

SEQUENCE: 87

| | | | | | | |
|---|---|---|---|---|---|---|
| ccttcctcgc | ccgccatcat | aaatagccac | ccctcccagc | ttccttcgcc | acatcctctc | 60 |
| atcatcttct | ctcgtgtagc | acgcgcagcc | cgatccccaa | tcccctctcc | tcgcgagcct | 120 |
| cgtcgatccc | tcgcttcaag | gtatggctat | cgtcctccct | ctctctctct | ttaccttatc | 180 |
| tagatcggcg | atccatggtt | agggcctgct | agttctccgt | tcgtgtttgt | cgatggctgt | 240 |
| gaggcacaat | agatccgtcg | gcgttatgat | ggttagcctg | tcatgctctt | gcgatctgtg | 300 |
| gttcctttag | gaaaggcatt | aatttaatcc | ctgatggttc | gagatcggtg | atccatggtt | 360 |
| agtaccctaa | gctgtggagt | cgggtttaga | tccgcgctgt | tcgtaggcga | tctgttctga | 420 |
| ttgttaactt | gtcagtacct | gcgaatcctc | ggtggttcta | gctggttcgg | agatcagatc | 480 |
| gattccatta | tctgctatac | atcttgtttc | gttgcctagg | ctccgtttaa | tctatccatc | 540 |
| gtatgatgtt | agcctttgat | gtgattcgat | cgtgctagct | atgtcctgcg | gacttaattg | 600 |
| tcaggtccta | attttaggga | agactgttcc | aaaccatctg | ctggatttat | taaatttgga | 660 |
| tctggatgtg | tcatacacac | cttcataatt | aaaatggatg | gaaatatctc | ttatctttta | 720 |
| gatatggata | ggcattttata | tgatgctgtg | agttttacta | gtactttctt | agaatatatg | 780 |
| tacttttttta | gacggaatat | tgatatgtat | acatgtgtag | atacatgaag | caacatgctg | 840 |
| ctgtagtcta | ataattcctg | ttcatctaat | aatcaagtat | gtatatgttc | tgtgtgtttt | 900 |
| attggtatttt | gattagatat | atacatgctt | agatacatac | atgaagcagc | atgctgctac | 960 |
| agtttaatca | ttattgttta | tccaataaac | aaacatgctt | tttaatttat | cttgatatgc | 1020 |
| ttggatgacg | gaatatgcag | agattttaag | tacccagcat | catgagcatg | catgaccctg | 1080 |
| cgttagtatg | ctgtttattt | gcttgagact | cttttctttg | tagatactca | ccctgttttc | 1140 |
| tggtgatcct | actgcag | | | | | 1157 |

| SEQ ID NO: 88 | moltype = DNA   length = 54 |
|---|---|
| FEATURE | Location/Qualifiers |
| source | 1..54 |
| | mol_type = other DNA |
| | organism = Coix lacryma-jobi |

SEQUENCE: 88

| | | | | |
|---|---|---|---|---|
| ccttcctcgc | ccgccatcat | aaatagccac | ccctcccagc | ttccttcgcc acat | 54 |

| SEQ ID NO: 89 | moltype = DNA   length = 798 |
|---|---|
| FEATURE | Location/Qualifiers |
| source | 1..798 |
| | mol_type = other DNA |
| | organism = Coix lacryma-jobi |

SEQUENCE: 89

| | | | | | | |
|---|---|---|---|---|---|---|
| agcagactcg | cattatcgat | ggagctctac | caaactggcc | ctaggcatta | acctaccatg | 60 |
| gatcacatcg | taaaaaaaaa | accctaccat | ggatcctatc | tgttttcttt | ttgccctgaa | 120 |
| agagtgaagt | catcatcata | tttaccatgg | cgcgcgtagg | agcgcttcgt | cgaagaccca | 180 |
| tagggggggcg | gtactcgcac | cgtggttgtt | tcctgttatg | taatatcgga | tggggggagca | 240 |
| gtcggctagg | ttggtcccat | cggtactggt | cgtcccctag | tgcgctagat | gcgcgatgt | 300 |
| tgtcctcaaa | aactcttttc | ttcttaataa | caatcatacg | caaattttt | gcgtattcga | 360 |
| gaaaaaaaga | agattctatc | tgttttttttt | ttgaaatggc | tccaatttat | aggaggagcc | 420 |
| cgtttaacgg | cgtcgacaaa | tctaacggac | accaaccagc | gaatgagcga | acccaccagc | 480 |
| gccaagctag | ccaagcgaag | cagacgccgg | agacgctgac | accttgcct | tggcgcggga | 540 |
| tctccgtcgc | tggctcgctg | gctctggccc | cttcgcgaga | gttccggtcc | acctccacct | 600 |
| gtgtcggttt | ccaactccgt | tccgcttcg | cgtgggactt | gttccgttca | tccgttggcg | 660 |
| gcatccggaa | attgcgtggc | gtagagcacg | gggccctcct | ctcacacggc | acggaaccgt | 720 |
| cacgagctca | cggcaccggc | agcacggcgg | ggattccttc | cccaccaccg | ctccttccct | 780 |
| ttcccttcct | cgcccgcc | | | | | 798 |

| SEQ ID NO: 90 | moltype = DNA   length = 3393 |
|---|---|
| FEATURE | Location/Qualifiers |
| source | 1..3393 |
| | mol_type = other DNA |
| | organism = Coix lacryma-jobi |

SEQUENCE: 90

| | | | | | | |
|---|---|---|---|---|---|---|
| ggttctatac | aacaccacac | actgtgtgag | tgtgtgacca | gtggccaact | tttgttcagt | 60 |
| tcaacgatcc | tggcctttcc | gggcacccaa | tacactaatt | aatctattgc | agctaacctc | 120 |
| aaaagaaatg | catttgcagt | tgtctgtcct | aatcaatcta | ctagcagact | cacattattg | 180 |

```
atgtaggaaa taaaattcag cctgtgacgt ggatgcaaca actgcactgc acaggatacc   240
atcttagccg ttgtgtcaca atttgctttg ctaatgtttt gagaaaccca gctttgacaa   300
acgtaagatc gatgagggcc ttacgtttgg cacaatatgt attgtaatcc ggcacggcaa   360
gttagactcg gtagtgttta gccggcatct ttatgtttgg cacaatttaa tttaattcgg   420
catggtaggt tagactgcag cgtgagccgg tcattgcaag ttattatgac atgttagagc   480
atctccaaca agttggaaaa aatgacttgg tatatcatgg tatatcatga gttttagcaa   540
cttattaatt catttgacaa gtaaaaaaaa gatccctctt caacaatttg ctattccaac   600
tcgctaaaat aaaaaaaaat taggctcacc taggccgatc tgcgttgccg cgggagagga   660
gggtaaaaga ttttgcgcta ggagaggtgg aggaacaggg cgcgggagcc ggccacggtg   720
aaatcacggg atagcaacct cacccgcgcg cgcaaattta cgcgtgtggc atggaggaat   780
agaaagttgg aaaagatagc aagttcattt agggagttgt tggagaagaa tatttgtgct   840
tttaccaaat ttataagaat agcaagtgag aatagagagt tgttggagat gctcaacaaa   900
tatacacaat aaagtggtat aataagcggc aagttattat gacatatata agagcaagta   960
tacaataagg tgaactgtta tatcgatcga ttttttttg agcacatatc gatcgaattt   1020
attgtaagat agaaaagaga agatataaaa acttatagtg atgaacaata ataatataaa   1080
gattattttt aaactatgaa aacaataacc gaactactcg ctctcttcta attagtaaag   1140
taaaggcttc tcattgtata tatataaaaa aattcgttct gatttcttat attcaagacg   1200
gggagagtgc tgagtgctaa cttactagtc tacgagagaa gcttcaaatc aaacagtgta   1260
ctatagggct tacacaattt ttctgaggga agcgattgtc tgaaatgaac taaaaggctg   1320
agagctggaa aaagtagctt attctgattc tgtgaagtga ttctccatgc tgatttttaaa 1380
agtttatgat aaaaaatcaa agagaataac tttcagccac agaatcactt ctctcagaga   1440
atcaacttat atggagaatc agaatcagat ggagctctac caaactggcc ctaggcatta   1500
acctaccatg gatcacatcg taaaaaaaaa accctaccat ggatcctatc tgtttttcttt 1560
ttgccctgaa agagtgaagt catcatcata tttaccatgg cgcgcgtagg agcgcttcgt   1620
cgaagaccca taggggggcg gtactcgcac cgtggttgtt tcctgttatg taatatcgga   1680
tggggagca gtcggctagg ttggtcccat cggtactggt cgtcccctag tgcgctagat   1740
gcgcgatgtt tgtcctcaaa aactctttc ttcttaataa caatcatacg caaatttttt   1800
gcgtattcga gaaaaaaga agattctatc tgttttttttt tgaaatggc tccaattat   1860
aggaggagcc cgtttaacgg cgtcgacaaa tctaacggac accaaccagc gaatgagcga   1920
acccaccagc gccaagctag ccaagcgaag cagacgccg agacgctgac acccttgcct   1980
tggcgcggca tctccgtcgc tggctcgctg gctctggccc cttcgcgaga gttccggtcc   2040
acctccacct gtgtcggttt ccaactccgt tccgccttcg cgtgggactt gttccgttca   2100
tccgttggcg gcatccggaa attgcgtggc gtagagcacg gggccctcct ctcacacggc   2160
acgaaccgt cacgagctca cggcaccggc agcagcgcgg ggattccttc cccaccaccg   2220
ctccttccct ttcccttcct cgcccgccat cataaatagc caccccctccc agcttccttc   2280
gccacatcct ctcatcatct tctctcgtgt agcacgcgca gcccgatccc caatcccctc   2340
tcctcgcgag cctcgtcgat ccctcgcttc aaggtatggc tatcgtcctt cctctctctc   2400
tctttacctt atctagatcg gcgatccatg gttagggcct gctagttctc cgttcgtgtt   2460
tgtcgatggc tgtgaggcac aatagatccg tcggcgttat gatggttagc ctgtcatgct   2520
cttgcgatct gtggttcctt taggaaaggc attaatttaa tccctgatgg ttcgagatcg   2580
gtgatccatg gttagtaccc taagctgtgg agtcgggttt agatccgcgc tgttcgtagg   2640
cgatctgttc tgattgttaa cttgtcagta cctgcgaatc tcggtggtt ctagctggtt   2700
cggagatcag atcgattcca ttatctgcta tacatcttgt ttcgttgcct aggctccgtt   2760
taatctatcc atcgtatgat gttagccttt gatatgattc gatcgtgcta gctatgtcct   2820
gtggacttaa ttgtcaggtc ctaattttta ggaagactgt tccaaaccat ctgctggatt   2880
tattaaattt ggatctggat gtgtcacata caccttcata attaaaatgg atggaaatat   2940
ctcttatctt ttagatatgg ataggcattt atatgatgct gtgagttta ctagtactttt 3000
cttagaatat atgtactttt ttagacgaa tattgatatg tatacatgtg tagatacatg   3060
aagcaacatg ctgctgtagt ctaataattc ctgttcatct aataatcaag tatgtatatg   3120
ttctgtgtgt tttattggta tttgattaga tatatacatg cttagataca tacatgaagc   3180
agcatgctgc tacagtttaa tcattattgt ttatccaata aacaaactgg cttttttaatt 3240
tatcttgata tgcttggatg acggaatatg cagagatttt aagtacccag catcatgagc   3300
atgcatgacc ctgcgttagt atgctgttta tttgcttgag actctttctt ttgtagatac   3360
tcaccctgtt ttctggtgat cctactgcag gtg                                3393

SEQ ID NO: 91        moltype = DNA    length = 2287
FEATURE              Location/Qualifiers
source               1..2287
                     mol_type = other DNA
                     organism = Coix lacryma-jobi
SEQUENCE: 91
ggttctatac aacaccacac actgtgtgag tgtgtgacca gtggccaact tttgttcagt    60
tcaacgatcc tggcctttcc gggcacccaa tacactaatt aatctattgc agctaacctc   120
aaaagaaatg catttgcagt tgtctgtcct aatcaatcta ctagcagact cacattattg   180
atgtaggaaa taaaattcag cctgtgacgt ggatgcaaca actgcactgc acaggatacc   240
atcttagccg ttgtgtcaca atttgctttg ctaatgtttt gagaaaccca gctttgacaa   300
acgtaagatc gatgagggcc ttacgtttgg cacaatatgt attgtaatcc ggcacggcaa   360
gttagactcg gtagtgttta gccggcatct ttatgtttgg cacaatttaa tttaattcgg   420
catggtaggt tagactgcag cgtgagccgg tcattgcaag ttattatgac atgttagagc   480
atctccaaca agttggaaaa aatgacttgg tatatcatgg tatatcatga gttttagcaa   540
cttattaatt catttgacaa gtaaaaaaaa gatccctctt caacaatttg ctattccaac   600
tcgctaaaat aaaaaaaaat taggctcacc taggccgatc tgcgttgccg cgggagagga   660
gggtaaaaga ttttgcgcta ggagaggtgg aggaacaggg cgcgggagcc ggccacggtg   720
aaatcacggg atagcaacct cacccgcgcg cgcaaattta cgcgtgtggc atggaggaat   780
agaaagttgg aaaagatagc aagttcattt agggagttgt tggagaagaa tatttgtgct   840
tttaccaaat ttataagaat agcaagtgag aatagagagt tgttggagat gctcaacaaa   900
tatacacaat aaagtggtat aataagcggc aagttattat gacatatata agagcaagta   960
tacaataagg tgaactgtta tatcgatcga ttttttttg agcacatatc gatcgaattt   1020
attgtaagat agaaaagaga agatataaaa acttatagtg atgaacaata ataatataaa   1080
```

```
gattattttt aaactatgaa aacaataacc gaactactcg ctctcttcta attagtaaag   1140
taaaggcttc tcattgtata tatataaaaa aattcgttct gatttcttat attcaagacg   1200
gggagagtgc tgagtgctaa cttactagtc tacgagagaa gcttcaaatc aaacagtgta   1260
ctataggcgt tacacaattt ttctgaggga agcgattgtc tgaaatgaac taaaaggctg   1320
agagctggaa aaagtagctt attctgattc tgtgaagtga ttctccatgc tgattttaaa   1380
agtttatgat aaaaaatcaa agagaataac tttcagccac agaatcactt ctctcagaga   1440
atcaacttat atggagaatc agaatcagat ggagctctac caaactggcc ctaggcatta   1500
acctaccatg gatcacatcg taaaaaaaaa accctaccat ggatcctatc tgttttcttt   1560
ttgccctgaa agagtgaagt catcatcata tttaccatgg cgcgcgtagg agcgcttcgt   1620
cgaagaccca taggggggcg gtactcgcac cgtggttgtt tcctgttatg taatatcgga   1680
tgggggagca gtcggctagg ttggtccat cggtactggt cgtccctag tgcgctagat    1740
gcgcgatgtt tgtcctcaaa aactcttttc ttcttaataa caatcatacg caaatttttt   1800
gcgtattcga gaaaaaaaga agattctatc tgttttttt ttgaaatggc tccaatttat    1860
aggaggagcc cgtttaacgg cgtcgacaaa tctaacgaac accaaccagc gaatgagcga   1920
acccaccagc gccaagctag ccaagcgaag cagacggccg agacgctgac acccttgcct   1980
tggcgcggca tctccgtcgc tggctcgctg gctctggccc cttcgcgaga gttccggtcc   2040
acctccacct gtgtcggttt ccaactccgt tccgccttcg cgtgggactt gttccgttca   2100
tccgttggcg gcatccggaa attgcgtggc gtagagcacg gggccctcct ctcacacggc   2160
acggaaccgt cacgagctca cggcaccggc agcacgccgg ggattccttc cccaccaccg   2220
ctccttccct ttcccttcct cgcccgccat cataaatagc caccoctccc agcttccttc   2280
gccacat                                                            2287

SEQ ID NO: 92          moltype = DNA   length = 1020
FEATURE                Location/Qualifiers
source                 1..1020
                       mol_type = other DNA
                       organism = Coix lacryma-jobi
SEQUENCE: 92
gtatggctat cgtccttcct ctctctctct ttaccttatc tagatcggcg atccatggtt    60
agggcctgct agttctccgt tcgtgtttgt cgatggctgc gaggcacaat agatccgtcg   120
gcgttatgat ggttagcctg tcatgctctt gcgatctgtg gttcctttag gaaaggcatt   180
aatttaatcc ctgatggttc gagatcggtg atccatggtt agtaccctaa gctgtggagt   240
cgggtttaga tccgcgctgt tcgtaggcga tctgttctga ttgttaactt gtcagtacct   300
gcgaatcctc ggtggttcta gctggttcgg agatcagatc gattccatta tctgctatac   360
atcttgtttc gttgcctagg ctccgtttaa tctatccatc gtatgatgtt agcctttgat   420
atgattcgat cgtgctagct atgtcctgtg gacttaattg tcaggtccta attttttagga  480
agactgttcc aaaccatctg ctggatttat taaatttgga tctggatgtg tcacatacac   540
cttcataatt aaaatggatg gaaatatctc ttatctttta gatatggata ggcatttata   600
tgatgctgtg agttttacta gtacttttctt agaatatatg tacttttttta gacggaatat  660
tgatatgtat acatgtgtag acatgaag caacatgctg ctgtagtcta ataattcctg     720
ttcatctaat aatcaagtat gtatatgttc tgtgtgtttt attggtattt gattagatat    780
atacatgctt agatacatac atgaagcagc atgctgctac agtttaatca ttattgttta   840
tccaataaac aaaatgcttt tttaatttat cttgatatgc ttggatgacg gaatatgcag   900
agattttaag tacccagcat catgagcatg catgaccctg cgttagtatg ctgtttattt   960
gcttgagact cttttctttttg tagatactca ccctgttttc tggtgatcct actgcaggtg  1020

SEQ ID NO: 93          moltype = DNA   length = 3393
FEATURE                Location/Qualifiers
source                 1..3393
                       mol_type = other DNA
                       organism = Coix lacryma-jobi
SEQUENCE: 93
ggttctatac aacaccacac actgtgtgag tgtgtgacca gtggccaact tttgttcagt    60
tcaacgatcc tggcctttcc gggcacccaa tacactaatt aatctattgc agctaacctc   120
aaaagaaatg catttgcagt tgtctgtcct aatcaatcta ctagcagact cacattattg   180
atgtaggaaa taaaattcag cctgtgacgt ggatgcaaca actgcactgc acaggatacc   240
atcttagccg ttgtgtcaca atttgctttg ctaatgtttt gagaaaccca gctttgacaa   300
acgtaagatc gatgagggcc ttacgtttgg cacaatatgt attgtaatcc ggcacggcaa   360
gttagactcg gtagtgttta gccggcatct ttatgtttgg cacaatttaa tttaattcgg   420
catggtaggt tagactgcag cgtgagccag tcattgcaag ttattatgac atgttagagc   480
atctccaaca agttggaaaa aatgacttgg tatatcatgg tatatcatga gttttagcaa   540
cttattaatt catttgacaa gtaaaaaaaa gatccctctt caacaatttg ctattccaac   600
tcgctaaaat aaaaaaaaat taggctcacc taggccgatc tgccgttgccg cgggagagga   660
gggtaaaaga ttttgcgcta ggagaggtgg aggaacaggg aggcgagagc ggccacggtg   720
aaatcacggg atagcaacct cacccgcgcg cgcaaattta cgcgtgtggc atggaggaat   780
agaaagttgg aaaagatagc aagttcattt agggagttgt tggagaagaa tatttgtgct   840
tttaccaaat ttataagaat agcaagtgag aatagagagt tgttggagat gctcaacaaa   900
tatacacaat aaaatggtat aataagcggc aagttattat gacatatata agagcaagta   960
tacaataagg tgaactgtta tatcgatcga ttttttttg agcacatatc gatcgaattt    1020
attgtaagat agaaaagaga agatataaaa acttatagtg atgaacaata ataatataaa   1080
gattattttt aaactatgaa aacaataacc gaactactcg ctctcttcta attagtaaag   1140
taaaggcttc tcattgtata tatataaaaa aattcgttct gatttcttat attcaagacg   1200
gggagagtgc tgagtgctaa cttactagtc tacgagagaa gcttcaaatc aaacagtgta   1260
ctataggcgt tacacaattt ttctgaggga agcgattgtc tgaaatgaac taaaaggctg   1320
agagctggaa aaagtagctt attctgattc tgtgaagtga ttctccatgc tgattttaaa   1380
agtttatgat aaaaaatcaa agagaataac tttcagccac agaatcactt ctctcagaga   1440
atcaacttat atggagaatc agaatcagat ggagctctac caaactggcc ctaggcatta   1500
acctaccatg gatcacatcg taaaaaaaaa accctaccat ggatcctatc tgttttcttt   1560
ttgccctgaa agagtgaagt catcatcata tttaccatgg cgcgcgtagg agcgcttcgt   1620
```

-continued

```
cgaagaccca tagggggcg gtactcgcac cgtggttgtt tcctgttatg taatatcgga  1680
tgggggagca gtcggctagg ttggtccat cggtactggt cgtccctag tgcgctagat   1740
gcgcgatgtt tgtcctcaaa aactcttttc ttcttaataa caatcatacg caaattttt   1800
gcgtattcga gaaaaaaga agattctatc tgtttttttt ttgaaatggc tccaatttat   1860
aggaggagcc cgtttaacgg cgtcgacaaa tctaacggac accaaccagc gaatgagcga  1920
acccaccagc gccaagctag ccaagcgaag cagacggccg agacgctgac acccttgcct  1980
tggcgcggca tctccgtcgc tggctcgctg gctctggccc cttcgcgaga gttccggtcc  2040
acctccacct gtgtcggttt ccaactccgt tccgccttcg cgtgggactt gttccgttca  2100
tccgttggcg gcatccggaa attgcgtggc gtagagcacg gggccctcct ctcacacggc  2160
acggaaccgt cacgagctca cggcaccggc agcacggcgg ggattccttc cccaccaccg  2220
ctccttccct ttcccttcct cgcccgccat cataaatagc caccctccc agcttccttc    2280
gccacatcct ctcatcatct tctctcgtgt agcacgcgca gcccgatccc caatcccctc  2340
tcctcgcgag cctcgtcgat ccctcgcttc aaggtatggc tatcgtcctt cctctctctc  2400
tctttacctt atctagatcg gcgatccatg gttagggcct gctagttctc cgttcgtgtt  2460
tgtcgatggc tgtgaggcac aatagatccg tcggcgttat gatggttagc ctgtcatgct   2520
cttgcgatct gtggttcctt taggaaaggc attaatttaa tccctgatgg ttcgagatcg   2580
gtgatccatg gttagtaccc taagctgtgg agtcgggttt agatccgcgc tgttcgtagg   2640
cgatctgttc tgattgttaa cttgtcagta cctgcgaatc ctcggtggtt ctagctggtt   2700
cggagatcag atcgattcca ttatctgcta tacatcttgt ttcgttgcct aggctccgtt   2760
taatctatcc atcgtatgat gttagccttt gatatgattc gatcgtgcta gctatgtcct   2820
gtggacttaa ttgtcaggtc ctaattttta ggaagactgt tccaaaccat ctgctggatt   2880
tattaaattt ggatctggat gtgtcacata cacccttcata attaaaatgg atggaaatat  2940
ctcttatctt ttagatatgg ataggcatt  atatgatgct gtgagtttta ctagtacttt   3000
cttagaatat atgtactttt ttagacggaa tattgatatg tatacatgtg tagatacatg   3060
aagcaacatg ctgctgtagt ctaataattc ctgttcatct aataatcaag tatgtatatg   3120
ttctgtgtgt tttattggta tttgattaga tatatacatg cttagataca tacatgaagc   3180
agcatgctgc tacagtttaa tcattattgt ttatccaata aacaaacatg cttttttaatt  3240
tatcttgata tgcttggatg acggaatatg cagagatttt aagtacccag catcatgagc  3300
atgcatgacc ctgcgttagt atgctgttta tttgcttgag actctttctt ttgtagatac   3360
tcaccctgtt ttctggtgat cctactgcag gtc                                3393

SEQ ID NO: 94          moltype = DNA  length = 1020
FEATURE                Location/Qualifiers
source                 1..1020
                       mol_type = other DNA
                       organism = Coix lacryma-jobi
SEQUENCE: 94
gtatggctat cgtccttcct ctctctctct ttaccttatc tagatcggcg atccatggtt    60
agggcctgct agttctccgt tcgtgtttgt cgatgctgt gaggcacaat agatccgtcg    120
gcgttatgat ggttagcctg tcatgctctt gcgatctgtg gttcctttag gaaaggcatt    180
aatttaatcc ctgatggttc gagatcggtg atccatggtt agtaccctaa gctgtggagt   240
cgggtttaga tccgcgctgt tcgtaggcga tctgttctga ttgttaactt gtcagtacct   300
gcgaatcctc ggtggttcta gctggttcgg agatcagatc gattccatta tctgctatac   360
atcttgtttc gttgcctagg ctccgttaa  tctatccatc gtatgatgtt agcctttgat   420
atgattcgat cgtgctagct atgtcctgtg gacttaattg tcaggtccta attttagga   480
agactgttcc aaaccatctg ctggatttat taaatttgga tctggatgtg tcacatacac   540
cttcataatt aaaatggatg gaaatatctc ttatcttta gatatggata ggcatttata   600
tgatgctgtg agttttacta gtactttctt agaatatatg tacttttta gacggaatat   660
tgatatgtat acatgtgtag atacatgaag caacatgctc tgtagtcta ataattcctg    720
ttcatctaat aatcaagtat gtatgttc tgtgtgtttt attggtattt gattagatat    780
atacatgctt agatacatac atgaagcagc atgctgctac agtttaatca ttattgttta   840
tccaataaac aaacatgctt tttaattat cttgatatgc ttggatgacg gaatatgcag   900
agattttaag tacccagcat catgagcatg catgaccctg cgttagtatg ctgttattt    960
gcttgagact ctttctttg tagatactca ccctgttttc tggtgatcct actgcaggtc  1020

SEQ ID NO: 95          moltype = DNA  length = 2166
FEATURE                Location/Qualifiers
source                 1..2166
                       mol_type = other DNA
                       organism = Coix lacryma-jobi
SEQUENCE: 95
gtctacgaga gaagcttcaa atcaaacagt gtactatagg gcttacacaa ttttctgag    60
ggaagcgatt gtctgaaatg aactaaaagg ctgagagctg gaaaaagtag cttattctga   120
ttctgtgaag tgattctcca tgctgatttt aaaagtttat gataaaaaat caaagagaat   180
aactttcagc cacagaatca cttctctcag agaatcaact tatatggaga atcagaatca   240
gatggagctc taccaaactg gcctaggca ttaacctacc atggatcaca tcgtaaaaaa   300
aaaaccctac catggatcct atctgtttc ttttgccct gaaagagtga agtcatcatc    360
atatttacca tggcgcgcgt aggagcgctt cgtcgaagac ccataggggg gcggtactcg   420
caccgtggtt gtttcctgtt atgtaatatc ggatggggag cagtcggctag gttggtccc    480
catcggtact ggtcgtcccc tagtgcgcta gatgcgcgat gtttgtcctc aaaaactctt   540
ttcttcttaa taacaatcat acgcaaattt tttgcgtatt cgagaaaaaa agaagattct   600
atctgttttt ttttgaaat ggctccaatt tataggagga gcccgtttaa cggcgtcgac    660
aaatctaacg gacaccaacc agcgaatgag cgaacccacc agcgccaagc tagccaagcg   720
aagcagacgc tgacacccttg cttggcgcgg catctccgt cgctggctcg ctggctctgg    780
cctggctctg ggccttcgcg agagttccg gtccaccttcca cctgtgtcgg tttccaactc    840
cgttccgcct tcgcgtggga cttgttccgt tcatccgttg gcggcatccg gaaattgcgt   900
ggcgtagagc acggggcct cctctcacac ggcacggaac cgtcacgagc tcacggcacc   960
ggcagcacgg cggggattcc ttccccacca ccgctcctc ccttcccttt cctgcccgc    1020
catcataaat agccacccct cccagcttcc ttcgccacat cctctcatca tctttctctcg  1080
```

```
tgtagcacgc gcagcccgat ccccaatccc ctctcctcgc gagcctcgtc gatccctcgc    1140
ttcaaggtat ggctatcgtc cttcctctct ctctctttac cttatctaga tcggcgatcc    1200
atggttaggg cctgctagtt ctccgttcgt gtttgtcgat ggctgtgagg cacaatagat    1260
ccgtcggcgt tatgatggtt agcctgtcat gctcttgcga tctgtggttc ctttaggaaa    1320
ggcattaatt taatccctga tggttcgaga tcggtgatcc atggttagta ccctaagctg    1380
tggagtcggg tttagatccg cgctgttcgt aggcgatctg ttctgattgt taacttgtca    1440
gtacctgcga atcctcggtg gttctagctg gttcggagat cagatcgatt ccattatctg    1500
ctatacatct tgtttcgttg cctaggctcc gtttaatcta tccatcgtat gatgttagcc    1560
tttgatatga ttcgatcgtg ctagctatgt cctgtggact taattgtcag gtcctaattt    1620
ttaggaagac tgttccaaac catctgctgg atttattaaa tttggatctg gatgtgtcac    1680
atacaccttc ataattaaaa tggatggaaa tatctcttat cttttagata tggataggca    1740
tttatatgat gctgtgagtt ttactagtac tttcttagaa tatatgtact tttttagacg    1800
gaatattgat atgtatacat gtgtagatac atgaagcaac atgctgctgt agtctaataa    1860
ttcctgttca tctaataatc aagtatgtat atgttcgtgt gattttattg gtattttgatt   1920
agatatatac atgcttagat acatacatga agcagcatgc tgctacagtt taatcattat    1980
tgtttatcca ataaacaaac atgcttttta atttatcttg atatgcttgg atgacggaat    2040
atgcagagat tttaagtacc cagcatcatg agcatgcatg accctgcgtt agtatgctgt    2100
ttatttgctt gagactcttt cttttgtaga tactcaccct gttttctggt gatcctactg    2160
caggtg                                                                2166

SEQ ID NO: 96          moltype = DNA  length = 1060
FEATURE                Location/Qualifiers
source                 1..1060
                       mol_type = other DNA
                       organism = Coix lacryma-jobi
SEQUENCE: 96
gtctacgaga gaagcttcaa atcaaacagt gtactatagg gcttacacaa ttttttctgag   60
ggaagcgatt gtctgaaatg aactaaaagg ctgagagctg gaaaaagtag cttattctga    120
ttctgtgaag tgattctcca tgctgatttt aaaagtttat gataaaaaat caaagagaat    180
aactttcagc cacagaatca cttctctcag agaatcaact tatatggaga atcagaatca    240
gatggagctc taccaaactg gcccctaggca ttaacctacc atggatcaca tcgtaaaaaa   300
aaaaccctac catggatcct atctgttttc tttttgccct gaaagagtga agtcatcatc    360
atatttacca tggcgcgcgt aggagcgctt cgtcgaagac ccatagggggg gcggtactcg   420
caccgtggtt gtttcctgtt atgtaatatc ggatggggga gcagtcggct aggttggtcc    480
catcgtgact ggtcgtcccc tagtgcgcta gatgcgcgat gtttgtcctc aaaaactctt    540
ttcttcttaa taacaatcat acgcaaattt tttgcgtatt cgagaaaaaa agaagattct    600
atctgttttt tttttgaaat ggctccaatt tataggagga gcccgtttaa cggcgtcgac    660
aaatctaacg gacaccaacc agcgaatgag cgaacccacc agcgccaagc tagccaagcg    720
aagcagacgg ccgagacgct gacacccttg ccttggcgcg gcatctccgt cgctggctcg    780
ctggctctgg cccccttcgcg agagttccgg tccacctcca cctgtgtcgg tttccaactc    840
cgttccgcct tcgcgtggga cttgttccgt tcatccgttg gcggcatccg gaaattgcgt    900
ggcgtagagc acggggcccct cctctcacac ggcacggaac cgtcacgagc tcacggcacc   960
ggcagcacgg cggggattcc ttccccacca ccgctccttc cctttccctt cctcgcccgc   1020
catcataaat agccaccccct cccagcttcc ttcgccacat                         1060

SEQ ID NO: 97          moltype = DNA  length = 2166
FEATURE                Location/Qualifiers
source                 1..2166
                       mol_type = other DNA
                       organism = Coix lacryma-jobi
SEQUENCE: 97
gtctacgaga gaagcttcaa atcaaacagt gtactatagg gcttacacaa ttttttctgag   60
ggaagcgatt gtctgaaatg aactaaaagg ctgagagctg gaaaaagtag cttattctga    120
ttctgtgaag tgattctcca tgctgatttt aaaagtttat gataaaaaat caaagagaat    180
aactttcagc cacagaatca cttctctcag agaatcaact tatatggaga atcagaatca    240
gatggagctc taccaaactg gcccctaggca ttaacctacc atggatcaca tcgtaaaaaa   300
aaaaccctac catggatcct atctgttttc tttttgccct gaaagagtga agtcatcatc    360
atatttacca tggcgcgcgt aggagcgctt cgtcgaagac ccatagggggg gcggtactcg   420
caccgtggtt gtttcctgtt atgtaatatc ggatggggga gcagtcggct aggttggtcc    480
catcgtgact ggtcgtcccc tagtgcgcta gatgcgcgat gtttgtcctc aaaaactctt    540
ttcttcttaa taacaatcat acgcaaattt tttgcgtatt cgagaaaaaa agaagattct    600
atctgttttt tttttgaaat ggctccaatt tataggagga gcccgtttaa cggcgtcgac    660
aaatctaacg gacaccaacc agcgaatgag cgaacccacc agcgccaagc tagccaagcg    720
aagcagacgg ccgagacgct gacacccttg ccttggcgcg gcatctccgt cgctggctcg    780
ctggctctgg cccccttcgcg agagttccgg tccacctcca cctgtgtcgg tttccaactc    840
cgttccgcct tcgcgtggga cttgttccgt tcatccgttg gcggcatccg gaaattgcgt    900
ggcgtagagc acggggcccct cctctcacac ggcacggaac cgtcacgagc tcacggcacc   960
ggcagcacgg cggggattcc ttccccacca ccgctccttc cctttccctt cctcgcccgc   1020
catcataaat agccaccccct cccagcttcc ttcgccacat cctctcatca tcttctctca  1080
tgtagcacgc gcagcccgat ccccaatccc ctctcctcgc gagcctcgtc gatccctcgc   1140
ttcaaggtat ggctatcgtc cttcctctct ctctctttac cttatctaga tcggcgatcc    1200
atggttaggg cctgctagtt ctccgttcgt gtttgtcgat ggctgtgagg cacaatagat    1260
ccgtcggcgt tatgatggtt agcctgtcat gctcttgcga tctgtggttc ctttaggaaa    1320
ggcattaatt taatccctga tggttcgaga tcggtgatcc atggttagta ccctaagctg    1380
tggagtcggg tttagatccg cgctgttcgt aggcgatctg ttctgattgt taacttgtca    1440
gtacctgcga atcctcggtg gttctagctg gttcggagat cagatcgatt ccattatctg    1500
ctatacatct tgtttcgttg cctaggctcc gtttaatcta tccatcgtat gatgttagcc    1560
tttgatatga ttcgatcgtg ctagctatgt cctgtggact taattgtcag gtcctaattt    1620
ttaggaagac tgttccaaac catctgctgg atttattaaa tttggatctg gatgtgtcac    1680
```

```
atacaccttc ataattaaaa tggatggaaa tatctcttat cttttagata tggataggca    1740
tttatatgat gctgtgagtt ttactagtac tttcttagaa tatatgtact tttttagacg    1800
gaatattgat atgtatacat gtgtagatac atgaagcaac atgctgctgt agtctaataa    1860
ttcctgttca tctaataatc aagtatgtat atgttctgtg tgttttattg gtatttgatt    1920
agatatatac atgcttagat acatacatga agcagcatgc tgctacagtt taatcattat    1980
tgtttatcca ataaacaaac atgcttttta atttatcttg atatgcttgg atgacgaat     2040
atgcagagat tttaagtacc cagcatcatg agcatgcatg accctgcgtt agtatgctgt    2100
ttatttgctt gagactcttt cttttgtaga tactcaccct gttttctggt gatcctactg    2160
caggtc                                                               2166

SEQ ID NO: 98        moltype = DNA   length = 1943
FEATURE              Location/Qualifiers
source               1..1943
                     mol_type = other DNA
                     organism = Coix lacryma-jobi
SEQUENCE: 98
agcagactcg cattatcgat ggagctctac caaactggcc ctaggcatta acctaccatg    60
gatcacatcg taaaaaaaaa accctaccat ggatcctatc tgtttcttt ttgccctgaa     120
agagtgaagt catcatcata tttaccatgg cgcgcgtagg agcgcttcgt cgaagaccca    180
tagggggcg gtactcgcac cgtggttgtt tcctgttatg taatatcgga tgggggagca    240
gtcggctagg ttggtcccat cggtactggt cgtcccctag tgcgctagat gcgcgatgtt    300
tgtcctcaaa aactcttttc ttcttaataa caatcatacg caaattttt gcgtattcga    360
gaaaaaaga gattctatc tgtttttttt ttgaaatggc tccaatttat aggaggagcc      420
cgtttaacgg cgtcgacaaa tctaacggac accaaccagc gaatgagcga acccaccagc    480
gccaagctag ccaagcgaag cagacggccg agacgctgac acccttgcct ggcgcggca     540
tctccgtcgc tggctcgctg gctctggccc cttcgcgaga gttccggtcc acctccacct    600
gtgtcggttt ccaactccgt tccgccttcg cgtgggactt gttccgttca tccgttggcg    660
gcatccggaa attgcgtggc gtagagcacg gggcctcct ctcacacggc acggaaccgt     720
cacgagctca cggcaccggc agcacggcgg ggattcctc cccaccaccg ctccttccct     780
ttcccttcct cgcccgccat cataaatagc caccctccc agcttccttc gccacatcct    840
ctcatcatct tctctcgtgt agcacgcgca gcccgatccc caatccctc tcctcgcgag     900
cctcgtcgat ccctcgcttc aaggtatggc tatcgtcctt cctctctctc tcttaccttt    960
atctagatcg gcgatccatg gttagggcct gctagttctc cgttcgtgtt tgtcgatggc    1020
tgtgaggcac aatagatccg tcggcgttat gatggttagc ctgtcatgct cttgcgatct    1080
gtggttcctt taggaaaggc attaattaa tccctgatgg ttcgagatcg gtgatccatg     1140
gttagtaccc taagctgtgg agtcgggttt agatccgcgc tgttcgtagg cgatctgttc    1200
tgattgttaa cttgtcagta cctgcgaatc ctcggtggtt ctagctggtt cggagatcag    1260
atcgattcca ttatctgcta tacatcttgt ttcgttgcct aggctccgtt taatctatcc    1320
atcgtatgat gttagccttt gatatgattc gatcgtgcta gctatgtcct gtggacttaa    1380
ttgtcaggtc ctaattttta ggaagactgt tccaaccat ctgctggatt tattaaattt     1440
ggatctggat gtgtcacata caccttcata attaaatgg atggaaatat ctcttatctt    1500
ttagatatgg ataggcattt atatgatgct gtgagttta ctagtacttt cttagaatat     1560
atgtacttttt ttagacggaa tattgatatg tacatgtga tagatacatg aagcaacatg    1620
ctgctgtagt ctaataattc ctgttcatct aataatcaag tatgtatatg ttctgtgtgt    1680
tttattggta tttgattaga tatatacatg cttagataca tacatgaagc agcatgctgc    1740
tacagtttaa tcattattgt ttatccaata aacaaacatg cttttaatt tatcttgata     1800
tgcttggatg acggaatatg cagagatttt aagtacccag catcatgagc atgcatgacc    1860
ctgcgttagt atgctgttta tttgcttgag actcttctt ttgtagatac tcaccctgtt     1920
ttctggtgat cctactgcag gtc                                             1943

SEQ ID NO: 99        moltype = DNA   length = 1943
FEATURE              Location/Qualifiers
source               1..1943
                     mol_type = other DNA
                     organism = Coix lacryma-jobi
SEQUENCE: 99
agcagactcg cattatcgat ggagctctac caaactggcc ctaggcatta acctaccatg    60
gatcacatcg taaaaaaaaa accctaccat ggatcctatc tgtttctttt ttgccctgaa    120
agagtgaagt catcatcata tttaccatgg cgcgcgtagg agcgcttcgt cgaagaccca    180
tagggggcg gtactcgcac cgtggttgtt tcctgttatg taatatcgga tgggggagca    240
gtcggctagg ttggtcccat cggtactggt cgtcccctag tgcgctagat gcgcgatgtt    300
tgtcctcaaa aactcttttc ttcttaataa caatcatacg caaattttt gcgtattcga     360
gaaaaaaga gattctatc tgtttttttt ttgaaatggc tccaatttat aggaggagcc      420
cgtttaacgg cgtcgacaaa tctaacggac accaaccagc gaatgagcga acccaccagc    480
gccaagctag ccaagcgaag cagacggccg agacgctgac acccttgcct ggcgcggca     540
tctccgtcgc tggctcgctg gctctggccc cttcgcgaga gttccggtcc acctccacct    600
gtgtcggttt ccaactccgt tccgccttcg cgtgggactt gttccgttca tccgttggcg    660
gcatccggaa attgcgtggc gtagagcacg gggcctcct ctcacacggc acggaaccgt     720
cacgagctca cggcaccggc agcacggcgg ggattcctc cccaccaccg ctccttccct     780
ttcccttcct cgcccgccat cataaatagc caccctccc agcttccttc gccacatcct    840
ctcatcatct tctctcgtgt agcacgcgca gcccgatccc caatccctc tcctcgcgag     900
cctcgtcgat ccctcgcttc aaggtatggc tatcgtcctt cctctctctc tcttaccttt    960
atctagatcg gcgatccatg gttagggcct gctagttctc cgttcgtgtt tgtcgatggc    1020
tgtgaggcac aatagatccg tcggcgttat gatggttagc ctgtcatgct cttgcgatct    1080
gtggttcctt taggaaaggc attaattaa tccctgatgg ttcgagatcg gtgatccatg     1140
gttagtaccc taagctgtgg agtcgggttt agatccgcgc tgttcgtagg cgatctgttc    1200
tgattgttaa cttgtcagta cctgcgaatc ctcggtggtt ctagctggtt cggagatcag    1260
atcgattcca ttatctgcta tacatcttgt ttcgttgcct aggctccgtt taatctatcc    1320
atcgtatgat gttagccttt gatatgattc gatcgtgcta gctatgtcct gtggacttaa    1380
```

```
ttgtcaggtc ctaatttta ggaagactgt tccaaaccat ctgctggatt tattaaattt   1440
ggatctggat gtgtcacata caccttcata attaaaatgg atggaaatat ctcttatctt   1500
ttagatatgg ataggcattt atatgatgct gtgagtttta ctagtacttt cttagaaat    1560
atgtactttt ttagacggaa tattgatatg tacatgtg tagatacatg aagcaacatg    1620
ctgctgtagt ctaataattc ctgttcatct aataatcaag tatgtatatg ttctgtgtgt   1680
tttattggta tttgattaga tatatacatg cttagataca tacatgaagc agcatgctgc   1740
tacagtttaa tcattattgt ttatccaata aacaaacatg ctttttaatt tatcttgata   1800
tgcttggatg acgaaatatg cagagatttt aagtacccag catcatgagc atgcatgacc   1860
ctgcgttagt atgctgttta tttgcttgag actctttctt ttgtagatac tcaccctgtt   1920
ttctggtgat cctactgcag gtg                                           1943

SEQ ID NO: 100          moltype = DNA   length = 1943
FEATURE                 Location/Qualifiers
source                  1..1943
                        mol_type = other DNA
                        organism = Coix lacryma-jobi
SEQUENCE: 100
agcagactcg cattatcgat ggagctctac caaactggcc ctaggcatta acctaccatg     60
gatcacatcg taaaaaaaaa accctaccat ggatcctatc tgttttcttt ttgccctgaa    120
agagtgaagt catcatcata tttaccatgg cgcgcgtagg agcgcttcgt cgaagaccca    180
tagggggcg gtactcgcac cgtggttgtt tcctgttatg taatatcgga tgggggagca    240
gtcggctagg ttggtcccat cggtactggt cgtcccctag gatgcgatgt gcgcgatgtt    300
tgtcctcaaa aactcttttc ttcttaataa caatcatacg caaattttt gcgtattcga    360
gaaaaaaga agattctatc tgtttttttt ttgaaatggc tccaatttat aggaggagcc    420
cgtttaacgc cgtcgacaaa tctaacggac accaaccagc gaatgagcga acccaccagc    480
gccaagctag ccaagcgaag cagacggcc agacgctgcc accccttgcct tggcgcgaca    540
tctccgtcgc tggctcgctg gctctgcgcc cttcgcgaga gttccggtcc acctccacct    600
gtgtcggttt ccaactccgt tccgccttcg cgtgggactt gttccgttca tccgttggcg    660
gcatccggaa attgcgtggc gtagagcacg gggcctcct ctcacacggc acggaaccgt    720
cacgagctca cggcaccggc agcacggcgg ggattccttc cccaccaccg ctccttcccct    780
ttcccttcct cgcccgccat cataaatagc caccccctcc agcttccttc gccacatcct    840
ctcatcatct tctctcgtgt agcacgcgca gcccgatccc caatccctc tcctcgcgag    900
cctcgtcgat ccctcgcttc aaggtatggc tatcgtcctt cctctctctc tctttaccct    960
atctagatcg gcgatccatg gttagggcct gctagttctc cgttcgtgtt tgtcgatggc   1020
tgtgaggcac aatagatccg tcggcgttat gatggttagc ctgtcatgct cttgcgatct   1080
gtggttcctt taggaaaggc attaatttaa tccctgatgg ttcgagatcg gtgatccatg   1140
gttagtaccc taagctgtgg agtcgggttt agatccgcgc tgttcgtagg cgatctgttc   1200
tgattgttaa ccttgtcagta cctgcgaatc ctcggtggtt ctagctggtt cggagatcag   1260
atcgattcca ttatctgcta tacatcttgt ttcgttgcct aggctccgtt taatctatcc   1320
atcgtatgat gttagccttt gatatgattc gatcgtgcta gctatgtcct gtggacttaa   1380
ttgtcaggtc ctaatttta ggaagactgt tccaaaccat ctgctggatt tattaaattt   1440
ggatctggat gtgtcacata caccttcata attaaaatgg atggaaatat ctcttatctt   1500
ttagatatgg ataggcattt atatgatgct gtgagtttta ctagtacttt cttagaaat    1560
atgtactttt ttagacggaa tattgatatg tacatgtg tagatacatg aagcaacatg    1620
ctgctgtagt ctaataattc ctgttcatct aataatcaag tatgtatatg ttctgtgtgt   1680
tttattggta tttgattaga tatatacatg cttagataca tacatgaagc agcatgctgc   1740
tacagtttaa tcattattgt ttatccaata aacaaacatg ctttttaatt tatcttgata   1800
tgcttggatg acgaaatatg cagagatttt aagtacccag catcatgagc atgcatgacc   1860
ctgcgttagt atgctgttta tttgcttgag actctttctt ttgtagatac tcaccctgtt   1920
ttctggtgat cctactgcag gcg                                           1943

SEQ ID NO: 101          moltype = DNA   length = 1020
FEATURE                 Location/Qualifiers
source                  1..1020
                        mol_type = other DNA
                        organism = Coix lacryma-jobi
SEQUENCE: 101
gtatggctat cgtccttcct ctctctctct ttacctatc tagatcggcg atccatggtt     60
agggcctgct agttctccgt tcgtgtttgt cgatggctgt gaggcacaat agatccgtcg    120
gcgttatgat ggttagcctg tcatgctctt gcgatctgtg gttcctttag gaaaggcatt    180
aatttaatcc ctgatggttc gagatcggtg atccatggtt agtaccctaa gctgtgagt    240
cgggtttaga tccgcgctgt tcgtaggcga tctgttctga ttgttaactt gtcagtacct    300
gcgaatcctg gtggttctga gctggttcgg agatcagatc gattccatta tctgctatac    360
atcttgtttc gttgcctagg ctccgtttaa tctatccatc gtatgatgtt agcctttgat    420
atgattcgat cgtgctagct atgtcctgtg gacttaattg tcaggtccta atttttagga    480
agactgttcc aaaccatctg ctggatttat aaatttgga tctggatgtg tcacatacac    540
cttcataatt aaaatggatg gaaatatctc ttatcttta gatatggata ggcatttata    600
tgatgctgtg agttttacta gtacttttctt agaatatatg tactttttta gacggaaat    660
tgatatgtat acatgtag atacatgaag caacatgctg ctgtagtcta ataattcctg    720
ttcatctaat aatcaagtat gtatatgttc tgtgtgtttt attggtattt gattagatat    780
atacatgctt agatacatac atgaagcagc atgctgctac agtttaatca ttattgttta    840
tccaataaac aaacatgctt tttaatttat cttgatatgc ttggatgacg aaatatgcag    900
agattttaag tacccagcat catgagcatg catgaccctg cgttagtatg ctgttatttt    960
gcttgagact ctttctttg tagatactca ccctgttttc tggtgatcct actgcaggcg   1020

SEQ ID NO: 102          moltype = DNA   length = 1943
FEATURE                 Location/Qualifiers
source                  1..1943
                        mol_type = other DNA
```

```
                        organism = Coix lacryma-jobi
SEQUENCE: 102
agcagactcg cattatcgat ggagctctac caaactggcc ctaggcatta acctaccatg     60
gatcacatcg taaaaaaaaa accctaccat ggatcctatc tgttttcttt ttgccctgaa    120
agagtgaagt catcatcata tttaccatgg cgcgcgtagg agcgcttcgt cgaagaccca    180
taggggggcg gtactcgcac cgtggttgtt tcctgttatg taatatcgga tgggggagca    240
gtcggctagg ttggtcccat cggtactggt cgtcccctag tgcgctagat gcgcgatgtt    300
tgtcctcaaa aactcttttc ttcttaataa caatcatacg caaatttttt gcgtattcga    360
gaaaaaaaga agattctatc tgttttttt ttgaaatggc tccaatttat aggaggagcc    420
cgtttaacgg cgtcgacaaa tctaacggac accaaccagc gaatgagcga acccaccagc    480
gccaagctag ccaagcgaag cagacggccg agacgctgac accttgcct tggcgcggca     540
tctccgtcgc tggctcgctg gctctggccc cttcgcgaga gttccggtcc acctccacct    600
gtgtcggttt ccaactccgt tccgccttcg cgtgggactt gttccgttca tccgttggcg    660
gcatccggaa attgcgtggc gtagagcacg gggccctcct ctcacacggc acggaaccgt    720
cacgagctca cggcaccggc agcacggcgg ggattccttc cccaccaccg ctccttccct    780
ttcccttcct cgcccgccat cataaatagc caccctccc agcttccttc gccacatcct    840
ctcatcatct tctctcgtgt agcacgcgca gcccgatccc caatccctc tcctcgcgag     900
cctcgtcgat ccctcgcttc aaggtatggc tatcgtcctt cctctctctc tctttacctt    960
atctagatcg gcgatccatg gttagggcct gctagttctc cgttcgtgtt tgtcgatggc   1020
tgtgaggcac aatagatccg tcggcgttat gatggttagc ctgtcatgct cttgcgatct   1080
gtggttcctt taggaaaggc attaatttaa tccctgatgg ttcgagatcg gtgatccatg   1140
gttagtaccc taagctgtgg agtcgggttt agatccgcga cgttcgtagg cgatctgttc   1200
tgattgttaa cttgtcagta cctgcgaatc ctcggtggtt ctagctggtt cggagatcag   1260
atcgattcca ttatctgcta tacatcttgt ttcgttgcct aggctccgtt taatctatcc   1320
atcgtatgat gttagccttt gatatgattc gatcgtgcta gctatgtcct gtggacttaa   1380
ttgtcaggtc ctaattttta ggaagactgt tccaaaccat ctgctggatt tattaaattt   1440
ggatctggat gtgtcacata caccttcata attaaaatgt atggaaatat ctcttatcct   1500
ttagatatgg ataggcattt atatgatgct gtgagttttta ctagtacttt cttagaaatat   1560
atgtactttt ttagacggaa tattgatatg tatacatgtg tagatacatg aagcaacatg   1620
ctgctgtagt ctaataattc ctgttcatct aataatcaag tatgtatatg ttctgtgtgt   1680
tttattggta tttgattaga tatatacatg cttagataca tacatgaagc agcatgctgc   1740
tacagtttaa tcattattgt ttatccaata aacaaacatg ctttttaatt tatcttgata   1800
tgcttggatg acggaaatatg cagagatttt aagtacccag catcatgagc atgcatgacc   1860
ctgcgttagt atgctgttta tttgcttgag actctttctt ttgtagatac tcaccctgtt   1920
ttctggtgat cctactgcag gac                                            1943

SEQ ID NO: 103           moltype = DNA   length = 1020
FEATURE                  Location/Qualifiers
source                   1..1020
                         mol_type = other DNA
                         organism = Coix lacryma-jobi
SEQUENCE: 103
gtatggctat cgtccttcct ctctctctct ttaccttatc tagatcggcg atccatggtt     60
agggcctgct agttctccgt tcgtgtttgt cgatggctgt gaggcacaat agatccgtcg    120
gcgttatgat ggttagcctg tcatgctctt gcgatctgtg gttcctttag gaaaggcatt    180
aatttaatcc ctgatggttc gagatcgtg atccatggtt agtaccctaa gctgtggagt    240
cgggtttaga tccgcgctgt tcgtaggcga tcgttctga ttgttaactt gtcagtacct     300
gcgaatcctc ggtggttcta gctggttcgg agatcagatc gattccatta tctgctatac   360
atcttgtttc gttgcctagg ctccgtttaa tctatccatc gtatgatgtt agcctttgat   420
atgattcgat cgtgctagct atgtcctgtg gacttaattg tcaggtccta attttttagga   480
agactgttcc aaaccatctg ctggatttat taaatttgga tctggatgt tcacatacac     540
cttcataatt aaaatggatg aaatatctc ttatctttta gatatggata ggcatttata    600
tgatgctgtg agttttacta gtactttctt agaaatatg tacttttta gacgaaatat      660
tgatatgtat acatgtgtag atacatgaag caacatgctg ctgtagtcta ataattcctg   720
ttcatctaat aatcaagtat gtatgttc tgtgtgtttt attggtattt gattagatat       780
atacatgctt agatacatac atgaagcagc atgctgctac agtttaatca ttattgttta   840
tccaataaac aaacatgctt tttaatttat cttgatatgc ttggatgacg gaatatgcag    900
agattttaag tacccagcat catgagcatg catgaccctg cgttagtatg ctgtttattt    960
gcttgagact ctttctttttg tagatactca ccctgttttc tggtgatcct actgcaggac   1020

SEQ ID NO: 104           moltype = DNA   length = 1943
FEATURE                  Location/Qualifiers
source                   1..1943
                         mol_type = other DNA
                         organism = Coix lacryma-jobi
SEQUENCE: 104
agcagactcg cattatcgat ggagctctac caaactggcc ctaggcatta acctaccatg     60
gatcacatcg taaaaaaaaa accctaccat ggatcctatc tgttttcttt ttgccctgaa    120
agagtgaagt catcatcata tttaccatgg cgcgcgtagg agcgcttcgt cgaagaccca    180
taggggggcg gtactcgcac cgtggttgtt tcctgttatg taatatcgga tgggggagca    240
gtcggctagg ttggtcccat cggtactggt cgtcccctag tgcgctagat gcgcgatgtt    300
tgtcctcaaa aactcttttc ttcttaataa caatcatacg caaatttttt gcgtattcga    360
gaaaaaaaga agattctatc tgttttttt ttgaaatggc tccaatttat aggaggagcc    420
cgtttaacgg cgtcgacaaa tctaacggac accaaccagc gaatgagcga acccaccagc    480
gccaagctag ccaagcgaag cagacggccg agacgctgac accttgcct tggcgcggca     540
tctccgtcgc tggctcgctg gctctggccc cttcgcgaga gttccggtcc acctccacct    600
gtgtcggttt ccaactccgt tccgccttcg cgtgggactt gttccgttca tccgttggcg    660
gcatccggaa attgcgtggc gtagagcacg gggccctcct ctcacggc acggaaccgt      720
cacgagctca cggcaccggc agcacggcgg ggattccttc cccaccaccg ctccttccct    780
```

-continued

```
ttcccttcct cgcccgccat cataaatagc caccccctccc agcttccttc gccacatcct  840
ctcatcatct tctctcgtgt agcacgcgca gcccgatccc caatcccctc tcctcgcgag  900
cctcgtcgat ccctcgcttc aaggtatggc tatcgtcctt cctctctctc tctttacctt  960
atctagatcg gcgatccatg gttagggcct gctagttctc cgttcgtgtt tgtcgatggc 1020
tgtgaggcac aatagatccg tcggcgttat gatggttagc ctgtcatgct cttgcgatct 1080
gtggttcctt taggaaaggc attaaattaa tccctgatgg ttcgagatcg gtgatccatg 1140
gttagtaccc taagctgtgg agtcgggttt agatccgcgc tgttcgtagg cgatctgttc 1200
tgattgttaa cttgtcagta cctgcgaatc tcggtggtt ctagctggtt cggagatcag 1260
atcgattcca ttatctgcta tacatcttgt ttcgttgcct aggctccgtt taatctatcc 1320
atcgtatgat gttagccttt gatatgattc gatcgtgcta gctatgtcct gtggacttaa 1380
ttgtcaggtc ctaattttta ggaagactgt tccaaaccat ctgctggatt tattaaattt 1440
ggatctggat gtgtcacata caccttcata attaaaatgg atggaaatat ctcttatctt 1500
ttagatatgg ataggcattt atatgatgct gtgagttta ctagtactt cttagaatat 1560
atgtactttt ttagacggaa tattgatatg tatacatgtg tagatacatg aagcaacatg 1620
ctgctgtagt ctaataattc ctgttcatct aataatcaag tatgtatatg ttctgtgtgt 1680
tttattggta tttgattaga tatatacatg cttagataca tacatgaagc agcatgctgc 1740
tacagtttaa tcattattgt ttatccaata acaaacatg cttttttaatt tatcttgata 1800
tgcttggatg acggaaatatg cagagattt aagtacccag catcatgagc atgcatgacc 1860
ctgcgttagt atgctgttta tttgcttgag actctttctt ttgtagatac tcaccctgtt 1920
ttctggtgat cctactgcag acc                                        1943

SEQ ID NO: 105         moltype = DNA  length = 1020
FEATURE                Location/Qualifiers
source                 1..1020
                       mol_type = other DNA
                       organism = Coix lacryma-jobi
SEQUENCE: 105
gtatggctat cgtccttcct ctctctctct ttaccttatc tagatcggcg atccatggtt   60
agggcctgct agttctccgt tcgtgtttgt cgatggctgt gaggcacaat agatccgtcg  120
gcgttatgat ggttagcctg tcatgctctt gcgatctgtg gttcctttag gaaaggcatt  180
aatttaatcc ctgatggttc gagatcggtg atccatggtt agtacccta gctgtggagt  240
cgggtttaga tccgcgctgt tcgtaggcga tctgttctga ttgttaactt gtcagtacct  300
gcgaatcctc ggtggttcta gctggttcgg agatcagatc gattccatta tctgctatac  360
atcttgtttc gttgcctagg ctccgtttaa tctatccatc gtatgatgat agccttgat  420
atgattcgat cgtgctagct atgtcctgtg gacttaattg tcaggtccta attttagga  480
agactgttcc aaaccatctg ctggatttat taaattggga tctggatgtg tcacatacac  540
cttcataatt aaaatggatg gaaatatctc ttatcttta gatatggata ggcatttata  600
tgatgctgtg agttttacta gtactttctt agaatatatg tacttttta gacggaatat  660
tgatatgtat acatgtgtag atacatgaag caacatgctg ctgtagtcta ataattcctg  720
ttcatctaat aatcaagtat gtatatgttc tgtgtgtttt attggtattt gattagatat  780
atacatgctt agatacatac atgaagcagc atgctgctac agtttaatca ttattgttta  840
tccaataaac aaacatgctt tttaattat cttgatatgc ttggatgacg gaatatgcag  900
agattttaag tacccagcat catgagcatg catgaccctg cgttagtatg ctgttatttt  960
gcttgagact ctttctttg tagatactca ccctgttttc tggtgatcct actgcagacc 1020

SEQ ID NO: 106         moltype = DNA  length = 1943
FEATURE                Location/Qualifiers
source                 1..1943
                       mol_type = other DNA
                       organism = Coix lacryma-jobi
SEQUENCE: 106
agcagactcg cattatcgat ggagctctac caaactggcc ctaggcatta acctaccatg   60
gatcacatcg taaaaaaaaa accctaccat ggatcctatc tgtttctttt ttgccctgaa  120
agagtgaagt catcatcata tttaccatgg cgcgcgtagg agcgcttcgt cgaagaccca  180
taggggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaatttttt gcgtattcga  360
gaaaaaaaga agattctatc tgttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacgggcg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacgcgg ggattccttc cccaccaccg ctcctcccg  780
ttcccttcct cgcccgccat cataaatagc caccccctccc agcttccttc gccacatcct  840
ctcatcatct tctctcgtgt agcacgcgca gcccgatccc caatcccctc tcctcgcgag  900
cctcgtcgat ccctcgcttc aaggtatggc tatcgtcctt cctctctctc tctttacctt  960
atctagatcg gcgatccatg gttagggcct gctagttctc cgttcgtgtt tgtcgatggc 1020
tgtgaggcac aatagatccg tcggcgttat gatggttagc ctgtcatgct cttgcgatct 1080
gtggttcctt taggaaaggc attaaattaa tccctgatgg ttcgagatcg gtgatccatg 1140
gttagtaccc taagctgtgg agtcgggttt agatccgcgc tgttcgtagg cgatctgttc 1200
tgattgttaa cttgtcagta cctgcgaatc tcggtggtt ctagctggtt cggagatcag 1260
atcgattcca ttatctgcta tacatcttgt ttcgttgcct aggctccgtt taatctatcc 1320
atcgtatgat gttagccttt gatatgattc gatcgtgcta gctatgtcct gtggacttaa 1380
ttgtcaggtc ctaattttta ggaagactgt tccaaaccat ctgctggatt tattaaattt 1440
ggatctggat gtgtcacata caccttcata attaaaatgg atggaaatat ctcttatctt 1500
ttagatatgg ataggcattt atatgatgct gtgagttta ctagtactt cttagaatat 1560
atgtactttt ttagacggaa tattgatatg tatacatgtg tagatacatg aagcaacatg 1620
ctgctgtagt ctaataattc ctgttcatct aataatcaag tatgtatatg ttctgtgtgt 1680
```

```
tttattggta tttgattaga tatatacatg cttagataca tacatgaagc agcatgctgc   1740
tacagtttaa tcattattgt ttatccaata aacaaacatg cttttttaatt tatcttgata  1800
tgcttggatg acggaaatatg cagagatttt aagtacccag catcatgagc atgcatgacc  1860
ctgcgttagt atgctgttta tttgcttgag actctttctt ttgtagatac tcaccctgtt   1920
ttctggtgat cctactgcag ggg                                          1943

SEQ ID NO: 107         moltype = DNA  length = 1020
FEATURE                Location/Qualifiers
source                 1..1020
                       mol_type = other DNA
                       organism = Coix lacryma-jobi
SEQUENCE: 107
gtatggctat cgtccttcct ctctctctct ttaccttatc tagatcggcg atccatggtt   60
agggcctgct agttctccgt tcgtgtttgt cgatggctgt gaggcacaat agatccgtcg  120
gcgttatgat ggttagcctg tcatgctctt gcgatctgtg gttcctttag gaaaggcatt  180
aatttaatcc ctgatggttc gagatcggtg atccatggtt agtacccctaa gctgtggagt 240
cgggtttaga tccgcgctgt tcgtaggcga tctgttctga ttgttaactt gtcagtacct  300
gcgaatcctc ggtggttcta gctggttcgg agatcagatc gattccatta tctgctatac  360
atcttgtttc gttgcctagg ctccgtttaa tctatccatc gtatgatgtt agccctttgat 420
atgattcgat cgtgctagct atgtcctgtg gacttaattg tcaggtccta attttttagga 480
agactgttcc aaaccatctg ctggatttat taaatttgga tctggatgtg tcacatacac  540
cttcataatt aaaatggatg gaaatatctc ttatctttca gatatggata ggcatttata  600
tgatgctgtg agtttactaa gtactttctt agaatatatg tacttttttta gacggaatat  660
tgatatgtat acatgtgtag atacatgaag caacatgctg ctgtagtcta ataattcctg   720
ttcatctaat aatcaagtat gtatatgttc tgtgtgtttt attggtattt gattagatat   780
atacatgctt agatacatac atgaagcagc atgctgctac agttaatca ttattgttta   840
tccaatataaac aaacatgctt tttaattatat cttgatatgc ttggatgacg gaatatgcag  900
agattttaag tacccagcat catgagcatg catgaccctg cgttagtatg ctgtttattt   960
gcttgagact ctttctttttg tagatactca ccctgttttc tggtgatcct actgcagggg  1020

SEQ ID NO: 108         moltype = DNA  length = 1943
FEATURE                Location/Qualifiers
source                 1..1943
                       mol_type = other DNA
                       organism = Coix lacryma-jobi
SEQUENCE: 108
agcagactcg cattatcgat ggagctctac caaactggcc ctaggcatta acctaccatg   60
gatcacatcg taaaaaaaaa accctaccat ggatcctatc tgtttttcttt ttgccctgaa  120
agagtgaagt catcatcata tttaccatgg cgcgcgtaag acgcttcgt cgaagaccca   180
taggggggcg gtactcgcac cgtggttgtt tcctgttatg taatatcgga tgggggagca   240
gtcggctagg ttggtcccat cggtactggt cgtcccctag tgcgctagat gcgcgatgtt  300
tgtcctcaaa aactctttttc ttcttaataa caatcatacg caaattttttt gcgtattcga  360
gaaaaaaga agattctatc tgtttttttttt ttgaaatgct tccaatttat aggaggagcc  420
cgtttaacgg cgtcgacaaa tctaacggac accaaccagc gaatgagcga acccaccagc   480
gccaagctag ccaagcgaag cagacggccg agacgctgac acccttgcct ggcgcggca   540
tctccgtcgc tggctcgctg gctctggccc ttcgcgaga gttccggtcc acctccacct   600
gtgtcggttt ccaactccgt tccgccttcg cgtgggactt gttccgttca tccgttggcg  660
gcatccggaa attgcgtggc gtagagcacg gggccctcct ctcacacggc acggaaccgt   720
cacgagctca cggcaccggc agcacggcgg ggattccttc cccaccaccg ctcctttccct 780
ttcccttcct cgccccgccat cataaatagc caccccctccc agcttccttc gccacatcct  840
ctcatcatct tctctcgtgt agcacgcgca gcccgatcc caatccctc tcctcgcgag   900
cctcgtcgat ccctcgcttc aaggtatggc tatcgtcctt cctctctctc tctttacctt   960
atctagatcg gcgatccatg gttagggcct gctagttctc cgttcgtgtt tgtcgatggc   1020
tgtgaggcac aatagatccg tcggcgttat gatggttagc ctgtcatgct cttgcgatct  1080
gtggttcctt taggaaaggc attaatttaa tccctgatgg ttcgagatcg gtgatccatg  1140
gttagtaccc taagctgtgg agtcgggttt agatccgcgc tgttcgtagg cgatctgttc  1200
tgattgttaa cttgtcagta cctgcgaatc ctcggtggtt ctagctggtt cggagatcag  1260
atcgattcca ttatctgcta tacatcttgt ttcgttgcct aggctccgtt taatctatcc  1320
atcgtatgat gttagccttt gatatgattc gatcgtgcta tgtcctgtgg gacttaa    1380
ttgtcaggtc ctaattttta ggaagactgt tccaaaccat ctgctggatt tattaaattt   1440
ggatctggat gtgtcacata caccttcata attaaaatgg atggaaatat ctcttatctt  1500
ttagatatgg ataggcattt atatgatgct gtgagttta ctagtacttt cttagaatat  1560
atgtactttt ttagacggaa tattgatatg tatacatgtg tagatacatg aagcaacatg  1620
ctgctgtagt ctaataattc ctgttcatct aataatcaag tatgtatatg ttctgtgtgt  1680
tttattggta tttgattaga tatatacatg cttagataca tacatgaagc agcatgctgc  1740
tacagtttaa tcattattgt ttatccaata aacaaacatg cttttttaatt tatcttgata  1800
tgcttggatg acggaaatatg cagagatttt aagtacccag catcatgagc atgcatgacc  1860
ctgcgttagt atgctgttta tttgcttgag actctttctt ttgtagatac tcaccctgtt   1920
ttctggtgat cctactgcag ggt                                          1943

SEQ ID NO: 109         moltype = DNA  length = 1020
FEATURE                Location/Qualifiers
source                 1..1020
                       mol_type = other DNA
                       organism = Coix lacryma-jobi
SEQUENCE: 109
gtatggctat cgtccttcct ctctctctct ttaccttatc tagatcggcg atccatggtt   60
agggcctgct agttctccgt tcgtgtttgt cgatggctgt gaggcacaat agatccgtcg  120
gcgttatgat ggttagcctg tcatgctctt gcgatctgtg gttcctttag gaaaggcatt  180
```

```
aatttaatcc ctgatggttc gagatcggtg atccatggtt agtaccctaa gctgtggagt    240
cgggtttaga tccgcgctgt tcgtaggcga tctgttctga ttgttaactt gtcagtacct    300
gcgaatcctc ggtggttcta gctggttcgg agatcagatc gattccatta tctgctatac    360
atcttgtttc gttgcctagg ctccgtttaa tctatccatc gtatgatgtt agcctttgat    420
atgattcgat cgtgctagct atgtcctgtg gacttaattg tcaggtccta atttttagga    480
agactgttcc aaaccatctg ctggatttat taaatttgga tctggatgtg tcacatacac    540
cttcataatt aaaatggatg gaaatatctc ttatctttta gatatggata ggcatttata    600
tgatgctgtg agttttacta gtactttctt agaatatatg tacttttta gacggaatat     660
tgatatgtat acatgtgtag atacatgaag caacatgctg ctgtagtcta ataattcctg    720
ttcatctaat aatcaagtat gtatatgttc tgtgtgtttt attggtattt gattagatat    780
atacatgctt agatacatac atgaagcagc atgctgctac agtttaatca ttattgttta    840
tccaataaac aaacatgctt tttaatttat cttgatatgc ttggatgacg gaatatgcag    900
agattttaag tacccagcat catgagcatg catgaccctg cgttagtatg ctgtttattt    960
gcttgagact ctttctttg tagatactca ccctgttttc tggtgatcct actgcagggt    1020

SEQ ID NO: 110          moltype = DNA   length = 1943
FEATURE                 Location/Qualifiers
source                  1..1943
                        mol_type = other DNA
                        organism = Coix lacryma-jobi
SEQUENCE: 110
agcagactcg cattatcgat ggagctctac caaactggcc ctaggcatta acctaccatg    60
gatcacatcg taaaaaaaaa acctaccat ggatcctatc tgttttcttt ttgccctgaa     120
agagtgaagt catcatcata tttaccatgg cgcgcgtagg agcgcttcgt cgaagaccca    180
tagggggcg gtactcgcac cgtggttgtt tcctgttatg taatatcgga tgggggagca     240
gtcggctagg ttggtcccat cggtactggt cgtcccctag gctagtagct gcgcgatgtt    300
tgtcctcaaa aactctttc ttcttaataa caatcatacg caaatttttt gcgtattcga     360
gaaaaaaaga agattctatc tgtttttttt ttgaaatggc tccaatttat aggaggagcc    420
cgtttaacgc gtcgacaaa tctaacggac accaaccagc gaatgagcga acccaccagc    480
gccaagctag ccaagcgaag cagacggccg agacgctgac acccttgcct tggcgcggca    540
tctccgtcgc tggctcgctg gctctggccc cttcgcgaga gttccggtcc acctccacct    600
gtgtcggttt ccaactccgt tccgccttcg cgtgggactt gttccgttca tccgttggcg    660
gcatccggaa attgcgtggc gtagagcacg gggccctcct ctcacacggc acggaaccgt    720
cacgagctca cggccaccgg cagcacggcgg ggattccttc cccaccaccg ctccttcct    780
ttccttcct cgcccgccat cataaatagc caccctccc agcttcctc gccacatcct       840
ctcatcatct tctctcgtgt agcacgcgca gcccgatccc caatccctc tcctcgcgag    900
cctcgtcgat ccctcgcttc aaggtatggc tatcgtcctt cctctctctc tctttaccttt   960
atctagatcg gcgatccatg gttagggcct gctagttctc cgttcgtgtt tgtcgatggc    1020
tgtgaggcac aatagatccg tcggcgttat gatggttagc ctgtcatgct cttgcgatct    1080
gtggttcctt taggaaaggc attaaatttaa tccctgatgg ttcgagatcg gtgatccatg    1140
gttagtaccc taagctgtgg agtcgggttt agatccgcgc tgttcgtagg cgatctgttc    1200
tgattgttaa cttgtcagta cctgcgaatc ctcggtggtt ctagctggtt cggagatcag    1260
atcgattcca ttatctgcta tacatcttgt tcgttgccta aggctccgtt taatctatcc    1320
atcgtatgat gttagccttt gatatgattc gatcgtgcta gctatgtcct gtggacttaa    1380
ttgtcaggtc ctaattttta ggaagactgt tccaaaccat ctgctggatt tattaaattt    1440
ggatctggat gtgtcacata caccttcata attaaaatgg atggaaatat ctcttatctt    1500
ttagatatgg ataggcattt atatgatgct gtgagtttta ctagtacttt cttagaaatat    1560
atgtactttt ttagacggaa tattgatatg tatacatgtg tagatacatg aagcaacatg    1620
ctgctgtagt ctaataattc ctgttcatct aataatcaag tatgtatatg ttctgtgtgt    1680
tttattggta tttgattaga tatatacatg cttagataca tacatgaagc agcatgctgc    1740
tacagtttaa tcattattgt ttatccaata aacaaacatg cttttttaatt tatcttgata    1800
tgcttggatg acggaatatg cagagatttt aagtacccag catcatgagc atgcatgacc    1860
ctgcgttagt atgctgttta tttgcttgag actctttctt ttgtagatac tcaccctgtt    1920
ttctggtgat cctactgcag cgt                                           1943

SEQ ID NO: 111          moltype = DNA   length = 1020
FEATURE                 Location/Qualifiers
source                  1..1020
                        mol_type = other DNA
                        organism = Coix lacryma-jobi
SEQUENCE: 111
gtatggctat cgtccttcct ctctctctct ttaccttatc tagatcggcg atccatggtt    60
agggcctgct agttctccgt tcgtgtttgt cgatggctgt gaggcacaat agatccgtcg    120
gcgtttatgat ggttagcctg tcatgctctt gcgatctgtg gttccttag gaaaggcatt    180
aatttaatcc ctgatggttc gagatcggtg atccatggtt agtaccctaa gctgtggagt    240
cgggtttaga tccgcgctgt tcgtaggcga tctgttctga ttgttaactt gtcagtacct    300
gcgaatcctc ggtggttcta gctggttcgg agatcagatc gattccatta tctgctatac    360
atcttgtttc gttgcctagg ctccgtttaa tctatccatc gtatgatgtt agcctttgat    420
atgattcgat cgtgctagct atgtcctgtg gacttaattg tcaggtccta atttttagga    480
agactgttcc aaaccatctg ctggatttat taaatttgga tctggatgtg tcacatacac    540
cttcataatt aaaatggatg gaaatatctc ttatctttta gatatggata ggcatttata    600
tgatgctgtg agttttacta gtactttctt agaatatatg tacttttta gacggaatat     660
tgatatgtat acatgtgtag atacatgaag caacatgctg ctgtagtcta ataattcctg    720
ttcatctaat aatcaagtat gtatatgttc tgtgtgtttt attggtattt gattagatat    780
atacatgctt agatacatac atgaagcagc atgctgctac agtttaatca ttattgttta    840
tccaataaac aaacatgctt tttaatttat cttgatatgc ttggatgacg gaatatgcag    900
agattttaag tacccagcat catgagcatg catgaccctg cgttagtatg ctgtttattt    960
gcttgagact ctttctttg tagatactca ccctgttttc tggtgatcct actgcagcgt    1020
```

| SEQ ID NO: 112 | moltype = DNA   length = 1943 |
| --- | --- |
| FEATURE | Location/Qualifiers |
| source | 1..1943 |
| | mol_type = other DNA |
| | organism = Coix lacryma-jobi |

SEQUENCE: 112

```
agcagactcg cattatcgat ggagctctac caaactggcc ctaggcatta acctaccatg   60
gatcacatcg taaaaaaaaa accctaccat ggatcctatc tgttttcttt ttgccctgaa  120
agagtgaagt catcatcata tttaccatgg cgcgcgtagg agcgcttcgt cgaagaccca  180
tagggggggcg gtactcgcac cgtggttgtt tcctgttatg taatatcgga tgggggagca  240
gtcggctagg ttggtcccat cggtactggt cgtccctag tgcgctagat gcgcgatgtt  300
tgtcctcaaa aactcttttc ttcttaataa caatcatacg caaattttt gcgtattcga  360
gaaaaaaga agattctatc tgttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggcc agacgctgac accttgcct tggcgcggca  540
tctccggtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacggcgg ggattcct tc cccaccaccg ctccttccct  780
ttcccttcct cgcccgccat cataaatagc caccctccc agcttcctc gccacatcct  840
ctcatcatct tctctcgtgt agcacgcgca gcccgatccc caatccctc tcctcgcgag  900
cctcgtcgat ccctcgcttc aaggtatggc tatcgtcctt cctctctctc tctttaccctt  960
atctagatcg gcgatccatg gttagggcct gctagttctc cgttcgtgtt tgtcgatggc 1020
tgtgaggcac aatagatccg tcggcgttat gatggttagc ctgtcatgct cttgcgatct 1080
gtggttcctt taggaaaggc attaatttaa tccctgatgg ttcgagatcg gtgatccatg 1140
gttagtaccc taagctgtgg agtcgggttt agatccgtcg tgttcgtagg cgatctgttc 1200
tgattgttaa cttgtcagta cctgcgaatc ctcggtggtt ctagctggtt cggagatcag 1260
atcgattcca ttatctgcta tacatcttgt ttcgttgcct aggctccgtt taatctatcc 1320
atcgtatgat gttagccttt gatatgattc gatcgtgcta gctatgtcct gtggacttaa 1380
ttgtcaggtc ctaattttta ggaagactgt tccaaaccat ctgctggatt tattaaattt 1440
ggatctggat gtgtcacata caccttcata attaaaatgg atggaaatat ctcttatcttt 1500
ttagatatgg ataggcattt atatgatgct gtgagtttta ctagtacttt cttagaatat 1560
atgtactttt ttagacggaa tattgatatg tatacatgtg tagatacatg aagcaacatg 1620
ctgctgtagt ctaataattc ctgttcatct aataatcaag tatgtatatg ttctgtgtgt 1680
tttattggta tttgattaga tatatacatg cttagataca tacatgaagc agcatgctgc 1740
tacagtttaa tcattattgt ttatccaata aacaaacatg cttttaatt tatcttgata 1800
tgcttggatg acgaatatg cagagatttt aagtacccag catcatgagc atgcatgacc 1860
ctgcgttagt atgctgttta tttgcttgag actctttctt ttgtagatac tcaccctgtt 1920
ttctggtgat cctactgcag tgt                                         1943
```

| SEQ ID NO: 113 | moltype = DNA   length = 1020 |
| --- | --- |
| FEATURE | Location/Qualifiers |
| source | 1..1020 |
| | mol_type = other DNA |
| | organism = Coix lacryma-jobi |

SEQUENCE: 113

```
gtatggctat cgtccttcct ctctctctct ttaccttatc tagatcggcg atccatggtt   60
agggcctgct agttctccgt tcgtgtttgt cgatggctgt gaggcacaat agatccgtcg  120
gcgttatgat ggttagcctg tcatgctctt gcgatctgtg gttcctttag gaaaggcatt  180
aatttaatcc ctgatggttc gagatcggtg atccatggtt agtaccctaa gctgtggagt  240
cgggtttaga tccgcgctgt tcgtaggcga tctgttctga ttgttaactt gtcagtacct  300
gcgaatcctc ggtggttcta gctggtcgg agatcagatc gattccatta tctgctatac  360
atcttgtttc gttgcctagg ctccgtttaa tctatccatc gtatgatgtt agcctttgat  420
atgattcgat cgtgctagct atgtcctgtg gacttaattg tcaggtccta attttagga  480
agactgttcc aaaccatctg ctggatttat taaatttgga tctggatgtg tcacatacac  540
cttcataatt aaaatggatg gaaatatctc ttatcttta gatatggata ggcatttata  600
tgatgctgtg agttttacta gtactttctt agaatatatg tactttttta gacggaatat  660
tgatatgtat acatgtgtag atacatgaag caacatgctg ctgtagtcta ataattcctg  720
ttcatctaat aatcaagtat gtatatgttc tgtgtgttt attggtattt gattagatat  780
atacatgctt agatacatac atgaagcagc atgctgctac agtttaatca ttattgttta  840
tccaataaac aaacatgctt tttaatttat cttgatatgc ttggatgacg aatatgcag  900
agattttaag tacccagcat catgagcatg catgaccctg cgttagtatg ctgtttattt  960
gcttgagact ctttctttg tagatactca ccctgttttc tggtgatcct actgcagtgt 1020
```

| SEQ ID NO: 114 | moltype = DNA   length = 1848 |
| --- | --- |
| FEATURE | Location/Qualifiers |
| source | 1..1848 |
| | mol_type = other DNA |
| | organism = Coix lacryma-jobi |

SEQUENCE: 114

```
ctatctgttt tcttttgcc ctgaaagagt gaagtcatca tcatatttac catggcgcgc   60
gtaggagcgc ttcgtcgaag acccataggg ggcggtact cgcaccgtgg ttgtttcctg  120
ttatgtaata tcggatgggg gagcagtcgg ctaggttggt cccatcggta ctggtcgtcc  180
cctagtgcgc tagatgcgcg atgtttgtcc tcaaaaactc ttttcttctt aataacaatc  240
atacgcaaat tttttgcgta ttcgagaaaa aaagaagatt ctatctgttt ttttttttgaa  300
atggctccaa tttataggag gagcccgttt aacggcgtcg acaaatctaa cggacaccaa  360
ccagcgaatg agcgaaccca ccagcgccaa gctagccaag cgaagcagac ggccgagacg  420
ctgacaccct tgccttggcg cggcatctcc gtcgctggct cgctggctct ggccccttcg  480
cgagagttcc ggtccacctc cacctgtgtc ggttccaac tccgttccgc cttcgcgtgg  540
```

```
gacttgttcc gttcatccgt tggcggcatc cggaaattgc gtggcgtaga gcacggggcc   600
ctcctctcac acggcacgga accgtcacga gctcacggca ccggcagcac ggcggggatt   660
ccttccccac caccgctcct tcccttttccc ttcctcgccc gccatcataa atagccaccc  720
ctcccagctt ccttcgccac atcctctcat catcttctct cgtgtagcac gcgcagcccg   780
atccccaatc ccctctcctc gcgagcctcg tcgatccctc gcttcaaggt atggctatcg   840
tccttcctct ctctctcttt acctatctag atcggcgat ccatggttag ggcctgctag    900
ttctccgttc gtgtttgtcg atggctgtga ggcacaatag atccgtcggc gttatgatgg   960
ttagcctgtc atgctcttgc gatctgtggt tcctttagga aaggcattaa tttaatccct  1020
gatggttcga gatcggtgat ccatggttag tacctaagc tgtggagtcg ggtttagatc    1080
cgcgctgttc gtaggcgatc tgttctgatt gttaacttgt cagtacctgc gaatcctcgg  1140
tggttctagc tggttcggag atcagatcga ttccattatc tgctatacat cttgtttcgt  1200
tgcctaggct ccgtttaatc tatccatcgt atgatgttag cctttgatat gattcgatcg   1260
tgctagctat gtcctgtgga cttaattgtc aggtcctaat ttttaggaag actgttccaa   1320
accatctgct ggatttatta aatttggatc tggatgtgtc acatacacct tcataattaa   1380
aatggatgga aatatctctt atcttttaga tatggatagg catttatatg atgctgtgag   1440
ttttactagt acttcttag aatatatgta ctttttttaga cggaatattg atatgtatac   1500
atgtgtagat acatgaagca acatgctgct gtagtctaat aattcctgtt catctaataa   1560
tcaagtatgt atatgttctg tgtgttttat tggtatttga ttagatatat acatgcttag   1620
atacatacat gaagcagcat gctgctacag tttaatcatt attgtttatc caataaacaa   1680
acatgctttt taatttatct tgatatgctt ggatgacgga atatgcagag attttaagta   1740
cccagcatca tgagcatgca tgaccctgcg ttagtatgct gtttatttgc ttgagactct   1800
ttcttttgta gatactcacc ctgttttctg gtgatcctac tgcaggtc                1848

SEQ ID NO: 115          moltype = DNA   length = 1507
FEATURE                 Location/Qualifiers
source                  1..1507
                        mol_type = other DNA
                        organism = Coix lacryma-jobi
SEQUENCE: 115
caaatctaac ggacaccaac cagcgaatga gcgaacccac cagcgccaag ctagccaagc   60
gaagcagacg gccgagacgc tgacaccctt gccttggcgc ggcatctccg tcgctggctc   120
gctggctctg gccccttcgc gagagttccg gtccacctcc acctgtgtcg gtttccaact   180
ccgttccgcc ttcgcgtggg acttgttccg ttcatccgtt ggcggcatcc ggaaattgcg   240
tggcgtagag cacggggccc tcctctcaca cggcacggaa ccgtcacgag ctcacggcac   300
cggcagcacg gcggggattc cttccccacc accgctcctt ccctttccct tcctcgcccg   360
ccatcataaa tagccacccc tcccagcttc cttcgccaca tcctctcatc atcttctctc   420
gtgtagcacg cgcagcccga tccccaatcc cctctcctcg cgagcctcgt cgatccctcg   480
cttcaaggta tggctatcgt ccttcctctc tctctcttta cctatctag atcggcgatc    540
catggttagg gcctgctagt tctccgttcg tgtttgtcga tggctgtgag gcacaataga   600
tccgtcggcg ttatgatggt tagcctgtca tgctcttgcg atctgtggtt cctttaggaa   660
aggcattaat ttaatccctg atggttcgag atcggtgatc catggttagt accctaagct   720
gtggagtcgg gtttagatcc gcgctgttcg taggcgatct gttctgattg ttaacttgtc   780
agtacctgcg aatcctcggt ggttctagct ggttcggaga tcagatcgat tccattatct   840
gctatacatc ttgtttcgtt gcctaggctc cgtttaatct atccatcgta tgatgttagc   900
ctttgatatg attcgatcgt gctagctatg tcctgtggac ttaattgtca ggtcctaatt   960
tttaggaaga ctgttccaaa ccatctgctg gatttattaa atttggatct ggatgtgtca  1020
catacacctt cataattaaa atggatggaa atatctctta tcttttagat atggataggc  1080
atttatatga tgctgtgagt tttactagta cttcttaga atatatgtac tttttttagac  1140
ggaatattga tatgtataca tgtgtagata catgaagcaa catgctgctg tagtctaata  1200
attcctgttc atctaataat caagtatgta tatgttctgt gtgttttatt ggtatttgat  1260
tagatatata catgcttaga tacatacatg aagcagcatg ctgctacagt ttaatcatta  1320
ttgtttatcc aataaacaaa catgcttttt aatttatctt gatatgcttg gatgacgaa   1380
tatgcagaga ttttaagtac ccagcatcat gagcatgcat gaccctgcgt tagtatgctg  1440
tttatttgct tgagactctt tcttttgtag atactcaccc tgttttctgg tgatcctact  1500
gcaggtc                                                            1507

SEQ ID NO: 116          moltype = DNA   length = 1160
FEATURE                 Location/Qualifiers
source                  1..1160
                        mol_type = other DNA
                        organism = Coix lacryma-jobi
SEQUENCE: 116
ccttcctcgc ccgccatcat aaatagccac ccctcccagc ttccttcgcc acatcctctc   60
atcatcttct ctcgtgtagc acgcgcagcc cgatccccaa tcccctcctc gcgagcctcg   120
cgtcgatccc tcgcttcaag gtatggctat cgtccttcct ctctctctct ttaccttatc   180
tagatcggcg atccatggtt agggcctgct agttctccgt tcgtgtttgt cgatggctgt   240
gaggcacaat agatccgtcg cgttatgat ggttagcctg tcatgctctt gcgatctgtg    300
gttcctttag gaaaggcatt aatttaatcc ctgatggttc gagatcggtg atccatggtt   360
agtaccctaa gctgtggagt cgggtttaga tccgcgctgt taggcgatc tgttctgta    420
ttgttaactt gtcagtacct gcgaatcctc ggtggttcta gctggttcgg agatcagatc   480
gattccatta tctgctatac atcttgtttc gttgcctagg ctccgtttaa tctatccatc   540
gtatgatgtt agcctttgat atgattcgat cgtgctagct atgtcctgtg acttaattg    600
tcaggtccta attttaggaa agactgttcc aaaccatctg ctggatttat taaatttgga   660
tctggatgtg tcacatacac cttcataatt aaaatggatg gaaatatctc ttatctttta   720
gatatggata ggcatttata tgatgctgtg agttttacta gtactttctt agaatatatg   780
tactttttta gacggaatat tgatatgtat acatgtgtag atacatgaag caacatgctg   840
ctgtagtcta taattcctg ttcatctaat aatcaagtat gtatatgttc tgtgtgtttt    900
attggtattt gattagatat acatgctt agatacatac atgaagcagc atgctgctac    960
agtttaatca ttattgttta tccaataaac aaacatgctt tttaatttat cttgatatgc  1020
```

| SEQ ID NO: 117 | moltype = DNA length = 2625 |
|---|---|
| FEATURE | Location/Qualifiers |
| source | 1..2625 |
| | mol_type = other DNA |
| | organism = Setaria italica |

SEQUENCE: 117

```
actgccgcga cacgcctcac tggcgggagg gctccgagcg ctctctcccc ggcggccggc    60
ggagcagcga tctggattgg agagaataga ggaaagagag ggaaaggag agagatagcg   120
caaagagctg aaaagataag gttgtgcggg ctgtggtgat tagaggacca ctaatccctc   180
catctcctaa tgacgcggtg cccaagacca gtgccgcggc acaccagcgt ctaagtgaac   240
ttccgctaac cttccggtca ttgcgcctga aagatgtcat gtggcgaggc cccctctca    300
gtagattgcc aactgcctac cgtgccactc ttccatgcat gattgctccc gtctatcccg   360
tttctcacaa cagatagaca acagtaagca tcactaaagc aagcatgtgt agaaccttaa   420
aaaaaggctt atactaccag tatactatca accagcatgc cgttttttgaa gtatccagga   480
ttagaagctt ctactgcgct tttatattat agctgtggac ctgtggtaac cttctctttt   540
tggcgcttgc ttaatctcgg ccgtgctggt ccatgcttag gcactaggca gagatagagc   600
cggggggtgaa tggggctaaa gctcagctgc tcgaggggcc gtgggctggt ttccactagc   660
ctacagctgt gccacgtgcg gccgcgcaag ccgaagcaag cacgctgagc cgttggacag   720
cttgtcataa tgccattacg tggattacac gtaactggcc ctgtaactac tcgttcggcc   780
atcatcaaac gacgacgtcc gctaggcgac gacacgggta atgcacgcag ccacccaggc   840
gcgcgcgcta gcggagcacg tcaggtgac acgggcgtcg tgacgcttcc gagttgaagg   900
ggttaacgcc agaaacagtg tttggccagg gtatgaacaa gcacaaaaat attcacacga   960
aagaatggaa gtatggagct gctactgtgt aaatgccaag caggaaactc acgcccgcta  1020
acatccaacg gccaacagct cgacgtgccg gtcagcagag catcggaaca ctggtgattg  1080
gtggagccgg cagtatgcgc cccagcacgg ccgaggtggt ggtggcccgt ggccctgctg  1140
tctgcgcgcc tcgggacaac ttgaaactgg gccaccgcct cgtcgcaact cgcaaccgct  1200
tggcggaaga aaggaatggc tcgtagggc ccgggtagaa tcgaagaatg ttgcgctggg  1260
cttcgattca cataacatgg gcctgaagct ctaaaacgac ggcccggtcg ccgcgcgatg  1320
gaaagagacc ggatcctcct cgtgaattct ggaaggccac acgagagcga cccaccaccg  1380
acgcggagga gtcgtgcgtg gtccaacacg gccggcgggc tgggctgcga ccttaaccag  1440
caaggcgcac cacgacccgc cccgccctcg aggcataaat accctcccat cccgttgccg  1500
caagactcag atcagattcc gatcccagt tcttccccaa tcaccttgtg gtctctcgtg  1560
tcgcggttcc cagggacgcc tccggctcgt cgctcgacag cgatctccgc cccagcaagg  1620
tatagattca gttccttgct ccgatcccaa tctggttgag atgttgctcc gatgcgactt  1680
gattatgtca tatatctgcg gtttgcaccg atctgaagc taggtttct cgagcgaccc  1740
agttatttgc aatttgcgat tgctcgtttt gttgcgcagc gtagttattg tttgagtaa   1800
tcgaggattt gtatgcggcg tcggcgctac ctgcttaatc acgccatgtg acgcggttac  1860
ttgcagaggc tgggttctgt tatgtcgtga tctaagaatc tagattaggc tcagtcgttc  1920
ttgctgtcga ctagtttgtt ttgatatcca tgtagtacaa agttacttaa atttaggtcc  1980
aatatatttt gcatgctttt ggcctgttat tcttgccaac aagttgtcct ggtaaaaagt  2040
agatgtgaaa gtcacgtatt gggacaaatt gatggttag tgctatagtt ctatagttct  2100
gtgatacatc tatctgattt ttttttggtct attggtgcct aacttatctg aaaatcatgg  2160
aacatgaggc tagtttgatc atggtttagt tcattgtgat taataatgta tgatttagta  2220
gctatttttgg tgatcgtgtc attttatttg tgaatgaat cattgtatgt aaatgaagc   2280
agttcagggg ttacgatgta gctggctttg tattctaaag gctgctatta ttcatccatc  2340
gatttcacct atatgtaatc cagagctttt gatgtgaaat ttgtctgatc cttcactagg  2400
aaggacagaa cattgttaat attttggcac atctgtctta ttctcatcct ttgtttgaa   2460
atgttagcct gttcaaacag atactgttgt aatgtcctag ttatatagg acatatgtgt  2520
tctctattga gtttatggac ttttgtgtgt gaagttatat ttcattttgc tcaaaactca  2580
tgtttgcaag ctttctgaca ttattctatt gttctgaaac aggtg                  2625
```

| SEQ ID NO: 118 | moltype = DNA length = 1006 |
|---|---|
| FEATURE | Location/Qualifiers |
| source | 1..1006 |
| | mol_type = other DNA |
| | organism = Setaria italica |

SEQUENCE: 118

```
gtatagattc agttccttgc tccgatccca atctggttga gatgttgctc cgatgcgact    60
tgattatgtc atatatctgc ggtttgcacc gatctgaagc taggtttc tcgagcgacc   120
cagttatttg caatttgcga tttgctcgtt tgttgcgcag cgtagtttat gtttggagta   180
atcgaggatt tgtatgcggc gtcggcgcta cctgcttaat cacgccatgt gacgcggtta   240
cttgcagagg ctgggttctg ttatgtcgtg atctaagaat ctagattagg ctcagtcgtt   300
cttgctgtcg actagtttgt tttgatatcc atgtagtaca agttacttaa atttaggtc    360
caatatattt tgcatgcttt tggcctgtta ttcttgccaa caagttgtcc tggtaaaaag   420
tagatgtgaa agtcacgtat tgggacaaat tgatggttta gtgctatagt tctatagttc   480
tgtgatacat ctatctgatt ttttttggtc tattggtgcc taacttatct gaaaatcatg   540
gaacatgagg ctagtttgat catggtttag ttcattgtga ttaataatgt atgatttagt   600
agctattttg tgatcgtgt cattttatt gtgaatgaa tcattgtatg taaatgaagc    660
tagttcaggg gttacgatgt agctggcttt gtattctaaa ggctgctatt attcatccat   720
cgatttcacc tatatgtaat ccagagcttt tgatgtctgat ccttcactag               780
gaaggacaga acattgttaa tattttggca catctgtctt attctcatcc tttgtttgaa    840
catgttagcc tgttcaaaca gatactgttg taatgtccta gttatatagg acatatgtg    900
ttctctattg agtttatgga cttttgtgtg tgaagttata tttcattttg ctcaaaactc    960
atgtttgcaa gctttctgac attattctat tgttctgaaa caggtg                  1006
```

| SEQ ID NO: 119 | moltype = DNA length = 2625 |
|---|---|
| FEATURE | Location/Qualifiers |
| source | 1..2625 |
| | mol_type = other DNA |
| | organism = Setaria italica |

SEQUENCE: 119

```
actgccgcga cacgcctcac tggcgggagg gctccgagcg ctctctcccc ggcggccggc    60
ggagcagcga tctggattgg agagaataga ggaaagagag ggaaaaggag agagatagcg   120
caaagagctg aaaagataag gttgtgcggg ctgtggtgat tagaggacca ctaatccctc   180
catctcctaa tgacgcggtg cccaagacca gtgccgcggc acaccagcgt ctaagtgaac   240
ttccgctaac cttccggtca ttgcgcctga aagatgtcat gtggcgaggc ccccctctca   300
gtagattgcc aactgcctac cgtgccactc ttccatgcat gattgctccc gtctatcccg   360
tttctcacaa cagatagaca acagtaagca tcactaaagc aagcatgtgt agaaccttaa   420
aaaaaggctt atactaccag tatactatca accagcatgc cgttttgaa gtatccagga   480
ttagaagctt ctactgcgct tttatattat agctgtggac ccgtggtaac ctttctcttt   540
tggcgcttgc ttaatctcgg ccgtgctggt ccatgcttag gcactaggca gagatagagc   600
cggggggtgaa tgggctaaa gctcagctgc tcgaggggcc gtgggctggt ttccactagc   660
ctacagctgt gccacgtgcg gccgcgcaag ccgaagcaag cacgctgagc cgttggacag   720
cttgtcataa tgccattacg tggattacac gtaactggcc ctgtaactac tcgttcggcc   780
atcatcaaac gacgacgtcc gctaggcgac gacacgggta atgcacgcag ccacccaggc   840
gcgcgcgcta gcggagcacg tcaggtgac acgggcgtcg tgacgcttcc gagttgaagg   900
ggttaacgcc agaaacagtg tttggccagg gtatgaacaa acaaaaaat attcacacga   960
aagaatggaa gtatggagct gctactgtgt aaatgccaag caggaaactc acgcccgcta  1020
acatccaacg gccaacagct cgacgtgccg gtcagcagag catcggaaca ctggtgattg  1080
gtggagccga cagtatgcgc cccagcacgg ccgaggtggt ggtggcccgt ggccctgctg  1140
tctgcgcgac tcgggacaac ttgaaactgg gccaccgcct cgtcgcaact cgcaaccgt  1200
tggcggaaga aaggaatggc tcgtaggggc ccgggtagaa tcgaagaatg ttgcgctggg  1260
cttcgattca cataacatgg gcctgaagct ctaaaacgac ggcccggtcg ccgcgcgatg  1320
gaaagagacc ggatcctcct cgtgaattct ggaaggccac acgagagcga cccaccaccg  1380
acgcggagga gtcgtgcgtg gtccaacacg gccggcgggc tgggctgcga ccttaaccag  1440
caaggcacgc cacgacccgc cccgccctcg aggcataaat accctcccat cccgttgccg  1500
caagactcag atcagattcc gatcccagt tcttccccaa tcaccttgtg gtctctcgtg  1560
tcgcggttcc cagggacgcc tccggctcgt cgctcgacag cgatctccgc cccagcaagg  1620
tatagattca gttccttgct ccgatcccaa tctggttgag atgttgctcc gatgcgactt  1680
gattatgtca tatatctgcg gtttgcaccg atctgaagcc tagggtttct cgagcgaccc  1740
agttatttgc aatttgcgat ttgctcgttt gttgcgcagc gtagtttatg tttggagtaa  1800
tcgaggattt gtatgcggcg tcggcgctac ctgcttaatc acgccatgtg acgcggttac  1860
ttgcagaggc tgggttctgt tatgtcgtga tctaagaatc tagattaggc tcagtcgttc  1920
ttgctgtcga ctagtttgtt ttgatatcca tgtagtacaa gttacttaaa attttaggtcc  1980
aatatatttt gcatgctttt ggcctgttat tcttgccaac aagttgtcct ggtaaaaagt  2040
agatgtgaaa gtcacgtatt gggacaaatt gatggtttag tgctatagtt ctatagttct  2100
gtgatacatc tatctgattt ttttttggtct attggtgcct aacttatctg aaaatcatgg  2160
aacatgaggc tagtttgatc atggtttagt tcattgtga ttaataatgt atgatttagt  2220
agctattttg tgatcgtgtc attttatttt tgaatggaat cattgtatg taaatgaagc  2280
agttcagggg ttacgatgta gctggctttg tattctaaag gctgctatta ttcatccatc  2340
gatttcacct atatgtaatc cagagctttt gatgtgaaat ttgtctgatc cttcactagg  2400
aaggacagaa cattgttaat attttggcac atctgtctta ttctcatcct ttgtttgaac  2460
atgttagcct gttcaaacag atactgttgt aatgtcctag ttatataggt acatatgtgt  2520
tctctattga gtttatggac ttttgtgtgt gaagttatat ttcattttgc tcaaaactca  2580
tgtttgcaag ctttctgaca ttattctatt gttctgaaac agggt              2625
```

| SEQ ID NO: 120 | moltype = DNA length = 1006 |
|---|---|
| FEATURE | Location/Qualifiers |
| source | 1..1006 |
| | mol_type = other DNA |
| | organism = Setaria italica |

SEQUENCE: 120

```
gtatagattc agttccttgc tccgatccca atctggttga gatgttgctc cgatgcgact    60
tgattatgtc atatatctgc ggtttgcacc gatctgaagc ctaggggtttc tcgagcgacc  120
cagttatttg caatttgcga tttgctcgtt tgttgcgcag cgtagtttat gtttggagta   180
atcgaggatt tgtatgcggc gtcggcgcta cctgcttaat cacgccatgt gacgcggtta   240
cttgcagagg ctgggttctg ttatgtcgtg atctaagaat ctagattagg ctcagtcgtt   300
cttgctgtcg actagtttgt tttgatatcc atgtagtaca agttacttaa aatttaggtc   360
caatatattt tgcatgcttt tggcctgtta ttcttgccaa caagttgtcc tggtaaaaag   420
tagatgtgaa agtcacgtat tgggacaaat tgatggttta gtgctatagt tctatagttc   480
tgtgatacat ctatctgatt ttttttggtc tattggtgcc taacttatct gaaaatcatg   540
gaacatgagg ctagtttgat catggtttag ttcattgtga ttaataatgt atgatttagt   600
agctattttg tgatcgtgtg cattttattt tgaatggaa tcattgtatg taaatgaagc   660
tagttcaggg gttacgatgt agctggcttt gtattctaaa ggctgctatt attcatccat   720
cgatttcacc tatatgtaat ccagagcttt tgatgtgaaa tttgtctgat ccttcactag   780
gaaggacaga acattgttaa tattttggca catctgtctt attctcatcc tttgtttgaa   840
catgttagcc tgttcaaaca gatactgttg taatgtccta gttatatagg tacatatgtg   900
ttctctattg agtttatgga cttttgtgtg tgaagttata tttcattttg ctcaaaactc   960
atgtttgcaa gctttctgac attattctat tgttctgaaa caggqt                  1006
```

| SEQ ID NO: 121 | moltype = DNA length = 2625 |
|---|---|
| FEATURE | Location/Qualifiers |
| source | 1..2625 |
| | mol_type = other DNA |

```
                        organism = Setaria italica
SEQUENCE: 121
actgccgcga cacgcctcac tggcgggagg gctccgagcg ctctctcccc ggcggccggc    60
ggagcagcga tctggattgg agagaataga ggaaagagag ggaaaggag agagatagcg    120
caaagagctg aaaagataag gttgtgcggg ctgtggtga tagaggacca ctaatccctc    180
catctcctaa tgacgcggtg cccaagacca gtgccgcggc acaccagcgt ctaagtgaac   240
ttccgctaac cttccggtca ttgcgcctga aagatgtcat gtggcgaggc ccccctctca   300
gtagattgcc aactgcctac cgtgccactc ttccatgcat gattgctccc gtctatcccg   360
tttctcacaa cagatagaca acagtaagca tcactaaagc aagcatgtgt agaaccttaa   420
aaaaaggctt atactaccag tatactatca accagcatgc cgttttttgaa gtatccagga   480
ttagaagctt ctactgcgct tttatattat agctgtggac ccgtggtaac ctttctcttt   540
tggcgcttgc ttaatctcgg ccgtgctggt ccatgcttag gcactaggca gagatagagc   600
cggggggtgaa tggggctaaa gctcagctgc tcgagggggcc gtgggctggt ttccactagc   660
ctacagctgt gccacgtgcg gccgcgcaag ccgaagcaag cacgctgagc cgttggacag   720
cttgtcataa tgccattacg tggattacac gtaactggcc ctgtaactac tcgttcggcc   780
atcatcaaac gacgacgtcc gctaggcgac gacacgggta atgcacgcag ccacccaggc   840
gcgcgcgcta gcggagcacg tcaggtgac acgggcgtcg tgacgcttcc gagttgaagg   900
ggttaacgcc agaaacagtg tttggccagg gtatgaacat aacaaaaaat attcacacga   960
aagaatggaa gtatgagagct gctactgtgt aaatgccaag caggaaactc acgcccgcta  1020
acatccaacg gccaacagct cgacgtgccg gtcagcagaga catcggaaca ctggtgattg  1080
gtggagccga cagtatgcgc cccagcacgg ccgaggtggt ggtggcccgt ggccctgctg  1140
tctgcgacac tcgggacaac ttgaaactgg gccaccgcct cgtcgcaact cgcaacccgt  1200
tggcggaaga aaggaatggc tcgtagggggc ccgggtagaa tcgaagaatg ttgcgctggg  1260
cttcgattca cataacatgg gcctgaagct ctaaaacgac ggcccggtcg ccgcgcgatg  1320
gaaagagacc ggatcctcct cgtgaattct ggaaggccac acgagagcga cccaccaccg  1380
acgcggagga gtcgtgcgtg gtccaacacg gccggcgggc tgggctgcga ccttaaccag  1440
caaggcacgc cacgacccgc cccgccctcg aggcataaat accctcccat cccgttgccg  1500
caagactcag atcagattcc gatccccagt tcttccccaa tcaccttgtg gtctctcgtg  1560
tcgcggttcc cagggacgcc tccggctcgt cgctcgacag cgatctccgc cccagcaagg  1620
tatagattca gttccttgct ccgatcccaa tctggttgga atgttgctcc gatgcgactt  1680
gattatgtca tatatctgcg gtttgcaccg atctgaagcc tagggttttct cgagcgaccc  1740
agttatttgc aatttgcgat ttgctcgttt gttgcgcagc gtagtttatg tttggagtaa  1800
tcgaggattt gtatgcggcg tcggcgctac ctgcttaatc acgccatgtg acgcggttac  1860
ttgcagaggc tgggttctgt tatgtcgtga tctaagaatc tagattaggc tcagtcgttc  1920
ttgctgtcga ctagtttgtt ttgatatcca tgtagtaca agttacttaa aatttaggtc   1980
aatatatttt gcatgctttt ggcctgttat tcttgccaac aagttgtcct ggtaaaaagt  2040
agatgtgaaa gtcacgtatt gggacaaatt gatggtttag tgctatagtt ctatagttct  2100
gtgatacatc tatctgattt ttttttggtct attggtgcct aacttatctg aaaatcatgg  2160
aacatgagc tagtttgatc atggtttagt tcattgtga ttaataatgt atgatttagt    2220
gctatttttgg tgatcgtgtc atttttattt tgaatggaat cattgtatgt aaatgaagct  2280
agttcagggg ttacgatgta gctggctttg tattctaaag gctgctatta ttcatccatc  2340
gatttcacct atatgtaatc cagagctttt gatgtgaaat ttgtctgatc cttcactagg  2400
aaggacagaa cattgttaat attttggcac atctgtctta ttctcatcct ttgtttgaac  2460
atgttagcct gttcaaacag atactgttgt aatgtcctag ttatataggt acatatgtgt  2520
tctctattga gtttatggac ttttgtgtgt gaagttatat ttcattttgc tcaaaactca  2580
tgtttgcaag ctttctgaca ttattctatt gttctgaaac agacc             2625

SEQ ID NO: 122           moltype = DNA   length = 1006
FEATURE                  Location/Qualifiers
source                   1..1006
                         mol_type = other DNA
                         organism = Setaria italica
SEQUENCE: 122
gtatagattc agttccttgc tccgatccca atctggttga gatgttgctc cgatgcgact    60
tgattatgtc atatatctgc ggtttgcacc gatctgaagc ctaggggttc tcgagcgacc   120
cagttatttg caatttgcga tttgctcgtt tgttgcgcag cgtagtttat gtttggagta   180
atcgaggatt tgtatgcggc gtcggcgcta cctgcttaat cacgccatgt gacgcggtta   240
cttgcagagg ctgggttctg ttatgtcgtg atctaagaat ctagattagg ctcagtcgtt   300
cttgctgtcg actagtttgt tttgatatcc atgtagtaca agttacttaa aatttaggtc   360
caatatatttt tgcatgcttt tggcctgtta ttcttgccaa caagttgtcc tggtaaaaag   420
tagatgtgaa agtcacgtat tgggacaaat tgatggttta gtgctatagt tctatagttc   480
tgtgatacat ctatctgatt ttttttggtc tattggtgcc taacttatct gaaaatcatg   540
gaacatgagc tagtttgat catggtttag ttcattgtga ttaataatgt atgatttagt   600
agctattttg gtgatcgtgt catttttattt tgaatggatg cattgtatg taaatgaagct   660
tagttcaggg gttacgatgt agctggctt tgtattctaaa ggctgctatt attcatccat   720
cgatttcacc tatatgtaat ccagagcttt tgatgtgaaa tttgtctgat ccttcactag   780
gaaggacaga acattgttaa tattttggca catctgtctt attctcatcc tttgtttgaa   840
catgttagcc tgttcaaaca gatactgttg taatgtccta gttatatagg tacatatgtg   900
ttctctattg agtttatgga cttttgtgtg tgaagttata tttcattttg ctcaaaactc   960
atgtttgcaa gctttctgac attattctat tgttctgaaa cagacc               1006

SEQ ID NO: 123           moltype = DNA   length = 2167
FEATURE                  Location/Qualifiers
source                   1..2167
                         mol_type = other DNA
                         organism = Setaria italica
SEQUENCE: 123
gccgtttttg aagtatccag gattagaagc ttctactgcg cttttatatt atagctgtgg    60
acctgtggta acctttctct tttggcgctt gcttaatctc ggccgtgctg gtccatgctt   120
```

```
aggcactagg cagagataga gccggggtg aatggggcta aagctcagct gctcgagggg    180
ccgtgggctg gtttccacta gcctacagct gtgccacgtg cggccgcgca agccgaagca    240
agcacgctga gccgttggac agcttgtcat aatgccatta cgtggattac acgtaactgg    300
ccctgtaact actcgttcgg ccatcatcaa acgacgacgt ccgctaggcg acgacacggg    360
taatgcacgc agccacccag gcgcgcgcgc tagcggagca cggtcaggtg acacgggcgt    420
cgtgacgctt ccgagttgaa gggggttaacg ccagaaacag tgtttggcca gggtatgaac    480
ataacaaaaa atattcacac gaaagaatgg aagtatggag ctgctactgt gtaaatgcca    540
agcaggaaac tcacgcccgc taacatccaa cggccaacag ctcgacgtgc cggtcagcag    600
agcatcggaa cactggtgat tggtggagcc ggcagtatgc gcccagcac ggccgaggtg     660
gtggtgggcc gtggccctgc tgtctgcgcg gctcgggaca acttgaaact gggccaccgc    720
ctcgtcgcaa ctcgcaaccc gttggcgaa gaaaggaatg gctcgtaggg gcccgggtag     780
aatcgaagaa tgttgcgctg ggcttcgatt cacataacat gggcctgaag ctctaaaacg    840
acggcccggt cgccgcgcga tggaaagaga ccggatcctc ctcgtgaatt ctggaaggcc    900
acacgagagc gaccaccacc cgacgcggag gagtcgtgcg tggtccaaca cggccggcgg    960
gctgggctgc gaccttaacc agcaaggcac gccacgaccc gccccgcct cgaggcataa    1020
ataccctccc atcccgttgc cgcaagactc agatcagatt ccgatcccca gttcttcccc    1080
aatcaccttg tggtctctcg tgtcgcggtt cccagggacg cctccggctc gtcgctcgac    1140
agcgatctcc gccccagcaa ggtatagatt cagttccttg ctccgatccc aatctggttg    1200
agatgttgct ccgatgcgac ttgattatgt catatatctg cggtttgcac cgatctgaag    1260
cctaggtttt ctcgagcgac ccagttattt gcaatttgcg atttgctcgt ttgttgcgca    1320
gcgtagttta tgtttggagt aatcgaggat ttgtatgcgg cgtcggcgct acctgcttaa    1380
tcacgccatg tgacgcggtt acttgcagag gctgggtcct gttatgtcgt gatctaagaa    1440
tctagattag gctcagtcgt tcttgctgtc gactagtttg ttttgatatc catgtagtac    1500
aagttactta aaatttaggt ccaatatatt ttgcatgctt ttggcctgtt attcttgcca    1560
acaagttgtc ctggtaaaaa gtagatgtga aagtcacgta ttgggacaaa ttgatggttt    1620
agtgctatag ttctatagtt ctgtgataca tctatctgat tttttttttggt ctattggtgc  1680
ctaacttatc tgaaaatcat ggaacatgag gctagtttga tcatggttta gttcattgtg    1740
attaataatg tatgatttag tagctatttt ggtgatcgtg tcatttttatt tgtgaatgga    1800
atcattgtat gtaaatgaag ctagttcagg ggttacgatg tagctggctt tgtattctaa    1860
aggctgctat tattcatcca tcgatttcac ctatatgtaa tccagagctt ttgatgtgaa    1920
atttgtctga tccttcacta ggaaggacag aacattgtta atattttggc acatctgtct    1980
tattctcatc ctttgtttga acatgttagc ctgttcaaac agatactgtt gtaatgtcct    2040
agttatatag gtacatatgt gttctctatt gagtttatgg acttttgtgt gtgaagttat    2100
atttcatttt gctcaaaact catgtttgca agctttctga cattattcta ttgttctgaa    2160
acaggtg                                                              2167
```

SEQ ID NO: 124         moltype = DNA   length = 1813
FEATURE                Location/Qualifiers
source                 1..1813
                       mol_type = other DNA
                       organism = Setaria italica
SEQUENCE: 124

```
cacgggtaat gcacgcagcc acccaggcgc gcgcgctagc ggagcacggt caggtgacac     60
gggcgtcgtg acgcttccga gttgaagggg ttaacgccag aaacagtgtt tggccagggt   120
atgaacataa caaaaatat tcacacgaaa gaatggaagt atggagctgc tactgtgtaa    180
atgccaagca ggaaactcac gcccgctaac atccaacggc caacagctcg acgtgccggt    240
cagcagagca tcggaacact ggtgattggt ggagccggca gtatgcgcac cagcacggcc    300
gaggtggtgg tggcccgtgg ccctgctgtc tgcgcggctc gggacaactt gaaactgggc    360
caccgcctcg tcgcaactcg caacccgttg gcggaagaaa ggaatggctc gtaggggccc    420
gggtagaatc gaagaatgtt gcgctgggct tcgattcaca taacatgggc ctgaagctct    480
aaaacgaccc ggtcgcc gcgcgatgga aagagacggg atcctcctcg tgaattctga     540
aaggccacac gagagcgacc caccaccgac gcggaggagt cgtgcgtggt ccaacacggc    600
cggcgggctg ggctgcgacc ttaaccagca aggcacgcca cgacccgccc cgccctcgag    660
gcataaatac cctcccatcc cgttgccgca agactcagat cagattccga tccccagttc    720
ttcccaatc accttgtggt ctctcgtgtc gcggttccca gggacgcctc cggctcgtc    780
ctcgacagcg atctccgccc cagcaaggta tagattcagt tccttgctcc gatcccaatc    840
tggttgagat gttgctccga tgcgacttga ttatgtcata tatctgcggt ttgcaccgat    900
ctgaagccta gggtttctcg agcgacccag ttatttgcaa tttgcgattt gctcgtttgt    960
tgcgcagcgt agtttatgtt tggagtaatc gaggatttgt atgcggcgtc ggcgctacct   1020
gcttaatcac gccatgtgac gcggttactt gcagaggctg ggttctgtta tgtcgtgatc   1080
taagaatcta gattaggctc agtcgttctt gctgtcgact agtttgtttt gatatccatg   1140
tagtacaagt tacttaaaat ttaggtccaa tatattttgc atgcttttgg cctgttattc   1200
ttgccaacaa gttgtcctgg taaaaagtag atgtgaaagt cacgtattgg gacaaattga   1260
tggttagtg ctatagttct atagttctgt gatacatcta tctgattttt ttttggtgc    1320
tggtgcctaa cttatctgaa aatcatggaa catgaggcta gtttgatcat ggtttagttc   1380
attgtgatta ataatgtatg atttagtagc tattttggtg atcgtgtcat tttatttgtg   1440
aatggaatca ttgtatgtaa atgaagctag ttcaggggtt acgatgtagc tggctttgta   1500
ttctaaaggc tgctattatt catccatcga tttcacctat atgtaatcca gagcttttga   1560
tgtgaaattt gtctgatcct tcactaggaa ggacagaaca tgttaatat tttggcacat   1620
ctgtcttatt ctcatccttt gtttgaacat gttagcctgt tcaaacagat actgttgtaa   1680
tgtcctagtt atataggtac atatgtgttc tctattgagt ttatggactt ttgtgtgtga   1740
agttatattt cattttgctc aaaactcatg tttgcaagct ttctgacatt attctattgt   1800
tctgaaacag gtg                                                      1813
```

SEQ ID NO: 125         moltype = DNA   length = 1813
FEATURE                Location/Qualifiers
source                 1..1813
                       mol_type = other DNA
                       organism = Setaria italica -continued

```
SEQUENCE: 125
cacgggtaat gcacgcagcc acccaggcgc gcgcgctagc ggagcacggt caggtgacac    60
gggcgtcgtg acgcttccga gttgaagggg ttaacgccag aaacagtgtt tggccagggt   120
atgaacataa caaaaatat tcacacgaaa gaatggaagt atggagctgc tactgtgtaa    180
atgccaagca ggaaactcac gcccgctaac atccaacggc caacagctcg acgtgccggt   240
cagcagagca tcggaacact ggtgattggt ggagccggca gtatgcgccc cagcacgggc   300
gaggtggtgg tggcccgtgg ccctgctgtc tgccgggctc gggacaactt gaaactgggc   360
caccgcctcg tcgcaactcg caacccgttg gcggaagaaa ggaatggctc gtaggggccc   420
gggtagaatc gaagaatgtt gcgctgggct tcgattcaca taacatgggc ctgaagctct   480
aaaacgacgg cccggtcgcc gcgcgatgga aagagaccgg atcctcctcg tgaattctgg   540
aaggccacac gagagcgacc caccaccgac gcggaggagt cgtgcgtggt ccaacacggc   600
cggcgggctg ggctgcgacc ttaaccagca aggcacgcca cgacccgccc cgccctcgag   660
gcataaatac cctcccatcc cgttgccgca agactcagat cagattccga tcccccagttc 720
ttccccaatc accttgtggt ctctcgtgtc gcggttccca gggacgcctc cggctcgtcg   780
ctcgacagcg atctccgccc cagcaaggta tagattcagt tccttgctcc gatcccaatc   840
tggttgagat gttgctccga tgcgacttga ttatgtcata tatctgcggt ttgcaccgat   900
ctgaagccta gggtttctcg agcgacccag ttatttgcaa tttgcgattt gctcgtttgt   960
tgcgcagcgt agtttatgtt tggagtaatc gaggattgt atgcggcgtc ggcgctacct   1020
gcttaatcac gccatgtgac gcggttactt gcagaggctg ggttctgtta tgtcgtgatc   1080
taagaatcta gattaggctc agtcgttctt gctgtcgact agtttgttt gatatccatg    1140
tagtacaagt tacttaaaat ttaggtccaa tatattttgc atgcttttgg cctgttattc   1200
ttgccaacaa gttgtcctgg taaaaagtag atgtgaaagt cacgtattgg gacaaattga   1260
tggtttagtg ctatagttct atagttctgt gatacatcta tctgattttt tttggtctat   1320
tggtgcctaa cttatctgaa aatcatggaa catgaggcta gtttgatcat ggtttagttc   1380
attgtgatta ataatgtatg attttagtagc tattttggtg atcgtgtcat tttatttgtg   1440
aatggaatca ttgtatgtaa atgaagctag ttcaggggtt acgatgtagc tggcttttga   1500
ttctaaaggc tgctattatt catccatcga tttcacctat atgtaatcca gagctttga    1560
tgtgaaattt gtctgatcct tcactaggaa ggacagaaca ttgttaatat tttggcacat   1620
ctgtcttatt ctcatccttt gtttgaacat gttagcctgt tcaaacagat actgttgtaa   1680
tgtcctagtt atataggtac atatgtgttc tctattgagt ttatgactt ttgtgtgtga    1740
agtatatttt cattttgctc aaaactcatg tttgcaagct ttctgacatt attctattgt   1800
tctgaaacag ggt                                                      1813
```

```
SEQ ID NO: 126          moltype = DNA  length = 1813
FEATURE                 Location/Qualifiers
source                  1..1813
                        mol_type = other DNA
                        organism = Setaria italica
SEQUENCE: 126
cacgggtaat gcacgcagcc acccaggcgc gcgcgctagc ggagcacggt caggtgacac    60
gggcgtcgtg acgcttccga gttgaagggg ttaacgccag aaacagtgtt tggccagggt   120
atgaacataa caaaaatat tcacacgaaa gaatggaagt atggagctgc tactgtgtaa    180
atgccaagca ggaaactcac gcccgctaac atccaacggc caacagctcg acgtgccggt   240
cagcagagca tcggaacact ggtgattggt ggagccggca gtatgcgccc cagcacgggc   300
gaggtggtgg tggcccgtgg ccctgctgtc tgccgggctc gggacaactt gaaactgggc   360
caccgcctcg tcgcaactcg caacccgttg gcggaagaaa ggaatggctc gtaggggccc   420
gggtagaatc gaagaatgtt gcgctgggct tcgattcaca taacatgggc ctgaagctct   480
aaaacgacgg cccggtcgcc gcgcgatgga aagagaccgg atcctcctcg tgaattctgg   540
aaggccacac gagagcgacc caccaccgac gcggaggagt cgtgcgtggt ccaacacggc   600
cggcgggctg ggctgcgacc ttaaccagca aggcacgcca cgacccgccc cgccctcgag   660
gcataaatac cctcccatcc cgttgccgca agactcagat cagattccga tcccccagttc 720
ttccccaatc accttgtggt ctctcgtgtc gcggttccca gggacgcctc cggctcgtcg   780
ctcgacagcg atctccgccc cagcaaggta tagattcagt tccttgctcc gatcccaatc   840
tggttgagat gttgctccga tgcgacttga ttatgtcata tatctgcggt ttgcaccgat   900
ctgaagccta gggtttctcg agcgacccag ttatttgcaa tttgcgattt gctcgtttgt   960
tgcgcagcgt agtttatgtt tggagtaatc gaggattgt atgcggcgtc ggcgctacct   1020
gcttaatcac gccatgtgac gcggttactt gcagaggctg ggttctgtta tgtcgtgatc   1080
taagaatcta gattaggctc agtcgttctt gctgtcgact agtttgttt gatatccatg    1140
tagtacaagt tacttaaaat ttaggtccaa tatattttgc atgcttttgg cctgttattc   1200
ttgccaacaa gttgtcctgg taaaaagtag atgtgaaagt cacgtattgg gacaaattga   1260
tggtttagtg ctatagttct atagttctgt gatacatcta tctgattttt tttggtctat   1320
tggtgcctaa cttatctgaa aatcatggaa catgaggcta gtttgatcat ggtttagttc   1380
attgtgatta ataatgtatg attttagtagc tattttggtg atcgtgtcat tttatttgtg   1440
aatggaatca ttgtatgtaa atgaagctag ttcaggggtt acgatgtagc tggcttttga   1500
ttctaaaggc tgctattatt catccatcga tttcacctat atgtaatcca gagctttga    1560
tgtgaaattt gtctgatcct tcactaggaa ggacagaaca ttgttaatat tttggcacat   1620
ctgtcttatt ctcatccttt gtttgaacat gttagcctgt tcaaacagat actgttgtaa   1680
tgtcctagtt atataggtac atatgtgttc tctattgagt ttatgactt ttgtgtgtga    1740
agtatatttt cattttgctc aaaactcatg tttgcaagct ttctgacatt attctattgt   1800
tctgaaacag ggc                                                      1813
```

```
SEQ ID NO: 127          moltype = DNA  length = 1006
FEATURE                 Location/Qualifiers
source                  1..1006
                        mol_type = other DNA
                        organism = Setaria italica
SEQUENCE: 127
gtatagattc agttccttgc tccgatccca atctggttga gatgttgctc cgatgcgact    60
tgattatgtc atatatctgc ggtttgcacc gatctgaagc ctaggggttc tcgagcgacc   120
```

```
cagttatttg caatttgcga tttgctcgtt tgttgcgcag cgtagtttat gtttggagta    180
atcgaggatt tgtatgcggc gtcggcgcta cctgcttaat cacgccatgt gacgcggtta    240
cttgcagagg ctgggttctg ttatgtcgtg atctaagaat ctagattagg ctcagtcgtt    300
cttgctgtcg actagtttgt tttgatatcc atgtagtaca agttacttaa aatttaggtc    360
caatatattt tgcatgcttt tggcctgtta ttcttgccaa caagttgtcc tggtaaaaag    420
tagatgtgaa agtcacgtat tgggacaaat tgatggttta gtgctatagt tctatagttc    480
tgtgatacat ctatctgatt ttttttggtc tattggtgcc taacttatct gaaaatcatg    540
gaacatgagg ctagtttgat catggtttag ttcattgtga ttaataatgt atgatttagt    600
agctattttg gtgatcgtgt cattttattt gtgaatggaa tcattgtatg taaatgaagc    660
tagttcaggg gttacgatgt agctggcttt gtattctaaa ggctgctatt attcatccat    720
cgatttcacc tatatgtaat ccagagcttt tgatgtgaaa tttgtctgat ccttcactag    780
gaaggacaga acattgttaa tattttggca catctgtctt attctcatcc tttgtttgaa    840
catgttagcc tgttcaaaca gatactgttg taatgtccta gttatatagg tacatatgtg    900
ttctctattg agtttatgga cttttgtgtg tgaagttata tttcattttg ctcaaaactc    960
atgtttgcaa gctttctgac attattctat tgttctgaaa cagggc                  1006

SEQ ID NO: 128         moltype = DNA  length = 2634
FEATURE                Location/Qualifiers
source                 1..2634
                       mol_type = other DNA
                       organism = Setaria viridis
SEQUENCE: 128
actgccgcga cacgcctcac tggcgggagg gctccgagcg ctctctcccc ggcggccggc     60
ggagcagcga tctggattgg agagaataga ggaaagagag ggaaaaggag agagatagcg    120
caaagagctg aaaagataag gttgtgcggg ctgtggtgat tagaggacca ctaatccctc    180
catctcctaa tgacgcggtg cccaagacca gtccgcggcc acaccagcgt ctaagtgaac    240
ttccgctaac cttccggtca ttgcgcctga aagatgtcat atggcgaggc cccctctca    300
gtagattgcc aactgcctac cgtgccactc ttccatgcat gattgctccc gtctatcccg    360
tttctcacaa cagatagaca acagtaagca tcactaaagc aagcatgtgt agaaccttaa    420
aaaaaggctt atactaccag tatactatca accagcatgc cgtttttgaa gtatccagga    480
ttagaagctt ctactgcgct tttatattat agctgtggac ctgtggtaac ctttctcttt    540
tggcgcttgc ttaatctcgg ccgtgctggt ccatgcttag gcactaggca gagatagagc    600
cggggggtgaa tggggctaaa gctcagctgc tcgaggggcc gtgggctggt ttccactagc    660
ctacagctgt gccacgtgcg gccgcgcaag ccgaagcaag cacgctgagc cgttggacga    720
cttgtcataa tgccattacg tggattacag gtaactgcc ctgtaactac tcgttcggcc    780
atcatcaaac gacgacgtcc gctaggcgac gacacgggta atgcacgcag ccacccaggc    840
gcgcgcgcta gcggagcacg gtcaggtgac acgggcgtcg tgacgcttcc gagttgaagg    900
ggttaacgcc agaaacagtg tttggccagg gtatgaacat aacaaaaaat attcacacga    960
aagaatggaa gtatggagct gctactgtgt aaatgccaag caggaaactc acgcccgcta   1020
acatccaacg gccaacagct cgacgtgccg gtcagcagag acatcggaac actggtgatt   1080
ggtggagccg gcagtatgcg ccccagcacg gccgaggtgg tggtgcccg tggccctgct   1140
gtctgcgcgg ctcgggacaa cttgaaactg ggccaccgcc tcgtcgcaac tcgcaacccg   1200
ttggcggaag aaaggaatgg ctcgtagggg cccgggtaga atccaagaat gtgcgctgg   1260
gcttcgattc acataacatg ggcctgaagc tctaaaacga cggcccgtc accgggcgat   1320
ggaaagagac cggatcctcc tcgtgaattc tggaaggcca cacagagcg acccaccacc   1380
gacgcggagg agtcgtgcgt ggtccaacac ggccggcggg ctgggctgcg accttaacca   1440
gcaaggcacg ccacgacccg cctcgccctc gaggcataaa taccctccca tcccgttgcc   1500
gcaagactca gatcagattc cgatcccag ttcttcccca atcaccttgt ggtctctcgt   1560
gtcgcggttc ccaggacgc ctccggctcg tcgctcgaca gcgatctccg ccccagcaag   1620
gtatagattc agttccttgc tccgatccca atctggttga gatgttgctc cgatgcgact   1680
tgattatgtc atatatctgc ggtttgcacc gatctgaagc ctagggtttc tcgagcgacc   1740
cagttgtttg caatttgcga tttgctcgtt tgttgcgcat cgtagtttat gtttggagta   1800
atcgaggatt tgtatgcggc gtcggcgcta cctgcttaat cacgccatgt gacgcggtta   1860
cttgcagagg ctgggttagt gggttctgtt atgtcgtgat ctaagaatct agattaggct   1920
cagtcgttct tgctgtcgac tagtttgttt tgatatccat gtagtacaag ttacttaaaa   1980
tttaggtcca atatattttg catgcttttg gcctgttatt cttgccaaca agttgtcctg   2040
gtaaaaagta gatgtgaaag tcacgtattg ggacaaattg atggttaagt gctatagttc   2100
tatagttctg tgatacatct atctgatttt ttttggtcta ttggtgccta acttatctga   2160
aaatcatgga acatgaggct agtttgatca tggtttagtt cattgtgatt aataatgtat   2220
gatttagtag ctatttttgg gtgatcgtgtca ttttattgt gaatggaatc attgtatgta   2280
aatgaagcta gttcagggt tatgatgtag ctggctttgt attctaaagg ctgctattat   2340
tcatccatcg atttcaccta tatgtaatcc agagctttcg atgtgaaatt tgtctgatcc   2400
ttcactagga aggacagaac attgttaata ttttggcaca tctgtcttat tctcatcctt   2460
tgtttgaaca tgttagcctg ttcaaacaga tactgttgta atgtcctagt tatataggta   2520
catatgtgtt ctctattgag tttatggact tttgtgtgtg aagttatatt tcattttgct   2580
caaaactcat gtttgcaagc tttctgacat tattctattg ttctgaaaca ggtg          2634

SEQ ID NO: 129         moltype = DNA  length = 1014
FEATURE                Location/Qualifiers
source                 1..1014
                       mol_type = other DNA
                       organism = Setaria viridis
SEQUENCE: 129
gtatagattc agttccttgc tccgatccca atctggttga gatgttgctc cgatgcgact     60
tgattatgtc atatatctgc ggtttgcacc gatctgaagc ctagggtttc tcgagcgacc    120
cagttgtttg caatttgcga tttgctcgtt tgttgcgcat cgtagtttat gtttggagta    180
atcgaggatt tgtatgcggc gtcggcgcta cctgcttaat cacgccatgt gacgcggtta    240
cttgcagagg ctgggttagt gggttctgtt atgtcgtgat ctaagaatct agattaggct    300
cagtcgttct tgctgtcgac tagtttgttt tgatatccat gtagtacaag ttacttaaaa    360
```

```
tttaggtcca atatattttg catgcttttg gcctgttatt cttgccaaca agttgtcctg  420
gtaaaaagta gatgtgaaag tcacgtattg gacaaattg  atggttaagt gctatagttc  480
tatagttctg tgatacatct atctgatttt ttttggtcta ttggtgccta acttatctga  540
aaatcatgga acatgaggct agtttgatca tggtttagtt cattgtgatt aataatgtat  600
gatttagtag ctattttggt gatcgtgtca ttttatttgt gaatggaatc attgtatgta  660
aatgaagcta gttcagggt  tatgatgtag ctggctttgt attctaaagg ctgctattat  720
tcatccatcg atttcaccta tatgtaatcc agagctttcg atgtgaaatt tgtctgatcc  780
ttcactagga aggacagaac attgttaata ttttggcaca tctgtcttat tctcatcctt  840
tgtttgaaca tgttagcctg ttcaaacaga tactgttgta atgtcctagt tatataggta  900
catatgtgtt ctctattgag tttatggact tttgtgtgtg aagttatatt tcattttgct  960
caaaactcat gtttgcaagc tttctgacat tattctattg ttctgaaaca ggtg         1014

SEQ ID NO: 130       moltype = DNA  length = 2634
FEATURE              Location/Qualifiers
source               1..2634
                     mol_type = other DNA
                     organism = Setaria viridis
SEQUENCE: 130
actgccgcga cacgcctcac tggcgggagg gctccgagcg ctctctcccc ggcggccggc   60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcgcc acaccagcgt ctaagtgaac  240
ttccgctaac cttccggtca ttgcgcctga aagatgtcat gtggcgaggc cccctctca   300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagctgcc cgttttgaa  gtatccagga  480
ttagaagctt ctactgcgct tttatattat agctgtggac ctgtggtaac cttctcttt   540
tggcgcttgc ttaatctcgg ccgtgctggt ccatgcttag gcactaggca gagatagagc  600
cgggggtgaa tgggctaaa  gctcagctgc tcgaggggcc gtgggctggt ttccactagc  660
ctacagctgt gccacgtgcg gccgcgcaag ccgaagcaag cacgctgagc cgttggacag  720
cttgtcataa tgccattacg tggattacag gtaactggcc ctgtaactac tcgttcggcc  780
atcatcaaac gacgacgtcc gctaggcgac gacacgggta atgcacgcag ccacccaggc  840
gcgcgcgcta gcggagcacg tcaggtgac  acgggcgtcg tgacgcttcc gagttgaagg  900
ggtaacgcc  agaaacagtg tttggccagg gtatgaacat aacaaaaaat attcacacga  960
aagaatggaa gtatggagct gctactgtgt aaatgccaag caggaaactc acgcccgcta 1020
acatccaacg gccaacagct cgacgtgccg gtcagcagag acatcggaac actggtgatt 1080
ggtggagccg gcagtatgcg ccccagcacg gccgaggtgg tggtgcccg  tggcctgct  1140
gtctgcgcgg ctcgggacaa cttgaaactg gccaccgcc  tcgtcgcaac tcgcaacccg 1200
ttggcggaag aaaggaatgg ctcgtagggg cccgggtaga atccaagaat gttgcgctgg 1260
gcttcgattc acataacatg ggcctgaagc tctaaaacga cggcccgtc  accgggcgat 1320
ggaaagagac cggatcctcc tcgtgaattc tggaaggcca cacgagagcg acccaccacc 1380
gacgcggagg agtcgtgcgt ggtccaacac ggccggcggg ctgggctgcg accttaacca 1440
gcaaggcacg ccacgacccg cctcgccctc gaggcataaa taccctccca tcccgttgtg 1500
gcaagactca gatcagattc cgatcccag  ttcttcccca atcaccttgt ggtctctcgt 1560
gtcgcggttc ccaggacgc  ctccggctcg tcgtcgaca  gcgatctccg ccccagcaag 1620
gtatagattc agttccttgc tccgatccca atctggttga gatgttgctc cgatgcgact 1680
tgattatgtc atatatctgc ggtttgcacc gatctgaagc ctagggtttc tcgagcgacc 1740
cagttgtttg caatttgcga tttgctcgtt tgttgcgcat cgtagtttat gtttggagta 1800
atcgaggatt tgtatgcggc gtcggcgcta cctgcttaat cacgccatgt gacgcggtta 1860
cttgcagagg ctgggttagt gggttctgtt atgtcgtgat ctaagaatct agattaggct 1920
cagtcgttct tgctgtcgac tagtttgttt tgatatccat gtagtacaag ttacttaaaa 1980
tttaggtcca atatattttg catgcttttg gcctgttatt cttgccaaca agttgtcctg 2040
gtaaaaagta gatgtgaaag tcacgtattg gacaaattg  atggttaagt gctatagttc 2100
tatagttctg tgatacatct atctgatttt ttttggtcta ttggtgccta acttatctga 2160
aaatcatgga acatgaggct agtttgatca tggtttagtt cattgtgatt aataatgtat 2220
gatttagtag ctattttggt gatcgtgtca ttttatttgt gaatggaatc attgtatgta 2280
aatgaagcta gttcagggt  tatgatgtag ctggctttgt attctaaagg ctgctattat 2340
tcatccatcg atttcaccta tatgtaatcc agagctttcg atgtgaaatt tgtctgatcc 2400
ttcactagga aggacagaac attgttaata ttttggcaca tctgtcttat tctcatcctt 2460
tgtttgaaca tgttagcctg ttcaaacaga tactgttgta atgtcctagt tatataggta 2520
catatgtgtt ctctattgag tttatggact tttgtgtgtg aagttatatt tcattttgct 2580
caaaactcat gtttgcaagc tttctgacat tattctattg ttctgaaaca gggt         2634

SEQ ID NO: 131       moltype = DNA  length = 1014
FEATURE              Location/Qualifiers
source               1..1014
                     mol_type = other DNA
                     organism = Setaria viridis
SEQUENCE: 131
gtatagattc agttccttgc tccgatccca atctggttga gatgttgctc cgatgcgact   60
tgattatgtc atatatctgc ggtttgcacc gatctgaagc ctagggtttc tcgagcgacc  120
cagttgtttg caatttgcga tttgctcgtt tgttgcgcat cgtagtttat gtttggagta  180
atcgaggatt tgtatgcggc gtcggcgcta cctgcttaat cacgccatgt gacgcggtta  240
cttgcagagg ctgggttagt gggttctgtt atgtcgtgat ctaagaatct agattaggct  300
cagtcgttct tgctgtcgac tagtttgttt tgatatccat gtagtacaag ttacttaaaa  360
tttaggtcca atatattttg catgcttttg gcctgttatt cttgccaaca agttgtcctg  420
gtaaaaagta gatgtgaaag tcacgtattg gacaaattg  atggttaagt gctatagttc  480
tatagttctg tgatacatct atctgatttt ttttggtcta ttggtgccta acttatctga  540
aaatcatgga acatgaggct agtttgatca tggtttagtt cattgtgatt aataatgtat  600
```

```
gatttagtag ctattttggt gatcgtgtca ttttatttgt gaatggaatc attgtatgta   660
aatgaagcta gttcagggggt tatgatgtag ctggctttgt attctaaagg ctgctattat   720
tcatccatcg atttcaccta tatgtaatcc agagctttcg atgtgaaatt tgtctgatcc   780
ttcactagga aggacagaac attgttaata ttttggcaca tctgtcttat tctcatcctt   840
tgtttgaaca tgttagcctg ttcaaacaga tactgttgta atgtcctagt tatataggta   900
catatgtgtt ctctattgag tttatggact tttgtgtgtg aagttatatt tcattttgct   960
caaaactcat gtttgcaagc tttctgacat tattctattg ttctgaaaca gggt         1014

SEQ ID NO: 132          moltype = DNA  length = 2176
FEATURE                 Location/Qualifiers
source                  1..2176
                        mol_type = other DNA
                        organism = Setaria viridis
SEQUENCE: 132
gccgttttttg aagtatccag gattagaagc ttctactgcg cttttatatt atagctgtgg   60
acctgtggta acctttctct tttggcgctt gcttaatctc ggccgtgctg gtccatgctt   120
aggcactagg cagagataga gccggggggtg aatgggggcta aagctcagct gctcgagggg   180
ccgtgggctg gtttccacta gcctacagct gtgccacgtg cggccgcgca agccgaagca   240
agcacgctga gccgttggac agcttgtcat aatgccatta cgtggattac aggtaactga   300
ccctgtaact actcgttcgg ccatcatcaa acgacgacgt ccgctaggcg acgacacggg   360
taatgcacgc agccacccag gcgcgcgcgc tagcggagca cggtcaggtg acacgggcgt   420
cgtgacgctt ccgagttgaa gggggttaacg ccagaaacag tgtttggccg ggtgatgaac   480
ataacaaaaa atattcacac gaaagaatgg aagtatggag ctgctactgt gtaaatgcca   540
agcaggaaac tcacgcccgc taacatccaa cggccaacag ctcgacgtgc cggtcagcag   600
agacatcgga acactggtga ttggtggagc cggcagtatg cgcccagca cggccgaggt    660
ggtggtggcc cgtggccctg tcgtctgcgc ggctcgggac aacttgaaac tgggccaccg   720
cctcgtcgca actcgcaacc cgttggcgga agaaaggaat ggctcgtagg ggcccggggta    780
gaatccaaga atgttgcgct gggcttcgat tcacataaca tgggcctgaa gctctaaaac   840
gacggccggg tcaccgggcg atggaaagag accggatcct cctcgtgaat tctggaaggc   900
cacacgagag cgacccacca ccgacgcgga ggagtcgtgc gtggtccaac acggccgggcg   960
ggctgggctg cgaccttaac cagcaaggca cgccacgacc cgcctcgccc tcgaggcata   1020
aataccctcc catcccgttg ccgcaagact cagatcagat tccgatcccc agttcttccc   1080
caatcacctt gtggtctctc gtgtcgcggt tcccaggggac gcctccggct cgtcgctcga   1140
cagcgatctc cgccccagca aggtatagat tcagttcctt gctccgatcc caatctggtt   1200
gagatgttgc tccgatgcga cttgattatg tcatatatct gcggtttgca ccgatctgga   1260
gcctaggggtt tctcgagcga cccagttgtt tgcaatttgc gatttgctcg tttgttgcgc   1320
atcgtagttt atgtttggag taatcgagga tttgatgcg cgtcggcgc tacctgctta    1380
atcacgccat gtgacgcgt tacttgcaga ggctgggtta gtgggttctg ttatgtcgtg    1440
atctaagaat ctagattagg ctcagtcgtt cttgctgtca actagtttgt tttgatatcc   1500
atgtagtaca agttacttaa aatttaggtc caatatattt tgcatgcttt tggcctgtta   1560
ttcttgccaa caagttgtcc tggtaaaaag tagatgtgaa agtcacgtat gggacaaat    1620
tgatggttaa gtgctatagt tctatagttc tgtgatacat ctatctgatt tttttttggtc   1680
tattggtgcc taacttatct gaaaatcatg gaacatgagg ctagtttgat catggttttag   1740
ttcattgtga ttaataatgt atgatttagt agctatttttg gtgatcgtgt cattttattt   1800
gtgaatggaa tcattgtatg taaatgaagc tagttcaggg gttatgatgt agctggcttt   1860
gtattctaaa ggctgctatt attcatccat cgatttcacc tatatgtaat ccagagcttt   1920
cgatgtgaaa tttgtctgat ccttcactag gaaggacaga acattgttaa tattttggca   1980
catctgtctt attctcatcc tttgtttgaa catgttagcc tgttcaaaca gatactgttg   2040
taatgtccta gttatatagg tacatatgtg ttctctattg agtttatgga cttttgtgtg   2100
tgaagttata tttcattttg ctcaaaactc atgtttgcaa gctttctgac attattctat   2160
tgttctgaaa caggtg                                                    2176

SEQ ID NO: 133          moltype = DNA  length = 1822
FEATURE                 Location/Qualifiers
source                  1..1822
                        mol_type = other DNA
                        organism = Setaria viridis
SEQUENCE: 133
cacgggtaat gcacgcagcc acccaggcgc gcgcgctagc ggagcacggt caggtgacac    60
gggcgtcgtg acgcttccga gttgaagggg ttaacgccag aaacagtgtt tggccaggggt   120
atgaacataa caaaaatat tcacacgaaa gaatggaagt atggagctgc tactgtgtaa    180
atgccaagca ggaaactcac gcccgctaac atccaacggc caacagctcg acgtgccggt   240
cagcagagac atcggaacac tggtgattgg tggagccggc agtatgcgcc ccagcacggc   300
cgaggtggtg gccccgtg gcccctgctgt tgcgcgcgcg cggggacaact tgaaactggg    360
ccaccgcctc gtcgcaactc gcaacccgtt ggcggaagaa aggaatggct cgtaggggcc   420
cgggtagaat ccaagaatgt tgcgctgggc ttcgattcac ataacatggg cctgaagctc   480
taaaacgacg gccggtcac cgggcgatgg aaagagaccg gatcctcctt gtgaattctg    540
gaaggccaca cgagagcgac ccaccaccga cgcggaggag tcgtgcgtgg tccaacacgg   600
ccggggcggct gggctgcgac cttaaccagc aaggcacgcc acgacccgcc tcgccctcga   660
ggcataaaata ccctcccatc ccgttgccgc aagactcaga tcagattccg atccccagtt   720
cttccccaat caccttgtgg tctctcgtgt cgcggttccc agggacgcct ccggctcgtc   780
gctcgacagc gatctccgcc ccagcaaggt atagattcag ttccttgctc cgatcccaat   840
ctggttgaga tgttgctccg atgcgacttg attatgtcat atatctgcgg tttgcaccga   900
tctgaagcct aggggtttctc gagcgaccca gttgtttgca atttgcgatt tgctcgtttg   960
ttgcgcatcg tagtttatgt ttggagtaat cgaggatttg atgcggcgt ggcgctacc    1020
tgcttaatca cgccatgtga cgcggttact tgcagaggct gggttagtgg ttcgtttat    1080
gtcgtgatct aagaatctag attaggctca gtcgttcttg ctgtcgacta gtttgtttttg   1140
atatccatgt agtacaagtt acttaaaatt taggtccaat atattttgca tgcttttggc   1200
ctgttattct tgccaacaag ttgtcctggt aaaaagtaga tgtgaaagtc acgtattggg   1260
```

```
acaaattgat ggttaagtgc tatagttcta tagttctgtg atacatctat ctgatttttt    1320
ttggtctatt ggtgcctaac ttatctgaaa atcatggaac atgaggctag tttgatcatg    1380
gtttagttca ttgtgattaa taatgtatga tttagtagct attttggtga tcgtgtcatt    1440
ttatttgtga atggaatcat tgtatgtaaa tgaagctagt tcaggggtta tgatgtagct    1500
ggctttgtat tctaaaggct gctattattc atccatcgat ttcacctata tgtaatccag    1560
agctttcgat gtgaaatttg tctgatcctt cactaggaag gacagaacat tgttaatatt    1620
ttggcacatc tgtcttattc tcatcctttg tttgaacatg ttagcctgtt caaacagata    1680
ctgttgtaat gtcctagtta tataggtaca tatgtgttct ctattgagtt tatggacttt    1740
tgtgtgtgaa gttatatttc attttgctca aaactcatgt ttgcaagctt tctgacatta    1800
ttctattgtt ctgaaacagg tg                                             1822

SEQ ID NO: 134           moltype = DNA   length = 1822
FEATURE                  Location/Qualifiers
source                   1..1822
                         mol_type = other DNA
                         organism = Setaria viridis
SEQUENCE: 134
cacgggtaat gcacgcagcc acccaggcgc gcgcgctagc ggagcacggt caggtgacac      60
gggcgtcgtg acgcttccga gttgaagggg ttaacgccag aaacagtgtt tggccagggt     120
atgaacataa caaaaaatat tcacacgaaa gaatggaagt atggagctgc tactgtgtaa     180
atgccaagca ggaaactcac gcccgctaac atccaacggc caacagctcg acgtgccggt     240
cagcagagac atcggaacac tggtgattgg tggagccggc agtatgcgcc ccagcacggc     300
cgaggtggtg gtggcccgtg gccctgctgt ctgcgcggct cgggacaact tgaaactggg     360
ccaccgcctc gtcgcaactc gcaacccgtt ggcggaagaa aggaatggct cgtaggggcc     420
cgggtagaat ccaagaatgt tgcgctgggc ttcgattcac ataacatggg cctgaagctc     480
taaaacgacg gcccggtcac cgggcgatgg aaagagaccg gatcctcctc gtgaattctg     540
gaaggccaca cgagagcgac ccaccaccga cgcggaggag tcgtgcgtgg tccaacacgg     600
ccggcgggct gggctgcgac cttaaccagc aaggcacgcc acgacccgcc tcgccctcga     660
ggcataaata ccctcccatc ccgttgccgc aagactcaga tcagattccg atccccagtt     720
cttcccaat caccttgtgg tctctcgtgt cgcggttccc agggacgacct tcggctcgtc     780
gctcgacagc gatctccgcc ccagcaaggt atagattcag ttccttgctc cgatcccaat     840
ctggttgaga tgttgctccg atgcgacttg attatgtcat atatctgcgg tttgcaccga     900
tctgaagcct agggtttctc gagcgaccca gttgtttgca atttgcgatt tgctcgtttg     960
ttgcgcatcg tagtttatgt ttggagtaat cgaggatttg tatgcggcgt cggcgctatc    1020
tgcttaatca cgccatgtga cgcggttact tgcagaggct gggttagtgg gttctgttat    1080
gtcgtgatct aagaatctag attaggctca gtcgttcttg ctgtcgacta gtttgttttg    1140
atatccatgt agtacaagtt acttaaaatt taggtccaat atattttgca tgcttttggc    1200
ctgttattct tgccaacaag ttgtcctggt aaaaagtaga tgtgaaagtc acgtattggg    1260
acaaattgat ggttaagtgc tatagttcta tagttctgtg atacatctat ctgatttttt    1320
ttggtctatt ggtgcctaac ttatctgaaa atcatggaac atgaggctag tttgatcatg    1380
gtttagttca ttgtgattaa taatgtatga tttagtagct attttggtga tcgtgtcatt    1440
ttatttgtga atggaatcat tgtatgtaaa tgaagctagt tcaggggtta tgatgtagct    1500
ggctttgtat tctaaaggct gctattattc atccatcgat ttcacctata tgtaatccag    1560
agctttcgat gtgaaatttg tctgatcctt cactaggaag gacagaacat tgttaatatt    1620
ttggcacatc tgtcttattc tcatcctttg tttgaacatg ttagcctgtt caaacagata    1680
ctgttgtaat gtcctagtta tataggtaca tatgtgttct ctattgagtt tatggacttt    1740
tgtgtgtgaa gttatatttc attttgctca aaactcatgt ttgcaagctt tctgacatta    1800
ttctattgtt ctgaaacagg tg                                             1822

SEQ ID NO: 135           moltype = DNA   length = 681
FEATURE                  Location/Qualifiers
source                   1..681
                         mol_type = other DNA
                         organism = Setaria viridis
SEQUENCE: 135
cacgggtaat gcacgcagcc acccaggcgc gcgcgctagc ggagcacggt caggtgacac      60
gggcgtcgtg acgcttccga gttgaagggg ttaacgccag aaacagtgtt tggccagggt     120
atgaacataa caaaaaatat tcacacgaaa gaatggaagt atggagctgc tactgtgtaa     180
atgccaagca ggaaactcac gcccgctaac atccaacggc caacagctcg acgtgccggt     240
cagcagagac atcggaacac tggtgattgt tggagccggc agtatgcgcc ccagcacggc     300
cgaggtggtg gtggcccgtg gccctgctgt ctgcgcggct cgggacaact tgaaactggg     360
ccaccgcctc gtcgcaactc gcaacccgtt ggcggaagaa aggaatggct cgtaggggcc     420
cgggtagaat ccaagaatgt tgcgctgggc ttcgattcac ataacatggg cctgaagctc     480
taaaacgacg gcccggtcac cgggcgatgg aaagagaccg gatcctcctc gtgaattctg     540
gaaggccaca cgagagcgac ccaccaccga cgcggaggag tcgtgcgtgg tccaacacgg     600
ccggcgggct gggctgcgac cttaaccagc aaggcacgcc acgacccgcc tcgccctcga     660
ggcataaata ccctcccatc c                                               681

SEQ ID NO: 136           moltype = DNA   length = 1822
FEATURE                  Location/Qualifiers
source                   1..1822
                         mol_type = other DNA
                         organism = Setaria viridis
SEQUENCE: 136
cacgggtaat gcacgcagcc acccaggcgc gcgcgctagc ggagcacggt caggtgacac      60
gggcgtcgtg acgcttccga gttgaagggg ttaacgccag aaacagtgtt tggccagggt     120
atgaacataa caaaaaatat tcacacgaaa gaatggaagt atggagctgc tactgtgtaa     180
atgccaagca ggaaactcac gcccgctaac atccaacggc caacagctcg acgtgccggt     240
cagcagagac atcggaacac tggtgattgg tggagccggc agtatgcgcc ccagcacggc     300
```

```
cgaggtggtg gtggcccgtg gccctgctgt ctgcgcggct cgggacaact tgaaactggg   360
ccaccgcctc gtcgcaactc gcaacccgtt ggcggaagaa aggaatggct cgtaggggcc   420
cgggtagaat ccaagaatgt tgcgctgggc ttcgattcac ataacatggg cctgaagctc   480
taaaacgacg gcccggtcac cgggcgatgg aaagagaccg gatcctcctt gtgaattctg   540
gaaggccaca cgagagcgac ccaccaccga cgcggaggga tcgtcgtgg tccaacacgg   600
ccggcgggct gggctgcgac cttaaccagc aaggcacgcc acgacccgcc tcgcccctcga  660
ggcataaaata ccctcccatc ccgttgccgc aagactcaga tcagattccg atccccagtt   720
cttccccaat caccttgtgg tctctcgtgt cgcggttccc agggacgcct ccggctcgtc   780
gctcgacagc gatctccgcc ccagcaaggt atagattcag ttccttgctc cgatcccaat   840
ctggttgaga tgttgctccg atgcgacttg attatgtcat atatctgcgg tttgcaccga   900
tctgaagcct agggtttctc gagcgaccca gttgtttgca atttgcgatt tgctcgtttg   960
ttgcgcatcg tagtttatgt ttggagtaat cgaggatttg tatgcggcgt cggcgctacc  1020
tgcttaatca cgccatgtga cgcggttact tgcagaggct gggttagtgg gttctgttat  1080
gtcgtgatct aagaatctag attaggctca gtcgttcttg ctgtcgacta gttgttttg  1140
atatccatgt agtacaagtt acttaaaatt taggtccaat atattttgca tgcttttggc  1200
ctgttattct tgccaacaag ttgtcctggt aaaaagtaga tgtgaaagtc acgtattggg  1260
acaaattgat ggttaagtgc tatagttcta tagttctgtg atacatctat ctgatttttt  1320
ttggtctatt ggtgcctaac ttatctgaaa atcatgaaac atgaggctag tttgatcatg  1380
gtttagttca ttgtgattaa taatgtatga tttagtagct attttggtga tcgtgtcatt  1440
ttatttgtga atggaatcat tgtatgtaaa tgaagctagt tcaggggtta tgatgtagct  1500
ggcttttgtat tctaaaggct gctattattc atccatcgat ttcacctata tgtaatccag  1560
agcttttcgat gtgaaatttg tctgatcctt cactaggaag gacagaacat tgttaatatt  1620
ttggcacatc tgtcttattc tcatccctttg tttgaacatg ttagcctgtt caaacagata  1680
ctgttgtaat gtcctagtta tataggtaca tatgtgttct ctattgagtt tatggacttt  1740
tgtgtgtgaa gttatatttc attttgctca aaactcatgt ttgcaagctt tctgacatta  1800
ttctattgtt ctgaaacagg gt                                            1822

SEQ ID NO: 137          moltype = DNA  length = 1925
FEATURE                 Location/Qualifiers
source                  1..1925
                        mol_type = other DNA
                        organism = Zea mays
                        sub_species = Mexicana
SEQUENCE: 137
gtcgtgcccc tctctagaga taatgagcat tgcatgtcta agttataaaa aattaccaca    60
tatttttttt tgtcacactt gtgtttgaag tgcagtttat ctatctctat acatatattt   120
aaacttcact atatgaataa tatagtctat agtattaaaa taatatcaat gttttagatg   180
attatataac tgaactgcta gacatggtct aaaggacaac cgagtatttt gacaacatga   240
ctctacagtt ttatcttttt agtgtgcatg tgttcttttt acttttgcaa atagcttcac   300
ctatataata cttcatccat tttattagta catccattta ctaaattttt agtacatcta   360
ttttattcta ttttagcctc taaattaaga aaacttaaac tctattttag tttttttattt  420
aataatttag atataaaata gaataaaata aagtgactaa aaaataacta aataccttt    480
aagaaataaa aaaactaagg aaccatttt cttgttccga tagataatg acagcctgtt   540
caacgccgtc gacgagtcta acggacacca accagcgaac cagcagcgtc gcgtcgggcc   600
aagcgaagca gacggcacgg catctctgta gctgcctctg gaccccctctc gagagttccg   660
ctccaccgtt ggacttgctc cgctgtcggc atccagaaat tgcgtggcgg agcggcagac   720
gtgagccggc acggcaggcg gcctcctctc acggcaccgg cagctacggg ggattccttt   780
cccaccgctc cttcgctttc ccttcctcgc ccgccgtaat aaatagaccc cctccacacc   840
ctctttcccc aacctcgtgt tcgttcggag cgcgcacaca cacaaccaga tctcccccaa   900
atccaccgt cggcacctcc gcttcaaggt acgccgctca tcctcctccc cccctctct    960
ctaccttctc tagatcggcg tttcggttcca tggttagggc ccggtagttc tacttctgtt  1020
catgtttgtg ttagatccgt gttttgtgtta gatccgtgct gctagatttc gtacacggat  1080
gcgacctgta catcagacat gttctgattg ctaacttgcc agtgttttctc tttggggaat  1140
cctgggatgc ctctagccgt tccgcagacg ggatcgattt catgaatttt tttttgtttcg  1200
ttgcataggg tttggttttgc cctttttcctt tatttcaata tatgccgtgc acttgtttgt  1260
cgggtcatct tttcatgttt tttttggctt ggttgtgatg atgtggtctg gttgggcggt  1320
cgttctagat cggagtagaa tactgtttca aactaccttgg tggatttatt aaaggatctg  1380
tatgtatgtg ccatacatct tcatagttac gagtttaaga tgatggatgg aaatatcgat  1440
ctaggatagg tatacatgtt gatgcgggtt ttactgattga atatacagag atgctttttt  1500
ttcgccttggt tgtgatgatg tggtctgttc gggcggtcgt tctagatcgg agtagaaatc  1560
tgtttcaaac tacctggtgg atttattaat tttggatctg tatgtgtgtc atacatcttc   1620
atagttacga gtttaagatc gatggaaata tcgatctagg ataggtatac atgttgatgt   1680
gggttttact gatgcatata catggcatat gcagcatcta ttcatatgct ctaaccttga  1740
gtacctatct attataataa acaagtatgt tttataatta ttttgatctc gatatactgg  1800
gatgatggca tatgcagcag ctatatgtgg atttttttag ccctgccttc atacgctatt  1860
tattgcttg gtactgtttc ttttgtcgat gctcaccctg ttgtttggtg atacttctgc  1920
aggtc                                                               1925

SEQ ID NO: 138          moltype = DNA  length = 997
FEATURE                 Location/Qualifiers
source                  1..997
                        mol_type = other DNA
                        organism = Zea mays
                        sub_species = Mexicana
SEQUENCE: 138
gtacgccgct catcctcctc ccccccctct ctctaccttc tctagatcgg cgtttcggtc    60
catggttagg gccggtagt tctacttctg ttcatgtttg tgttagatcc gtgtttgtgt   120
tagatccgtg ctgctagatt tcgtacacgg atgcgacctg tacatcagac atgttctgat   180
tgctaacttg ccagtgtttc tctttgggga atcctgggat ggctctagcc gttccgcaga   240
```

```
cgggatcgat ttcatgaatt ttttttgttt cgttgcatag ggtttggttt gcccttttcc    300
tttatttcaa tatatgccgt gcacttgttt gtcgggtcat cttttcatgt ttttttggc    360
ttggttgtga tgatgtggtc tggttgggcg gtcgttctag atcggagtag aatactgttt    420
caaactacct ggtggattta ttaaaggatc tgtatgtatg tgccatacat cttcatagtt    480
acgagtttaa gatgatggat ggaaatatcg atctaggata ggtatacatg ttgatgcggg    540
ttttactgat gcatatacag agatgctttt ttttcgcttg gttgtgatga tgtggtctgg    600
tcgggcggtc gttctagatc ggagtagaat actgttcaa actacctggt ggatttatta    660
attttggatc tgtatgtgtg tcatacatct tcatagttac gagtttaaga tcgatggaaa    720
tatcgatcta ggataggtat acatgttgat gtgggtttta ctgatgcata tacatggcat    780
atgcagcatc tattcatatg ctctaacctt gagtacctat ctattataat aaacaagtat    840
gttttataat tattttgatc ttgatatact tggatgatgg catatgcagc agctatatgt    900
ggatttttt agccctgcct tcatacgcta tttatttgct tggtactgtt tcttttgtcg    960
atgctcaccc tgttgtttgg tgatacttct gcaggtc                             997

SEQ ID NO: 139        moltype = DNA   length = 1925
FEATURE               Location/Qualifiers
source                1..1925
                      mol_type = other DNA
                      organism = Zea mays
                      sub_species = Mexicana
SEQUENCE: 139
gtcgtgcccc tctctagaga taatgagcat tgcatgtcta agttataaaa aattaccaca     60
tattttttt tgtcacactt gtgtttgaag tgcagtttat ctatctctat acatatattt    120
aaacttcact atatgaataa tatagtctat agtattaaaa taatatcaat gttttagatg    180
attatataac tgaactgcta gacatggtct aaaggacaac cgagtatttt gacaacatga    240
ctctacagtt ttatcttttt agtgtgcatg tgttctttta acttttgcaa atagcttcac    300
ctatataata cttcatccat tttattagta catccattta ctaaattttt agtacatcta    360
ttttattcta ttttagcctc taaattaaga aaacttaaac tctatttag ttttttattt    420
aataatttag atataaaata gaataaaata aagtgactaa aaaataacta aatacctttt    480
aagaaataaa aaaactaagg aaccatttt cttgttccga gtagataatg acagcctgtc    540
caacgccgtc gacgagtcta acggacacca accagcagca cagcagcgtc gcgtcgggcc    600
aagcgaagca gacggcacgg catctctgta gctgcctctg gaccctctc gagagttccg    660
ctccaccgtt ggacttgctc cgctgtcggc atccagaaat tgcgtggcgg agcggcagac    720
gtgagccggc acggcaggcg gcctcctctc acggcacggg cagctacggg ggattccttt    780
cccaccgctc cttcgctttc ccttcctcgc ccgccgtaat aaatagaccc cctccacacc    840
ctctttcccc aacctcgtgt tcgttcggag cgcgcacaca cacaaccaga tctcccccaa    900
atccaccccg cggcacctcc gcttcaaggt acgccgctca tcctcctccc cccctctct    960
ctaccttctc tagatcggcg tttcggtcca tggttagggc ccggtagttc tacttctgtt   1020
catgttgtg ttagatccgt gttgtgtta gatccgtgct gctagattc gtacacgat      1080
gcgacctgta catcagacat gttctgattg ctaacttgcc agtgtttctc tttggggaat   1140
cctgggatgg ctctagccgt tccgcagacg ggatcgattt catgaatttt ttttgttcg    1200
ttgcataggg ttggttgc ccttttctt tatttcaata tatgccgtgc acttgttgt       1260
cgggtcatct tttcatgttt tttttggctt ggttgtggtc gttgggcgtg gttgggcgtg   1320
cgttctagat cggagtagaa tactgtttca aactacctgg tggatttatt aaaggatctg   1380
tatgtatgtg ccatacatct tcatagttac gagtttaaga tgatggatgg aaatatcgat   1440
ctaggatagg tatacatgtt gatgcgggtt ttactgatgc atatacagag atgctttttt   1500
ttcgcttggt tgtgatgatg tggtctggtc gggcggtcgt tctagatcgg agtagaaatc   1560
tgtttcaaac tacctggtgg atttattaat tttggatctg tatgtgtc atacatcttc    1620
atagttacga gtttaagatc gatggaaata tcgatctagg ataggtatac atgttgatgt   1680
gggttttact gatgcatata catggcatat gcagcatcta ttcatatgct ctaaccttga   1740
gtacctatct attataataa acaagtatgt tttataatta ttttgatctt gatatactg   1800
gatgatggca tatgcagcag ctatatgtgg attttttag ccctgccttc atacgctatt   1860
tatttgcttg gtactgtttc ttttgtcgat gctcaccctg ttgtttggtg atacttctgc   1920
agggt                                                              1925

SEQ ID NO: 140        moltype = DNA   length = 997
FEATURE               Location/Qualifiers
source                1..997
                      mol_type = other DNA
                      organism = Zea mays
                      sub_species = Mexicana
SEQUENCE: 140
gtacgccgct catcctcctc ccccccctct ctctaccttc tctagatcgg cgtttcggtc     60
catggttagg gcccggtagt tctacttctg ttcatgtttg tgttagatcc gtgttttgtt   120
tagatccgtg ctgctagatt tcgtacacga tgcgacctg tacatcagac atgttctgat    180
tgctaacttg ccagtgtttc tctttgggga atcctgggat ggctctagcc gttccgcaga   240
cgggatcgat ttcatgaatt ttttttgttt cgttgcatag ggtttggttt gcccttttcc   300
tttatttcaa tatatgccgt gcacttgttt gtcgggtcat cttttcatgt ttttttggc    360
ttggttgtga tgatgtggtc tggttgggcg gtcgttctag atcggagtag aatactgttt    420
caaactacct ggtggattta ttaaaggatc tgtatgtatg tgccatacat cttcatagtt    480
acgagtttaa gatgatggat ggaaatatcg atctaggata ggtatacatg ttgatgcggg    540
ttttactgat gcatatacag agatgctttt ttttcgcttg gttgtgatga tgtggtctgg    600
tcgggcggtc gttctagatc ggagtagaat actgttcaa actacctggt ggatttatta    660
attttggatc tgtatgtgtg tcatacatct tcatagttac gagtttaaga tcgatggaaa    720
tatcgatcta ggataggtat acatgttgat gtgggtttta ctgatgcata tacatggcat    780
atgcagcatc tattcatatg ctctaacctt gagtacctat ctattataat aaacaagtat    840
gttttataat tattttgatc ttgatatact tggatgatgg catatgcagc agctatatgt    900
ggatttttt agccctgcct tcatacgcta tttatttgct tggtactgtt tcttttgtcg    960
atgctcaccc tgttgtttgg tgatacttct gcagggt                             997
```

| SEQ ID NO: 141 | moltype = DNA length = 1974 |
| --- | --- |
| FEATURE | Location/Qualifiers |
| source | 1..1974 |
| | mol_type = other DNA |
| | organism = Zea mays |
| | sub_species = Mexicana |

SEQUENCE: 141

```
gtcgtgcccc tctctagaga taaagagcat tgcatgtcta agttataaaa aattaccaca   60
tatttttttt gtcacacttg tttgaagtgc agtttatcta tctttataca tatatttaaa  120
ctttactcta cgaataatat aatctatagt actacaataa tatcagtgtt ttagagaatc  180
atataaatga acagttagac atggtctaaa ggacaattga gtattttgac aacaggactc  240
tacagtttta tcttttagt gtgcatgtgt tctcctttt tttttgcaaa tagcttcacc  300
tatataatac ttcatccatt ttattagtac atccatttag ggtttagggt taatggtttt  360
tatagactaa ttttttagt acatctattt tattctattt tagcctctaa attaagaaaa  420
ctaaaactct atttagttt ttttatttaa taatttagat ataaaataga ataaaataaa  480
gtgactaaaa attaaacaaa taccctttaa gaaattaaaa aaactaagga aacattttc  540
ttgtttcgag tagataatgc cagcctgtta aacgccgtcg acgagtctaa cggacaccaa  600
ccagcgaacc agcagcgtcg cgtcgggcca agcgaagcag acggcacggc atctctgtcg  660
ctgcctctgg acccctctcg agagttccgc tccaccgttg gacttgctcc gctgtcggca  720
tccagaaatt gcgtggcgga gcggcagacg tgagccggca cggcaggcgg cctcctctc  780
ctctcacggc accggcagct acgggggatt cctttcccac cgctccttcg ctttccttc  840
ctcgcccgcc gtaataaata gacaccccct ccacccttc tttccccaac ctcgtgttgt  900
tcggagcgca cacacacaca accagatctc ccccaaatcc acccgtcggc acctccgctt  960
caaggtacgc cgctcatcct cccccccccc tctctacctt ctctagatcg gcgttccggt 1020
ccatggttag ggcccggtag ttctacttct gttcatgttt gtgttagatc cgtgttgtg 1080
ttagatccgt gctgctagcg ttcgtacacg gatgcgacct gtacgtcaga cacgttctga 1140
ttgctaactt gccagtgttt ctctttggggg aatcctggga tggctctagc cgttccgcag 1200
acgggatcga tttcatgatt ttttgtttt cgttgcatag ggtttggttt gccttttcc 1260
tttatttcaa tatatgccgt gcacttgttt gtcgggtcat cttttcatgc ttttttttgt 1320
cttggttgtg atgatgtggt ctggttggggc ggtcgttcta gatcggagaa gaattctgtt 1380
tcaaactacc tggtggattt attaattttg gatctgtatg tgtgtgccat acatattcat 1440
agttacgaat tgaagatgat ggatggaaat atcgatctag gataggtata catgttgatg 1500
cgggttttac tgatgcatat acagagatgc tttttgttcg cttggttgtg atgatgtggt 1560
ctggttgggc ggtcgttcat tcgttctaga tcggataga atactgttc aaactacctg 1620
gtgtatttat taattttgga actgtatgtg tgtgtcatac atcttcatag ttacgagttt 1680
aagatggatg gaaatatcga tctaggatag gtatacatgt tgatgtgggt tttactgatg 1740
catatacatg atggcatatg cagcatctat tcatatgctc taaccttgag tacctatcta 1800
ttataataaa caagtcgtt ttataattat tttgatcttg atatacttgg atgatggcat 1860
atgcagcagc tatatgtgga ttttttagc cctgccttca tacgctattt atttgcttgg 1920
tactgtttct tttgtcgatg ctcaccctgt tgtttggtga tacttctgca ggtc        1974
```

| SEQ ID NO: 142 | moltype = DNA length = 1010 |
| --- | --- |
| FEATURE | Location/Qualifiers |
| source | 1..1010 |
| | mol_type = other DNA |
| | organism = Zea mays |
| | sub_species = Mexicana |

SEQUENCE: 142

```
gtacgccgct catcctcccc ccccctctc taccttctct agatcggcgt tccggtccat   60
ggttagggcc cggtagttct acttctgttc atgtttgtt tagatccgtg tttgtgttag  120
atccgtgctg ctagcgttcg tacacggatg cgacctgtac gtcagacacg ttctgattgc  180
taacttgcca gtgtttctct ttggggaatc ctgggatggc tctagccgtt ccgcagacgg  240
gatcgatttc atgatttttt tgtttcgtt gcataggggt tggttgccc ttttccttta  300
tttcaatata tgccgtgcac ttgttgtcg ggtcatcttt tcatgcttt tttgtcttg  360
gttgtgatga tgtggtctgg ttgggcggtc gttctagatc ggagaagaat tctgtttcaa  420
actacctggt ggatttatta attttggatc tgtatgtgtg tgccatacat attcatagtt  480
acgaattgaa gatgatggat ggaaatatcg atcgaggata ggtatacatg ttgatgcggg  540
ttttactgat gcatatacag agatgctttt tgttcgcttg gttgtgatga tgtggtctgg  600
ttgggcggtc gttcattcgt tctagatcgg agtagaatac tgtttcaaac tacctggtgt  660
atttattaat tttggaactg tatgtgtgtg tcatacatct tcatagttac gagtttaaga  720
tggatggaaa tatcgatcta ggataggtat acatgttgat gtgggtttta ctgatgcata  780
tacatgatgg catatgcagc atctattcat atgctctaac cttgagtacc tatctattat  840
aataaacaag tatgttttat aattattttg atcttgatat acttggatga tggcatatga  900
agcagctata tgtggatttt ttagccctg ccttcatacg ctatttattt gcttggtact  960
gtttcttttg tcgatgctca ccctgttgtt tggtgatact tctgcaggtc             1010
```

| SEQ ID NO: 143 | moltype = DNA length = 1974 |
| --- | --- |
| FEATURE | Location/Qualifiers |
| source | 1..1974 |
| | mol_type = other DNA |
| | organism = Zea mays |
| | sub_species = Mexicana |

SEQUENCE: 143

```
gtcgtgcccc tctctagaga taaagagcat tgcatgtcta agttataaaa aattaccaca   60
tatttttttt gtcacacttg tttgaagtgc agtttatcta tctttataca tatatttaaa  120
ctttactcta cgaataatat aatctatagt actacaataa tatcagtgtt ttagagaatc  180
atataaatga acagttagac atggtctaaa ggacaattga gtattttgac aacaggactc  240
tacagtttta tcttttagt gtgcatgtgt tctcctttt tttttgcaaa tagcttcacc  300
```

```
tatataatac ttcatccatt ttattagtac atccatttag ggtttagggt taatggtttt    360
tatagactaa tttttttagt acatctattt tattctattt tagcctctaa attaagaaaa    420
ctaaaactct attttagttt tttatttaa taatttagat ataaaataga ataaaataaa    480
gtgactaaaa attaaacaaa tacccttttaa gaaattaaaa aaactaagga aacattttc    540
ttgtttcgag tagataatgc cagcctgtta aacgccgtac acgagtctaa cggacaccaa    600
ccagcgaacc agcagcgtcg cgtcgggcca agcgaagcag acggcacggc atctctgtcg    660
ctgcctctgg acccctctcg agagttccgc tccaccgttg gacttgctcc gctgtcggca    720
tccagaaatt gcgtggcgga gcggcagacg tgagccggca cggcaggcgg cctcctcctc    780
ctctcacggc accggcagct acgggggatt cctttcccac cgctccttcg ctttccttc    840
ctcgcccgcc gtaataaata gacacccct ccacacctt ttccccaac ctcgtgttgt    900
tcggagcgca cacacacaca accagatctc ccccaaatcc cccgtcggc acctccgctt    960
caaggtacgc cgctcatcct ccccccccc tctctacctt ctctagatcg gcgttccggt   1020
ccatggttag ggcccggtag ttctacttct gttcatgttt gtgttagatc cgtgtttgtg   1080
ttagatccgt gctgctagcg ttcgtacacg gatgcgaccc gtacgtcaga cacgttctga   1140
ttgctaactt gccagtgttt ctctttgggg aatcctggga tggctctagc cgttccgcag   1200
acgggatcga tttcatgatt tttttgttt cgttgcatag ggtttggttt gcccttttcc   1260
tttatttcaa tatatgccgt gcacttgttt gtcgggtcat cttttcatgc ttttttttgt   1320
cttggttgtg atgatgtggt ctggtttggc ggtcgttcta gatcggagaa gaattctgct   1380
tcaaactacc tggtggattt attaattttg gatctgtatg tgtgtgccat acatattcat   1440
agttacgaat tgaagatgat ggatggaaat atcgatctag gataggtata catgttgatg   1500
cgggttttac tgatgcatat acagagatgc tttttgttcg cttggttgtg atgatgtggt   1560
ctggttgggc ggtcgttcat tcgttctaga tcggagtaga atactgtttc aaactacctg   1620
gtgtatttat taattttgga actgtatgtg tgtgtcatac atcttcatag ttacgagttt   1680
aagatggatg gaaatatcga tctaggatag gtatacatgt tgatgtgggt tttactgatg   1740
catatacatg atggcatatg cagcatctat tcatatgctc taaccttgag tacctatcta   1800
ttataataaa caagtcttgt ttataattat tttgatcttg atatacttgg atgatggcat   1860
atgcagcagc tatatgtgga ttttttttagc cctgccttca tacgctattt atttgcttgg   1920
tactgtttct tttgtcgatg ctcaccctgt tgtttggtga tacttctgca gggt        1974

SEQ ID NO: 144         moltype = DNA  length = 1010
FEATURE                Location/Qualifiers
source                 1..1010
                       mol_type = other DNA
                       organism = Zea mays
                       sub_species = Mexicana
SEQUENCE: 144
gtacgccgct catcctcccc ccccctctc taccttctct agatcggcgt tccggtccat     60
ggttagggcc cggtagttct acttctgttc atgtttgtgt tagatccgtg tttgtgttag    120
atccgtgctg ctagcgttcg tacacggatg cgacctgtac gtcagacacg ttctgattgc    180
taacttgcca gtgtttctct ttggggaatc ctgggatggc tctagccgtt ccgcagacgg    240
gatcgatttc atgatttttt ttgtttcgtt gcataggtt tggtttgccc tttcctttta    300
tttcaatata tgccgtgcac ttgttgtcg ggtcatcttt tcatgctttt ttttgtcttg    360
gttgtgatga tgtggtctgg ttgggcggtc gttctagatc ggagaagaat tctgtttcaa    420
actacctggt ggatttatta attttggatc tgtatgtgtg tgccatacat attcatagtt    480
acgaattgaa gatgatggat ggaaatatcg atctaggata ggtatacatg ttgatgcggg    540
ttttactgat gcatatacag agatgctttt tgttcgcttg gttgtgatga tgtggtctgg    600
ttgggcggtc gttcattcgt tctagatcgg agtagaatac tgtttcaaac tacctggtgt    660
atttattaat tttggaactg tatgtgtgtg tcatacatct tcatagttac gagtttaaga    720
tggatggaaa tatcgatcta ggataggtat acatgttgat gtgggtttta ctgatgcata    780
tacatgatgg catatgcagc atctattcat atgctctaac cttgagtacc tatctattat    840
aataaacaag tatgttttat aattattttg atcttgata acttggatga tggcatatgc    900
agcagctata tgtggatttt tttagccctg ccttcatacg ctatttattt gcttggtact    960
gtttcttttg tcgatgctca ccctgttgtt tggtgatact tctgcagggt             1010

SEQ ID NO: 145         moltype = DNA  length = 2008
FEATURE                Location/Qualifiers
source                 1..2008
                       mol_type = other DNA
                       organism = Zea mays
                       sub_species = Mexicana
SEQUENCE: 145
gtcgtgcccc tctctagaga taaagagcat tgcatgtcta agtataaaa aattaccaca     60
tatttttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tattttgaca atctacagtt    240
ttatctttt agtgtgcatg tgatctctct gttttttttg caaatagctt gacctatata    300
atactttcatc cattttatta gtacatccat ttaggatta gggttgatgg tttctataga    360
ctaattttta gtacatccat tttattcttt ttagtctcta aatttttaa aactaaaact    420
ctattttagt tttttattta ataatttaga tataaaatga aataaaataa attgactaca    480
aataaaacaa ataccctta agaaataaaa aaactaagca aacattttc ttgtttcgag    540
tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
acccctctcg agagttccgc tccaccgttg gacttgctcc gctgtcggca tccagaaatt    720
gcgtggcgga gcggcagacg tgaggcggca cggcaggcgg cctcctcctc ctctcacggc    780
accggcagct acgggggatt cctttcccac cgctccttcg ctttccttc ctcgcccgcc    840
gtaataaata gacacccct ccacacctc tttcccaac ctcgtgttcg ttcggagcgc    900
acacacacgc aaccagatct cccccaaatc cagccgtcgg cacctccgct tcaaggtacg    960
ccgctcatcc tcccccccc cctctctcta ccttctctag atcggcgatc cggtccatgg   1020
ttagggcccg gtagttctac ttctgttcat gtttgtgtta gagcaaacat gttcatgttc   1080
```

```
atgtttgtga tgatgtggtc tggttgggcg gtcgttctag atcggagtag gatactgttt    1140
caagctacct ggtggattta ttaattttgt atctgtatgt gtgtgccata catcttcata    1200
gttacgagtt taagatgatg gatggaaata tcgatctagg ataggtatac atgttgatgc    1260
gggttttact gatgcatata cagagatgct ttttttctcg cttggttgtg atgatatggt    1320
ctggttgggc ggtcgttcta gatcggagta gaatactgtt tcaaactacc tggtggattt    1380
attaaaggat aaagggtcgt tctagatcgg agtagaatac tgtttcaaac tacctggtgg    1440
atttattaaa ggatctgtat gtatgtgcct acatcttcat agttacgagt ttaagatgat    1500
ggatggaaat atcgatctag gataggtata catgttgatg cgggttttac tgatgcatat    1560
acagagatgc ttttttttcgc ttggttgtga tgatgtggtc tggttgggcg gtcgttctag    1620
atcggagtag aatactgttt caaactacct ggtggattta ttaattttgt atctttatgt    1680
gtgtgccata catcttcata gttacgagtt taagatgatg gatggaaata ttgatctagg    1740
ataggtatac atgttgatgt gggttttact gatgcatata catgatggca tatgcggcat    1800
ctattcatat gctctaacct tgagtaccta tctattataa taaacaagta tgttttataa    1860
ttattttgat cttgatatac ttggatgatg gcatatgcag cagctatatg tggattttct    1920
agccctgcct tcatacgcta tttatttgct tggtactgtt tcttttgtcc gatgctcacc    1980
ctgttgttgg gtgatacttc tgcaggtc                                       2008

SEQ ID NO: 146        moltype = DNA   length = 1053
FEATURE               Location/Qualifiers
source                1..1053
                      mol_type = other DNA
                      organism = Zea mays
                      sub_species = Mexicana
SEQUENCE: 146
gtacgccgct catcctcccc ccccccctct ctctaccttc tctagatcgg cgatccggtc      60
catggttagg gcccggtagt tctacttctg ttcatgtttg tgttagagca aacatgttca     120
tgttcatgtt tgtgatgatg tggtctggtt gggcggtcgt tctagatcgg agtaggatac     180
tgtttcaagc tacctggtgg atttattaat tttgtatctg tatgtgtgtg ccatacatct     240
tcatagttac gagtttaaga tgatggatgg aaatatcgat ctaggatagg tatacatgtt     300
gatgcgggtt ttactgatgc atatacagag atgctttttt tctcgcttgg ttgtgatgat     360
atggtctggt tgggcggtcg ttctagatcg gagtagaata ctgtttcaaa ctacctggtg     420
gatttattaa aggataaagg gtcgttctag atcggagtag aatactgttt caaactacct     480
ggtggattta ttaaaggatc tgtatgtatg tgcctacatc ttcatagtta cgagtttaag     540
atgatggatg gaaatatcga tctaggatag gtatacatgt tgatgcgggt tttactgatg     600
catatacaga gatgcttttt ttcgcttggt tgtgatgatg tggtctggtt gggcggtcgt     660
tctagatcgg agtagaatac tgtttcaaac tacctggtgg atttattaat tttgtatctt     720
tatgtgtgtg ccatacatct tcatagttac gagtttaaga tgatggatgg aaatattgat     780
ctaggatagg tatacatgtt gatgtgggtt ttactgatgc atatacatga tggcatatgc     840
ggcatctatt catatgctct aaccttgagt acctatctat tataataaac aagtatgtgt     900
tataattatt ttgatcttga tacttggat tgatggcata tgcagcagct atatgtggat     960
tttttagccc tgccttcata cgctatttat ttgcttggta ctgtttcttt tgtccgatgc    1020
tcaccctgtt gttgggtgat acttctgcag gtc                                 1053

SEQ ID NO: 147        moltype = DNA   length = 2008
FEATURE               Location/Qualifiers
source                1..2008
                      mol_type = other DNA
                      organism = Zea mays
                      sub_species = Mexicana
SEQUENCE: 147
gtcgtgcccc tctctagaga taaagagcat tgcatgtcta aagtataaaa aattaccaca      60
tatttttttg tcacacttat ttgaagtgta gtttatctat ctctatacat atatttaaac     120
ttcactctac aaataatata gtctataata ctaaaataat attagtgttt tagaggatca     180
tataaataaa ctgctagaca tggtctaaag gataattgaa tattttgaca atctacagtt     240
ttatcttttt agtgtgcatg tgatctctct gttttttttg caaatagctt gacctatata     300
atacttcatc cattttatta gtacatccat ttaggattta gggttgatgg tttctataga     360
ctaatttttta gtacatccat tttattcttt ttagtctcta aatttttaa aactaaaact     420
ctattttagt tttttattta ataatttaga tataaaatga aataaaataa attgactaca     480
aataaaacaa atacccttta agaaataaaa aaactaagca aacattttttc ttgtttcgag     540
tagataatga caggctgttc aacgccgtcg acgagtctaa cggacaccaa ccagcgaacc     600
agcagcgtcg cgtcgggcca agcgaagcag acggcacggc atctctgtag ctgcctctgg     660
accccttctcg agagttccgc tccacgttg gacttgctcc gctgtcggca tccagaaatt     720
gcgtggcgga gcggcagacg tgaggcggca cggcaggcgg cctcttcctc ctctcacggc     780
accggcagct acggggatt ccttttcccac cgctccttcc ctttccttc ctcgcccgtc     840
gtaataaata gacacccccct ccacaccctc tttccccaac ctcgtgttcg ttcggagcgc     900
acacacgc aaccagatct cccccaaatc cagccgtcgg cacctccgct tcaaggtacg     960
ccgctcatcc tcccccccc cctctctcta ccttctctag atcggcgatc cggtccatgg    1020
ttagggcccg gtagttctac ttctgttcat gtttgtgtta gagcaaacat gttcatgttc    1080
atgtttgtga tgatgtggtc tggttgggcg gtcgttctag atcggagtag gatactgttt    1140
caagctacct ggtggattta ttaattttgt atctgtatgt gtgtgccata catcttcata    1200
gttacgagtt taagatgatg gatggaaata tcgatctagg ataggtatac atgttgatgc    1260
gggttttact gatgcatata cagagatgct ttttttctcg cttggttgtg atgatatggt    1320
ctggttgggc ggtcgttcta gatcggagta gaatactgtt tcaaactacc tggtggattt    1380
attaaaggat aaagggtcgt tctagatcgg agtagaatac tgtttcaaac tacctggtgg    1440
atttattaaa ggatctgtat gtatgtgcct acatcttcat agttacgagt ttaagatgat    1500
ggatggaaat atcgatctag gataggtata catgttgatg cgggttttac tgatgcatat    1560
acagagatgc ttttttcgc ttggttgtga tgatgtggtc tggttgggcg gtcgttctag    1620
atcggagtag aatactgttt caaactacct ggtggattta ttaattttgt atctttatgt    1680
gtgtgccata catcttcata gttacgagtt taagatgatg gatggaaata ttgatctagg    1740
```

```
ataggtatac atgttgatgt gggttttact gatgcatata catgatggca tatgcggcat   1800
ctattcatat gctctaacct tgagtaccta tctattataa taaacaagta tgttttataa   1860
ttattttgat cttgatatac ttggatgatg gcatatgcag cagctatatg tggattttt   1920
agccctgcct tcatacgcta tttatttgct tggtactgtt tcttttgtcc gatgctcacc   1980
ctgttgtttg gtgatacttc tgcaggtc                                      2008

SEQ ID NO: 148          moltype = DNA   length = 1053
FEATURE                 Location/Qualifiers
source                  1..1053
                        mol_type = other DNA
                        organism = Zea mays
                        sub_species = Mexicana
SEQUENCE: 148
gtacgccgct catcctcccc ccccccctct ctctaccttc tctagatcgg cgatccggtc     60
catggttagg gcccggtagt tctacttctg ttcatgtttg tgttagagca aacatgttca    120
tgttcatgtt tgtgatgatg tggtctggtt gggcggtcgt tctagatcgg agtaggatac    180
tgtttcaagc tacctggtgg attattaat tttgtatctg tatgtgtgtg ccatacatct    240
tcatagttac gagtttaaga tgatggatgg aaatatcgat ctaggatagg tatacatgtt    300
gatgcgggtt ttactgatgc atatacagag atgctttttt tctcgcttgg ttgtgatgat    360
atggtctggt tgggcggtcg ttctagatcg gagtagaata ctgtttcaaa ctacctggtg    420
gatttattaa aggataaagg gtcgttctag atcggagtag aatactgttt caaactacct    480
ggtggattta ttaaaggatc tgtatgtatg tgcctacatc ttcatagtta cgagtttaag    540
atgatggatg gaaatatcga tctaggatag gtatacatgt tgatgcgggt tttactgatg    600
catatacaga gatgcttttt ttcgcttggt tgtgatgatg tggtctggtt gggcggtcgt    660
tctagatcgg agtagaatac tgtttcaaac tacctggtgg atttattaat tttgtatctt    720
tatgtgtgtg ccatacatct tcatagttac gagtttaaga tgatggatgg aaatattgat    780
ctaggatagg tatacatgtt gatgtgggtt ttactgatgc atatacatga tggcatatgc    840
ggcatctatt catatgctct aaccttgagt acctatctat tataataaac aagtatgttt    900
tataattatt ttgatcttga tatacttgga tgatggcata tgcagcagct atatgtggat    960
tttttagccc tgccttcata cgctatttat ttgcttggta ctgtttcttt tgtccgatgc   1020
tcaccctgtt gtttggtgat acttctgcag gtc                                1053

SEQ ID NO: 149          moltype = DNA   length = 2008
FEATURE                 Location/Qualifiers
source                  1..2008
                        mol_type = other DNA
                        organism = Zea mays
                        sub_species = Mexicana
SEQUENCE: 149
gtcgtgcccc tctctagaga taaagagcat tgcatgtcta aagtataaaa aattaccaca     60
tatttttttg tcacacttat ttgaagtgta gtttatctat ctctatacat atatttaaac    120
ttcactctac aaataatata gtctataata ctaaataat attagtgttt tagaggatca    180
tataaataaa ctgctagaca tggtctaaag gataattgaa tattttgaca atctacagtt    240
ttatcttttt agtgtgcatg tgatctctct gttttttttg caaatagctt gacctatata    300
atacttcatc cattttatta gtacatccat ttaggattta gggttgatgg tttctataga    360
ctaattttta gtacatccat tttattcttt ttagtctcta aattttttaa aactaaaact    420
ctattttagt tttttattta ataatttaga tataaaatga aataaaataa attgactaca    480
aataaaacaa atacccttta agaaataaaa aaactaagca aacatttttc ttgtttcgag    540
tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
accccctcg agagttccgc tccaccgttg gacttgctcc gctgtcggca tccagaaatt    720
gcgtggcgga gcggcagacg tgaggcggca cggcaggcgg cctcttcctc ctctcacggc    780
accggcagct acgggggatt cctttcccac cgctccttcg cttcccttc ctcgcccgcc    840
gtaataaata gacaccccct ccacaccctc tttcccaac ctcgtgttcg ttcggagcgc    900
acacacacgc aaccagatct cccccaaatc cagccgtccg cacctccgct tcaaggtacg    960
ccgctcatcc tcccccccc cctctctcta ccttctctag atcggcgatc cggtccatgg   1020
ttagggcccg gtagtctac ttctgttcat gtttgtgtta gagcaaacat gttcatgttc    1080
atgtttgtga tgatggtc tggttgggcg tcgttctag atcggagtag gatactgttt    1140
caagctacct ggtggattta ttaattttgt atctgtatgt gtgtgccata catcttcata    1200
gttacgagtt taagatgatg gatgggaata tcgatctagg ataggtatac atgttgatgc    1260
gggttttact gatgcatata cagagatgct ttttttctcg cttggttgtg atgatatggt    1320
ctggttgggc ggtcgttcta gatcggagta gaatactgtt tcaaactacc tggtggattt    1380
attaaaggat aaagggtcgt tctagatcgg agtagaatac tgtttcaaac tacctggtgg    1440
atttattaaa ggatctgtat gtatgtgcct acatcttcat agttacgagt ttaagatgat    1500
ggatggaaat atcgatctag gataggtata catgttgatg cgggttttac tgatgcatat    1560
acagagatgc tttttttcgc ttggttgtga tgatgtggtc tggttgggcg gtcgttctag    1620
atcggagtag aatactgttt caaactacct ggtggattta ttaattttgt atctttatgt    1680
gtgtgccata catcttcata gttacgagtt taagatgatg gatggaaata ttgatctagg    1740
ataggtatac atgttgatgt gggttttact gatgcatata catgatggca tatgcggcat    1800
ctattcatat gctctaacct tgagtaccta tctattataa taaacaagta tgttttataa    1860
ttattttgat cttgatatac ttggatgatg gcatatgcag cagctatatg tggattttt   1920
agccctgcct tcatacgcta tttatttgct tggtactgtt tcttttgtcc gatgctcacc   1980
ctgttgtttg gtgatacttc tgcagggt                                      2008

SEQ ID NO: 150          moltype = DNA   length = 1053
FEATURE                 Location/Qualifiers
source                  1..1053
                        mol_type = other DNA
                        organism = Zea mays
```

```
                         sub_species = Mexicana
SEQUENCE: 150
gtacgccgct catcctcccc cccccctct ctctaccttc tctagatcgg cgatccggtc   60
catggttagg gcccggtagt tctacttctg ttcatgtttg tgttagagca aacatgttca  120
tgttcatgtt tgtgatgatg tggtctggtt gggcggtcgt tctagatcgg agtaggatac  180
tgtttcaagc tacctggtgg atttattaat tttgtatctg tatgtgtgtg ccatacatct  240
tcatagttac gagtttaaga tgatggatgg aaatatcgat ctaggatagg tatacatgtt  300
gatgcgggtt ttactgatgc atatacagag atgctttttt tctcgcttgg ttgtgatgat  360
atggtctggt tgggcggtcg ttctagatcg gagtagaata ctgtttcaaa ctacctggtg  420
gatttattaa aggataaagg gtcgttctag atcggagtag aatactgttt caaactacct  480
ggtggattta ttaaaggatc tgtatgtatg tgcctacatc ttcatagtta cgagtttaag  540
atgatggatg gaaatatcga tctaggatag gtatacatgt tgatgcgggt ttactgatg   600
catatacaga gatgctttt tttcgcttggt tgtgatgatg tggtctggtt gggcggtcgt  660
tctagatcgg agtagaatac tgtttcaaac tacctggtgg atttattaat tttgtatctt  720
tatgtgtgtg ccatacatct tcatagttac gagtttaaga tgatggatgg aaatattgat  780
ctaggatagg tatacatgtt gatgtgggtt ttactgatgc atatacatga tggcatatgc  840
ggcatctatt catatgctct aaccttgagt acctatctat tataataaac aagtatgttt  900
tataattatt ttgatcttga tacttggat gatggcata tgcagcagct atatgtggat   960
tttttagccc tgccttcata cgctatttat ttgcttggta ctgtttctt tgtccgatgc 1020
tcaccctgtt gttgggtgat acttctgcag ggt                             1053

SEQ ID NO: 151         moltype = DNA  length = 1635
FEATURE                Location/Qualifiers
source                 1..1635
                       mol_type = other DNA
                       organism = Sorghum bicolor
SEQUENCE: 151
ccaagtccaa atgtcaattc ccttgaagat gatctatttt tatcttttgc attttgttat   60
ggaagtttgc aaatagcaac aaatgctaag tcaatttgcc aaagtctttg gagatgctct  120
tagtctataa ttgaacaata tttgtaaaat acaaaaaaaa atagtactat ttttattta   180
aaaaatttt ggaagtaaac aaggccgagg atggggaaac ggaagtccaa cacgtcgttt   240
tctaagttgg gctcaaaagc ccatcacgga actgacctgc tatgggtcgg aggagagcgc   300
gtccagatgt tccagaggc tggtggtggt gggccaaacg cggaactccg ccaccgccac    360
ggcctcgtgc gcaagcgcag cgcgttgccg tgagccgtga cgtaaccctc cgttgcccac   420
gataaaagct ccacccccga ccccggcccc ccgatttccc ctacggacca gtctccccc   480
gatcgcaatc gcgaattcgt cgcaccatcg gcacgcagca gaacgaagca aggctctccc   540
catcggctcg tcaaggtatg cgttccctag atttgttccc ttcctctctc ggtttgtcta   600
tatatatgca tgtatggtcg attcccgatc tcgtcgattc tcggtttcgc cttccgtacg   660
aagattcgtt tagattgttc atattgttctg ttgtgttacc agattgatcg gatcaacttg   720
atccagttat cttcgctcct ccgattagat ccgtttctat ttcagtatat atatactagt   780
atagtatcta gggttcacac tgtgaccga ctggttactt ggaattgatc cgtgctgagt    840
tcagttgttg ccgtccataa aggcccgtgc tattgtctgt tctgaaacga aatcctgtag   900
atttcttagg gttagtgttc aattcatcaa aaggttgatt agtgaattat caaatttgag   960
agggttaaat cattctcatc atgttgtctc gaatgtaatc ccaaagatat tatagactgt 1020
gtttcgattt gatggattga tttgtgtatc atctaaatca acaaggctaa gtcatcagtt 1080
catagaatca tgtttaggtt tccgttcaat agactagttt tatcaatata taaaattata 1140
agaagggtag ggtaaatcac gttgcctcaa atgccatcct gtatggtttg gtttcaattc 1200
aattagtttg gttgattagg gtatgctctg gattaagatg gttaaatctt ccctagcatc 1260
ttccctgcct atccttactt gatccgtttc ggatatgttg gaagtacagc gagcttattt 1320
catgttgata gtgacccctt tcagattata ctattgaata ttgtatgttt gccacttctg 1380
tatgttgaat tatcctgcta aattagcaat ggaattagca tattggcaat tggtatgcat 1440
ggacctaatc aggacggatg tggttatgtt agtttcaatt cattgtcaat tcattgttca 1500
cctgcgttag atatatatga tgattttac gtgtagttca tagttcttga gttttggatc 1560
tttcttatct gatatatgct ttcctgtgcc tgtgctttat tgtgtcttac catgcgattt 1620
ttgtctatgc aggtc                                                 1635

SEQ ID NO: 152         moltype = DNA  length = 1080
FEATURE                Location/Qualifiers
source                 1..1080
                       mol_type = other DNA
                       organism = Sorghum bicolor
SEQUENCE: 152
gtatgcgttc cctagatttg ttccccttcct ctctcggttt gtctatatat atgcatgtat   60
ggtcgattcc cgatctcgtc gattctcggt ttcgccttcc gtacgaagat tcgtttagat  120
tgttcatatg ttctgttgtg ttaccagatt gatcggatca acttgatcca gttatcttcg  180
ctcctccgat tagatccgtt tctatttcag tatatatata ctagtatagt atctagggtt  240
cacactgttg accgactggt tacttggaat tgatccgtgc tgagttcagt tgttgccgtc  300
cataaaggcc cgtgctattg tctgttctga aacgaaatcc tgtagattt ttaggggtag   360
tgttcaattc atcaaaaggt tgattagtga attatcaaat ttgagagggt taaatcattc  420
tcatcatgtt gtctcgaatg taatcccaaa gatattatag actgtgtttc gatttgatgg  480
attgatttgt gtatcatcta aatcaacaag gctaagtcat cagttcatag aatcatgttt  540
aggtttccgt tcaatagact agttttatca atatataaaa ttataagaag ggtagggtaa  600
atcacgttgc tcaaatgcc atcctgtatg gtttggtttc aattcaatta gtttggttga   660
ttagggtatg ctctggatta agatggttaa atcttcccta gcatcttccc tgcctatcct  720
tacttgatcc gtttcggata tgttggaagt acagcgagct tatttcatgt tgatagtgac  780
ccctttcaga ttatactatt gaatattgta tgtttgccac ttctgtatgt tgaattatcc  840
tgctaaatta gcaatggaat tagcatattg gcaattggta tgcatggacc taatcaggac  900
ggatgtggtt atgttagttt caattcattg tcaattcatt gttcacctgc gttagatata  960
tatgatgatt tttacgtgta gttcatagtt cttgagtttt ggatctttct tatctgatat 1020
```

```
atgctttcct gtgcctgtgc tttattgtgt cttaccatgc gattttgtc tatgcaggtc  1080

SEQ ID NO: 153          moltype = DNA   length = 2067
FEATURE                 Location/Qualifiers
source                  1..2067
                        mol_type = other DNA
                        organism = Sorghum bicolor
SEQUENCE: 153
cattaaaagt cattatgtgc atgcgtcgta actaacatgg atatgttgct gcactatctc   60
ctcgcactag ctgcgcatga taaagccaca agccaaaatt aattattatg ggtgagaata  120
aatacgtacc agcaccggcc atagaaaaag tacattatta aaggtctaat ttggaaacag  180
tctgaaaacg acgtgcgctg cagaggtaaa tgtaattttc ggcactaaaa ccattatcaa  240
ctaattcatt caataacagt tatttagaaa atgtatagct cgctctaaaa aaacagttta  300
gaaaaacagt caaaataatt cgaccaacaa acagttaata aggttcatta aatatataat  360
gcacggtgct atttgatctt ttaaaggaaa aagaggaata gtcgtgggcg ccaggcggga  420
attggggcgc gggagtctgc cggacgacgc gttccgtccg aacggccgga cccgacgagg  480
ccccccccgcc gccccacgtc gcagaaccgt ccgtgggtgg taatctggcc gggtacacca  540
gccgtcccct tgggcggcct cacagcactg ggctcacacg tgagttttgt tctgggcttc  600
ggatcgcacc atatgggcct cggcatcaga aagacgggc ccgtctggga tagaagagac  660
aggaacctcc tcgtggattc cagaagccag ccacgagcga ccaccgacgc ggaggatact  720
cgtcgtccaa gtcaacacg gcgggcgggc gggcggacgc gtgggctggg ctaactgcct  780
aaccttaacc tccaaggcac gccaaggcc gcttctccca cccgacataa atatcccccc  840
atccaggcaa ggcgcagagc ctcagaccag attccgatca atcacccata agctccccc   900
aaatctgttc ctcgtctccc gtctcgcggt ttcctacttc cctcggacgc ctccggcaag  960
tcgctcgacc gcgcgattcc gcccgctcaa ggtatcaact cggttcacca ctccaatcta 1020
cgtctgattt agatgttact tccatctatg tctaattag atgttactcc gatgcgattg 1080
gattatgttt atgcggtttg cactgctctg gaaactggaa tctagggttt cgagtgattt 1140
gatcgatcgc gatctgtgat ttcgttgcgc cttgtgtatg cttggagtga tctaggcttg 1200
tatatgcgga atcgcgatct gacgcggttg ctttgtagag gctggggtc taggctgtga 1260
ttttagaatc aaataaagct gttccttacc gtagatgttt cctacagtc ctgtccagta 1320
ctccagtgct atattcacat tgtttgaggc ttgagttttg tcgatcagtg gtcatgagaa 1380
aaatatatct catgatttta gaggcaccta ttgggaaagg tagatggttc cgttttacat 1440
gtttatagac cttgtggca tggctccttt gttctatggg tgctttattt tcctgaataa 1500
cagtaatgcg agactggtct atgggtgctt tgaccagtaa tgcgagacta gttatttgat 1560
catggtgcag ttcctagtga ttacgaacaa caatttggta gctcagttca ttcagcattg 1620
gtttctacga tccttatcat tttacttctg aatgaattta tttatttaag atattacagt 1680
gcaataaact gctgtataat atcagtaaca aactgctatt actagtaaat gcctagattc 1740
ataataattc attattctac ttgaaaatga tcttaggcct tttatgcgg tcctacgcat 1800
ccttccacag gacttgctgt ttgtttgttt tttgtaatcc ctcgctggga cgcagaatgg 1860
ttcatctgtg ctaataattt ttttgcatat ataagtttat agttctcatt attcatgtgg 1920
ctatggtagc ctgtaaaatc tattgtaata acatattagt cagccataca tctgttccaa 1980
cttgctcaat tgcaaatcat atctccactt aaagcacatg tttgcaagct ttctgacaag 2040
tttctttgtg tttgattgaa acaggtg                                     2067

SEQ ID NO: 154          moltype = DNA   length = 1076
FEATURE                 Location/Qualifiers
source                  1..1076
                        mol_type = other DNA
                        organism = Sorghum bicolor
SEQUENCE: 154
gtatcaactc ggttcaccac tccaatctac gtctgattta gatgttactt ccatctatgt   60
ctaatttaga tgttactccg atgcgattgg attatgttta tgcggtttgc actgctctgg  120
aaactggaat ctagggtttc gagtgatttg atcgatcgcg atctgtgatt tcgttgcgcc  180
ttgtgtatgc ttggagtgat ctaggcttgt atatgcggca tcgcgatctg acgcggttgc  240
tttgtagagg ctgggggtct aggctgtgat tttagaatca aataaagctg ttccttaccg  300
tagatgtttc ctacatgttc tgtccagtac tccagtgcta tattcacatt gtttgaggct  360
tgagttttgt cgatcagtgg tcatgagaaa aatatatctc atgattttag aggcacctat  420
tgggaaaggt agatggttcc gttttacatg ttttatagac cttgtggcat ggctcctttg  480
ttctatgggt gctttatttt cctgaataac agtaatgcga gactggtcta tgggtgcttt  540
gaccagtaat gcgagactag ttatttgatc atggtgcagt tcctagtgat tacgaacaac  600
aatttggtag ctcagttcat tcagcattgg tttctacgat ccttatcatt ttacttctga  660
atgaatttat ttatttaaga tattacagtg caataaactg ctgtataatc tcagtaacaa  720
actgctatta ctagtaaatg cctagattca ataattca ttattctact tgaaaatgat  780
cttaggcctt tttatgcggt cctacgcatc cttccacagg acttgctgtt tgtttgttt   840
ttgtaatccc tcgctgggac gcagaatggt tcatctgtgc taataatttt tttgcatata  900
taagtttata gttctcatta ttcatgtggc tatggtagcc tgtaaaatct attgtaataa  960
catattagtc agccatacat ctgttccaac ttgctcaatt gcaaatcata tctccactta 1020
aagcacatgt ttgcaagctt tctgacaagt tctttgtgt ttgattgaaa caggtg      1076

SEQ ID NO: 155          moltype = DNA   length = 2067
FEATURE                 Location/Qualifiers
source                  1..2067
                        mol_type = other DNA
                        organism = Sorghum bicolor
SEQUENCE: 155
cattaaaagt cattatgtgc atgcgtcgta actaacatgg atatgttgct gcactatctc   60
ctcgcactag ctgcgcatga taaagccaca agccaaaatt aattattatg ggtgagaata  120
aatacgtacc agcaccggcc atagaaaaag tacattatta aaggtctaat ttggaaacag  180
tctgaaaacg acgtgcgctg cagaggtaaa tgtaattttc ggcactaaaa ccattatcaa  240
```

```
ctaattcatt caataacagt tatttagaaa atgtatagct cgctctaaaa aaacagttta    300
gaaaaacagt caaaataatt cgaccaacaa acagttaata aggttcatta aatatataat    360
gcacggtgct atttgatctt ttaaaggaaa aagaggaata gtcgtgggcg ccaggcggga    420
attgggcgc gggagtctgc cggacgacgc gttccgtccg aacggccgga cccgacgagg     480
ccccccgcc gccccacgtc gcagaaccgt ccgtgggtgg taatctggcc gggtacacca     540
gccgtcccct tgggcggcct cacagcactg ggctcacacg tgagttttgt tctgggcttc    600
ggatcgcacc atatgggcct cggcatcaga aagacgggc ccgtctggga tagaagagac     660
aggaacctcc tcgtggattc cagaagccag ccacgagcga ccaccgacgc ggaggatact    720
cgtcgtccaa gtccaacacg gcgggcgggc gggcggacgc gtgggctggg ctaactgcct    780
aaccttaacc tccaaggcac gccaaggcc gcttctccca cccgacataa atatccccc      840
atccaggcaa ggcgcagagc ctcagaccag attccgatca atcacccata agctccccc    900
aaatctgttc ctcgtctccc gtctcgcggt ttcctacttc cctcggacgc ctccggcaag    960
tcgctcgacc gcgcgattcc gcccgctcaa ggtatcaact cggttcacca ctccaatcta    1020
cgtctgattt agatgttact tccatctatg tctaatttag atgttactcc gatgcgattg    1080
gattatgttt atgcggtttg cactgctctg gaaactggaa tctagggttt cgagtgattt    1140
gatcgatcgc gatctgtgat ttcgttgcgc cttgtgtatg cttggagtga tctaggcttg    1200
tatatgcgga atcgcgatct gacgcggttg ctttgtagag gctggggtc taggctgtga     1260
ttttagaatc aaataaagct gttccttacc gtagatgttt cctacactgt ctgtccagta    1320
ctccagtgct atattcacat tgtttgaggc ttgagttttg tcgatcagtg gtcatgagaa    1380
aaatatatct catgatttta gaggcaccta tgggaaagg tagatggttc cgttttacat     1440
gttttataga ccttgtggca tggctccttt gttctatggg tgctttattt tcctgaataa    1500
cagtaatgcg agactggtct atgggtgctt tgaccagtaa tgcgagacta gttatttgat    1560
catggtgcag ttcctagtga ttacgaacaa caatttggta gctcagttca ttcagcattg    1620
gtttctacga tccttatcat tttacttctg aatgaattta tttatttaag atattacagt    1680
gcaataaact gctgtataat atcagtaaca aactgctatt actagtaaat gcctagattc    1740
ataataattc attattctac ttgaaaatga tcttaggcct ttttatgcgg tcctacgcat    1800
ccttccacag gacttgctgt tgtttgttt tttgtaatcc ctcgctggga gcagaatggt    1860
ttcatctgtg ctaataattt ttttgcatat ataagtttat agttctcatt attcatgtgg    1920
ctatggtagc ctgtaaaatc tattgtaata acatattagt cagccataca tctgttccaa    1980
cttgctcaat tgcaaatcat atctccactt aaagcacatg tttgcaagct ttctgacaag    2040
tttctttgtg tttgattgaa acagggt                                        2067
```

```
SEQ ID NO: 156          moltype = DNA   length = 1076
FEATURE                 Location/Qualifiers
source                  1..1076
                        mol_type = other DNA
                        organism = Sorghum bicolor
SEQUENCE: 156
gtatcaactc ggttcaccac tccaatctac gtctgattta gatgttactt ccatctatgt    60
ctaatttaga tgttactccg atgcgattgg attatgttta tgcggtttgc actgctctgg    120
aaactggaat ctagggtttc gagtgatttg atcgatcgcg atctgtgatt tcgttgcgcc    180
ttgtgtatgc ttggagtgat ctaggcttgt atatgcggca tcgcgatctg acgcggttgc    240
tttgtagagg ctggggtct aggctgtgat tttagaatca aataaagctg ttccttaccg     300
tagatgtttc ctacatgttc tgtccagtac tccagtgcta tattcacatt gtttgaggct    360
tgagttttgt cgatcagtgg tcatgagaaa aatatatctc atgattttag aggcacctat    420
tgggaaaggt agatggttcc gttttacatg ttttatagac cttgtggcat ggctcctttg    480
ttctatgggt gctttatttt cctgaataac agtaatgcga gactggtcta tgggtgcttt    540
gaccagtaat gcgagactag ttatttgatc atggtgcagt tcctagtgat tacgaacaac    600
aatttggtag ctcagttcat tcagcattgg tttctacgat ccttatcatt ttacttctga    660
atgaatttat ttatttaaga tattacagtg caataaactg ctgtataata tcagtaacaa    720
actgctatta ctagtaaatg cctagattca ataattca ttattctact tgaaaatgat      780
cttaggcctt tttatgcggt cctacgcatc cttccacagg acttgctgtt tgtttgtttt    840
ttgtaatccc tcgctgggac gcagaatggt tcatctgtgc taataatttt tttgcatata    900
taagtttata gttctcatta ttcatgtggc tatggtagcc tgtaaaatct attgtaataa    960
catattagtc agccatacat ctgttccaac ttgctcaatt gcaaatcata tctccactta    1020
aagcacatgt ttgcaagctt tctgacaagt ttctttgtgt ttgattgaaa cagggt        1076
```

```
SEQ ID NO: 157          moltype = DNA   length = 2003
FEATURE                 Location/Qualifiers
source                  1..2003
                        mol_type = other DNA
                        organism = Sorghum bicolor
SEQUENCE: 157
agaagtaaaa aaaagttcg tttcagaatc ataaaggtaa gttaaaaaaa gaccatacaa      60
aaaagaggta tttaatgata aactataatc cagaatttgt taggatagta tataagaata    120
agaccttgtt tagtttcaaa aaaatttgca aaatttttcca gattcctcgt cacatcaaat   180
ctttagaggt atgcatggag tattaaatat agacaagacc taaataagaa aacatgaaat    240
gttcacgaaa aaaatcaagc caatgcatga tcgaagcaaa cggtatagta acggtgttaa    300
cctgatccat tgatctttgt aatctttaac ggccaccttac ggcgggcagc aaacggcgtc   360
cccctcctcg atatctccgc ggcggcctct ggcttttttcc gcggaattgc gcggtgggga   420
cggattccac gagaccgcaa cgcaaccgcc tctcgccgct gggccccaca ccgctcggtg    480
ccgtagcccg tagcctcacg ggattctttc tcctcctcc ccgtgtata aattggcttc      540
atccctcc tgcctcatcc atccaaatcc cactcccaa tccatcccg tcggagaaat        600
tcatcgaagc gaagcgaagc gaatcctccc gatcctctca aggtacgcga ggtttcgaat    660
cccctccaga cccctcgtat gctttccctg ttcgttttcg tcgtagcgtt tgattaggta    720
tgctttccct gttcgtgttc gtcgtagggt tcgattaggt cgtgtgaggc catggcctgc    780
tgtgataaat ttatttgttg ttatatcgga tctgtagtcg atttgggggt cgtggtgtag    840
atccgcgggc tgtgatgaag ttatttggtg tgattgtgct cgcgtgattc tgcgcgttga    900
gctcgagtag atctgatggt tggacgaccg attggttcgt tggctggctg cgctaaggtt    960
```

```
gggctgggct catgttgcgt tcgctgttgc gcgtgattcc gcggatggac ttgcgcttga  1020
ttgccgccag atcacgttac gattatgtga tttcgtttgg aacttttag atttgtagct    1080
tctgcttatt atatgacaga tgcgcctact gctcatatgc ctgtggtaaa taatggatgg   1140
ctgtgggtca aactagttga ttgtcgagtc atgtatcata tacaggtgta tagacttgcg   1200
tctaattgtt tgcatgttgc agttatatga tttgttttgt attgtttgtt ccactcatct   1260
aggctgtaaa agggacacta cttattagct tgttgtttaa tcttttatt agtagattat    1320
attggtaatg ttttactaat tattattatg ttatatgtga cttctgctca tgcctgatta   1380
taatcataga tcactgtagt tgattgttga atcatgtgtc aaatacccgt atacataaca   1440
ctacacattt gcttagttgt ttccttaact catgcaaatt gaacaccatg tatgatttgc   1500
atggtgctgt aatgttaaat actacagtcc tgttggtact tgtttagtaa gaatctgctt   1560
catacaacta tatgctatgc ctgatgataa tcatatatct ttgtgtaatt aataattagt   1620
tgactgttga ataatgtatc gagtacatac catggcacaa ttgcttagtc acttccttaa   1680
ccatgcatat tgaactgacc ccttcatgtt ctgctgaatt gttctattct gattagacca   1740
tacatcatgt attgcaatct ttatttgcaa ttgtaatgta atggttcggt tctcaaatgt   1800
taaatgctat agttgtgcta ctttctaatg ttaaatgcta tagctgtgct acttgtaaga   1860
tctgcttcat agtttagtta aattaggatg atgagctttg atgctgtaac tttgtttgat   1920
tatgttcata gttgatcagt ttttgttaga ctcacagtaa cttatggtct cactcttctt   1980
ctggtctttg atgtttgcag cgg                                           2003

SEQ ID NO: 158         moltype = DNA  length = 1361
FEATURE                Location/Qualifiers
source                 1..1361
                       mol_type = other DNA
                       organism = Sorghum bicolor
SEQUENCE: 158
gtacgcgagt tttcgaatcc cctccagacc cctcgtatgc tttccctgtt cgttttcgtc   60
gtagcgtttg attaggtatg ctttccctgt tcgtgttcgt cgtagggttc gattaggtcg   120
tgtgaggcca tggcctgctg tgataaattt atttgttgtt atatcggatc tgtagtcgat   180
ttgggggtcg tggtgtagat ccgcgggctg tgatgaagtt atttggtgtg attgtgctcg   240
cgtgattctg cgcgttgagc tcgagtagat ctgatgggtg gacgaccgat tggttcgttg   300
gctggctgcg ctaaggttgg gctgggctca tgttgcgttc gctgttgcgc gtgattccgc   360
ggatggactt cgcgcttgatt gccgccagat cacgttacga ttatgtgatt tcgtttggaa   420
ctttttagat ttgtagcttc tgcttattat atgacagatg cgcctactgc tcatatgcct   480
gtggtaaata atggatggct gtgggtcaaa ctagttgatt gtcgagtcat gtatcatata   540
caggtgtata gacttgcgtc taattgtttg catgttgcag ttatatgatt tgttttagat   600
tgtttgttcc actcatctag gctgtaaaag ggacactact tattagcttg ttgtttaatc   660
ttttttattag tagattatat tggtaatgtt ttactaatta ttattatgtt atatgtgact   720
tctgctcatg cctgattata atcatagatc actgtagttg attgttgaat catgtgtcaa   780
atacccgtat acataacact acacatttgc ttagttgttt ccttaactca tgcaaattga   840
acaccatgta tgatttgcat ggtgctgtaa tgttaaatac tacagtcctg ttggtacttg   900
tttagtaaga atctgcttca tacaactata tgctatgcct gatgataatc atatatcttt   960
gtgtaattaa taattagttg actgttgaat aatgtatcga gtacatacca tggcacaatt   1020
gcttagtcac ttccttaacc atgcatattg aactgacccc ttcatgttct gctgaattgt   1080
tctattctga ttagaccata tcatcatgta tgcaatcttt atttgcaatt gtaatgtaat   1140
ggttcggttc tcaaatgtta aatgctatag ttgtgctact ttctaatgtt aaatgctata   1200
gctgtgctac ttgtaagatc tgcttcatag tttagttaaa ttaggatgat gagctttgat   1260
gctgtaactt tgtttgatta tgttcatagt tgatcagttt ttgttagact cacagtaact   1320
tatggtctca ctcttcttct ggtctttgat gtttgcagcg g                       1361

SEQ ID NO: 159         moltype = DNA  length = 1812
FEATURE                Location/Qualifiers
source                 1..1812
                       mol_type = other DNA
                       organism = synthetic construct
SEQUENCE: 159
atggtccgtc ctgtagaaac cccaacccgt gaaatcaaaa aactcgacgg cctgtgggca   60
ttcagtctgg atcgcgaaaa ctgtggaatt gatcagcgtt ggtgggaaag cgcgttacaa   120
gaaagccggg caattgctgt gccaggcagt tttaacgatc agttcgccga tgcagatatt   180
cgtaattatg cgggcaacgt ctggtatcag cgcgaagtct ttataccgaa aggttgggca   240
ggccagcgta tcgtgctgcg tttcgatgcg gtcactcatt acggcaaagt gtgggtcaat   300
aatcaggaag tgatggagca tcagggcggc tatacgccat tgaagccga tgtcacgccg   360
tatgttattg ccgggaaaag tgtacgtatc ccgtttgtg tgaacaacga actgaactgg   420
cagactatcc cgccgggaat ggtgattacc gacgaaaacg caagaaaaa gcagtcttac   480
ttccatgatt tctttaacta tgccggaatc catcgcagtc aatgctctta caccacgccg   540
aacacctggg tggacgatat caccgtggtg acgcatgtcg cgcaagactg taaccacgcg   600
tctgttgact ggcaggtggt ggccaatggt gatgtcagcg ttgaactgcg tgatgcggat   660
caacaggtgg ttgcaactgg acaaggcact agcgggactt gcaagtggt gaatccgcac   720
ctctggcaac cgggtgaagg ttatctctat gaactgtgcg tcacagccaa aagccagaca   780
gagtgtgata tctacccgct tcgcgtcgg atccggtcag tggcagtgaa gggcgaacag   840
ttcctgatta ccacaaaacc gttctacttt actggctttg tcgtcatgag agatgcggac   900
ttgcgtggca aaggattcga taacgtgctg atggtgcacg accacgcatt aatggactgg   960
attggggcca actcctaccg tacctcgcat taccttacg ctgaagagat gctcgactgg   1020
gcagatgaac atggcatcgt ggtgattgat gaaactgctg ctgtcggctt taacctctct   1080
ttaggcattg gtttcgaagc gggcaacaag ccgaaagaac tgtacagcga agaggcagtc   1140
aacgggaaa ctcagcaagc gcacttacga gcgattaaag agctgatagc cgtgacaaa   1200
aaccacccaa gcgtggtgat gtggagtatt gccaacgaac cggataccg tccgcaaggt   1260
gcacgggaat atttcgcgcc actggcgaa gcaacgcgta aactcgaccc gacgcgtccg   1320
atcacctgcg tcaatgtaat gttctgcgac gctcacaccg ataccatcag cgatctcttt   1380
gatgtgctgt gcctgaaccg ttattacgga tggtatgtcc aaagcggcga tttggaaacg   1440
```

```
gcagagaagg tactggaaaa agaacttctg gcctggcagg agaaactgca tcagccgatt    1500
atcatcaccg aatacggcgt ggatacgtta gccgggctgc actcaatgta caccgacatg    1560
tggagtgaag agtatcagtg tgcatggctg gatatgtatc accgcgtctt tgatcgcgtc    1620
agcgccgttg tcggtgaaca ggtatggaat tcgccgattt tgcgacctc gcaaggcata    1680
ttgcgcgttg gcggtaacaa gaaagggatc ttcactcgcg accgcaaacc gaagtcggcg    1740
gcttttctgc tgcaaaaacg ctggactggc atgaacttcg tgaaaaacc gcagcaggga    1800
ggcaaacaat ga                                                         1812

SEQ ID NO: 160          moltype = DNA  length = 2001
FEATURE                 Location/Qualifiers
source                  1..2001
                        mol_type = other DNA
                        organism = synthetic construct
SEQUENCE: 160
atggtccgtc ctgtagaaac cccaacccgt gaaatcaaaa aactcgacgg cctgtgggca    60
ttcagtctgg atcgcgaaaa ctgtggaatt gatcagcgtt ggtgggaaag cgcgttacaa    120
gaaagccggg caattgctgt gccaggcagt tttaacgatc agttcgccga tgcagatatt    180
cgtaattatg cgggcaacgt ctggtatcag cgcgaagtct ttataccgaa aggttgggca    240
ggccagcgta tcgtgctgcg tttcgatgcg gtcactcatt acggcaaagt gtgggtcaat    300
aatcaggaag tgatggagca tcagggcggc tatacgccat ttgaagccga tgtcacgccg    360
tatgttattg ccgggaaaag tgtacgtaag tttctgcttc tacctttgat atatatataa    420
taattatcat taattagtag taatataata tttcaaatat tttttcaaa ataaaagaat    480
gtagtatata gcaattgctt ttctgtagtt tataagtgtg tatattttaa tttataactt    540
ttctaatata tgaccaaaat tgttgatgt gcaggtatca ccgtttgtgt gaacaacgaa    600
ctgaactggc agactatccc gccgggaatg gtgattaccg acgaaacgg caagaaaaag    660
cagtcttact tccatgattt cttaactat gccggaatcg atcgcagcgt aatgctctac    720
accacgccga acacctgggt ggacgatatc accgtggtga cgcatgtcgc gcaagactgt    780
aaccacgcgt ctgttgactg gcaggtggtg gccaatggtg atgtcagcgt tgaactgcgt    840
gatgcggatc aacaggtggt tgcaactgga caaggcacta gcgggacttt gcaagtggtg    900
aatccgacc tctggcaacc gggtgaaggt tatctcgtaa actgtgcgt cacagccaaa    960
agccagacag agtgtgatat ctacccgctt cgcgtcggca tccggtcagt ggcagtgaag    1020
ggcgaacagt tcctgattaa ccacaaaccg ttctacttta ctggctttgg tcgtcatgaa    1080
gatgcggact tgcgtggcaa aggattcgat aacgtgctga tggtgcacga ccacgcatta    1140
atggactgga ttggggccaa ctcctaccgt acctcgcatt accttacgc tgaagagatg    1200
ctcgactggg cagatgaaca tggcatcgtg gtgattgatg aaactgctgc tgtcggcttt    1260
aacctctctt taggcattgg tttcgaagcg ggcaacaagc cgaaagaact gtacagcgaa    1320
gaggcagtca acggggaaac tcagcaagcg cacttacagg cgattaaaga gctgatagcg    1380
cgtgacaaaa accaccccaag cgtggtgatg tggagtattg ccaacgaacc ggataccgt    1440
ccgcaggtg cacgggaata tttcgcgcca ctggccgaag caacgcgtaa actcgacccg    1500
acgcgtccga tcacctgcgt caatgtaatg ttctgcgacg ctcacaccga taccatcagc    1560
gatctctttg atgtgctgtg cctgaaccgt tattacggat ggtatgtcca aagcggcgat    1620
ttggaaacgg cagagaaggt actggaaaaa gaacttctgg cctggcagga gaaactgcat    1680
cagccgatta tcatcaccga atacggcgtg gatacgttac cgggctgca ctcaatgtac    1740
accgacatgt ggagtgaaga gtatcagtgt gcatggctgg atatgtatca ccgcgtcttt    1800
gatcgcgtca gcgccgtcgt cggtgaacag gtatggaatt cgccgatttt gcgacctcg    1860
caaggcatat tgcgcgttgg cggtaacaag aaagggatct tcactcgcga ccgcaaaccg    1920
aagtcggcgg cttttctgct gcaaaaacgc tggactggca tgaacttcgg tgaaaaaccg    1980
cagcagggag gcaaacaatg a                                              2001

SEQ ID NO: 161          moltype = DNA  length = 253
FEATURE                 Location/Qualifiers
source                  1..253
                        mol_type = other DNA
                        organism = Agrobacterium tumefaciens
SEQUENCE: 161
gatcgttcaa acatttggca ataaagtttc ttaagattga atcctgttgc cggtcttgcg    60
atgattatca tataatttct gttgaattac gttaagcatg taataattaa catgtaatgc    120
atgacgttat ttatgagatg gtttttatg attagagtcc cgcaattata catttaatac    180
gcgatagaaa acaaaatata gcgcgcaaac taggataaat tatcgcgcgc ggtgtcatct    240
atgttactag atc                                                        253

SEQ ID NO: 162          moltype = DNA  length = 210
FEATURE                 Location/Qualifiers
source                  1..210
                        mol_type = other DNA
                        organism = Triticum aestivum
SEQUENCE: 162
ctgcatgcgt ttggacgtat gctcattcag gttggagcca atttggttga tgtgtgtgcg    60
agttcttgcg agtctgatga gacatctctg tattgtgttt cttcccag tgttttctgt    120
acttgtgtaa tcggctaatc gccaacagat tcggcgatga taaatgaga aataaattgt    180
tctgattttg agtgcaaaaa aaaaggaatt                                      210

SEQ ID NO: 163          moltype = DNA  length = 1204
FEATURE                 Location/Qualifiers
source                  1..1204
                        mol_type = other DNA
                        organism = synthetic construct
SEQUENCE: 163
ggtccgattg agacttttca acaaagggta atatccggaa acctcctcgg attccattgc    60
```

```
ccagctatct gtcactttat tgtgaagata gtggaaaagg aaggtggctc ctacaaatgc    120
catcattgcg ataaaggaaa ggccatcgtt gaagatgcct ctgccgacag tggtcccaaa    180
gatggacccc cacccacgag gagcatcgtg gaaaagaag acgttccaac cacgtcttca     240
aagcaagtgg attgatgtga tggtccgatt gagactttc aacaagggt aatatccgga      300
aacctcctcg gattccattg cccagctatc tgtcacttta ttgtgaagat agtggaaaag    360
gaaggtggct cctacaaatg ccatcattgc gataaaggaa aggccatcgt tgaagatgcc    420
tctgccgaca gtggtcccaa agatggaccc ccacccacga ggagcatcgt ggaaaaagaa    480
gacgttccaa ccacgtcttc aaagcaagtg gattgatgtg atatctccac tgacgtaagg    540
gatgacgcac aatcccacta tccttcgcaa gaccettcct ctatataagg aagttcattt    600
catttggaga ggacacgctg acaagctgac tctagcagat cctctagaac catcttccac    660
acactcaagc cacactattg gagaacacac agggacaaca caccataaga tccaagggag    720
gcctccgccg ccgccggtaa ccaccccgcc cctctcctct ttctttctcc gttttttttt    780
ccgtctcggt ctcgatcttt ggccttgta gtttgggtgg gcgagaggcg gcttcgtgcg     840
cgcccagatc ggtgcgcggg aggggcggga tctcgcggcg ggcggcgtgaa               900
tccggcccgg atctcgcggg gaatgggct ctcggatgta gatctgcgat ccgccgttgt      960
tgggggagat gatgggggt ttaaaatttc cgccgtgcta aacaagatca ggaagagggg     1020
aaaagggcac tatggtttat attttttatat atttctgctg cttcgtcagg cttagatgtg   1080
ctagatcttt cttttcttctt tttgtgggta gaatttgaat ccctcagcat tgttcatcgg   1140
tagttttct ttcatgatt tgtgacaaat gcagcctcgt gcggagcttt tttgtaggta     1200
gaag                                                                1204

SEQ ID NO: 164         moltype = DNA  length = 1399
FEATURE                Location/Qualifiers
source                 1..1399
                       mol_type = other DNA
                       organism = Oryza sativa
SEQUENCE: 164
tcgaggtcat tcatatgctt gagaagagag tcgggatagt ccaaaataaa acaaaggtaa     60
gattacctgg tcaaaagtga aaacatcagt taaaagtgg tataaagtaa aatatccgta     120
ataaaaggtg gcccaaagtg aaatttactc ttttctacta ttataaaaat tgaggatgtt    180
tttgtcggta ctttgatacg tcattttgt atgaattgat ttttaagttt attcgctttt     240
ggaaatgcat atctgtattt gagtcgggtt ttaagttcgt ttgctttgt aaatacagag     300
ggatttgtat aagaaatatc tttagaaaaa cccatatgct aatttgacat aatttttgag    360
aaaaatatat attcaggcga attctcacaa tgaacaataa taagattaaa atagctttcc    420
cccgttgcag cgcatgggta ttttttctag taaaaataaa agataaactt agactcaaaa    480
catttacaaa aacaaccct aaagttccta aagcccaaag tgctatccac gatccatagc      540
aagcccagcc caacccaacc caacccaacc caccccagtc cagccaactg gacaatagtc     600
tccacacccc cccactatca ccgtgagttg tccgcacgca ccgcacgtct cgcagccaaa    660
aaaaaaaaga aagaaaaaaa agaaaaagaa aaaacagcag gtgggtccgg gtcgtggggg    720
ccggaaacgc gaggaggatc gcgagccagc gacgaggccg gccctccctc cgcttccaaa    780
gaaacgcccc ccatcgccac tatatacata cccccccctc tcctcccatc cccccaaccc    840
taccaccacc accaccacca cctccacctc ctccccctc gctgccggac gacgagctcc     900
tccccctcc ccctccgccg ccgccgcgcc ggtaaccacc ccgccccctct cctcttctt     960
tctccgtttt tttttccgtc tcggtctcga tctttggcct tggtagtttg ggtgggcgag   1020
aggcggcttc gtgcgcgcc agatcggtgc gcgggagggg cgggatctcg cggctggggc    1080
tctcgccggc gtggatccgg cccggatctc gcggggaatg gggctctcgg atgtagatct   1140
gcgatccgcc gttgttgggg gagatgatgg ggggtttaaa atttccgcgt gctaaacaa    1200
gatcaggaag agggggaaaag ggcactatgg tttatatttt tatatattc tgctgcttcg   1260
tcaggcttag atgtgctaga tcttttcttttc ttctttttgt gggtagaatt tgaatccctc  1320
agcattgttc atcggtagtt ttttcttca tgatttgtga caaatgcagc ctcgtgcgga    1380
gctttttttgt aggtagaag                                               1399

SEQ ID NO: 165         moltype = DNA  length = 2181
FEATURE                Location/Qualifiers
source                 1..2181
                       mol_type = other DNA
                       organism = Oryza sativa
SEQUENCE: 165
gacaacaaca tgcttctcat caacatggag ggaagaggga gggagaaagt gtcgcctggt     60
cacctccatt gtcacactag ccactggcca gctctcccac accaccaatg ccaggggcga    120
gctttagcac agccaccgct tcacctccac caccgcacta ccctagcttc gcccaacagc    180
caccgtcaac gcctcctctc cgtcaacata agagagagag agaagaggag agtagccatg    240
tgggaggag gaatagtaca tggggcctac cgttggcaa gttattttgg gttgccaagt      300
taggccaata aggggaggga tttggccatc cggttgggaa ggtattggg gtagtatctt      360
tttactagaa ttgtcaaaaa aaatagttt gagagccatt tggagaggat gttgcctgtt    420
agaggtgctc ttaggacatc aaattccata aaaacatcag aaaaattctc tcgatgaaga    480
tttataacca ctaaaactgc cctcaattcg aagggagttc aaaacaatta aaatcatgtt    540
cgaattgagt ttcaatttca cttttaaccc tttgaaatct caatggtaaa acatcaaccg    600
gtcaggtagc atggttcttt ttattccttt caaaaagagt taattacaaa cagaatcaaa    660
actaacagtt aggcccaagg cccatccgag caaacaatag atcatgggcc aggcctgcca    720
ccaccctccc cctcctggct cccgctcttg aatttcaaaa tccaaaaata tcggcacgac    780
tggccgccga cggagcgggc ggaaaatgac ggaacaaccc ctcgaattct accccaacta    840
cgcccaccaa cccacacgcc actgacaatc cggtcccacc cttgtgggcc cacctacaag    900
cgagacgtca gtcgctcgca gcaacagtg ggccaccctc ccagtgagcg gcgggtagat     960
ctggactctt acccacccac actaaacaaa acgcatgaa tatttgcac taaaaccctc     1020
agaaaaatc cgatattcca aaccagtaca gttcctgacc gttggaggag ccaaagtggaa   1080
gcggagtgta aaattgggaa acttaatcga ggggggtaaa cgcaaaaacg ccgaggcgcc   1140
tcccgctcta tagaaagggg aggagtggga ggtggaaacc ctaccacacc gcagagaaag   1200
gcgtcttcgt actcgcctct ctccgcgccc tcctccgccc ccgctcgccg ccgttcgtct   1260
```

```
ccgccgccac cggctagcca tccaggtaaa acaaacaaaa acggatctga tgcttccatt  1320
cctccgtttc tcgtagtagc gcgcttcgat ctgtgggtgg atctgggtga tcctggggtg  1380
tggttcgttc tgtttgatag atctgtcggt ggatctggcc ttctgtggtt gtcgatgtcc  1440
ggatctgcgt tttgatcagt ggtagttcgt ggatctggcg aaatgttttg gatctggcag  1500
tgagacgcta agaatcggga aatgatgcaa tattagggcg gtttcggatg gggatccact  1560
gaattagtct gtctccctgc tgataatctg ttccttttg gtagatctgg ttagtgtatg   1620
tttgtttcgg atagatctga tcaatgcttg tttgttttt caaattttct acctaggttg   1680
tataggaatg gcatgcggat ctggttggat tgccatgatc cgtgctgaaa tgcccctttg   1740
gttgatggat cttgatattt tactgctgtt cacctagatt tgtactcccg tttatactta   1800
atttgttgct tattatgaat agatctgtaa cttaggcaca tgtatggacg gagtatgtgg   1860
atctgtagta tgtacattgc tgcgagctaa gaactatttc agagcaagca cagaaaaaaa  1920
tatttagaca gattgggcaa ctatttgatg gtctttggta tcatgctttg tagtgctcgt   1980
ttctgcgtag taatctttg atctgatctg aagataggtg ctattatatt cttaaaggtc   2040
attagaacgc tatctgaaag gctgtattat gtggattggt tcacctgtga ctccctgttc   2100
gtcttgtctt gataaatcct gtgataaaaa aaattcttaa ggcgtaattt gttgaaatct   2160
tgttttgtcc tatgcagcct g                                            2181

SEQ ID NO: 166           moltype = DNA   length = 1653
FEATURE                  Location/Qualifiers
source                   1..1653
                         mol_type = other DNA
                         organism = synthetic construct
SEQUENCE: 166
atggaagacg ccaaaaacat aaagaaaggc ccggcgccat tctatcctct agaggatgga  60
accgctggag agcaactgca taaggctatg aagagatacg cccggttcc tggaacaatt    120
gcttttacag atgcacatat cgaggtgaac atcacgtacg cggaatactt cgaaatgtcc   180
gttcggttgg cagaagctat gaaacgatat gggctgaata caaatcacag aatcgtcgta  240
tgcagtgaaa actctcttca attctttatg ccggtgttgg gcgcgttatt tatcggagtt   300
gcagttgcgc ccgcgaacga catttataat gaacgtgaat tgctcaacag tatgaacatt  360
tcgcagccta ccgtagtgtt tgtttccaaa aaggggttgc aaaaaatttt gaacgtgcaa  420
aaaaaattac caataatcca gaaaattatt atcatggatt ctaaaacgga ttaccaggga  480
tttcagtcga tgtacacgtt cgtcacatct catctacctc ccggttttaa tgaatacgat  540
tttgtaccag agtcctttga tcgtgacaaa acaattgcac tgataatgaa ttcctctgga  600
tctactgggt tacctaaggg tgtggccctt ccgcataga actgcctgcgt cagattctcg   660
catgccagag atcctatttt tggcaatcaa atcattccgg atactgcgat tttaagtgtt  720
gttccattcc atcacggttt tggaatgttt actacactcg gatatttgat atgtggattt  780
cgagtcgtct taatgtatag atttgaagaa gagctgtttt tacgatccct tcaggattac  840
aaaattcaaa gtgcgttgct agtaccaacc ctatttttct tcttcgccaa aagcactctg  900
attgacaaat acgatttatc taatttacac gaaattgctt ctgggggcgc acctctttcg  960
aaagaagtcg gggaagcggt tgcaaaacgc ttccatcttc cagggatacg acaaggatat  1020
gggctcactg agactacatc agctattctg attacacccg agggggatga taaaccgggc  1080
gcggtcggta aagttgttcc attttttgaa gcgaaggttg tggatctgga taccgggaaa  1140
acgctgggcg ttaatcagag aggcgaatta tgtgtcagag gacctatgat tatgtccggg  1200
tatgtaaaca atccggaagc gaccaacgcc ttgattgaca aggatggatg gctacattct  1260
ggagacatag cttactggga cgaagacgaa cacttcttca tagttgaccg cttgaagtct  1320
ttaattaaat acaaaggata tcaggtggcc cccgctgaat tggaatcgat attgttacaa  1380
caccccaaca tcttcgacgc gggcgtggca ggtcttcccg acgatgacgc cggtgaactt  1440
cccgccgccg ttgttgtttt ggagcacgga aagacgatga cggaaaaaga gatcgtggat  1500
tacgtcgcca gtcaagtaac aaccgcgaaa aagttgcgcg aggagttgt gtttgtggac   1560
gaagtaccga aaggtcttac cggaaaactc gacgcaagaa aaatcagaga gatcctcata  1620
aaggccaaga agggcggaaa gtccaaattg taa                               1653

SEQ ID NO: 167           moltype = DNA   length = 936
FEATURE                  Location/Qualifiers
source                   1..936
                         mol_type = other DNA
                         organism = synthetic construct
SEQUENCE: 167
atggcttcca aggtgtacga ccccgagcaa cgcaaacgca tgatcactgg gcctcagtgg  60
tgggctcgct gcaagcaaat gaacgtgctg gactccttca tcaactacta tgattccgag  120
aagcacgccg agaacgccgt gatttttctg catggtaacg ctgcctccag ctacctgtgg  180
aggcacgtcg tgcctcacat cgagcccgtg gctagatgca tcatccctga tctgatcgga  240
atgggtaagt ccggcaagag cgggaatggc tcatatcgcc tcctggatca ctacaagtac  300
ctcaccgctt ggttcgagct gctgaacctt ccaaagaaaa tcatctttgt gggccacgac  360
tgggggggctt gtctggcctt tcactactcc tacgagcacc aagacaagat caaggccatc  420
gtccatgctg agagtgtcgt ggacgtgatc gagtcctggg acgagtggcc tgacatcgag  480
gaggatatcg ccctgatcaa gagcgaagag ggcgagaaaa tggtgcttga gaataacttc  540
ttcgtcgaga ccatgctccc aagcaagatc atgcggaaac tggagcctga ggagttcgct  600
gcctacctgg agccattcaa ggagaagggc gaggttagac ggctaccct ctcctggcct  660
cgcgagatcc ctctcgttaa gggaggcaag cccgacgtcg tccagattgt ccgcaactac  720
aacgcctacc tcgggccag cgacgatctg cctaagatgt tcatcgagtc cgaccctggg  780
ttctttttcca acgctattgt cgagggagct aagaagttcc ctaacaccga gttcgtgaag  840
gtgaagggc tccacttcag ccaggaggac gctccagatg aaatgggtaa gtacatcaag  900
agcttcgtgg agcgcgtgct gaagaacgag cagtaa                            936

SEQ ID NO: 168           moltype = DNA   length = 675
FEATURE                  Location/Qualifiers
source                   1..675
                         mol_type = other DNA
```

```
                        organism = synthetic construct
SEQUENCE: 168
ggtccgatgt gagactttc aacaaagggt aatatccgga aacctcctcg gattccattg    60
cccagctatc tgtcactta ttgtgaagat agtggaaaag gaaggtggct cctacaaatg    120
ccatcattgc gataaaggaa aggccatcgt tgaagatgcc tctgccgaca gtggtcccaa   180
agatggaccc ccacccacga ggagcatcgt ggaaaaagaa gacgttccaa ccacgtcttc   240
aaagcaagtg gattgatgtg atggtccgat gtgagacttt tcaacaaagg gtaatatccg   300
gaaacctcct cggattccat tgcccagcta tctgtcactt tattgtgaag atagtggaaa   360
aggaaggtgg ctcctacaaa tgccatcatt gcgataaagg aaaggccatc gttgaagatg   420
cctctgccga cagtggtccc aaagatggac ccccacccac gaggagcatc gtggaaaaag   480
aagacgttcc aaccacgtct tcaaagcaag tggattgatg tgatatctcc actgacgtaa   540
gggatgacgc acaatcccac tatccttcgc aagaccttc ctctatataa ggaagttcat    600
ttcatttgga gaggaaccat cttccacaca ctcaagccac actattggag aacacacagg   660
gacaacacac cataa                                                    675

SEQ ID NO: 169         moltype = DNA   length = 622
FEATURE                Location/Qualifiers
source                 1..622
                       mol_type = other DNA
                       organism = Cauliflower mosaic virus
SEQUENCE: 169
ggtccgattg agacttttca acaaagggta atatccggaa acctcctcgg attccattgc    60
ccagctatct gtcactttat tgtgaagata gtggaaaagg aaggtggctc ctacaaatgc   120
catcattgcg ataaaggaaa ggccatcgtt gaagatgcct ctgccgacag tggtcccaaa   180
gatggacccc acccacgag gagcatcgtg aaaaagaag acgttccaac cacgtcttca    240
aagcaagtgg attgatgtga tggtccgatt gagacttttc aacaaaggga atatccgga    300
aacctcctcg gattccattg cccagctatc tgtcacttta ttgtgaagat agtggaaaag   360
gaaggtggct cctacaaatg ccatcattgc gataaaggaa aggccatcgt tgaagatgcc   420
tctgccgaca gtggtcccaa agatggaccc ccacccacga ggagcatcgt ggaaaaagaa   480
gacgttccaa ccacgtcttc aaagcaagtg gattgatgtg atatctccac tgacgtaagg   540
gatgacgcac aatcccacta tctagacgca agacccttcc tctatataag gaagttcatt   600
tcatttggag aggacacgct ga                                            622

SEQ ID NO: 170         moltype = DNA   length = 1446
FEATURE                Location/Qualifiers
source                 1..1446
                       mol_type = other DNA
                       organism = synthetic construct
SEQUENCE: 170
ggtccgattg agacttttca acaaagggta atatccggaa acctcctcgg attccattgc    60
ccagctatct gtcactttat tgtgaagata gtggaaaagg aaggtggctc ctacaaatgc   120
catcattgcg ataaaggaaa ggccatcgtt gaagatgcct ctgccgacag tggtcccaaa   180
gatggacccc acccacgag gagcatcgtg aaaaagaag acgttccaac cacgtcttca    240
aagcaagtgg attgatgtga tggtccgatt gagacttttc aacaaagggt aatatccgga   300
aacctcctcg gattccattg cccagctatc tgtcacttta ttgtgaagat agtggaaaag   360
gaaggtggct cctacaaatg ccatcattgc gataaaggaa aggccatcgt tgaagatgcc   420
tctgccgaca gtggtcccaa agatggaccc ccacccacga ggagcatcgt ggaaaaagaa   480
gacgttccaa ccacgtcttc aaagcaagtg gattgatgtg atatctccac tgacgtaagg   540
gatgacgcac aatcccacta tccttcgcaa gaccttcct ctatataagg aagttcattt    600
catttggaga ggacacgctg acaagctgac tctagcagat ctaccgtctt cggtacgcgc   660
tcactcgcc ctctgccttt gttactgcca cgtttctctc aatgctctct tgtgtggtga    720
ttgctgagag tggtttagct ggatctagaa ttacactctg aaatcgtgtt ctgcctgtgc   780
tgattacttg ccgtcctttg tagcagcaaa atatagggac atggtagtac gaaacgaaga   840
tagaacctac acagcaatac gagaaatgtg taatttggtg cttagcggta tttatttaag   900
cacatgttgg tgttataggg cacttggatt cagaagtttg ctgttaattt aggcacaggc   960
ttcatactac atgggtcaat agtatagga ttcatattat aggcgatact ataataattt    1020
gttcgtctgc agagcttatt atttgccaaa attagatatt cctattctgt ttttgttgt    1080
gtgctgttaa attgttaacg cctgaaggaa taaatataaa tgacgaaatt tgatgtttta   1140
tctctgctcc ttattgtga ccataagtca agatcagatg cacttgtttt aaatattgtt    1200
gtctgaagaa ataagtactg acagtatttt gatgcattga tctgcttgtt tgttgtaaca   1260
aaatttaaaa ataaagagtt tccttttgt tgctctcctt acctcctgat ggtatctagt    1320
atctaccaac tgcactata ttgcttctct ttacatacgt atcttgctcg atgccttctc    1380
cctagtgtta accagtgtta ctcacatagt ctttgctcat tcattgtaa tgcagatacc   1440
aagcgg                                                              1446

SEQ ID NO: 171         moltype = DNA   length = 1165
FEATURE                Location/Qualifiers
source                 1..1165
                       mol_type = other DNA
                       organism = synthetic construct
SEQUENCE: 171
ggtccgatgt gagactttc aacaaagggt aatatccgga aacctcctcg gattccattg    60
cccagctatc tgtcactta ttgtgaagat agtggaaaag gaaggtggct cctacaaatg    120
ccatcattgc gataaaggaa aggccatcgc tgaagatgcc tctgccgaca gtggtcccaa   180
agatggaccc ccacccacga ggagcatcgt ggaaaaagaa gacgttccaa ccacgtcttc   240
aaagcaagtg gattgatgtg atggtccgat gtgagacttt tcaacaaagg gtaatatccg   300
gaaacctcct cggattccat tgcccagcta tctgtcactt tattgtgaag atagtggaaa   360
aggaaggtgg ctcctacaaa tgccatcatt gcgataaagg aaaggccatc gttgaagatg   420
cctctgccga cagtggtccc aaagatggac ccccacccac gaggagcatc gtggaaaaag   480
```

```
aagacgttcc aaccacgtct tcaaagcaag tggattgatg tgatatctcc actgacgtaa    540
gggatgacgc acaatcccac tatccttcgc aagacccttc ctctatataa ggaagttcat    600
ttcatttgga gaggacacgc tgacaagctg actctagcag atcctctaga accatcttcc    660
acacactcaa gccacactat tggagaacac acagggacaa cacaccataa gatccaaggg    720
aggcctccgc cgccgccggt aaccaccccg cccctctcct cttcttcttct ccgtttttt    780
ttccgtctcg gtctcgatct ttggccttgg tagtttgggt gggcgagagg cggcttcgtg    840
cgcgcccaga tcggtgcgcg ggaggggcgg gatctcgcgg ggaatggggc tctcggatgt    900
agatctgcga tccgccgttg ttgggggaga tgatgggggg tttaaaattt gcgccgtgct    960
aaacaagatc aggaagaggg gaaaagggca ctatgggtta tatttttata tattctgtg   1020
gcttcgtcag gcttagatgt gctagatctt tctttcttct tttttgtgggt agaatttgaa  1080
tccctcagca ttgttcatcg gtagtttttt ttttcatgat ttgtgacaaa tgcagcctcg  1140
tgcgagcttt ttttgtaggt agaag                                         1165

SEQ ID NO: 172          moltype = DNA  length = 1751
FEATURE                 Location/Qualifiers
source                  1..1751
                        mol_type = other DNA
                        organism = synthetic construct
SEQUENCE: 172
tcgaggtcat tcatatgctt gagaagagag tcgggatagt ccaaaataaa acaaaggtaa    60
gattacctgg tcaaaagtga aaacatcagt taaaggtgg tataaagtaa aatatcggta    120
ataaaaggtg gcccaaagtg aaatttactc ttttctacta ttataaaaat tgaggatgtt    180
tttgtcggta ctttgatacg tcatttttgt atgaattgat ttttaagttt attcgctttt    240
ggaaatgcat atctgtattt gagtcgggtt ttaagttcgt ttgcttttgt aaatacagag    300
ggatttgtat aagaaatatc tttagaaaaa cccatatgct aatttgacat aatttttgag    360
aaaaatatat attcaggcga attagcttag gcctcatcgt tgaagatgcc tctgccgaca    420
gtggtcccaa agatggaccc ccacccacga ggagcatcgt ggaaaaagaa gacgttccaa    480
ccacgtcttc aaagcaagtg gattgatgtg atatctccac tgacgtaagg gatgacgcac    540
aatcccacta tccttcgagg cctcatcgtt gaagatgcct ctgccgacag tggtcccaaa    600
gatggacccc cacccacgag gagcatcgtg gaaaaagaag acgttccaac cacgtcttca    660
aagcaagtgg attgatgtga tatctccact gacgtaaggg atgacgcaca atcccactat    720
ccttcgaagc taattctcac aatgaacaat aataagatta aaatagcttt ccccgttgc    780
agcgcatggg tatttttttct agtaaaaata aagataaac ttagactcaa aacatttaca    840
aaaacaaccc ctaaagttcc taaagccaa agtgctatcc acgatccata gcaagcccaa    900
cccaacccaa cccaacccaa cccacccag tccagccaac tggacaatag tctccacacc    960
cccccactat caccgtgagt tgtccgcacg caccgcacgt ctcgcagcca aaaaaaaaa   1020
gaaagaaaaa aaagaaaaag aaaaaacagc aggtgggtcc gggtcgtggg ggccggaaac  1080
gcgaggagga tcgcgagcca gcgacgaggc cggccctccc tccgcttcca aagaaacgcc  1140
cccatcgcc actatataca tacccccccc tctcctcccca tccccccaac cctaccacca  1200
ccaccaccac cacctccacc tcctcccccc tcgctgccgg acgacgagct cctccccct   1260
cccccctccgc cgccgccgcg ccggtaacca ccccgcccct ctcctctttc tttctccgtt  1320
tttttttccg tctcggtctc gatctttggc cttggtagtt tgggtgggcg agaggcggct  1380
tcgtgcgcgc ccagatcggt gcgcggggag ggcgggatct cgcggcgcg gtctctgcga  1440
gcgtggatcc ggcccggatc tcgcggggaa tggggctctc ggatgtagat ctgcgatccg  1500
ccgttgttgg gggagatgat ggggggttta aaatttccgc cgtgctaaac aagatcagga  1560
agaggggaaa agggcactat ggtttatatt tttatatatt tctgctgctt cgtcaggctt  1620
agatgtgcta gatctttctt tcttcttttt gtgggtagaa tttgaatccc tcagcattgt  1680
tcatcggtag ttttctttt catgatttgt gacaaatgca gcctcgtgcg gagctttttt  1740
gtaggtagaa g                                                        1751

SEQ ID NO: 173          moltype = DNA  length = 1101
FEATURE                 Location/Qualifiers
source                  1..1101
                        mol_type = other DNA
                        organism = synthetic construct
SEQUENCE: 173
ggtccgattg agactttca acaaagggta atatccggaa acctcctcgg attccattgc     60
ccagctatct gtcactttat tgtgaagata gtggaaaagg aaggtggctc ctacaaatgc   120
catcattgcg ataaaggaaa ggccatcgtt gaagatgcct ctgccgacag tggtcccaaa   180
gatggacccc cacccacgag gagcatcgtg gaaaaagaag acgttccaac cacgtcttca   240
aagcaagtgg attgatgtga tggtccgatt gagactttc aacaaagggt aatatccgga   300
aacctcctcg gattccattg cccagctatc tgtcactta ttgtgaagat agtggaaaag   360
gaaggtggct cctacaaatg ccatcattgc gataaaggaa aggccatcgt tgaagatgcc   420
tctgccgaca gtggtcccaa agatggaccc ccacccacga ggagcatcgt ggaaaaagaa   480
gacgttccaa ccacgtcttc aaagcaagtg gattgatgtg atatctccac tgacgtaagg   540
gatgacgcac aatcccacta tccttcgcaa gaccttcct ctatataagg aagttcattt   600
catttggaga ggacacgctg accgccgccg ccggtaacca ccccgcccct ctcctcttc   660
ttctccgtt ttttttccg tctcggtctc gatctttggc cttggtagtt tgggtgggcg   720
agaggcggct tcgtgcgcgc ccagatcggt gcgcggggag ggcgggatct cgcggcgctg  780
gctctcgccg gcgtggatcc ggcccggatc tcgcggggaa tggggctctc ggatgtagat  840
ctgcgatccg ccgttgttgg gggagatgat ggggggttta aaatttccgc cgtgctaaac  900
aagatcagga agaggggaaa agggcactat ggtttatatt tttatatatt tctgctgctt  960
cgtcaggctt agatgtgcta gatctttctt tcttcttttt gtgggtagaa tttgaatccc 1020
tcagcattgt tcatcggtag ttttctttt catgatttgt gacaaatgca gcctcgtgcg 1080
gagctttttt gtaggtagaa g                                             1101

SEQ ID NO: 174          moltype = DNA  length = 200
FEATURE                 Location/Qualifiers
source                  1..200
```

```
                    mol_type = other DNA
                    organism = Cauliflower mosaic virus
SEQUENCE: 174
aaatcaccag tctctctcta caaatctatc tctctctatt tttctccaga ataatgtgtg    60
agtagttccc agataaggga attagggttc ttatagggtt tcgctcatgt gttgagcata   120
taagaaaccc ttagtatgta tttgtatttg taaaatactt ctatcaataa aatttctaat   180
tcctaaaacc aaaatccagt                                               200

SEQ ID NO: 175      moltype = DNA  length = 300
FEATURE             Location/Qualifiers
source              1..300
                    mol_type = other DNA
                    organism = Oryza sativa
SEQUENCE: 175
attaatcgat cctccgatcc cttaattacc ataccattac accatgcatc aatatccata    60
tatatataaa cccttcgca cgtacttata ctatgttttg tcatacatat atatgtgtcg    120
aacgatcgat ctatcactga tatgatatga ttgatccatc agcctgatct ctgtatcttg   180
ttatttgtat accgtcaaat aaaagtttct tccacttgtg ttaataatta gctactctca   240
tctcatgaac cctatatata actagtttaa tttgctgtca attgaacatg atgatcgatg   300

SEQ ID NO: 176      moltype = DNA  length = 623
FEATURE             Location/Qualifiers
source              1..623
                    mol_type = other DNA
                    organism = Cauliflower mosaic virus
SEQUENCE: 176
ggtccgatgt gagacttttc aacaaagggt aatatccgga aacctcctcg gattccattg    60
cccagctatc tgtcacttta ttgtgaagat agtggaaaag gaaggtggct cctacaaatg   120
ccatcattgc gataaaggaa aggccatcgt tgaagatgcc tctgccgaca gtggtcccaa   180
agatgaccct ccaccacga ggagcatcgt ggaaaaagaa gacgttccaa ccacgtcttc   240
aaagcaagtg gattgatgtg atggtccgat gtgagacttt tcaacaaagg gtaatatccg   300
gaacctcct cggattccat tgcccagcta tctgtcactt tattgtgaag atagtggaaa   360
aggaaggtgg ctcctacaaa tgccatcatt gcgataaagg aaaggccatc gttgaagatg   420
cctctgccga cagtggtccc aaagatggac cccacccaa gaggagcatc gtggaaaaag   480
aagacgttcc aaccacgtct tcaaagcaag tggattgatg tgatatctcc actgacgtaa   540
gggatgacgc acaatcccac tatccttcgc aagacccttc ctctatataa ggaagttcat   600
ttcatttgga gaggacacgc tga                                           623

SEQ ID NO: 177      moltype =    length =
SEQUENCE: 177
000

SEQ ID NO: 178      moltype = DNA  length = 804
FEATURE             Location/Qualifiers
source              1..804
                    mol_type = other DNA
                    organism = Zea mays
SEQUENCE: 178
accgtcttcg gtacgcgctc actccgccct ctgcctttgt tactgccacg tttctctgaa    60
tgctctcttg tgtggtgatt gctgagagtg gtttagctgg atctagaatt acactctgaa   120
atcgtgttct gcctgtgctg attacttgcc gtcctttgta gcagcaaaat atagggacat   180
ggtagtacga aacgaagata gaacctacac agcaatacga gaaatgtgta atttggtgct   240
tagcggtatt tatttaagca catgttggtg ttatagggca cttggattca gaagtttgct   300
gttaatttag gcacaggctt catactacat gggtcaatag tatagggatt catattatag   360
gcgatactat aataatttgt tcgtctgcag agcttattat ttgccaaaat tagatattcc   420
tattctgttt ttgtttgtgt gctgttaaat tgttaacgcc tgaaggaata aatataaatg   480
acgaaatttt gatgtttatc tctgctcctt tattgtgacc ataagtcaag atcagatgca   540
cttgttttaa atattgttgt ctgaagaaat aagtactgac agtattttga tgcattgatc   600
tgcttgtttg ttgtaacaaa atttaaaaat aaagagtttc cttttgttg ctctccttac   660
ctcctgatgg tatctagtat ctaccaactg acactatatt gcttctcttt acatacgatt   720
cttgctcgat gccttctccc tagtgttgac cagtgttact cacatagtct ttgctcattt   780
cattgtaatg cagataccaa gcgg                                          804

SEQ ID NO: 179      moltype = DNA  length = 1396
FEATURE             Location/Qualifiers
source              1..1396
                    mol_type = other DNA
                    organism = Oryza sativa
SEQUENCE: 179
tcgaggtcat tcatatgctt gagaagagag tcgggatagt ccaaaataaa acaaaggtaa    60
gattacctgg tcaaaagtga aaacatcagt taaaggtgg tataaagtaa aatatcggta   120
ataaaggta gcccaaagtg aaatttactc ttttctacta ttataaaaat tgaggatgtt   180
tttgtcggta ctttgatacg tcattttgt atgaattggt tttaagttt attcgctttt   240
ggaaatgcat atctgtattt gagtcgggtt ttaagttcgt ttgcttttgt aaatacagag   300
ggatttgtat aagaaatatc tttagaaaaa cccatatgct aatttgacat aatttttgag   360
aaaaatatat attcaggcga attctcacaa tgaacaataa taagattaaa atagctttcc   420
cccgttgcag cgcatgggta ttttttctag taaaaataaa agataaactt agactcaaaa   480
catttacaaa aacaacccct aaagttccta agcccaaagt tgctatccac gatccatagc   540
aagcccagcc caacccaacc caacccagcc caccccagtc agccaactg gacaatagtc   600
```

```
tccacacccc cccactatca ccgtgagttg tccgcacgca ccgcacgtct cgcagccaaa    660
aaaaaaaaga aagaaaaaaa agaaaaagaa aaaacagcag gtgggtccgg gtcgtggggg    720
ccggaaacgc gaggaggatc gcgagccagc gacgaggccg gccctccctc cgcttccaaa    780
gaaacgcccc ccatcgccac tatatacata cccccccctc tcctcccatc cccccaaccc    840
taccaccacc accaccacca cctccacctc ctccccctc gctgccggac gacgagctcc    900
tccccctcc cctccgccg ccgccgcgcc ggtaaccacc ccgcccctct cctctttctt    960
tctccgtttt tttttccgtc tcggtctcga tctttggcct tggtagtttg ggtgggcgag  1020
aggcggcttc gtgccgccca gatcggtgcg cgggaggggc gggatctcgc ggctggctct  1080
cgccccgtg gatccggccc ggatctcgcg gggaatgggg ctctcggatg tagatctgcg  1140
atccgccgtt gttggggccg atgatggggc ccttaaaatt tccgccgtgc taaacaagat  1200
caggaagagg ggaaaagggc actatggttt atatttttat atatttctgc tgcttcgtca  1260
ggcttagatg tgctagatct ttctttcttc tttttgtggg tagaatttaa tccctcagca  1320
ttgttcatcg gtagttttc ttttcatgat tcgtgacaaa tgcagcctcg tgcggacgtt  1380
tttttgtagg tagaag                                                 1396

SEQ ID NO: 180           moltype = DNA  length = 2625
FEATURE                  Location/Qualifiers
source                   1..2625
                         mol_type = other DNA
                         organism = Setaria italica
SEQUENCE: 180
actgccgcga cacgcctcac tggcgggagg gctccgagcg ctctctcccc ggcggccggc    60
ggagcagcga tctggattgg agagaataga ggaaagagag ggaaaaggag agagatagcg   120
caaagagctg aaaagataag gttgtgcggg ctgtggtgat tagaggacca ctaatccctc   180
catctcctaa tgacgcggtg cccaagacca gtgccgcggc acaccagcgt ctaagtgaac   240
ttccgctaac cttccggtca ttgcgcctga aagatgtcat gtggcgaggc cccctctca   300
gtagattgcc aactgcctac cgtgccactc ttccatgcat gattgctccc gtctatcccg   360
tttctcacaa cagatagaca acagtaagca tcactaaagc aagcatgtgt agaaccttaa   420
aaaaaggctt atactaccag tatactatca accagcatgc cgttttgaa gtatccagga   480
ttagaagctt ctactgcgct tttatattat agctgtgaac ccgtggtaac cttttctctt   540
tggcgcttgc ttaatctcgg ccgtgctggt ccatgcttag gcactaggca gagatagagc   600
cgggggtgaa tggggctaaa gctcagctgc tcgaggggcc gtgggctggt ttccactagc   660
ctacagctgt gccacgtgcg gccgcgcaag ccgaagcaag cacgctgagc cgttggacag   720
cttgtcataa tgccattacg tggattacac gtaactggcc ctgtaactac tcgttcgttg   780
atcatcaaac gacgacgtcc gctaggcgac gacacgggta atgcacgcag ccacccaggc   840
gcgcgcgcta gcggagcacg gtcaggtgac acgggcgtcg tgacgcttcc gagttgaagg   900
ggttaacgcc agaaacagtg tttggccagg gtatgaacat aacaaaaaat attcacacga   960
aagaatggaa gtatggagct gctactgtgt aaatgccaag caggaaactc acgcccgcta  1020
acatccaacg gccaacagct cgactgccg gtcagcagag catcggaaca ctggtgattg   1080
gtggagccgg cagtatgcgc cccagcacgg ccgaggtggt ggtggccgt ggccctgctg  1140
tctgcgcggc tcgggacaac ttgaaactgg gccaccgcct cgtcgcaact cgcaacccgt  1200
tggcggaaga aaggaatggc tcgtaggggc ccgggtagaa tcgaagaatg ttgcgctggg  1260
cttcgattca cataacatgg gcctgaagct ctaaaacgag ggcccggtcg ccgcgcgtta  1320
gaaagagacc ggatcctcct cgtgaattct ggaaggccac acgagagcga cccaccaccg  1380
acgcggagga gtcgtgcgtg gtccaacacg gccggcgggc tgggctgcga ccttaaccag  1440
caaggcacgc cacgacccgc cccgcctcg aggcataaat accctcccat cccgttgccg  1500
caagactcag atcagattcc gatcccccagt tcttccccaa tcaccttgtg gtctctcgtg  1560
tcgcggttcc cagggacgcc tccggctcgt cgctcgacag cgatctccgc cccagcaagg  1620
tatagattca gttccttgct ccgatcccaa tctggttgag atgttgctcc gatgcgactt  1680
gattatgtca tatatctgcg gtttgcaccg atctgaagcc tagggtttct cgagcgaccc  1740
agttatttgc aatttgcgat ttgctcgttt gttgcgcagc gtagtttatg tttggagtaa  1800
tcgaggattt gtatgcggcg tcggcgctac ctgcttaatc acgccatgtg acgcggttac  1860
ttgcagaggc tgggttctgt tatgtcgtga tctaagaatc tagattaggc tcagtcgttc  1920
ttgctgtcga ctagtttgtt ttgatatcca tgtagtacaa gttacttaaa atttaggtcc  1980
aatatatttt gcatgctttt ggcctgttat tcttgccaac aagttgtcct ggtaaaaagt  2040
agatgtgaaa gtcacgtatt gggacaaatt gatggtttag tgctatagtt ctatagttct  2100
gtgatacatc tatctgattt ttttggtct attggtgcct aacttatctg aaaatcatgg  2160
aacatgaggc tagtttgatc atggtttagt tcattgtgat taataatgta tgatttagta  2220
gctattttgg tgatcgtgtc atttttatttg tgaatgaat cattgtatgt aaatgaagct  2280
agttcagggg ttacgatgta gctggctttg tattctaaag gctgctatta ttcatccatc  2340
gatttcacct atatgtaatc cagagctttt gatgtgaaat ttgtctgatc cttcactagg  2400
aaggacagaa cattgttaat attttggcac atctgtctta ttctcatcct ttgtttgaac  2460
atgttagcct gttcaaacag atactgttgt aatgtcctag ttataggt acatatgtgt  2520
tctctattga gtttatggac ttttgtgtgt gaagttatat ttcatttgc tcaaaactca  2580
tgtttgcaag ctttctgaca ttattctatt gttctgaaac aggtg                 2625

SEQ ID NO: 181           moltype = DNA  length = 2008
FEATURE                  Location/Qualifiers
source                   1..2008
                         mol_type = other DNA
                         organism = Zea mays
                         sub_species = Mexicana
SEQUENCE: 181
gtcgtgcccc tctctagaga taaagagcat tgcatgtcta aagtataaaa aattaccaca    60
tatttttttg tcacacttat ttgaagtgta gtttatctat ctctatacat atatttaaac   120
ttcactctac aaataatata gtctataata ctaaaataat attagtgttt tagaggatca   180
tataaataaa ctgctagaca tggtctaaag gataattgaa tattttgaca atctacagtt   240
ttatcttttt agtgtgcatg tgatctctct gtttttttg caaatagctt gacctatata   300
atacttcatc cattttatta gtacatccat ttaggattta gggttgatgg tttctataga   360
```

```
ctaattttta gtacatccat tttattcttt ttagtctcta aattttttaa aactaaaact    420
ctattttagt tttttattta ataatttaga tataaaatga aataaaataa attgactaca    480
aataaaacaa atacccttta agaaataaaa aaactaagca aacattttc ttgtttcgag    540
tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
accctctcg  agagttccgc tccaccgttg gacttgctcc gctgtcggca tccagaaatt    720
gcgtggcgga gcgcagacg  tgaggcggca cggcaggcgg cctcttcctc ctctcacggc    780
accggcagct acggggatt  cctttcccac cgctccttcg cttcccttc  ctcgcccgcc    840
gtaataaata gacacccct  ccacaccctc tttcccaac  ctcgtgtcg  ttcggagcgc    900
acacacacgc aaccagatct cccccaaatc cagccgtcgg cacctccgct tcaaggtacg    960
ccgctcatcc tccccccccc cctctctcta ccttctctag atcggcgatc cggtccatgg   1020
ttagggcccg gtagttctac ttctgttcat gtttgtgtta gagcaaacat gttcatgttc   1080
atgtttgtga tgatgtggtc tggttgggcg gtcgttctag atcggagtag gatactgttt   1140
caagctacct ggtggattta ttaattttgt atctgtatgt gtgtgccata catcttcata   1200
gttacgagtt taagatgatg gatggaaata tcgatctagg ataggtatac atgttgatgc   1260
gggttttact gatgcatata cagagatgct ttttttctcg cttggttgtg atgatatggt   1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
atttattaaa ggatctgtat gtatgtgcct acatcttcat agttacgagt ttaagatgat   1500
ggatggaaat atcgatctag gataggtata catgttgatg cgggttttac tgatgcatat   1560
acagagatgc ttttttcgc  ttggttgtga tgatgtggtc tggttgggcg gtcgttctag   1620
atcggagtag aatactgttt caaactacct ggtggattta ttaattttgt atctttatgt   1680
gtgtgccata catcttcata gttacgagtt taagatgatg gatggaaata ttgatctagg   1740
ataggtatac atgttgatgt gggttttact gatgcatata catgatggca tatgcggcat   1800
ctattcatat gctctaacct tgagtaccta tctattataa taaacaagta tgttttataa   1860
ttatttgat  cttgatatac ttggatgatg gcatatgcag cagctatatg tggatttttt   1920
agccctgcct tcatacgcta tttatttgct tggtactgtt tcttttgtcc gatgctcacc   1980
ctgttgttgg gtgatacttc tgcagcgg                                      2008

SEQ ID NO: 182          moltype = DNA  length = 1053
FEATURE                 Location/Qualifiers
source                  1..1053
                        mol_type = other DNA
                        organism = Zea mays
                        sub_species = Mexicana
SEQUENCE: 182
gtacgccgct catcctcccc ccccccctct ctctaccttc tctagatcgg cgatccggtc     60
catggttagg gcccggtagt tctacttctg ttcatgtttg tgttagagca aacatgttca    120
tgttcatgtt tgtgatgatg tggtctggtt gggcggtcgt tctagatcgg agtaggatac    180
tgtttcaagc tacctggtgg atttattaat tttgtatctg tatgtgtgtg ccatacatct    240
tcatagttac gagtttaaga tgatggatgg aaatatcgat ctaggatagg tatacatgtt    300
gatgcgggtt ttactgatgc atatacagag atgctttttt tctcgcttgg ttgtgatgat    360
atggtctggt tgggcggtcg ttctagatcg gagtagaata ctgtttcaaa ctacctggtg    420
gatttattaa aggataaagg gtcgttctag atcggagtag aatactgttt caaactacct    480
ggtggattta ttaaaggatc tgtatgtatg tgcctacatc ttcatagtta cgagtttaag    540
atgatggatg gaaatatcga tctaggatag gtatacatgt tgatgcgggt ttactgatg    600
catatacaga gatgcttttt tcgcttggt tgtgatgtcg gtctggttgg gcggtcgt    660
tctagatcgg agtagaatac tgtttcaaac tacctggtgg atttattaat tttgtatctt    720
tatgtgtgtg ccatacatct tcatagttac gagtttaaga tgatggatgg aaatattgat    780
ctaggatagg tatacatgtt gatgtgggtt ttactgatgc atatacatga tggcatatgc    840
ggcatctatt catatgctct aaccttgagt acctatctat tataaacaag tagtttataa    900
tataattatt ttgatcttga tatacttgga tgatggcata tgcagcagct atatgtggat    960
tttttagccc tgccttcata cgctatttat ttgcttggta ctgtttcttt tgtccgatgc   1020
tcaccctgtt gttgggtgat acttctgcag cgg                                1053

SEQ ID NO: 183          moltype = DNA  length = 2625
FEATURE                 Location/Qualifiers
source                  1..2625
                        mol_type = other DNA
                        organism = Setaria italica
SEQUENCE: 183
actgccgcga cacgcctcac tggcgggagg gctccgagcg ctctctcccc ggcggccggc     60
ggagcagcga tctggattgg agagaataga ggaaagagag ggaaaaggag agagatagcg    120
caaagacgtg aaaagataag gttgtgcggg ctgtggtgat tagaggacca ctaatccctc    180
catctcctaa tgacgcggtg cccaagacca gtgccgcggc acaccagcgt ctaagtgaac    240
ttccgctaac cttccggtca ttgcgcctga aagatgtcat gtggcgaggc ccccctctca    300
gtagattgcc aactgcctac cgtgccactc ttccatgcat gattgctccc gtctatcccg    360
tttctcacaa cagatagaca acagtaagca tcactaaagc aagcatgtgt agaaccttaa    420
aaaaaggctt atactaccag tatactatca accagtgtcg cgttttgaa gtatccagga    480
ttagaagctt ctactgcgct tttatattat agctgtggac ccgtggtaac ctttctcttt    540
tggcgcttgc ttaatctcgg ccgtgctggt ccatgcttag gcactaggca gagatagagc    600
cggggtgaa  tggggctaaa gctcagctgc tcgaggggcc gtgggctggt ttccactagc    660
ctacagctgt gccacgtgcg gccgcgcaag ccgaagcaag cacgctgagc cgttggacag    720
cttgtcataa tgccattacg tggattacac gtaactgact tcgttcgctg                780
atcatcaaac gacgacgtcc gctaggcgac gacacgggta atgcacgcag ccacccagcc    840
gcgcgcgcta gcggagcacg gtcaggtgac acgggcgtcg tgacgcttcc gagttgaagg    900
ggttaacgcc agaaacagtg tttggccagg gtatgaacat aacaaaaaat attcacacga    960
aagaatggaa gtatggagct gctactgtgt aaatgccaag caggaaactc acgcccgcta   1020
acatccaacg gccaacagct cgacgtgccg gtcagcagag catcggaaca ctggtgattg   1080
```

```
                                                              -continued
gtggagccgg cagtatgcgc cccagcacgg ccgaggtggt ggtggcccgt ggccctgctg    1140
tctgcgcggc tcgggacaac ttgaaactgg gccaccgcct cgtcgcaact cgcaacccgt    1200
tggcggaaga aaggaatggc tcgtaggggc ccgggtagaa tcgaagaatg ttgcgctggg    1260
cttcgattca cataacatgg gcctgaagct ctaaaacgac ggcccggtcg ccgcgcgatg    1320
gaaagagacc ggatcctcct cgtgaattct ggaaggccac acgagagcga cccaccaccg    1380
acgcggagga gtcgtgcgtg gtccaacacg gccggcgggc tgggctgcga ccttaaccag    1440
caaggcacgc cacgacccgc cccgccctcg aggcataaat accctcccat cccgttgccg    1500
caagactcag atcagattcc gatcccccagt tcttccccaa tcaccttgtg gtctctcgtg    1560
tcgcggttcc cagggacgcc tccggctcgt cgctcgacag cgatctccgc cccagcaagg    1620
tatagattca gttccttgct ccgatcccaa tctggttgag atgttgctcc gatgcgactt    1680
gattatgtca tatatctgcg gtttgcaccg atctgaagcc tagggtttct cgagcgaccc    1740
agttatttgc aatttgcgat ttgctcgttt gttgcgcagc gtagtttatg tttggagtaa    1800
tcgaggattt gtatgcggcg tcggcgctac ctgcttaatc acgccatgtg acgcggttac    1860
ttgcagaggc tgggttctgt tatgtcgtga tctaagaatc tagattaggc tcagtcgttc    1920
ttgctgtcga ctagtttgtt ttgatatcca tgtagtacaa gttacttaaa atttaggtcc    1980
aatatatttt gcatgctttt ggcctgttat tcttgccaac aagttgtcct ggtaaaaagt    2040
agatgtgaaa gtcacgtatt gggacaaatt gatggtttag tgctatagtt ctatagttct    2100
gtgatacatc tatctgattt tttttggtct attggtgcct aacttatctg aaaatcatgg    2160
aacatgaggc tagtttgatc atggtttagt tcattgtgat taataatgta tgatttagta    2220
gctattttgg tgatcgtgtc attttatttg tgaatggaat cattgtatgt aaatgaagct    2280
agttcagggg ttacgatgta gctggctttg tattctaaag gctgctatta ttcatccatc    2340
gatttcacct atatgtaatc cagagctttt gatgtgaaat ttgtctgatc cttcactagg    2400
aaggacagaa cattgttaat attttggcac atctgtctta ttctcatcct ttgtttgaac    2460
atgttagcct gttcaaacag atactgttgt aatgtcctag ttatataggt acatatgtgt    2520
tctctattga gtttatggac ttttgtgtgt gaagttatat ttcattttgc tcaaaactca    2580
tgtttgcaag ctttctgaca ttattctatt gttctgaaac aggtg                   2625
```